United States Patent
Devine et al.

(10) Patent No.: US 11,452,915 B2
(45) Date of Patent: Sep. 27, 2022

(54) USER INTERFACES FOR WORKOUT CONTENT

(71) Applicant: Apple Inc., Cupertino, CA (US)

(72) Inventors: Lynne Devine, San Francisco, CA (US); Joel A. Angelone, San Francisco, CA (US); Julie A. Arney, Los Gatos, CA (US); Niharika Milind Bedekar, San Francisco, CA (US); Jay Blahnik, San Francisco, CA (US); Gary Ian Butcher, Los Gatos, CA (US); Edward Chao, Palo Alto, CA (US); David Clark, Corona Del Mar, CA (US); Alan C. Dye, San Francisco, CA (US); Hanwen Fan, San Jose, CA (US); Eamon F. Gilravi, San Francisco, CA (US); Anders Kalle Haglunds, Sunnyvale, CA (US); Brett L. Lareau, San Jose, CA (US); Emily Pedersen, Los Altos Hills, CA (US); Danvin Ruangchan, San Jose, CA (US); Matthew J. Sundstrom, Campbell, CA (US); Eduardo Valencia Paz, San Francisco, CA (US); Molly Pray Wiebe, San Francisco, CA (US); Aled Hywel Williams, Llandeilo (GB)

(73) Assignee: Apple Inc., Cupertino, CA (US)

( * ) Notice: Subject to any disclaimer, the term of this patent is extended or adjusted under 35 U.S.C. 154(b) by 54 days.

(21) Appl. No.: 17/031,543

(22) Filed: Sep. 24, 2020

(65) Prior Publication Data
US 2021/0255758 A1 Aug. 19, 2021

Related U.S. Application Data

(60) Provisional application No. 63/078,311, filed on Sep. 14, 2020, provisional application No. 63/036,374, (Continued)

(51) Int. Cl.
*G06F 3/048* (2013.01)
*A63B 24/00* (2006.01)
(Continued)

(52) U.S. Cl.
CPC ........ *A63B 24/0062* (2013.01); *A61B 5/4866* (2013.01); *A63B 24/0006* (2013.01);
(Continued)

(58) Field of Classification Search
CPC ............ A63B 24/0062; A63B 24/0006; A63B 24/0075; A63B 71/0622;
(Continued)

(56) References Cited

U.S. PATENT DOCUMENTS

| | | | |
|---|---|---|---|
| 4,205,628 A | 6/1980 | Null | |
| 4,842,266 A | 6/1989 | Sweeney et al. | |

(Continued)

FOREIGN PATENT DOCUMENTS

| | | |
|---|---|---|
| CA | 2815518 A1 | 5/2012 |
| CN | 1337638 A | 2/2002 |

(Continued)

OTHER PUBLICATIONS

US 2002/0018582 A1, 02/2002, Hagiwara et al. (withdrawn)
(Continued)

*Primary Examiner* — David Phantana-angkool
(74) *Attorney, Agent, or Firm* — Dentons US LLP

(57) ABSTRACT

In some embodiments, an electronic device performs techniques related to displaying personalized workout suggestions based on completed workouts. In some embodiments, an electronic device performs techniques related to starting an audio-based workout. In some embodiments, an electronic device performs techniques related to displaying information about a workout during playback of workout content. In some embodiments, an electronic device per-
(Continued)

forms techniques related to displaying information about physical activity of a user relative to a group of users. In some embodiments, an electronic device performs techniques related to coordinating display of workout content among multiple devices.

66 Claims, 168 Drawing Sheets

Related U.S. Application Data filed on Jun. 8, 2020, provisional application No. 62/977,076, filed on Feb. 14, 2020.

(51) Int. Cl.

| | |
|---|---|
| A63B 71/06 | (2006.01) |
| A61B 5/00 | (2006.01) |
| G16H 20/30 | (2018.01) |
| G06F 3/0484 | (2022.01) |
| H04W 12/55 | (2021.01) |
| G06F 3/04842 | (2022.01) |
| G06F 3/16 | (2006.01) |
| G06F 3/0482 | (2013.01) |
| G06F 3/0481 | (2022.01) |
| G16H 40/63 | (2018.01) |
| G16H 50/70 | (2018.01) |

(52) U.S. Cl.
CPC ...... *A63B 24/0075* (2013.01); *A63B 71/0622* (2013.01); *G06F 3/0481* (2013.01); *G06F 3/0482* (2013.01); *G06F 3/0484* (2013.01); *G06F 3/04842* (2013.01); *G06F 3/167* (2013.01); *G16H 20/30* (2018.01); *G16H 40/63* (2018.01); *G16H 50/70* (2018.01); *H04W 12/55* (2021.01); *A63B 2024/0009* (2013.01); *A63B 2024/0015* (2013.01); *A63B 2024/0065* (2013.01); *A63B 2024/0068* (2013.01); *A63B 2071/0655* (2013.01)

(58) Field of Classification Search
CPC .... A63B 2024/0009; A63B 2024/0015; A63B 2024/0065; A63B 2024/0068; A63B 2071/0655; H04W 12/55; A61B 5/4866; G06F 3/0484; G06F 3/04842; G06F 3/167; G16H 20/30

See application file for complete search history.

(56) References Cited

U.S. PATENT DOCUMENTS

| | | |
|---|---|---|
| 5,423,863 A | 6/1995 | Felblinger et al. |
| 5,458,548 A | 10/1995 | Crossing et al. |
| 5,463,725 A | 10/1995 | Henckel et al. |
| 5,474,077 A | 12/1995 | Suga |
| 5,583,542 A | 12/1996 | Capps et al. |
| 5,602,981 A | 2/1997 | Hargrove |
| 5,642,731 A | 7/1997 | Kehr |
| 5,677,708 A | 10/1997 | Matthews et al. |
| 5,685,723 A | 11/1997 | Ladin et al. |
| 5,712,995 A | 1/1998 | Cohn |
| 5,767,835 A | 6/1998 | Obbink et al. |
| 5,788,655 A | 8/1998 | Yoshimura et al. |
| 5,825,349 A | 10/1998 | Meier et al. |
| 5,845,122 A | 12/1998 | Nielsen et al. |
| 5,864,868 A | 1/1999 | Contois |
| 5,886,697 A | 3/1999 | Naughton et al. |
| 5,969,283 A | 10/1999 | Looney et al. |
| 6,013,008 A | 1/2000 | Fukushima |
| 6,055,543 A | 4/2000 | Christensen et al. |
| 6,088,649 A | 7/2000 | Kadaba et al. |
| 6,095,949 A | 8/2000 | Arai |
| 6,095,984 A | 8/2000 | Amano et al. |
| 6,097,371 A | 8/2000 | Siddiqui et al. |
| 6,097,385 A | 8/2000 | Robinson |
| 6,118,450 A | 9/2000 | Proehl et al. |
| 6,141,007 A | 10/2000 | Elterman et al. |
| 6,154,210 A | 11/2000 | Anderson |
| 6,160,551 A | 12/2000 | Naughton et al. |
| 6,167,469 A | 12/2000 | Safai et al. |
| 6,237,010 B1 | 5/2001 | Hui et al. |
| 6,244,988 B1 | 6/2001 | Delman |
| 6,245,982 B1 | 6/2001 | Suzuki et al. |
| 6,248,946 B1 | 6/2001 | Dwek |
| 6,292,273 B1 | 9/2001 | Dow et al. |
| 6,301,586 B1 | 10/2001 | Yang et al. |
| 6,302,789 B2 | 10/2001 | Harada et al. |
| 6,317,784 B1 | 11/2001 | Mackintosh et al. |
| 6,334,025 B1 | 12/2001 | Yamagami et al. |
| 6,346,951 B1 | 2/2002 | Mastronardi |
| 6,356,971 B1 | 3/2002 | Katz et al. |
| 6,374,177 B1 | 4/2002 | Lee et al. |
| 6,380,947 B1 | 4/2002 | Stead |
| 6,416,471 B1 | 7/2002 | Kumar et al. |
| 6,462,760 B1 | 10/2002 | Cox et al. |
| 6,564,213 B1 | 5/2003 | Ortega et al. |
| 6,603,477 B1 | 8/2003 | Tittle |
| 6,639,584 B1 | 10/2003 | Li |
| 6,705,972 B1 | 3/2004 | Takano et al. |
| 6,713,312 B2 | 3/2004 | Blalock et al. |
| 6,731,312 B2 | 5/2004 | Robbin |
| 6,784,925 B1 | 8/2004 | Tomat et al. |
| 6,837,827 B1 | 1/2005 | Lee et al. |
| 6,866,613 B1 | 3/2005 | Brown et al. |
| 6,920,619 B1 | 7/2005 | Milekic |
| 6,950,989 B2 | 9/2005 | Rosenzweig et al. |
| 7,020,514 B1 | 3/2006 | Wiesel |
| 7,128,693 B2 | 10/2006 | Brown et al. |
| 7,164,410 B2 | 1/2007 | Kupka |
| 7,251,454 B2 | 7/2007 | White |
| 7,302,272 B2 | 11/2007 | Ackley |
| 7,380,212 B2 | 5/2008 | Cody et al. |
| 7,444,390 B2 | 10/2008 | Tadayon et al. |
| 7,453,444 B2 | 11/2008 | Geaghan |
| 7,559,034 B1 | 7/2009 | Paperny et al. |
| 7,627,828 B1 | 12/2009 | Collison et al. |
| 7,662,065 B1 | 2/2010 | Kahn et al. |
| 7,695,406 B2 | 4/2010 | Waters |
| 7,739,148 B2 | 6/2010 | Suzuki et al. |
| 7,779,358 B1 | 8/2010 | Gupta et al. |
| 7,791,755 B2 | 9/2010 | Mori |
| 7,823,080 B2 | 10/2010 | Miyajima et al. |
| 7,970,240 B1 | 6/2011 | Chao et al. |
| 7,996,788 B2 | 8/2011 | Carmichael |
| 8,024,658 B1 | 9/2011 | Fagans et al. |
| 8,060,229 B2 | 11/2011 | Gupta et al. |
| 8,105,208 B2 | 1/2012 | Oleson et al. |
| 8,106,856 B2 | 1/2012 | Matas et al. |
| 8,132,116 B1 | 3/2012 | Schendel |
| 8,152,640 B2 | 4/2012 | Shirakawa et al. |
| 8,259,132 B2 | 9/2012 | Buchheit |
| 8,305,355 B2 | 11/2012 | Forstall et al. |
| 8,321,006 B1 | 11/2012 | Snyder et al. |
| 8,339,420 B2 | 12/2012 | Hiraoka et al. |
| 8,341,557 B2 | 12/2012 | Pisula et al. |
| 8,456,431 B2 | 6/2013 | Victor |
| 8,458,617 B2 | 6/2013 | Victor et al. |
| 8,464,173 B2 | 6/2013 | Victor et al. |
| 8,475,339 B2 | 7/2013 | Hwang et al. |
| 8,496,563 B2 | 7/2013 | Komatsu et al. |
| 8,676,170 B2 | 3/2014 | Porrati et al. |
| 8,768,648 B2 | 7/2014 | Panther et al. |
| 8,780,069 B2 | 7/2014 | Victor et al. |
| 8,784,115 B1 | 7/2014 | Chuang |
| 8,825,445 B2 | 9/2014 | Hoffman et al. |
| 8,863,016 B2 | 10/2014 | Victor et al. |
| 8,934,963 B1 | 1/2015 | Farazi |
| 8,957,865 B2 | 2/2015 | Cieplinski et al. |
| 8,966,399 B2 | 2/2015 | Chiang et al. |
| 8,990,006 B1 | 3/2015 | Wallace et al. |

(56) References Cited

U.S. PATENT DOCUMENTS

| | | |
|---|---|---|
| 9,020,538 B1 | 4/2015 | White et al. |
| 9,224,291 B2 | 12/2015 | Moll-Carrillo et al. |
| 9,230,076 B2 | 1/2016 | King et al. |
| 9,310,907 B2 | 4/2016 | Victor et al. |
| 9,459,792 B2 | 10/2016 | Matas et al. |
| 9,557,881 B1 | 1/2017 | Jain et al. |
| 9,589,445 B2 | 3/2017 | White et al. |
| 9,712,629 B2 | 7/2017 | Molettiere et al. |
| 9,734,477 B2 | 8/2017 | Weast et al. |
| 9,813,642 B1 | 11/2017 | Chen et al. |
| 9,817,481 B2 | 11/2017 | Pantelopouios et al. |
| 9,854,653 B1 | 12/2017 | Ackmann et al. |
| 9,880,805 B1 * | 1/2018 | Guralnick ............... G06F 3/165 |
| 9,940,682 B2 | 4/2018 | Hoffman et al. |
| 10,056,006 B1 | 8/2018 | Hsu-Hoffman et al. |
| 10,220,258 B2 | 3/2019 | Gu et al. |
| 10,226,195 B2 | 3/2019 | Briante et al. |
| 10,282,070 B2 | 5/2019 | Victor |
| 10,300,334 B1 | 5/2019 | Chuang |
| 10,304,347 B2 | 5/2019 | Wilson et al. |
| 10,339,830 B2 | 7/2019 | Han et al. |
| 10,398,381 B1 | 9/2019 | Heneghan et al. |
| 10,489,508 B2 | 11/2019 | Zhai et al. |
| 10,736,543 B2 | 8/2020 | Chen et al. |
| 10,777,314 B1 * | 9/2020 | Williams ............... A61B 5/1118 |
| 11,103,161 B2 * | 8/2021 | Williams ............... H04W 4/029 |
| 11,107,569 B1 | 8/2021 | Devoto |
| 11,152,100 B2 * | 10/2021 | Crowley ............... A61B 5/7455 |
| 11,202,598 B2 * | 12/2021 | Soli ........ G06F 3/0414 |
| 11,209,957 B2 * | 12/2021 | Dryer ................. G06F 3/04847 |
| 11,317,833 B2 * | 5/2022 | Williams ............... H04W 4/029 |
| 2001/0014184 A1 | 8/2001 | Bubie et al. |
| 2001/0049470 A1 | 12/2001 | Mault et al. |
| 2002/0008763 A1 | 1/2002 | Kawamura et al. |
| 2002/0021758 A1 | 2/2002 | Chui et al. |
| 2002/0045960 A1 | 4/2002 | Phillips et al. |
| 2002/0054233 A1 | 5/2002 | Juen |
| 2002/0057292 A1 | 5/2002 | Holtz |
| 2002/0057461 A1 | 5/2002 | Dow et al. |
| 2002/0070982 A1 | 6/2002 | Hill et al. |
| 2002/0086774 A1 | 7/2002 | Warner |
| 2002/0106199 A1 | 8/2002 | Ikeda |
| 2002/0118121 A1 | 8/2002 | Lehrman et al. |
| 2002/0135621 A1 | 9/2002 | Angiulo et al. |
| 2003/0023178 A1 | 1/2003 | Bischoff et al. |
| 2003/0048291 A1 | 3/2003 | Dieberger |
| 2003/0064860 A1 | 4/2003 | Yamashita et al. |
| 2003/0081135 A1 | 5/2003 | Boll |
| 2003/0108241 A1 | 6/2003 | Colmenarez et al. |
| 2003/0122787 A1 | 7/2003 | Zimmerman et al. |
| 2003/0128192 A1 | 7/2003 | Van Os |
| 2003/0128241 A1 | 7/2003 | Watanabe et al. |
| 2003/0134714 A1 | 7/2003 | Oishi et al. |
| 2003/0149990 A1 | 8/2003 | Anttila et al. |
| 2003/0169288 A1 | 9/2003 | Misawa |
| 2003/0179229 A1 | 9/2003 | Van et al. |
| 2003/0181291 A1 | 9/2003 | Ogawa |
| 2003/0182628 A1 | 9/2003 | Lira |
| 2003/0197687 A1 | 10/2003 | Shetter |
| 2003/0216971 A1 | 11/2003 | Sick et al. |
| 2003/0226695 A1 | 12/2003 | Mault |
| 2004/0014567 A1 | 1/2004 | Mendel |
| 2004/0046886 A1 | 3/2004 | Ambiru et al. |
| 2004/0077462 A1 | 4/2004 | Brown et al. |
| 2004/0119758 A1 | 6/2004 | Grossman et al. |
| 2004/0128286 A1 | 7/2004 | Yasushi et al. |
| 2004/0135904 A1 | 7/2004 | Shiota et al. |
| 2004/0158555 A1 | 8/2004 | Seedman et al. |
| 2004/0183830 A1 | 9/2004 | Cody et al. |
| 2004/0205504 A1 | 10/2004 | Phillips |
| 2004/0207722 A1 | 10/2004 | Koyama et al. |
| 2004/0236189 A1 | 11/2004 | Hawthorne et al. |
| 2005/0041035 A1 | 2/2005 | Nagatomo et al. |
| 2005/0062130 A1 | 3/2005 | Ciancio et al. |
| 2005/0071767 A1 | 3/2005 | Kirkland et al. |
| 2005/0073601 A1 | 4/2005 | Battles et al. |
| 2005/0075214 A1 | 4/2005 | Brown et al. |
| 2005/0076307 A1 | 4/2005 | Robbin |
| 2005/0079905 A1 | 4/2005 | Martens |
| 2005/0083406 A1 | 4/2005 | Cozier |
| 2005/0088418 A1 | 4/2005 | Nguyen |
| 2005/0102635 A1 | 5/2005 | Jiang et al. |
| 2005/0104848 A1 | 5/2005 | Yamaguchi et al. |
| 2005/0113650 A1 | 5/2005 | Pacione et al. |
| 2005/0124324 A1 | 6/2005 | Thomas et al. |
| 2005/0134719 A1 | 6/2005 | Beck |
| 2005/0139852 A1 | 6/2005 | Chen et al. |
| 2005/0160377 A1 | 7/2005 | Sciammarella et al. |
| 2005/0165627 A1 | 7/2005 | Fotsch et al. |
| 2005/0172311 A1 | 8/2005 | Hjelt et al. |
| 2005/0183026 A1 | 8/2005 | Amano et al. |
| 2005/0195221 A1 | 9/2005 | Berger et al. |
| 2005/0197063 A1 | 9/2005 | White et al. |
| 2005/0216867 A1 | 9/2005 | Marvit et al. |
| 2005/0228735 A1 | 10/2005 | Duquette |
| 2005/0272564 A1 | 12/2005 | Pyles et al. |
| 2006/0001652 A1 | 1/2006 | Chiu et al. |
| 2006/0004685 A1 | 1/2006 | Pyhalammi et al. |
| 2006/0017692 A1 | 1/2006 | Wehrenberg et al. |
| 2006/0020174 A1 | 1/2006 | Matsumura et al. |
| 2006/0025218 A1 | 2/2006 | Hotta |
| 2006/0026521 A1 | 2/2006 | Hotelling et al. |
| 2006/0026535 A1 | 2/2006 | Hotelling et al. |
| 2006/0026536 A1 | 2/2006 | Hotelling et al. |
| 2006/0052727 A1 | 3/2006 | Palestrant |
| 2006/0061663 A1 | 3/2006 | Park |
| 2006/0072028 A1 | 4/2006 | Hong |
| 2006/0077266 A1 | 4/2006 | Nurmi et al. |
| 2006/0080386 A1 | 4/2006 | Roykkee et al. |
| 2006/0088228 A1 | 4/2006 | Marriott et al. |
| 2006/0098109 A1 | 5/2006 | Ooki |
| 2006/0106741 A1 | 5/2006 | Janarthanan |
| 2006/0112335 A1 | 5/2006 | Hofmeister et al. |
| 2006/0136246 A1 | 6/2006 | Tu |
| 2006/0136839 A1 | 6/2006 | Makela et al. |
| 2006/0164535 A1 | 7/2006 | Oyama |
| 2006/0170669 A1 | 8/2006 | Walker et al. |
| 2006/0184800 A1 | 8/2006 | Rosenberg |
| 2006/0184966 A1 | 8/2006 | Hunleth et al. |
| 2006/0240959 A1 | 10/2006 | Huang |
| 2006/0250524 A1 | 11/2006 | Roche |
| 2006/0279532 A1 | 12/2006 | Olszewski et al. |
| 2007/0016868 A1 | 1/2007 | Nurmi |
| 2007/0021269 A1 | 1/2007 | Shum |
| 2007/0031115 A1 | 2/2007 | Oshikiri et al. |
| 2007/0032733 A1 | 2/2007 | Burton |
| 2007/0033069 A1 | 2/2007 | Rao et al. |
| 2007/0050726 A1 | 3/2007 | Wakai et al. |
| 2007/0055940 A1 | 3/2007 | Moore et al. |
| 2007/0056727 A1 | 3/2007 | Newman |
| 2007/0061748 A1 | 3/2007 | Hirose |
| 2007/0071256 A1 | 3/2007 | Ito |
| 2007/0081740 A1 | 4/2007 | Ciudad et al. |
| 2007/0097421 A1 | 5/2007 | Sorensen et al. |
| 2007/0113726 A1 | 5/2007 | Oliver et al. |
| 2007/0136093 A1 | 6/2007 | Rankin et al. |
| 2007/0136778 A1 | 6/2007 | Birger et al. |
| 2007/0143433 A1 | 6/2007 | Daigle |
| 2007/0150839 A1 | 6/2007 | Danninger |
| 2007/0160345 A1 | 7/2007 | Sakai et al. |
| 2007/0169614 A1 | 7/2007 | Sasaki et al. |
| 2007/0179938 A1 | 8/2007 | Ikeda et al. |
| 2007/0186154 A1 | 8/2007 | Anthony et al. |
| 2007/0188518 A1 | 8/2007 | Vale et al. |
| 2007/0192741 A1 | 8/2007 | Yoritate et al. |
| 2007/0204225 A1 | 8/2007 | Berkowitz et al. |
| 2007/0209004 A1 | 9/2007 | Layard |
| 2007/0229678 A1 | 10/2007 | Barrus |
| 2007/0236475 A1 | 10/2007 | Wherry |
| 2007/0245236 A1 | 10/2007 | Lee et al. |
| 2007/0245257 A1 | 10/2007 | Chan et al. |
| 2007/0249949 A1 | 10/2007 | Hadley |
| 2007/0253025 A1 | 11/2007 | Terayoko |
| 2007/0271065 A1 | 11/2007 | Gupta et al. |

(56) References Cited

U.S. PATENT DOCUMENTS

| | | |
|---|---|---|
| 2008/0019591 A1 | 1/2008 | Iwayama et al. |
| 2008/0020803 A1 | 1/2008 | Rios et al. |
| 2008/0027673 A1 | 1/2008 | Trumm |
| 2008/0030456 A1 | 2/2008 | Asadi et al. |
| 2008/0040668 A1 | 2/2008 | Ala-Rantaia |
| 2008/0051919 A1 | 2/2008 | Sakai et al. |
| 2008/0052945 A1 | 3/2008 | Matas et al. |
| 2008/0057941 A1 | 3/2008 | Scott et al. |
| 2008/0058626 A1 | 3/2008 | Miyata et al. |
| 2008/0059888 A1 | 3/2008 | Dunko |
| 2008/0066010 A1 | 3/2008 | Brodersen et al. |
| 2008/0076637 A1 | 3/2008 | Gilley et al. |
| 2008/0082145 A1 | 4/2008 | Skwarek et al. |
| 2008/0086318 A1 | 4/2008 | Gilley et al. |
| 2008/0096726 A1 | 4/2008 | Riley et al. |
| 2008/0133697 A1 | 6/2008 | Stewart et al. |
| 2008/0134070 A1 | 6/2008 | Kobayashi et al. |
| 2008/0141135 A1 | 6/2008 | Mason et al. |
| 2008/0147664 A1 | 6/2008 | Fujiwara et al. |
| 2008/0150731 A1 | 6/2008 | Laukkanen et al. |
| 2008/0155478 A1 | 6/2008 | Stross |
| 2008/0161161 A1 | 7/2008 | Pipinich et al. |
| 2008/0161707 A1 | 7/2008 | Farringdon et al. |
| 2008/0165141 A1 | 7/2008 | Christie |
| 2008/0180404 A1 | 7/2008 | Han et al. |
| 2008/0200312 A1 | 8/2008 | Tagliabue |
| 2008/0216022 A1 | 9/2008 | Lorch et al. |
| 2008/0229226 A1 | 9/2008 | Rowbottom et al. |
| 2008/0254767 A1 | 10/2008 | Jin |
| 2008/0262946 A1 * | 10/2008 | Wren .................... G06Q 30/06 705/27.1 |
| 2008/0297482 A1 | 12/2008 | Weiss |
| 2008/0300110 A1 | 12/2008 | Smith et al. |
| 2008/0320419 A1 | 12/2008 | Matas et al. |
| 2009/0007017 A1 | 1/2009 | Anzures et al. |
| 2009/0012988 A1 | 1/2009 | Brown |
| 2009/0013350 A1 | 1/2009 | Ohlfs et al. |
| 2009/0021576 A1 | 1/2009 | Linder et al. |
| 2009/0047645 A1 | 2/2009 | Dibenedetto et al. |
| 2009/0051946 A1 | 2/2009 | Hibi |
| 2009/0055748 A1 | 2/2009 | Dieberger et al. |
| 2009/0118100 A1 | 5/2009 | Oliver et al. |
| 2009/0128516 A1 | 5/2009 | Rimon et al. |
| 2009/0140997 A1 | 6/2009 | Jeong et al. |
| 2009/0158326 A1 | 6/2009 | Hunt et al. |
| 2009/0164567 A1 | 6/2009 | Hara |
| 2009/0170532 A1 | 7/2009 | Lee et al. |
| 2009/0192823 A1 | 7/2009 | Hawkins et al. |
| 2009/0193351 A1 | 7/2009 | Lee et al. |
| 2009/0210078 A1 | 8/2009 | Crowley |
| 2009/0216556 A1 | 8/2009 | Martin et al. |
| 2009/0222056 A1 | 9/2009 | Lindh et al. |
| 2009/0233771 A1 | 9/2009 | Quatrochi et al. |
| 2009/0259134 A1 | 10/2009 | Levine |
| 2009/0259967 A1 | 10/2009 | Davidson et al. |
| 2009/0262088 A1 | 10/2009 | Moll-Carrillo et al. |
| 2009/0268949 A1 | 10/2009 | Ueshima et al. |
| 2009/0287103 A1 | 11/2009 | Pillai |
| 2009/0319243 A1 | 12/2009 | Suarez-Rivera et al. |
| 2010/0031202 A1 | 2/2010 | Morris et al. |
| 2010/0042949 A1 | 2/2010 | Chen |
| 2010/0048358 A1 | 2/2010 | Tchao et al. |
| 2010/0058238 A1 | 3/2010 | Ben Moshe |
| 2010/0060586 A1 | 3/2010 | Pisula et al. |
| 2010/0062818 A1 | 3/2010 | Haughay et al. |
| 2010/0062905 A1 | 3/2010 | Rottier et al. |
| 2010/0064255 A1 | 3/2010 | Rottier et al. |
| 2010/0076331 A1 | 3/2010 | Chan et al. |
| 2010/0079291 A1 | 4/2010 | Kroll et al. |
| 2010/0121700 A1 | 5/2010 | Wigder et al. |
| 2010/0137106 A1 | 6/2010 | Oshima et al. |
| 2010/0145209 A1 | 6/2010 | Lee et al. |
| 2010/0149211 A1 | 6/2010 | Tossing et al. |
| 2010/0153833 A1 | 6/2010 | Siegel et al. |
| 2010/0169819 A1 | 7/2010 | Bestle et al. |
| 2010/0179832 A1 | 7/2010 | Van et al. |
| 2010/0191701 A1 | 7/2010 | Beyda et al. |
| 2010/0194692 A1 | 8/2010 | Orr et al. |
| 2010/0198453 A1 | 8/2010 | Dorogusker et al. |
| 2010/0214442 A1 | 8/2010 | Uemura et al. |
| 2010/0241955 A1 | 9/2010 | Price et al. |
| 2010/0253807 A1 | 10/2010 | Matsumoto et al. |
| 2010/0262634 A1 | 10/2010 | Wang |
| 2010/0281374 A1 | 11/2010 | Schulz et al. |
| 2010/0283754 A1 | 11/2010 | Nakao et al. |
| 2010/0292600 A1 | 11/2010 | Dibenedetto et al. |
| 2010/0298899 A1 | 11/2010 | Donnelly et al. |
| 2010/0305965 A1 | 12/2010 | Benjamin et al. |
| 2010/0309149 A1 | 12/2010 | Blumenberg et al. |
| 2010/0331145 A1 | 12/2010 | Lakovic et al. |
| 2011/0003665 A1 | 1/2011 | Burton et al. |
| 2011/0016120 A1 | 1/2011 | Haughay et al. |
| 2011/0032105 A1 | 2/2011 | Hoffman et al. |
| 2011/0066051 A1 | 3/2011 | Moon et al. |
| 2011/0069017 A1 | 3/2011 | Victor |
| 2011/0071869 A1 | 3/2011 | Obrien et al. |
| 2011/0074699 A1 | 3/2011 | Marr et al. |
| 2011/0098928 A1 | 4/2011 | Hoffman et al. |
| 2011/0099299 A1 | 4/2011 | Vasudevan et al. |
| 2011/0106553 A1 | 5/2011 | Tanaka et al. |
| 2011/0112418 A1 | 5/2011 | Feild et al. |
| 2011/0125041 A1 | 5/2011 | Fischell et al. |
| 2011/0137678 A1 | 6/2011 | Williams |
| 2011/0137836 A1 | 6/2011 | Kuriyama et al. |
| 2011/0159469 A1 | 6/2011 | Hwang et al. |
| 2011/0167369 A1 | 7/2011 | Van |
| 2011/0179097 A1 | 7/2011 | Ala-Rantala |
| 2011/0201911 A1 | 8/2011 | Johnson et al. |
| 2011/0213276 A1 | 9/2011 | Sarussi et al. |
| 2011/0227872 A1 | 9/2011 | Huska et al. |
| 2011/0230169 A1 | 9/2011 | Ohki |
| 2011/0230986 A1 | 9/2011 | Lafortune et al. |
| 2011/0246509 A1 | 10/2011 | Migita et al. |
| 2011/0246918 A1 | 10/2011 | Henderson |
| 2011/0261079 A1 | 10/2011 | Ingrassia et al. |
| 2011/0275940 A1 | 11/2011 | Nims et al. |
| 2011/0306389 A1 | 12/2011 | Nagayama |
| 2011/0307821 A1 | 12/2011 | Martens |
| 2011/0314422 A1 | 12/2011 | Cameron et al. |
| 2012/0015778 A1 | 1/2012 | Lee et al. |
| 2012/0015779 A1 | 1/2012 | Powch et al. |
| 2012/0030623 A1 | 2/2012 | Hoellwarth |
| 2012/0034897 A1 | 2/2012 | Kreitzer et al. |
| 2012/0036460 A1 | 2/2012 | Cieplinski et al. |
| 2012/0041767 A1 | 2/2012 | Hoffman et al. |
| 2012/0042039 A1 | 2/2012 | Mark |
| 2012/0042272 A1 | 2/2012 | Hong et al. |
| 2012/0059664 A1 | 3/2012 | Georgiev et al. |
| 2012/0071770 A1 | 3/2012 | Grey et al. |
| 2012/0092383 A1 | 4/2012 | Hysek et al. |
| 2012/0105225 A1 | 5/2012 | Valtonen |
| 2012/0116550 A1 | 5/2012 | Hoffman et al. |
| 2012/0117506 A1 | 5/2012 | Koch et al. |
| 2012/0150759 A1 | 6/2012 | Tarjan |
| 2012/0159380 A1 | 6/2012 | Kocienda et al. |
| 2012/0179319 A1 | 7/2012 | Gilman et al. |
| 2012/0232414 A1 | 9/2012 | Mollicone et al. |
| 2012/0253485 A1 | 10/2012 | Weast et al. |
| 2012/0274508 A1 | 11/2012 | Brown et al. |
| 2012/0283855 A1 | 11/2012 | Hoffman et al. |
| 2012/0290109 A1 | 11/2012 | Engelberg et al. |
| 2012/0302840 A1 | 11/2012 | Kubo |
| 2012/0302843 A1 | 11/2012 | Otsubo et al. |
| 2012/0317167 A1 | 12/2012 | Rahman et al. |
| 2012/0326873 A1 | 12/2012 | Utter |
| 2013/0021368 A1 | 1/2013 | Lee et al. |
| 2013/0054150 A1 | 2/2013 | Sacks et al. |
| 2013/0054720 A1 | 2/2013 | Kang et al. |
| 2013/0061175 A1 | 3/2013 | Matas et al. |
| 2013/0067050 A1 | 3/2013 | Kotteri et al. |
| 2013/0081083 A1 | 3/2013 | Yu et al. |
| 2013/0093715 A1 | 4/2013 | Marsden et al. |
| 2013/0106603 A1 | 5/2013 | Weast et al. |
| 2013/0106684 A1 | 5/2013 | Weast et al. |

(56) References Cited

U.S. PATENT DOCUMENTS

| | | |
|---|---|---|
| 2013/0110264 A1 | 5/2013 | Weast et al. |
| 2013/0115583 A1 | 5/2013 | Gordon et al. |
| 2013/0132028 A1 | 5/2013 | Crankson et al. |
| 2013/0137073 A1 | 5/2013 | Nacey et al. |
| 2013/0138734 A1 | 5/2013 | Crivello et al. |
| 2013/0141233 A1 | 6/2013 | Jacobs et al. |
| 2013/0151285 A1 | 6/2013 | Mclaren et al. |
| 2013/0158367 A1 | 6/2013 | Pacione et al. |
| 2013/0179837 A1 | 7/2013 | Eriksson et al. |
| 2013/0184613 A1 | 7/2013 | Homsi et al. |
| 2013/0185097 A1 | 7/2013 | Saria et al. |
| 2013/0187923 A1 | 7/2013 | Yoshimoto et al. |
| 2013/0188322 A1 | 7/2013 | Lowe et al. |
| 2013/0197679 A1 | 8/2013 | Balakrishnan et al. |
| 2013/0198661 A1 | 8/2013 | Matas |
| 2013/0198672 A1 | 8/2013 | Yoon et al. |
| 2013/0203475 A1 | 8/2013 | Shin et al. |
| 2013/0215119 A1 | 8/2013 | Vanhoecke |
| 2013/0217979 A1 | 8/2013 | Blackadar et al. |
| 2013/0231575 A1 | 9/2013 | Erkkila et al. |
| 2013/0231711 A1 | 9/2013 | Kaib |
| 2013/0233097 A1 | 9/2013 | Hayner et al. |
| 2013/0239049 A1 | 9/2013 | Perrodin et al. |
| 2013/0262155 A1 | 10/2013 | Hinkamp |
| 2013/0263055 A1 | 10/2013 | Victor |
| 2013/0263719 A1 | 10/2013 | Watterson et al. |
| 2013/0324210 A1 | 12/2013 | Doig et al. |
| 2013/0325358 A1 | 12/2013 | Oshima et al. |
| 2013/0325394 A1 | 12/2013 | Yuen et al. |
| 2013/0325396 A1 | 12/2013 | Yuen et al. |
| 2013/0330694 A1 | 12/2013 | Watterson |
| 2013/0332286 A1 | 12/2013 | Medelius et al. |
| 2013/0345978 A1 | 12/2013 | Lush et al. |
| 2014/0037107 A1 | 2/2014 | Marino et al. |
| 2014/0038781 A1 | 2/2014 | Foley et al. |
| 2014/0039840 A1 | 2/2014 | Yuen et al. |
| 2014/0067096 A1 | 3/2014 | Aibara |
| 2014/0074825 A1 | 3/2014 | Wood et al. |
| 2014/0081666 A1 | 3/2014 | Teller et al. |
| 2014/0089836 A1 | 3/2014 | Damani et al. |
| 2014/0092291 A1 | 4/2014 | Aoshima et al. |
| 2014/0108998 A1 | 4/2014 | Chaudhri et al. |
| 2014/0139637 A1 | 5/2014 | Mistry et al. |
| 2014/0165000 A1 | 6/2014 | Fleizach et al. |
| 2014/0176346 A1 | 6/2014 | Brumback et al. |
| 2014/0176475 A1 | 6/2014 | Myers et al. |
| 2014/0180786 A1 | 6/2014 | Sullivan |
| 2014/0189584 A1 | 7/2014 | Weng et al. |
| 2014/0200691 A1 | 7/2014 | Lee et al. |
| 2014/0218369 A1 | 8/2014 | Yuen et al. |
| 2014/0225925 A1 | 8/2014 | Hayashi et al. |
| 2014/0228647 A1 | 8/2014 | Sakamoto et al. |
| 2014/0239065 A1 | 8/2014 | Zhou et al. |
| 2014/0240122 A1 | 8/2014 | Roberts et al. |
| 2014/0240349 A1 | 8/2014 | Tuukkanen |
| 2014/0244009 A1 | 8/2014 | Mestas |
| 2014/0245161 A1 | 8/2014 | Yuen et al. |
| 2014/0257537 A1 | 9/2014 | Stroupe et al. |
| 2014/0274413 A1 | 9/2014 | Chelst |
| 2014/0275852 A1 | 9/2014 | Hong et al. |
| 2014/0275854 A1 | 9/2014 | Venkatraman et al. |
| 2014/0277628 A1 | 9/2014 | Nieminen et al. |
| 2014/0278229 A1 | 9/2014 | Hong et al. |
| 2014/0282011 A1 | 9/2014 | Dellinger et al. |
| 2014/0282153 A1 | 9/2014 | Christiansen et al. |
| 2014/0282262 A1 | 9/2014 | Gregotski et al. |
| 2014/0288680 A1 | 9/2014 | Hoffman et al. |
| 2014/0310598 A1 | 10/2014 | Sprague et al. |
| 2014/0310643 A1 | 10/2014 | Karmanenko et al. |
| 2014/0331314 A1 | 11/2014 | Fujioka |
| 2014/0336796 A1 | 11/2014 | Agnew |
| 2014/0337041 A1 | 11/2014 | Madden et al. |
| 2014/0337450 A1 | 11/2014 | Choudhary et al. |
| 2014/0337451 A1 | 11/2014 | Choudhary et al. |
| 2014/0344723 A1 | 11/2014 | Malik et al. |
| 2014/0344951 A1 | 11/2014 | Brewer |
| 2014/0358473 A1 | 12/2014 | Goel et al. |
| 2014/0358584 A1 | 12/2014 | Worden et al. |
| 2014/0371887 A1 | 12/2014 | Hoffman et al. |
| 2014/0372898 A1 | 12/2014 | Ayres et al. |
| 2015/0004578 A1* | 1/2015 | Gilley .................. G16H 10/20 434/236 |
| 2015/0018632 A1 | 1/2015 | Khair |
| 2015/0039616 A1 | 2/2015 | Rolston et al. |
| 2015/0046814 A1 | 2/2015 | Haughay et al. |
| 2015/0057943 A1 | 2/2015 | Self et al. |
| 2015/0058263 A1 | 2/2015 | Landers |
| 2015/0065095 A1 | 3/2015 | Seo et al. |
| 2015/0065302 A1 | 3/2015 | Ou et al. |
| 2015/0067513 A1 | 3/2015 | Zambetti et al. |
| 2015/0067811 A1 | 3/2015 | Agnew et al. |
| 2015/0074571 A1 | 3/2015 | Marti et al. |
| 2015/0081059 A1 | 3/2015 | Hwang et al. |
| 2015/0081060 A1 | 3/2015 | Hwang et al. |
| 2015/0081529 A1 | 3/2015 | Lee et al. |
| 2015/0083970 A1 | 3/2015 | Koh et al. |
| 2015/0098309 A1 | 4/2015 | Adams et al. |
| 2015/0100245 A1 | 4/2015 | Huang et al. |
| 2015/0106025 A1 | 4/2015 | Keller et al. |
| 2015/0112700 A1 | 4/2015 | Sublett et al. |
| 2015/0113553 A1 | 4/2015 | Pan |
| 2015/0118657 A1 | 4/2015 | Shrake et al. |
| 2015/0124067 A1 | 5/2015 | Bala et al. |
| 2015/0130719 A1 | 5/2015 | Wehrenberg et al. |
| 2015/0130830 A1 | 5/2015 | Nagasaki et al. |
| 2015/0142689 A1 | 5/2015 | Squires |
| 2015/0153943 A1 | 6/2015 | Wang |
| 2015/0164349 A1 | 6/2015 | Gopalakrishnan et al. |
| 2015/0177979 A1 | 6/2015 | Johansson et al. |
| 2015/0180746 A1 | 6/2015 | Day et al. |
| 2015/0181314 A1 | 6/2015 | Swanson |
| 2015/0185967 A1* | 7/2015 | Ly .................. G06F 3/0488 715/720 |
| 2015/0193805 A1 | 7/2015 | Filipiak |
| 2015/0196804 A1 | 7/2015 | Koduri et al. |
| 2015/0199494 A1 | 7/2015 | Koduri et al. |
| 2015/0205492 A1 | 7/2015 | Nobil |
| 2015/0205930 A1 | 7/2015 | Shaanan et al. |
| 2015/0217163 A1 | 8/2015 | Amis et al. |
| 2015/0220883 A1 | 8/2015 | Bfar et al. |
| 2015/0251053 A1 | 9/2015 | Hoffman et al. |
| 2015/0269848 A1 | 9/2015 | Yuen et al. |
| 2015/0293592 A1 | 10/2015 | Cheong et al. |
| 2015/0297134 A1 | 10/2015 | Albert et al. |
| 2015/0301691 A1 | 10/2015 | Qin |
| 2015/0324751 A1 | 11/2015 | Orenstein et al. |
| 2015/0331589 A1 | 11/2015 | Kawakita |
| 2015/0343709 A1 | 12/2015 | Gerstle et al. |
| 2015/0347711 A1 | 12/2015 | Soli et al. |
| 2015/0350861 A1 | 12/2015 | Soli et al. |
| 2015/0351655 A1 | 12/2015 | Coleman |
| 2015/0374310 A1 | 12/2015 | Lee |
| 2016/0000379 A1 | 1/2016 | Pougatchev et al. |
| 2016/0004432 A1 | 1/2016 | Bernstein et al. |
| 2016/0015275 A1 | 1/2016 | Samadani et al. |
| 2016/0019360 A1 | 1/2016 | Pahwa et al. |
| 2016/0027282 A1 | 1/2016 | Lee |
| 2016/0048263 A1 | 2/2016 | Hiraga et al. |
| 2016/0048298 A1 | 2/2016 | Choi et al. |
| 2016/0058336 A1 | 3/2016 | Blahnik et al. |
| 2016/0058337 A1 | 3/2016 | Blahnik et al. |
| 2016/0062582 A1 | 3/2016 | Wilson et al. |
| 2016/0065505 A1 | 3/2016 | Iskander |
| 2016/0070275 A1 | 3/2016 | Anderson et al. |
| 2016/0072896 A1 | 3/2016 | Petersen et al. |
| 2016/0085937 A1 | 3/2016 | Dettinger et al. |
| 2016/0107031 A1 | 4/2016 | Palatsi et al. |
| 2016/0110355 A1 | 4/2016 | Charania et al. |
| 2016/0135731 A1 | 5/2016 | Drennan |
| 2016/0140828 A1 | 5/2016 | Deforest |
| 2016/0156584 A1 | 6/2016 | Hum et al. |
| 2016/0196635 A1 | 7/2016 | Cho et al. |
| 2016/0210099 A1 | 7/2016 | Hampapuram et al. |
| 2016/0216868 A1 | 7/2016 | Victor et al. |

(56) References Cited

U.S. PATENT DOCUMENTS

| | | |
|---|---|---|
| 2016/0220225 A1 | 8/2016 | Wang et al. |
| 2016/0235374 A1 | 8/2016 | Miller et al. |
| 2016/0246880 A1 | 8/2016 | Battiah et al. |
| 2016/0250517 A1 | 9/2016 | Tilvis et al. |
| 2016/0255162 A1 | 9/2016 | Frieder et al. |
| 2016/0256082 A1 | 9/2016 | Ely et al. |
| 2016/0256741 A1 | 9/2016 | Holma et al. |
| 2016/0263435 A1 | 9/2016 | Venkatraman et al. |
| 2016/0278659 A1 | 9/2016 | Kaib et al. |
| 2016/0278667 A1 | 9/2016 | Villard et al. |
| 2016/0279475 A1 | 9/2016 | Aragones et al. |
| 2016/0283483 A1 | 9/2016 | Jiang et al. |
| 2016/0301794 A1 | 10/2016 | Schlakman et al. |
| 2016/0302680 A1 | 10/2016 | Narusawa et al. |
| 2016/0302717 A1 | 10/2016 | Tawa et al. |
| 2016/0321831 A1 | 11/2016 | Nakamura et al. |
| 2016/0324457 A1 | 11/2016 | Dagum |
| 2016/0328736 A1 | 11/2016 | Wang et al. |
| 2016/0332025 A1 | 11/2016 | Repka |
| 2016/0346607 A1 | 12/2016 | Rapfogel |
| 2016/0371464 A1 | 12/2016 | Bricker |
| 2016/0375306 A1 | 12/2016 | Gu et al. |
| 2016/0379511 A1 | 12/2016 | Dawson et al. |
| 2017/0001073 A1 | 1/2017 | Krueger et al. |
| 2017/0011210 A1 | 1/2017 | Cheong et al. |
| 2017/0014037 A1 | 1/2017 | Coppola et al. |
| 2017/0019587 A1 | 1/2017 | Matas et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0032168 A1 | 2/2017 | Kim |
| 2017/0053542 A1 | 2/2017 | Wilson et al. |
| 2017/0065224 A1 | 3/2017 | Rahko et al. |
| 2017/0095695 A1 | 4/2017 | Mangusson et al. |
| 2017/0139554 A1 | 5/2017 | Nakabayashi et al. |
| 2017/0143262 A1 | 5/2017 | Kurunmaki et al. |
| 2017/0153606 A1 | 6/2017 | Pitis et al. |
| 2017/0153804 A1 | 6/2017 | Kim et al. |
| 2017/0161014 A1 | 6/2017 | Kikugawa et al. |
| 2017/0169295 A1 | 6/2017 | Park et al. |
| 2017/0192625 A1 | 7/2017 | Kim et al. |
| 2017/0209766 A1 | 7/2017 | Riley et al. |
| 2017/0237694 A1 | 8/2017 | Choudhary et al. |
| 2017/0239524 A1 | 8/2017 | Lee et al. |
| 2017/0243508 A1 | 8/2017 | Cheng et al. |
| 2017/0266494 A1 | 9/2017 | Crankson et al. |
| 2017/0269792 A1 | 9/2017 | Xu et al. |
| 2017/0274149 A1 | 9/2017 | Aeschlimann |
| 2017/0274267 A1 | 9/2017 | Blahnik |
| 2017/0281026 A1 | 10/2017 | Nick et al. |
| 2017/0281057 A1 | 10/2017 | Blahnik et al. |
| 2017/0294174 A1 | 10/2017 | Albadawi et al. |
| 2017/0300186 A1 | 10/2017 | Kuhar et al. |
| 2017/0301039 A1 | 10/2017 | Dyer et al. |
| 2017/0319941 A1 | 11/2017 | Smith et al. |
| 2017/0329933 A1 | 11/2017 | Brust et al. |
| 2017/0330297 A1 | 11/2017 | Cronin et al. |
| 2017/0333752 A1 | 11/2017 | Korkala et al. |
| 2017/0337033 A1 | 11/2017 | Duyan et al. |
| 2017/0348562 A1 | 12/2017 | Jung et al. |
| 2017/0354845 A1 | 12/2017 | Williams et al. |
| 2017/0357382 A1 | 12/2017 | Miura et al. |
| 2017/0357520 A1 | 12/2017 | De Vries et al. |
| 2018/0000426 A1 | 1/2018 | Li |
| 2018/0001184 A1 | 1/2018 | Tran et al. |
| 2018/0032234 A1 | 2/2018 | Michalske |
| 2018/0053200 A1 | 2/2018 | Cronin et al. |
| 2018/0056132 A1 | 3/2018 | Foley et al. |
| 2018/0065025 A1 | 3/2018 | Toda et al. |
| 2018/0068019 A1 | 3/2018 | Novikoff et al. |
| 2018/0074462 A1 | 3/2018 | Helder et al. |
| 2018/0074464 A1 | 3/2018 | Essery et al. |
| 2018/0078182 A1 | 3/2018 | Chen et al. |
| 2018/0126248 A1 | 5/2018 | Dion et al. |
| 2018/0137937 A1 | 5/2018 | Gass et al. |
| 2018/0140903 A1 | 5/2018 | Poure et al. |
| 2018/0150709 A1 | 5/2018 | Ha |
| 2018/0189077 A1 | 7/2018 | Gupta et al. |
| 2018/0206766 A1 | 7/2018 | Blahnik et al. |
| 2018/0272190 A1 | 9/2018 | Miura et al. |
| 2018/0294053 A1 | 10/2018 | Runyon et al. |
| 2018/0318647 A1 | 11/2018 | Foley et al. |
| 2018/0329584 A1 | 11/2018 | Williams et al. |
| 2018/0339195 A1 | 11/2018 | Bernotas |
| 2018/0345078 A1 | 12/2018 | Blahnik et al. |
| 2018/0367862 A1 | 12/2018 | Horii et al. |
| 2019/0008467 A1 | 1/2019 | Averina et al. |
| 2019/0025995 A1 | 1/2019 | Williams |
| 2019/0034049 A1 | 1/2019 | Williams et al. |
| 2019/0034050 A1 | 1/2019 | Williams et al. |
| 2019/0073081 A1 | 3/2019 | Takahashi et al. |
| 2019/0089701 A1 | 3/2019 | Mercury et al. |
| 2019/0104951 A1 | 4/2019 | Valys et al. |
| 2019/0184234 A1 | 6/2019 | Packles et al. |
| 2019/0209777 A1 | 7/2019 | O'Connell et al. |
| 2019/0232110 A1 | 8/2019 | Williams et al. |
| 2019/0232111 A1 | 8/2019 | Williams et al. |
| 2019/0274565 A1 | 9/2019 | Soli et al. |
| 2019/0279520 A1 | 9/2019 | Wilson et al. |
| 2019/0313012 A1 | 10/2019 | Matas |
| 2019/0336044 A1 | 11/2019 | Williams et al. |
| 2019/0336045 A1 | 11/2019 | Williams et al. |
| 2019/0336827 A1 | 11/2019 | Intonato et al. |
| 2019/0339849 A1* | 11/2019 | Williams ............. G06F 1/1626 |
| 2019/0342616 A1 | 11/2019 | Domm et al. |
| 2019/0387982 A1 | 12/2019 | Buller |
| 2020/0004409 A1 | 1/2020 | Victor |
| 2020/0014967 A1 | 1/2020 | Putnam |
| 2020/0054931 A1* | 2/2020 | Martin ................. A61B 5/486 |
| 2020/0098278 A1 | 3/2020 | Doti et al. |
| 2020/0101365 A1 | 4/2020 | Wilson et al. |
| 2020/0160961 A1* | 5/2020 | Wadhawan ........ A63B 24/0059 |
| 2020/0257434 A1 | 8/2020 | Victor |
| 2020/0297249 A1 | 9/2020 | Williams et al. |
| 2020/0356222 A1 | 11/2020 | Clarke et al. |
| 2020/0356590 A1 | 11/2020 | Clarke et al. |
| 2020/0357522 A1 | 11/2020 | Pahwa et al. |
| 2020/0381100 A1 | 12/2020 | Williams et al. |
| 2020/0382613 A1 | 12/2020 | Sundstrom et al. |
| 2021/0007632 A1 | 1/2021 | Blahnik et al. |
| 2021/0007633 A1 | 1/2021 | Blahnik et al. |
| 2021/0093919 A1* | 4/2021 | Lyke ..................... G16H 50/20 |
| 2021/0110908 A1 | 4/2021 | Blahnik et al. |
| 2021/0113116 A1 | 4/2021 | Chen et al. |
| 2021/0113137 A1 | 4/2021 | Soli et al. |
| 2021/0117072 A1 | 4/2021 | Victor |
| 2021/0145321 A1 | 5/2021 | Chen et al. |
| 2021/0191584 A1 | 6/2021 | Williams et al. |
| 2021/0193293 A1 | 6/2021 | Blahnik et al. |
| 2021/0243356 A1 | 8/2021 | Matas et al. |
| 2021/0252337 A1 | 8/2021 | Devine et al. |
| 2021/0252341 A1 | 8/2021 | Devine et al. |
| 2021/0252369 A1 | 8/2021 | Devine et al. |
| 2021/0255747 A1 | 8/2021 | Devine et al. |
| 2021/0255826 A1* | 8/2021 | Devine ............... G06F 3/04817 |
| 2021/0350900 A1 | 11/2021 | Blahnik et al. |
| 2021/0379447 A1* | 12/2021 | Lee ......................... A61B 5/11 |
| 2022/0047918 A1 | 2/2022 | Williams et al. |
| 2022/0062707 A1* | 3/2022 | Bedekar ................ G16H 20/30 |
| 2022/0121299 A1 | 4/2022 | De Vries et al. |

FOREIGN PATENT DOCUMENTS

| | | |
|---|---|---|
| CN | 1397904 A | 2/2003 |
| CN | 1404233 A | 3/2003 |
| CN | 1585943 A | 2/2005 |
| CN | 1717918 A | 1/2006 |
| CN | 1756273 A | 4/2006 |
| CN | 101150810 A | 3/2008 |
| CN | 101541387 A | 9/2009 |
| CN | 101651870 A | 2/2010 |
| CN | 101836894 A | 9/2010 |
| CN | 101978374 A | 2/2011 |
| CN | 102339201 A | 2/2012 |

(56) References Cited

FOREIGN PATENT DOCUMENTS

| | | |
|---|---|---|
| CN | 102448555 A | 5/2012 |
| CN | 102804238 A | 11/2012 |
| CN | 102989159 A | 3/2013 |
| CN | 103154954 A | 6/2013 |
| CN | 103212197 A | 7/2013 |
| CN | 103370924 A | 10/2013 |
| CN | 103403627 A | 11/2013 |
| CN | 104288983 A | 1/2015 |
| CN | 104501043 A | 4/2015 |
| CN | 104508426 A | 4/2015 |
| CN | 104815428 A | 8/2015 |
| CN | 106537397 A | 3/2017 |
| CN | 106709235 A | 5/2017 |
| CN | 106878550 A | 6/2017 |
| EP | 0871177 A2 | 10/1998 |
| EP | 1124175 A2 | 8/2001 |
| EP | 1148412 A2 | 10/2001 |
| EP | 1577746 A2 | 9/2005 |
| EP | 1615114 A2 | 1/2006 |
| EP | 1840717 A1 | 10/2007 |
| EP | 1935339 A1 | 6/2008 |
| EP | 2025368 A2 | 2/2009 |
| EP | 2045703 A2 | 4/2009 |
| EP | 2060970 A1 | 5/2009 |
| EP | 2068237 A2 | 6/2009 |
| EP | 2509074 A2 | 10/2012 |
| EP | 3122038 A1 | 1/2017 |
| FR | 2830093 A3 | 3/2003 |
| GB | 2420260 A | 5/2006 |
| JP | 3-217976 A | 9/1991 |
| JP | 6-187118 A | 7/1994 |
| JP | 6-309138 A | 11/1994 |
| JP | 8-106469 A | 4/1996 |
| JP | 10-93848 A | 4/1998 |
| JP | 11-164175 A | 6/1999 |
| JP | 11-168694 A | 6/1999 |
| JP | 11-341425 A | 12/1999 |
| JP | 2000-138883 A | 5/2000 |
| JP | 2000-138888 A | 5/2000 |
| JP | 2000-148591 A | 5/2000 |
| JP | 2000-163031 A | 6/2000 |
| JP | 2000-221879 A | 8/2000 |
| JP | 2000-244673 A | 9/2000 |
| JP | 2000-350134 A | 12/2000 |
| JP | 2001-76078 A | 3/2001 |
| JP | 2001-136303 A | 5/2001 |
| JP | 2001-265481 A | 9/2001 |
| JP | 2001-309019 A | 11/2001 |
| JP | 2002-152559 A | 5/2002 |
| JP | 2002-190007 A | 7/2002 |
| JP | 2003-102868 A | 4/2003 |
| JP | 2003-163820 A | 6/2003 |
| JP | 2003-337863 A | 11/2003 |
| JP | 2003-338975 A | 11/2003 |
| JP | 2003-345491 A | 12/2003 |
| JP | 2003-348432 A | 12/2003 |
| JP | 2004-15586 A | 1/2004 |
| JP | 2004-32346 A | 1/2004 |
| JP | 2004-102609 A | 4/2004 |
| JP | 2004-113466 A | 4/2004 |
| JP | 2004-145291 A | 5/2004 |
| JP | 2004-153832 A | 5/2004 |
| JP | 2004-288208 A | 10/2004 |
| JP | 2004-336536 A | 11/2004 |
| JP | 2004-336711 A | 11/2004 |
| JP | 2005-38101 A | 2/2005 |
| JP | 2005-79814 A | 3/2005 |
| JP | 2005-92386 A | 4/2005 |
| JP | 2005-100084 A | 4/2005 |
| JP | 2005-515530 A | 5/2005 |
| JP | 2005-150836 A | 6/2005 |
| JP | 2005-175991 A | 6/2005 |
| JP | 2005-182320 A | 7/2005 |
| JP | 2005-202483 A | 7/2005 |
| JP | 2005-202651 A | 7/2005 |
| JP | 2005-303728 A | 10/2005 |
| JP | 2005-321516 A | 11/2005 |
| JP | 2005-339420 A | 12/2005 |
| JP | 2006-67344 A | 3/2006 |
| JP | 2006-139340 A | 6/2006 |
| JP | 2006-140865 A | 6/2006 |
| JP | 2006-195592 A | 7/2006 |
| JP | 2006-203809 A | 8/2006 |
| JP | 2006-230679 A | 9/2006 |
| JP | 2006-236249 A | 9/2006 |
| JP | 2007-515775 A | 6/2007 |
| JP | 2007-525775 A | 9/2007 |
| JP | 2007-260288 A | 10/2007 |
| JP | 2007-330513 A | 12/2007 |
| JP | 2008-104758 A | 5/2008 |
| JP | 2008-106469 A | 5/2008 |
| JP | 2008-518330 A | 5/2008 |
| JP | 2008-183339 A | 8/2008 |
| JP | 2009-78134 A | 4/2009 |
| JP | 2009-112731 A | 5/2009 |
| JP | 2010-12335 A | 1/2010 |
| JP | 2010-517725 A | 5/2010 |
| JP | 2010-122901 A | 6/2010 |
| JP | 2010-162297 A | 7/2010 |
| JP | 2010-181280 A | 8/2010 |
| JP | 2011-125633 A | 6/2011 |
| JP | 2011-183101 A | 9/2011 |
| JP | 2011-192126 A | 9/2011 |
| JP | 2011-198184 A | 10/2011 |
| JP | 2011-206323 A | 10/2011 |
| JP | 2011-259253 A | 12/2011 |
| JP | 2012-20134 A | 2/2012 |
| JP | 2012-35071 A | 2/2012 |
| JP | 2012-59264 A | 3/2012 |
| JP | 2012-524640 A | 10/2012 |
| JP | 2012-230503 A | 11/2012 |
| JP | 2013-103020 A | 5/2013 |
| JP | 2013-117690 A | 6/2013 |
| JP | 2013-140171 A | 7/2013 |
| JP | 2013-544140 A | 12/2013 |
| JP | 2014-500740 A | 1/2014 |
| JP | 5771242 B2 | 8/2015 |
| JP | 2016-502875 A | 2/2016 |
| JP | 2016-52512 A | 4/2016 |
| JP | 2016-517329 A | 6/2016 |
| JP | 2016-528016 A | 9/2016 |
| JP | 2016-177151 A | 10/2016 |
| JP | 2016-202751 A | 12/2016 |
| JP | 2017-134689 A | 8/2017 |
| JP | 2017-211994 A | 11/2017 |
| JP | 2017-532069 A | 11/2017 |
| KR | 10-2005-0101162 A | 10/2005 |
| KR | 10-2006-0032793 A | 4/2006 |
| KR | 10-2006-0117570 A | 11/2006 |
| KR | 10-2011-0017076 A | 2/2011 |
| KR | 10-2012-0023657 A | 3/2012 |
| KR | 10-2012-0076559 A | 7/2012 |
| KR | 10-2013-0043698 A | 5/2013 |
| KR | 10-2013-0111569 A | 10/2013 |
| KR | 10-2013-0111570 A | 10/2013 |
| KR | 10-2013-0135282 A | 12/2013 |
| KR | 10-2015-0026635 A | 3/2015 |
| KR | 10-2016-0027943 A | 3/2016 |
| KR | 10-2017-0003608 A | 1/2017 |
| KR | 10-2017-0029014 A | 3/2017 |
| KR | 10-2019-0141702 A | 12/2019 |
| WO | 1999/41682 A2 | 8/1999 |
| WO | 1999/54807 A1 | 10/1999 |
| WO | 2001/29702 A2 | 4/2001 |
| WO | 2002/27530 A2 | 4/2002 |
| WO | 2002/080176 A2 | 10/2002 |
| WO | 2003/023593 A1 | 3/2003 |
| WO | 2003/081458 A1 | 10/2003 |
| WO | 2005/070289 A1 | 8/2005 |
| WO | 2005/093550 A2 | 10/2005 |
| WO | 2005/103863 A2 | 11/2005 |
| WO | 2006/020305 A2 | 2/2006 |
| WO | 2006/047697 A2 | 5/2006 |
| WO | 2008/030779 A2 | 3/2008 |

(56) References Cited

FOREIGN PATENT DOCUMENTS

| WO | 2008/085737 | A1 | 7/2008 |
|----|-------------|----|--------|
| WO | 2009/084141 | A1 | 7/2009 |
| WO | 2009/129402 | A1 | 10/2009 |
| WO | 2010/126825 | A1 | 11/2010 |
| WO | 2012/021507 | A2 | 2/2012 |
| WO | 2012/061438 | A2 | 5/2012 |
| WO | 2012/061440 | A2 | 5/2012 |
| WO | 2012/078079 | A2 | 6/2012 |
| WO | 2012/086910 | A1 | 6/2012 |
| WO | 2013/052789 | A1 | 4/2013 |
| WO | 2013/109762 | A1 | 7/2013 |
| WO | 2013/109777 | A1 | 7/2013 |
| WO | 2013/109916 | A1 | 7/2013 |
| WO | 2013/173838 | A2 | 11/2013 |
| WO | 2014/200730 | A1 | 12/2014 |
| WO | 2014/207294 | A1 | 12/2014 |
| WO | 2015/027133 | A1 | 2/2015 |
| WO | 2015/179592 | A1 | 11/2015 |
| WO | 2015/198488 | A1 | 12/2015 |
| WO | 2016/036472 | A1 | 3/2016 |
| WO | 2016/036582 | A2 | 3/2016 |
| WO | 2017/037242 | A1 | 3/2017 |
| WO | 2018/213066 | A1 | 11/2018 |
| WO | 2018/222313 | A1 | 12/2018 |
| WO | 2019/017508 | A1 | 1/2019 |
| WO | 2019/024603 | A1 | 2/2019 |
| WO | 2019/183422 | A1 | 9/2019 |
| WO | 2019/217249 | A2 | 11/2019 |
| WO | 2019/231982 | A1 | 12/2019 |

OTHER PUBLICATIONS

Communication of the Board of Appeal received for European Patent Application No. 15771747.1, dated Aug. 25, 2021, 9 pages.
Notice of Allowance received for Japanese Patent Application No. 2019-563407, dated Aug. 20, 2021, 4 pages (1 page of English Translation and 3 pages of Official Copy).
Notice of Allowance received for Korean Patent Application No. 10-2020-7026035, dated Aug. 23, 2021, 4 pages (2 page of English Translation and 2 pages of Official Copy).
Office Action received for Australian Patent Application No. 2020239748, dated Sep. 1, 2021, 4 pages.
Office Action received for European Patent Application No. 21168916.1, dated Aug. 23, 2021, 8 pages.
Applicant-Initiated Interview Summary received for U.S. Appl. No. 16/987,275, dated Feb. 3, 2022, 4 pages.
Applicant-Initiated Interview Summary received for U.S. Appl. No. 17/157,728, dated Feb. 3, 2022, 5 pages.
Intention to Grant received for Danish Patent Application No. PA202070615, dated Jan. 27, 2022, 2 pages.
Notice of Acceptance received for Australian Patent Application No. 2020239752, dated Jan. 31, 2022, 3 pages.
Notice of Allowance received for U.S. Appl. No. 17/192,161, dated Feb. 16, 2022, 8 pages.
Office Action received for Australian Patent Application No. 2021201130, dated Jan. 27, 2022, 2 pages.
Office Action received for Danish Patent Application No. PA202070616, dated Jan. 27, 2022, 2 pages.
Office Action received for Japanese Patent Application No. 2020-160053, dated Jan. 31, 2022, 8 pages (4 pages of English Translation and 4 pages of Official Copy).
Applicant-Initiated Interview Summary received for U.S. Appl. No. 17/192,161, dated Sep. 29, 2021, 3 pages.
Corrected Notice of Allowance received for U.S. Appl. No. 16/820,383, dated Oct. 5, 2021, 2 pages.
Extended European Search Report received for European Patent Application No. 21159939.4, dated Sep. 28, 2021, 13 pages.
Final Office Action received for U.S. Appl. No. 17/030,318, dated Sep. 30, 2021, 28 pages.
International Search Report and Written Opinion received for PCT Patent Application No. PCT/US2021/017736, dated Sep. 2, 2021, 25 pages.
Non-Final Office Action received for U.S. Appl. No. 16/418,786, dated Oct. 4, 2021, 10 pages.
Notice of Allowance received for U.S. Appl. No. 17/035,367, dated Sep. 23, 2021, 7 pages.
Office Action received for Danish Patent Application No. PA202070614, dated Sep. 28, 2021, 4 pages.
Decision on Appeal received for U.S. Appl. No. 16/584,783, dated Oct. 14, 2021, 12 pages.
Final Office Action received for U.S. Appl. No. 17/192,161, dated Oct. 18, 2021, 22 pages.
Non-Final Office Action received for U.S. Appl. No. 17/030,321, dated Oct. 18, 2021, 28 pages.
Office Action received for Danish Patent Application No. PA202070613, dated Sep. 30, 2021, 4 pages.
Advisory Action received for U.S. Appl. No. 16/377,892, dated Apr. 9, 2021, 4 pages.
Advisory Action received for U.S. Appl. No. 16/378,136, dated Apr. 12, 2021, 4 pages.
Applicant Initiated Interview Summary received for U.S. Appl. No. 15/608,848, dated Apr. 13, 2021, 4 pages.
Final Office Action received for U.S. Appl. No. 17/030,321, dated Apr. 2, 2021, 28 pages.
Non-Final Office Action received for U.S. Appl. No. 16/888,629, dated Mar. 31, 2021, 14 pages.
Non-Final Office Action received for U.S. Appl. No. 17/030,318, dated Apr. 2, 2021, 28 pages.
Notice of Acceptance received for Australian Patent Application No. 2021200787, dated Mar. 19, 2021, 3 pages.
Notice of Allowance received for U.S. Appl. No. 16/820,383, dated Mar. 31, 2021, 11 pages.
Office Action received for Australian Patent Application No. 2020239743, dated Mar. 25, 2021, 8 pages.
Office Action received for Japanese Patent Application No. 2018-184532, dated Mar. 1, 2021, 11 pages (6 pages of English Translation and 5 pages of Official Copy).
International Preliminary Report on Patentability received for PCT Patent Application No. PCT/US2020/025997, dated Nov. 18, 2021, 10 pages.
International Preliminary Report on Patentability received for PCT Patent Application No. PCT/US2020/031442, dated Nov. 18, 2021, 21 pages.
Non-Final Office Action received for U.S. Appl. No. 16/987,275, dated Nov. 23, 2021, 17 pages.
Notice of Allowance received for U.S. Appl. No. 16/888,629, dated Nov. 9, 2021, 11 pages.
Notice of Allowance received for U.S. Appl. No. 16/894,309, dated Nov. 5, 2021, 12 pages.
Office Action received for Danish Patent Application No. PA202070615, dated Nov. 16, 2021, 4 pages.
Office Action received for European Patent Application No. 20721342.2, dated Nov. 4, 2021, 9 pages.
Non-Final Office Action received for U.S. Appl. No. 17/192,161, dated May 13, 2021, 28 pages.
Notice of Allowance received for Chinese Patent Application No. 201680047983.1, dated Apr. 28, 2021, 3 pages (1 page of English Translation and 2 pages of Official Copy).
Notice of Allowance received for U.S. Appl. No. 16/377,892, dated May 24, 2021, 9 pages.
Office Action received for Japanese Patent Application No. 2018-138559, dated Apr. 9, 2021, 30 pages (6 pages of English Translation and 24 pages of Official Copy).
Summons to Oral Proceedings received for European Patent Application No. 15771747.1, mailed on Apr. 29, 2021, 8 pages.
Supplemental Notice of Allowance received for U.S. Appl. No. 16/584,776, dated May 13, 2021, 4 pages.
Applicant-Initiated Interview Summary received for U.S. Appl. No. 17/031,854, dated Feb. 25, 2022, 5 pages.
Applicant-Initiated Interview Summary received for U.S. Appl. No. 17/031,859, dated Feb. 25, 2022, 4 pages.

(56) References Cited

OTHER PUBLICATIONS

Applicant-Initiated Interview Summary received for U.S. Appl. No. 17/031,874, dated Feb. 25, 2022, 4 pages.
Notice of Allowance received for U.S. Appl. No. 16/894,309, dated Feb. 25, 2022, 9 pages.
Notice of Allowance received for U.S. Appl. No. 16/994,352, dated Mar. 2, 2022, 14 pages.
Notice of Allowance received for U.S. Appl. No. 17/157,728, dated Feb. 24, 2022, 7 pages.
Office Action received for Australian Patent Application No. 2020239748, dated Feb. 11, 2022, 2 pages.
Office Action received for Chinese Patent Application No. 201910858933.7, dated Dec. 30, 2021, 9 pages (4 pages of English Translation and 5 pages of Official Copy).
Office Action received for Chinese Patent Application No. 201911401161.0, dated Jan. 24, 2022, 6 pages (3 pages of English Translation and 3 pages of Official Copy).
Supplemental Notice of Allowance received for U.S. Appl. No. 17/030,318, dated Feb. 22, 2022, 2 pages.
Corrected Notice of Allowance received for U.S. Appl. No. 16/418,786, dated Jan. 5, 2022, 3 pages.
Non-Final Office Action received for U.S. Appl. No. 16/820,383, dated Jan. 10, 2022, 18 pages.
Non-Final Office Action received for U.S. Appl. No. 17/031,854, dated Dec. 27, 2021, 13 pages.
Notice of Allowance received for U.S. Appl. No. 17/030,318, dated Jan. 5, 2022, 8 pages.
Office Action received for Indian Patent Application No. 202014041563, dated Dec. 30, 2021, 6 pages.
Applicant-Initiated Interview Summary received for U.S. Appl. No. 17/192,161, dated Dec. 24, 2021, 4 pages.
Decision of Appeal received for European Patent Application No. 15771747.1, dated Dec. 14, 2021, 21 pages.
International Preliminary Report on Patentability received for PCT Patent Application No. PCT/US2020/035199, dated Dec. 16, 2021, 14 pages.
Non-Final Office Action received for U.S. Appl. No. 17/031,859, dated Dec. 24, 2021, 16 pages.
Notice of Allowance received for Chinese Patent Application No. 201380081349.6, dated Dec. 17, 2021, 2 pages (1 page of English Translation and 1 page of Official Copy).
Notice of Allowance received for Korean Patent Application No. 10-2021-7038005, dated Dec. 14, 2021, 4 pages (2 pages of English Translation and 2 pages of Official Copy).
Notice of Allowance received for U.S. Appl. No. 16/584,783, dated Dec. 20, 2021, 7 pages.
Office Action received for Chinese Patent Application No. 202010606407.4, dated Nov. 18, 2021, 6 pages (3 pages of English Translation and 3 pages of Official Copy).
Office Action received for Chinese Patent Application No. 202110363565.6, dated Nov. 16, 2021, 16 pages (9 pages of English Translation and 7 pages of Official Copy).
Office Action received for Indian Patent Application No. 202014041571, dated Dec. 17, 2021, 5 pages.
Office Action received for Japanese Patent Application No. 2020-160052, dated Dec. 17, 2021, 10 pages (5 pages of English Translation and 5 pages of Official Copy).
Search Report and Opinion received for Danish Patent Application No. PA202170113, dated Nov. 30, 2021, 9 pages.
Summons to Attend Oral Proceedings received for European Patent Application No. 20182116.2, mailed on Dec. 21, 2021, 7 pages.
Supplemental Notice of Allowance received for U.S. Appl. No. 16/894,309, dated Dec. 24, 2021, 2 pages.
Applicant-Initiated Interview Summary received for U.S. Appl. No. 16/377,892, dated Mar. 26, 2021, 2 pages.
Applicant-Initiated Interview Summary received for U.S. Appl. No. 16/378,136, dated Mar. 26, 2021, 2 pages.
Applicant-Initiated Interview Summary received for U.S. Appl. No. 16/418,786, dated Mar. 30, 2021, 4 pages.
Decision on Appeal received for Korean Patent Application No. 10-2019-7025538, dated Feb. 24, 2021, 20 pages (4 pages of English Translation and 16 pages of Official Copy).
Notice of Allowance received for Korean Patent Application No. 10-2019-7025538, dated Mar. 10, 2021, 5 pages (2 pages of English Translation and 3 pages of Official Copy).
Notice of Allowance received for U.S. Appl. No. 16/144,864, dated Mar. 30, 2021, 2 pages.
Office Action received for European Patent Application No. 18727543.3, dated Mar. 26, 2021, 7 pages.
Search Report and Opinion received for Danish Patent Application No. PA202070815, dated Mar. 16, 2021, 8 pages.
Applicant Initiated Interview Summary received for U.S. Appl. No. 16/994,352, dated Nov. 2, 2021, 4 pages.
Notice of Allowance received for Japanese Patent Application No. 2020-115940, dated Oct. 22, 2021, 4 pages (1 page of English Translation and 3 pages of Official Copy).
Notice of Allowance received for U.S. Appl. No. 15/608,848, dated Oct. 29, 2021, 7 pages.
Office Action received for Australian Patent Application No. 2020239752, dated Oct. 25, 2021, 5 pages.
Office Action received for Chinese Patent Application No. 201780034203.4, dated Sep. 24, 2021, 7 pages (3 pages of English Translation and 4 pages of Official Copy).
Office Action received for Danish Patent Application No. PA202070815, dated Oct. 18, 2021, 2 pages.
Office Action received for Korean Patent Application No. 10-2021-7031939, dated Oct. 19, 2021, 11 pages (5 pages of English Translation and 6 pages of Official Copy).
Supplemental Notice of Allowance received for U.S. Appl. No. 17/035,367, dated Oct. 27, 2021, 3 pages.
Final Office Action received for U.S. Appl. No. 16/994,352, dated Dec. 6, 2021, 14 pages.
Minutes of the Oral Proceedings received for European Patent Application No. 15771747.1, mailed on Dec. 1, 2021, 4 pages.
Non-Final Office Action received for U.S. Appl. No. 17/157,728, dated Nov. 26, 2021, 18 pages.
Notice of Acceptance received for Australian Patent Application No. 2020267396, dated Dec. 7, 2021, 3 pages.
Notice of Allowance received for Japanese Patent Application No. 2018-138559, dated Dec. 3, 2021, 3 pages (1 page of English Translation and 2 pages of Official Copy).
Notice of Allowance received for U.S. Appl. No. 16/418,786, dated Dec. 9, 2021, 9 pages.
Office Action received for European Patent Application No. 20203526.7, dated Nov. 23, 2021, 9 pages.
Final Office Action received for U.S. Appl. No. 17/031,859, dated Apr. 16, 2021, 14 pages.
Final Office Action received for U.S. Appl. No. 17/031,874, dated Apr. 16, 2021, 17 pages.
Notice of Allowance received for Japanese Patent Application No. 2019-162293, dated Apr. 9, 2021, 4 pages (1 page of English Translation and 3 pages of Official Copy).
Notice of Allowance received for U.S. Appl. No. 16/138,809, dated Apr. 16, 2021, 11 pages.
Office Action received for Danish Patent Application No. PA202170113, dated Apr. 15, 2021, 2 pages.
Corrected Notice of Allowance received for U.S. Appl. No. 16/377,892, dated Aug. 11, 2021, 3 pages.
Corrected Notice of Allowance received for U.S. Appl. No. 16/378,136, dated Aug. 11, 2021, 2 pages.
Corrected Notice of Allowance received for U.S. Appl. No. 16/820,383, dated Aug. 13, 2021, 2 pages.
Corrected Notice of Allowance received for U.S. Appl. No. 16/820,383, dated Aug. 19, 2021, 2 pages.
Final Office Action received for U.S. Appl. No. 17/192,161, dated Aug. 16, 2021, 22 pages.
Gym Book—Strength Training Planner, Logger and Analyzer, GymBookApp, Available Online at: https://web.archive.org/web/20160401104508/https://gymbookapp.com/, Apr. 1, 2016, 10 pages.
Notice of Acceptance received for Australian Patent Application No. 2020256383, dated Aug. 3, 2021, 3 pages.

(56) References Cited

OTHER PUBLICATIONS

Notice of Allowance received for U.S. Appl. No. 15/608,848, dated Aug. 25, 2021, 9 pages.
Office Action received for Chinese Patent Application No. 201780034203.4, dated Jul. 14, 2021, 12 pages (5 pages of English Translation and 7 pages of Official Copy).
Office Action received for Japanese Patent Application No. 2018-138559, dated Jul. 26, 2021, 37 pages (5 pages of English Translation and 32 pages of Official Copy).
Office Action received for Japanese Patent Application No. 2020-079486, dated Jul. 16, 2021, 10 pages (5 pages of English Translation and 5 pages of Official Copy).
Notice of Allowance received for U.S. Appl. No. 16/377,892, dated Sep. 9, 2021, 9 pages.
Notice of Allowance received for U.S. Appl. No. 16/378,136, dated Sep. 22, 2021, 7 pages.
Office Action received for Australian Patent Application No. 2020239743, dated Sep. 3, 2021, 4 pages.
Office Action received for Japanese Patent Application No. 2019-044107, dated Jul. 30, 2021, 9 pages (5 pages of English Translation and 4 pages of Official Copy).
Office Action received for Korean Patent Application No. 10-2021-7026284, dated Aug. 31, 2021, 10 pages (4 pages of English Translation and 6 pages of Official Copy).
Applicant-Initiated Interview Summary received for U.S. Appl. No. 16/820,383, dated Mar. 11, 2021, 2 pages.
Notice of Acceptance received for Australian Patent Application No. 2019250251, dated Feb. 18, 2021, 3 pages.
Notice of Allowance received for U.S. Appl. No. 15/925,652, dated Mar. 9, 2021, 9 pages.
Notice of Allowance received for U.S. Appl. No. 16/144,864, dated Mar. 12, 2021, 2 pages.
Office Action received for Chinese Patent Application No. 202010606407.4, dated Jan. 27, 2021, 16 pages (7 pages of English Translation and 9 pages of Official Copy).
Office Action received for Japanese Patent Application No. 2019-563407, dated Feb. 5, 2021, 5 pages (2 pages of English Translation and 3 pages of Official Copy).
Corrected Notice of Allowance received for U.S. Appl. No. 16/888,629, dated Jan. 21, 2022, 2 pages.
Corrected Notice of Allowance received for U.S. Appl. No. 17/030,318, dated Jan. 24, 2022, 2 pages.
Non-Final Office Action received for U.S. Appl. No. 17/031,874, dated Jan. 24, 2022, 18 pages.
Notice of Acceptance received for Australian Patent Application No. 2020239743, dated Jan. 13, 2022, 3 pages.
Notice of Allowance received for Chinese Patent Application No. 201780034203.4, dated Jan. 17, 2022, 2 pages (1 page of English Translation and 1 page of Official Copy).
Notice of Allowance received for Chinese Patent Application No. 202010606407.4, dated Jan. 24, 2022, 2 pages (1 page of English Translation and 1 page of Official Copy).
Notice of Allowance received for Japanese Patent Application No. 2018-184532, dated Jan. 17, 2022, 4 pages (1 page of English Translation and 3 pages of Official Copy).
Office Action received for German Patent Application No. 112007000067.8, dated Apr. 23, 2009, 15 pages (7 pages of English Translation and 8 pages of Official Copy).
Office Action received for German Patent Application No. 112007000067.8, dated Sep. 14, 2010, 4 pages (2 pages of English Translation and 2 pages of Official Copy).
Office Action received for Japanese Patent Application No. 2020-160054, dated Jan. 21, 2022, 8 pages (4 pages of English Translation and 4 pages of Official Copy).
Summons to Oral Proceedings received for German Patent Application No. 112007000067.8, mailed on Dec. 8, 2021, 11 pages (5 pages of English Translation and 6 pages of Official Copy).
Supplemental Notice of Allowance received for U.S. Appl. No. 16/894,309, dated Jan. 25, 2022, 2 pages.

Applicant-Initiated Interview Summary received for U.S. Appl. No. 16/888,629, dated Aug. 4, 2021, 5 pages.
Applicant-Initiated Interview Summary received for U.S. Appl. No. 17/030,318, dated Jul. 30, 2021, 4 pages.
Applicant-Initiated Interview Summary received for U.S. Appl. No. 17/030,321, dated Jul. 30, 2021, 2 pages.
Non-Final Office Action received for U.S. Appl. No. 16/994,352, dated Jul. 30, 2021, 11 pages.
Notice of Allowance received for Japanese Patent Application No. 2020-000492, dated Jul. 16, 2021, 4 pages (1 page of English Translation and 3 pages of Official Copy).
Office Action received for Australian Patent Application No. 2020239748, dated Apr. 21, 2021, 6 pages.
Applicant-Initiated Interview Summary received for U.S. Appl. No. 17/031,859, dated Feb. 26, 2021, 4 pages.
Applicant-Initiated Interview Summary received for U.S. Appl. No. 17/031,874, dated Feb. 26, 2021, 4 pages.
Decision to Refuse received for European Patent Application No. 18154145.9, dated Feb. 17, 2021, 20 pages.
Final Office Action received for U.S. Appl. No. 16/5894,309, dated Feb. 24, 2021, 30 pages.
Minutes of the Oral Proceedings received for European Patent Application No. 18154145.9, dated Feb. 12, 2021, 8 pages.
Notice of Acceptance received for Australian Patent Application No. 2017277971, dated Feb. 17, 2021, 3 pages.
Office Action received for Chinese Patent Application No. 201380081349.6, dated Jan. 5, 2021, 16 pages (7 pages of English Translation and 9 pages of Official Copy).
Office Action received for Chinese Patent Application No. 201680047983.1, dated Feb. 1, 2021, 6 pages (3 pages of English Translation and 3 pages of Official Copy).
Office Action received for Korean Patent Application No. 10-2020-7026035, dated Feb. 19, 2021, 13 pages (6 pages of English Translation and 7 pages of Official Copy).
Supplemental Notice of Allowance received for U.S. Appl. No. 16/584,776, dated Feb. 18, 2021, 3 pages.
European Search Report received for European Patent Application No. 21168916.1, dated Jul. 14, 2021, 5 pages.
Notice of Allowance received for Korean Patent Application No. 10-2019-7025781, dated Jun. 29, 2021, 5 pages (2 pages of English Translation and 3 pages of Official Copy).
Notice of Allowance received for Korean Patent Application No. 10-2019-7033834, dated Jul. 3, 2021, 4 pages (2 page of English Translation and 2 pages of Official Copy).
Notice of Allowance received for U.S. Appl. No. 16/138,809, dated Jul. 20, 2021, 6 pages.
Notice of Allowance received for U.S. Appl. No. 16/820,383, dated Jul. 21, 2021, 11 pages.
Office Action received for Chinese Patent Application No. 201380081349.6, dated Jun. 2, 2021, 17 pages (8 pages of English Translation and 9 pages of Official Copy).
Office Action received for Chinese Patent Application No. 201910858933.7, dated Jun. 29, 2021, 8 pages (3 pages of English Translation and 5 pages of Official Copy).
Supplemental Notice of Allowance received for U.S. Appl. No. 15/627,069, dated Jul. 12, 2021, 2 pages.
Applicant-Initiated Interview Summary received for U.S. Appl. No. 16/894,309, dated Jun. 25, 2021, 4 pages.
Applicant-Initiated Interview Summary received for U.S. Appl. No. 17/031,859, dated Jun. 30, 2021, 4 pages.
Applicant-Initiated Interview Summary received for U.S. Appl. No. 17/031,874, dated Jun. 30, 2021, 4 pages.
Applicant-Initiated Interview Summary received for U.S. Appl. No. 17/192,161, dated Jun. 29, 2021, 4 pages.
Decision to Grant received for Danish Patent Application No. PA201670656, dated Jun. 21, 2021, 2 pages.
Decision to Grant received for German Patent Application No. 112015002326.7, dated Jun. 15, 2021, 10 pages (1 page of English Translation and 9 pages of Official Copy).
European Search Report received for European Patent Application No. 21165295.3, dated Jun. 18, 2021, 4 pages.
Invitation to Pay Additional Fees received for PCT Patent Application No. PCT/US2021/017736, dated Jun. 15, 2021, 14 pages.

(56) References Cited

OTHER PUBLICATIONS

Notice of Allowance received for U.S. Appl. No. 15/627,069, dated Jun. 17, 2021, 14 pages.
Office Action received for Chinese Patent Application No. 202010606407.4, dated Jun. 2, 2021, 12 pages (5 pages of English Translation and 7 pages of Official Copy).
Office Action received for European Patent Application No. 19721883.7, dated Jun. 15, 2021, 9 pages.
Office Action received for European Patent Application No. 21165295.3, dated Jul. 1, 2021, 10 pages.
Corrected Notice of Allowance received for U.S. Appl. No. 16/378,136, dated Jun. 11, 2021, 2 pages.
Non-Final Office Action received for U.S. Appl. No. 17/035,367, dated Jun. 11, 2021, 11 pages.
Notice of Allowance received for U.S. Appl. No. 16/378,136, dated Jun. 3, 2021, 7 pages.
Office Action received for Australian Patent Application No. 2020239752, dated Jun. 4, 2021, 8 pages.
Office Action received for Australian Patent Application No. 2020256383, dated Jun. 4, 2021, 3 pages.
Office Action received for European Patent Application No. 20182116.2, dated May 25, 2021, 9 pages.
Office Action received for Japanese Patent Application No. 2020-115940, dated May 7, 2021, 3 pages (1 page of English Translation and 2 pages of Official Copy).
Search Report and Opinion received for Danish Patent Application No. PA202070612, dated Jun. 7, 2021, 9 pages.
Decision to Grant received for European Patent Application No. 17180535.1, dated Feb. 4, 2021, 2 pages.
Examiner's Answer to Appeal Brief received for U.S. Appl. No. 16/584,783, dated Feb. 17, 2021, 9 pages.
Non-Final Office Action received for U.S. Appl. No. 15/608,848, dated Feb. 12, 2021, 14 pages.
Notice of Allowance received for U.S. Appl. No. 16/144,753, dated Feb. 10, 2021, 8 pages.
Notice of Allowance received for U.S. Appl. No. 16/144,864, dated Feb. 9, 2021, 13 pages.
Search Report and Opinion received for Danish Patent Application No. PA202070616, dated Feb. 3, 2021, 8 pages.
Supplemental Notice of Allowance received for U.S. Appl. No. 15/925,652, dated Feb. 17, 2021, 3 pages.
Supplemental Notice of Allowance received for U.S. Appl. No. 16/556,023, dated Feb. 3, 2021, 2 pages.
CBS This Morning, "This smart mirror puts a personal trainer in your reflection", Available on: https://www.youtube.com/watch?v=nSmTTZcpVGg, Oct. 13, 2018, 4 pages.
Applicant Initiated Interview Summary received for U.S. Appl. No. 16/894,309, dated Jan. 26, 2021, 3 pages.
Adeniyi, "How to connect a second PS4 controller to a PlayStation 4 console", Online available on: https://www.youtube.com/watch?v=mOZX_SrNISE, May 28, 2017, 2 pages.
Allison, "Working out with Fiit's wearable-powered boutique fitness classes", Online available at: <https://www.wareable.com/wearable-tech/fiit-fitness-classesreview-3849>, May 14, 2018, 8 pages.
Applicant-Initiated Interview Summary received for U.S. Appl. No. 15/627,069, dated Jan. 22, 2021, 4 pages.
Decision to Refuse received for European Patent Application No. 17810749.6, dated Jan. 29, 2021, 24 pages.
Extended European Search Report received for European Patent Application No. 20203526.7, dated Jan. 29, 2021, 13 pages.
Final Office Action received for U.S. Appl. No. 16/377,892, dated Jan. 28, 2021, 11 pages.
Final Office Action received for U.S. Appl. No. 16/378,136, dated Jan. 28, 2021, 9 pages.
Hamilton, "Peloton Tips", Online available on: <https://www.youtube.com/watch?app=desktop&v=OneXtB0kaD4>, Oct. 22, 2015, 3 pages.
Intention to Grant received for Danish Patent Application No. PA201670656, dated Jan. 18, 2021, 2 pages.

Minutes of the Oral Proceedings received for European Patent Application No. 17810749.6, mailed on Jan. 26, 2021, 8 pages.
Notice of Acceptance received for Australian Patent Application No. 2019264623, dated Jan. 4, 2021, 3 pages.
Notice of Allowance received for Chinese Patent Application No. 201710439448.7, dated Jan. 26, 2021, 2 pages (1 page of English Translation and 1 page of Official Copy).
Notice of Allowance received for U.S. Appl. No. 16/584,776, dated Feb. 1, 2021, 9 pages.
Office Action received for European Patent Application No. 16837432.0, dated Jan. 27, 2021, 7 pages.
Office Action received for Japanese Patent Application No. 2020-000492, dated Dec. 11, 2020, 6 pages (3 pages English Translation and 3 pages of Official Copy).
Office Action received for Korean Patent Application No. 10-2019-7033834, dated Jan. 22, 2021, 13 pages (6 pages of English Translation and 7 pages of Official Copy).
Result of Consultation received for European Patent Application No. 17810749.6, dated Jan. 18, 2021, 3 pages.
Result of Consultation received for European Patent Application No. 17810749.6, dated Jan. 21, 2021, 18 pages.
Search Report and Opinion received for Danish Patent Application No. PA202070613, dated Jan. 22, 2021, 9 pages.
Search Report and Opinion received for Danish Patent Application No. PA202070615, dated Jan. 22, 2021, 9 pages.
Supplemental Notice of Allowance received for U.S. Appl. No. 15/925,652, dated Jan. 26, 2021, 3 pages.
Vicky's Blog, "How to Log In to PS4 Automatically with Particular User?", Online available on: https://www.youtube.com/watch?v=kqdIzXAvOkY, May 30, 2018, 3 pages.
Yoyodavid, "How to Use Multiple Accounts on the Playstation 4", Online available at: https://www.youtube.com/watch?v=5V21obRMeKE, Jan. 9, 2014, 3 pages.
Corrected Notice of Allowance received for U.S. Appl. No. 17/192,161, dated Mar. 23, 2022, 2 pages.
Non-Final Office Action received for U.S. Appl. No. 16/418,786, dated Mar. 28, 2022, 14 pages.
Non-Final Office Action received for U.S. Appl. No. 17/153,703, dated Mar. 30, 2022, 10 pages.
Notice of Allowance received for Australian Patent Application No. 2020239748, dated Mar. 7, 2022, 3 pages.
Notice of Allowance received for U.S. Appl. No. 17/197,628, dated Mar. 23, 2022, 35 pages.
Office Action received for Japanese Patent Application No. 2020-079486, dated Mar. 11, 2022, 8 pages (4 pages of English Translation and 4 pages of Official Copy).
Summons to Attend Oral Proceedings received for European Patent Application No. 18197554.1, mailed on Mar. 23, 2022, 7 pages.
T&GG Channel, "Canon IXUS 700 / Screenshots of deleting an image", Online available at: https://www.youtube.com/watch?v=8BL_L5hKZUM, May 2015, 2 pages.
Office Action received for Danish Patent Application No. PA 2020 70612, dated Mar. 1, 2022, 2 pages.
Office Action received for Korean Patent Application No. 10-2021-7036310, dated Feb. 23, 2022, 6 pages (2 pages of English Translation and 4 pages of Official Copy).
Summons to Attend Oral Proceedings received for European Patent Application No. 13811085.3, mailed on Mar. 3, 2022, 3 pages.
Supplemental Notice of Allowance received for U.S. Appl. No. 17/030,318, dated Mar. 16, 2022, 2 pages.
Office Action received for Danish Patent Application No. PA202070616, dated May 5, 2022, 3 pages.
Applicant-Initiated Interview Summary received for U.S. Appl. No. 17/381,570, dated Apr. 26, 2022, 5 pages.
Brief Communication Regarding Oral Proceedings received for European Patent Application No. 20182116.2, dated Apr. 13, 2022, 3 pages.
Corrected Notice of Allowance received for U.S. Appl. No. 17/157,728, dated Apr. 14, 2022, 6 pages.
Corrected Notice of Allowance received for U.S. Appl. No. 17/192,161, dated Apr. 22, 2022, 2 pages.
Notice of Acceptance received for Australian Patent Application No. 2021203636, dated Apr. 14, 2022, 3 pages.

(56) References Cited

OTHER PUBLICATIONS

Office Action received for Australian Patent Application No. 2021202225, dated Apr. 7, 2022, 3 pages.
Office Action received for Chinese Patent Application No. 202110783860.7, dated Mar. 10, 2022, 15 pages (5 pages of English Translation and 10 pages of Official Copy).
Supplemental Notice of Allowance received for U.S. Appl. No. 17/030,321, dated Apr. 15, 2022, 2 pages.
Board Decision received for Chinese Patent Application No. 201380081349.6, dated Nov. 23, 2020, 2 pages (1 page of English Translation and 1 page of Official Copy).
International Search Report and Written Opinion received for PCT Patent Application No. PCT/US2020/035199, dated Oct. 30, 2020, 20 pages.
Invitation to Pay Additional Fees received for PCT Patent Application No. PCT/US2020/035199, dated Sep. 8, 2020, 12 pages.
Non-Final Office Action received for U.S. Appl. No. 16/820,383, dated Dec. 14, 2020, 11 pages.
Non-Final Office Action received for U.S. Appl. No. 17/030,318, dated Dec. 3, 2020, 22 pages.
Non-Final Office Action received for U.S. Appl. No. 17/030,321, dated Dec. 15, 2020, 25 pages.
Non-Final Office Action received for U.S. Appl. No. 17/031,859, dated Dec. 15, 2020, 13 pages.
Notice of Allowance received for U.S. Appl. No. 16/144,753, dated Dec. 4, 2020, 22 pages.
Result of Consultation received for European Patent Application No. 18154145.9, dated Nov. 30, 2020, 17 pages.
Applicant-Initiated Interview Summary received for U.S. Appl. No. 16/138,809, dated Dec. 16, 2020, 7 pages.
Non-Final Office Action received for U.S. Appl. No. 17/031,874, dated Dec. 28, 2020, 14 pages.
Result of Consultation received for European Patent Application No. 17810749.6, dated Dec. 15, 2020, 3 pages.
Applicant-Initiated Interview Summary received for U.S. Appl. No. 15/925,652, dated Nov. 3, 2020, 4 pages.
Applicant-Initiated Interview Summary received for U.S. Appl. No. 16/144,753, dated Nov. 4, 2020, 3 pages.
Corrected Notice of Allowance received for U.S. Appl. No. 16/450,531, dated Oct. 30, 2020, 2 pages.
Office Action received for Korean Patent Application No. 10-2019-7025781, dated Oct. 30, 2020, 10 pages (4 pages of English Translation and 6 pages of Official Copy).
Bagala et al., "Evaluation of Accelerometer-Based Fall Detection Algorithms on Real-World Falls", PloS ONE, vol. 7, No. 5, May 2012, 9 pages.
Advisory Action received for U.S. Appl. No. 16/144,864. dated Jul. 29, 2019, 6 pages.
Advisory Action received for U.S. Appl. No. 10/497,076, dated Aug. 2, 2011, 3 pages.
Advisory Action received for U.S. Appl. No. 10/497,076, dated Oct. 28, 2008, 3 pages.
Advisory Action received for U.S. Appl. No. 14/732,773, dated Aug. 23, 2019, 6 pages.
Advisory Action received for U.S. Appl. No. 14/732,773, dated Nov. 9, 2018, 6 pages.
Advisory Action received for U.S. Appl. No. 14/839,922, dated Mar. 24, 2017, 4 pages.
Advisory Action received for U.S. Appl. No. 16/144,849, dated Aug. 12, 2019, 5 pages.
Advisory Action received for U.S. Appl. No. 16/144,864, dated Jul. 6, 2020, 6 pages.
Apple, "iPhone User's Guide", Available at <http://mesnotices.20minutes.fr/manuel-notice-mode-emploi/APPLE/IPHONE%2D%5FE#>, Retrieved on Mar. 27, 2008, Jun. 2007, 137 pages.
Applicant-Initiated Interview Summary received for U.S. Appl. No. 15/608,848, dated May 12, 2020, 5 pages.
Applicant-Initiated Interview Summary received for U.S. Appl. No. 15/627,069, dated Nov. 4, 2019, 6 pages.
Applicant-Initiated Interview Summary received for U.S. Appl. No. 16/144,735, dated Jun. 18, 2020, 3 pages.
Applicant-Initiated Interview Summary received for U.S. Appl. No. 16/144,753, dated Jun. 18, 2020, 3 pages.
Applicant-Initiated Interview Summary received for U.S. Appl. No. 16/144,849, dated Jan. 21, 2020, 6 pages.
Applicant-Initiated Interview Summary received for U.S. Appl. No. 16/144,864, dated Apr. 29, 2020, 4 pages.
Applicant-Initiated Interview Summary received for U.S. Appl. No. 15/600,243, dated Nov. 1, 2019, 6 pages.
Applicant-Initiated Interview Summary received for U.S. Appl. No. 15/608,848, dated Nov. 1, 2019, 3 pages.
Applicant-Initiated Interview Summary received for U.S. Appl. No. 15/627,069, dated Jul. 20, 2020, 5 pages.
Applicant-Initiated Interview Summary received for U.S. Appl. No. 15/705,849, dated Feb. 14, 2020, 3 pages.
Applicant-Initiated Interview Summary received for U.S. Appl. No. 15/705,849, dated Jun. 29, 2020, 3 pages.
Applicant-Initiated Interview Summary received for U.S. Appl. No. 16/138,809, dated Jun. 9, 2020, 4 pages.
Applicant-Initiated Interview Summary received for U.S. Appl. No. 16/144,864, dated Jun. 22, 2020, 3 pages.
Applicant-Initiated Interview Summary received for U.S. Appl. No. 16/450,531, dated Aug. 11, 2020, 5 pages.
Board Opinion received for Chinese Reexamination Patent Application No. 200780001142.8, dated Oct. 21, 2014, 13 pages (1 page of English Translation and 12 pages of Official Copy).
Bott, Ed, "Chapter 14. Playing and Recording Digital Music", Special Edition Using Microsoft Windows Millennium Edition, Nov. 2000, pp. 329-341.
Certificate of Examination received for Australian Patent Application No. 2018101855, dated Aug. 6, 2019, 2 pages.
Certification of Examination received for Australian Patent Application No. 2018100158, dated Oct. 23, 2018, 2 pages.
Cho, H.S., "Satisfactory Innovative Smart-watch (fitbit force) . . . review after seven days of use, such as the amount of sleep and movement (improving sleep is the object of X-Blue", Online Available at: https://x-blueuv.blogspot.com/2013/12/fitbit-force.html, Dec. 3, 2013, 8 pages (2 pages of English Translation and 6 pages of Official Copy).
CNET, "Google Fit's automatic activity tracking is getting smarter on Android Wear", Available online at: https://www.youtube.com/watch?v=IttzICid_d8, May 18, 2016, 1 page.
Codrington, Simon, "Intuitive Scrolling Interfaces with CSS Scroll Snap Points", Online Available at: https://www.sitepoint.com/intuitive-scrolling-interfaces-with-css-scroll-snap-points/, Dec. 8, 2015, 14 pages.
Corrected Notice of Allowance received for U.S. Appl. No. 12/566,994, dated Jan. 22, 2015, 2 pages.
Corrected Notice of Allowance received for U.S. Appl. No. 13/666,943, dated Aug. 11, 2016, 2 pages.
Corrected Notice of Allowance received for U.S. Appl. No. 14/732,773, dated Feb. 10, 2020, 3 pages.
Corrected Notice of Allowance received for U.S. Appl. No. 14/732,773, dated Mar. 24, 2020, 3 pages.
Corrected Notice of Allowance received for U.S. Appl. No. 15/183,663, dated Feb. 25, 2019, 3 pages.
Corrected Notice of Allowance received for U.S. Appl. No. 15/183,663, dated Mar. 27, 2019, 2 pages.
Corrected Notice of Allowance received for U.S. Appl. No. 15/281,524, dated Jun. 3, 2019, 2 pages.
Corrected Notice of Allowance received for U.S. Appl. No. 15/600,243, dated Feb. 5, 2020, 3 pages.
Corrected Notice of Allowance received for U.S. Appl. No. 15/600,243, dated Mar. 13, 2020, 3 pages.
Corrected Notice of Allowance received for U.S. Appl. No. 15/600,243, dated Mar. 31, 2020, 5 pages.
Cyclespeed Tours, "The Most Useful Data Fields to Display on Your Garmin", Online Available at: https://www.youtube.com/watch?v=AN0Eo50yxdg, Nov. 16, 2016, 3 pages.
DC Rainmaker, "Garmin Fenix3 New Auto Climb Functionality", Available online at https://www.youtube.com/watch?v=iuavOSNpVRc, Feb. 19, 2015, 1 page.

(56) References Cited

OTHER PUBLICATIONS

Decision to Grant received for Danish Patent Application No. PA201870379, dated Jul. 5, 2019, 2 pages.
Decision to Grant received for European Patent Application No. 09756118.7, dated Jul. 13, 2017, 2 pages.
Decision to Grant received for European Patent Application No. 11178259.5, dated Apr. 4, 2019, 3 pages.
Decision to Grant received for Japanese Patent Application No. 2009-526943, dated Dec. 2, 2011, 3 pages (Official Copy Only) (See Communication under 37 CFR § 1.98(a) (3)).
Decision to Grant received for the European Patent Application No. 07814633.9, dated Sep. 2, 2010, 3 pages.
Decision to Grant received for the European Patent Application No. 10172417.7, dated Nov. 14, 2013, 3 pages.
Decision to Grant received for the European Patent Application No. 11178257.9, dated Jun. 20, 2013, 3 pages.
Decision to Refuse received for European Patent Application No. 13811085.3, dated Sep. 11, 2018, 21 pages.
Decision to Refuse received for European Patent Application No. 15771747.1, dated Aug. 10, 2018, 22 pages.
"DwProgressBar v2: Stepping and Events", Online available at davidwalsh.name/dwprogressbar-2-stepping-events-mootools-progress-bar, retrieved from the Wayback Machine, Aug. 31, 2008, 4 pages.
European Search Report received for the European Application No. 11178259.5, dated Oct. 31, 2011, 8 pages.
European Search Report received for the European Patent Application No. 10172417.7, dated Jan. 7, 2011, 4 pages.
Evergreen et al., "Bar Chart", Better Evaluation, Available Online at: https://www.betterevaluation.org/en/evaluation-options/BarChart, Oct. 31, 2014, 8 pages.
Examiner's Pre-Review Report received for Japanese Patent Application No. 2018-138559, dated Jul. 29, 2020, 6 pages (3 pages of English Translation and 3 pages of Official Copy).
Ex-Parte Quayle Action received for U.S. Appl. No. 12/567,570, dated Oct. 3, 2012, 6 pages.
Extended European Search Report received for European Patent Application No. 11178257.9, dated Oct. 31, 2011, 5 pages.
Extended European Search Report received for European Patent Application No. 16837432.0, dated Mar. 11, 2019, 10 pages.
Extended European Search Report received for European Patent Application No. 18154145.9, dated Mar. 2, 2018, 8 pages.
Extended European Search Report received for European Patent Application No. 18197554.1, dated Jun. 3, 2019, 11 pages.
Extended European Search Report received for European Patent Application No. 17180535.1, dated Oct. 30, 2017, 9 pages.
Final Office Action received for U.S. Appl. No. 10/497,076 dated Feb. 10, 2012, 25 pages.
Final Office Action received for U.S. Appl. No. 10/497,076, dated Apr. 26, 2013, 30 pages.
Final Office Action received for U.S. Appl. No. 10/497,076, dated Feb. 2, 2011, 22 pages.
Final Office Action received for U.S. Appl. No. 10/497,076, dated Jun. 12, 2008, 31 pages.
Final Office Action received for U.S. Appl. No. 10/497,076, dated Oct. 6, 2009, 29 pages.
Final Office Action received for U.S. Appl. No. 12/205,847, dated Apr. 25, 2012, 42 pages.
Final Office Action received for U.S. Appl. No. 12/567,405, dated Dec. 17, 2012, 19 pages.
Final Office Action received for U.S. Appl. No. 12/567,553, dated Mar. 12, 2012, 15 pages.
Final Office Action received for U.S. Appl. No. 14/732,773, dated Jul. 13, 2018, 48 pages.
Final Office Action received for U.S. Appl. No. 14/732,773, dated Jun. 21, 2019, 32 pages.
Final Office Action received for U.S. Appl. No. 14/839,922, dated Dec. 14, 2016, 22 pages.
Final Office Action received for U.S. Appl. No. 15/281,524, dated Dec. 27, 2018, 6 pages.
Final Office Action received for U.S. Appl. No. 15/608,848, dated Aug. 21, 2020, 15 pages.
Final Office Action received for U.S. Appl. No. 15/608,848, dated Jun. 26, 2019, 27 pages.
Final Office Action received for U.S. Appl. No. 15/627,069, dated Mar. 2, 2020, 22 pages.
Final Office Action received for U.S. Appl. No. 15/705,849, dated May 1, 2020, 17 pages.
Final Office Action received for U.S. Appl. No. 15/925,652, dated Aug. 1, 2019, 30 pages.
Final Office Action received for U.S. Appl. No. 16/138,809, dated Aug. 27, 2020, 24 pages.
Final Office Action received for U.S. Appl. No. 16/144,735, dated May 4, 2020, 12 pages.
Final Office Action received for U.S. Appl. No. 16/144,753, dated Sep. 22, 2020, 9 pages.
Final Office Action received for U.S. Appl. No. 16/144,849, dated Jun. 7, 2019, 29 pages.
Final Office Action received for U.S. Appl. No. 16/144,864, dated May 17, 2019, 24 pages.
Final Office Action received for U.S. Appl. No. 16/144,864, dated May 28, 2020, 29 pages.
"Fitbit App", Available online at: <http://web.archive.org/web/20180114083150/https://www.fitbit.com/au/app>, Jan. 14, 2018, 8 pages.
Garmin, "Fenix 5x Owner's Manual", Online Available at:—https://web.archive.org/web/20180127170640/https://static.garmin.com/pumac/fenix5x_OM_EN.pdf, Jan. 27, 2018, 42 pages.
"Graphs and Charts", Online available at: <https://www.teachervision.com/lesson-planning/graph-chart-teacher-resources, retrieved on Dec. 12, 2018, 4 pages.
Helm, Josh, "Microsoft® Windows Media™ Player Version 7—New features and Walk-through", 2000, 20 pages.
Hinckley et al., "Sensing Techniques for Mobile Interaction", Symposium on User Interface Software and Technology, CHI Letters, vol. 2, No. 2, 2000, pp. 91-100.
Intention to Grant received for Danish Patent Application No. PA201570668, dated Mar. 27, 2017, 2 pages.
Intention to Grant received for Danish Patent Application No. PA201870379, dated May 2, 2019, 2 pages.
Intention to Grant received for European Patent Application No. 09756118.7, dated Mar. 2, 2017, 8 pages.
Intention to Grant received for European Patent Application No. 10172417.7, dated Jul. 9, 2013, 10 pages.
Intention to Grant received for European Patent Application No. 11178257.9, dated Jan. 30, 2013, 9 pages.
Intention to Grant received for European Patent Application No. 11178259.5, dated Nov. 8, 2018, 16 pages.
Intention to Grant received for European Patent Application No. 17180535.1, dated Sep. 24, 2020, 7 pages.
Intention to Grant received for the European Patent Application No. 07814633.9, dated Mar. 19, 2010, 4 pages.
International Preliminary Examination Report on Patentability received for PCT Patent Application No. PCT/US2002/000484, dated Aug. 4, 2003, 7 pages.
International Preliminary Report on Patentability received for PCT Application No. PCT/US2016/037686, dated Mar. 1, 2018, 12 pages.
International Preliminary Report on Patentability received for PCT Patent Application No. PCT/US2007/077441, dated Mar. 10, 2009, 9 pages.
International Preliminary Report on Patentability received for PCT Patent Application No. PCT/US2009/057899, dated Apr. 5, 2012, 14 pages.
International Preliminary Report on Patentability received for PCT Patent Application No. PCT/US2013/073195, dated Jun. 16, 2016, 10 pages.
International Preliminary Report on Patentability received for PCT Patent Application No. PCT/US2015/047282, dated Mar. 16, 2017, 26 pages.
International Preliminary Report on Patentability received for PCT Patent Application No. PCT/US2017/035554, dated Dec. 20, 2018, 39 pages.

(56) References Cited

OTHER PUBLICATIONS

International Preliminary Report on Patentability received for PCT Patent Application No. PCT/US2018/031662, dated Nov. 28, 2019, 12 pages.
International Search Report and Written Opinion received for PCT Patent Application No. PCT/US2002/000484, dated Jul. 11, 2002, 1 page.
International Search Report and Written Opinion received for PCT Patent Application No. PCT/US2009/057899, dated Jun. 14, 2010, 19 pages.
International Search Report and Written Opinion received for PCT Patent Application No. PCT/US2015/047282, dated May 9, 2016, 33 pages.
International Search Report and Written Opinion received for PCT Patent Application No. PCT/US2016/037686, dated Sep. 9, 2016, 19 pages.
International Search Report and Written Opinion received for PCT Patent Application No. PCT/US2017/035554, dated Sep. 22, 2017, 42 pages.
International Search Report and Written Opinion received for PCT Patent Application No. PCT/US2018/031662, dated Sep. 27, 2018, 17 pages.
International Search Report and Written Opinion received for PCT Patent Application No. PCT/US2019/024570, dated Aug. 8, 2019, 18 pages.
International Search Report and Written Opinion received for PCT Patent Application No. PCT/US2020/025997, dated Jul. 1, 2020, 16 pages.
International Search Report and Written Opinion received for PCT Patent Application No. PCT/US2020/025997, dated Jul. 14, 2020, 15 pages.
International Search Report and Written Opinion received for PCT Patent Application No. PCT/US2007/077441, dated May 8, 2008, 13 pages.
International Search Report received for PCT Patent Application No. PCT/US2013/073195, dated Jun. 23, 2014, 3 pages.
International Written Opinion received for PCT Patent Application No. PCT/US2013/073195, dated Jun. 23, 2014, 8 pages.
Invitation to Pay Addition Fees and Partial International Search Report received for PCT Patent Application No. PCT/US2018/031662, dated Jul. 16, 2018, 13 pages.
Invitation to Pay Additional Fees received for PCT Patent Application No. PCT/US2007/077441, dated Jan. 28, 2008, 5 pages.
Invitation to Pay Additional Fees received for PCT Patent Application No. PCT/US2015/047282, dated Dec. 22, 2015, 7 pages.
Invitation to Pay Additional Fees received for PCT Patent Application No. PCT/US2017/035554, dated Jul. 20, 2017, 2 pages.
Jenbsjourney, "Wondering About a Fitbit?", Available at: https://jenbsjourney.blogspot.kr/2013/08/wondering-about-fitbit.html, Aug. 6, 2013, 12 pages.
Jobs, Steve, "iPhone Introduction in 2007 (Complete)", Available at <https://www.youtube.com/watch?v=9hUIxyE2Ns8>, Jan. 10, 2013, 3 pages.
Karlson et al., "AppLens and LaunchTile: Two Designs for One-Handed Thumb Use on Small Devices", CHI 2005, Papers: Small Devices 1, Apr. 2-7, 2005, pp. 201-210.
Kyocera WX300K, "Way to Use a Camera", JP, Nov. 18, 2005, pp. 206-212. (Official Copy Only) (See Communication under 37 CFR § 1.98(a) (3)).
"Microsoft Support Webcasts", Windows Media Player 7: New features and Walk-through Transcript, Jul. 13, 2000, 7 pages.
Microsoft Windows,"Microsoft Windows (Copyright 2009)", 2 pages.
Minutes of Oral Proceedings received for European Patent Application No. 11178259.5, mailed on Nov. 2, 2018, 9 pages.
Minutes of Oral Proceedings received for European Patent Application No. 13811085.3, mailed on Sep. 11, 2018, 3 pages.
Minutes of Oral Proceedings received for European Patent Application No. 15771747.1, mailed on Aug. 10, 2018, 11 pages.
Mugs, Online Available at: https://web.archive.org/web/20151029034349/http://le-mugs.com/, Oct. 29, 2015, 14 pages.
"Multi-Set Bar Chart", The Data Visualization Catalogue, Available Online at: https://datavizcatalogue.com/methods/multiset_barchart.html, Feb. 8, 2014, 3 pages.
"My CalStep", http://www.surprisesoftware.com/mycalstep/, retrieved from the Wayback Machine, May 9, 2007, 2 pages.
Non-Final Office Action received for U.S. Appl. No. 09/757,000, dated Jan. 30, 2003, 11 pages.
Non-Final Office Action received for U.S. Appl. No. 09/757,000, dated Jun. 19, 2003, 11 pages.
Non-Final Office Action received for U.S. Appl. No. 10/497,076, dated Jan. 8, 2009, 29 pages.
Non-Final Office Action received for U.S. Appl. No. 10/497,076, dated May 13, 2010, 24 pages.
Non-Final Office Action received for U.S. Appl. No. 10/497,076, dated Oct. 3, 2012, 24 pages.
Non-Final Office Action received for U.S. Appl. No. 10/497,076, dated Oct. 13, 2011, 24 pages.
Non-Final Office Action received for U.S. Appl. No. 10/497,076, dated Sep. 13, 2007, 19 pages.
Non-Final Office Action received for U.S. Appl. No. 11/848,210, dated Jun. 30, 2011, 8 pages.
Non-Final Office Action received for U.S. Appl. No. 12/205,847, dated Oct. 3, 2011, 59 pages.
Non-Final Office Action received for U.S. Appl. No. 12/566,994, dated Dec. 13, 2013, 10 pages.
Non-Final Office Action received for U.S. Appl. No. 12/566,994, dated Jan. 9, 2013, 15 pages.
Non-Final Office Action received for U.S. Appl. No. 12/566,994, dated Jun. 13, 2014, 12 pages.
Non-Final Office Action received for U.S. Appl. No. 12/567,405, dated Jan. 16, 2014, 19 pages.
Non-Final Office Action received for U.S. Appl. No. 12/567,405, dated May 17, 2012, 14 pages.
Non-Final Office Action received for U.S. Appl. No. 12/567,460, dated Aug. 4, 2011, 13 pages.
Non-Final Office Action received for U.S. Appl. No. 12/567,553, dated Sep. 16, 2011, 11 pages.
Non-Final Office Action received for U.S. Appl. No. 12/849,767, dated Jul. 9, 2012, 16 pages.
Non-Final Office Action received for U.S. Appl. No. 13/361,912, dated Mar. 22, 2012, 8 pages.
Non-Final Office Action received for U.S. Appl. No. 13/909,001, dated Sep. 26, 2013, 7 pages.
Non-Final Office Action received for U.S. Appl. No. 13/909,002, dated Jun. 23, 2015, 6 pages.
Non-Final Office Action received for U.S. Appl. No. 14/732,773, dated Feb. 8, 2019, 32 pages.
Non-Final Office Action received for U.S. Appl. No. 14/732,773, dated Jan. 19, 2018, 45 pages.
Non-Final Office Action received for U.S. Appl. No. 14/839,916, dated Feb. 4, 2016, 19 pages.
Non-Final Office Action received for U.S. Appl. No. 14/839,916, dated May 1, 2017, 18 pages.
Non-Final Office Action received for U.S. Appl. No. 14/839,922, dated Aug. 17, 2016, 25 pages.
Non-Final Office Action received for U.S. Appl. No. 14/839,922, dated Feb. 25, 2016, 20 pages.
Non-Final Office Action received for U.S. Appl. No. 15/088,450, dated Jul. 23, 2018, 12 pages.
Non-Final Office Action received for U.S. Appl. No. 15/183,663, dated Jul. 9, 2018, 13 pages.
Non-Final Office Action received for U.S. Appl. No. 15/281,524, dated Jun. 19, 2018, 23 pages.
Non-Final Office Action received for U.S. Appl. No. 15/600,243, dated Jun. 27, 2019, 17 pages.
Non-Final Office Action received for U.S. Appl. No. 15/608,848, dated Feb. 6, 2020, 12 pages.
Non-Final Office Action received for U.S. Appl. No. 15/608,848, dated Nov. 2, 2018, 21 pages.
Non-Final Office Action received for U.S. Appl. No. 15/627,069, dated Jun. 21, 2019, 22 pages.

(56) References Cited

OTHER PUBLICATIONS

Non-Final Office Action received for U.S. Appl. No. 15/627,069, dated May 26, 2020, 25 pages.
Non-Final Office Action received for U.S. Appl. No. 15/705,849, dated Nov. 12, 2019, 15 pages.
Non-Final Office Action received for U.S. Appl. No. 15/925,652, dated Apr. 5, 2019, 28 pages.
Non-Final Office Action received for U.S. Appl. No. 15/925,652, dated Aug. 7, 2020, 39 pages.
Non-Final Office Action received for U.S. Appl. No. 16/138,809, dated Feb. 28, 2020, 22 pages.
Non-Final Office Action received for U.S. Appl. No. 16/144,735, dated Feb. 19, 2020, 10 pages.
Non-Final Office Action received for U.S. Appl. No. 16/144,753, dated Mar. 5, 2020, 9 pages.
Non-Final Office Action received for U.S. Appl. No. 16/144,849, dated Dec. 31, 2018, 28 pages.
Non-Final Office Action received for U.S. Appl. No. 16/144,849, dated Sep. 17, 2019, 9 pages.
Non-Final Office Action received for U.S. Appl. No. 16/144,864, dated Dec. 18, 2018, 19 pages.
Non-Final Office Action received for U.S. Appl. No. 16/144,864, dated Jan. 31, 2020, 29 pages.
Non-Final Office Action received for U.S. Appl. No. 16/377,892, dated May 21, 2020, 9 pages.
Non-Final Office Action received for U.S. Appl. No. 16/378,136, dated Jun. 2, 2020, 8 pages.
Non-Final Office Action received for U.S. Appl. No. 16/418,786, dated Apr. 24, 2020, 16 pages.
Non-Final Office Action received for U.S. Appl. No. 16/450,531, dated Jun. 10, 2020, 10 pages.
Non-Final Office Action received for U.S. Appl. No. 13/666,943, dated Oct. 26, 2015, 12 pages.
Notice of Acceptance received for Australian Patent Application No. 2011265412, dated Nov. 12, 2014, 2 pages.
Notice of Acceptance received for Australian Patent Application No. 2015201028, dated Mar. 21, 2017, 3 pages.
Notice of Acceptance received for Australian Patent Application No. 2015312215, dated Oct. 9, 2017, 3 pages.
Notice of Acceptance received for Australian Patent Application No. 2017201548, dated Sep. 3, 2018, 3 pages.
Notice of Acceptance received for Australian Patent Application No. 2018214074, dated Aug. 6, 2019, 3 pages.
Notice of Acceptance received for Australian Patent Application No. 2019201583, dated Jul. 15, 2019, 3 pages.
Notice of Acceptance received for Australian Patent Application No. 2019222943, dated May 5, 2020, 3 pages.
Notice of Acceptance received for Australian Patent Application No. 2020204153, dated Jul. 6, 2020, 3 pages.
Notice of Allowance received for Canadian Patent Application No. 2,935,875, dated May 3, 2017, 1 page.
Notice of Allowance received for Canadian Patent Application No. 2,984,527, dated Apr. 30, 2020, 1 page.
Notice of Allowance received for Chinese Patent Application No. 201580037927.5, dated Oct. 17, 2019, 3 pages (1 page of English Translation and 2 pages of Official Copy).
Notice of Allowance received for Chinese Patent Application No. 201810105846.X, dated Feb. 18, 2020, 2 pages (1 page of English Translation and 1 page of Official Copy).
Notice of Allowance received for Danish Patent Application No. PA201570666, dated Sep. 15, 2016, 1 page.
Notice of Allowance received for Danish Patent Application No. PA201570668, dated Oct. 30, 2017, 2 pages.
Notice of Allowance received for Japanese Patent Application No. 2013-140171, dated May 29, 2015, 4 pages (Official Copy only) (See Communication under 37 CFR § 1.98(a) (3)).
Notice of Allowance received for Japanese Patent Application No. 2014-259225, dated Feb. 27, 2017, 3 pages. (Official Copy Only) (See Communication under 37 CFR § 1.98(a) (3)).
Notice of Allowance received for Japanese Patent Application No. 2015-129152, dated May 8, 2017, 3 pages (Official Copy only) (See Communication under 37 CFR § 1.98(a) (3)).
Notice of Allowance received for Japanese Patent Application No. 2016-535045, dated Mar. 2, 2018, 4 pages (1 page of English Translation and 3 pages of Official Copy).
Notice of Allowance received for Japanese Patent Application No. 2016-557650, dated Apr. 9, 2019, 4 pages (1 page of English Translation and 3 pages of Official Copy).
Notice of Allowance received for Japanese Patent Application No. 2017-057997, dated Apr. 23, 2018, 4 pages (1 page of English Translation and 3 pages of Official Copy).
Notice of Allowance received for Japanese Patent Application No. 2017-132229, dated Jun. 25, 2018, 4 pages (1 page of English Translation and 3 pages of Official Copy).
Notice of Allowance received for Japanese Patent Application No. 2018-068846, dated Dec. 9, 2019, 4 pages (1 page of English Translation and 3 pages of Official Copy).
Notice of Allowance received for Korean Patent Application No. 10-2016-7014577, dated May 30, 2019, 5 pages (2 pages of English Translation and 3 pages of Official Copy).
Notice of Allowance received for Korean Patent Application No. 10-2016-7033638, dated May 31, 2017, 5 pages (2 pages of English Translation and 3 pages of Official Copy).
Notice of Allowance received for Taiwanese Patent Application No. 104128685, dated May 3, 2017, 3 pages (Official Copy Only) (See Communication under 37 CFR § 1.98(a) (3)).
Notice of Allowance received for the Canadian Patent Application No. 2,853,273, dated Jan. 12, 2016, 1 page.
Notice of Allowance received for U.S. Appl. No. 09/757,000, dated Dec. 15, 2003, 4 pages.
Notice of Allowance received for U.S. Appl. No. 11/848,210, dated Dec. 20, 2011, 5 pages.
Notice of Allowance received for U.S. Appl. No. 12/205,847, dated Aug. 20, 2012, 13 pages.
Notice of Allowance received for U.S. Appl. No. 12/566,994, dated May 22, 2013, 9 pages.
Notice of Allowance received for U.S. Appl. No. 12/566,994, dated Oct. 6, 2014, 8 pages.
Notice of Allowance received for U.S. Appl. No. 12/567,405, dated Jun. 11, 2014, 9 pages.
Notice of Allowance received for U.S. Appl. No. 12/567,460, dated Apr. 10, 2013, 9 pages.
Notice of Allowance received for U.S. Appl. No. 12/567,460, dated Aug. 10, 2012, 8 pages.
Notice of Allowance received for U.S. Appl. No. 12/567,460, dated Dec. 24, 2012, 8 pages.
Notice of Allowance received for U.S. Appl. No. 12/567,460, dated Jan. 18, 2012, 8 pages.
Notice of Allowance received for U.S. Appl. No. 12/567,553, dated Apr. 2, 2013, 9 pages.
Notice of Allowance received for U.S. Appl. No. 12/567,553, dated Aug. 10, 2012, 8 pages.
Notice of Allowance received for U.S. Appl. No. 12/567,553, dated Dec. 24, 2012, 8 pages.
Notice of Allowance received for U.S. Appl. No. 12/567,553, dated Jun. 12, 2012, 8 pages.
Notice of Allowance received for U.S. Appl. No. 12/567,570, dated Dec. 19, 2012, 7 pages.
Notice of Allowance received for U.S. Appl. No. 12/567,570, dated Mar. 27, 2013, 8 pages.
Notice of Allowance received for U.S. Appl. No. 12/849,767, dated Apr. 25, 2014, 5 pages.
Notice of Allowance received for U.S. Appl. No. 12/849,767, dated Jan. 8, 2013, 9 pages.
Notice of Allowance received for U.S. Appl. No. 13/361,912, dated Jul. 2, 2012, 7 pages.
Notice of Allowance received for U.S. Appl. No. 13/666,943, dated Jun. 2, 2016, 9 pages.
Notice of Allowance received for U.S. Appl. No. 13/666,943, dated Jun. 17, 2015, 7 pages.
Notice of Allowance received for U.S. Appl. No. 13/909,001, dated Mar. 3, 2014, 7 pages.

(56) References Cited

OTHER PUBLICATIONS

Notice of Allowance received for U.S. Appl. No. 13/909,002, dated Dec. 4, 2015, 7 pages.
Notice of Allowance received for U.S. Appl. No. 14/732,773, dated Dec. 18, 2019, 21 pages.
Notice of Allowance received for U.S. Appl. No. 14/839,916, dated Aug. 31, 2016, 11 pages.
Notice of Allowance received for U.S. Appl. No. 14/839,916, dated Jan. 10, 2018, 19 pages.
Notice of Allowance received for U.S. Appl. No. 14/839,922, dated Jan. 26, 2018, 2 pages.
Notice of Allowance received for U.S. Appl. No. 14/839,922, dated Jul. 6, 2017, 8 pages.
Notice of Allowance received for U.S. Appl. No. 14/839,922, dated Nov. 2, 2017, 8 pages.
Notice of Allowance received for U.S. Appl. No. 15/088,450, dated Dec. 13, 2018, 7 pages.
Notice of Allowance received for U.S. Appl. No. 15/183,663, dated Jan. 17, 2019, 6 pages.
Notice of Allowance received for U.S. Appl. No. 15/281,524, dated Apr. 11, 2019, 7 pages.
Notice of Allowance received for U.S. Appl. No. 15/600,243, dated Dec. 12, 2019, 7 pages.
Notice of Allowance received for U.S. Appl. No. 15/616,480, dated Jan. 3, 2019, 8 pages.
Notice of Allowance received for U.S. Appl. No. 15/705,849, dated Jul. 28, 2020, 10 pages.
Notice of Allowance received for U.S. Appl. No. 16/144,671, dated Feb. 10, 2020, 17 pages.
Notice of Allowance received for U.S. Appl. No. 16/144,735, dated Jul. 21, 2020, 13 pages.
Notice of Allowance received for U.S. Appl. No. 16/144,849, dated Apr. 17, 2020, 2 pages.
Notice of Allowance received for U.S. Appl. No. 16/144,849, dated Mar. 6, 2020, 9 pages.
Notice of Allowance received for U.S. Appl. No. 16/144,864, dated Jul. 28, 2020, 27 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.
Notice of Allowance received for U.S. Appl. No. 16/144,864, dated Sep. 29, 2020, 2 pages.
Notice of Allowance received for U.S. Appl. No. 16/403,184, dated Oct. 11, 2019, 9 pages.
Notice of Allowance received for U.S. Appl. No. 16/450,531 dated Sep. 25, 2020, 7 pages.
Notice of Allowance received for U.S. Appl. No. 16/588,950, dated Feb. 10, 2020, 9 pages.
Notice of Allowance received for U.S. Appl. No. 16/588,950, dated May 5, 2020, 9 pages.
Notice of Allowance received for U.S. Appl. No. 16/791,257, dated Jun. 12, 2020, 11 pages.
Office Action received for Australian Patent Application No. 2015201028, dated Mar. 15, 2016, 2 pages.
Office Action received for Australian Patent Application No. 2015312215, dated Oct. 13, 2016, 3 pages.
Office Action received for Australian Patent Application No. 2017100667, dated Aug. 3, 2017, 9 pages.
Office Action received for Australian Patent Application No. 2017201548, dated Feb. 26, 2018, 2 pages.
Office Action received for Australian Patent Application No. 2017277971, dated Aug. 12, 2020, 3 pages.
Office Action received for Australian Patent Application No. 2017277971, dated Jun. 3, 2020, 3 pages.
Office Action received for Australian Patent Application No. 2018100158, dated Apr. 23, 2018, 5 pages.
Office Action received for Australian Patent Application No. 2018101855, dated Feb. 22, 2019, 4 pages.
Office Action received for Australian Patent Application No. 2018200428, dated Mar. 7, 2018, 4 pages.
Office Action received for Australian Patent Application No. 2018200428, dated Nov. 15, 2018, 4 pages.
Office Action received for Australian Patent Application No. 2018214074, dated May 9, 2019, 2 pages.
Office Action received for Australian Patent Application No. 2018268972, dated Jul. 9, 2020, 4 pages.
Office Action received for Australian Patent Application No. 2019100495, dated Mar. 6, 2020, 3 pages.
Office Action received for Australian Patent Application No. 2019100495, dated Mar. 16, 2020, 3 pages.
Office Action received for Australian Patent Application No. 2019100495, dated Sep. 17, 2019, 7 pages.
Office Action received for Australian Patent Application No. 2019222943, dated Oct. 3, 2019, 3 pages.
Office Action received for Australian Patent Application No. 2019250251, dated Aug. 6, 2020, 3 pages.
Office Action received for Australian Patent Application No. 2019264623, dated Sep. 14, 2020, 3 pages.
Office Action received for Canadian Patent Application No. 2,853,273, dated Feb. 23, 2015, 5 pages.
Office Action received for Canadian Patent Application No. 2,984,527 dated Sep. 11, 2018, 5 pages.
Office Action received for Canadian Patent Application No. 2,984,527, dated Jul. 25, 2019, 4 pages.
Office Action received for Chinese Patent Application No. 201380081349.6, dated Feb. 26, 2019, 12 pages (6 pages of English Translation and 6 pages of Official Copy).
Office Action received for Chinese Patent Application No. 201380081349.6, dated Jan. 16, 2020, 11 pages (6 pages of English Translation and 5 pages of Official Copy).
Office Action received for Chinese Patent Application No. 201380081349.6, dated Jul. 15, 2019, 10 pages (5 pages of English Translation and 5 pages of Official Copy).
Office Action received for Chinese Patent Application No. 201380081349.6, dated Jul. 15. 2020, 9 pages (4 pages of English Translation and 5 pages of Official Copy).
Office Action received for Chinese Patent Application No. 201580037927.5, dated Apr. 22, 2019, 9 pages (4 pages of English Translation and 5 pages of Official Copy).
Office Action received for Chinese Patent Application No. 201580037927.5, dated Jul. 20, 2018, 21 pages (6 pages of English Translation and 15 pages of Official Copy).
Office Action received for Chinese Patent Application No. 20.1680047983.1, dated Jul. 1, 2020, 6 pages (3 pages of English Translation and 3 pages of Official Copy).
Office Action received for Chinese Patent Application No. 201680047983.1, dated Mar. 18, 2019, 18 pages (6 pages of English Translation and 12 pages of Official Copy).
Office Action received for Chinese Patent Application No. 201680047983.1, dated Nov. 28, 2019, 9 pages (4 pages of English Translation and 5 pages of Official Copy).
Office Action received for Chinese Patent Application No. 201710439448.7, dated Mar. 27, 2020, 13 pages (7 pages of English Translation and 6 pages of Official Copy).
Office Action received for Chinese Patent Application No. 201810105846.X, dated Aug. 27, 2019, 12 pages (5 pages of English Translation and 7 pages of Official Copy).
Office Action received for Chinese Patent Application No. 201810105846.X, dated Feb. 25, 2019, 10 pages (5 pages of English Translation and 5 pages of Official Copy).
Office Action received for Chinese Patent Application No. 201810105846.X, dated Nov. 28, 2019, 9 pages (5 pages of English Translation and 4 pages of Official Copy).
Office Action received for Chinese Patent Application No. 201910858933.7, dated Aug. 18, 2020, 14 pages (7 pages of English Translation and 7 pages of Official Copy).
Office Action received for Danish Patent Application No. PA201570666, dated Feb. 2, 2016, 9 pages.
Office Action received for Danish Patent Application No. PA201570666, dated Jun. 27, 2016, 4 pages.

(56) References Cited

OTHER PUBLICATIONS

Office Action received for Danish Patent Application No. PA201570668, dated Apr. 8, 2016, 8 pages.
Office Action received for Danish Patent Application No. PA201570668, dated Sep. 9, 2016, 3 pages.
Office Action received for Danish Patent Application No. PA201670656, dated Jul. 1, 2020, 4 pages.
Office Action received for Danish Patent Application No. PA201670656, dated Jun. 14, 2017, 3 pages.
Office Action received for Danish Patent Application No. PA201670656, dated May 2, 2019, 4 pages.
Office Action received for Danish Patent Application No. PA201670656, dated May 30, 2018, 5 pages.
Office Action received for Danish Patent Application No. PA201670656, dated Nov. 3, 2016, 8 pages.
Office Action received for Danish Patent Application No. PA201770191, dated Jan. 25, 2018, 3 pages.
Office Action received for Danish Patent Application No. PA201770191, dated Nov. 21, 2018, 4 pages.
Office Action received for Danish Patent Application No. PA201770191, dated Oct. 25, 2019, 4 pages.
Office Action received for Danish Patent Application No. PA201770423, dated Jun. 12, 2018, 7 pages.
Office Action received for Danish Patent Application No. PA201770423, dated Mar. 29, 2019, 6 pages.
Office Action received for Danish Patent Application No. PA201870378, dated Feb. 25, 2019, 3 pages.
Office Action received for Danish Patent Application No. PA201870378, dated Jan. 6, 2020, 3 pages.
Office Action received for Danish Patent Application No. PA201870379, dated Feb. 28, 2019, 3 pages.
Office Action received for Danish Patent Application No. PA201870380, dated Mar. 5, 2020, 2 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Office Action received for Danish Patent Application No. PA201970532, dated May 29, 2020, 3 pages.
Office Action received for European Patent Application No. 02713375.0, dated Feb. 27, 2009, 5 pages.
Office Action received for European Patent Application No. 07814633.9. dated Aug. 10, 2009, 3 pages.
Office Action received for European Patent Application No. 09756118.7, dated Feb. 13, 2013, 5 pages.
Office Action received for European Patent Application No. 09756118.7, dated Mar. 7, 2014, 7 pages.
Office Action received for European Patent Application No. 09756118.7, dated Oct. 8, 2015, 6 pages.
Office Action received for European Patent Application No. 10172417.7, dated Oct. 31, 2011, 6 pages.
Office Action received for European Patent Application No. 11178259.5, dated Jan. 4, 2013, 8 pages.
Office Action received for European Patent Application No. 11178259.5, dated Nov. 10, 2015, 4 pages.
Office Action received for European Patent Application No. 13811085.3, dated Apr. 20, 2018, 15 pages.
Office Action received for European Patent Application No. 16837432.0, dated Jan. 10, 2020, 7 pages.
Office Action received for European Patent Application No. 17180535.1, dated Oct. 8, 2018, 6 pages.
Office Action received for European Patent Application No. 17180535.1, dated Oct. 14, 2019, 8 pages.
Office Action received for European Patent Application No. 17810749.6, dated Aug. 20, 2019, 9 pages.
Office Action received for European Patent Application No. 18154145.9, dated Apr. 3, 2018, 6 pages.
Office Action received for European Patent Application No. 18197554.1, dated Jun. 15, 2020, 4 pages.
Office Action received for European Patent Application No. 19721883.7, dated Jan. 10, 2020, 4 pages.
Office Action received for European Patent Application No. 19721883.7, dated May 28, 2020, 11 pages.
Office Action received for European Patent Application No. 02713375.0, dated Feb. 24, 2010, 4 pages.
Office Action received for European Patent Application No. 02713375.0, dated Feb. 24, 2014, 5 pages.
Office Action received for European Patent Application No. 15771747.1, dated Oct. 31, 2017, 7 pages.
Office Action received for German Patent Application No. 112015002326.7, dated Feb. 20, 2019, 7 pages (2 pages of English Translation and 5 pages of Official Copy).
Office Action received for Indian Patent Application No. 9044/CHENP/2014, dated Jan. 24, 2020, 6 pages.
Office action received for Indian Patent Application No. 2797/CHEN/P2008, dated Jan. 29, 2014, 3 pages.
Office Action received for Japanese Patent Application No. 2013-140171, dated Jul. 22, 2014, 4 pages (2 pages of English Translation and 2 pages of Official copy).
Office Action received for Japanese Patent Application No. 2014-259225, dated May 27, 2016, 4 pages (2 pages of English Translation and 2 pages of Official Copy).
Office Action received for Japanese Patent Application No. 2014-259225, dated Nov. 20, 2015, 2 pages (Official Copy Only) (See Communication under 37 CFR § .1.98(a) (3)).
Office Action received for Japanese Patent Application No. 2015-129152, dated Sep. 23, 2016, 3 pages (1 page of English Translation and 2 pages of Official Copy).
Office Action received for Japanese Patent Application No. 2016-535045, dated May 12, 2017, 10 pages (5 pages of English Translation and 5 pages of Official Copy).
Office Action received for Japanese Patent Application No. 2016-557650, dated Apr. 13, 2018, 9 pages (5 pages of English Translation and 4 pages of Official Copy).
Office Action received for Japanese Patent Application No. 2016-557650, dated Aug. 10, 2017, 10 pages (5 pages of English Translation and 5 pages of Official Copy).
Office Action received for Japanese Patent Application No. 2016-557650, dated Nov. 9, 2018, 6 pages (3 pages of English Translation and 3 pages of Official Copy).
Office Action received for Japanese Patent Application No. 2017-057997, dated Jan. 9, 2018, 6 pages (3 pages of English Translation and 3 pages of official Copy).
Office Action received for Japanese Patent Application No. 2017-132229, dated Mar. 16, 2018, 7 pages (3 pages of English Translation and 4 pages of Official Copy).
Office Action received for Japanese Patent Application No. 2018-014096, dated Aug. 28, 2020, 4 pages (2 pages of English Translation and 2 pages of Official Copy).
Office Action received for Japanese Patent Application No. 2018-014096, dated Jan. 6, 2020, 17 pages (8 pages of English Translation and 9 pages of Official-Copy).
Office Action received for Japanese Patent Application No. 2018-014096, dated Jun. 29, 2018, 20 pages (11 pages of English Translation and 9 pages of Official Copy).
Office Action received for Japanese Patent Application No. 2018-014096, dated May 8, 2019, 14 pages (7 pages of English,Translation and 7 pages of Official Copy).
Office Action received for Japanese Patent Application No. 2018-014096, dated Nov. 6, 2018, 15 pages (7 pages of English Translation and 8 pages of Official Copy).
Office Action received for Japanese Patent Application No. 2018-068846, dated Jan. 8, 2019, 6 pages (3 pages of English Translation and 3 pages of Official Copy).
Office Action received for Japanese Patent Application No. 2018-138559, dated Jan. 27, 2020, 7 pages (3 pages of English Translation and 4 pages of Official Copy).
Office Action received for Japanese Patent Application No. 2018-138559, dated May 13, 2019, 10 pages (5 pages of English Translation and 5 pages of Official Copy).

(56) References Cited

OTHER PUBLICATIONS

Office Action received for Japanese Patent Application No. 2019-044107, dated May 29, 2020, 6 pages (3 pages of English Translation and 3 pages of Official Copy).
Office Action received for Japanese Patent Application No. 2019-162293, dated Jan. 31, 2020, 8 pages (4 pages of English Translation and 4 pages of Official Copy).
Office Action received for Japanese Patent Application No. 2019-162293, dated Jul. 27, 2020, 9 pages (5 pages of English Translation and 4 pages of Official Copy).
Office Action received for Korean Patent Application No. 10-2016-7014577, dated Dec. 26, 2017, 14 pages (6 pages of English Translation and 8 pages of Official Copy).
Office Action received for Korean Patent Application No. 10-2016-7014577, dated Oct. 31, 2018, 11 pages (5 pages of English Translation and 6 pages of Official Copy).
Office Action received for Korean Patent Application No. 10-2016-7033638, dated Jan. 31, 2017, 6 pages (2 pages of English Translation and 4 pages of Official Copy).
Office Action received for Korean Patent Application No. 10-2019-7025538, dated Aug. 15, 2020, 8 pages (4 pages of English Translation and 4 pages of Official Copy).
Office Action received for Korean Patent Application No. 10-2019-7025538, dated Feb. 17, 2020, 12 pages (6 pages of English Translation and 6 pages of Official Copy). .
Office Action received for Korean Patent Application No. 10-2019-7025781, dated Nov. 26, 2019, 10 pages (4 pages of English Translation and 6 pages of Official Copy).
Office Action received for Taiwanese Patent Application No. 104128685, dated Jan. 4, 2017, 40 pages (15 pages of English Translation and 25 pages of Official Copy).
Partial European Search Report received for European Patent Application No. 18197554.1, dated Jan. 22, 2019, 8 pages.
Partial Supplementary European Search Report received for European Patent Application No. 17810749.6, dated Apr. 25, 2019, 8 pages.
Person et al., "Using Windows 95" Special Edition, Published by Que Corporation, 2nd Edition, 1997, 5 pages.
Razykdreviews, "In Depth Review of Apple Watch Activity and Workout App", Available at: https://www.youtube.com/watch?v=GkKI3qIKOow>, May 11, 2015, 1 page.
Redmond, Wash, "Worldwide Popularity of Microsoft Windows Media Player 7", Microsoft PressPass, Aug. 2, 2000, 1 page.
Redmond, Wash, "Microsoft Unveils Windows Media Player 7", Microsoft Press Pass, Mar. 27, 2000, 4 pages.
Result of Consultation received for European Patent Application No. 18154145.9, dated Sep. 4, 2020, 3 pages.
Result of Consultation received for European Patent Application No. 19721883.7, dated Oct. 7, 2020, 3 pages.
Rizknows, "Garmin Connect Mobile App—REVIEW #2", Online available at: https://www.youtube.com/watch?v=7my3wMpeRbE, Oct. 22, 2015, 1 page.
Rizknows, "TomTom Multisport Cardio Review", Online available at :—https://www.youtube.com/watch?v=WoVCzLrSN9A, Sep. 4, 2015, 1 page.
Search report and opinion received for Danish Patent Application No. PA201770191, dated Jun. 30, 2017, 9 pages.
Search Report and Opinion received for Danish Patent Application No. PA201770423, dated Oct. 4, 2017, 10 pages.
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
Search Report and Opinion received for Danish Patent Application No. PA201970532, dated Nov. 8, 2019, 9 pages.
Skiljan Irfan, "IrfanView Help", Irfan View Screen Dumps, 1996-1999, 3 pages.
Smith, "Garmin Fenix 5 Activity/Smart Watch Review", Online Available at:—https://www.youtube.com/watch?v=6PkQxXQxpoU, Sep. 2, 2017, 1 page.
Sportstechguides, "Garmin Fenix 5: How to Add Power Data Fields", Online Available at:—https://www.youtube.com/watch?v=ZkPptnnXEiQ, Apr. 29, 2017, 2 pages.
Sportstechguides, "Garmin Fenix 5: How To Set Up Run Alerts", Online Available at:—https://www.youtube.com/watch?v=gSMwv8vIhB4, May 13, 2017, 2 pages.
Summons to Attend Oral Proceeding received for European Patent Application No. 10172417.7, mailed on Jan. 28, 2013, 6 pages.
Summons to Attend Oral Proceedings received for European Patent Application No. 09756118.7, mailed on Sep. 23, 2016, 8 pages.
Summons to Attend Oral Proceedings received for European Patent Application No. 11178259.5, mailed on Feb. 11, 2015, 9 pages.
Summons to Attend Oral Proceedings received for European Patent Application No. 11178259.5, mailed on Feb. 19, 2018, 12 pages.
Summons to attend oral proceedings received for European Patent Application No. 13811085.3, mailed on Jan. 26, 2018, 14 pages.
Summons to Attend Oral Proceedings received for European Patent Application No. 17810749.6, mailed on Aug. 12, 2020, 11 pages.
Summons to Attend Oral Proceedings received for European Patent Application No. 18154145.9, mailed on Sep. 17, 2020, 11 pages.
Summons to Attend Oral Proceedings received for European Patent Application No. 15771747.1, mailed on May 25, 2018, 17 pages.
Supplemental Notice of Allowance received for U.S. Appl. No. 15/616,480, dated Mar. 28, 2019, 2 pages.
Supplemental Notice of Allowance received for U.S. Appl. No. 16/144,849, dated Mar. 31, 2020, 2 pages.
Supplemental Notice of Allowance received for U.S. Appl. No. 16/403,184, dated Nov. 21, 2019, 3 pages.
Supplemental Notice of Allowance received for U.S. Appl. No. 16/588,950, dated Apr. 1, 2020, 2 pages.
Supplemental Notice of Allowance received for U.S. Appl. No. 16/588,950, dated Jul. 29, 2020, 2 pages.
Supplemental Notice of Allowance received for U.S. Appl. No. 16/588,950, dated Jun. 18, 2020, 2 pages.
Supplemental Notice of Allowance received for U.S. Appl. No. 16/791,257, dated Aug. 31, 2020, 3 pages.
Supplementary European Search Report received for European Patent Application No. 02713375.0, dated Oct. 2, 2009, 3 pages.
Supplementary European Search Report received for European Patent Application No. 17810749.6, dated Aug. 6, 2019, 6 pages.
Supplementary Search Report received for European Patent Application No. 02713375.0, dated Aug. 5, 2005, 3 pages.
"Support WebCast: Windows Media Player 7: New features and Walk-through", Microsoft Knowledge Base Article-324594, Jul. 13, 2000, 2 pages.
"Suunto Spartan Trainer Wrist HR 1.12", Online Available at:—https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Suunto, "Suunto Spartan—Heart Rate Zones", Online Available at :—https://www.youtube.com/watch?v=aixfoCnS0OU, Mar. 19, 2018, 2 pages.
Teunmo, "Data field; Visual Pace Alarm", Garmin Forum; Available online at:https://forums.garmin.com/forum/developers/connect-iq/connect-iq-showcase/115996-data-field-visual-pace-alarm, Nov. 17, 2015, 10 pages.
TomTom, "TomTom Runner & Multi-Sport Reference Guide", Online available at :—https://web.archive.org/web/20150908075934/http://download.tomtom.com/open/manuals/Runner_Multi-Sport/refman/TomTom-Runner-Muiti-Sport-RG-envgb.pdf, Sep. 8, 2015, 44 pages.
"Utilization of Galaxy S4-S Health, ChatOn and Samsung Hub", Available at: http://seeit.kr/1263, Jun. 12, 2013, 25 pages (Official Copy Only) (See Communication under 37 CFR § 1.98(a) (3)).
"Visual Pace Alarm app", Available Online at: https://apps.garmin.com/en-US/apps/3940f3a2-4847-4078-a911-d77422966c82, Oct. 19, 2016, 1 page.
Wesley, "Apple Watch Series 1", Online available at:—http://toolbox.info/blog/archives/1737-unknown.html, May 28, 2015, 5 pages (Official Copy Only) (See Communication under 37 CFR § 1.98(a) (3)).

(56) References Cited

OTHER PUBLICATIONS

Willcom, "Operation Manual for WS003SH", JP, Dec. 2005, 9 pages (Official Copy Only) (See Communication under 37 CFR § 1.98(a) (3)).
"WINAMP from Nullsoft", screen dumps of the media player having visual effect, version 2.62, 1997-2000, 2 pages.
"Windows Media Player", To view a visualization, 2000-2001, 2 pages.
Youtube, "Apple Watch Series 3", Online available at:—https://www.youtube.com/watch?v=iBPr9gEfkK8, Nov. 21, 2017, 15 pages (Official Copy Only) (See Communication under 37 CFR § 1.98(a) (3)).
Zlelik, "Garmin Fenix 5 Open Water Swimming Activity Demo", Online Available at:—https://www.youtube.com/watch?v=iSVhdvw2dcs, Jun. 9, 2017, 1 page.
Office Action received for Danish Patent Application No. PA202070612, dated May 10, 2022, 2 pages.
Office Action received for Danish Patent Application No. PA202070613, dated May 10, 2022, 2 pages.
Corrected Notice of Allowance received for U.S. Appl. No. 17/157,728, dated Apr. 4, 2022, 3 pages.
Non-Final Office Action received for U.S. Appl. No. 17/381,570, dated Apr. 1, 2022, 29 pages.
Notice of Acceptance received for Australian Patent Application No. 2021201130, dated Mar. 28, 2022, 3 pages.
Notice of Allowance received for Japanese Patent Application No. 2020-160054, dated Apr. 4, 2022, 4 pages (1 page of English Translation and 3 pages of Official Copy).
Notice of Allowance received for Korean Patent Application No. 10-2021-7031939, dated Apr. 5, 2022, 4 pages (1 page of English Translation and 3 pages of Official Copy).
Notice of Allowance received for U.S. Appl. No. 17/030,321, dated Apr. 1, 2022, 8 pages.
Office Action received for Australian Patent Application No. 2021203636, dated Mar. 23, 2022, 3 pages.
Supplemental Notice of Allowance received for U.S. Appl. No. 16/894,309, dated Apr. 8, 2022, 3 pages.
Supplemental Notice of Allowance received for U.S. Appl. No. 17/030,318, dated Apr. 4, 2022, 2 pages.
Final Office Action received for U.S. Appl. No. 16/418,786, dated Jan. 13, 2021, 14 pages.
Notice of Acceptance received for Australian Patent Application No. 2018268972, dated Dec. 18, 2020, 3 pages.
Notice of Allowance received for Japanese Patent Application No. 2018-014096, dated Jan. 5, 2021, 3 pages (1 page of English Translation and 2 pages of Official Copy).
Notice of Allowance received for Japanese Patent Application No. 2020-104679, dated Jan. 4, 2021, 4 pages (1 page of English Translation and 3 pages of Official Copy).
Notice of Allowance received for U.S. Appl. No. 16/556,023, dated Jan. 13, 2021, 8 pages.
Search Report and Opinion received for Danish Patent Application No. PA202070614, dated Jan. 14, 2021, 9 pages.
Supplemental Notice of Allowance received for U.S. Appl. No. 15/925,652, dated Jan. 6, 2021, 3 pages.
Applicant Initiated Interview Summary received for U.S. Appl. No. 16/584,776, dated May 13, 2020, 9 pages.
Applicant Initiated Interview Summary received for U.S. Appl. No. 16/584,783, dated May 4, 2020, 3 pages.
Applicant-Initiated Interview Summary received for U.S. Appl. No. 16/584,776, dated Nov. 25, 2020, 5 pages.
Corrected Notice of Allowance received for U.S. Appl. No. 16/450,531, dated Nov. 12, 2020, 2 pages.
Final Office Action received for U.S. Appl. No. 16/584,783, dated May 19, 2020, 19 pages.
International Preliminary Report on Patentability received for PCT Patent Application No. PCT/US2019/024570, dated Nov. 19, 2020, 10 pages.
International Search Report and Written Opinion received for PCT Patent Application No. PCT/US2020/031442, dated Oct. 30, 2020, 28 pages.
Invitation to Pay Additional Fees received for PCT Patent Application No. PCT/US2020/031442, dated Aug. 25, 2020, 22 pages.
Non-Final Office Action received for U.S. Appl. No. 16/584,776, dated Aug. 18, 2020, 36 pages.
Non-Final Office Action received for U.S. Appl. No. 16/584,776, dated Feb. 13, 2020, 31 pages.
Non-Final Office Action received for U.S. Appl. No. 16/584,783, dated Jan. 30, 2020, 18 pages.
Notice of Allowance received for U.S. Appl. No. 15/925,652, dated Nov. 20, 2020, 9 pages.
Office Action received for Chinese Patent Application No. 201710439448.7, dated Oct. 10, 2020, 19 pages (8 pages of English Translation and 11 pages of Official Copy).
Office Action received for Danish Patent Application No. PA201970535, dated May 20, 2020, 3 pages.
Office Action received for Danish Patent Application No. PA201970535, dated Oct. 27, 2020, 6 pages.
Office Action received for European Patent Application No. 20182116.2, dated Nov. 6, 2020, 9 pages.
Search Report and Opinion received for Danish Patent Application No. PA201970535, dated Nov. 5, 2019, 10 pages.
Applicant Initiated Interview Summary received for U.S. Appl. No. 15/608,848, dated Oct. 26, 2020, 3 pages.
Applicant-Initiated Interview Summary received for U.S. Appl. No. 16/377,892, dated Oct. 13, 2020, 5 pages.
Applicant-Initiated Interview Summary received for U.S. Appl. No. 16/378,136, dated Oct. 13, 2020, 4 pages.
European Search Report received for European Patent Application No. 20182116.2, dated Oct. 21, 2020, 4 pages.
Final Office Action received for U.S. Appl. No. 15/627,069, dated Oct. 20, 2020, 25 pages.
Non-Final Office Action received for U.S. Appl. No. 16/894,309, dated Oct. 15, 2020, 24 pages.
Notice of Allowance received for U.S. Appl. No. 15/705,849, dated Oct. 16, 2020, 14 pages.
Notice of Allowance received for U.S. Appl. No. 16/144,735, dated Oct. 28, 2020, 13 pages.
Notice of Allowance received for U.S. Appl. No. 16/556,023, dated Oct. 15, 2020, 8 pages.
Office Action received for Japanese Patent Application No. 2020-104679, dated Sep. 18, 2020, 13 pages (7 pages of English Translation and 6 pages of Official Copy).
Notice of Allowance received for Japanese Patent Application No. 2020-160052, dated Jun. 3, 2022, 4 pages (1 page of English Translation and 3 pages of Official Copy).
Office Action received for Korean Patent Application No. 10-2020-0123815, dated May 31, 2022, 10 pages (5 pages of English Translation and 5 pages of Official Copy).

\* cited by examiner

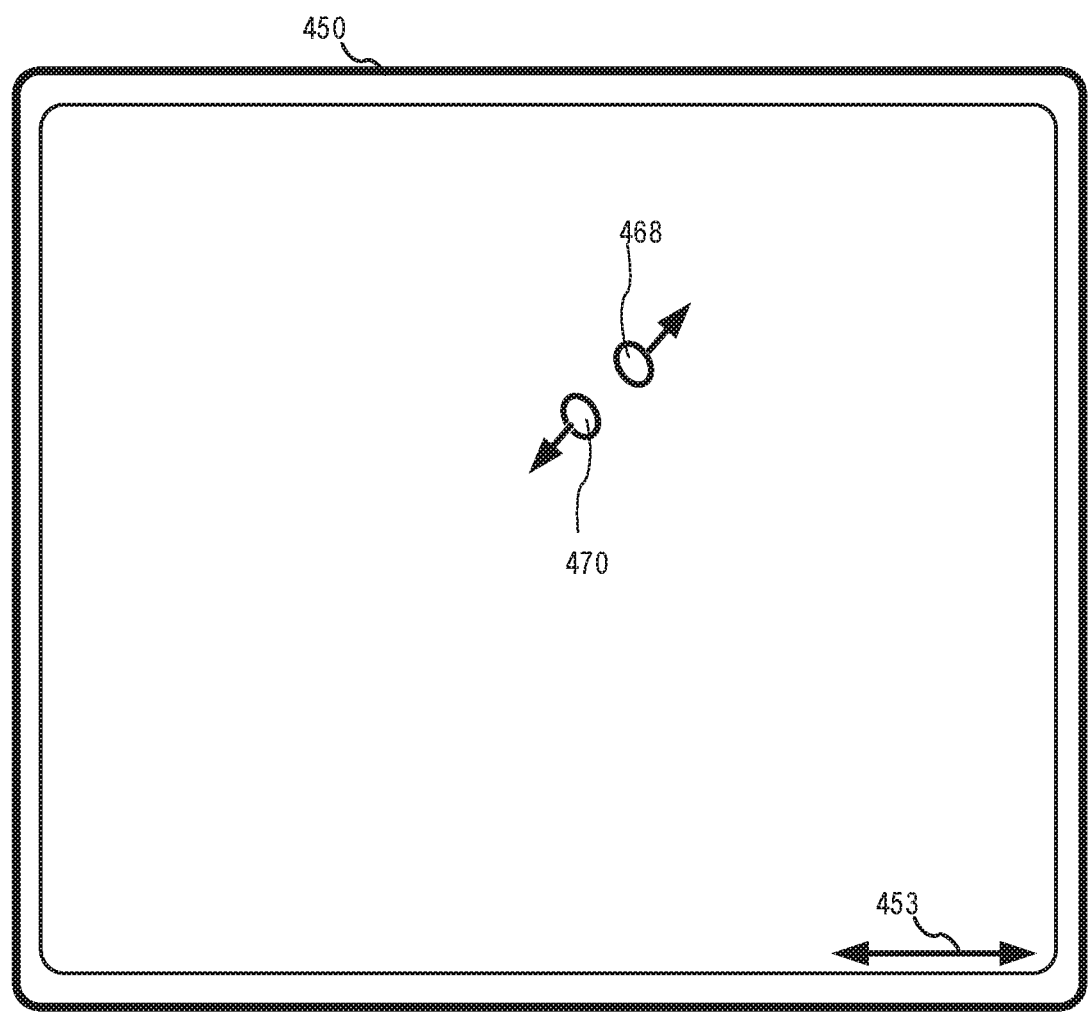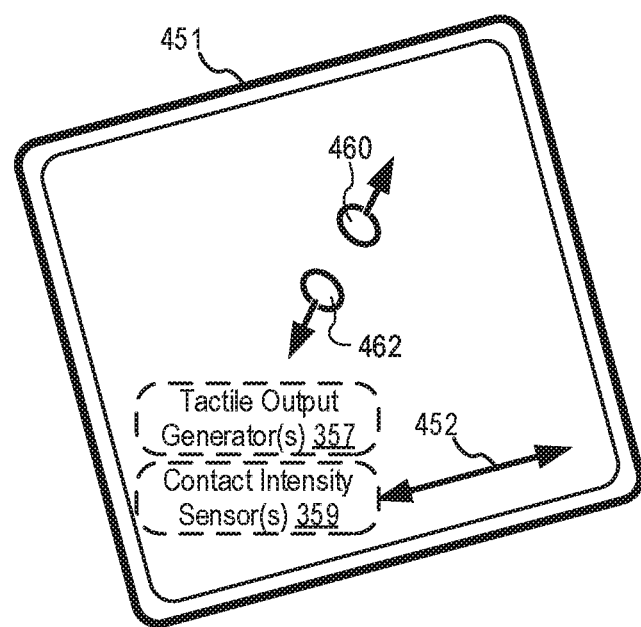
FIG. 4B

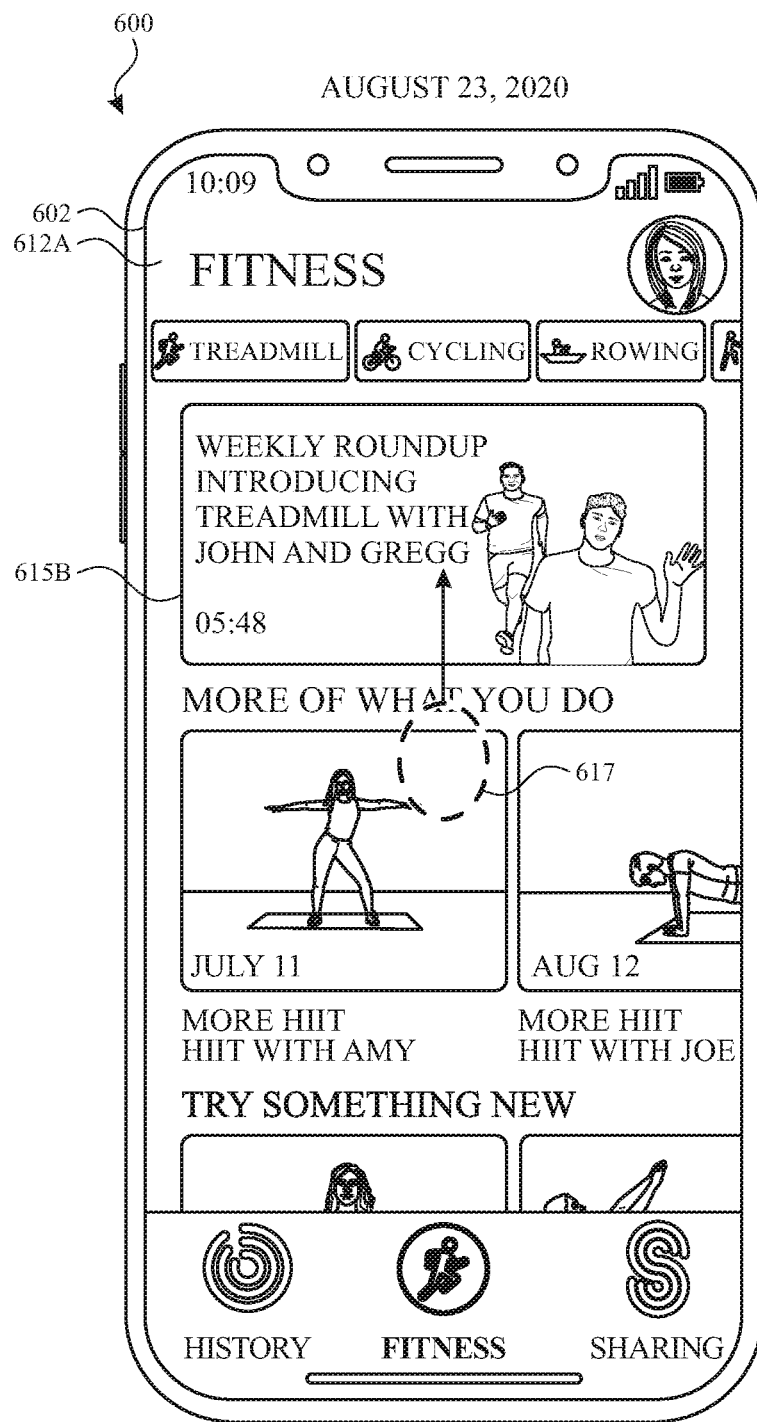
FIG. 6W1

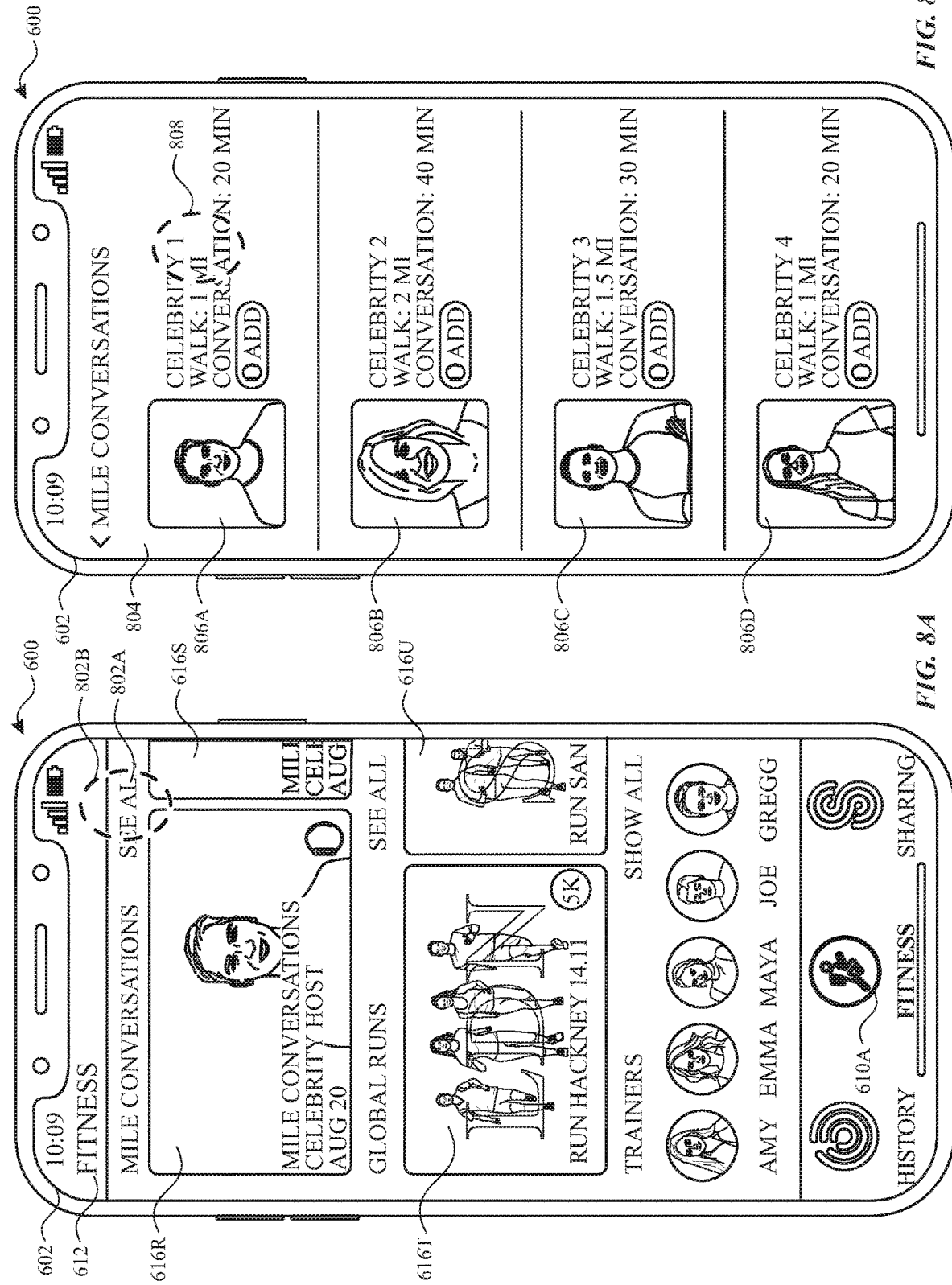

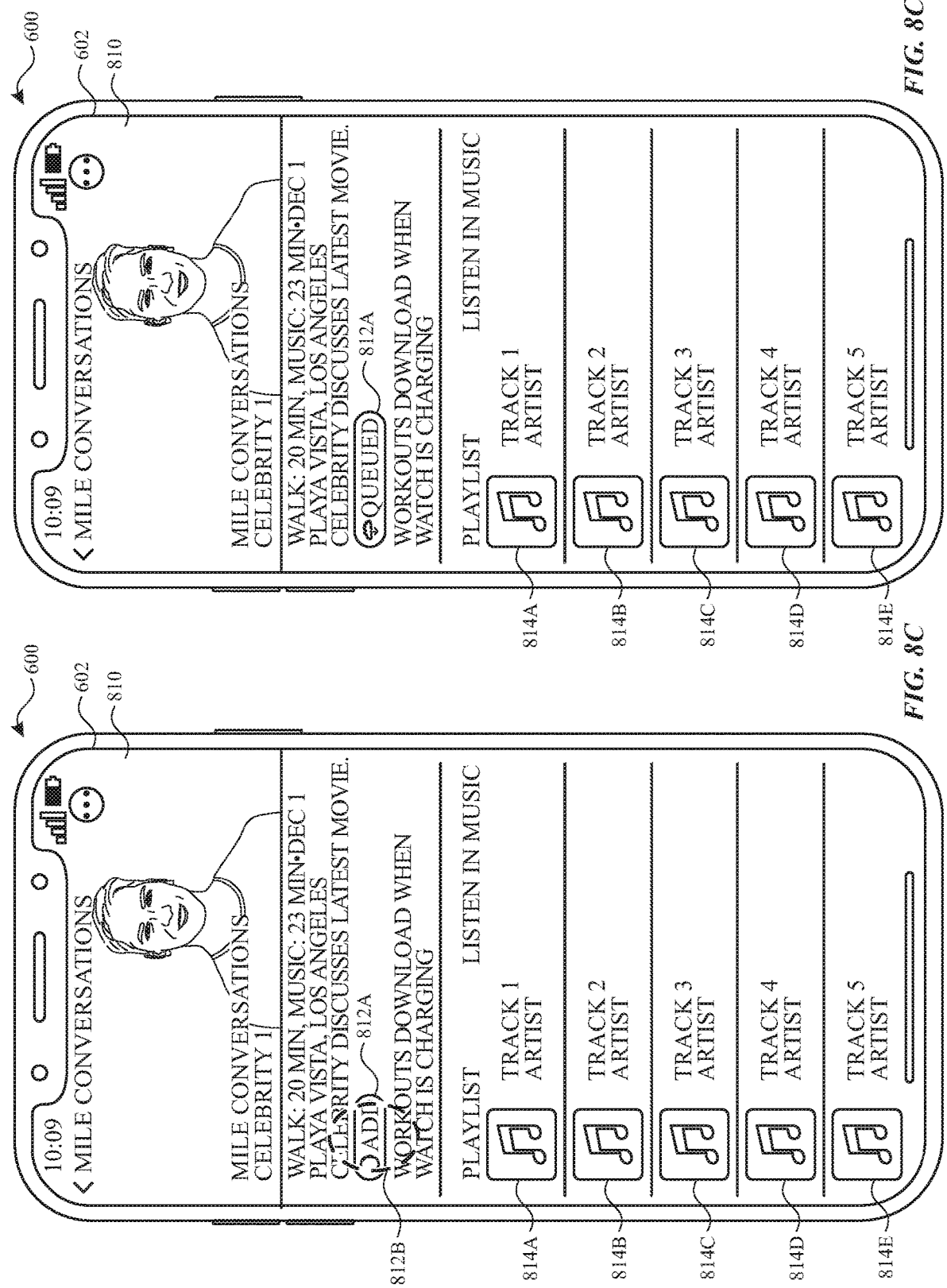

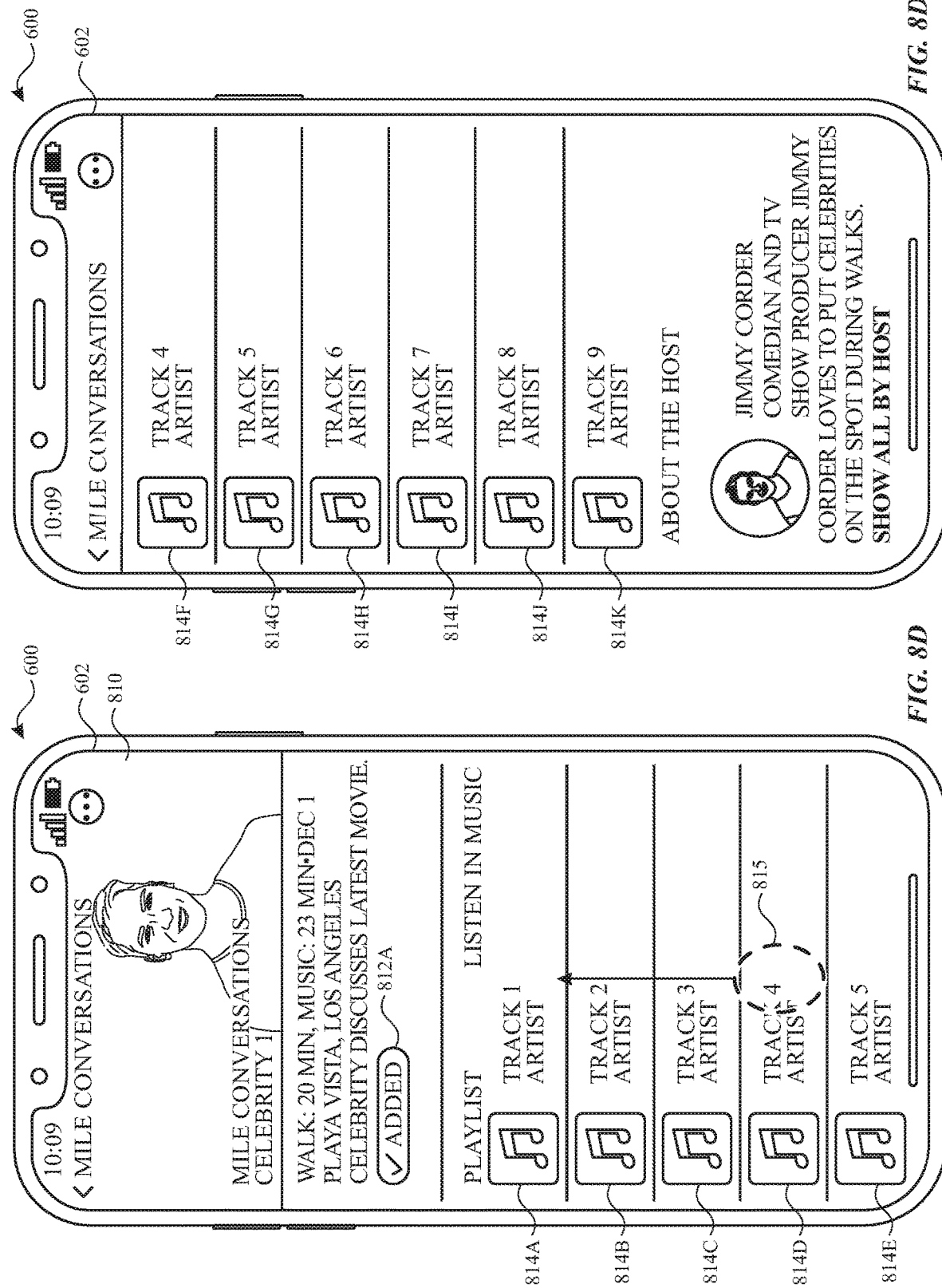

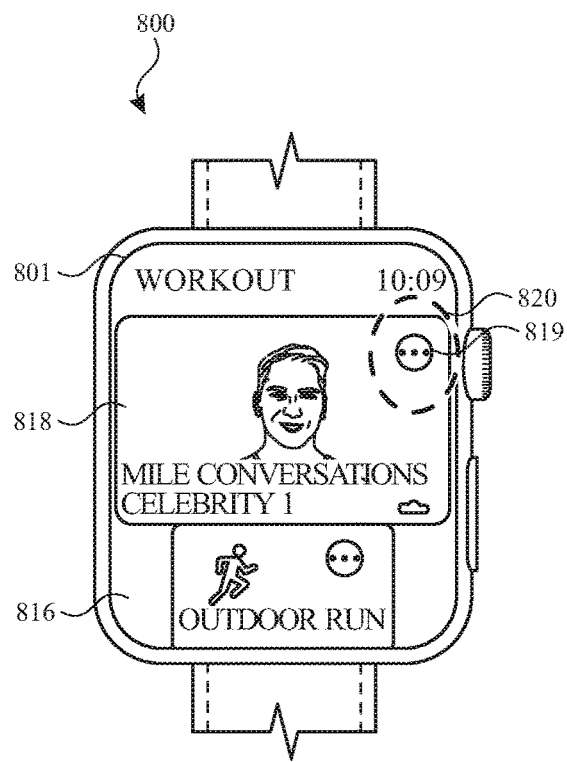
*FIG. 8E*
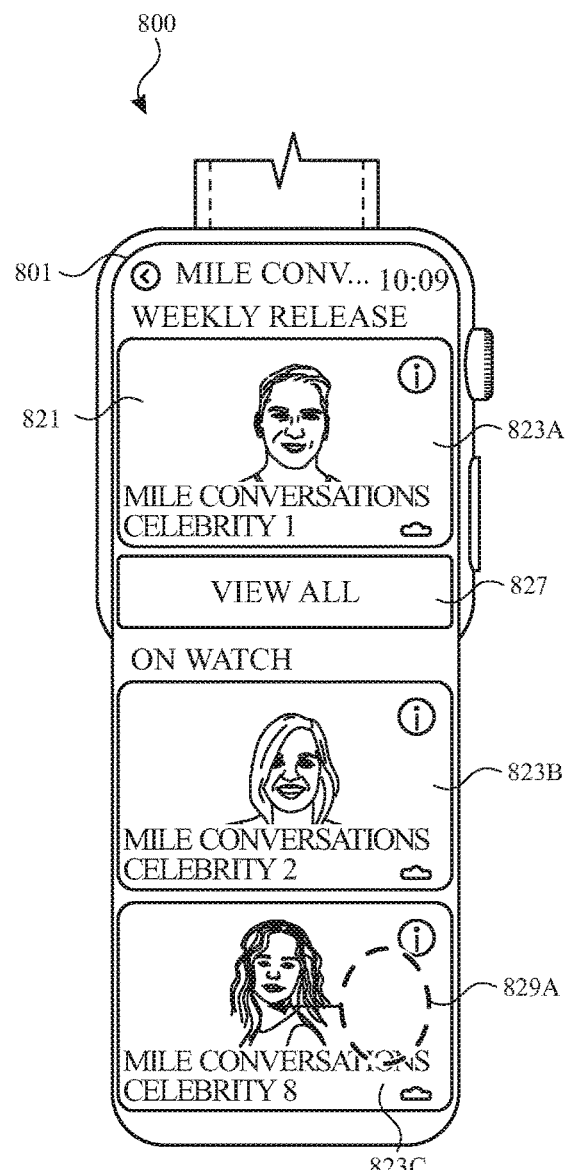
*FIG. 8E1*

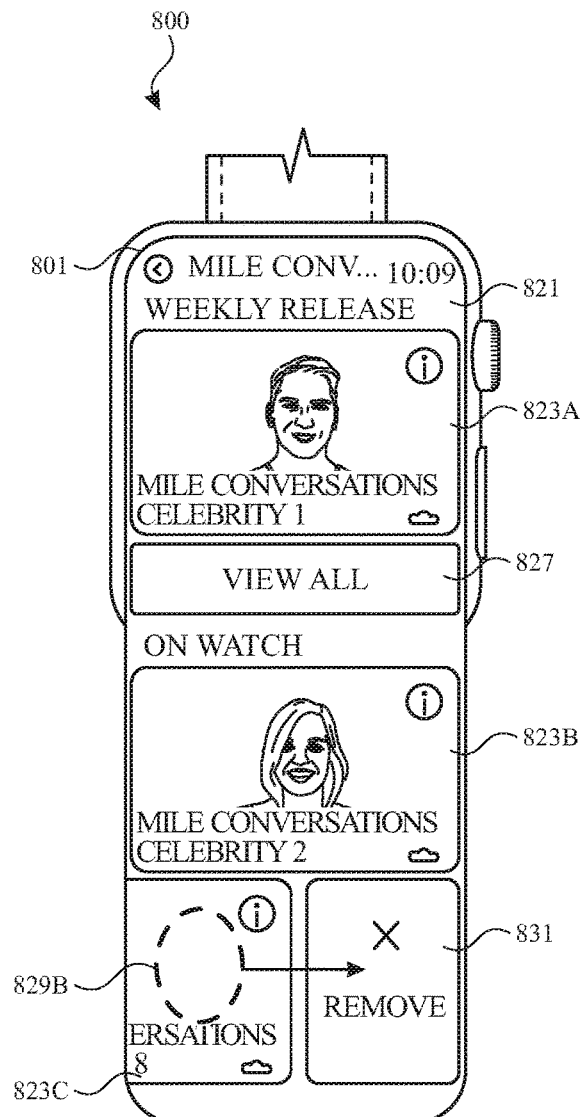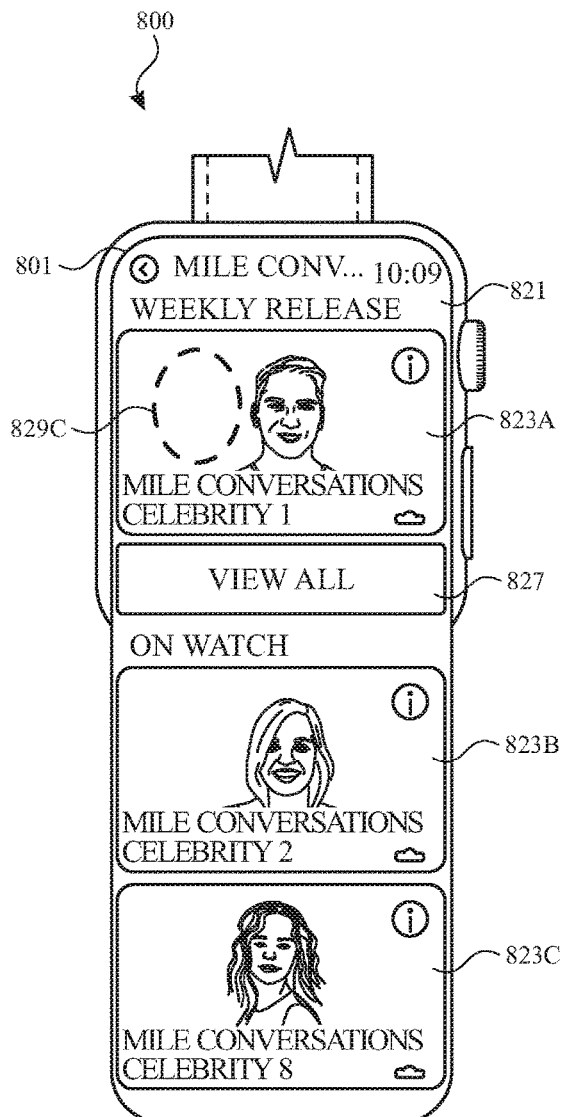
*FIG. 8E2*          *FIG. 8E3*

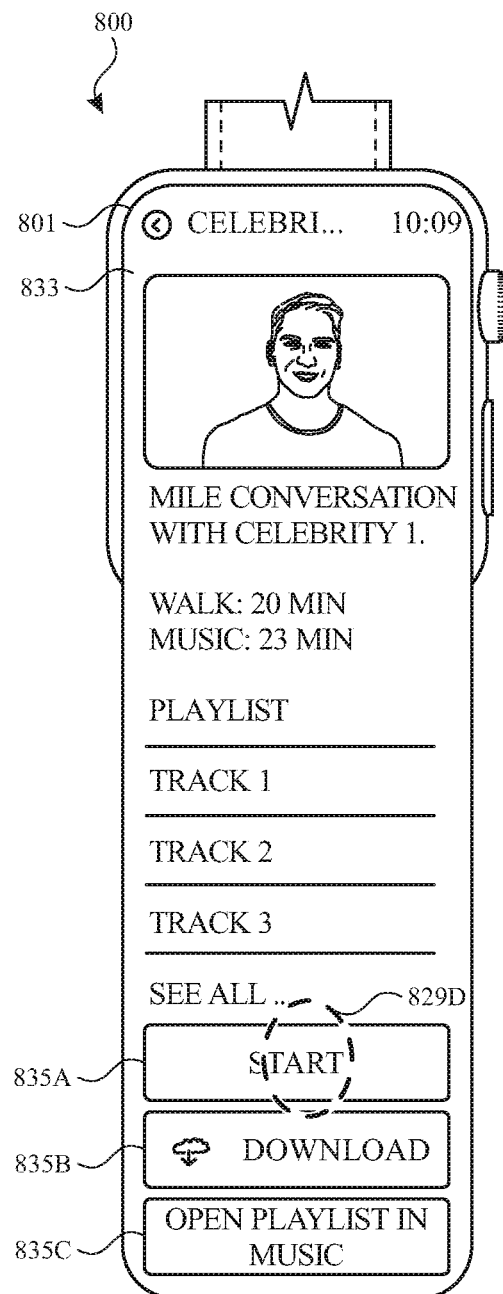
*FIG. 8E4*
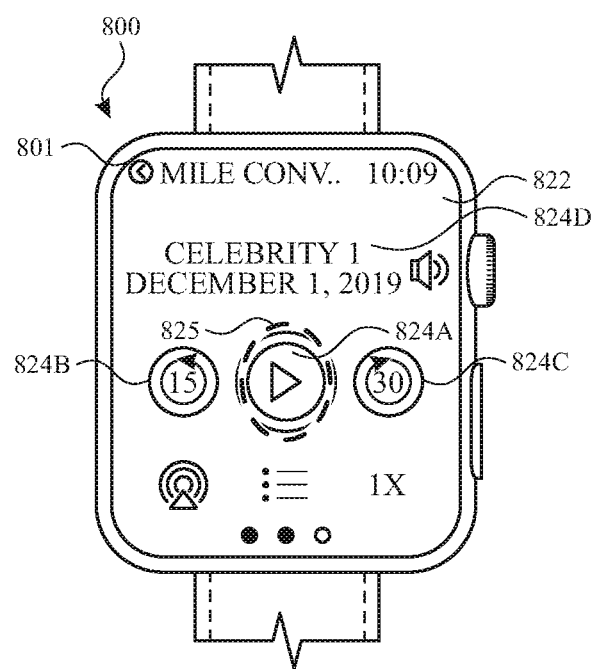
*FIG. 8F*

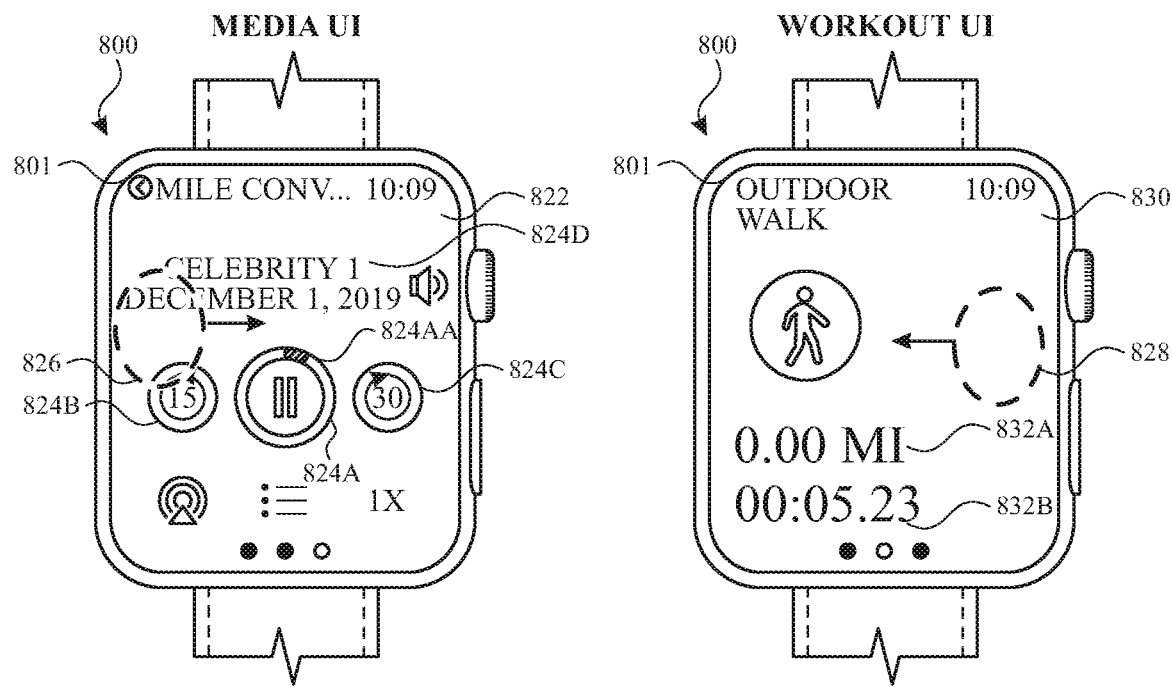
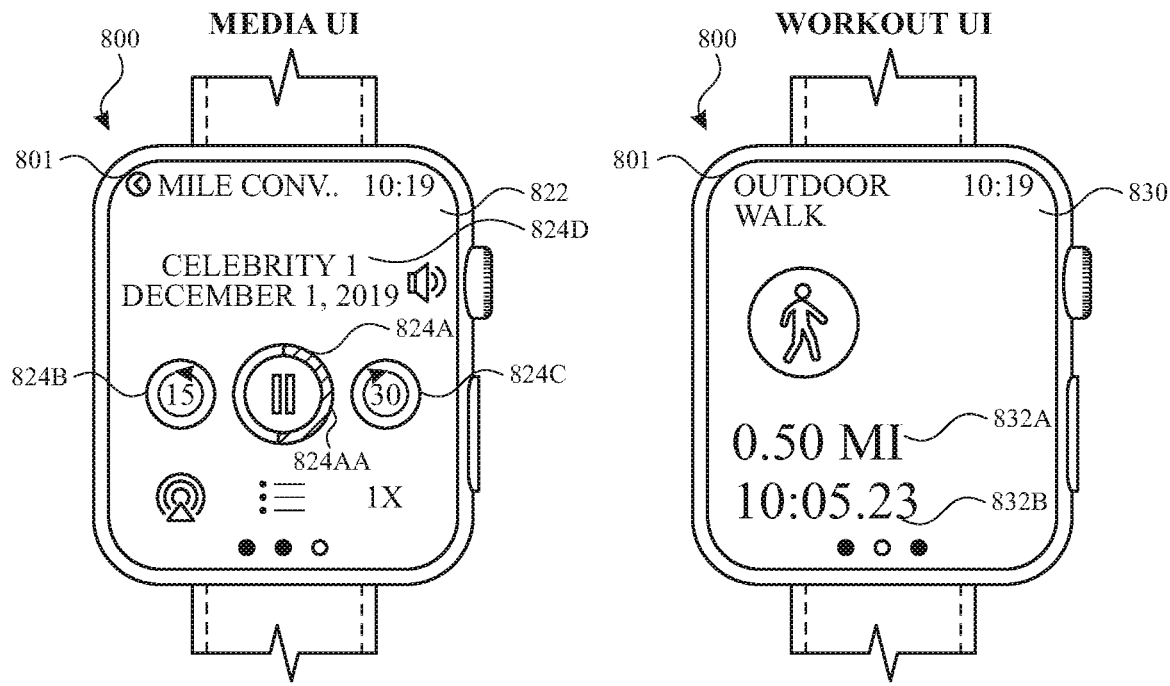
FIG. 8H

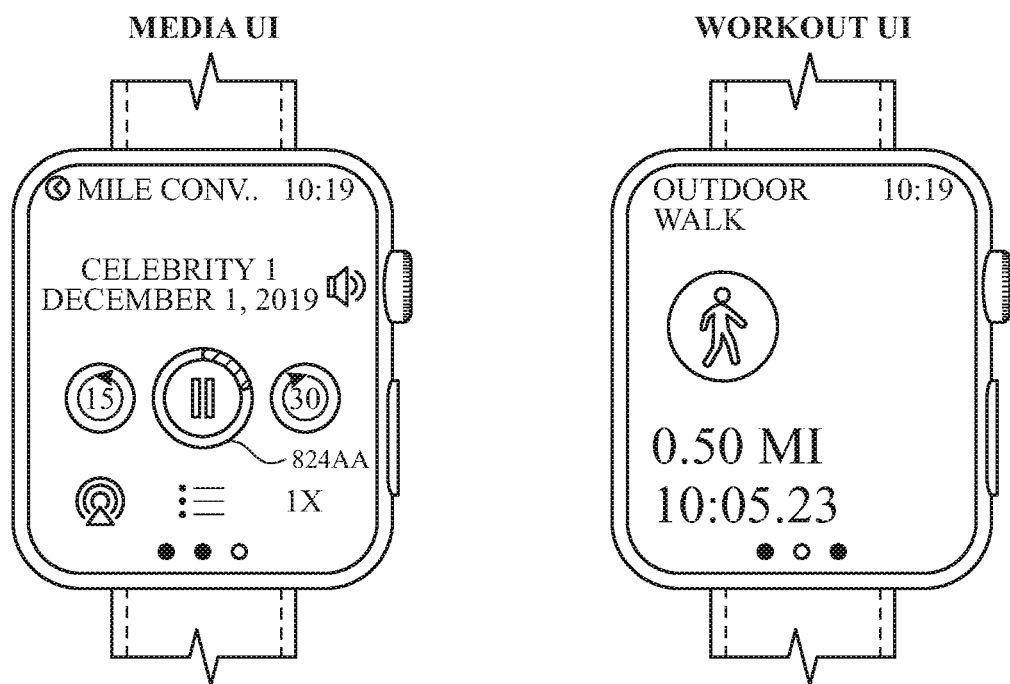
FIG. 8M1

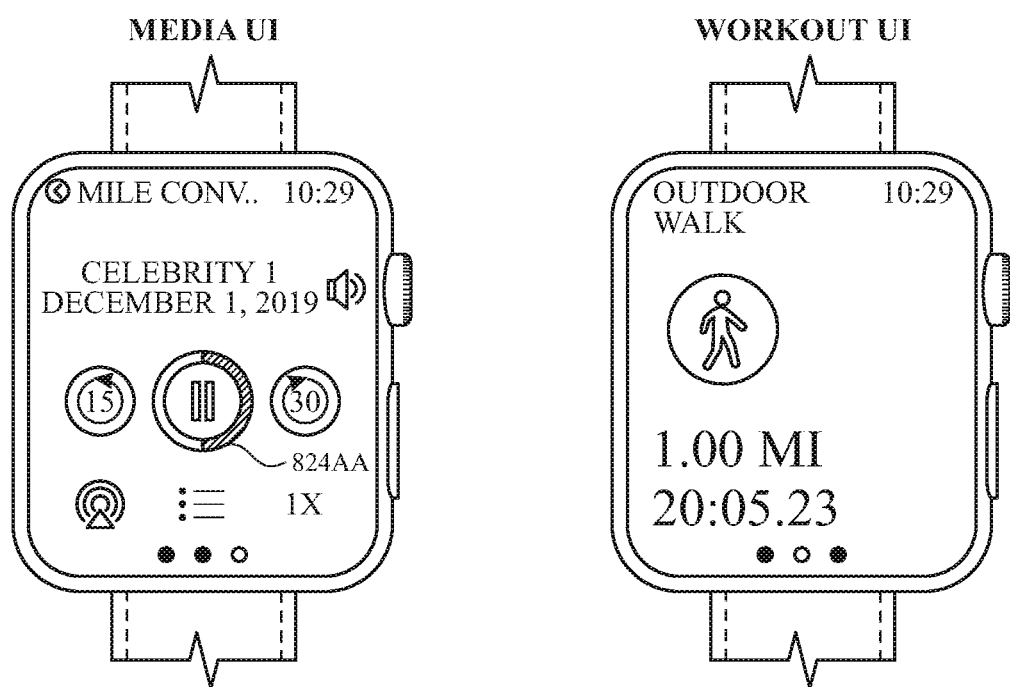
FIG. 8M2

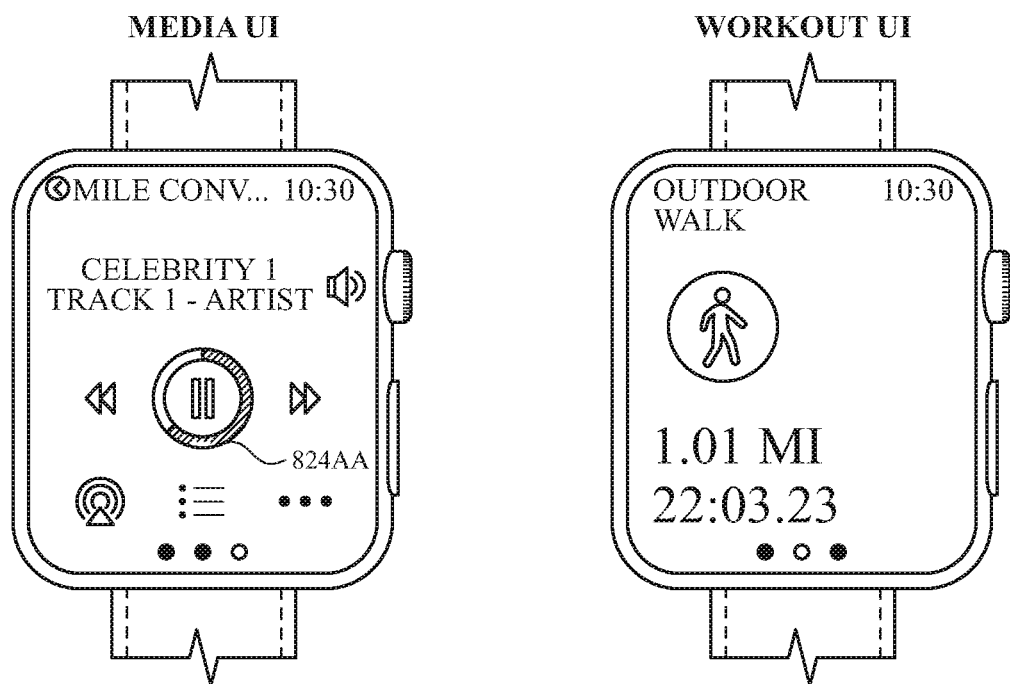
*FIG. 8M3*

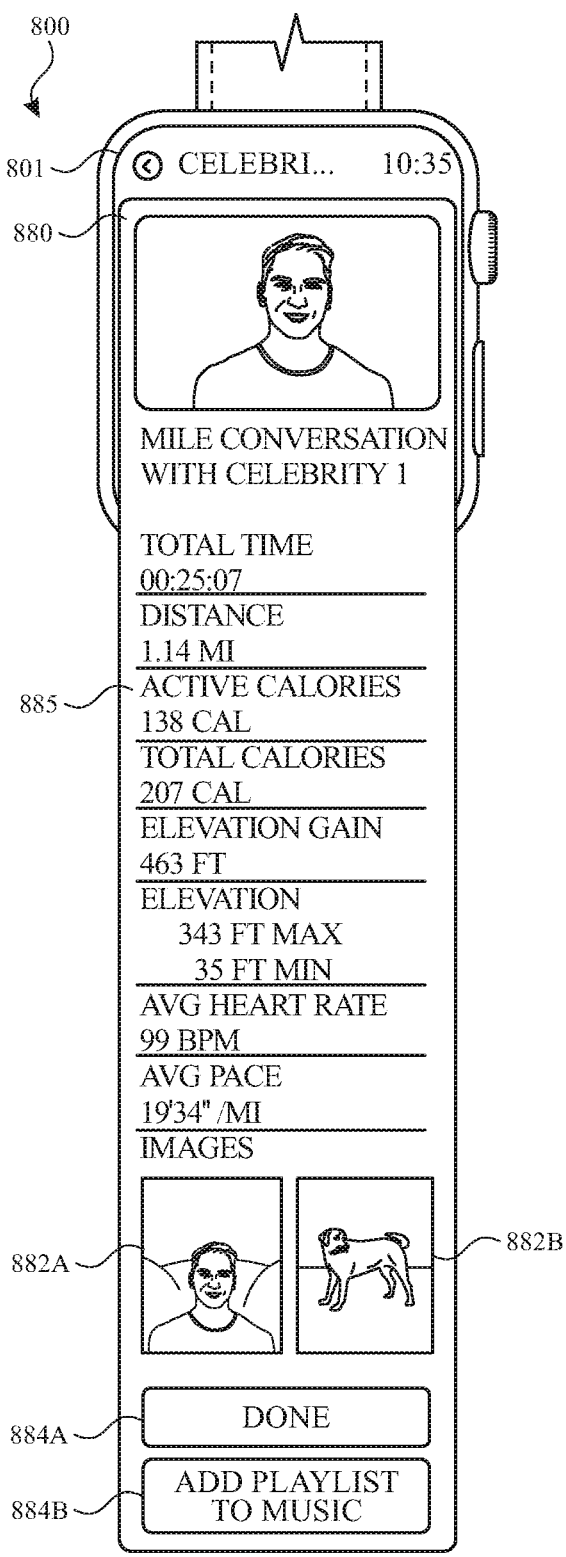
FIG. 8Q1

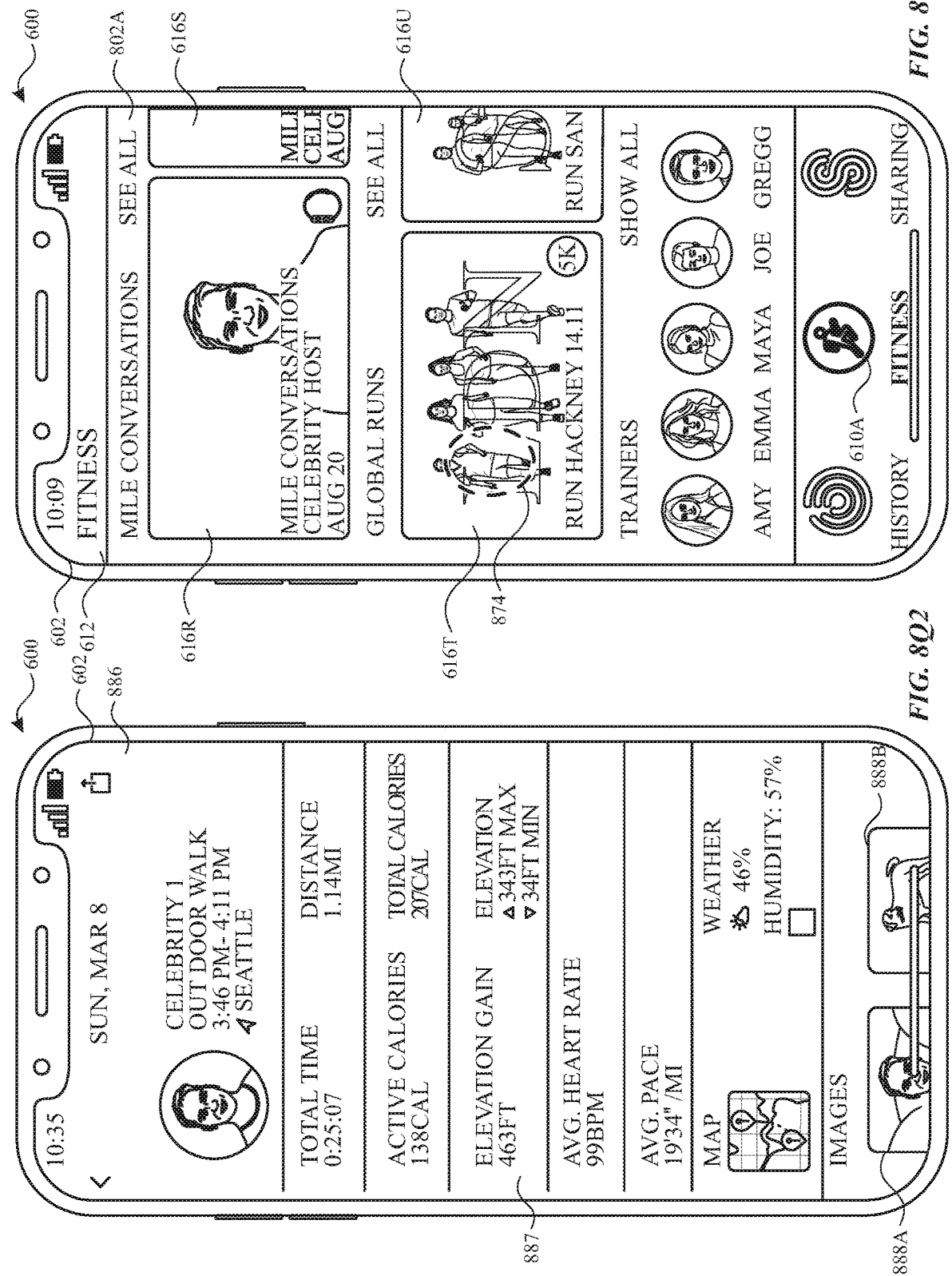

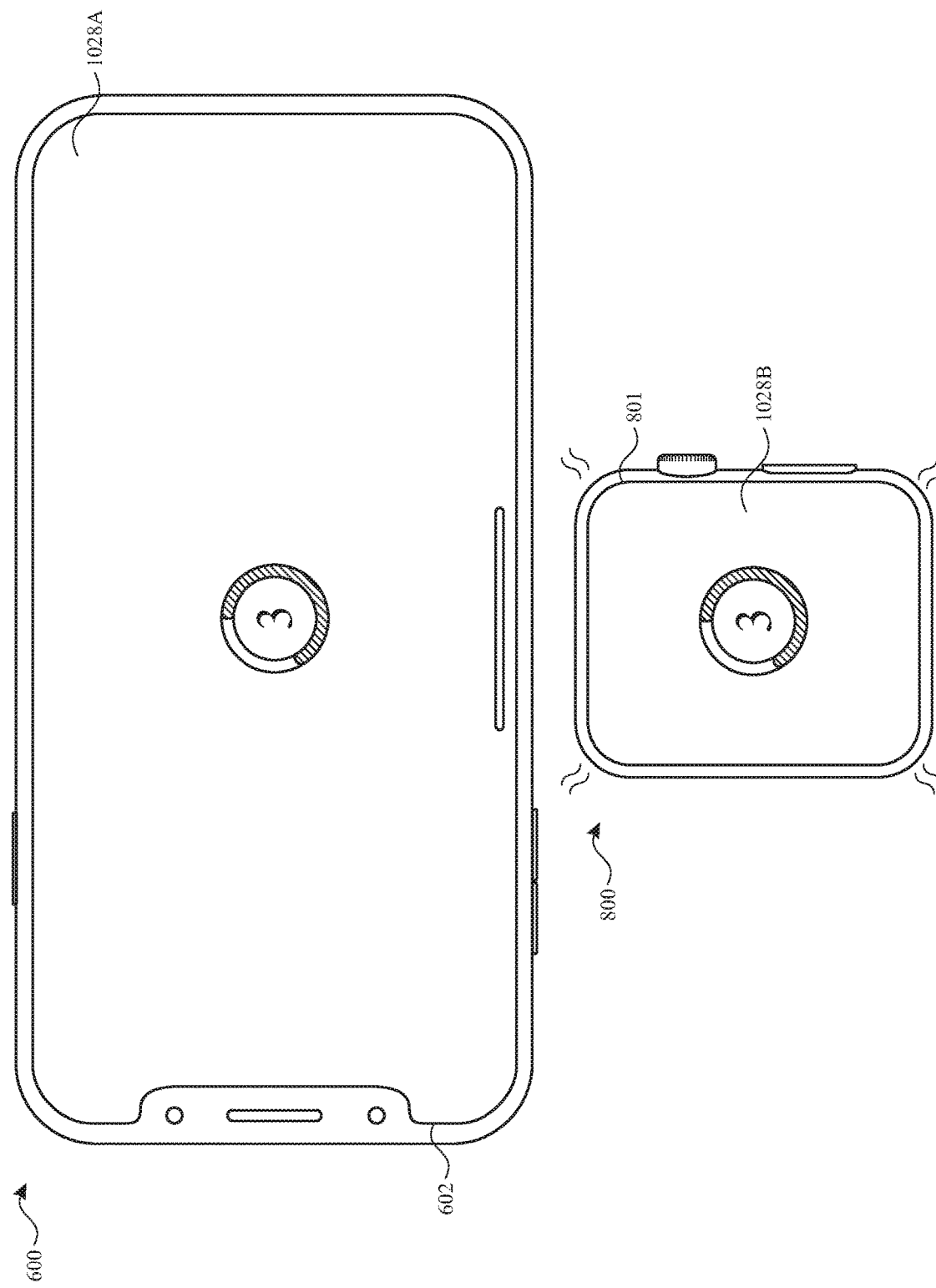

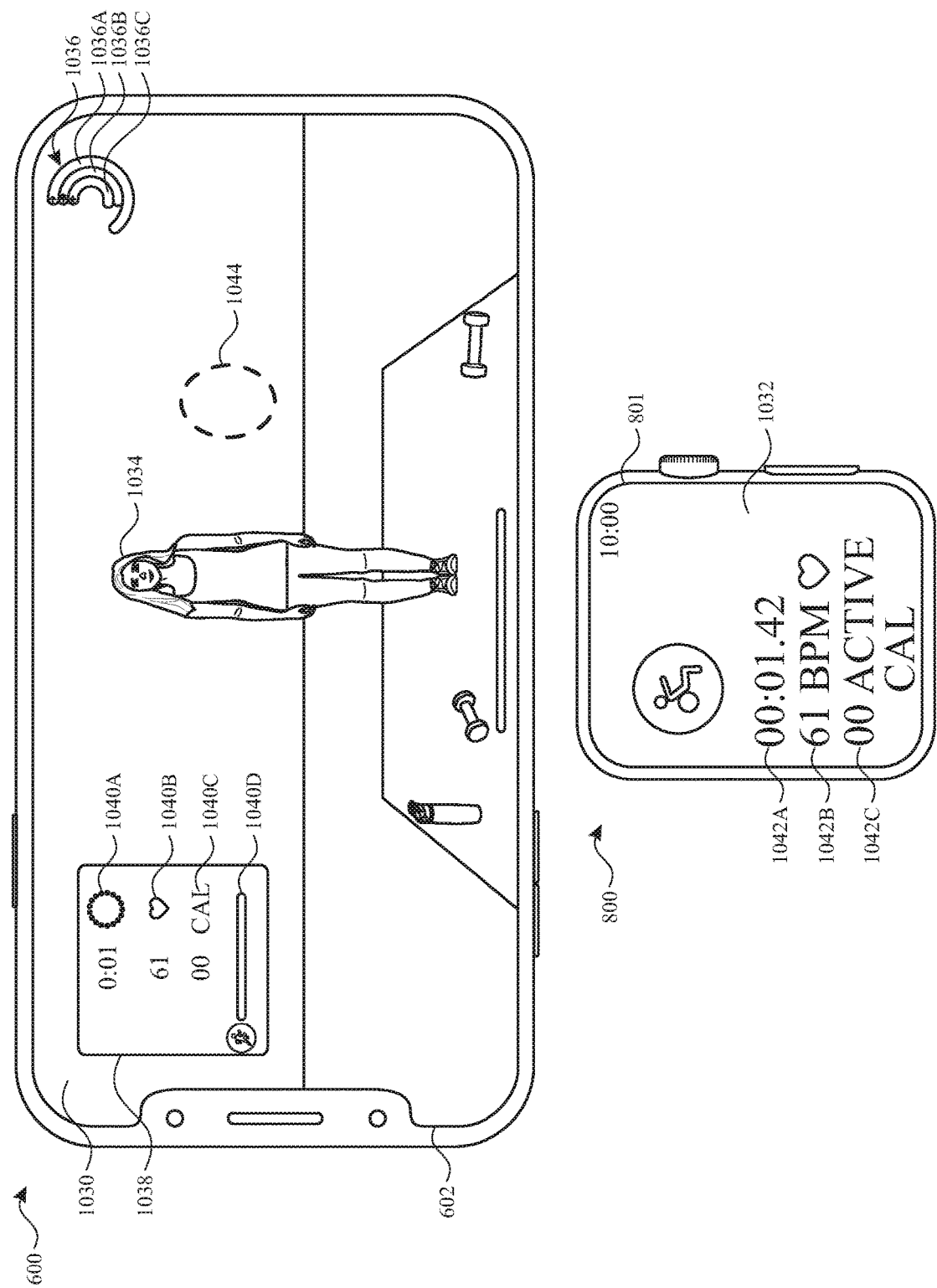

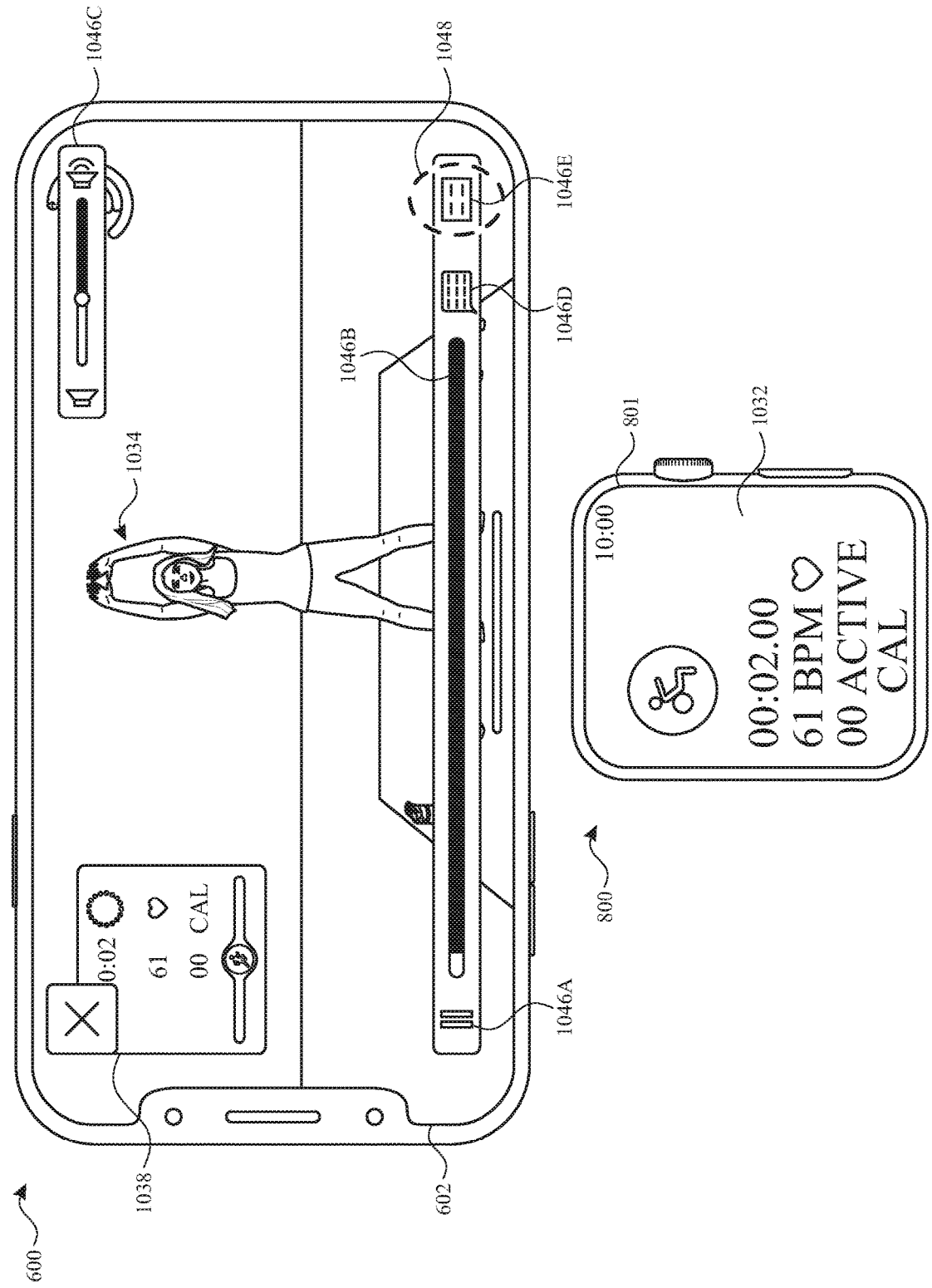

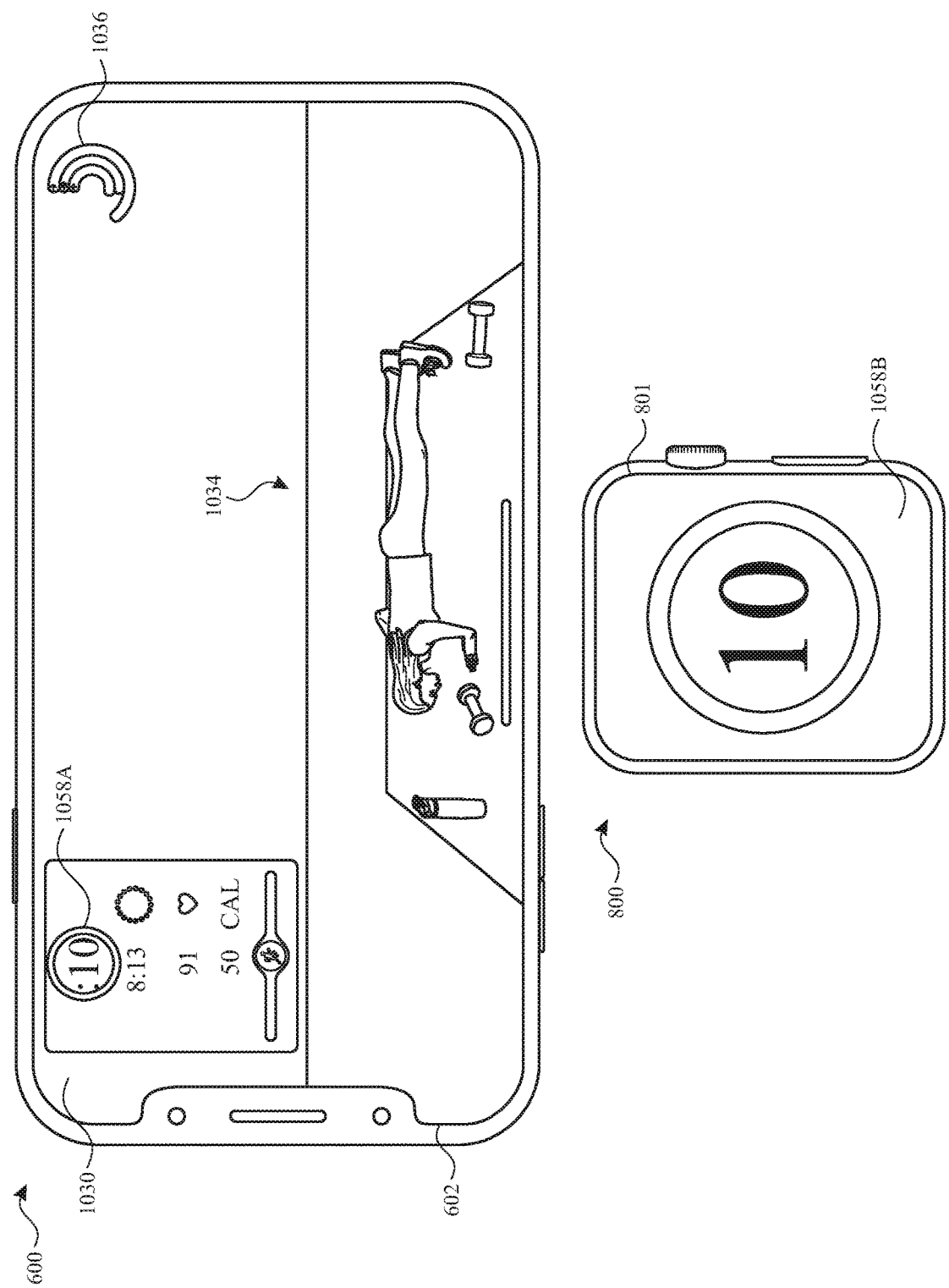

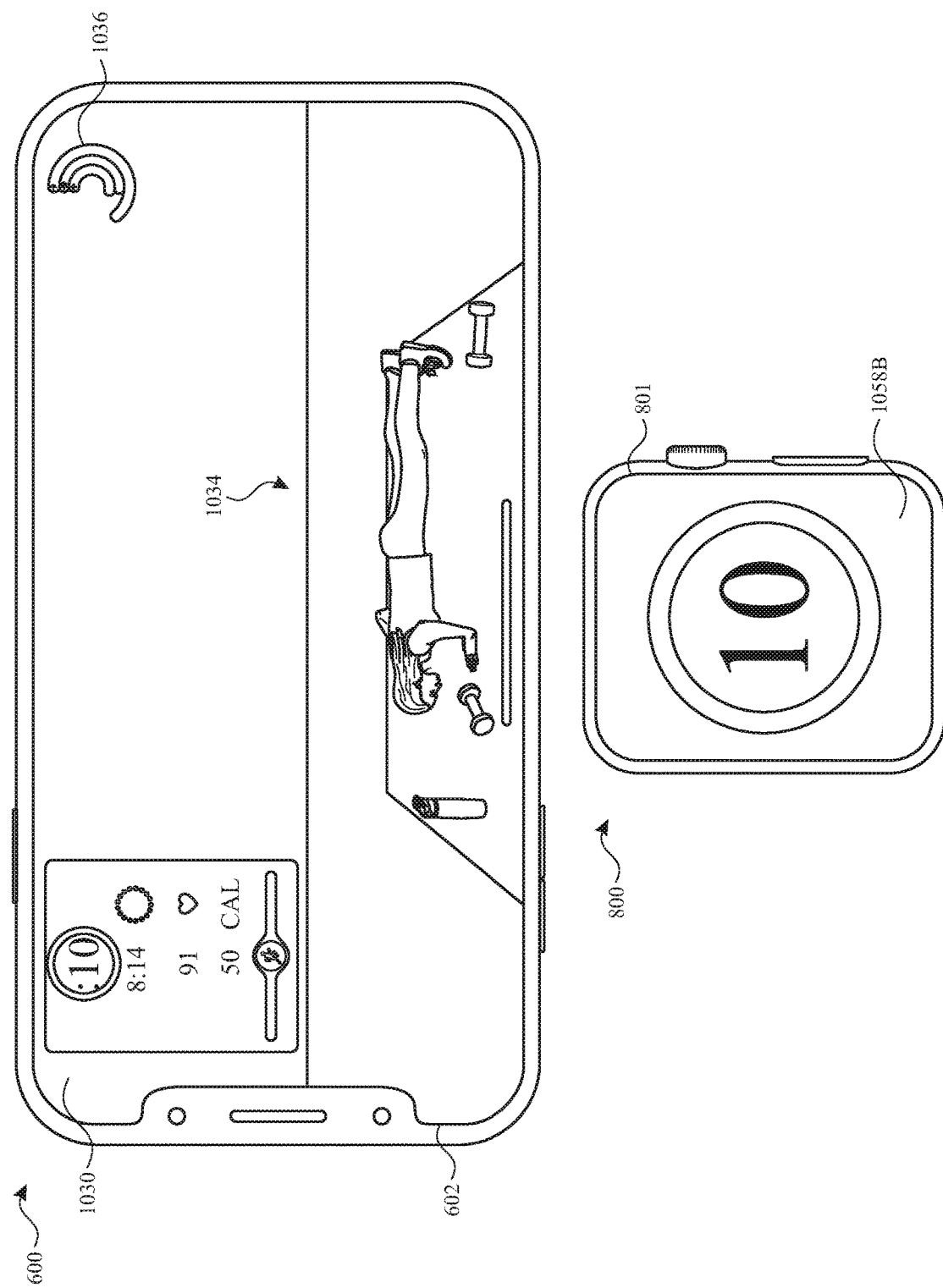
FIG. 10G2

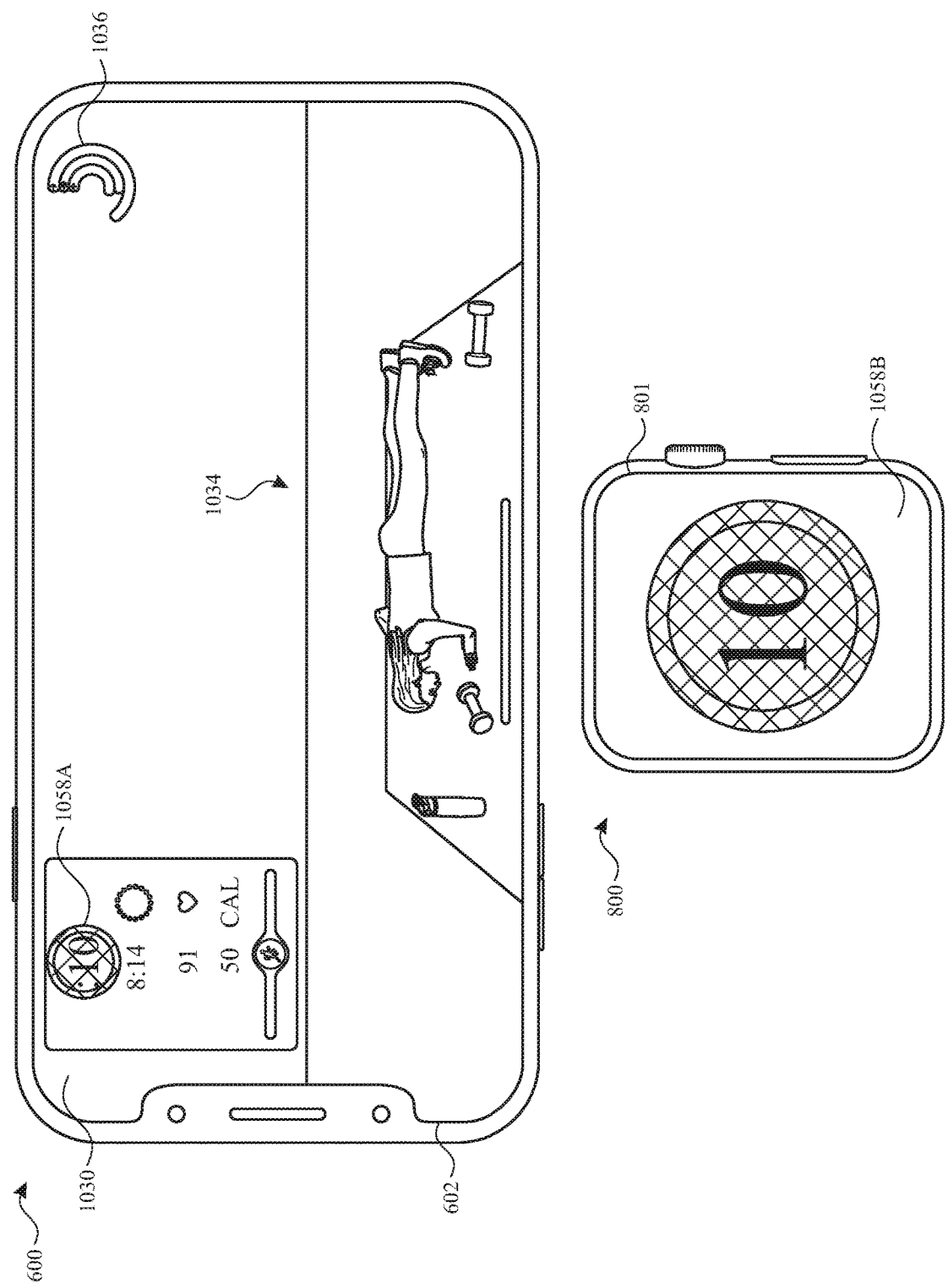
FIG. 10G3

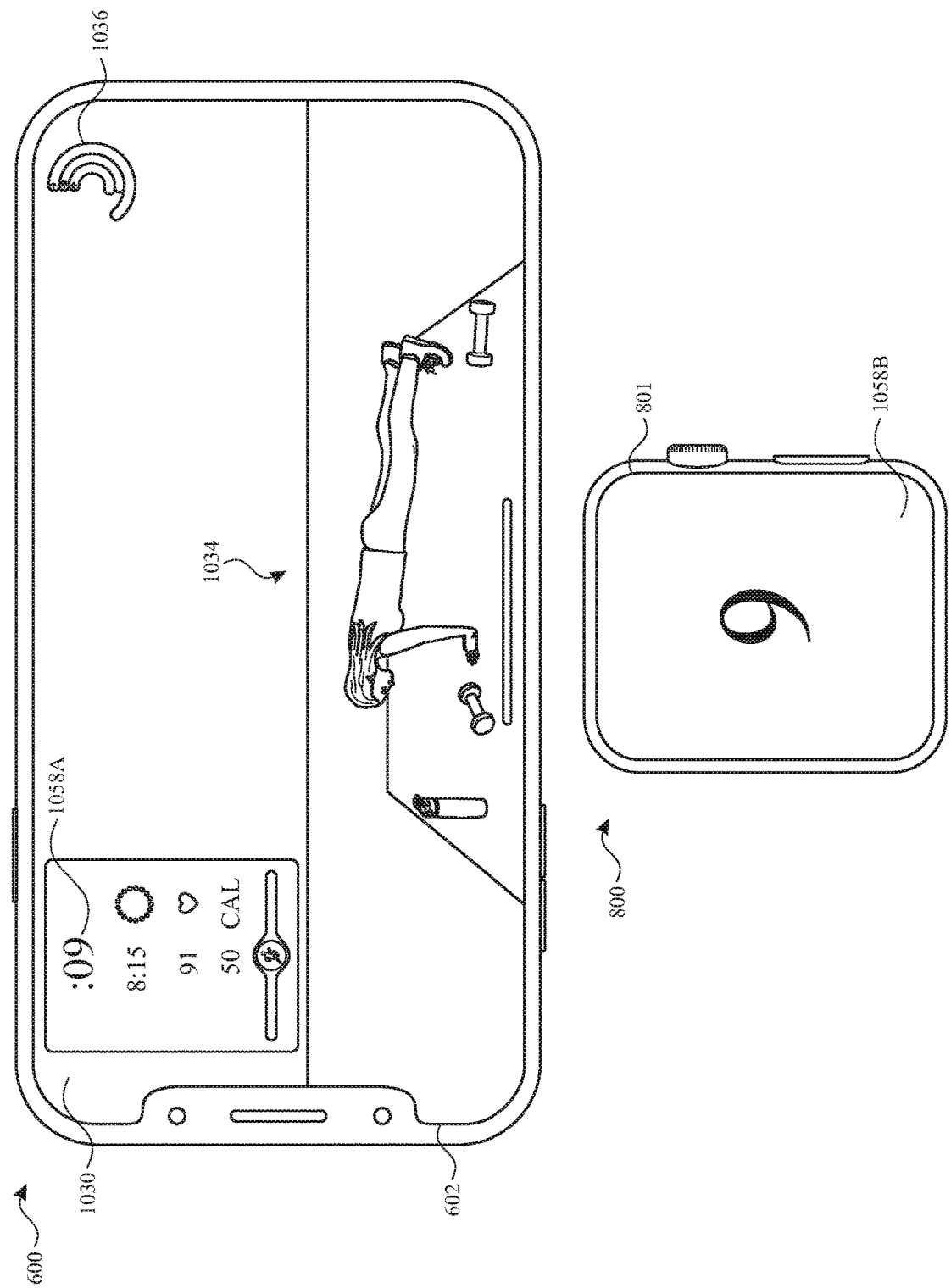

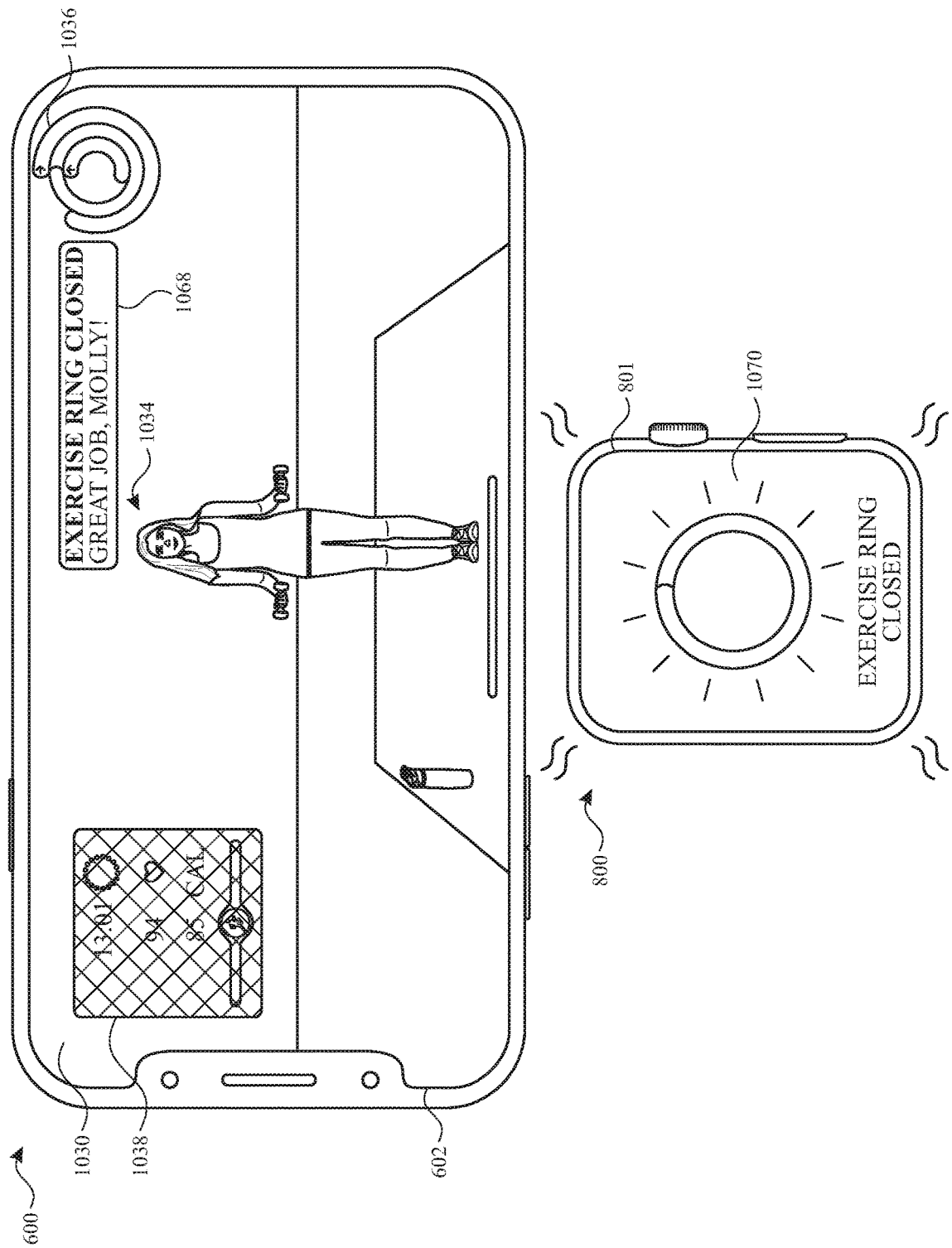

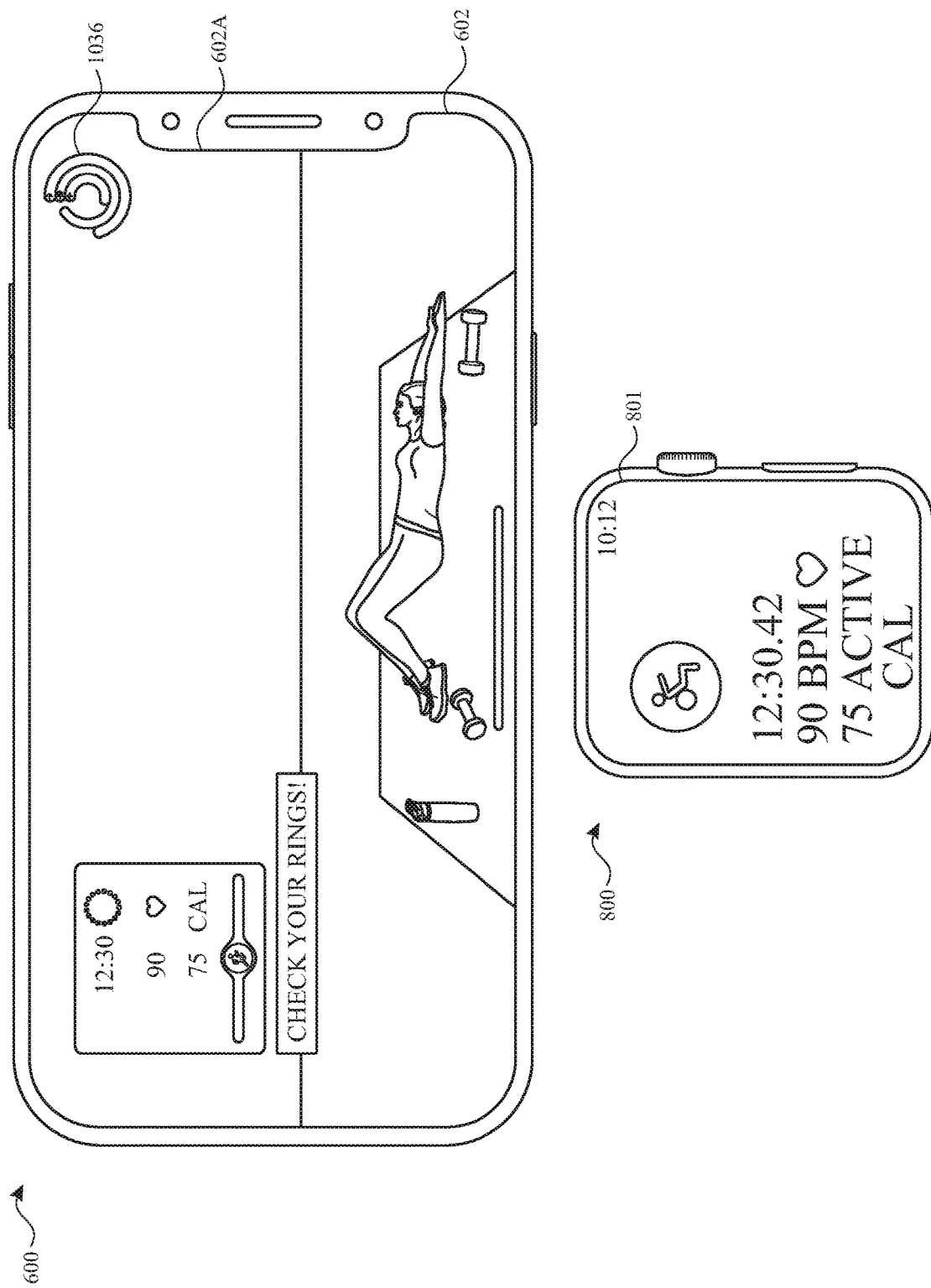
FIG. 10M1

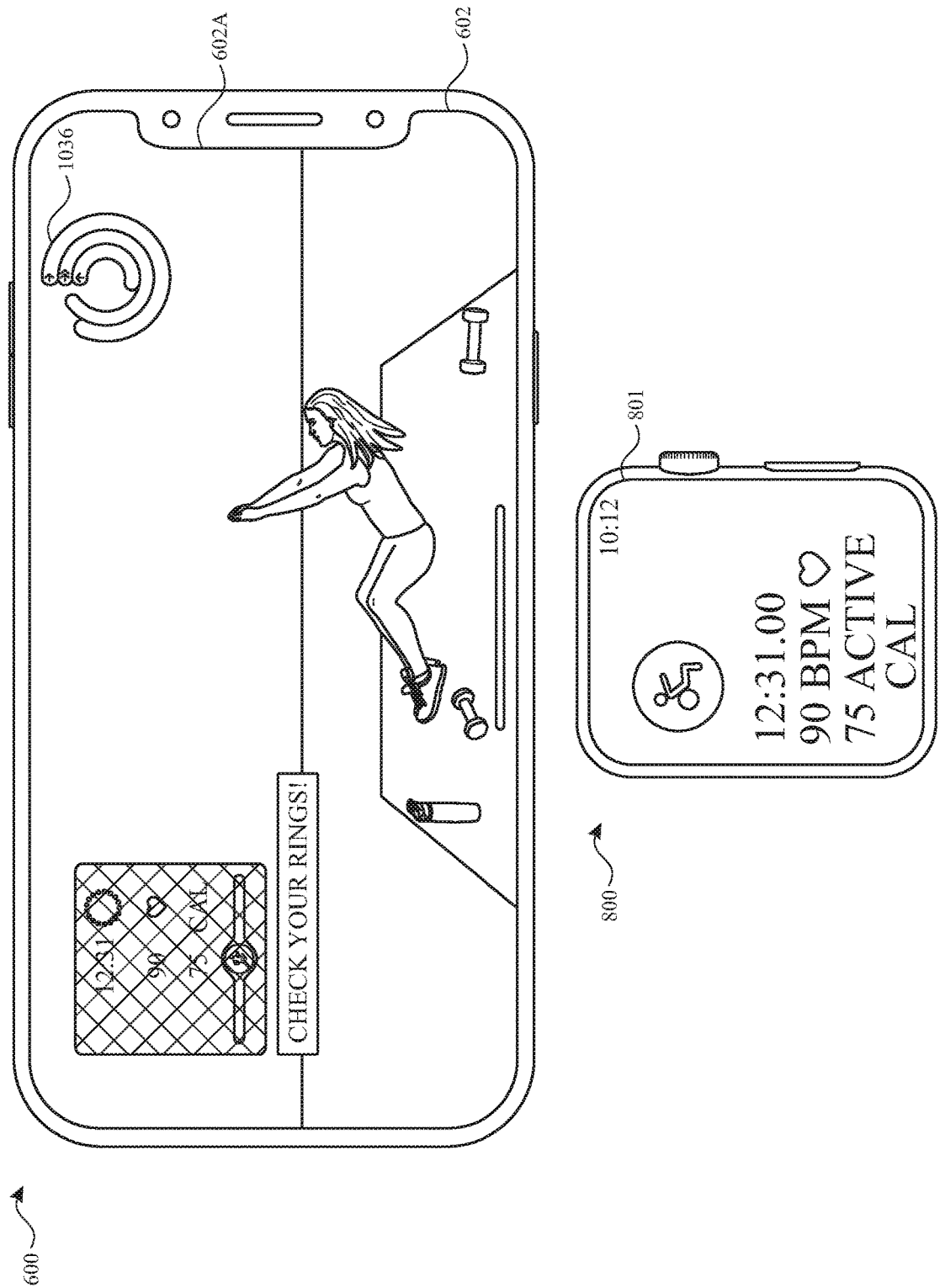
FIG. 10M2

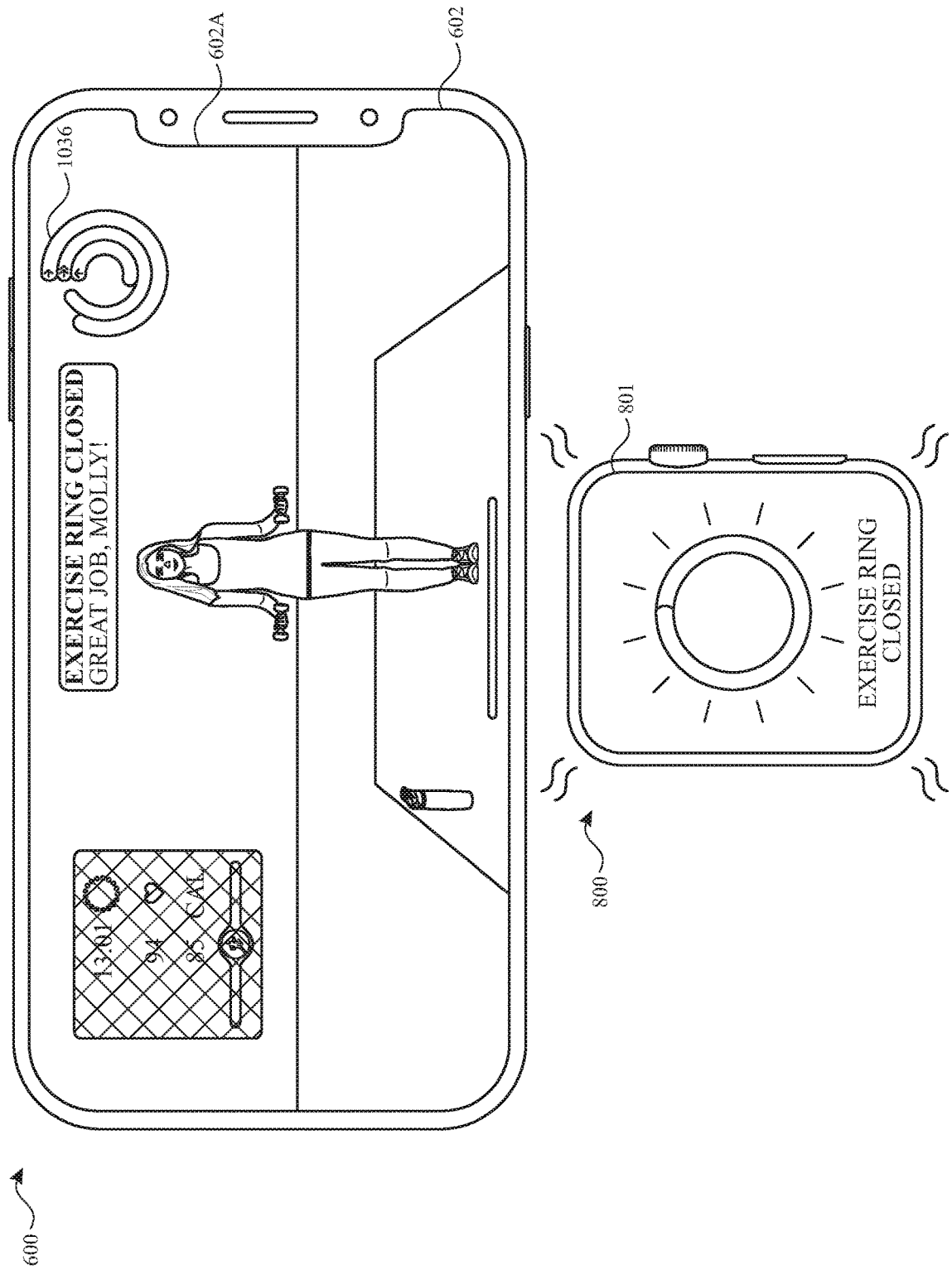
FIG. 10M3

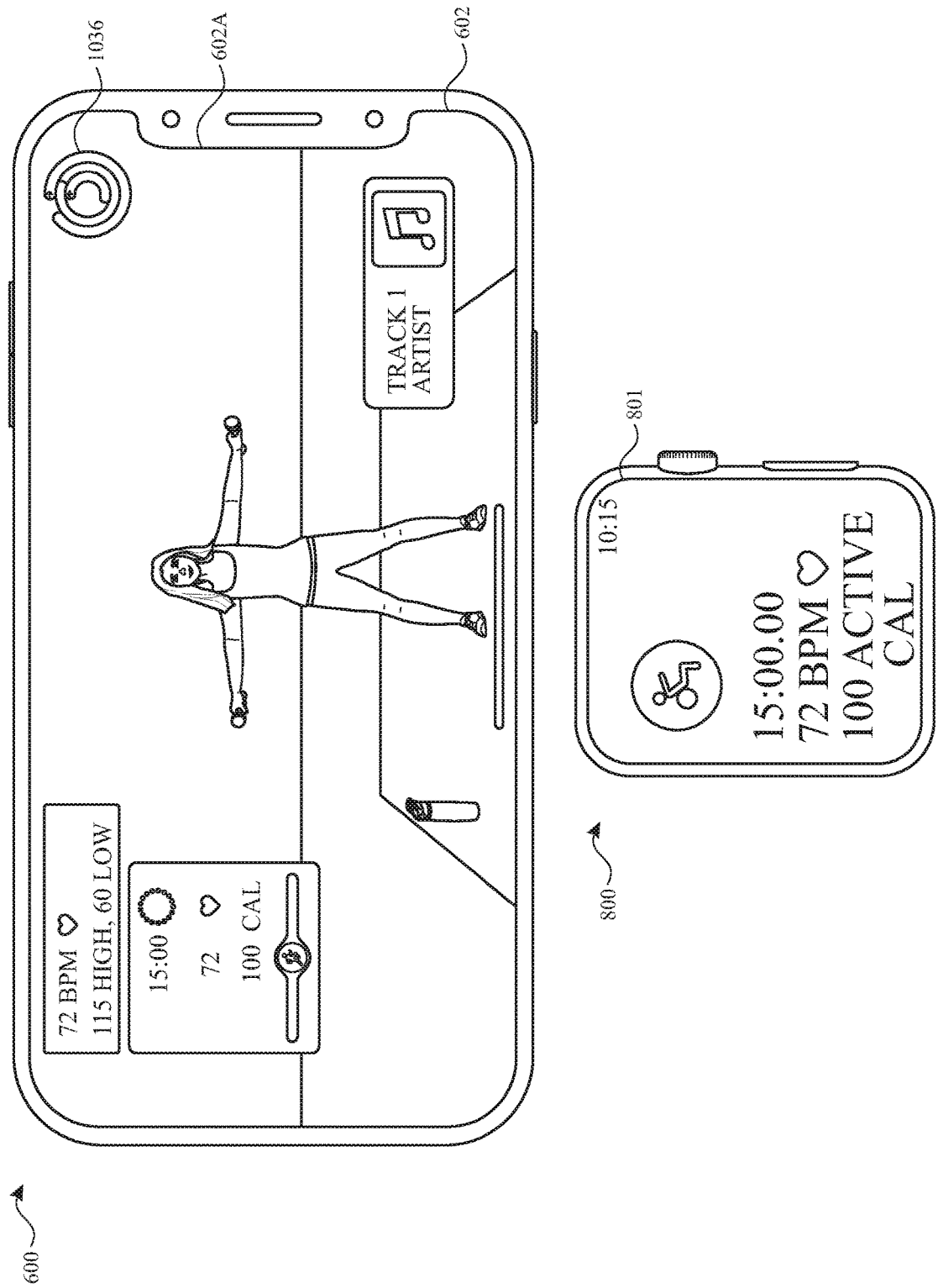
FIG. 10M4

1100 ⮕

1102
Cause concurrent display, via a display device, of video content and one or more representations of physical activity metrics corresponding to a user.

1104
The one or more representations of the physical activity metrics correspond to a predetermined amount of time preceding playback of the content.

1106
The one or more representations of the physical activity metrics are overlaid on the video content.

1108
While continuing to cause display of the video content:

1110
Receive activity data based on physical activity of the user during the display of the video content.

1112
The video content corresponds to a workout and the received activity data is based on physical activity of the user captured via one or more sensors that is in communication with the electronic device.

1114
In response to receiving the activity data:

1116
Update the display of the one or more representations of the physical activity metrics based on the received activity data.

*FIG. 11*

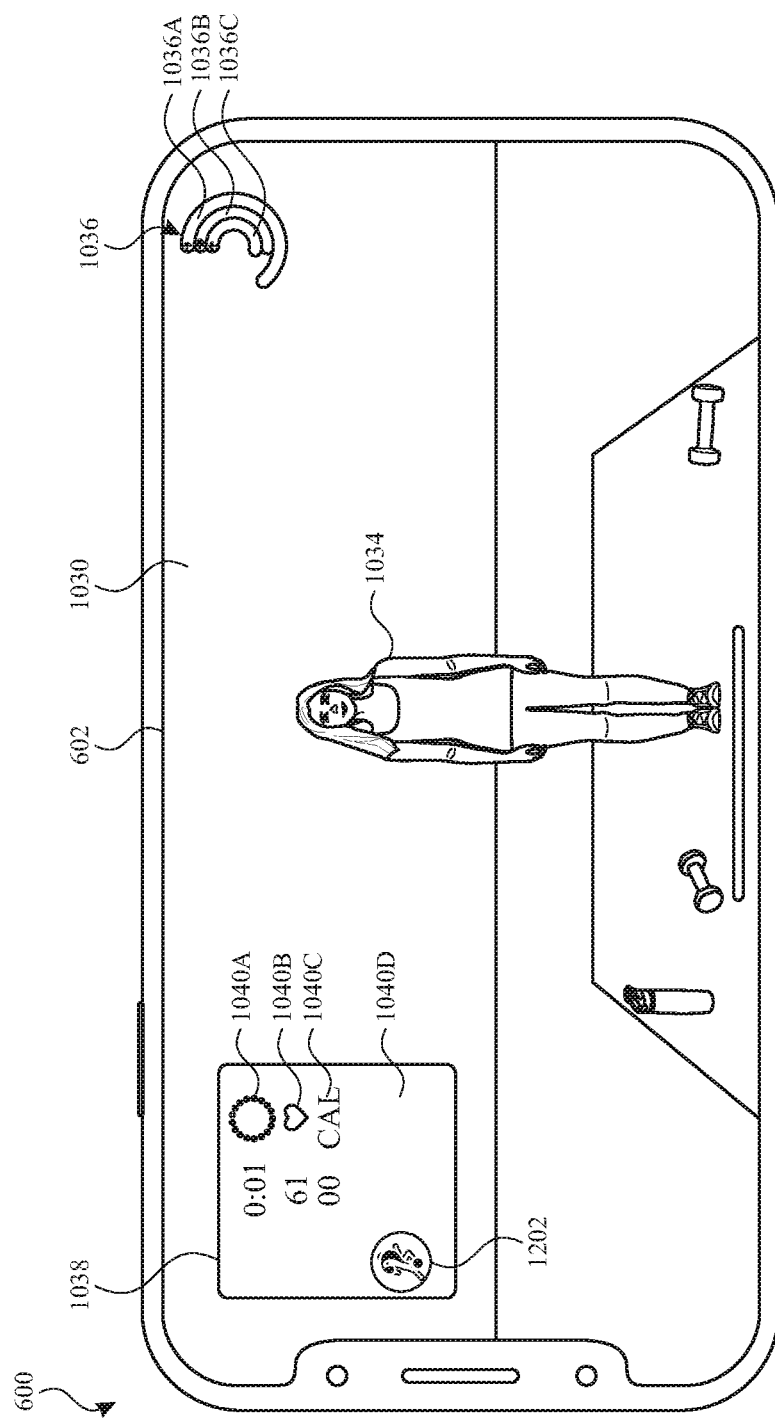

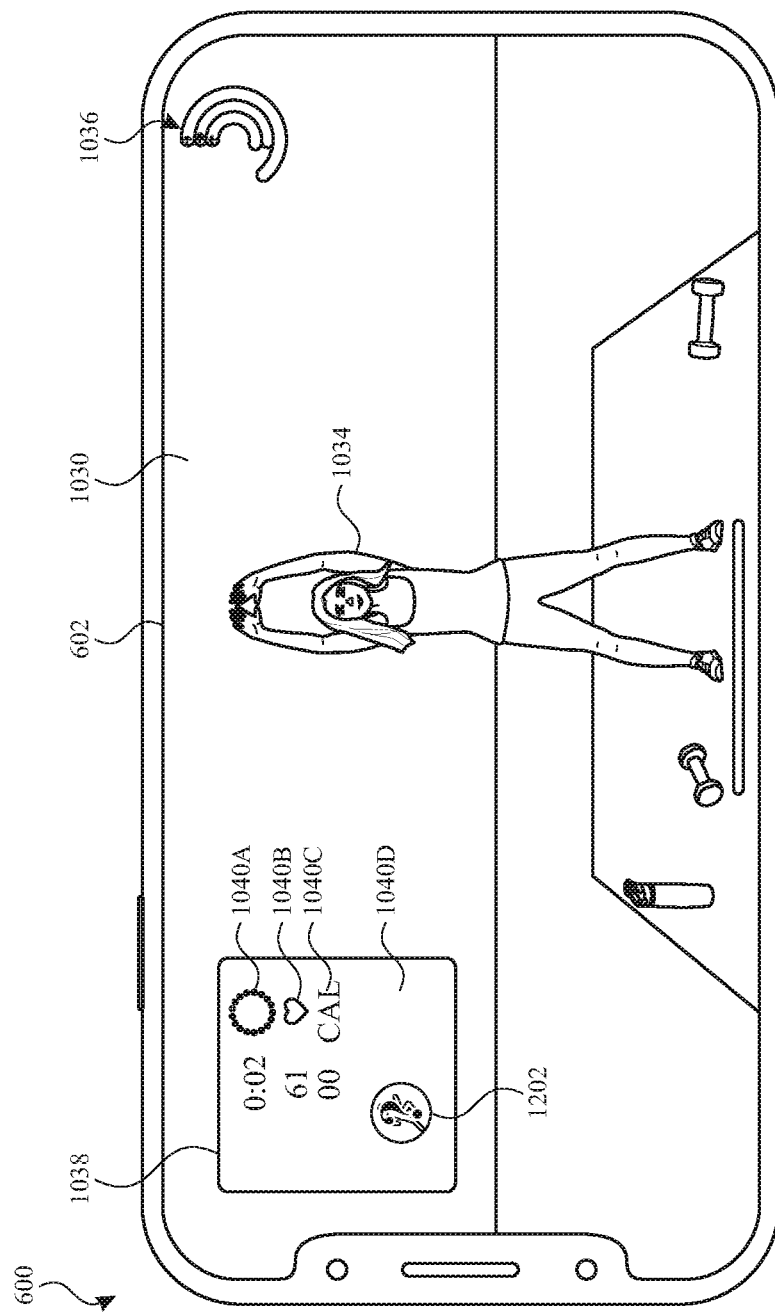

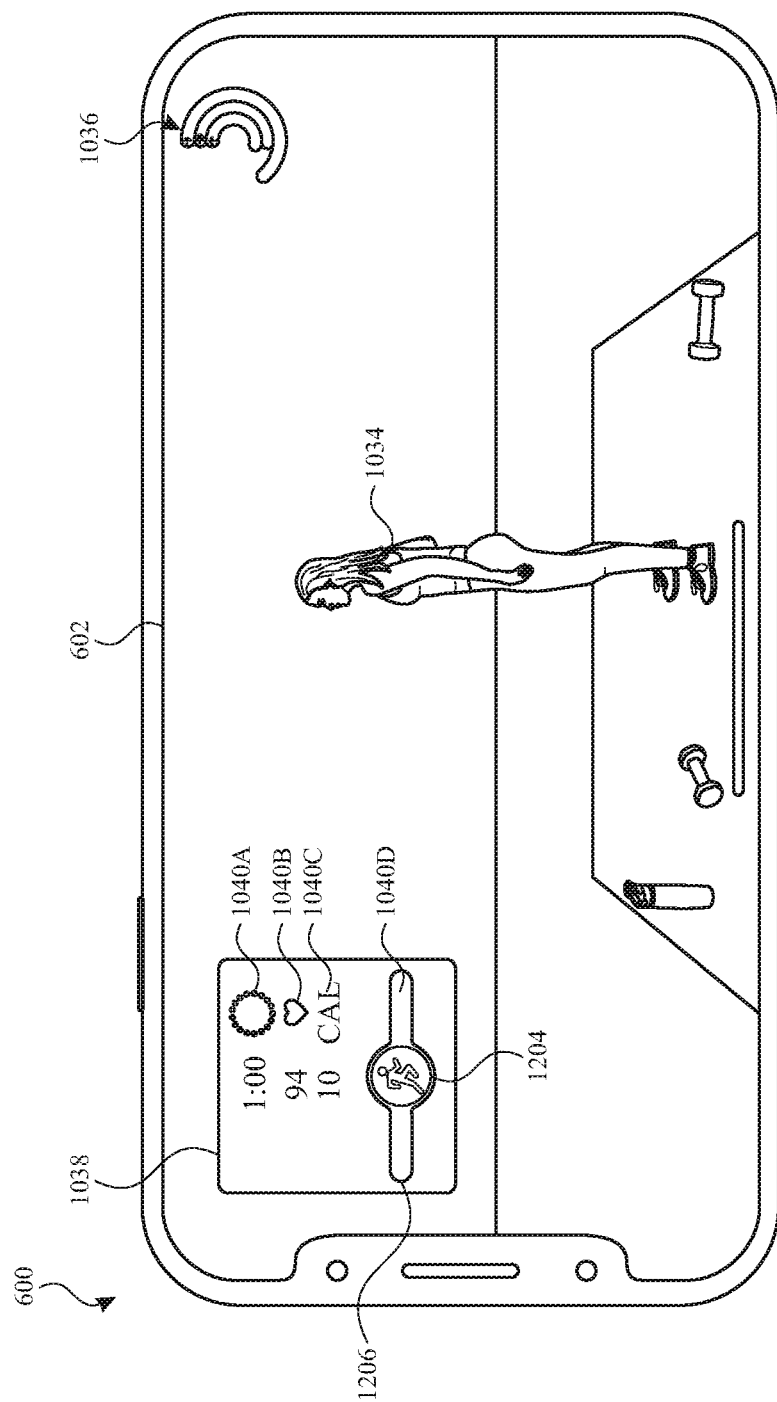

1300

1302
Cause concurrent display, via a display device, of video content and a workout intensity representation.

1304
The workout intensity representation has a visual characteristic based on a comparison between a physical activity metric for a user of the electronic device that corresponds to a first playback position of the video content and the physical activity metric for a group of users who participated in a workout while watching the video content based on the physical activity of the group of users that corresponds to the first playback position of the video content.

1306
The physical activity metric for the user corresponds to a representation of calories burned by the user.

1308
After the video has advanced from the first playback position to a second playback position:

1310
Receive activity data corresponding to the physical activity metric for the user.

1312
In response to receiving the activity data:

1314
Cause display, via the display device, of the workout intensity representation with the visual characteristic of the workout intensity representation changed based on the received activity data and based on a comparison between the physical activity metric for the user of the electronic device that corresponds to the second playback position of the video content and the physical activity metric for a group of users that corresponds to the second playback position of the video content.

1702
Cause display, via the display generation component, of a user interface, wherein the user interface includes: a plurality of workout suggestions displayed in a first region of the user interface, and one or more filtering options for filtering workout suggestions displayed concurrently with the plurality of workout suggestions.

1704
Detect, via the one or more input devices, a first user input directed to a first filtering option of the one or more filtering options.

1706
In accordance with a determination that the first user input directed to the first filtering option has been maintained for at least a predefined period of time:

1708
Cease to display at least a portion of the plurality of workout suggestions within the first region of the user interface, so that the first region of the user interface includes a first subset of workout suggestions from the plurality of workout suggestions that are associated with the first filtering option and does not include workout suggestions that are not associated with the first filtering option.

1710
While the first subset of workout suggestions is displayed in the first region of the user interface:

1712
Detect, via the one or more input devices, a second user input corresponding to navigation to a first workout suggestion of the first subset of workout suggestions.

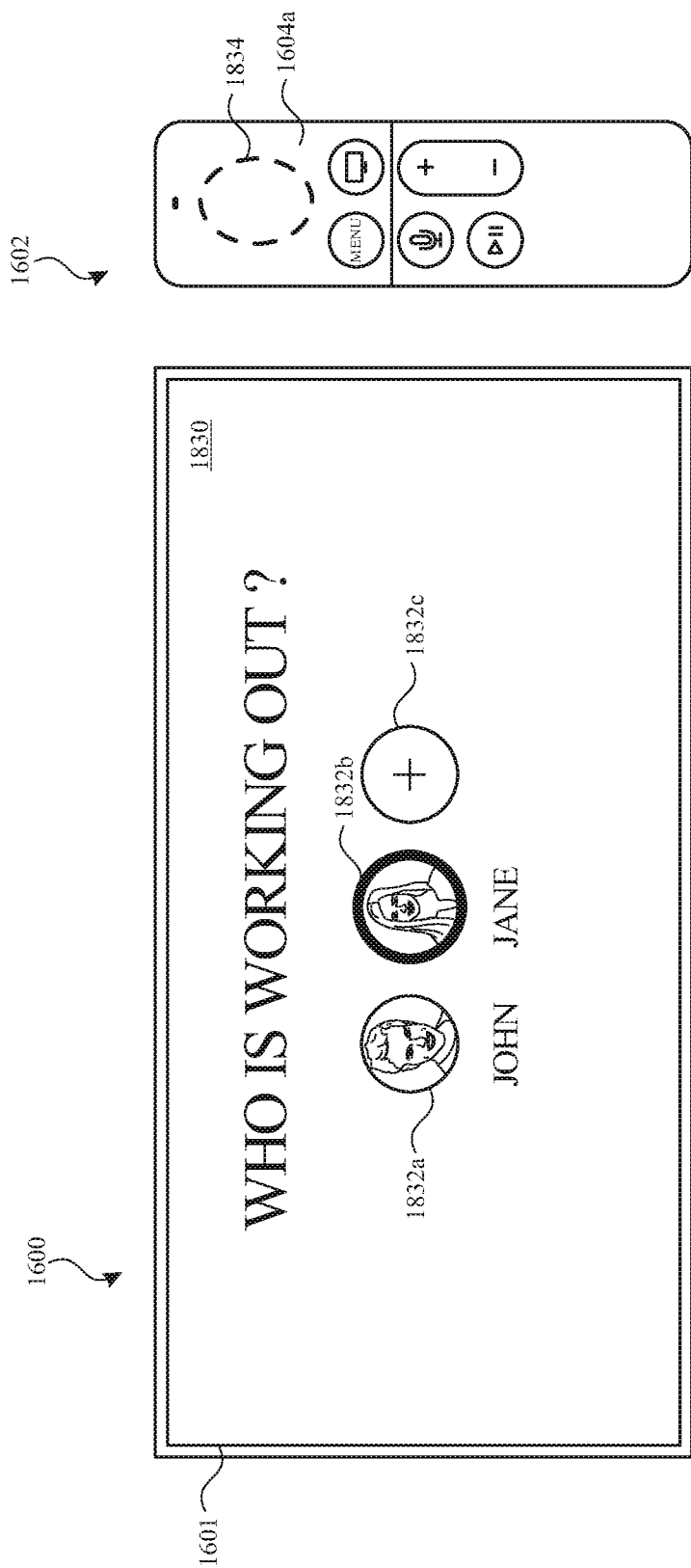

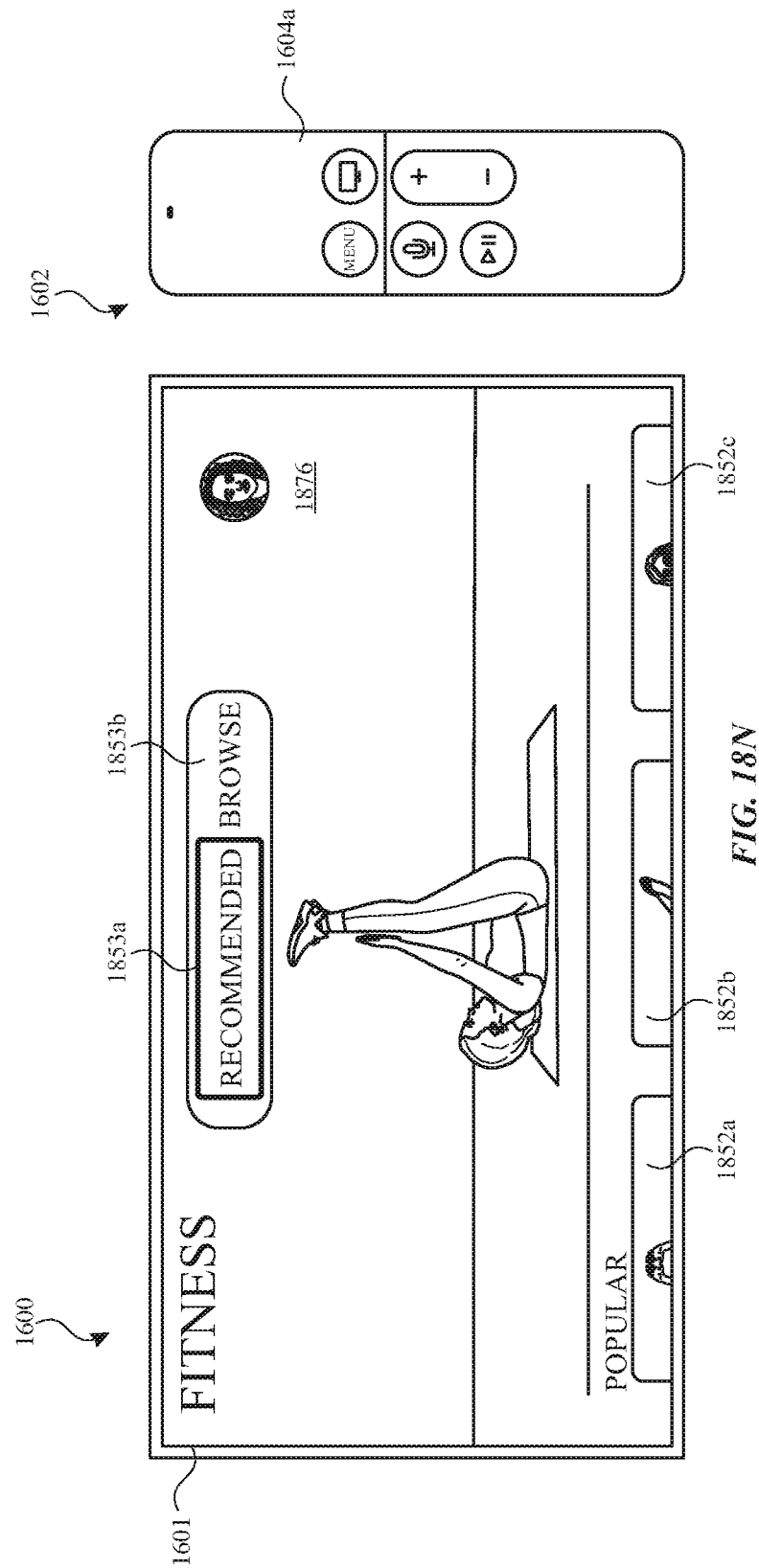

1904

1910
In accordance with a determination that the computer system meets proximity criteria relative to at least a first external electronic device of the first type and a second external electronic device of the first type:

1912
Initiate a process to display, via the display generation component, a disambiguation user interface different from the first workout suggestion user interface, wherein the disambiguation user interface includes:

1914
A first selectable user interface object that, when selected, initiates a process for displaying a second workout suggestion user interface associated with the first external electronic device, wherein the second workout suggestion user interface displays one or more workout suggestions associated with the first external electronic device.

1916
A second selectable user interface object that, when selected, initiates a process for displaying a third workout suggestion user interface different from the second workout suggestion user interface and associated with the second external electronic device, wherein the third workout suggestion user interface displays one or more workout suggestions associated with the second external electronic device.

*FIG. 19B*

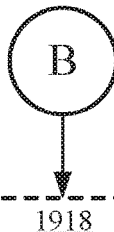

1918
Initiating the process to display the first workout suggestions user interface includes:

1920
Prior to display of the first workout suggestions user interface, cause the single external electronic device to output a notification requesting user confirmation to pair the single external electronic device with the computer system.

1922
User confirmation to pair the single external electronic device with the computer system includes user input of a personal identification number.

1924
User confirmation to pair the single external electronic device with the computer system includes a user input on a selectable user interface object.

1926
Cause the single external electronic device to generate a tactile output indicating that the single external electronic device is paired with the computer system.

FIG. 19C

USER INTERFACES FOR WORKOUT CONTENT

CROSS-REFERENCE TO RELATED APPLICATIONS

This application claims priority to U.S. Provisional Patent Application Ser. No. 63/078,311, entitled "USER INTERFACES FOR WORKOUT VIDEO CONTENT", filed Sep. 14, 2020; U.S. Provisional Patent Application Ser. No. 63/036,374, entitled "USER INTERFACES FOR WORKOUT VIDEO CONTENT", filed Jun. 8, 2020; and U.S. Provisional Patent Application Ser. No. 62/977,076, entitled "USER INTERFACES FOR WORKOUT CONTENT", filed Feb. 14, 2020, the contents of which are hereby incorporated by reference in their entirety.

FIELD

The present disclosure relates generally to computer user interfaces, and more specifically to techniques for navigating and outputting workout content.

BACKGROUND

As electronic devices, such as smartphones have become more widely used, their functions have grown beyond phone calls and text messaging. Providing an efficient method for using and implementing the various functions on these electronic devices can be complex and time-consuming.

BRIEF SUMMARY

As used herein, workout content refers to audio and/or video content that guides a user to perform a physical activity. Some techniques for navigating and outputting workout content using electronic devices, however, are generally cumbersome and inefficient. For example, some existing techniques use a complex and time-consuming user interface, which may include multiple key presses or keystrokes. Existing techniques require more time than necessary, wasting user time and device energy. This latter consideration is particularly important in battery-operated devices. As another example, some existing techniques for coordinating display of workout content among multiple devices are not intuitive and thus lead to erroneous inputs or require multiple key presses or keystrokes. Existing techniques require more time than necessary, wasting user time and device energy. This latter consideration is particularly important in battery-operated devices.

Accordingly, the present techniques provide electronic devices with faster, more efficient methods and interfaces for navigating and outputting workout content. Such methods and interfaces optionally complement or replace other methods for navigating and outputting workout content. Such methods and interfaces reduce the cognitive burden on a user and produce a more efficient human-machine interface. For battery-operated computing devices, such methods and interfaces conserve power and increase the time between battery charges.

In some embodiments, a method comprises: at an electronic device with a display: displaying, on the display, a selectable user interface object for displaying workout suggestions; detecting a user input corresponding to the selectable user interface object for displaying workout suggestions; and in response to detecting the user input corresponding to the selectable user interface object for displaying workout suggestions, displaying, on the display, a user interface for displaying workout suggestions that includes concurrently displaying: a plurality of selectable options that includes a first option that, when selected, causes the electronic device to initiate a process for displaying workout suggestions that share a first common workout parameter and a second option that, when selected, causes the electronic device to initiate a process for displaying workout suggestions that share a second common workout parameter; and a plurality of workout suggestions, wherein the plurality of workout suggestions are selected for display based on a workout history of a user of the electronic device.

In some embodiments, a non-transitory computer-readable storage medium stores one or more programs configured to be executed by one or more processors of an electronic device with a display, the one or more programs including instructions for: displaying, on the display, a selectable user interface object for displaying workout suggestions; detecting a user input corresponding to the selectable user interface object for displaying workout suggestions; and in response to detecting the user input corresponding to the selectable user interface object for displaying workout suggestions, displaying, on the display, a user interface for displaying workout suggestions that includes concurrently displaying: a plurality of selectable options that includes a first option that, when selected, causes the electronic device to initiate a process for displaying workout suggestions that share a first common workout parameter and a second option that, when selected, causes the electronic device to initiate a process for displaying workout suggestions that share a second common workout parameter; and a plurality of workout suggestions, wherein the plurality of workout suggestions are selected for display based on a workout history of a user of the electronic device.

In some embodiments, a transitory computer-readable storage medium stores one or more programs configured to be executed by one or more processors of an electronic device with a display, the one or more programs including instructions for: displaying, on the display, a selectable user interface object for displaying workout suggestions; detecting a user input corresponding to the selectable user interface object for displaying workout suggestions; and in response to detecting the user input corresponding to the selectable user interface object for displaying workout suggestions, displaying, on the display, a user interface for displaying workout suggestions that includes concurrently displaying: a plurality of selectable options that includes a first option that, when selected, causes the electronic device to initiate a process for displaying workout suggestions that share a first common workout parameter and a second option that, when selected, causes the electronic device to initiate a process for displaying workout suggestions that share a second common workout parameter; and a plurality of workout suggestions, wherein the plurality of workout suggestions are selected for display based on a workout history of a user of the electronic device.

In some embodiments, an electronic device comprises: a display; one or more processors; and memory storing one or more programs configured to be executed by the one or more processors, the one or more programs including instructions for: displaying, on the display, a selectable user interface object for displaying workout suggestions; detecting a user input corresponding to the selectable user interface object for displaying workout suggestions; and in response to detecting the user input corresponding to the selectable user interface object for displaying workout suggestions, displaying, on the display, a user interface for displaying workout suggestions that includes concurrently displaying: a plurality of selectable options that includes a first option that, when selected, causes the electronic device to initiate a process for displaying workout suggestions that share a first common workout parameter and a second option that, when selected, causes the electronic device to initiate a process for displaying workout suggestions that share a second common workout parameter; and a plurality of workout suggestions, wherein the plurality of workout suggestions are selected for display based on a workout history of a user of the electronic device.

In some embodiments, an electronic device comprises: a display; means for displaying, on the display, a selectable user interface object for displaying workout suggestions; means for detecting a user input corresponding to the selectable user interface object for displaying workout suggestions; and means, in response to detecting the user input corresponding to the selectable user interface object for displaying workout suggestions, for displaying, on the display, a user interface for displaying workout suggestions that includes concurrently displaying: a plurality of selectable options that includes a first option that, when selected, causes the electronic device to initiate a process for displaying workout suggestions that share a first common workout parameter and a second option that, when selected, causes the electronic device to initiate a process for displaying workout suggestions that share a second common workout parameter; and a plurality of workout suggestions, wherein the plurality of workout suggestions are selected for display based on a workout history of a user of the electronic device.

In some embodiments, a method comprises: at an electronic device with a display: displaying, on the display, a selectable user interface object for starting audio playback; detecting a user input corresponding to selection of the selectable user interface object for starting audio playback; and in response to detecting the user input corresponding to selection of the selectable user interface object for starting audio playback: causing audio playback of audio associated with a workout at an audio output device that is in communication with the electronic device; and causing recording of physical activity metrics corresponding to the workout, wherein the physical activity metrics are recorded by one or more sensors that are monitoring an activity level of a user of the electronic device.

In some embodiments, a non-transitory computer-readable storage medium stores one or more programs configured to be executed by one or more processors of an electronic device with a display, the one or more programs including instructions for: displaying, on the display, a selectable user interface object for starting audio playback; detecting a user input corresponding to selection of the selectable user interface object for starting audio playback; and in response to detecting the user input corresponding to selection of the selectable user interface object for starting audio playback: causing audio playback of audio associated with a workout at an audio output device that is in communication with the electronic device; and causing recording of physical activity metrics corresponding to the workout, wherein the physical activity metrics are recorded by one or more sensors that are monitoring an activity level of a user of the electronic device.

In some embodiments, a transitory computer-readable storage medium stores one or more programs configured to be executed by one or more processors of an electronic device with a display, the one or more programs including instructions for: displaying, on the display, a selectable user interface object for starting audio playback; detecting a user input corresponding to selection of the selectable user interface object for starting audio playback; and in response to detecting the user input corresponding to selection of the selectable user interface object for starting audio playback: causing audio playback of audio associated with a workout at an audio output device that is in communication with the electronic device; and causing recording of physical activity metrics corresponding to the workout, wherein the physical activity metrics are recorded by one or more sensors that are monitoring an activity level of a user of the electronic device.

In some embodiments, an electronic device comprises: a display; one or more processors; and memory storing one or more programs configured to be executed by the one or more processors, the one or more programs including instructions for: displaying, on the display, a selectable user interface object for starting audio playback; detecting a user input corresponding to selection of the selectable user interface object for starting audio playback; and in response to detecting the user input corresponding to selection of the selectable user interface object for starting audio playback: causing audio playback of audio associated with a workout at an audio output device that is in communication with the electronic device; and causing recording of physical activity metrics corresponding to the workout, wherein the physical activity metrics are recorded by one or more sensors that are monitoring an activity level of a user of the electronic device.

In some embodiments, an electronic device comprises: a display; means for displaying, on the display, a selectable user interface object for starting audio playback; means for detecting a user input corresponding to selection of the selectable user interface object for starting audio playback; and means, in response to detecting the user input corresponding to selection of the selectable user interface object for starting audio playback, for: causing audio playback of audio associated with a workout at an audio output device that is in communication with the electronic device; and causing recording of physical activity metrics corresponding to the workout, wherein the physical activity metrics are recorded by one or more sensors that are monitoring an activity level of a user of the electronic device.

In some embodiments, a method comprises: at an electronic device: causing concurrent display, via a display device, of video content and one or more representations of physical activity metrics corresponding to a user, wherein: the one or more representations of the physical activity metrics correspond to a predetermined amount of time that includes a period of time preceding playback of the content, and the one or more representations of the physical activity metrics are overlaid on the video content; and while continuing to cause display of the video content: receiving activity data based on physical activity of the user during the display of the video content; and in response to receiving the activity data, updating the display of the one or more representations of the physical activity metrics based on the received activity data.

In some embodiments, a non-transitory computer-readable storage medium stores one or more programs configured to be executed by one or more processors of an electronic device, the one or more programs including instructions for: causing concurrent display, via a display device, of video content and one or more representations of physical activity metrics corresponding to a user, wherein: the one or more representations of the physical activity metrics correspond to a predetermined amount of time that includes a period of time preceding playback of the content, and the one or more representations of the physical activity metrics are overlaid on the video content; and while continuing to cause display of the video content: receiving activity data based on physical activity of the user during the display of the video content; and in response to receiving the activity data, updating the display of the one or more representations of the physical activity metrics based on the received activity data.

In some embodiments, a transitory computer-readable storage medium stores one or more programs configured to be executed by one or more processors of an electronic device, the one or more programs including instructions for: causing concurrent display, via a display device, of video content and one or more representations of physical activity metrics corresponding to a user, wherein: the one or more representations of the physical activity metrics correspond to a predetermined amount of time that includes a period of time preceding playback of the content, and the one or more representations of the physical activity metrics are overlaid on the video content; and while continuing to cause display of the video content: receiving activity data based on physical activity of the user during the display of the video content; and in response to receiving the activity data, updating the display of the one or more representations of the physical activity metrics based on the received activity data.

In some embodiments, an electronic device comprises: one or more processors; and memory storing one or more programs configured to be executed by the one or more processors, the one or more programs including instructions for: causing concurrent display, via a display device, of video content and one or more representations of physical activity metrics corresponding to a user, wherein: the one or more representations of the physical activity metrics correspond to a predetermined amount of time that includes a period of time preceding playback of the content, and the one or more representations of the physical activity metrics are overlaid on the video content; and while continuing to cause display of the video content: receiving activity data based on physical activity of the user during the display of the video content; and in response to receiving the activity data, updating the display of the one or more representations of the physical activity metrics based on the received activity data.

In some embodiments, an electronic device comprises: means for causing concurrent display, via a display device, of video content and one or more representations of physical activity metrics corresponding to a user, wherein: the one or more representations of the physical activity metrics correspond to a predetermined amount of time that includes a period of time preceding playback of the content, and the one or more representations of the physical activity metrics are overlaid on the video content; and means, while continuing to cause display of the video content, for: receiving activity data based on physical activity of the user during the display of the video content; and in response to receiving the activity data, updating the display of the one or more representations of the physical activity metrics based on the received activity data.

In some embodiments, a method comprises: at an electronic device: causing concurrent display, via a display device, of: video content; and a workout intensity representation, wherein the workout intensity representation has a visual characteristic based on a comparison between a physical activity metric for a user of the electronic device that corresponds to a first playback position of the video content and the physical activity metric for a group of users who participated in a workout while watching the video content based on the physical activity of the group of users that corresponds to the first playback position of the video content; after the video has advanced from the first playback position to a second playback position, receiving activity data corresponding to the physical activity metric for the user; and in response to receiving the activity data, causing display, via the display device, of the workout intensity representation with the visual characteristic of the workout intensity representation changed based on the received activity data and based on a comparison between the physical activity metric for the user of the electronic device that corresponds to the second playback position of the video content and the physical activity metric for a group of users that corresponds to the second playback position of the video content.

In some embodiments, a non-transitory computer-readable storage medium stores one or more programs configured to be executed by one or more processors of an electronic device, the one or more programs including instructions for: causing concurrent display, via a display device, of: video content; and a workout intensity representation, wherein the workout intensity representation has a visual characteristic based on a comparison between a physical activity metric for a user of the electronic device that corresponds to a first playback position of the video content and the physical activity metric for a group of users who participated in a workout while watching the video content based on the physical activity of the group of users that corresponds to the first playback position of the video content; after the video has advanced from the first playback position to a second playback position, receiving activity data corresponding to the physical activity metric for the user; and in response to receiving the activity data, causing display, via the display device, of the workout intensity representation with the visual characteristic of the workout intensity representation changed based on the received activity data and based on a comparison between the physical activity metric for the user of the electronic device that corresponds to the second playback position of the video content and the physical activity metric for a group of users that corresponds to the second playback position of the video content.

In some embodiments, a transitory computer-readable storage medium stores one or more programs configured to be executed by one or more processors of an electronic device, the one or more programs including instructions for: causing concurrent display, via a display device, of: video content; and a workout intensity representation, wherein the workout intensity representation has a visual characteristic based on a comparison between a physical activity metric for a user of the electronic device that corresponds to a first playback position of the video content and the physical activity metric for a group of users who participated in a workout while watching the video content based on the physical activity of the group of users that corresponds to the first playback position of the video content; after the video has advanced from the first playback position to a second playback position, receiving activity data corresponding to the physical activity metric for the user; and in response to receiving the activity data, causing display, via the display device, of the workout intensity representation with the visual characteristic of the workout intensity representation changed based on the received activity data and based on a comparison between the physical activity metric for the user of the electronic device that corresponds to the second playback position of the video content and the physical activity metric for a group of users that corresponds to the second playback position of the video content.

In some embodiments, an electronic device comprises: one or more processors; and memory storing one or more programs configured to be executed by the one or more processors, the one or more programs including instructions for: causing concurrent display, via a display device, of: video content; and a workout intensity representation, wherein the workout intensity representation has a visual characteristic based on a comparison between a physical activity metric for a user of the electronic device that corresponds to a first playback position of the video content and the physical activity metric for a group of users who participated in a workout while watching the video content based on the physical activity of the group of users that corresponds to the first playback position of the video content; after the video has advanced from the first playback position to a second playback position, receiving activity data corresponding to the physical activity metric for the user; and in response to receiving the activity data, causing display, via the display device, of the workout intensity representation with the visual characteristic of the workout intensity representation changed based on the received activity data and based on a comparison between the physical activity metric for the user of the electronic device that corresponds to the second playback position of the video content and the physical activity metric for a group of users that corresponds to the second playback position of the video content.

In some embodiments, an electronic device comprises: means for causing concurrent display, via a display device, of: video content; and a workout intensity representation, wherein the workout intensity representation has a visual characteristic based on a comparison between a physical activity metric for a user of the electronic device that corresponds to a first playback position of the video content and the physical activity metric for a group of users who participated in a workout while watching the video content based on the physical activity of the group of users that corresponds to the first playback position of the video content; means, after the video has advanced from the first playback position to a second playback position, for receiving activity data corresponding to the physical activity metric for the user; and means, in response to receiving the activity data, for causing display, via the display device, of the workout intensity representation with the visual characteristic of the workout intensity representation changed based on the received activity data and based on a comparison between the physical activity metric for the user of the electronic device that corresponds to the second playback position of the video content and the physical activity metric for a group of users that corresponds to the second playback position of the video content.

In some embodiments, a method comprises: at an electronic device with a display, wherein the electronic device is in communication with a first external device and a second external device: displaying, on the display of the electronic device, a user interface corresponding to video content including a first selectable user interface object for enabling display of an activity session user interface associated with the video content on a display device that is in communication with the first external device; detecting a first sequence of one or more user inputs including selection of the first selectable user interface object; in response to detecting the first sequence of one or more user inputs including selection of the first selectable user interface object: causing the display device that is in communication with the first external device to display a first graphical user interface that is associated with the activity session; and while the display device is displaying the first graphical user interface that is associated with the activity session, a display device that is in communication with the second external device displays a second graphical user interface that is associated with starting the activity session and is different from the first graphical user interface, wherein a selection input directed to a portion of the second graphical user interface causes the display device that is in communication with the first external device to display an activity session user interface associated with the video content.

In some embodiments, a non-transitory computer-readable storage medium stores one or more programs configured to be executed by one or more processors of an electronic device with a display, the one or more programs including instructions for: displaying, on the display of the electronic device, a user interface corresponding to video content including a first selectable user interface object for enabling display of an activity session user interface associated with the video content on a display device that is in communication with the first external device, wherein the electronic device is in communication with a first external device and a second external device; detecting a first sequence of one or more user inputs including selection of the first selectable user interface object; in response to detecting the first sequence of one or more user inputs including selection of the first selectable user interface object: causing the display device that is in communication with the first external device to display a first graphical user interface that is associated with the activity session; and while the display device is displaying the first graphical user interface that is associated with the activity session, a display device that is in communication with the second external device displays a second graphical user interface that is associated with starting the activity session and is different from the first graphical user interface, wherein a selection input directed to a portion of the second graphical user interface causes the display device that is in communication with the first external device to display an activity session user interface associated with the video content.

In some embodiments, a transitory computer-readable storage medium stores one or more programs configured to be executed by one or more processors of an electronic device with a display, the one or more programs including instructions for: displaying, on the display of the electronic device, a user interface corresponding to video content including a first selectable user interface object for enabling display of an activity session user interface associated with the video content on a display device that is in communication with the first external device, wherein the electronic device is in communication with a first external device and a second external device; detecting a first sequence of one or more user inputs including selection of the first selectable user interface object; in response to detecting the first sequence of one or more user inputs including selection of the first selectable user interface object: causing the display device that is in communication with the first external device to display a first graphical user interface that is associated with the activity session; and while the display device is displaying the first graphical user interface that is associated with the activity session, a display device that is in communication with the second external device displays a second graphical user interface that is associated with starting the activity session and is different from the first graphical user interface, wherein a selection input directed to a portion of the second graphical user interface causes the display device that is in communication with the first external device to display an activity session user interface associated with the video content.

In some embodiments, an electronic device comprises: a display; one or more processors; and memory storing one or more programs configured to be executed by the one or more processors of the electronic device, the one or more programs including instructions for: displaying, on the display of the electronic device, a user interface corresponding to video content including a first selectable user interface object for enabling display of an activity session user interface associated with the video content on a display device that is in communication with the first external device, wherein the electronic device is in communication with a first external device and a second external device; detecting a first sequence of one or more user inputs including selection of the first selectable user interface object; in response to detecting the first sequence of one or more user inputs including selection of the first selectable user interface object: causing the display device that is in communication with the first external device to display a first graphical user interface that is associated with the activity session; and while the display device is displaying the first graphical user interface that is associated with the activity session, a display device that is in communication with the second external device displays a second graphical user interface that is associated with starting the activity session and is different from the first graphical user interface, wherein a selection input directed to a portion of the second graphical user interface causes the display device that is in communication with the first external device to display an activity session user interface associated with the video content.

In some embodiments, an electronic device comprises: a display; means for displaying, on the display of the electronic device, a user interface corresponding to video content including a first selectable user interface object for enabling display of an activity session user interface associated with the video content on a display device that is in communication with the first external device, wherein the electronic device is in communication with a first external device and a second external device; means for detecting a first sequence of one or more user inputs including selection of the first selectable user interface object; means, in response to detecting the first sequence of one or more user inputs including selection of the first selectable user interface object, for: causing the display device that is in communication with the first external device to display a first graphical user interface that is associated with the activity session; and while the display device is displaying the first graphical user interface that is associated with the activity session, a display device that is in communication with the second external device displays a second graphical user interface that is associated with starting the activity session and is different from the first graphical user interface, wherein a selection input directed to a portion of the second graphical user interface causes the display device that is in communication with the first external device to display an activity session user interface associated with the video content.

In some embodiments, a method comprises: at a computer system that is in communication with a display generation component and one or more input devices: causing display, via the display generation component, of a user interface, wherein the user interface includes: a plurality of workout suggestions displayed in a first region of the user interface, and one or more filtering options for filtering workout suggestions displayed concurrently with the plurality of workout suggestions; detecting, via the one or more input devices, a first user input directed to a first filtering option of the one or more filtering options; in accordance with a determination that the first user input directed to the first filtering option has been maintained for at least a predefined period of time: ceasing to display at least a portion of the plurality of workout suggestions within the first region of the user interface, so that the first region of the user interface includes a first subset of workout suggestions from the plurality of workout suggestions that are associated with the first filtering option and does not include workout suggestions that are not associated with the first filtering option; while the first subset of workout suggestions is displayed in the first region of the user interface, detecting, via the one or more input devices, a second user input corresponding to navigation to a first workout suggestion of the first subset of workout suggestions; and in response to detecting the second user input, causing display, via the display generation component, of a visual indication that the input is directed to the first workout suggestion while display of the first subset of workout suggestions is maintained in the first region of the user interface.

In some embodiments, a non-transitory computer-readable storage medium stores one or more programs configured to be executed by one or more processors of a computer system that is in communication with a display generation component and one or more input devices, the one or more programs including instructions for: causing display, via the display generation component, of a user interface, wherein the user interface includes: a plurality of workout suggestions displayed in a first region of the user interface, and one or more filtering options for filtering workout suggestions displayed concurrently with the plurality of workout suggestions; detecting, via the one or more input devices, a first user input directed to a first filtering option of the one or more filtering options; in accordance with a determination that the first user input directed to the first filtering option has been maintained for at least a predefined period of time: ceasing to display at least a portion of the plurality of workout suggestions within the first region of the user interface, so that the first region of the user interface includes a first subset of workout suggestions from the plurality of workout suggestions that are associated with the first filtering option and does not include workout suggestions that are not associated with the first filtering option; while the first subset of workout suggestions is displayed in the first region of the user interface, detecting, via the one or more input devices, a second user input corresponding to navigation to a first workout suggestion of the first subset of workout suggestions; and in response to detecting the second user input, causing display, via the display generation component, of a visual indication that the input is directed to the first workout suggestion while display of the first subset of workout suggestions is maintained in the first region of the user interface.

In some embodiments, a transitory computer-readable storage medium stores one or more programs configured to be executed by one or more processors of a computer system that is in communication with a display generation component and one or more input devices, the one or more programs including instructions for: causing display, via the display generation component, of a user interface, wherein the user interface includes: a plurality of workout suggestions displayed in a first region of the user interface, and one or more filtering options for filtering workout suggestions displayed concurrently with the plurality of workout suggestions; detecting, via the one or more input devices, a first user input directed to a first filtering option of the one or more filtering options; in accordance with a determination that the first user input directed to the first filtering option has been maintained for at least a predefined period of time: ceasing to display at least a portion of the plurality of workout suggestions within the first region of the user interface, so that the first region of the user interface includes a first subset of workout suggestions from the plurality of workout suggestions that are associated with the first filtering option and does not include workout suggestions that are not associated with the first filtering option; while the first subset of workout suggestions is displayed in the first region of the user interface, detecting, via the one or more input devices, a second user input corresponding to navigation to a first workout suggestion of the first subset of workout suggestions; and in response to detecting the second user input, causing display, via the display generation component, of a visual indication that the input is directed to the first workout suggestion while display of the first subset of workout suggestions is maintained in the first region of the user interface.

In some embodiments, a computer system comprises: one or more processors, wherein the computer system is in communication with a display generation component and one or more input devices; and memory storing one or more programs configured to be executed by the one or more processors, the one or more programs including instructions for: causing display, via the display generation component, of a user interface, wherein the user interface includes: a plurality of workout suggestions displayed in a first region of the user interface, and one or more filtering options for filtering workout suggestions displayed concurrently with the plurality of workout suggestions; detecting, via the one or more input devices, a first user input directed to a first filtering option of the one or more filtering options; in accordance with a determination that the first user input directed to the first filtering option has been maintained for at least a predefined period of time: ceasing to display at least a portion of the plurality of workout suggestions within the first region of the user interface, so that the first region of the user interface includes a first subset of workout suggestions from the plurality of workout suggestions that are associated with the first filtering option and does not include workout suggestions that are not associated with the first filtering option; while the first subset of workout suggestions is displayed in the first region of the user interface, detecting, via the one or more input devices, a second user input corresponding to navigation to a first workout suggestion of the first subset of workout suggestions; and in response to detecting the second user input, causing display, via the display generation component, of a visual indication that the input is directed to the first workout suggestion while display of the first subset of workout suggestions is maintained in the first region of the user interface.

In some embodiments, a computer system comprises: means for causing display, via a display generation component, of a user interface, wherein the user interface includes: a plurality of workout suggestions displayed in a first region of the user interface, and one or more filtering options for filtering workout suggestions displayed concurrently with the plurality of workout suggestions; means for detecting, via one or more input devices, a first user input directed to a first filtering option of the one or more filtering options; means for, in accordance with a determination that the first user input directed to the first filtering option has been maintained for at least a predefined period of time: ceasing to display at least a portion of the plurality of workout suggestions within the first region of the user interface, so that the first region of the user interface includes a first subset of workout suggestions from the plurality of workout suggestions that are associated with the first filtering option and does not include workout suggestions that are not associated with the first filtering option; means for, while the first subset of workout suggestions is displayed in the first region of the user interface, detecting, via the one or more input devices, a second user input corresponding to navigation to a first workout suggestion of the first subset of workout suggestions; and means for, in response to detecting the second user input, causing display, via the display generation component, of a visual indication that the input is directed to the first workout suggestion while display of the first subset of workout suggestions is maintained in the first region of the user interface.

In some embodiments, a method comprises: at a computer system that is in communication with a display generation component and one or more input devices: detecting, via the one or more input devices, a user input corresponding to a request to display a workout user interface; and in response to the request to display the workout user interface: in accordance with a determination that the computer system meets proximity criteria relative to a single external electronic device of a first type: initiating a process to display, via the display generation component, a first workout suggestion user interface, wherein the first workout suggestion user interface displays one or more workout suggestions associated with the single external electronic device, and in accordance with a determination that the computer system meets proximity criteria relative to at least a first external electronic device of the first type and a second external electronic device of the first type: initiating a process to display, via the display generation component, a disambiguation user interface different from the first workout suggestion user interface, wherein the disambiguation user interface includes: a first selectable user interface object that, when selected, initiates a process for displaying a second workout suggestion user interface associated with the first external electronic device, wherein the second workout suggestion user interface displays one or more workout suggestions associated with the first external electronic device, and a second selectable user interface object that, when selected, initiates a process for displaying a third workout suggestion user interface different from the second workout suggestion user interface and associated with the second external electronic device, wherein the third workout suggestion user interface displays one or more workout suggestions associated with the second external electronic device.

In some embodiments, a non-transitory computer-readable storage medium stores one or more programs configured to be executed by one or more processors of a computer system that is in communication with a display generation component and one or more input devices, the one or more programs including instructions for: detecting, via the one or more input devices, a user input corresponding to a request to display a workout user interface; and in response to the request to display the workout user interface: in accordance with a determination that the computer system meets proximity criteria relative to a single external electronic device of a first type: initiating a process to display, via the display generation component, a first workout suggestion user interface, wherein the first workout suggestion user interface displays one or more workout suggestions associated with the single external electronic device, and in accordance with a determination that the computer system meets proximity criteria relative to at least a first external electronic device of the first type and a second external electronic device of the first type: initiating a process to display, via the display generation component, a disambiguation user interface different from the first workout suggestion user interface, wherein the disambiguation user interface includes: a first selectable user interface object that, when selected, initiates a process for displaying a second workout suggestion user interface associated with the first external electronic device, wherein the second workout suggestion user interface displays one or more workout suggestions associated with the first external electronic device, and a second selectable user interface object that, when selected, initiates a process for displaying a third workout suggestion user interface different from the second workout suggestion user interface and associated with the second external electronic device, wherein the third workout suggestion user interface displays one or more workout suggestions associated with the second external electronic device.

In some embodiments, a transitory computer-readable storage medium stores one or more programs configured to be executed by one or more processors of a computer system that is in communication with a display generation component and one or more input devices, the one or more programs including instructions for: detecting, via the one or more input devices, a user input corresponding to a request to display a workout user interface; and in response to the request to display the workout user interface: in accordance with a determination that the computer system meets proximity criteria relative to a single external electronic device of a first type: initiating a process to display, via the display generation component, a first workout suggestion user interface, wherein the first workout suggestion user interface displays one or more workout suggestions associated with the single external electronic device, and in accordance with a determination that the computer system meets proximity criteria relative to at least a first external electronic device of the first type and a second external electronic device of the first type: initiating a process to display, via the display generation component, a disambiguation user interface different from the first workout suggestion user interface, wherein the disambiguation user interface includes: a first selectable user interface object that, when selected, initiates a process for displaying a second workout suggestion user interface associated with the first external electronic device, wherein the second workout suggestion user interface displays one or more workout suggestions associated with the first external electronic device, and a second selectable user interface object that, when selected, initiates a process for displaying a third workout suggestion user interface different from the second workout suggestion user interface and associated with the second external electronic device, wherein the third workout suggestion user interface displays one or more workout suggestions associated with the second external electronic device.

In some embodiments, a computer system comprises: one or more processors, wherein the computer system is in communication with a display generation component and one or more input devices; and memory storing one or more programs configured to be executed by the one or more processors, the one or more programs including instructions for: detecting, via the one or more input devices, a user input corresponding to a request to display a workout user interface; and in response to the request to display the workout user interface: in accordance with a determination that the computer system meets proximity criteria relative to a single external electronic device of a first type: initiating a process to display, via the display generation component, a first workout suggestion user interface, wherein the first workout suggestion user interface displays one or more workout suggestions associated with the single external electronic device, and in accordance with a determination that the computer system meets proximity criteria relative to at least a first external electronic device of the first type and a second external electronic device of the first type: initiating a process to display, via the display generation component, a disambiguation user interface different from the first workout suggestion user interface, wherein the disambiguation user interface includes: a first selectable user interface object that, when selected, initiates a process for displaying a second workout suggestion user interface associated with the first external electronic device, wherein the second workout suggestion user interface displays one or more workout suggestions associated with the first external electronic device, and a second selectable user interface object that, when selected, initiates a process for displaying a third workout suggestion user interface different from the second workout suggestion user interface and associated with the second external electronic device, wherein the third workout suggestion user interface displays one or more workout suggestions associated with the second external electronic device.

In some embodiments, a computer system comprises: means for detecting, via one or more input devices, a user input corresponding to a request to display a workout user interface; and means for, in response to the request to display the workout user interface: in accordance with a determination that the computer system meets proximity criteria relative to a single external electronic device of a first type: initiating a process to display, via a display generation component, a first workout suggestion user interface, wherein the first workout suggestion user interface displays one or more workout suggestions associated with the single external electronic device, and in accordance with a determination that the computer system meets proximity criteria relative to at least a first external electronic device of the first type and a second external electronic device of the first type: initiating a process to display, via the display generation component, a disambiguation user interface different from the first workout suggestion user interface, wherein the disambiguation user interface includes: a first selectable user interface object that, when selected, initiates a process for displaying a second workout suggestion user interface associated with the first external electronic device, wherein the second workout suggestion user interface displays one or more workout suggestions associated with the first external electronic device, and a second selectable user interface object that, when selected, initiates a process for displaying a third workout suggestion user interface different from the second workout suggestion user interface and associated with the second external electronic device, wherein the third workout suggestion user interface displays one or more workout suggestions associated with the second external electronic device.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for navigating and outputting workout content, thereby increasing the effectiveness, efficiency, and user satisfaction with such devices. Such methods and interfaces may complement or replace other methods for navigating and outputting workout content.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 4B illustrates an exemplary user interface for a multifunction device with a touch-sensitive surface that is separate from the display in accordance with some embodiments.

FIG. 11 is a flow diagram illustrating an exemplary process for displaying workout information, in accordance with some embodiments.

FIG. 13 is a flow diagram illustrating an exemplary process for displaying workout information, in accordance with some embodiments.

FIGS. 17A-17B are a flow diagram illustrating an exemplary process for displaying workout information, in accordance with some embodiments.

FIGS. 19A-19C are a flow diagram illustrating an exemplary process for displaying workout information, in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for navigating and outputting workout content. For example, a user would benefit from being shown particular workout suggestions that correspond to completed workouts. As another example, a user would benefit from being shown certain workouts metrics while workout content is outputted. Such techniques can reduce the cognitive burden on a user who navigates and outputting workout content, thereby enhancing productivity. Further, such techniques can reduce processor and battery power otherwise wasted on redundant user inputs.

Figure 7:
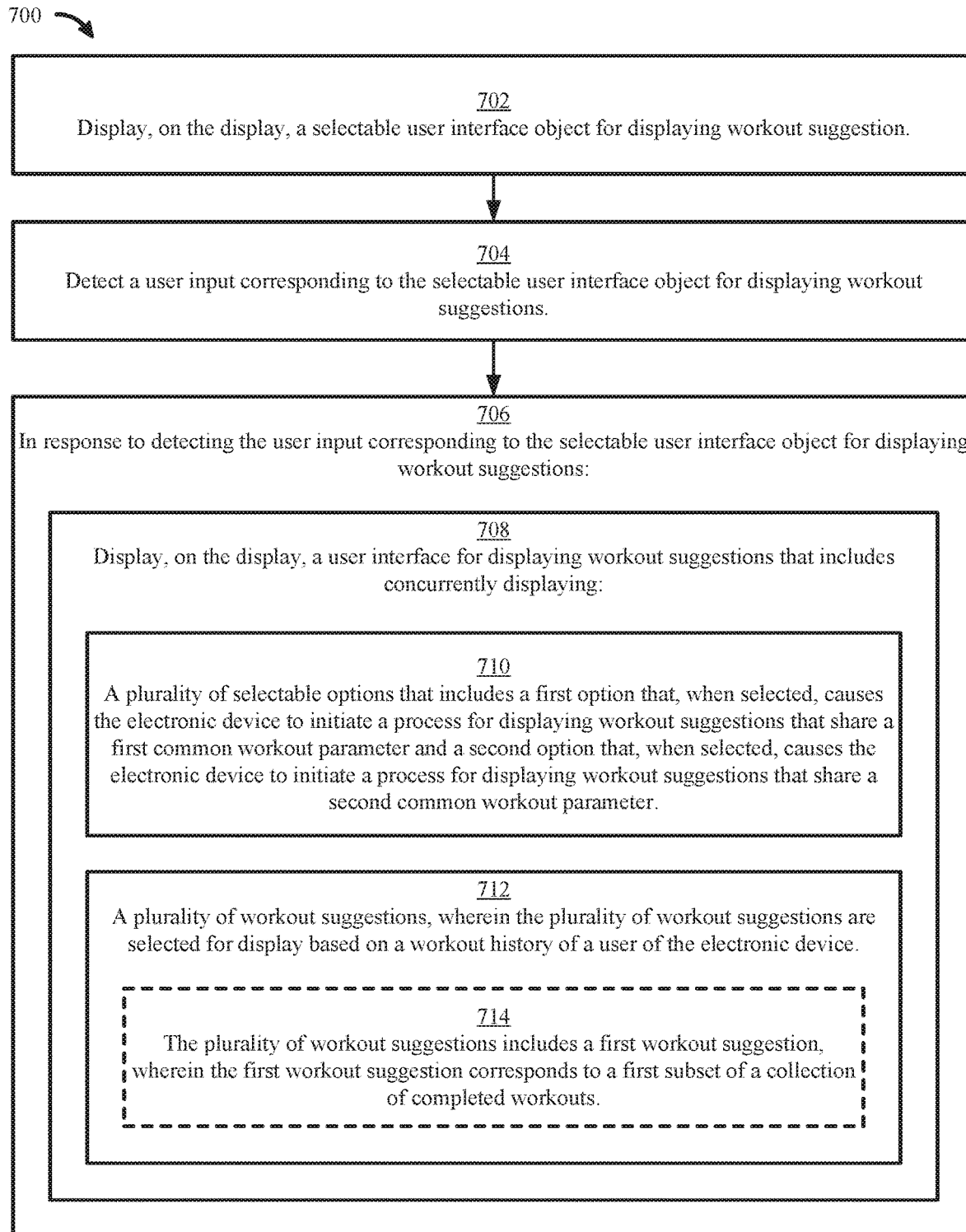
FIG. 7 is a flow diagram illustrating an exemplary process for displaying personalized workout suggestions based on completed workouts, in accordance with some embodiments.
Figure 8I:
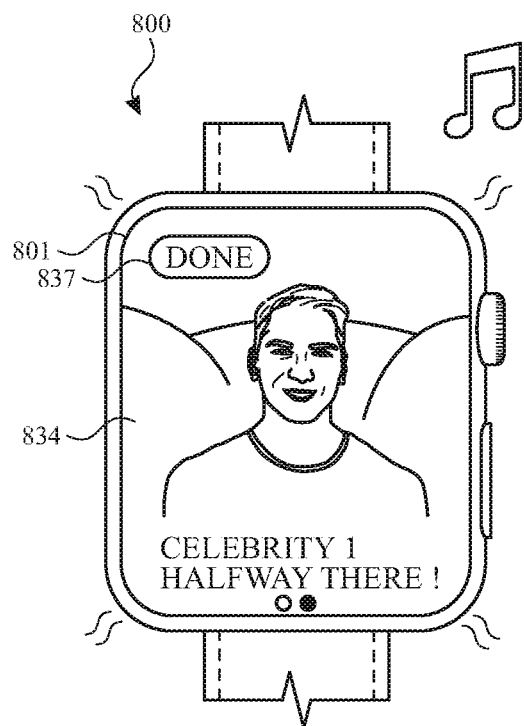
FIGS. 8A-8S illustrate exemplary user interfaces for starting an audio-based workout, in accordance with some embodiments.
Figure 8S:
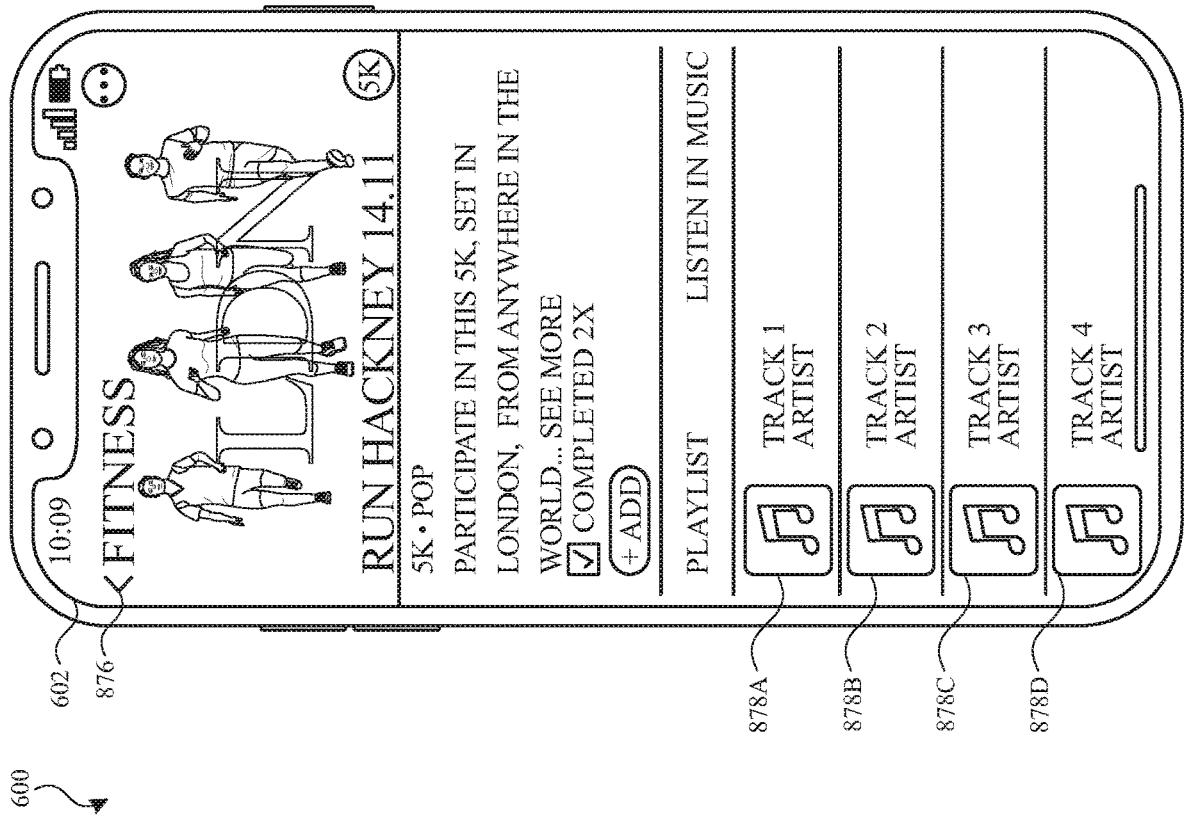
Figure 9:
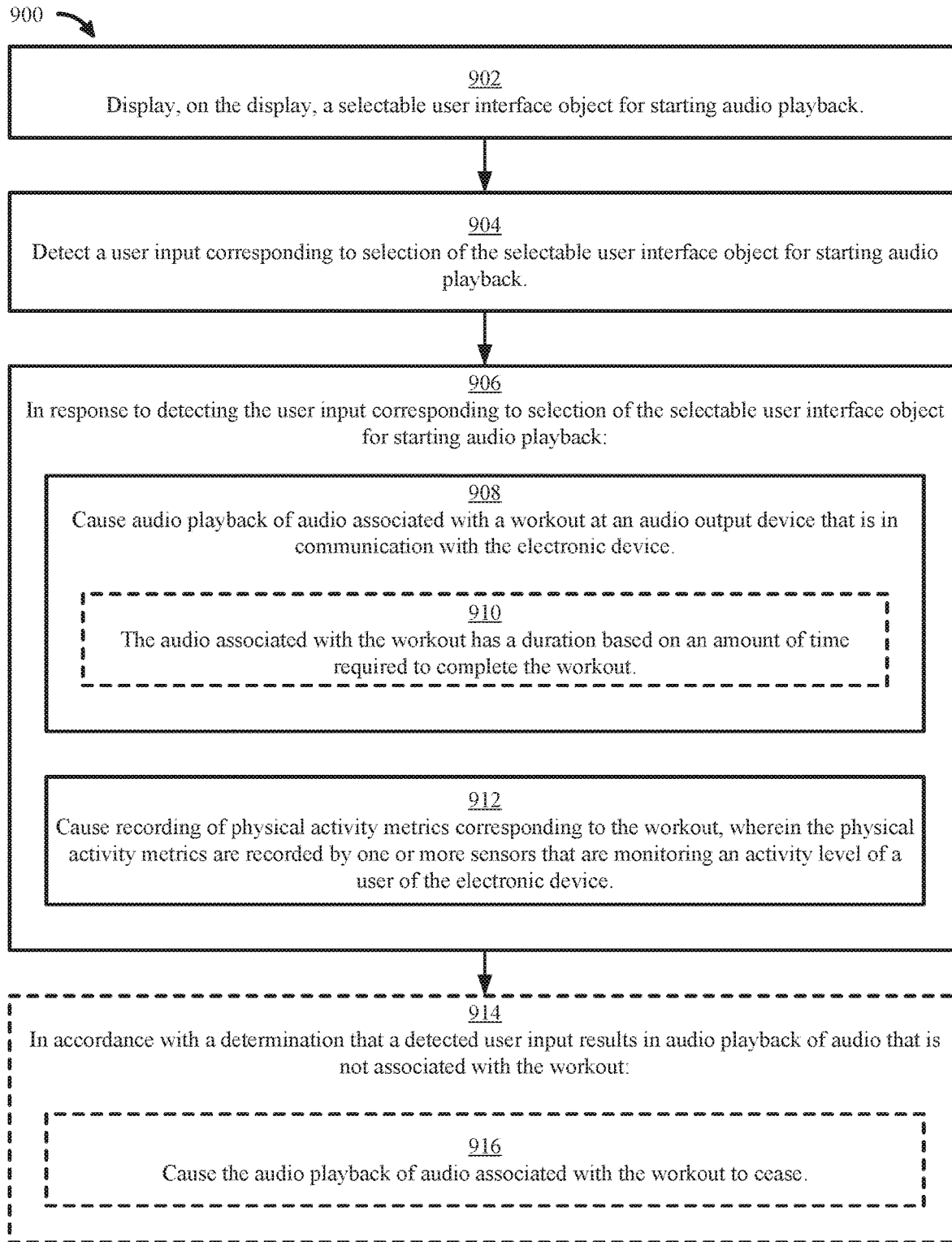
FIG. 9 is a flow diagram illustrating an exemplary process for starting an audio-based workout, in accordance with some embodiments.
Figure 10A:
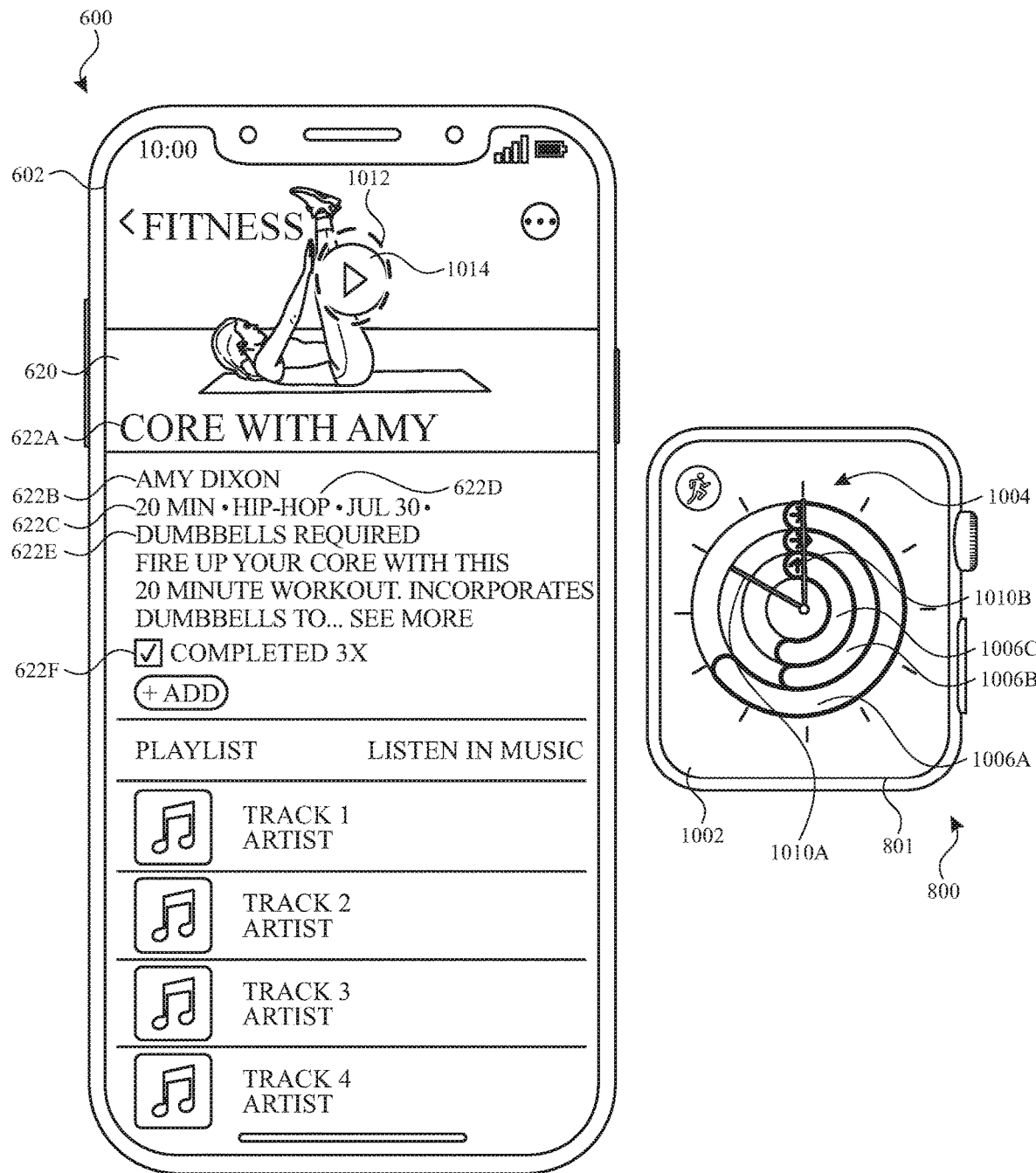
FIGS. 10A-10V illustrate exemplary user interfaces for displaying workout information, in accordance with some embodiments.
Figure 12C:
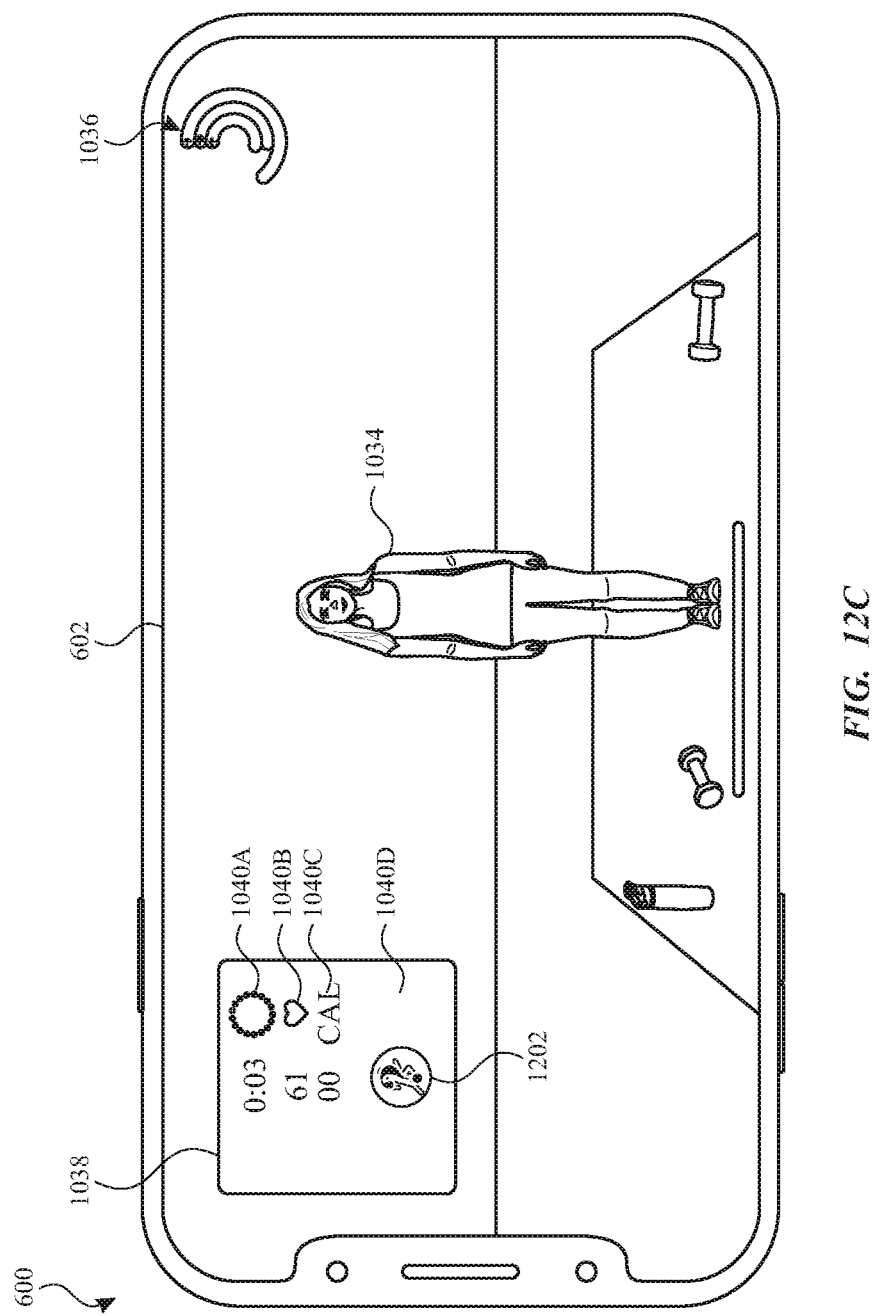
FIGS. 12A-12O illustrate exemplary user interfaces for displaying workout information, in accordance with some embodiments.
Figure 12D:
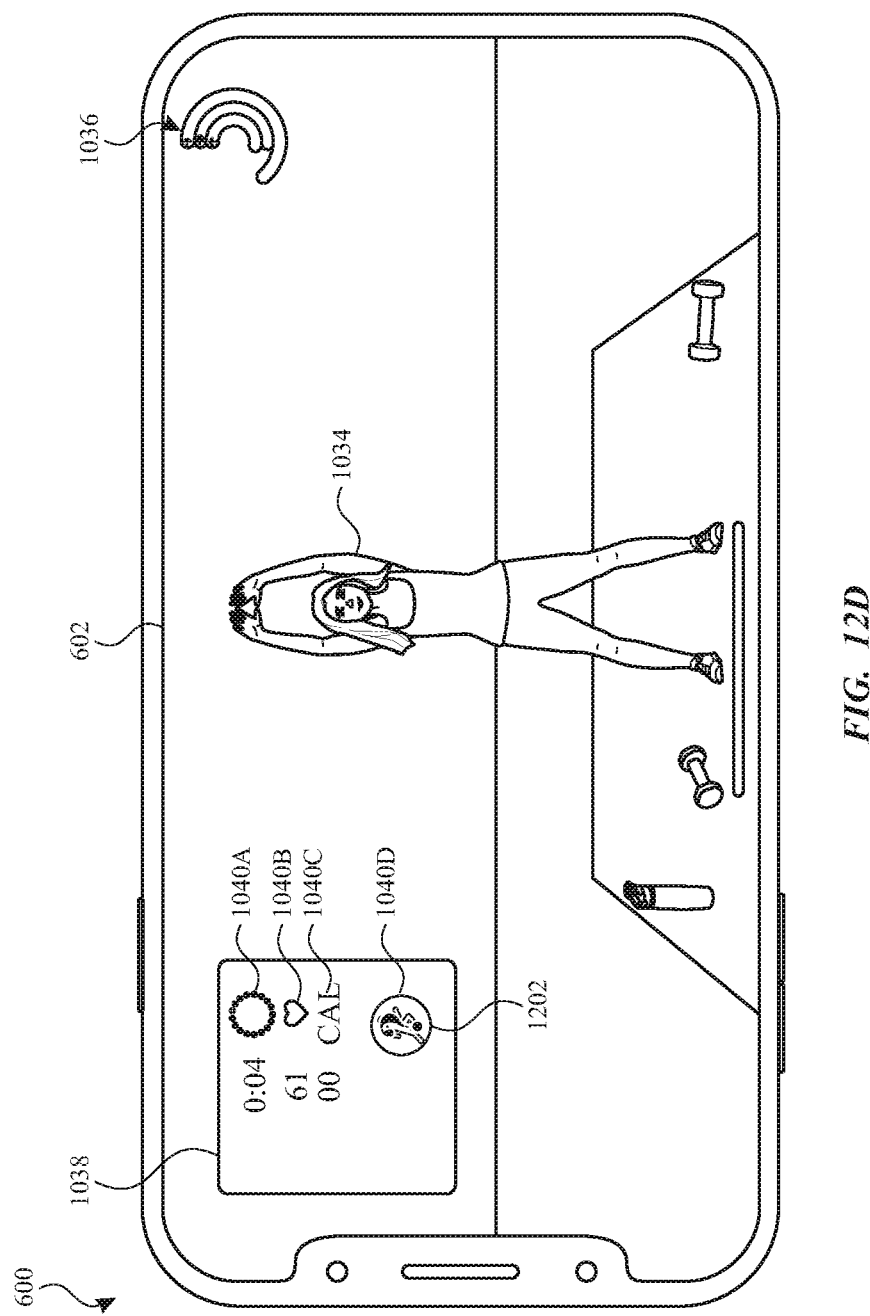
Figure 12E:
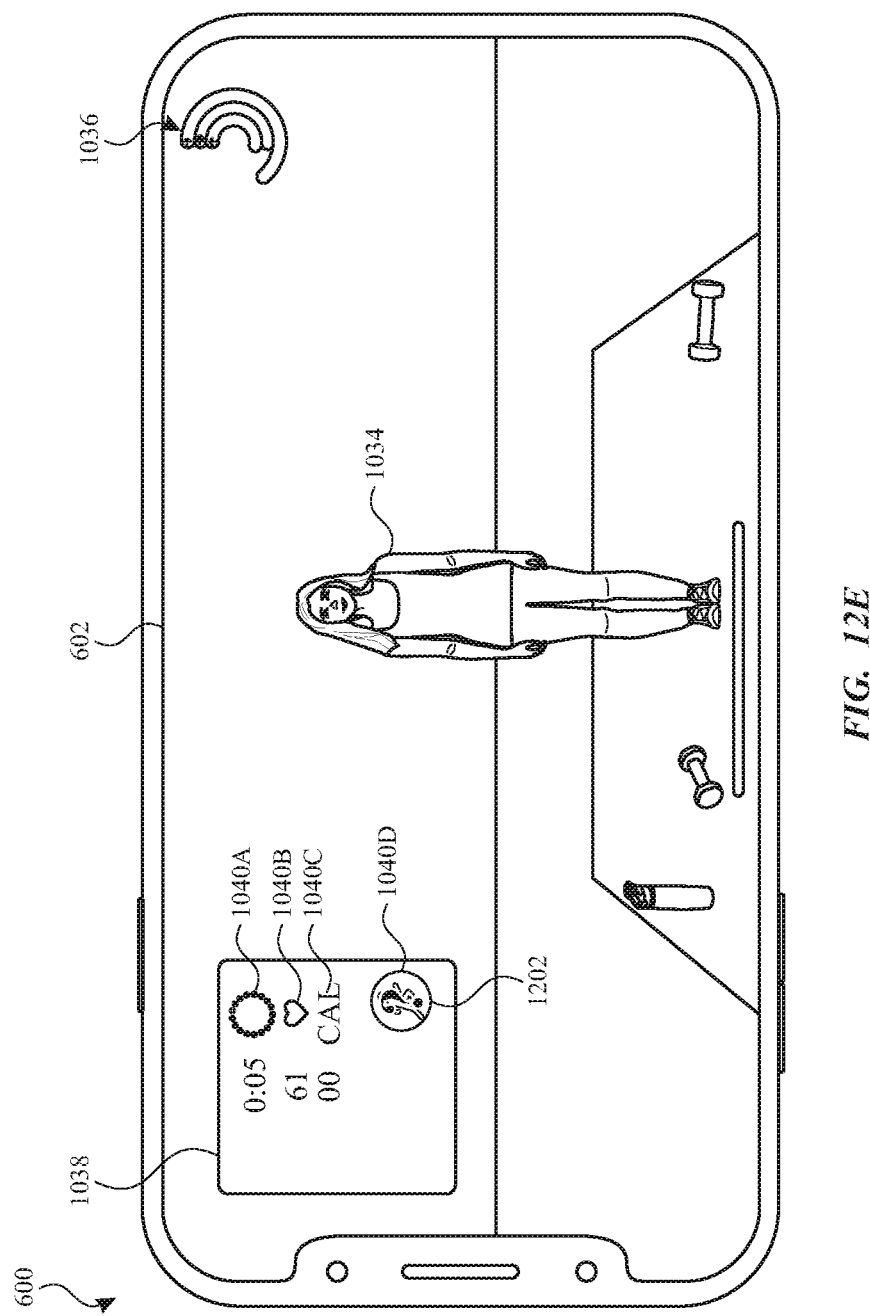
Figure 14A:
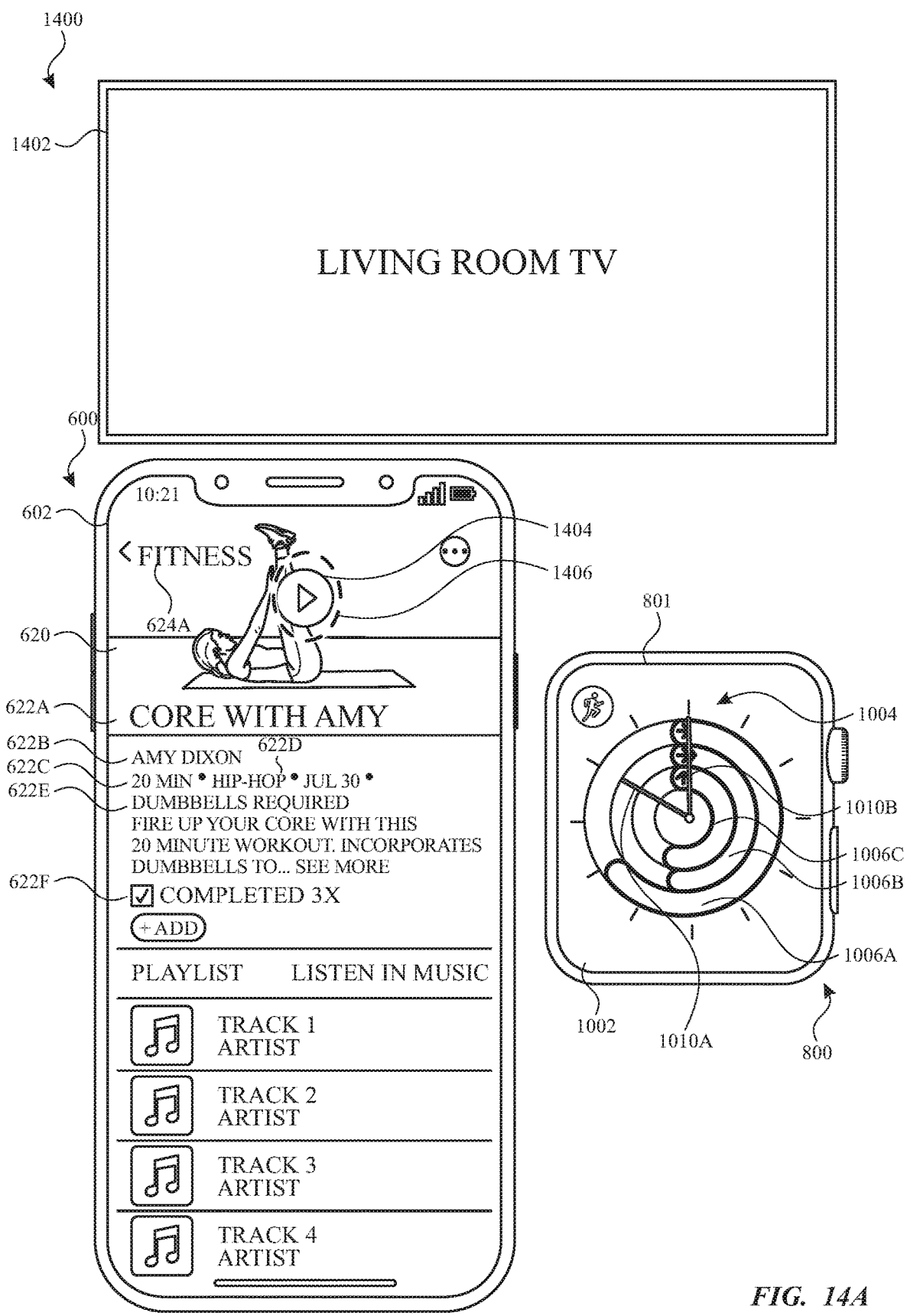
FIGS. 14A-14R illustrate exemplary user interfaces for coordinating display of workout content among multiple devices, in accordance with some embodiments.
Figure 14R:
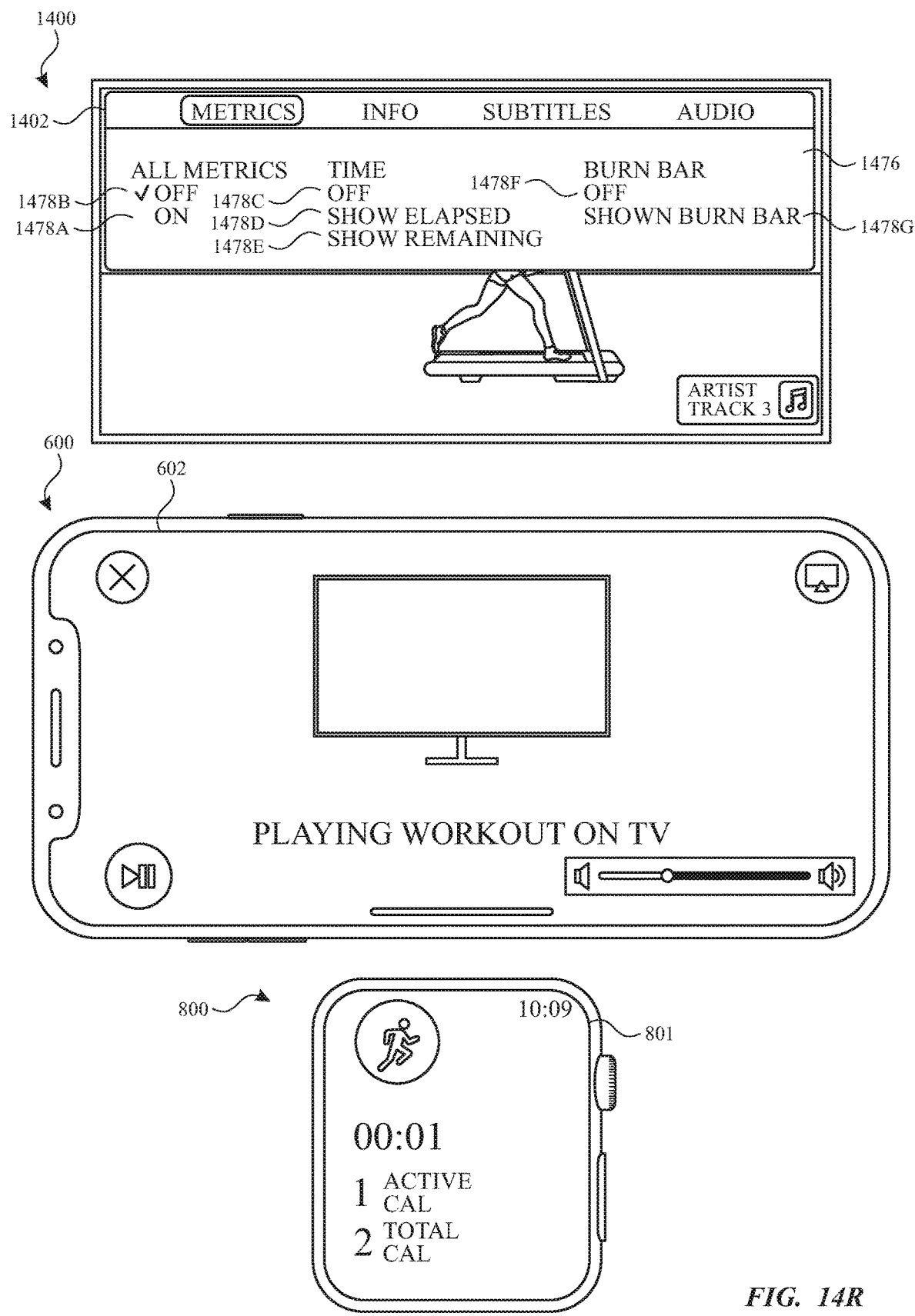
Figure 15:
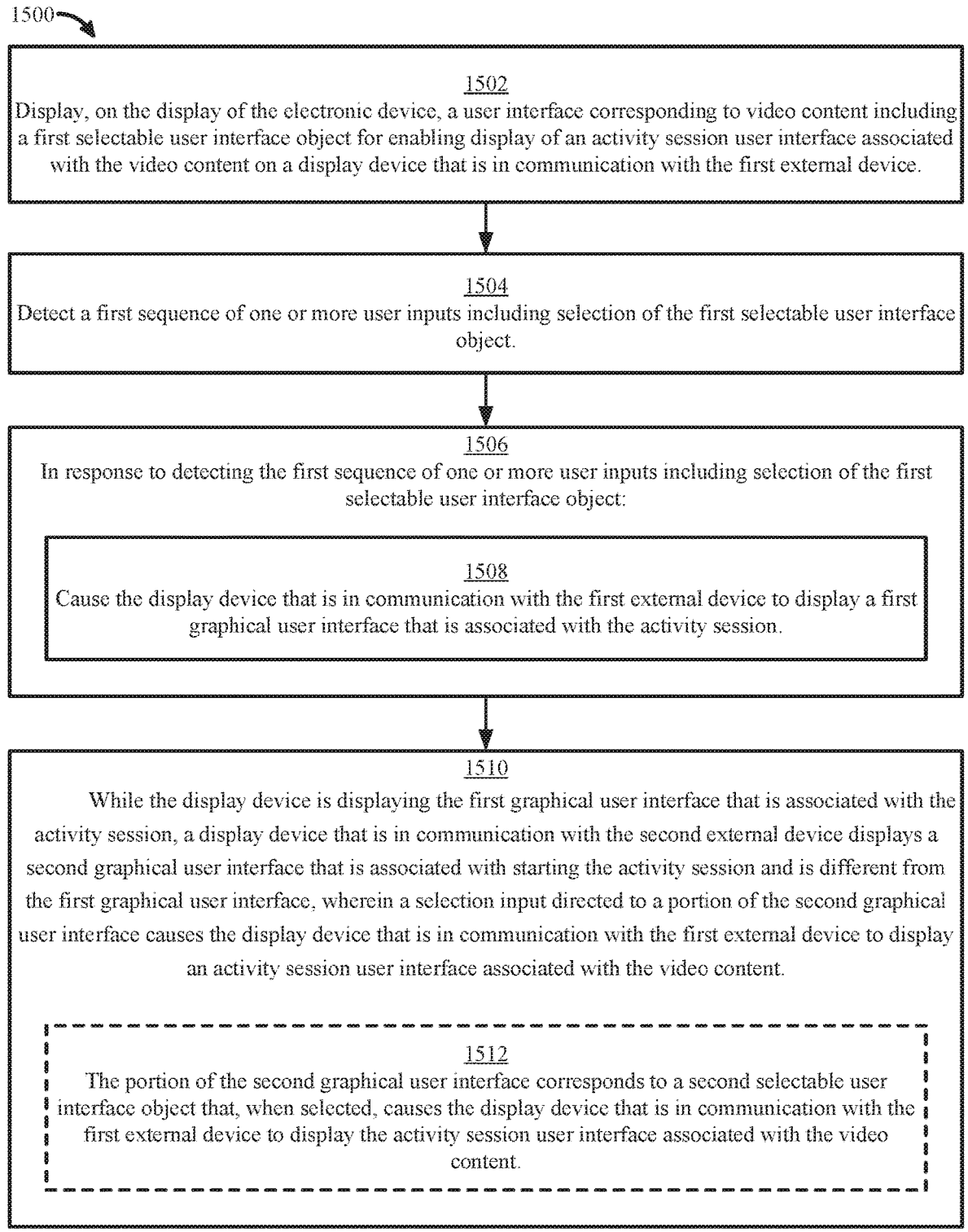
FIG. 15 is a flow diagram illustrating an exemplary process for coordinating display of workout content among multiple devices, in accordance with some embodiments.
Figure 16A:
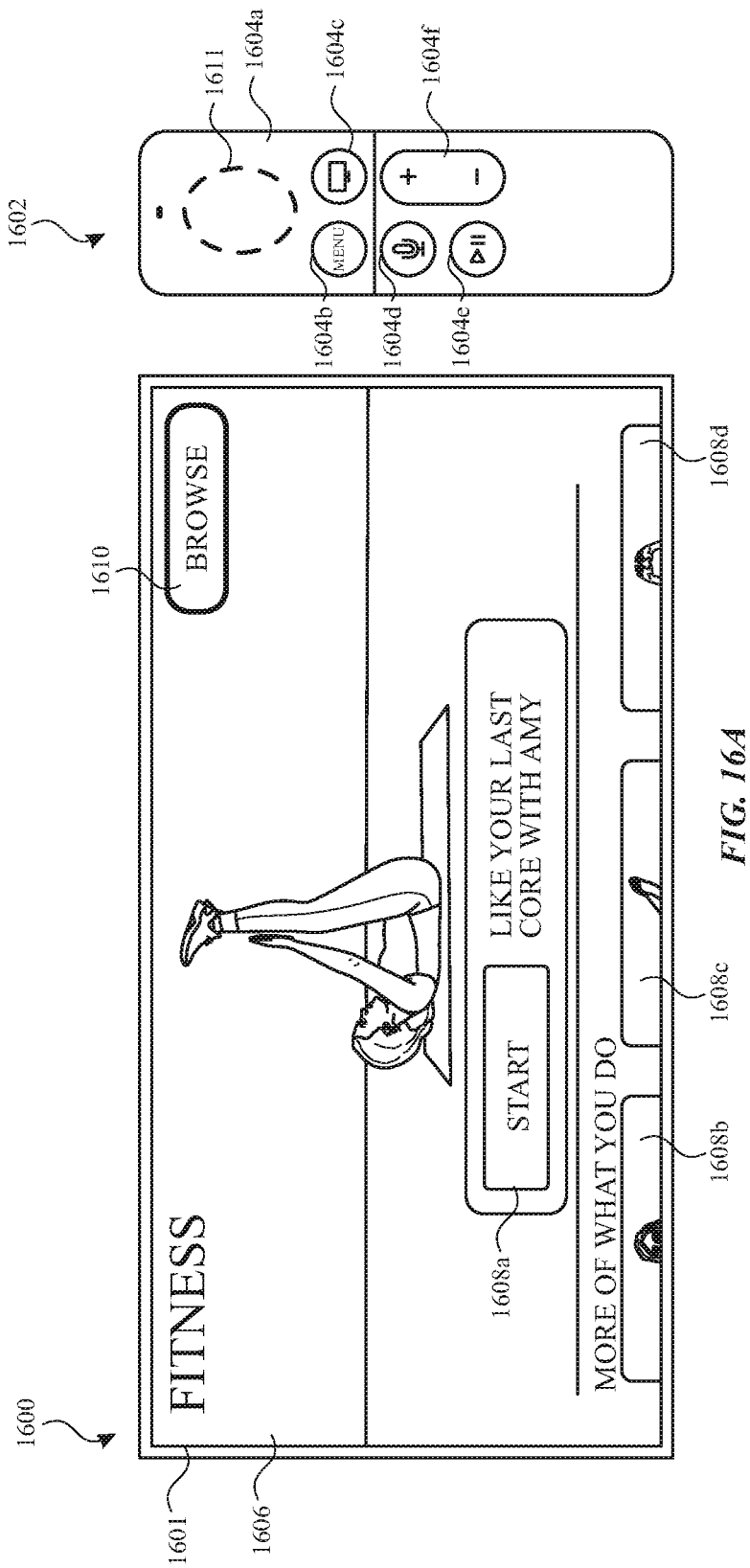
FIGS. 16A-16R illustrate exemplary user interfaces for displaying workout information, in accordance with some embodiments.
Figure 16R:
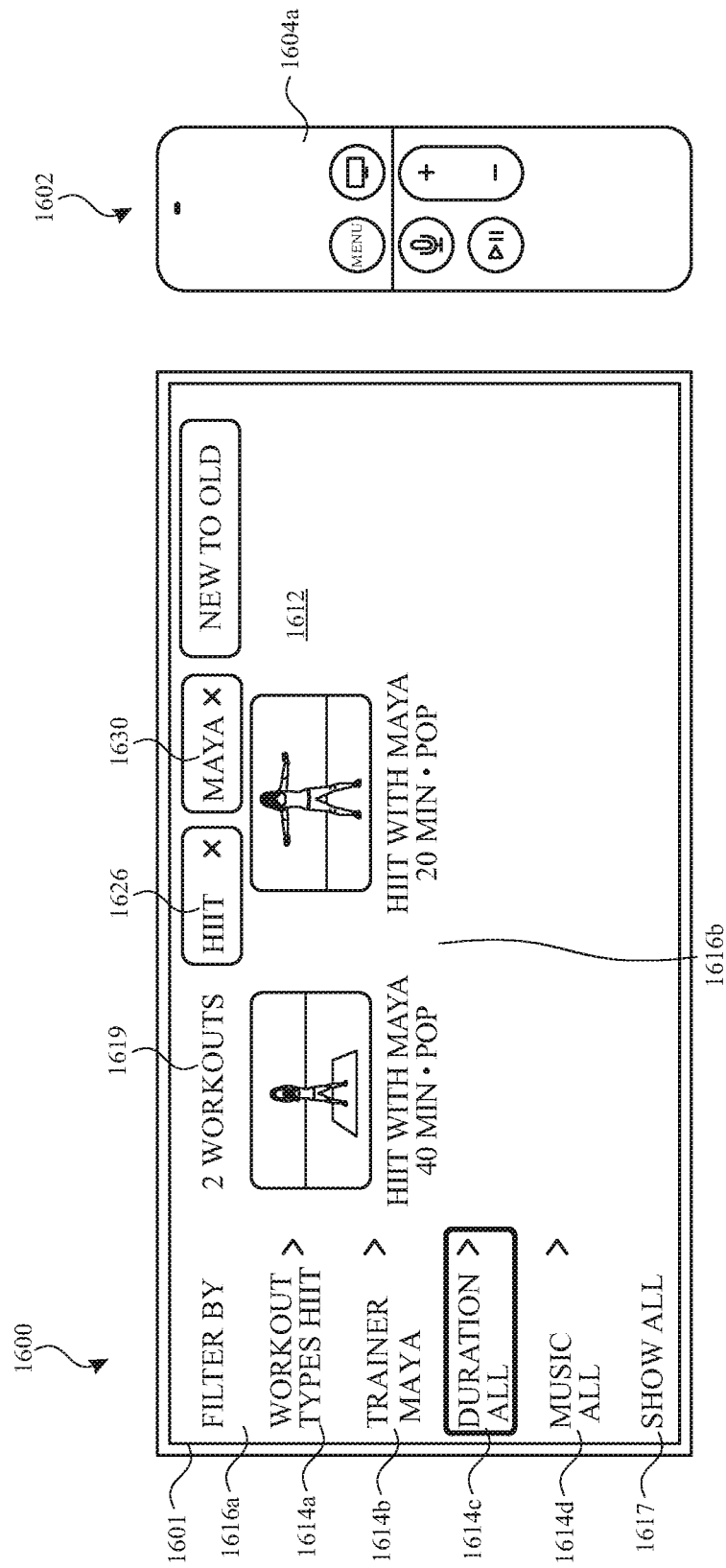
Figure 17B:
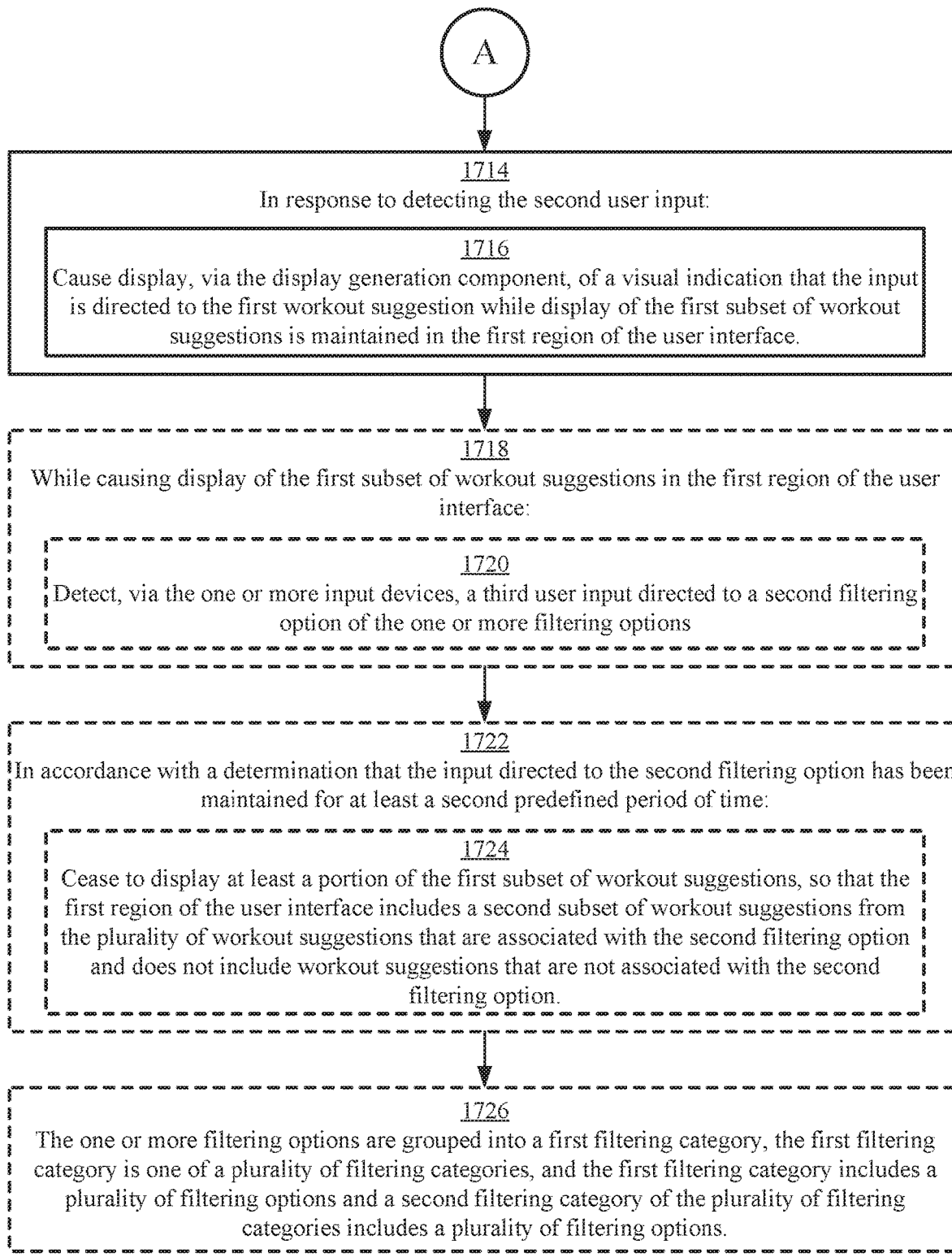
Figure 18A:
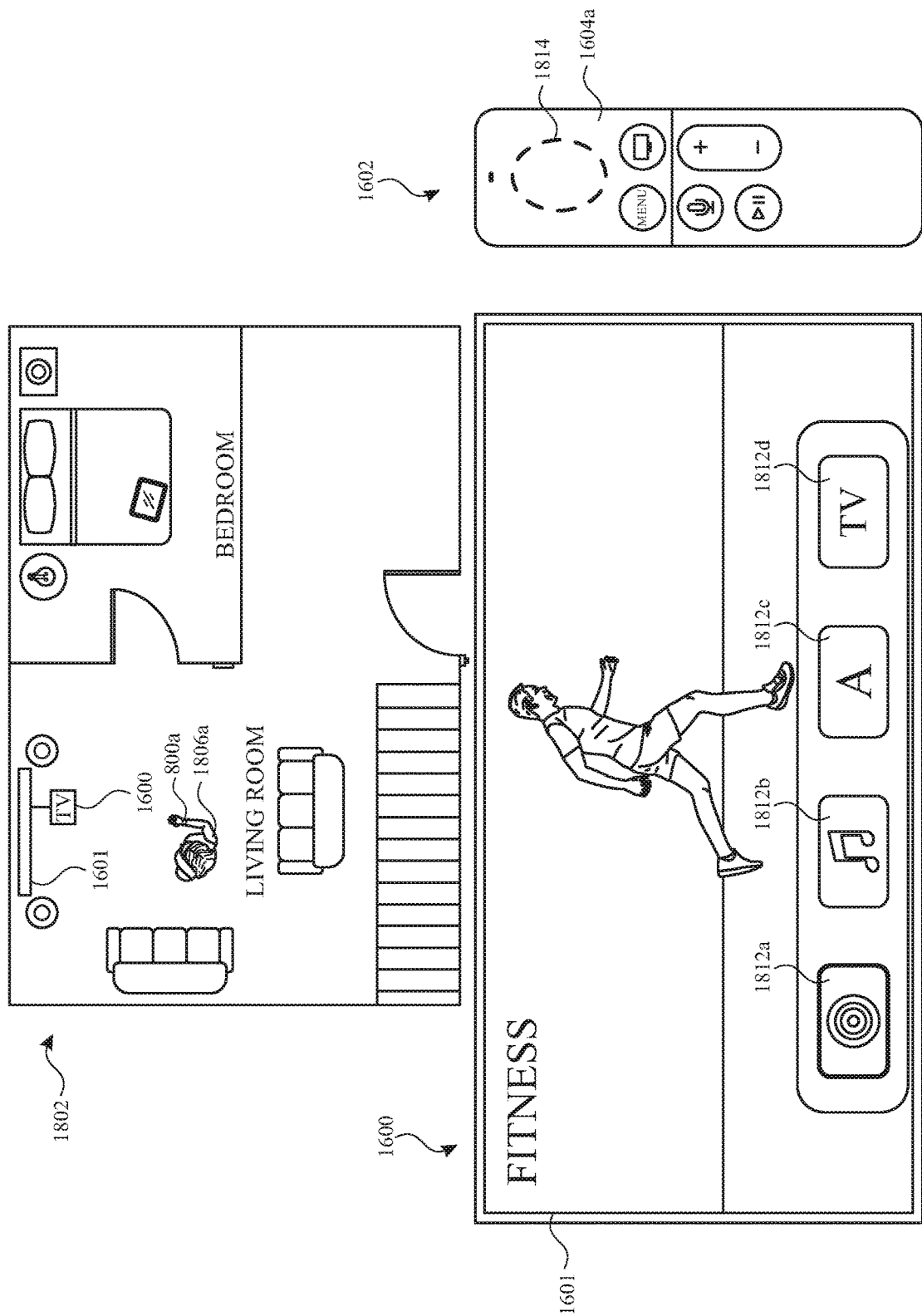
FIGS. 18A-18V illustrate exemplary user interfaces for displaying workout information, in accordance with some embodiments.
Figure 18V:
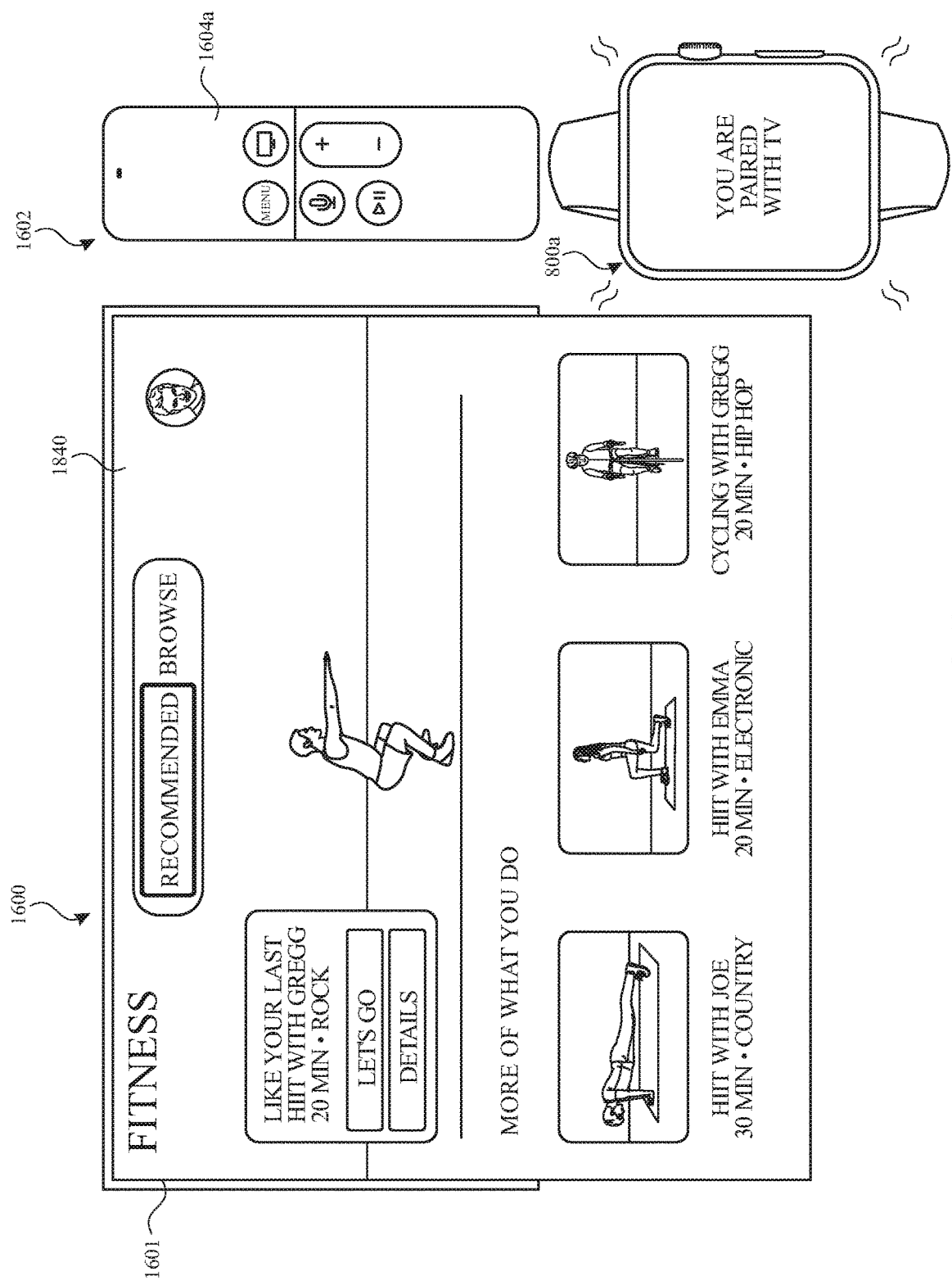
Figure 19A:
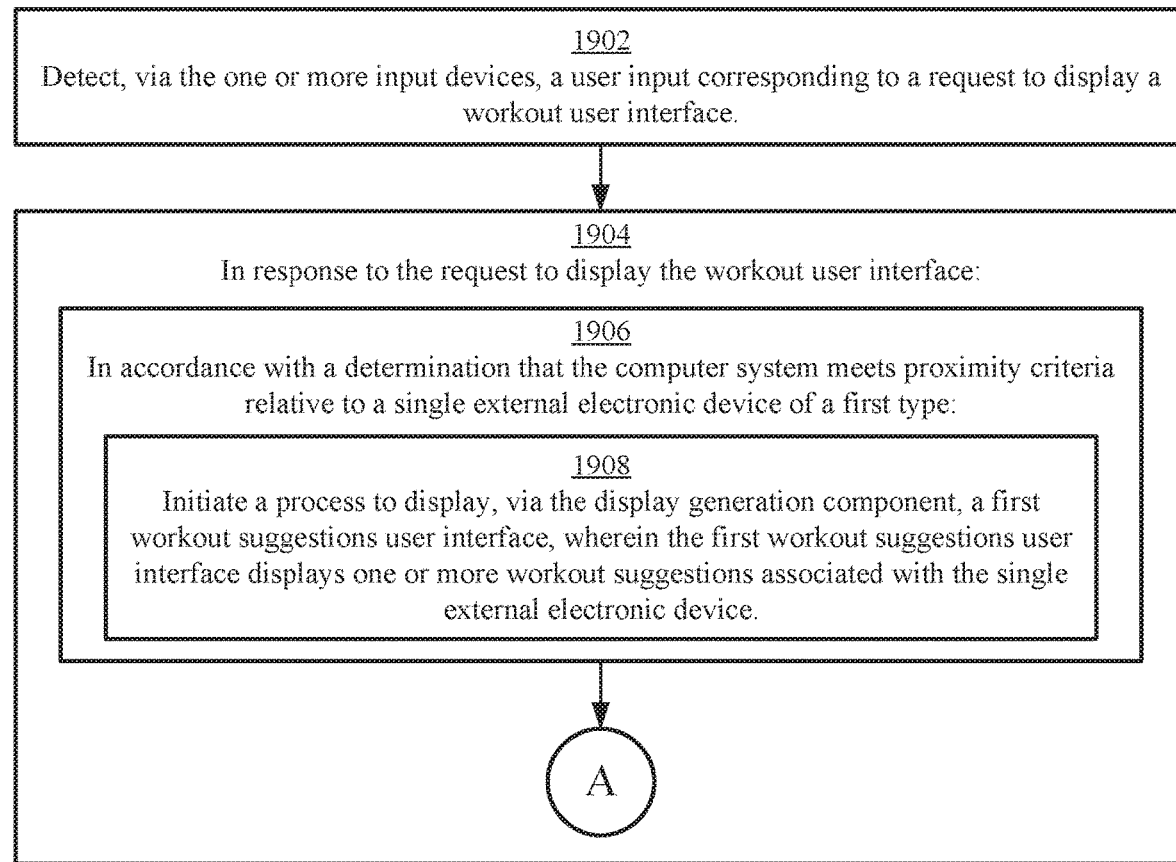

Below, FIGS. 1A-1B, 2, 3, 4A-4B, and 5A-5B provide a description of exemplary devices for performing the techniques for managing event notifications. FIGS. 6A-6EE illustrate exemplary user interfaces for displaying personalized workout suggestions based on completed workouts. FIG. 7 is a flow diagram illustrating an exemplary process for displaying personalized workout suggestions based on completed workouts, in accordance with some embodiments. The user interfaces in FIGS. 6A-6EE are used to illustrate the processes described below, including the processes in FIG. 7. FIGS. 8A-8S illustrate exemplary user interfaces for starting an audio-based workout. FIG. 9 is a flow diagram illustrating an exemplary process for starting an audio-based workout, in accordance with some embodiments. The user interfaces in FIGS. 8A-8S are used to illustrate the processes described below, including the processes in FIG. 9. FIGS. 10A-10V illustrate exemplary user interfaces for displaying workout information. FIG. 11 is a flow diagram illustrating an exemplary process for displaying workout information, in accordance with some embodiments. The user interfaces in FIGS. 10A-10V are used to illustrate the processes described below, including the processes in FIG. 11. FIGS. 12A-12O illustrate exemplary user interfaces for displaying workout information. FIG. 13 is a flow diagram illustrating an exemplary process for displaying workout information, in accordance with some embodiments. The user interfaces in FIGS. 12A-12O are used to illustrate the processes described below, including the processes in FIG. 13. FIGS. 14A-14R illustrate exemplary user interfaces for coordinating display of workout content among multiple devices. FIG. 15 is a flow diagram illustrating an exemplary process for coordinating display of workout content among multiple devices, in accordance with some embodiments. The user interfaces in FIGS. 14A-14R are used to illustrate the processes described below, including the processes in FIG. 15. FIGS. 16A-16R illustrate exemplary user interfaces for displaying workout information. FIGS. 17A-17B are a flow diagram illustrating an exemplary process for displaying workout information, in accordance with some embodiments. The user interfaces in FIGS. 16A-16R are used to illustrate the processes described below, including the processes in FIGS. 17A-17B. FIGS. 18A-18V illustrate exemplary user interfaces for displaying workout information. FIGS. 19A-19C are a flow diagram illustrating an exemplary process for displaying workout information, in accordance with some embodiments. The user interfaces in FIGS. 18A-18V are used to illustrate the processes described below, including the processes in FIGS. 19A-19C.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
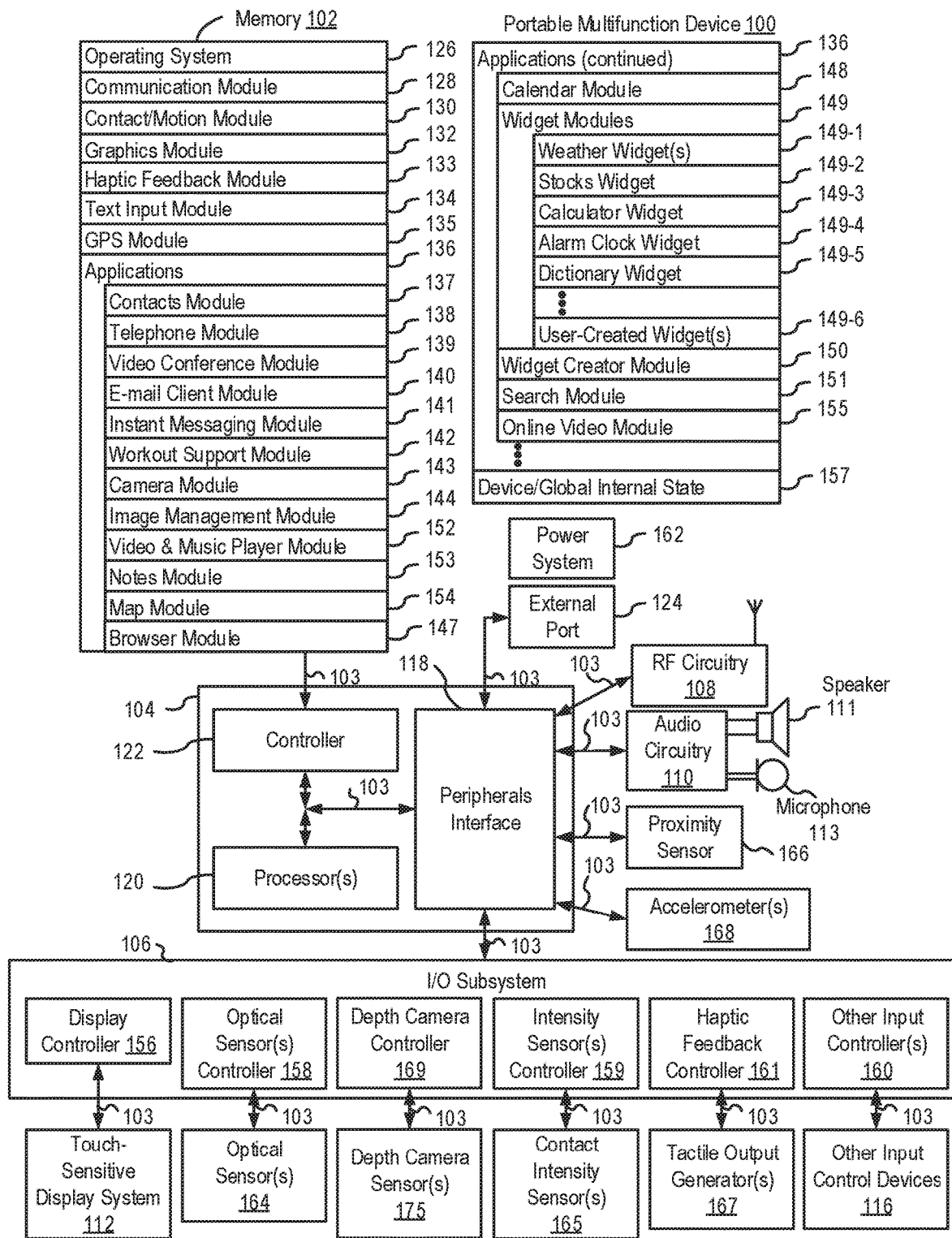
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures) as input. In some embodiments, the one or more input devices are integrated with the computer system. In some embodiments, the one or more input devices are separate from the computer system.

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch- Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
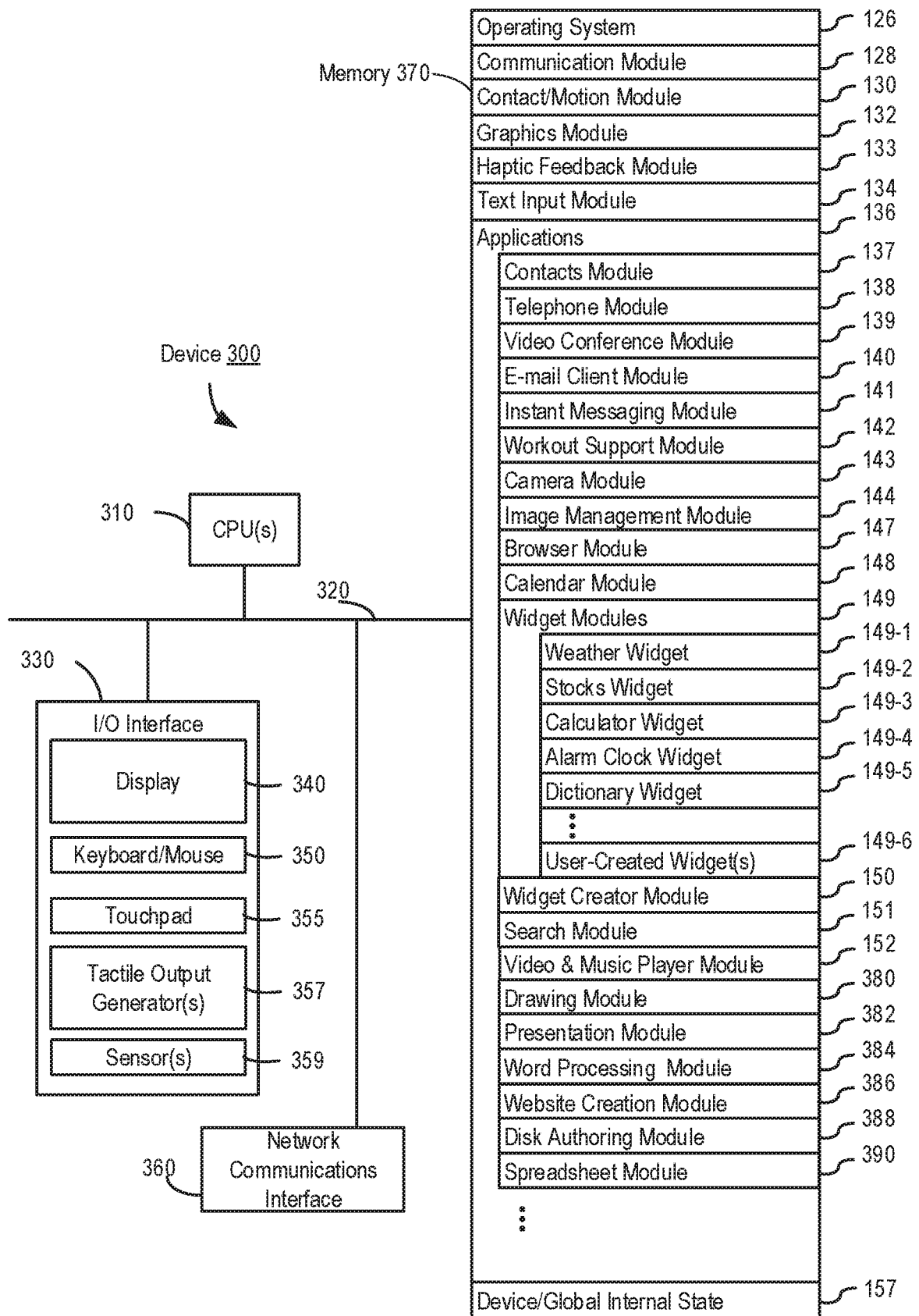
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
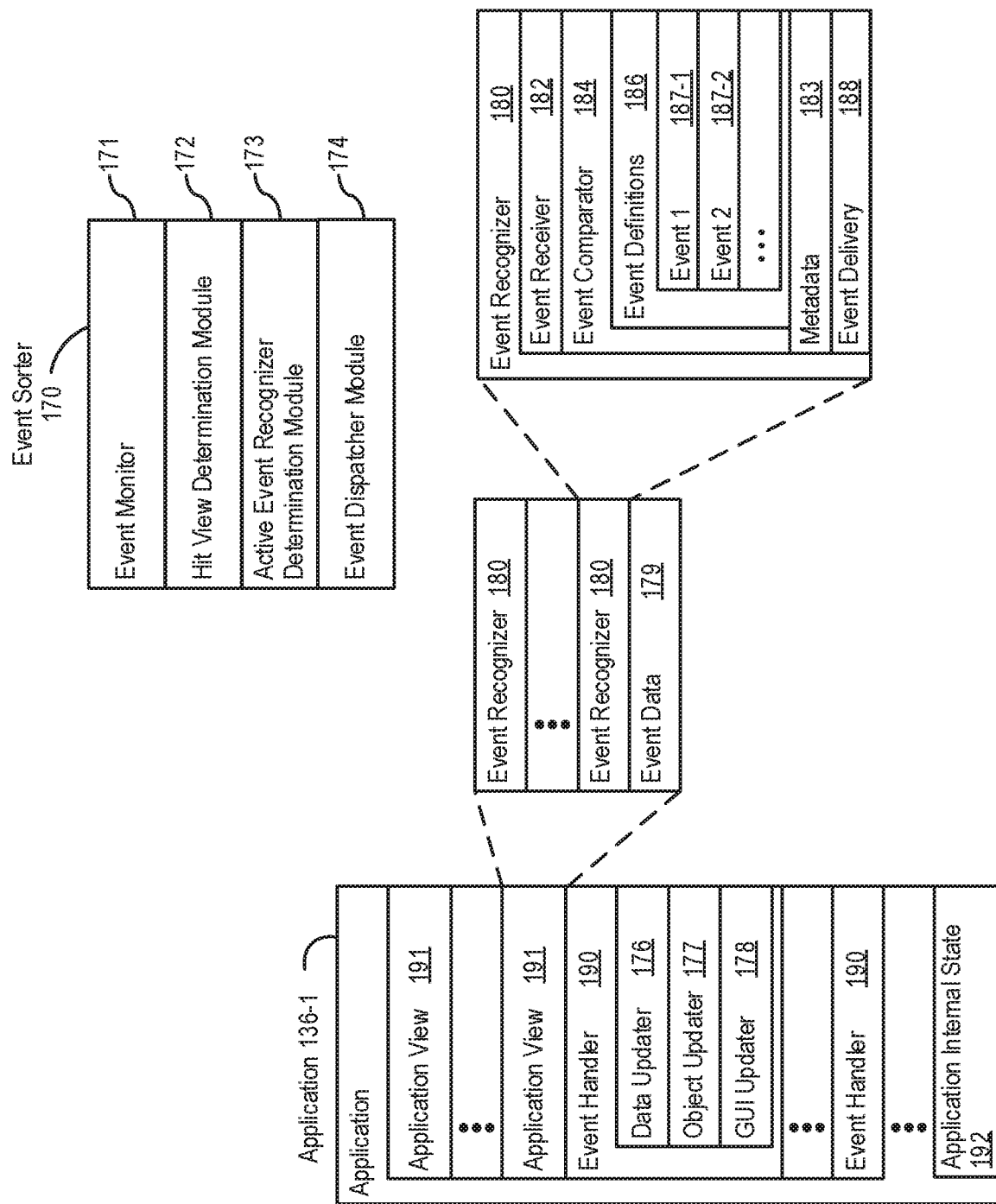
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
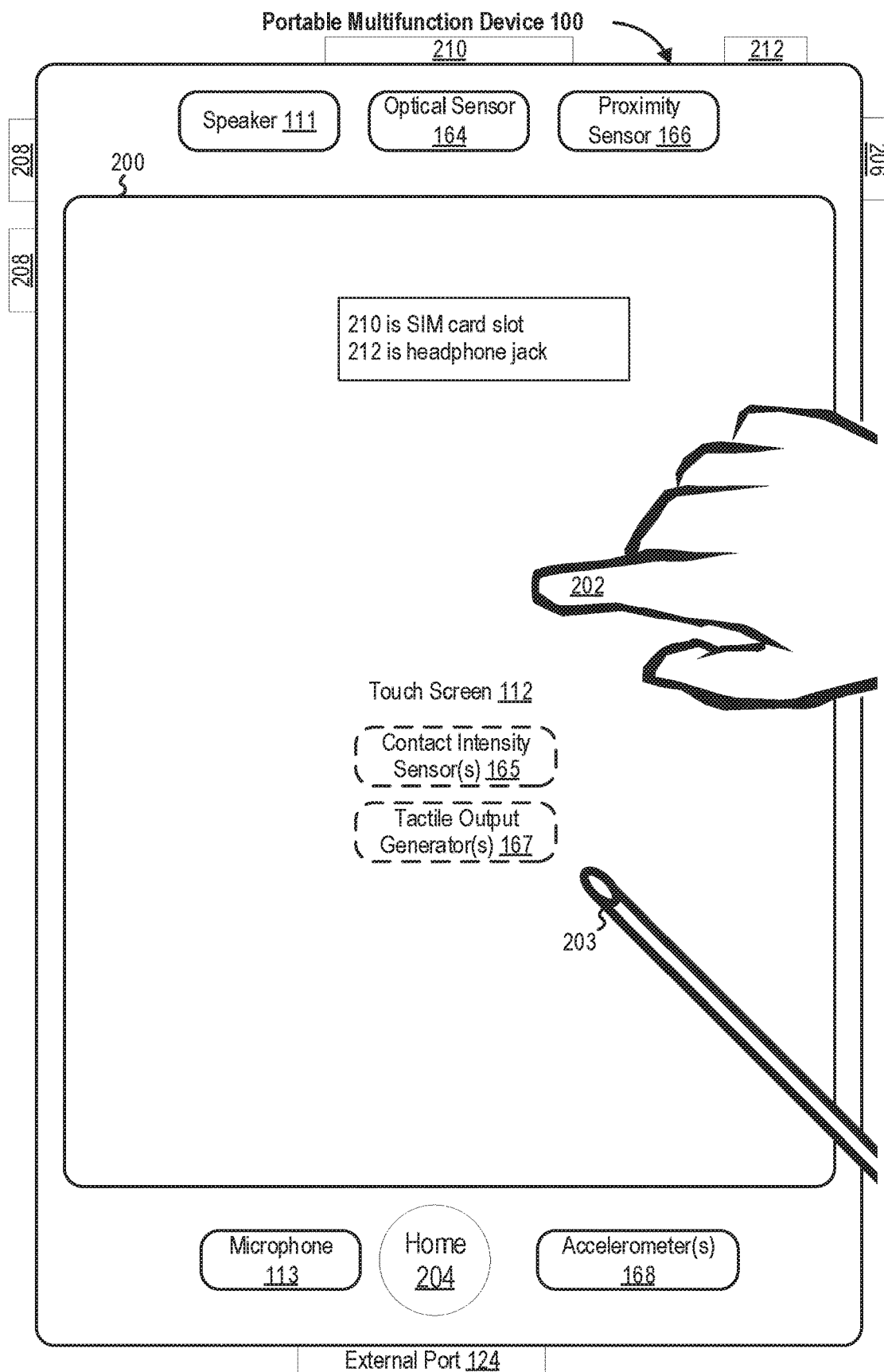
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
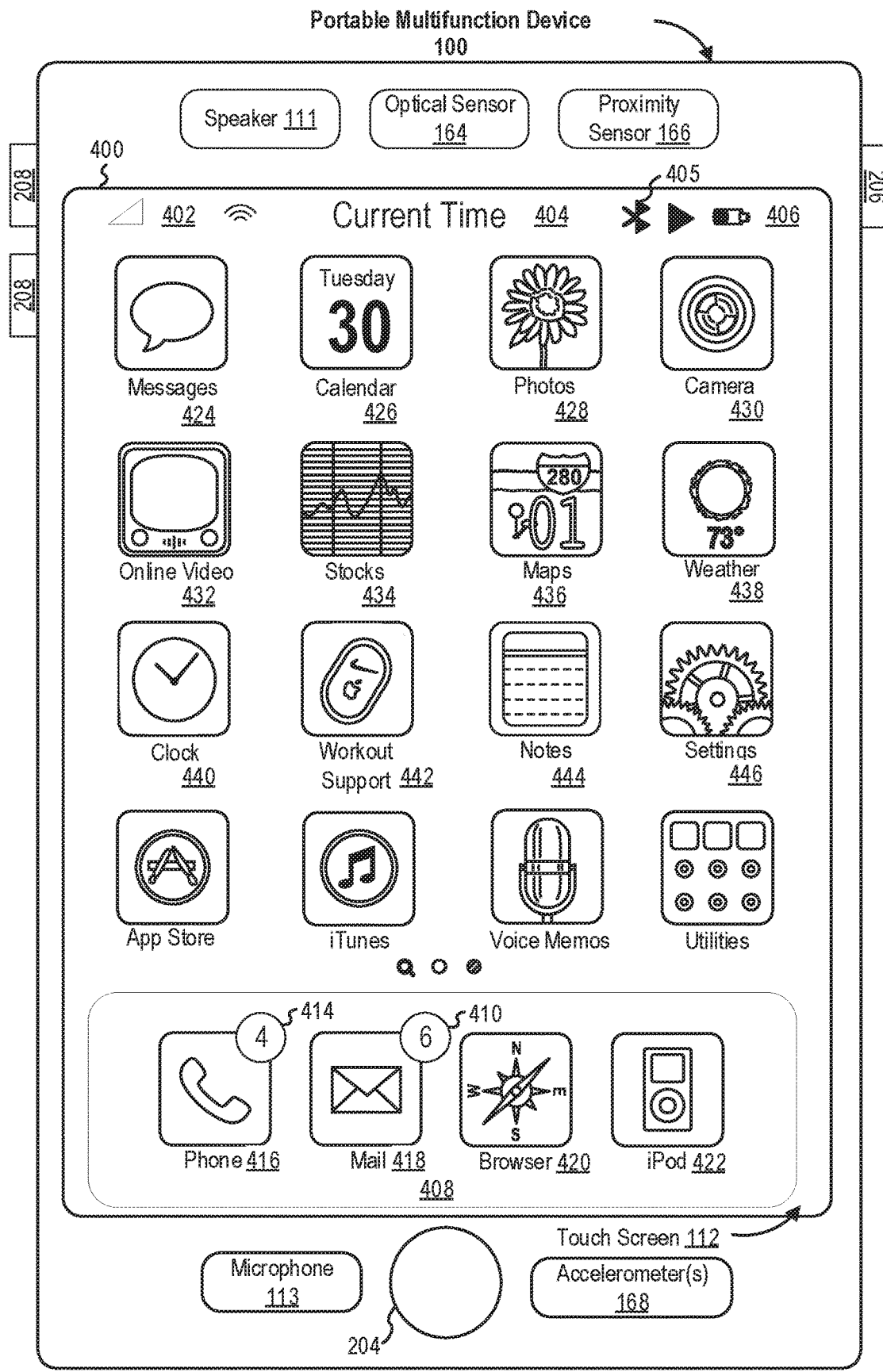
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

- Signal strength indicator(s) 402 for wireless communication(s), such as cellular and Wi-Fi signals;
- Time 404;
- Bluetooth indicator 405;
- Battery status indicator 406;
- Tray 408 with icons for frequently used applications, such as:
  - Icon 416 for telephone module 138, labeled "Phone," which optionally includes an indicator 414 of the number of missed calls or voicemail messages;
  - Icon 418 for e-mail client module 140, labeled "Mail," which optionally includes an indicator 410 of the number of unread e-mails;
  - Icon 420 for browser module 147, labeled "Browser;" and
  - Icon 422 for video and music player module 152, also referred to as iPod (trademark of Apple Inc.) module 152, labeled "iPod;" and
- Icons for other applications, such as:
  - Icon 424 for IM module 141, labeled "Messages;"
  - Icon 426 for calendar module 148, labeled "Calendar;"
  - Icon 428 for image management module 144, labeled "Photos;"
  - Icon 430 for camera module 143, labeled "Camera;"
  - Icon 432 for online video module 155, labeled "Online Video;"
  - Icon 434 for stocks widget 149-2, labeled "Stocks;"

Icon 436 for map module 154, labeled "Maps;"

Icon 438 for weather widget 149-1, labeled "Weather;"

Icon 440 for alarm clock widget 149-4, labeled "Clock;"

Icon 442 for workout support module 142, labeled "Workout Support;"

Icon 444 for notes module 153, labeled "Notes;" and

Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
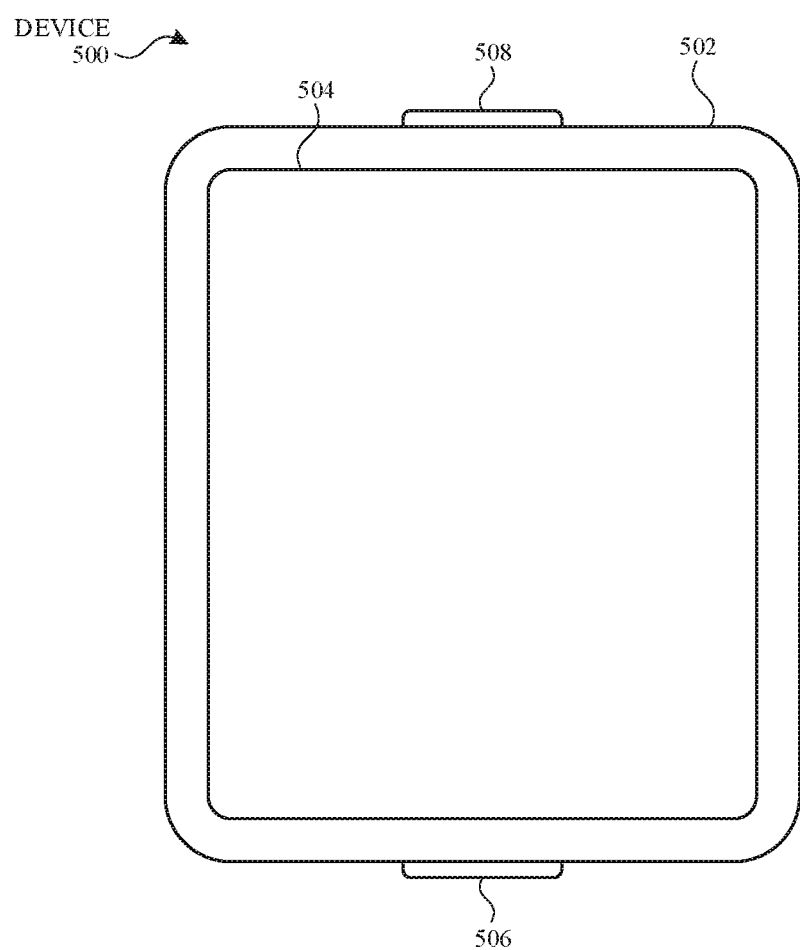
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
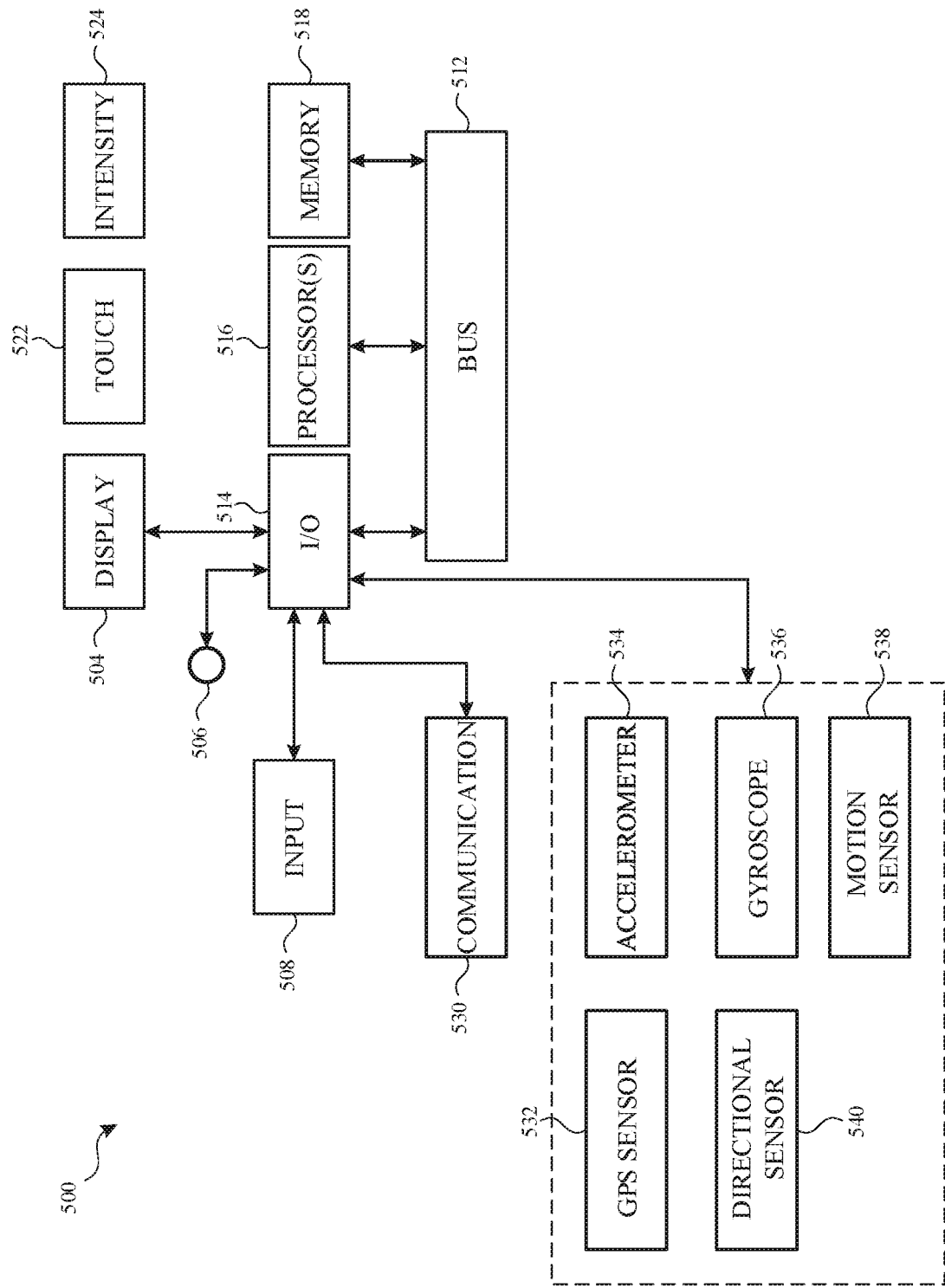
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700, 900, 1100, 1300, and 1500 (FIGS. 7, 9, 11, 13, and 15). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

Attention is now directed towards embodiments of user interfaces ("UI") and associated processes that are implemented on an electronic device, such as portable multifunction device 100, device 300, or device 500.

FIGS. 6A-6EE illustrate exemplary user interfaces for displaying personalized workout suggestions based on completed workouts, in accordance with some embodiments. In some embodiments, the personalized workout suggestions represent workout content (e.g., audio and/or video) that prompt a user to perform a particular type of physical activity for a predetermined duration of time. The user interfaces in these figures are used to illustrate the processes described below, including the processes in FIG. 7.

Figure 6A:
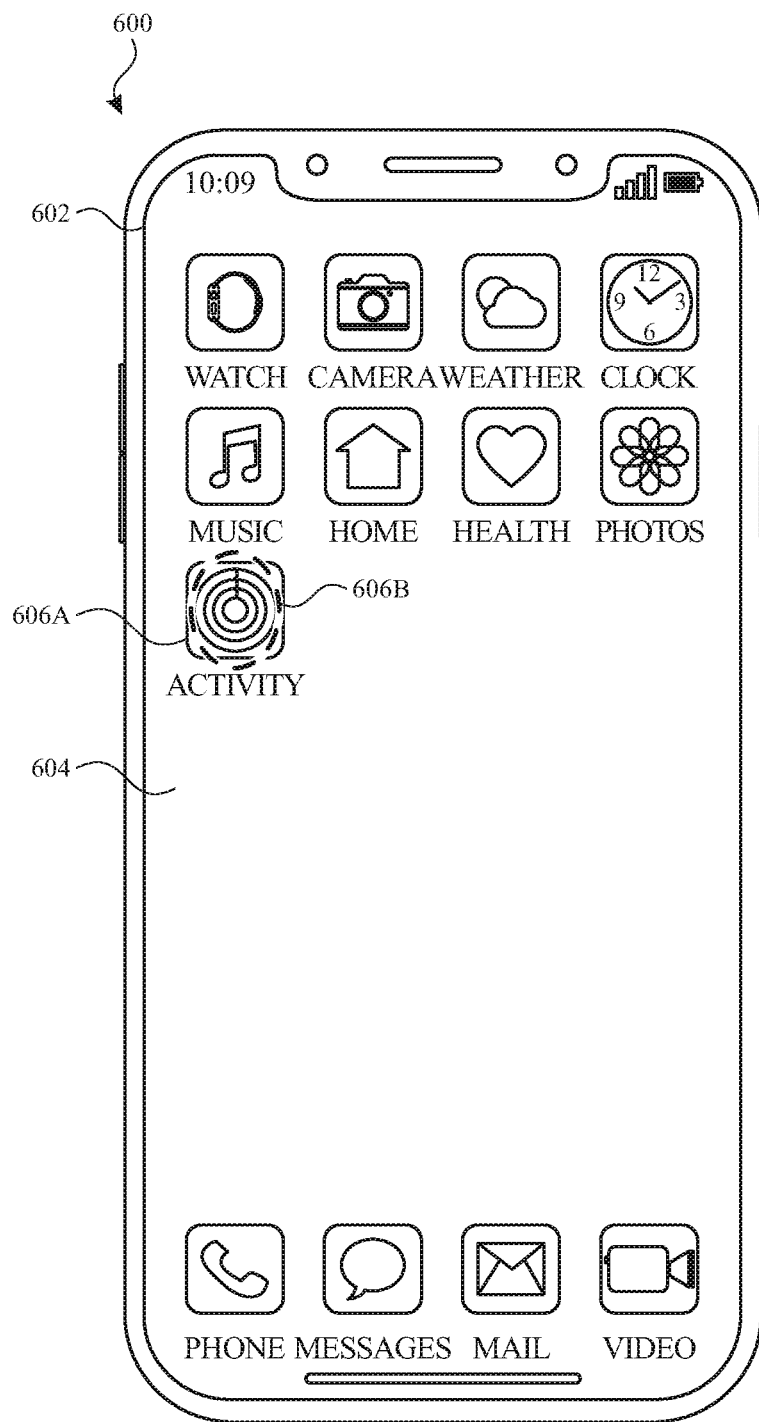
FIGS. 6A-6EE illustrate exemplary user interfaces for displaying personalized workout suggestions based on completed workouts, in accordance with some embodiments.

FIG. 6A depicts electronic device 600, which is a smartphone with display 602. Display 602 of electronic device 600 includes a touch-sensitive surface on which electronic device 600 can detect user gestures (e.g., tap, swipe, and/or drag). In some embodiments, electronic device 600 includes one or more features of electronic device 100, 300, and/or 500.

At FIG. 6A, while displaying home screen 604, electronic device 600 detects input 606B at a location corresponding to application icon 606A.

Figure 6B:
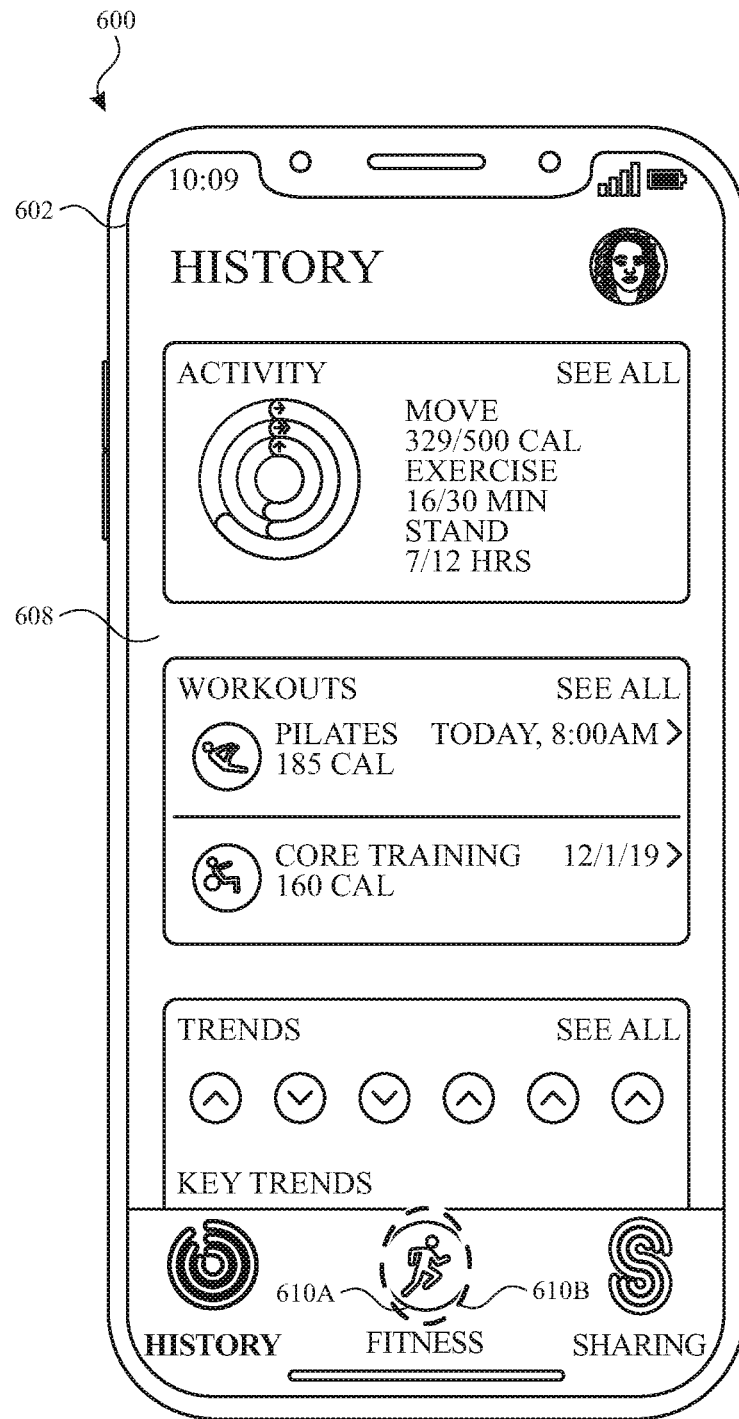

At FIG. 6B, in response to detecting input 606B, electronic device 600 launches an activity (e.g., physical activity) application. Launching the activity application includes replacing display of home screen 604 with history user interface 608 of the activity application. Additionally, electronic device 600 displays a plurality of options near the bottom of display 602, including option 610A. While displaying history user interface 608, electronic device 600 detects input 610B at a location corresponding to option 610A.

Figure 6C:
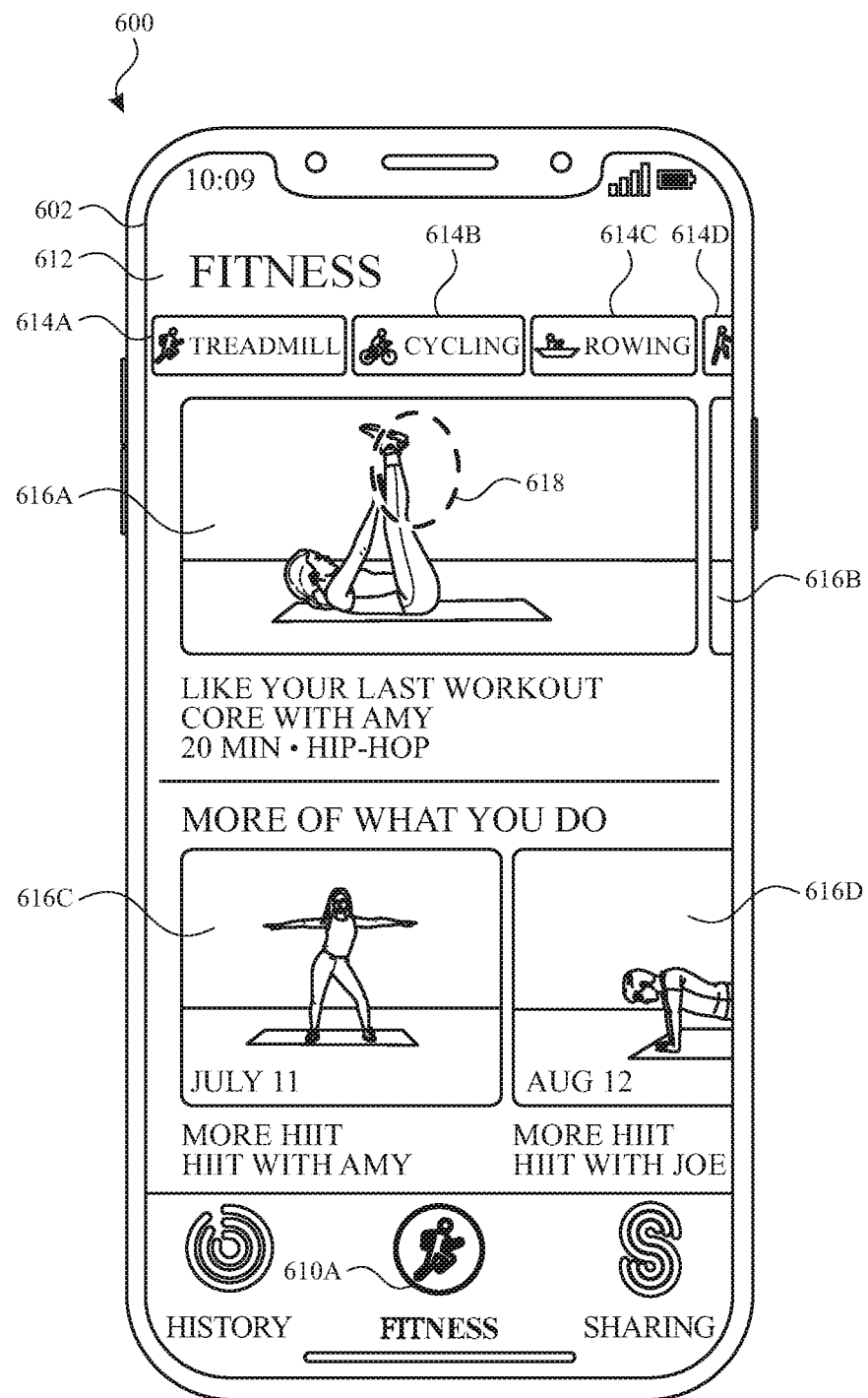

At FIG. 6C, in response to detecting input 610B, electronic device 600 replaces display of history user interface 608 with workout user interface 612. Workout user interface 612 includes options 614A-614D for filtering workouts based on exercise type (e.g., treadmill, cycling, rowing, core, high-intensity interval training (HIIT), yoga, and the like). Additionally, workout user interface 612 includes a plurality of workout suggestions for a user, where the workout suggestions are based on one or more workouts that have been completed by the user. For example, workout suggestion 616A represents a workout that shares one or more characteristics with a subset of workouts completed by the user (e.g., the most recently completed workout). Here, the user most recently completed a core workout with a different trainer, Emma. Accordingly, electronic device 600 provides workout suggestion 616A, as it represents a workout that has a shared characteristic with the user's most recently completed workout. In particular, the workout represented by workout suggestion 616A and the user's most recently completed workout have the same exercise type (core). Examples of shared characteristics include exercise type, duration, music, and trainer. Workout suggestion 616C, similar to workout suggestion 616A, shares one or more characteristics with a subset of workouts completed by the user. In contrast to workout suggestion 616A, which is based on the most recently completed workout, workout suggestion 616C is based on one or more workouts that have been completed in a predetermined amount of time (e.g., past 30, 60, or 90 days). For example, the user has completed ten workouts in the past 30 days, where the most common exercise type among the ten workouts is HIIT. As a result, electronic device 600 displays workout suggestion 616C, which represents a workout with the HIIT exercise type (e.g., the exercise type that is most common among the user's completed workouts in a predetermined period of time). While displaying workout user interface 612, electronic device 600 detects input 618 at a location corresponding to workout suggestion 616A.

Figure 6D:
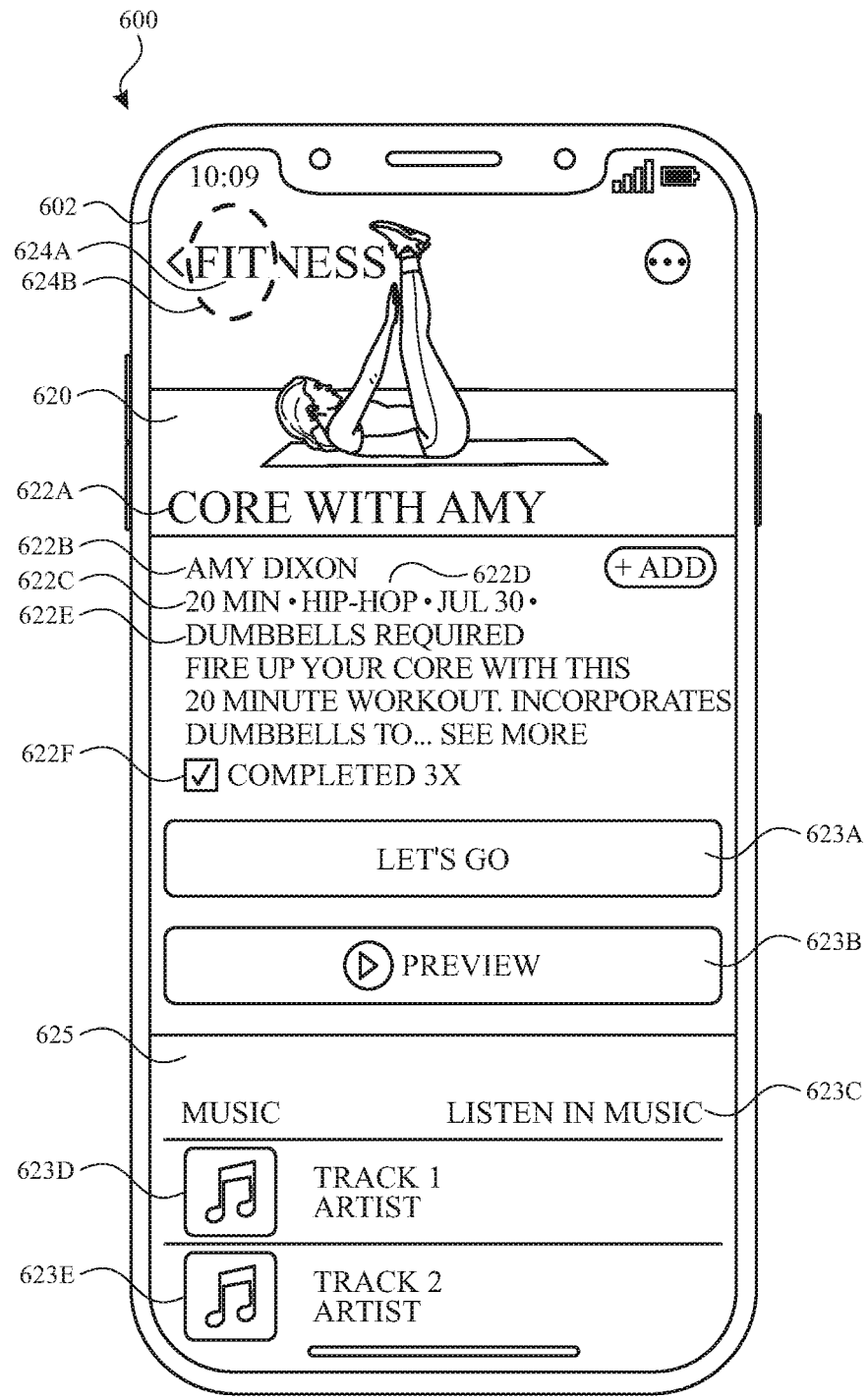

At FIG. 6D, in response to detecting input 618, electronic device 600 replaces display of workout user interface 612 with detail user interface 620. Detail user interface 620 includes characteristics of the workout represented by workout suggestion 616A. For example, detail user interface 620 includes exercise type 622A, trainer 622B, duration 622C, music 622D, required equipment 622E, and completion indication 622F.

Detail user interface 620 also includes an option 623A that can be selected by a user to play video content corresponding to the workout (e.g., a video that demonstrates the workout), and an option 623B that can be selected by a user to play a preview video corresponding to the workout. In some embodiments, the preview video is different from the video content corresponding to the workout. For example, the preview video can include a subset of the video content corresponding to the workout, and can be shorter in duration than the video content corresponding to the workout.

Detail user interface 620 also includes a music section 625 that identifies a music playlist comprising one or more music tracks that correspond to the workout. For example, the music section 625 can identify a music playlist comprising one or more music tracks that are played during the workout. The music section 625 includes an option 623C that is selectable by a user to open the full music playlist (e.g., all of the music tracks listed in the music section) in a separate music application. The music section 625 also includes options 623D, 623E, that correspond to individual music tracks, and are selectable by a user to open the individual music tracks in the separate music application (e.g., without opening other music tracks in the music playlist in the separate music application).

While displaying detail user interface 620, electronic device 600 detects input 624B at a location corresponding to option 624A.

Figure 6E:
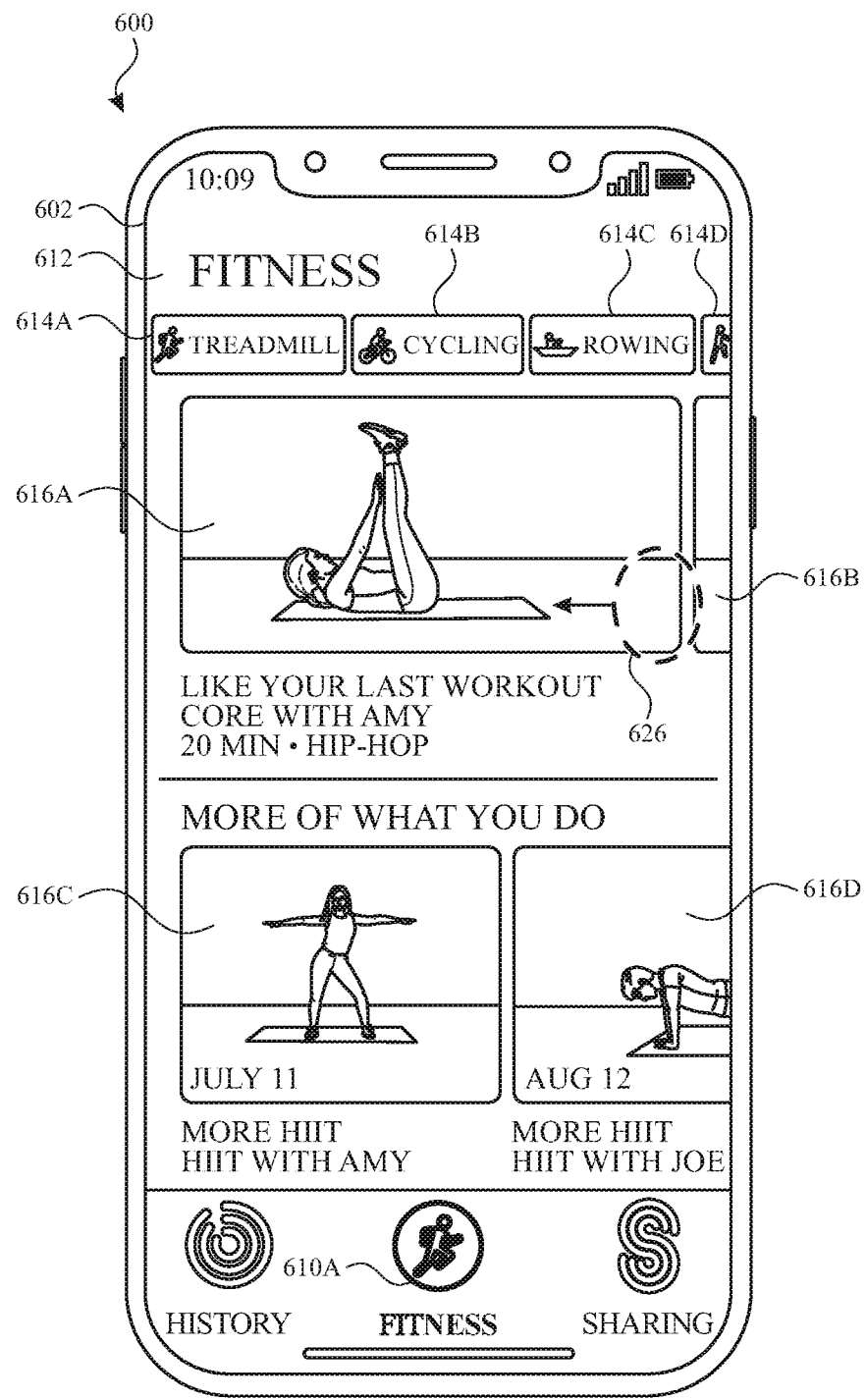

At FIG. 6E, in response to detecting input 624B, electronic device 600 replaces display of detail user interface 620 with workout user interface 612. While displaying detail user interface 620, electronic device 600 detects input 626 with movement in the right-to-left direction at a location corresponding to workout suggestion 616A.

Figure 6F:
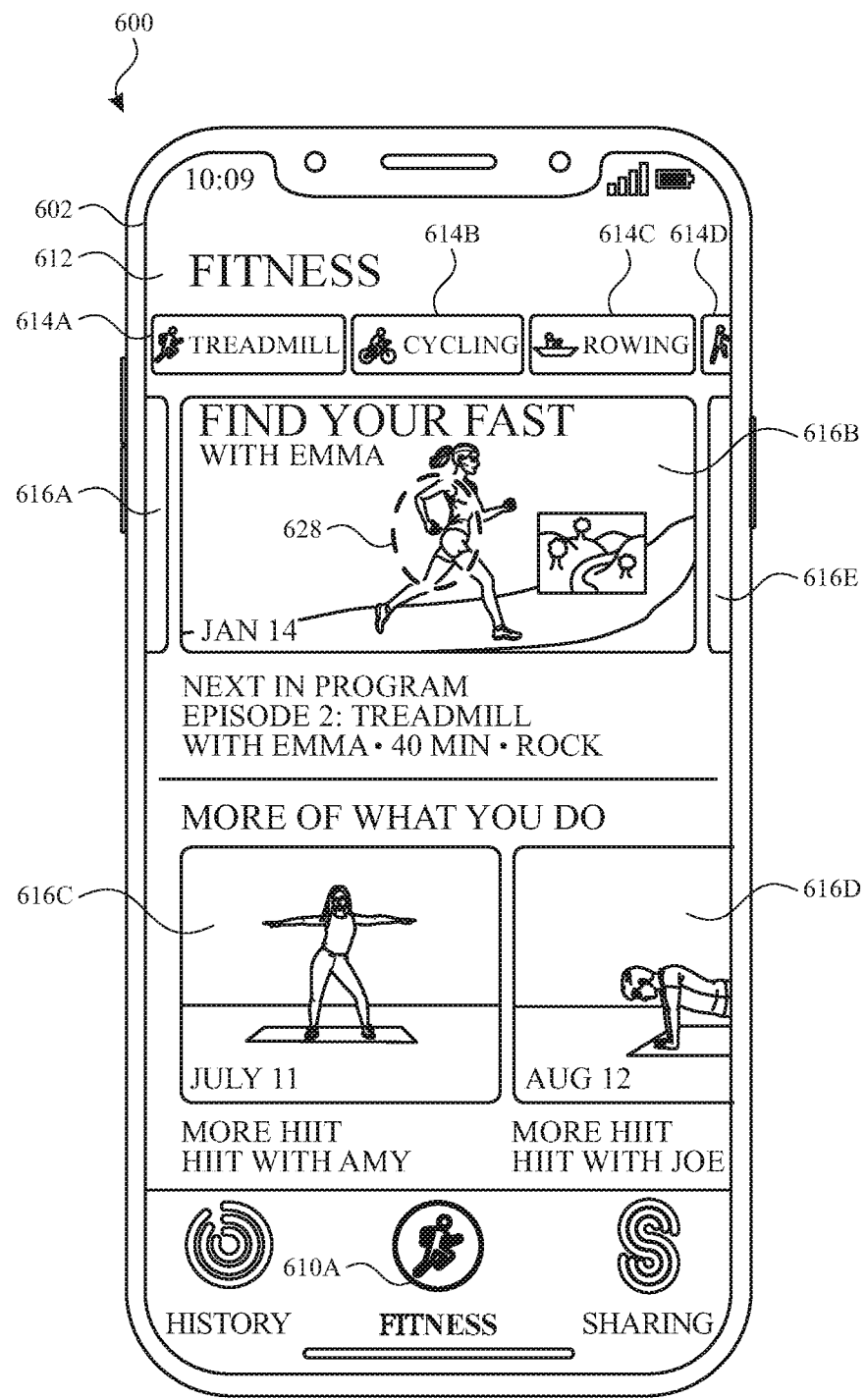

At FIG. 6F, in response to detecting input 626, electronic device 600 slides a portion of workout suggestion 616A off display 602, and slides workout suggestion 616B onto display 602. Additionally, electronic device 600 slides a portion of workout suggestion 616E onto display 602. In some embodiments, in response to detecting input 610B, electronic device 600 displays workout suggestion 616B instead of workout suggestion 616A (e.g., in accordance with a determination that the user has completed a workout that is part of a workout program, in accordance with a determination that the most recently completed workout is part of a workout program (e.g., predefined sequence of workouts or a workout series with multiple episodes). For example, in contrast to FIG. 6C, electronic device 600 displays workout suggestion 616B (Episode 2: Treadmill) as the first personalized suggestion in place of workout suggestion 616A (Core with Amy). In some embodiments, electronic device 600 displays workout suggestion 616B (Episode 2: Treadmill) as the first personalized suggestion if the user has completed a workout that is part of a workout program (Find Your Fast). Alternatively, as depicted in FIG. 6C, electronic device 600 displays workout suggestion 616A as the first personalized suggestion if the user has not completed a workout that is part of a workout program, in accordance with some embodiments. While displaying workout user interface 612, electronic device 600 detects input 628 at a location corresponding to workout suggestion 616B.

Figure 6G:
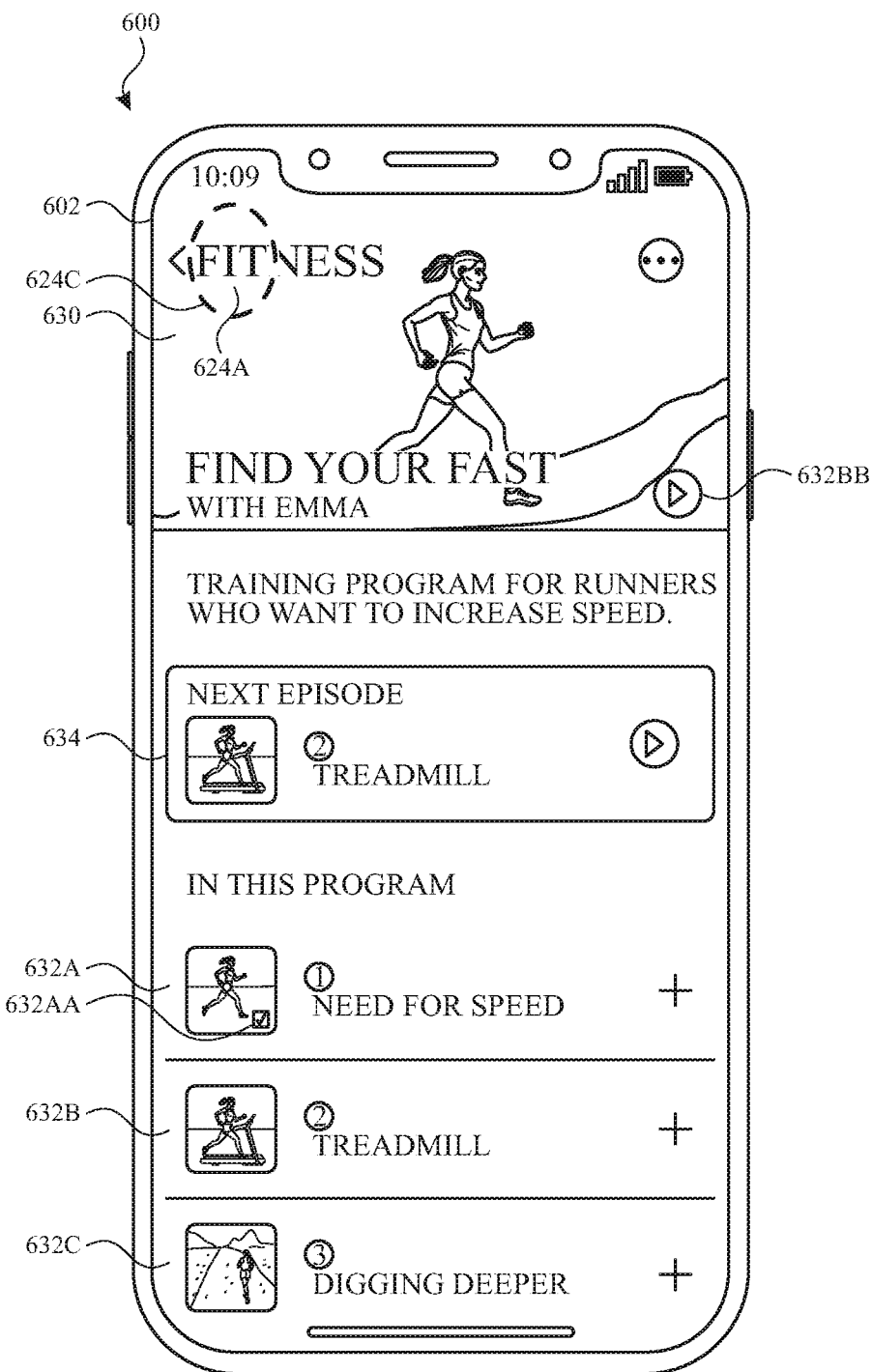

At FIG. 6G, in response to detecting input 628, electronic device 600 replaces display of workout user interface 612 with program user interface 630. Program user interface 630 includes a plurality of workout suggestions corresponding to a particular workout program (e.g., Find Your Fast). The workout program consists of a plurality of workout content items that are ordered in a predefined sequence. In accordance with a determination that a workout in the workout program has been completed, electronic device 600 visually emphasizes, using a border, the workout suggestion corresponding to the workout that comes next in the predefined sequence of workouts in the workout program. For example, electronic device 600 visually emphasizes workout suggestion 634 in accordance with a determination that the workout corresponding to workout suggestion 632A has been completed. Workout suggestion 634, which matches workout suggestion 632B, corresponds to the workout that is next in the sequence of workouts. Additionally, indication 632AA indicates that the workout corresponding to workout suggestion 632A has been completed. Program user interface 630 also includes an option 632BB that is selectable by a user to open and play a program introduction video. The program introduction video is separate and different from the workouts in the workout program. In some embodiments, the program introduction video comprises audio and/or visual clips (e.g., images or video clips) from some or all of the workouts in the workout program. In some embodiments, selection of a particular workout suggestion 632A, 632B, 632C causes display of a corresponding detail user interface (similar to the detail user interface 620 of FIG. 6D). In some embodiments, the detail user interface for each workout can include a selectable option for playing video content corresponding to the workout (e.g., playing a video that demonstrates the workout), and a separate selectable option for playing the program introduction video (e.g., similar to options 623A and 623B in FIG. 6D). While displaying program user interface 630, electronic device 600 detects input 624C at a location corresponding to option 624A.

Figure 6H:
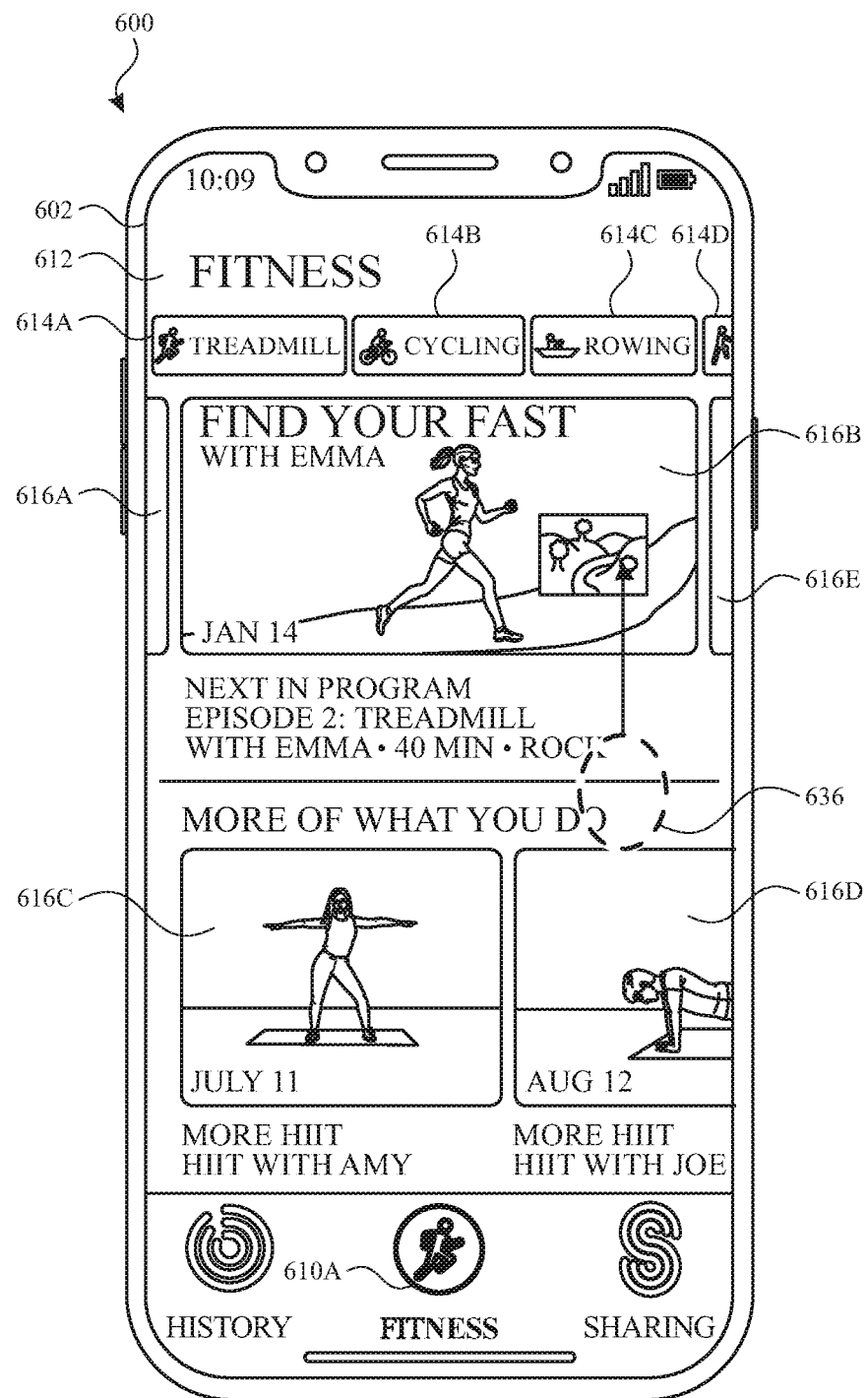

At FIG. 6H, in response to detecting input 624C, electronic device 600 replaces display of program user interface 630 with workout user interface 612. While displaying workout user interface 612, electronic device 600 detects input 636 with movement in an upward direction.

Figure 6I:
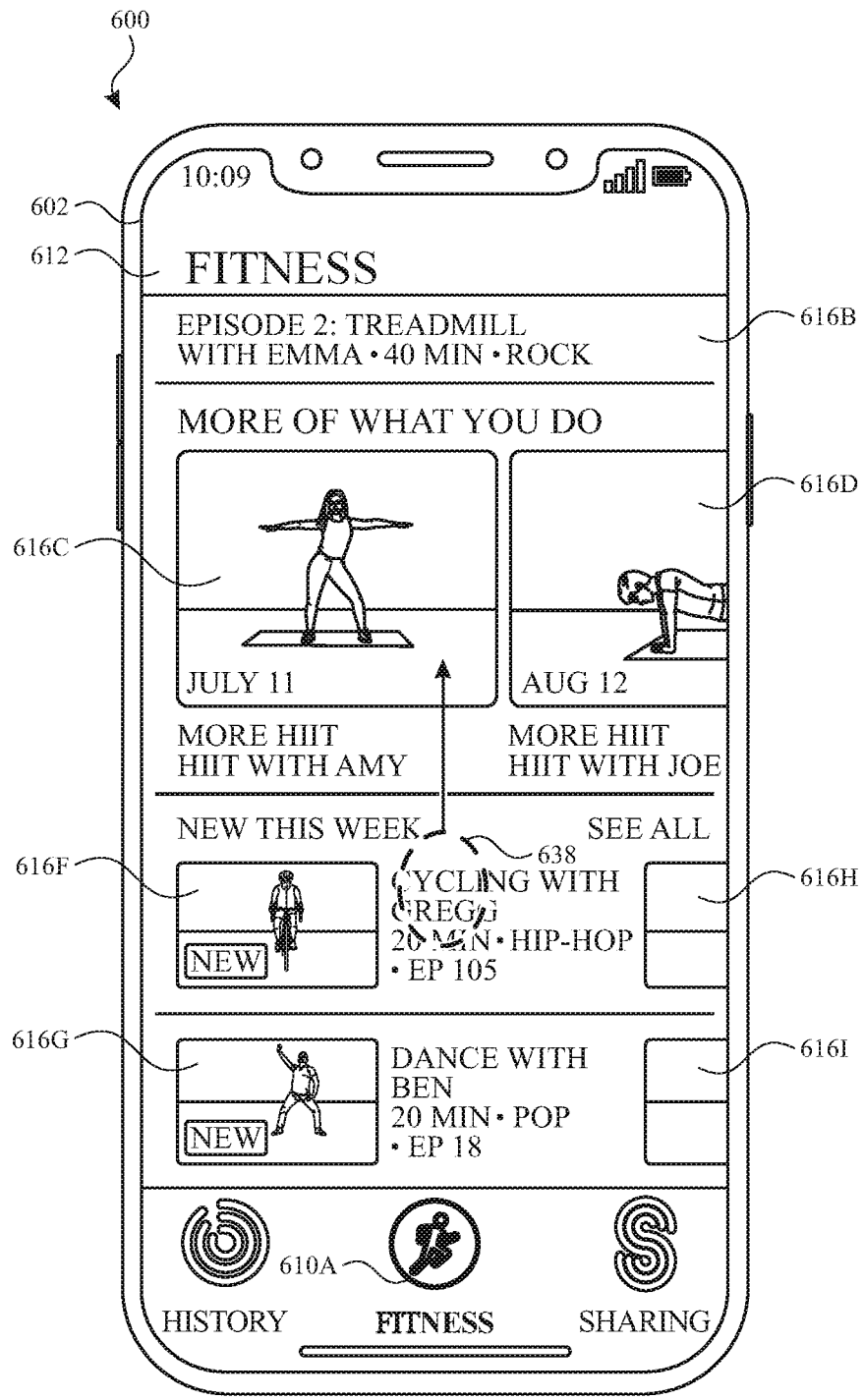
Figure 6J:
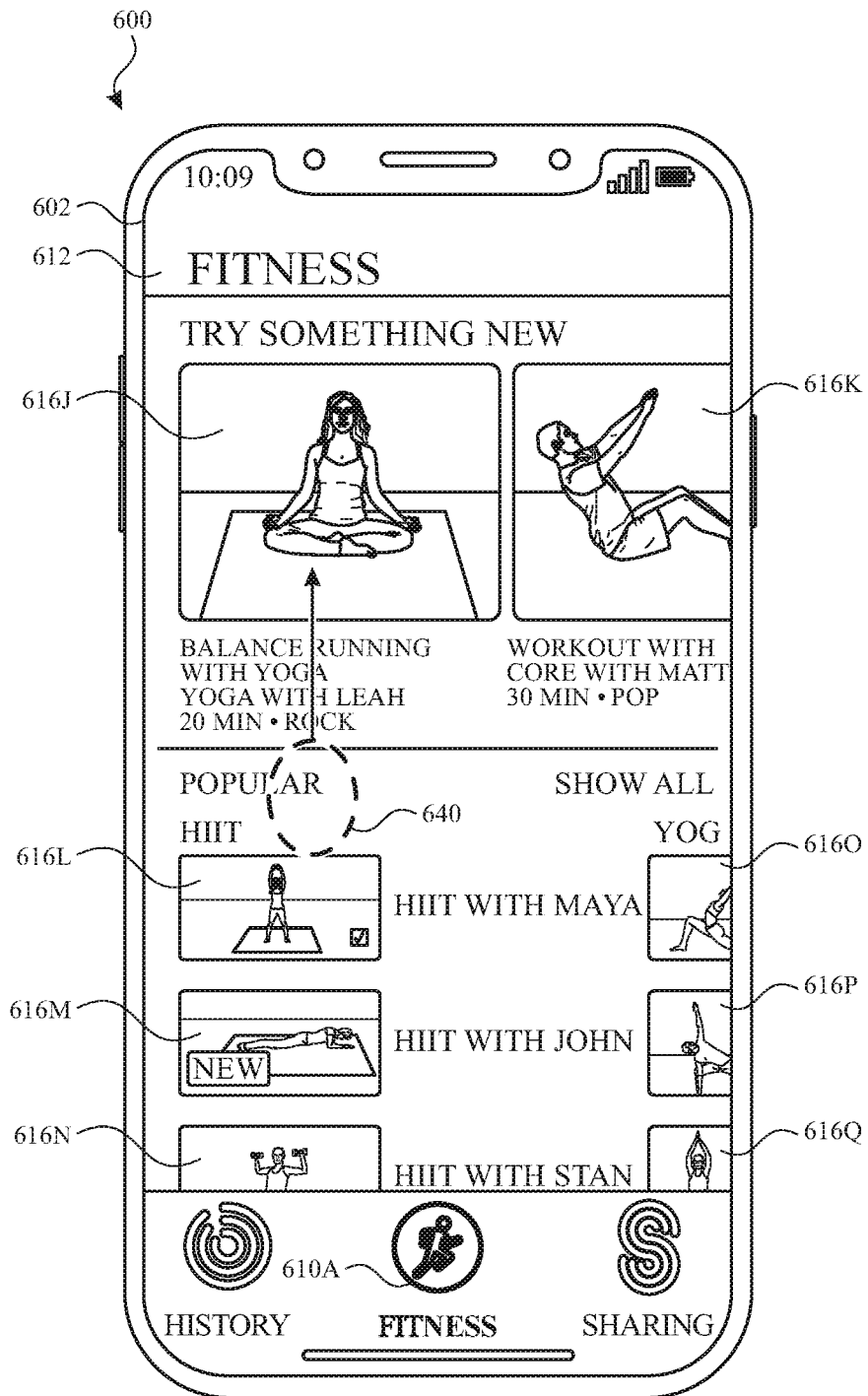

At FIG. 6I, in response to detecting input 636, electronic device 600 scrolls workout user interface 612. Scrolling workout user interface 612 includes sliding at least a portion of workout suggestions (e.g., 616A, 616B, and 616E) off display 602 (e.g., as shown in FIG. 6J). Scrolling workout user interface 612 includes modifying workout suggestion 616B to occupy a smaller portion of display 602 as compared to FIG. 6H. Scrolling workout user interface 612 includes sliding workout suggestions 616F-616I onto display 602. Workout suggestions 616F-616I represent workouts that have been recently made available (e.g., within a predetermined amount of time (e.g., past day, week, month)). Scrolling workout user interface 612 includes ceasing to display options 614A-614D. In some embodiments, electronic device 600 maintains display of options 614A-614D in response to detecting input 636. While displaying workout user interface 612, electronic device 600 detects input 638 with movement in an upward direction.

At FIG. 6J, in response to detecting input 638, electronic device 600 scrolls workout user interface 612. Scrolling workout user interface 612 includes sliding workout suggestions 616J-616Q onto display 602. Workout suggestions 616J-616Q represent new workouts that have not been completed by the user. In some embodiments, scrolling workout user interface 612 includes displaying workouts that are complementary to completed workouts. In some embodiments, a workout that is complementary to a completed workout is a workout that balances the physical activity performed in the completed workout. For example, running requires physical activity that can cause muscles to shorten. Accordingly, yoga is a complementary workout to running, as yoga promotes lengthening of muscles.

In some embodiments, completed workouts include workouts that are not accessible via workout user interface 612. For example, electronic device 600 determines that the user has completed a running workout, where the running workout is not represented in workout user interface 612. In some embodiments, in response to detecting input 638, electronic device 600 displays workout suggestion 616J based at least in part on a determination that the workout represented by workout suggestion 616J is complementary to completed workouts (e.g., yoga is complementary to running). In some embodiments, electronic device 600 displays workouts that do not share one or more characteristics with completed workouts. For example, electronic device 600 determines that the user has completed workouts with the core exercise type. In some embodiments, in response to detecting input 638, electronic device 600 displays workout suggestion 616K based at least in part on a determination that the workout represented by workout suggestion 616K does not share one or more characteristics with completed workouts (e.g., new trainer (e.g., Matt)) and/or does share one or more characteristics with completed workouts (e.g., same exercise type (e.g., core)). Additionally, scrolling workout user interface 612 includes sliding workout suggestions 616L-616Q onto display 602. Workout suggestions 616L-616Q represent popular workouts that have been frequently selected by a group of users. While displaying workout user interface 612, electronic device 600 detects input 640 with movement in an upward direction.

Figure 6K:
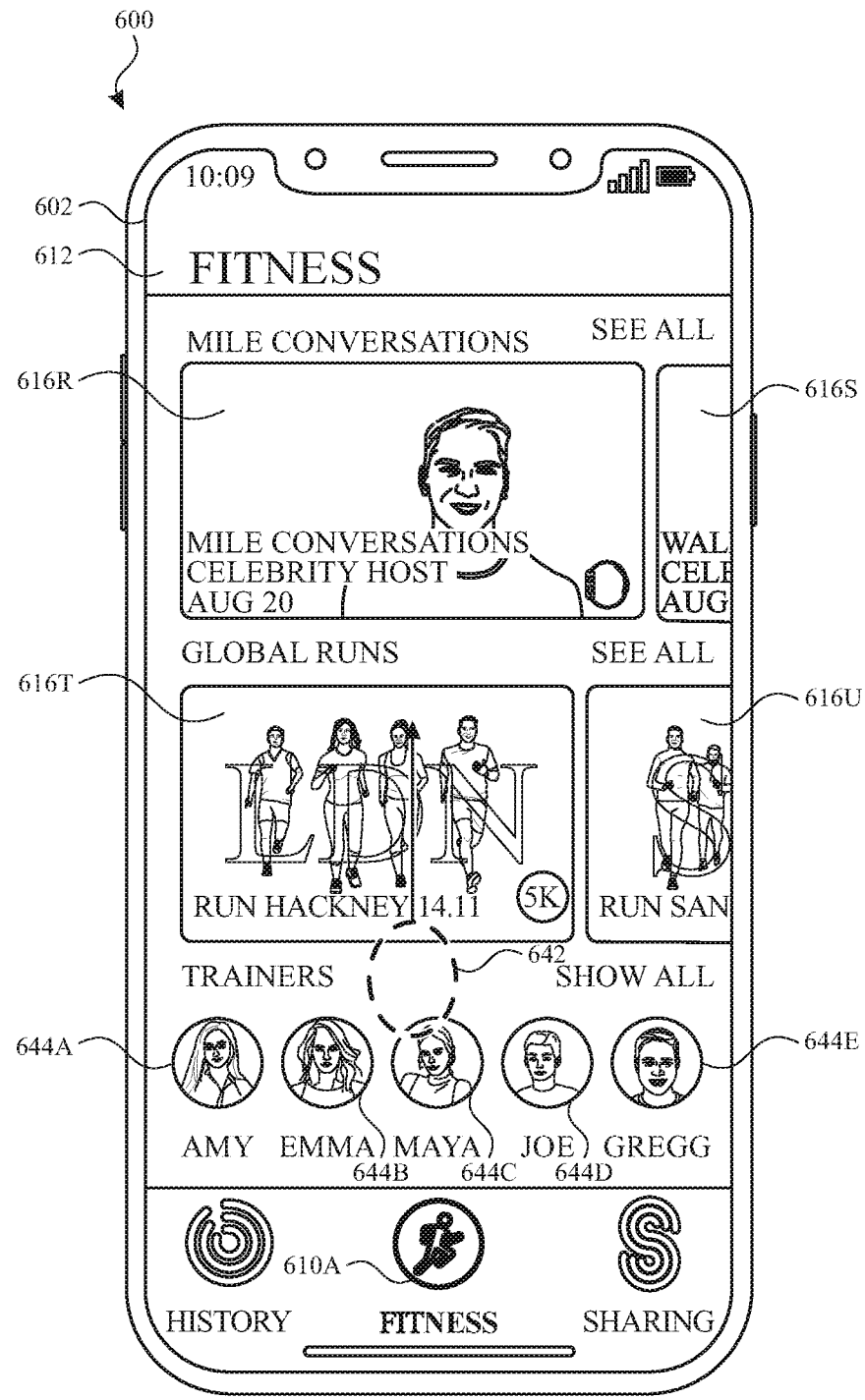

At FIG. 6K, in response to detecting input 640, electronic device 600 scrolls workout user interface 612. Scrolling workout user interface 612 includes sliding workout suggestions 616R-616U onto display 602. Workout suggestions 616R-616S represent audio content that has a duration corresponding to the amount of time required to walk a predefined distance (e.g., 1, 2, or 3 miles). Workout suggestions 616T-616U represent audio content corresponding to a predefined route at or near one or more physical locations (e.g., a 5 kilometer route in Hackney). Additionally, scrolling workout user interface 612 includes displaying options 644A-644E for filtering workouts based on the trainer. While displaying workout user interface 612, electronic device 600 detects input 642 with movement in an upward direction.

Figure 6L:
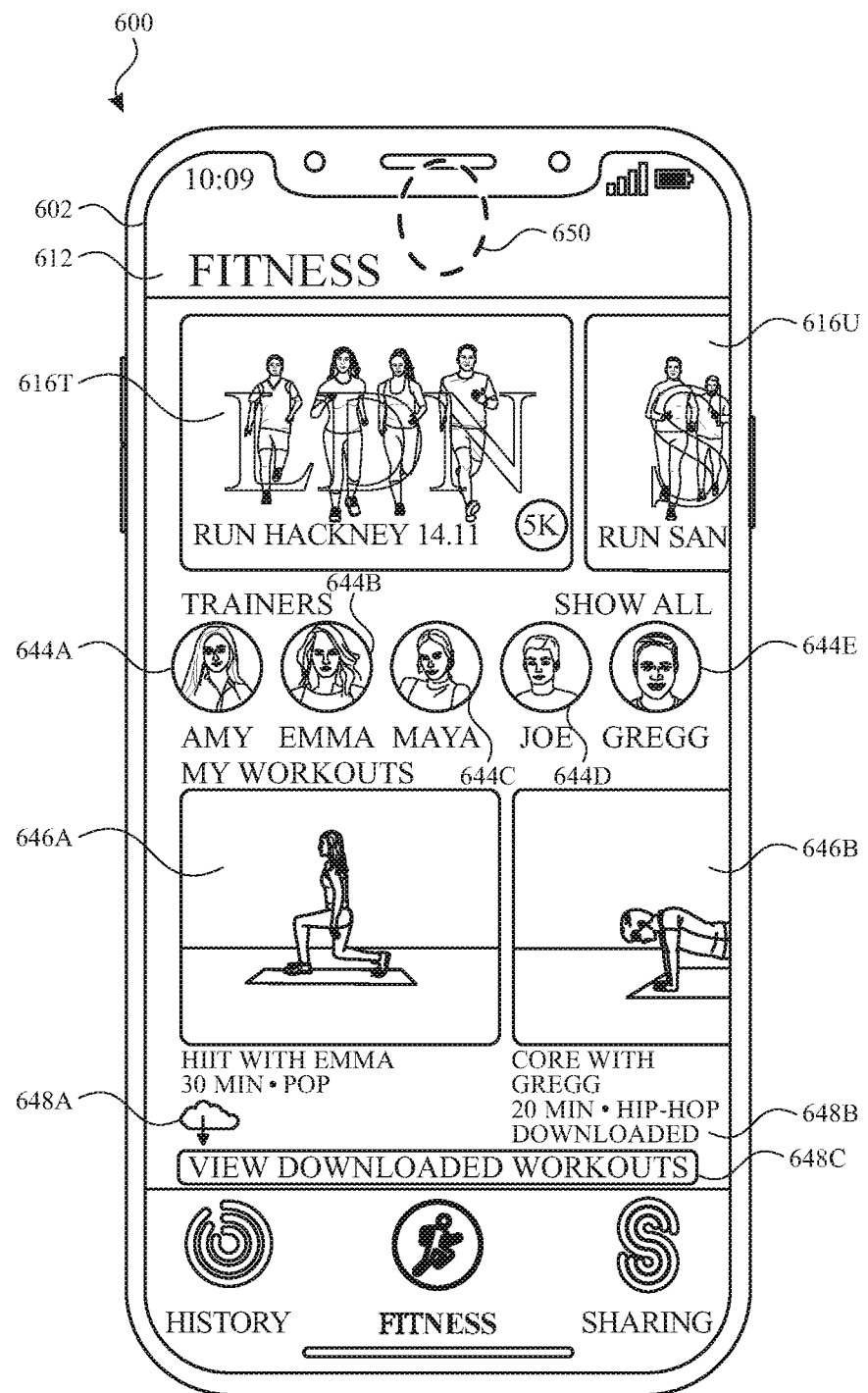

At FIG. 6L, in response to detecting input 642, electronic device 600 scrolls workout user interface 612 such that the end of workout user interface 612 has been reached. Scrolling workout user interface 612 includes displaying a library of workouts that the user has previously saved, including saved workouts 646A-646B. Workout user interface 612 includes option 648A which, when selected, initiates a process for downloading the workout content represented by saved workout 646A to electronic device 600. Additionally, workout user interface 612 includes indication 648B, which indicates that the workout content represented by saved workout 646B has already been downloaded to electronic device 600. Workout user interface 612 also includes option 648C which, when selected, replaces display of workout user interface 612 with a different user interface that displays all workouts that have already been downloaded to electronic device 600. While displaying workout user interface 612, electronic device 600 detects input 650 at a location within a predefined region near the top of display 602.

Figure 6M:
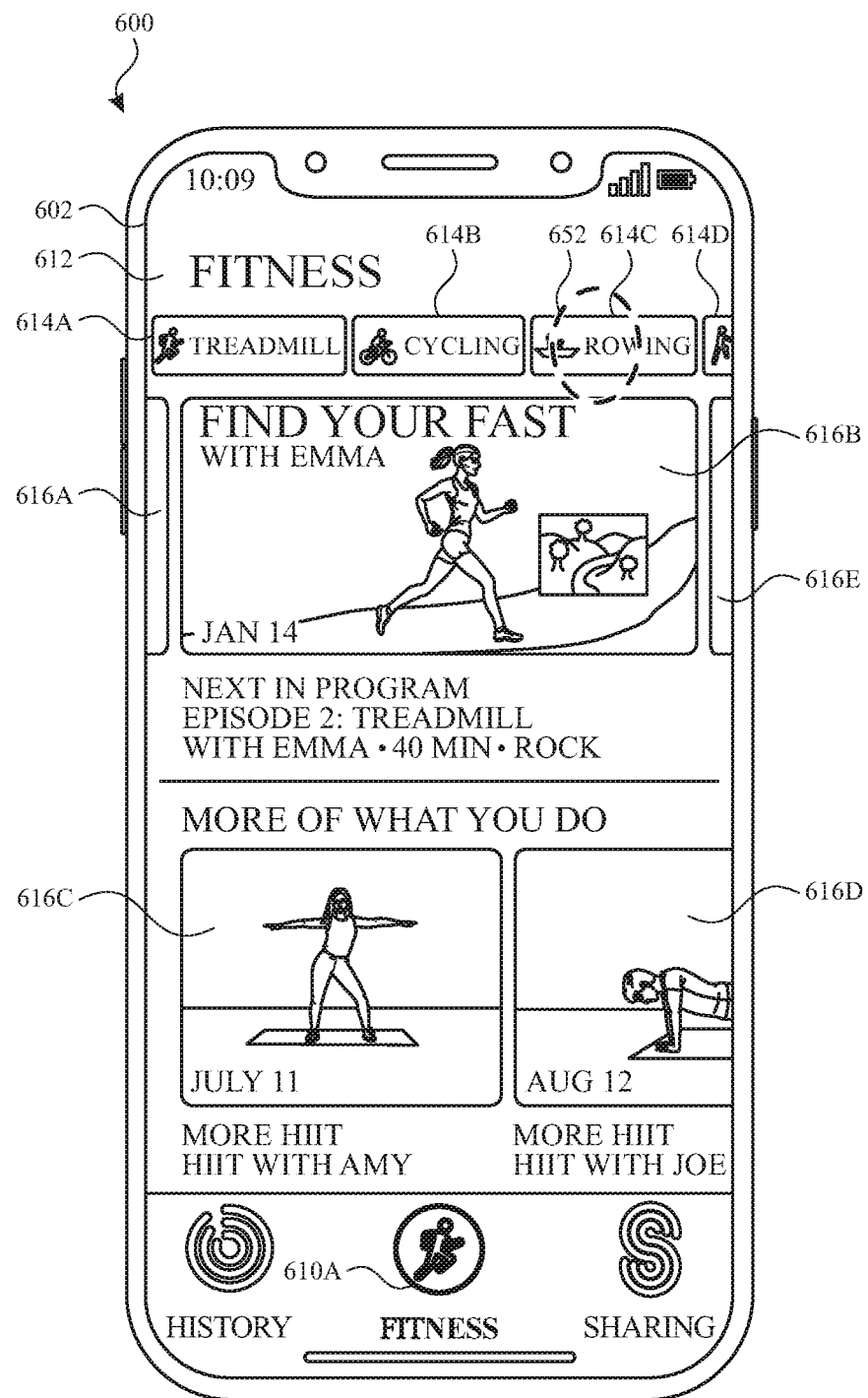

At FIG. 6M, in response to detecting input 650, electronic device 600 scrolls to the top of workout user interface 612, resulting in display of options 614A-614D. While displaying workout user interface 612, electronic device 600 detects input 652 at a location corresponding to option 614C.

Figure 6N:
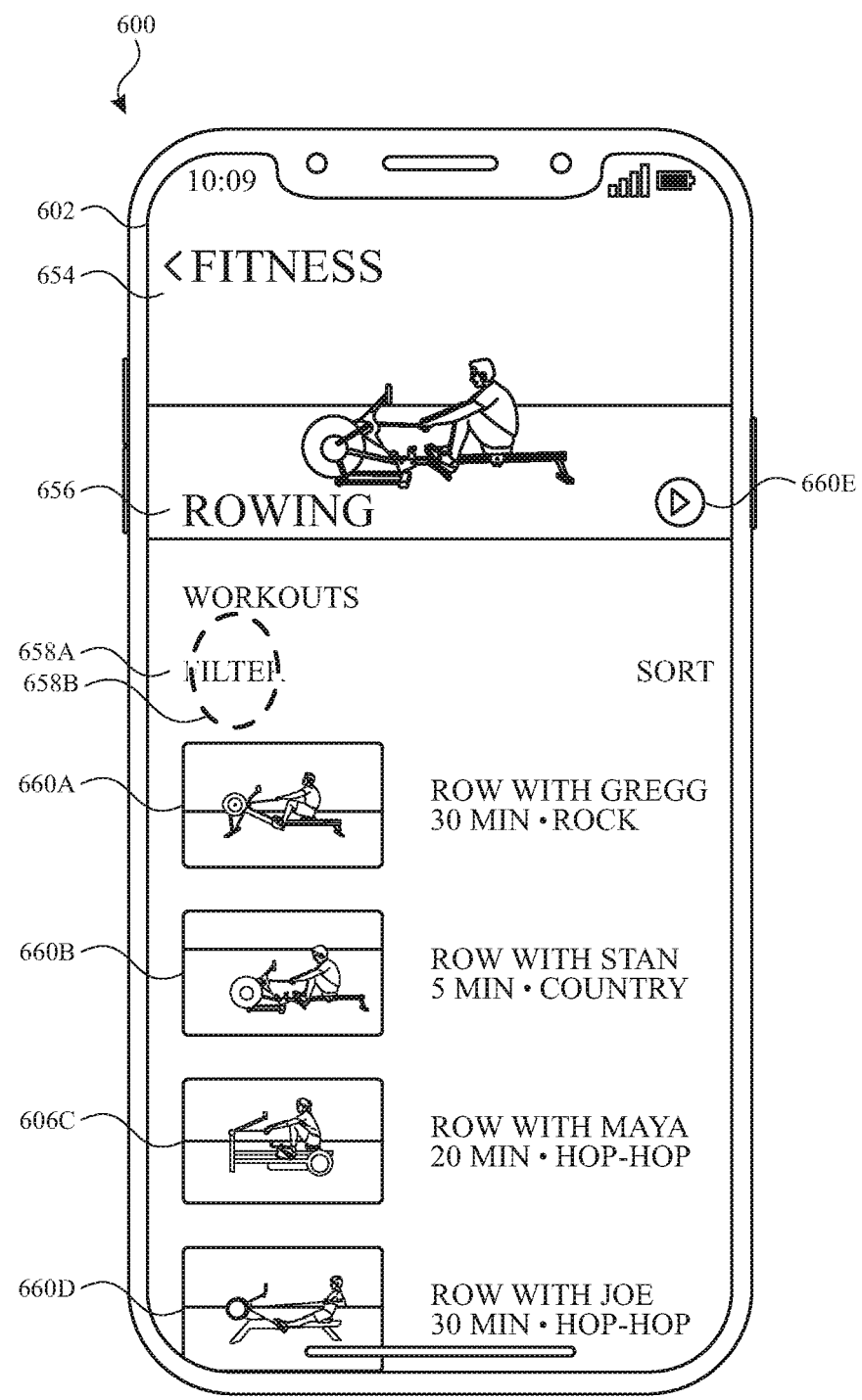

At FIG. 6N, in response to detecting input 652, electronic device 600 replaces display of workout user interface 612 with display of filter user interface 654. Filter user interface 654 includes filtered workout suggestions 660A-660D based on selected option 614C. Additionally, filter user interface 654 includes indication 656, which indicates the characteristic (e.g., rowing) that filtered workout suggestions 660A-660D have in common. In the depicted scenario, the filtered workout suggestions 660A-660D all have a particular workout type (or workout modality) in common (e.g., rowing).

The filter user interface 654 includes an option 660E that is selectable by a user to open and play a workout modality introduction video. The workout modality introduction video is separate and different from the workouts corresponding to filtered workout suggestions 660A-660D. In some embodiments, the workout modality introduction video can identify for a user any equipment that is required for the workout modality (e.g., a rowing machine can be required for the rowing workouts). While displaying filter user interface 654, electronic device 600 detects input 658B at a location corresponding to option 658A.

Figure 6O:
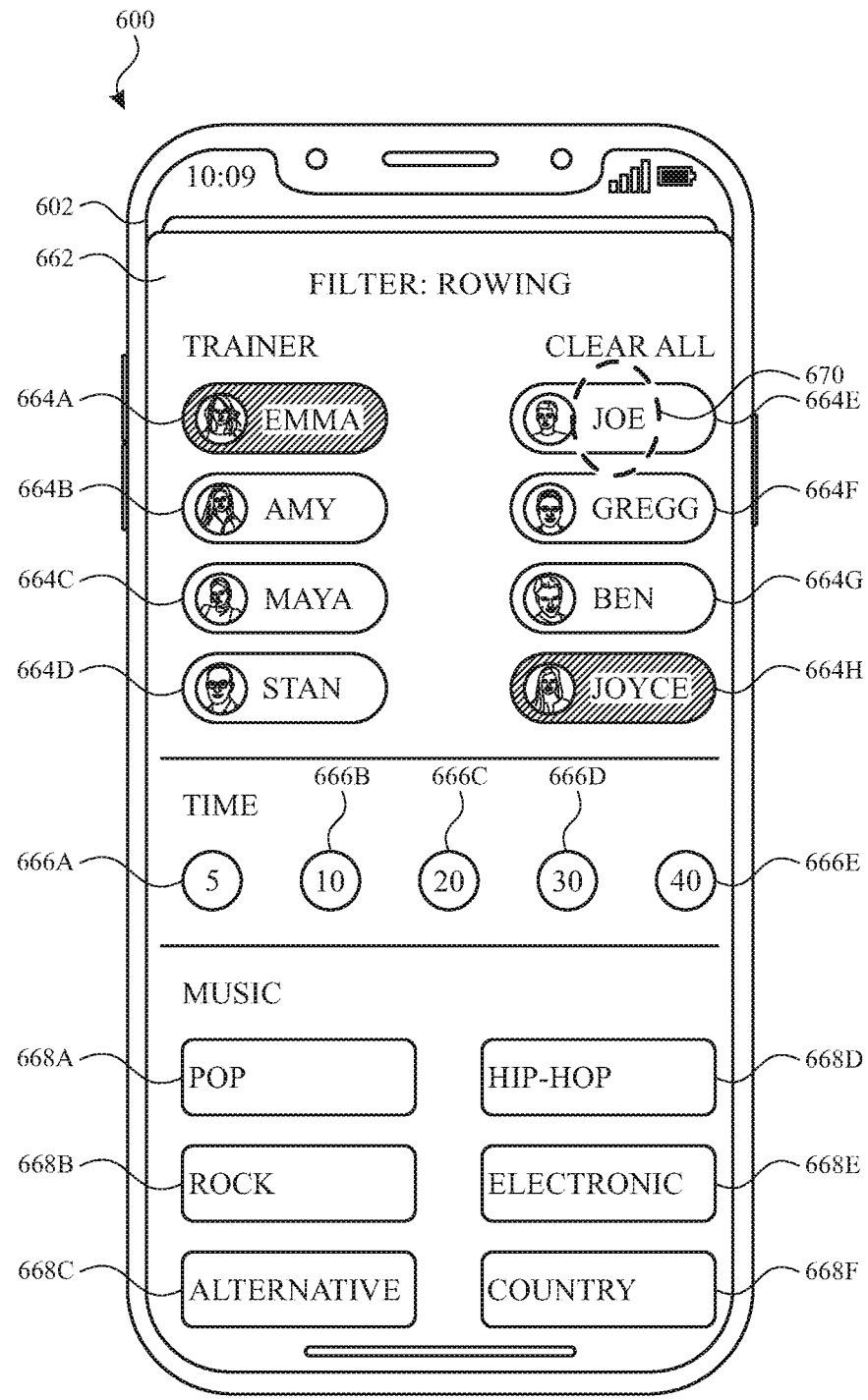

At FIG. 6O, in response to detecting input 658B, electronic device 600 displays filter user interface 662 with additional options for filtering workouts (e.g., in addition to exercise type, which is currently filtered for rowing). For example, filter user interface 662 includes options 664A-664H for filtering workouts based on the trainer, options 666A-666E for filtering workouts based on duration of the workout, and options 668A-668F for filtering workouts based on music genre. Electronic device 600 obscures (e.g., dims) options 664A and 664H based at least in part on a determination that the trainers represented by options 664A and options 664H do not satisfy the currently selected filter(s) (e.g., Emma and Joyce do not have any rowing workouts). While displaying filter user interface 662, electronic device 600 detects input 670 at a location corresponding to option 664E.

Figure 6P:
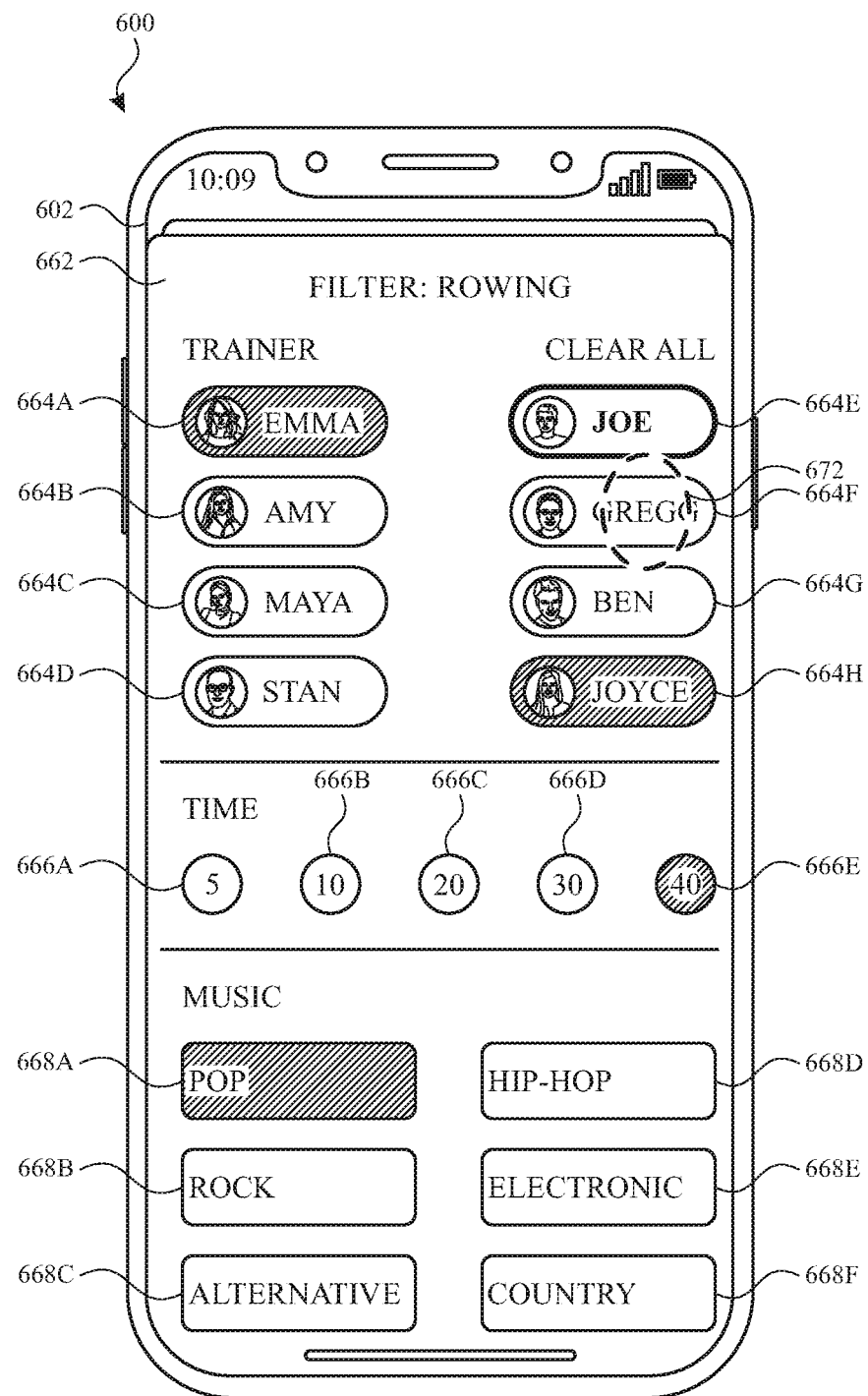

At FIG. 6P, in response to detecting input 670, electronic device 600 visually emphasizes option 664E to indicate that option 664E has been selected. Additionally, in response to detecting input 670, electronic device 600 obscures (e.g., dims) option 668A based at least in part on a determination that the music genre represented by option 668A does not satisfy the currently selected filter(s) (e.g., Joe does not have any workouts with pop music). Similarly, in response to detecting input 670, electronic device 600 obscures (e.g., dims) option 666E based at least in part on a determination that the duration represented by option 666E does not satisfy the currently selected filter(s) (e.g., Joe does not have any workouts with a duration of 40 minutes). While displaying filter user interface 662, electronic device 600 detects input 672 at a location corresponding to option 664F.

Figure 6Q:
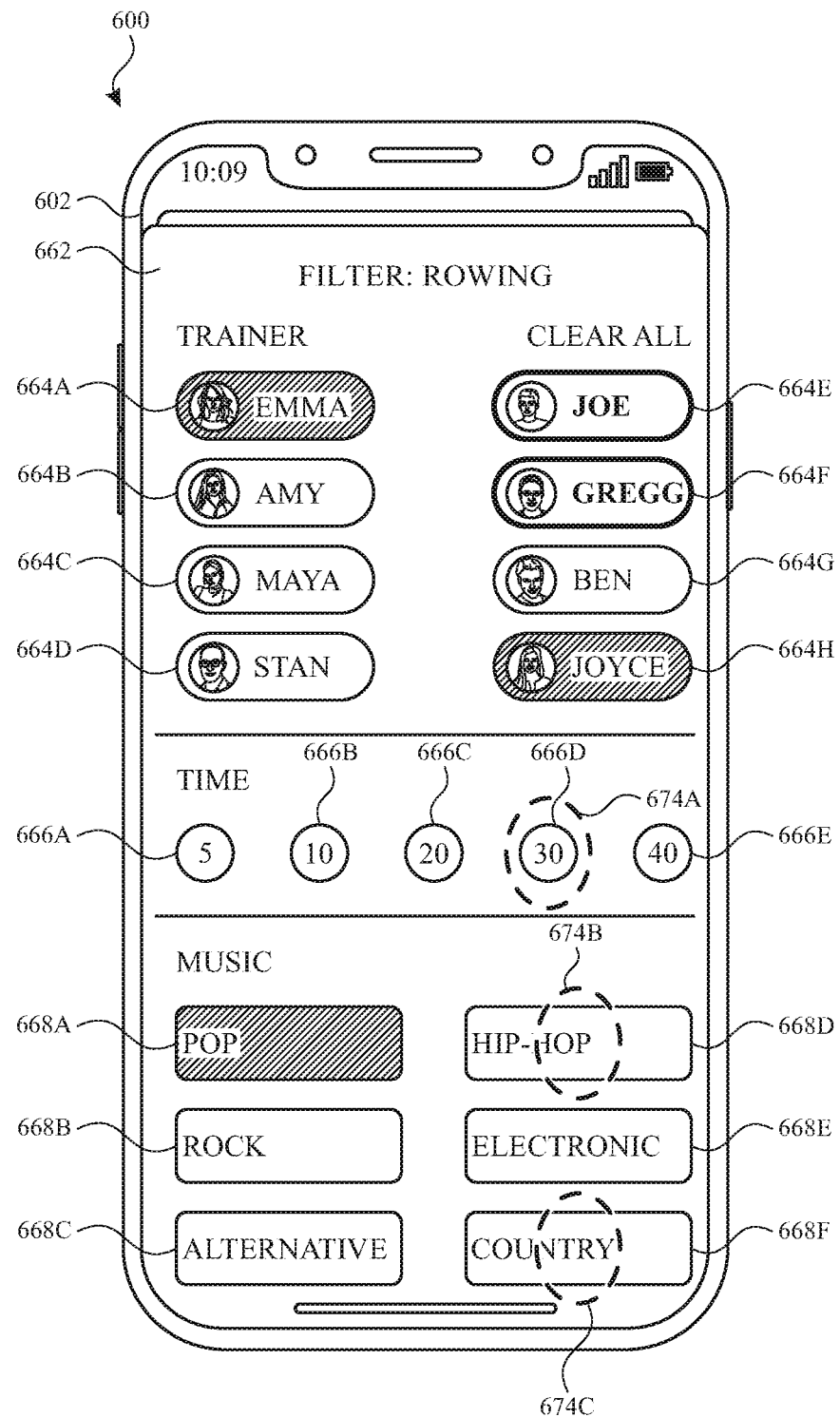

At FIG. 6Q, in response to detecting input 672, electronic device 600 visually emphasizes option 664F to indicate that option 664F has been selected. Additionally, in response to detecting input 670, electronic device 600 ceases to obscure (e.g., dim) option 666E based at least in part on a determination that the duration represented by option 666E does satisfy the currently selected filter(s) (e.g., Gregg has at least one workout with a duration of 40 minutes). While displaying filter user interface 662, electronic device 600 detects input 674A at a location corresponding to option 666D, input 674B at a location corresponding to option 668D, and input 674C at a location corresponding to option 668F.

Figure 6R:
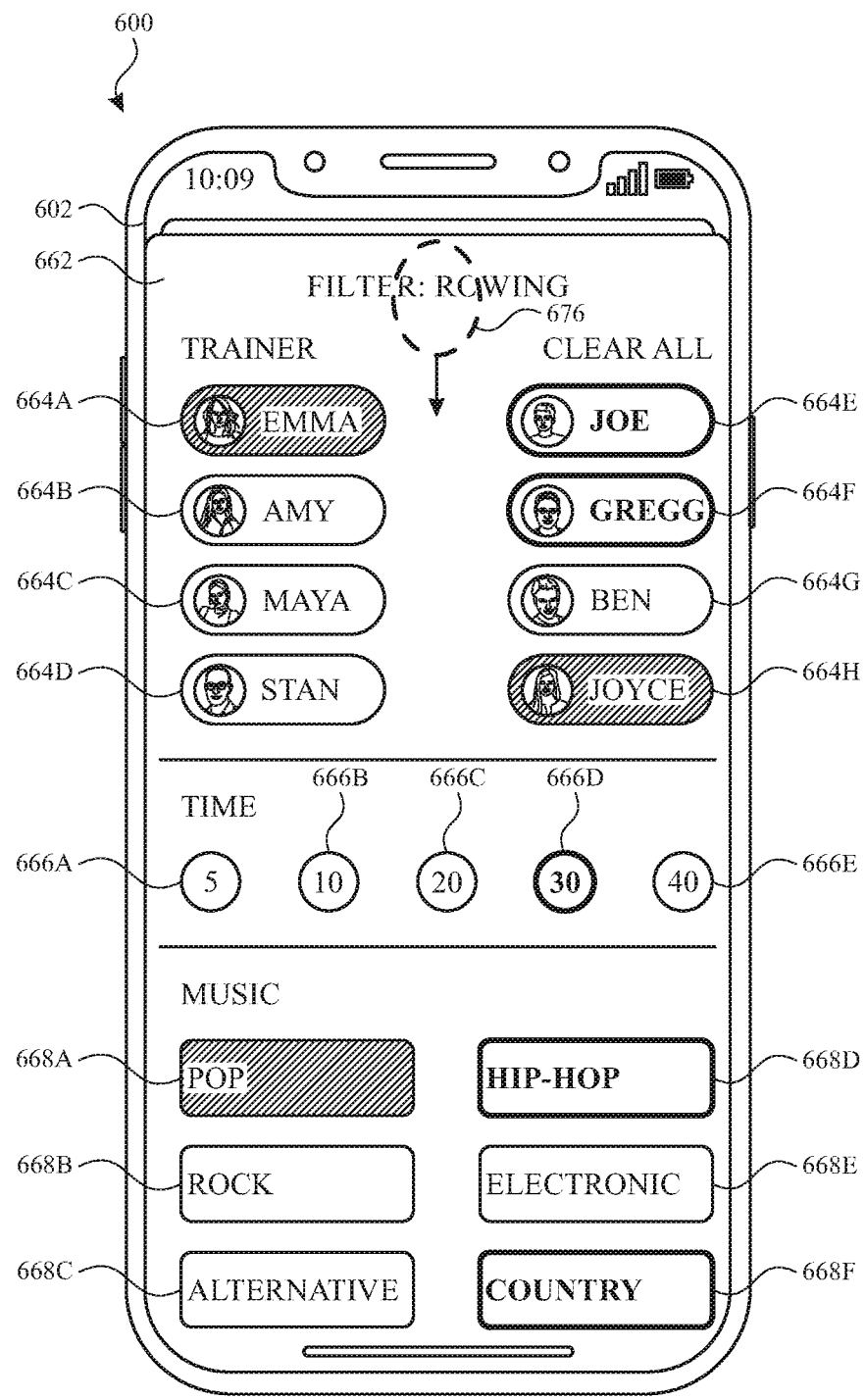

At FIG. 6R, in response to detecting the set of inputs (e.g., 674A-674C), electronic device 600 visually emphasizes options 666D, 668D, and 668F to indicate that the respective options have been selected. While displaying filter user interface 662, electronic device 600 detects input 676 with movement in a downward direction.

Figure 6S:
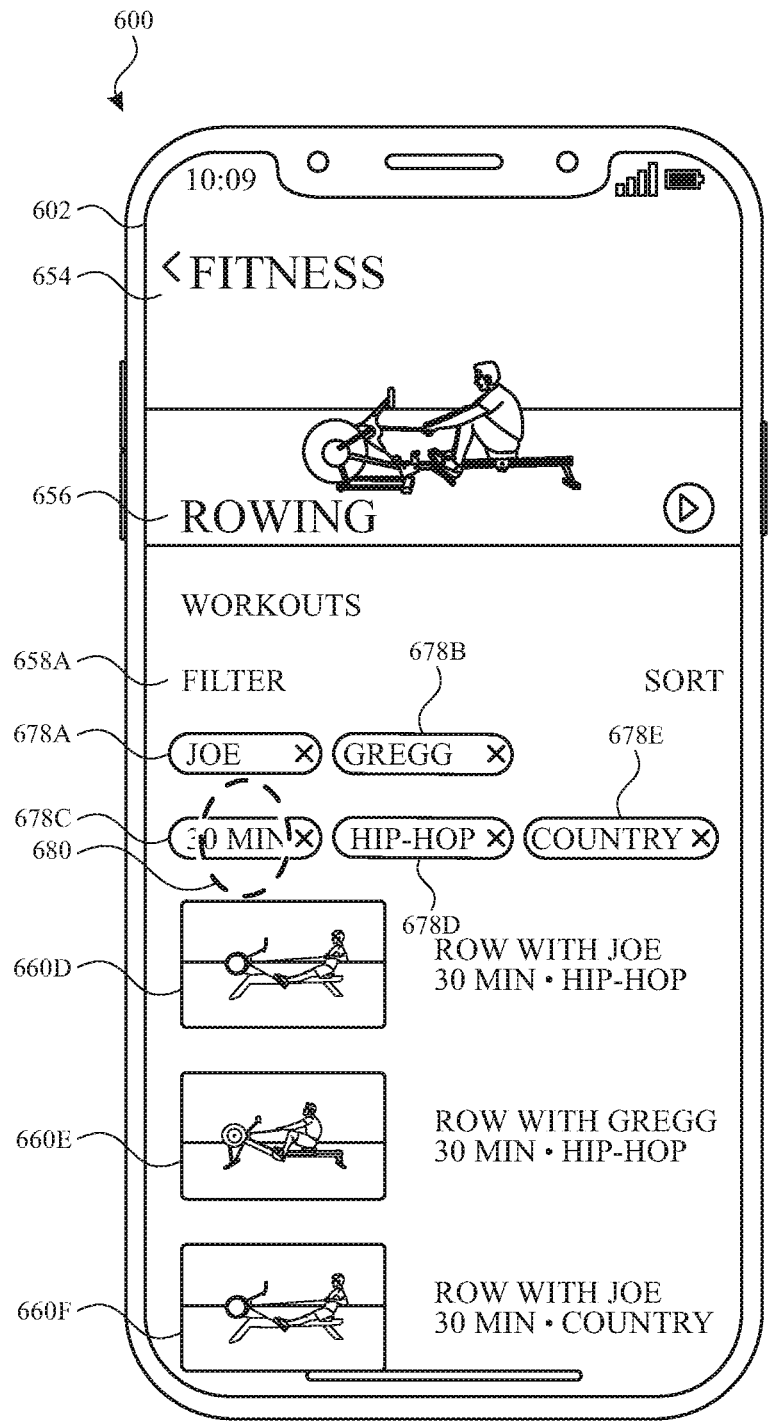

At FIG. 6S, in response to detecting input 676, electronic device 600 ceases to display filter user interface 662 and displays filter user interface 654 with updates to the filtered workout suggestions based on selections detected at filter user interface 662. Due to the filter selections, filter user interface 654 no longer includes filtered workout suggestions 660A-660C. Instead, filter user interface 654 has been updated to include filtered workout suggestions 660D-660F. Additionally, filter user interface 654 includes filter representations 678A-678E, where a respective filter representation corresponds to a filter option selected at filter user interface 662. While displaying filter user interface 654, electronic device 600 detects input 680 at a location corresponding to filter representation 678C.

Figure 6T:
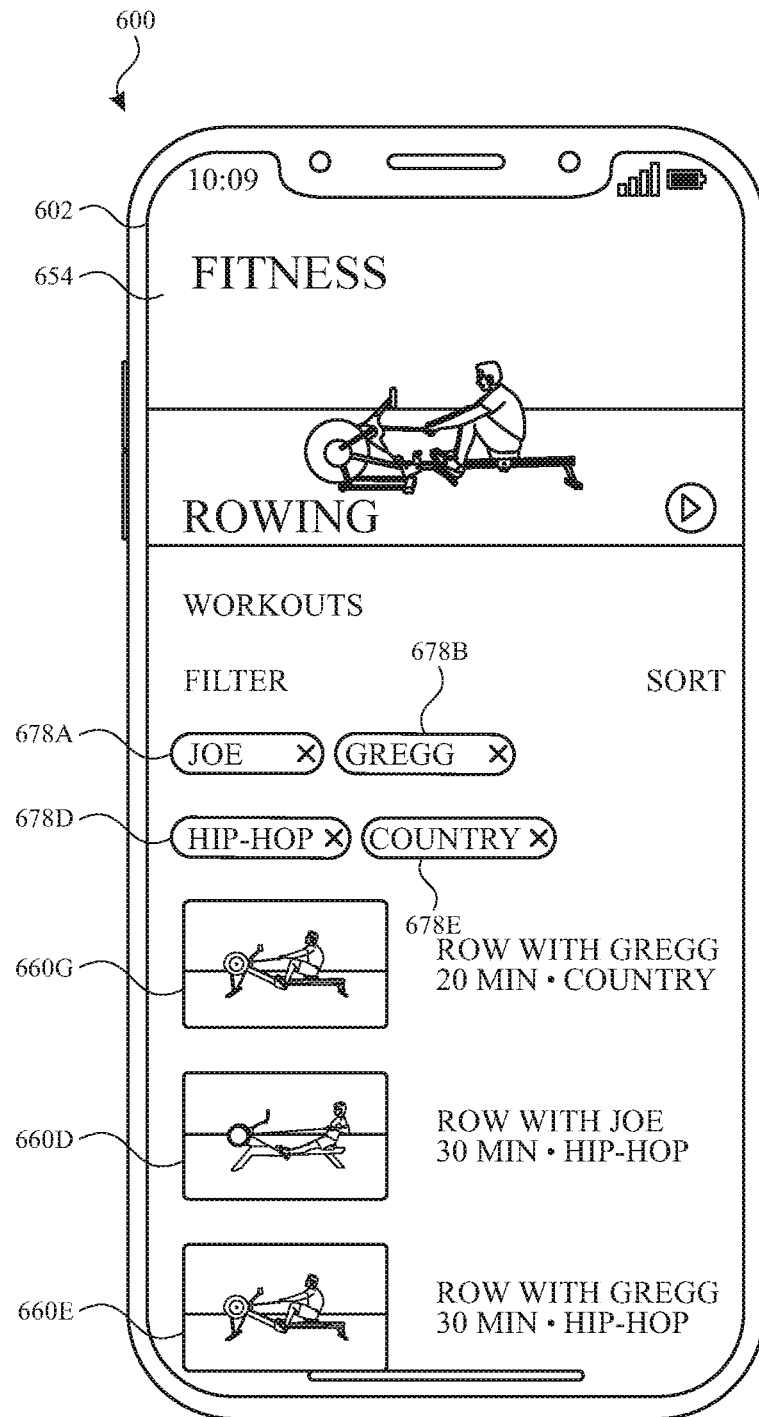

At FIG. 6T, in response to detecting input 680, electronic device 600 ceases to display filter representation 678C, as the 30 minute filter has been removed from the filter selections. Additionally, in response to detecting input 680, electronic device 600 updates the filtered workout suggestions based on the updated filter selections. Due to the updated filter selections, filter user interface 654 includes filtered workout suggestion 660G, which can be included with its 20 minute duration due to the removal of the 30 minute filter.

Figure 6U:
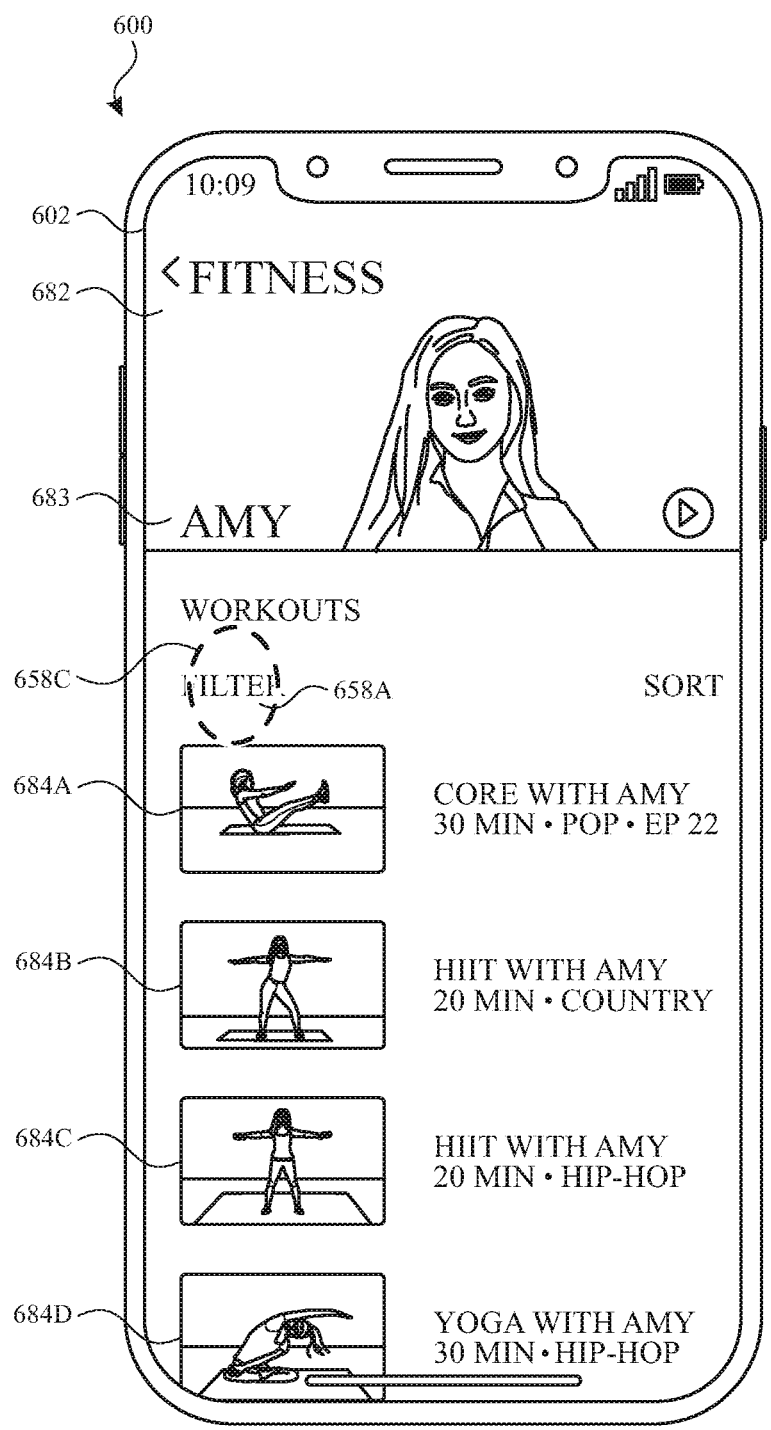

In some embodiments, instead of detecting selection of option 614C to filter based on exercise type, electronic device 600 detects selection of an option for filtering based on trainer. In some embodiments, electronic device 600 detects an input at a location corresponding to option 644A of FIG. 6L. At FIG. 6U, in response to detecting the input, electronic device 600 displays filter user interface 682. Filter user interface 682 includes filtered workout suggestions 684A-684D based on selected option 644A. Additionally, filter user interface 682 includes indication 683, which indicates the characteristic (e.g., Amy) that filtered workout suggestions 684-684D have in common. While displaying filter user interface 682, electronic device 600 detects input 658C at a location corresponding to option 658A.

Figure 6V:
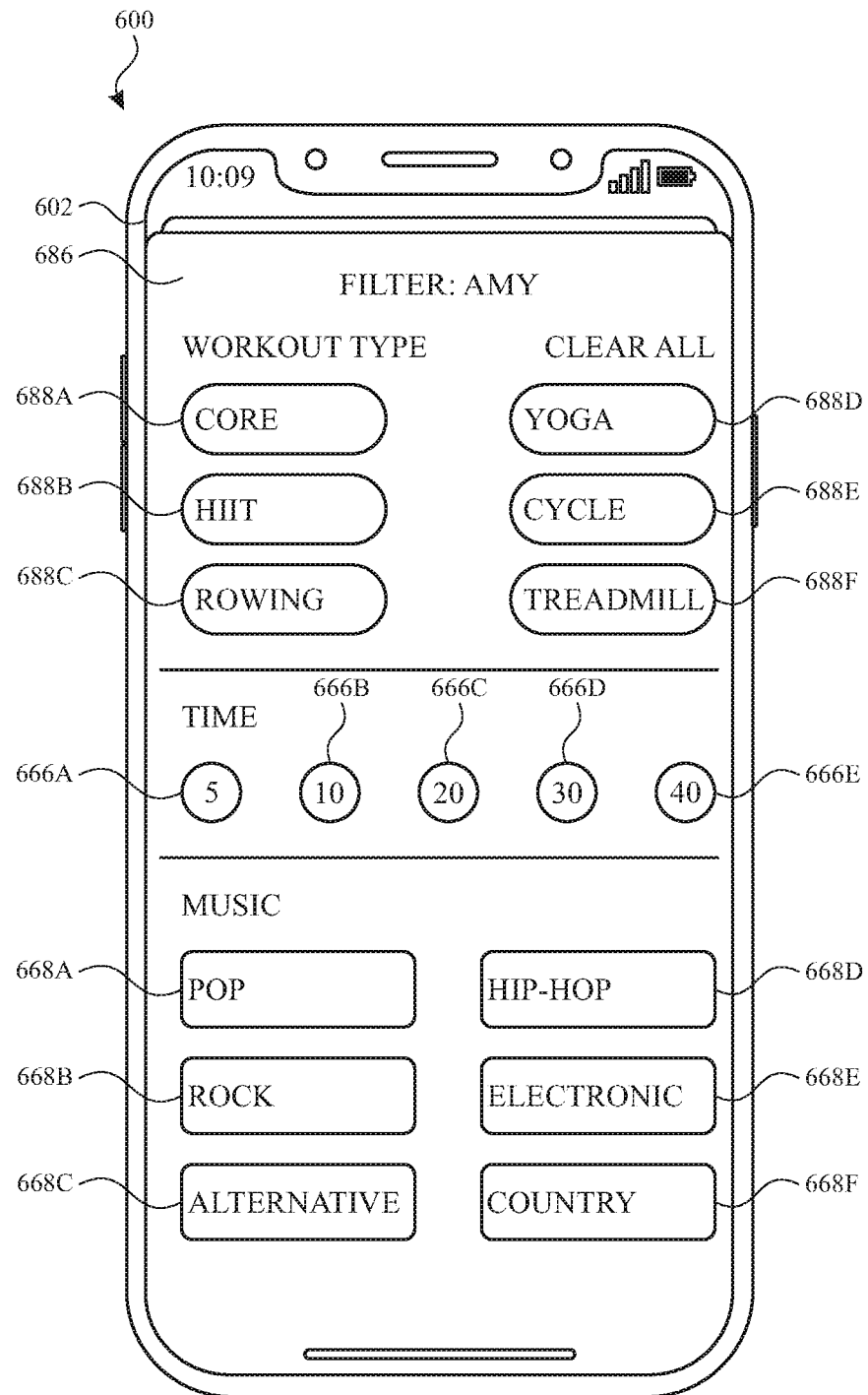

At FIG. 6V, in response to detecting input 658C, electronic device 600 displays filter user interface 686 with additional options for filtering workouts (e.g., in addition to trainer, which is currently filtered for Amy). For example, filter user interface 686 includes options 688A-688F for filtering workouts based on exercise (e.g., workout) type, options 666A-666E for filtering workouts based on duration of the workout, and options 668A-668F for filtering workouts based on music genre.

Figure 6W:
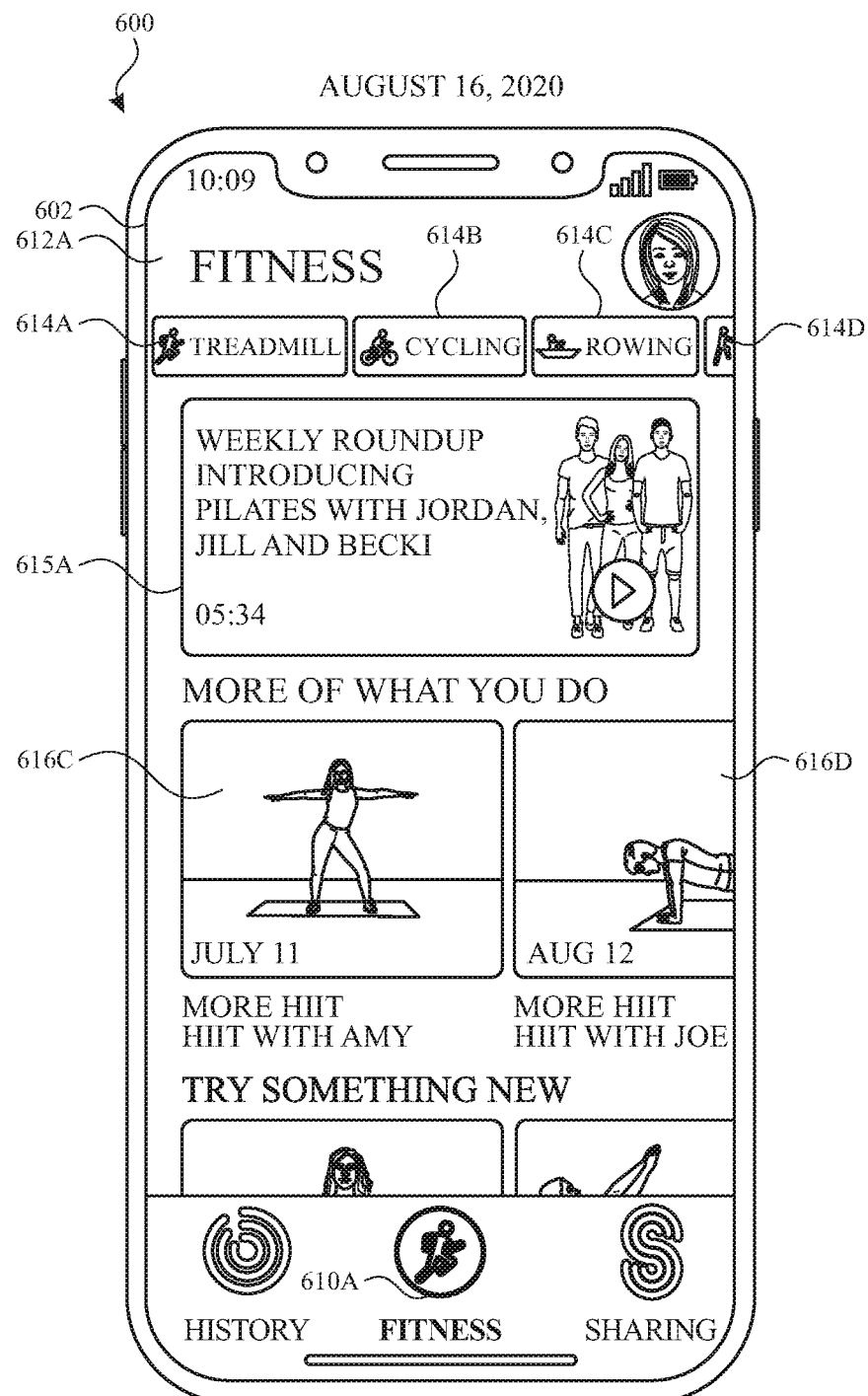

FIG. 6W depicts another example of a workout user interface 612A, similar to the workout user interface 612. The features described with reference to workout user interface 612A can be incorporated into workout user interface 612, and the features described with reference to workout user interface 612 can be incorporated into workout user interface 612A. Identical features in workout user interface 612A are labeled with the same reference numbers as used in workout user interface 612. Similar to workout user interface 612, workout user interface 612A includes options 614A-614D for filtering workouts based on exercise type, as well as workout suggestions 616C-616D that are selected based on the user's past workouts. Workout user interface 612A includes a weekly roundup option 615A. Selection of the weekly roundup option 615A causes playback of a weekly roundup video corresponding to a current week. For example, in some embodiments, a new weekly roundup video can be posted each week (e.g., each Sunday), and the weekly roundup video can introduce new workouts that were added to the workout application that week. In FIG. 6W, the current date is Aug. 16, 2020, and selection of the weekly roundup option 615A causes playback of a weekly roundup video corresponding to that week. In FIG. 6W1, the current date is Aug. 23, 2020, and a new weekly roundup option 615B corresponding to a different weekly roundup video (e.g., a weekly roundup video corresponding to the week of Aug. 23, 2020) is presented in the workout user interface 612A. At FIG. 6W1, while displaying workout user interface 612A, electronic device 600 detects input 617 with movement in an upward direction.

Figure 6X:
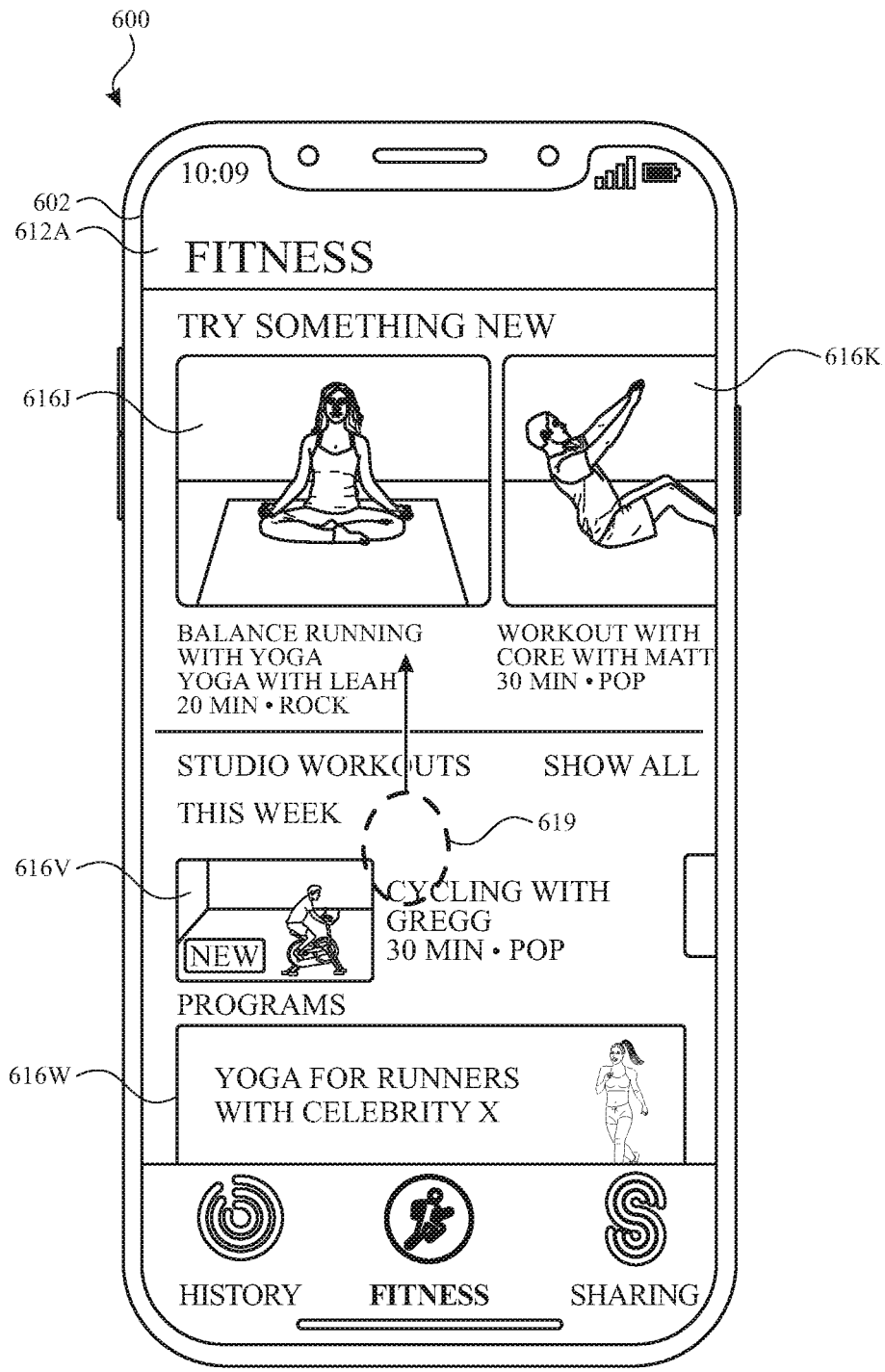

At FIG. 6X, in response to detecting input 617, electronic device 600 scrolls workout user interface 612A. Scrolling workout user interface 612A includes sliding workout suggestions 616J, 616K, 616V, 616W onto display 602. Workout suggestions 616J and 616K, like workout suggestions 616J and 616K in FIG. 6J, are workout suggestions that have been selected based on being complementary to previous workouts performed by the user. Workout suggestion 616V, like workout suggestions 616F, 616H, 616G, and 616I of FIG. 6I, are workout suggestions corresponding to new workouts that have been added to the application within the last week. Workout suggestion 616W, like workout suggestion 616B of FIG. 6H, is a workout suggestion corresponding to a workout program comprising an ordered series of workouts. While displaying workout user interface 612A, electronic device 600 detects input 619 with movement in an upward direction.

Figure 6Y:
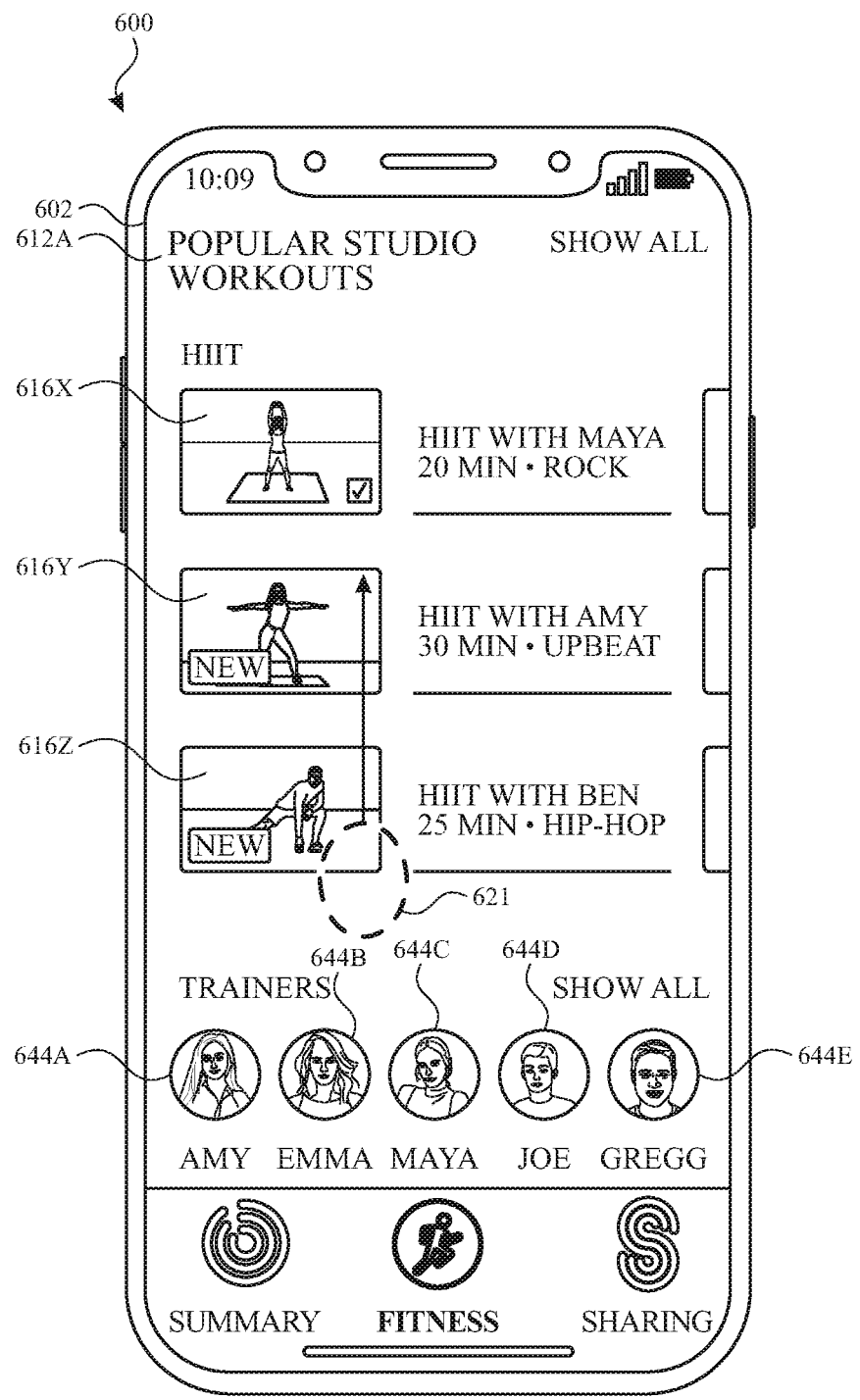

At FIG. 6Y, in response to detecting input 619, electronic device 600 scrolls workout user interface 612A. Scrolling workout user interface 612A includes sliding workout suggestions 616X, 616Y, and 616Z and options 644A-644E onto display 602. Workout suggestions 616X, 616Y, and 616Z, like workout suggestions 616L-616Q of FIG. 6J, are workout suggestions corresponding to workouts that are popular on the workout application. Options 644A-644E are identical to options 644A-644E of FIG. 6K, and can be selected to filter workout suggestions based on trainer. While displaying workout user interface 612A, electronic device 600 detects input 621 with movement in an upward direction.

Figure 6Z:
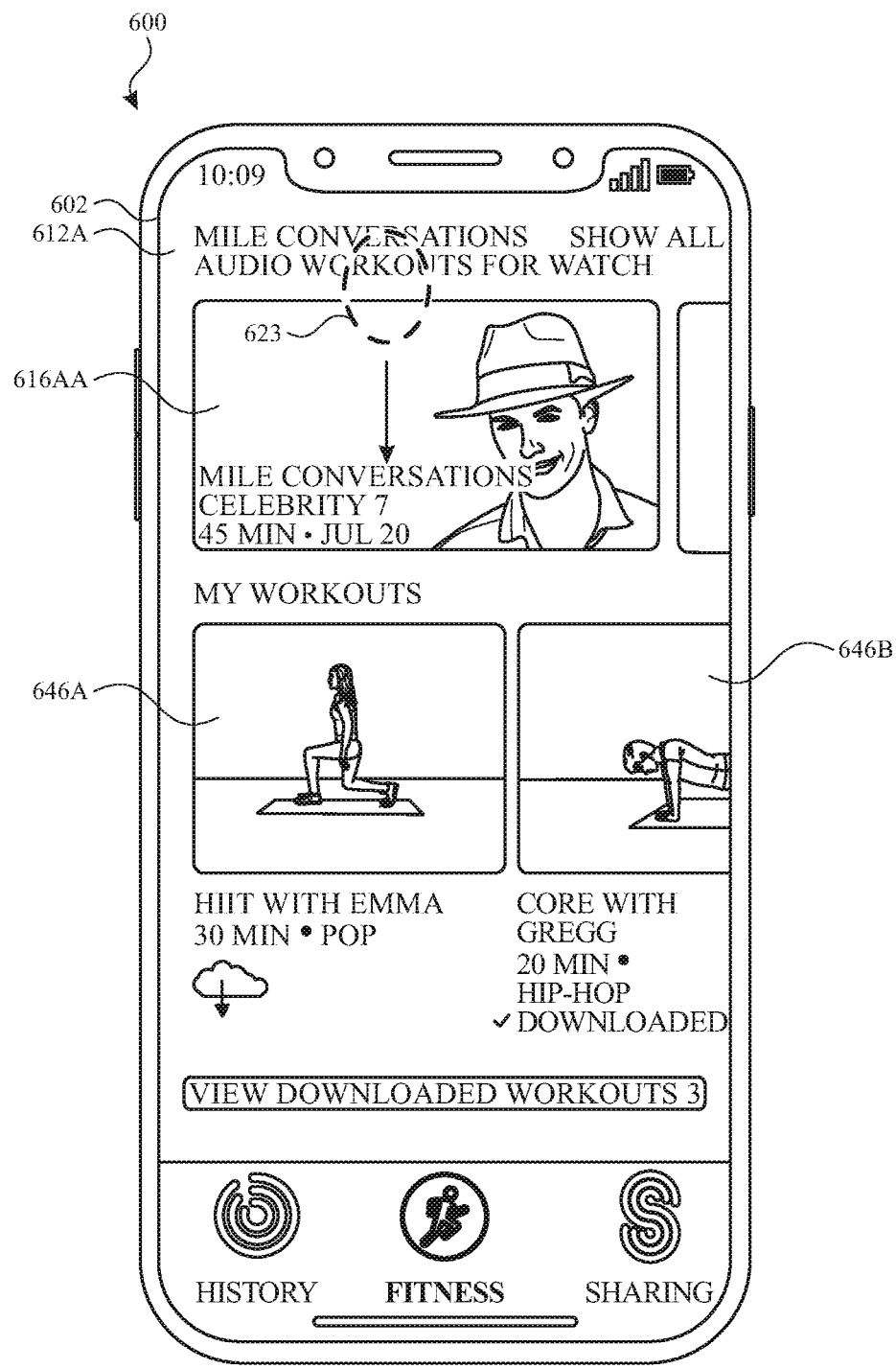
Figure 6A:
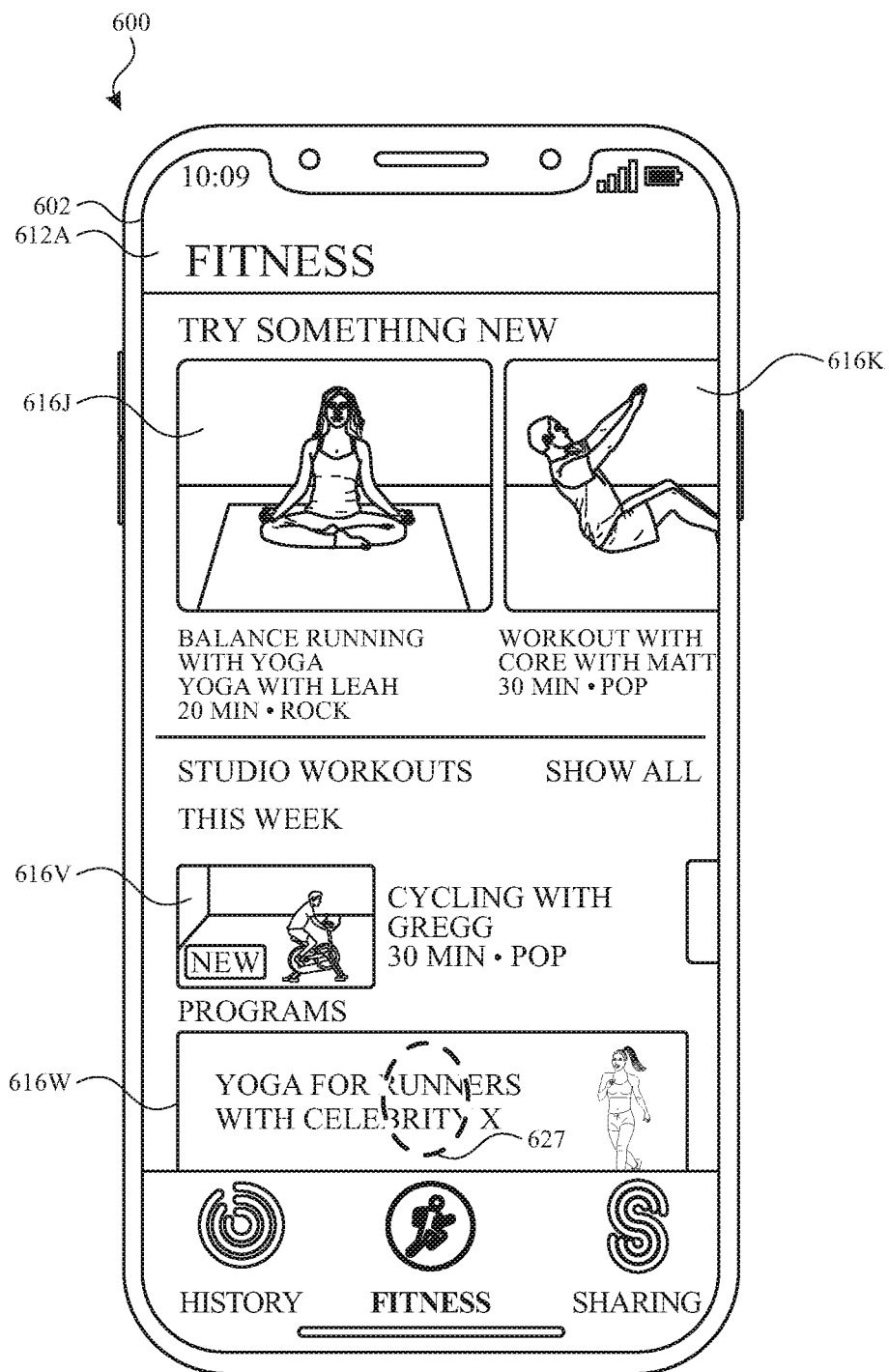
Figure 6B:
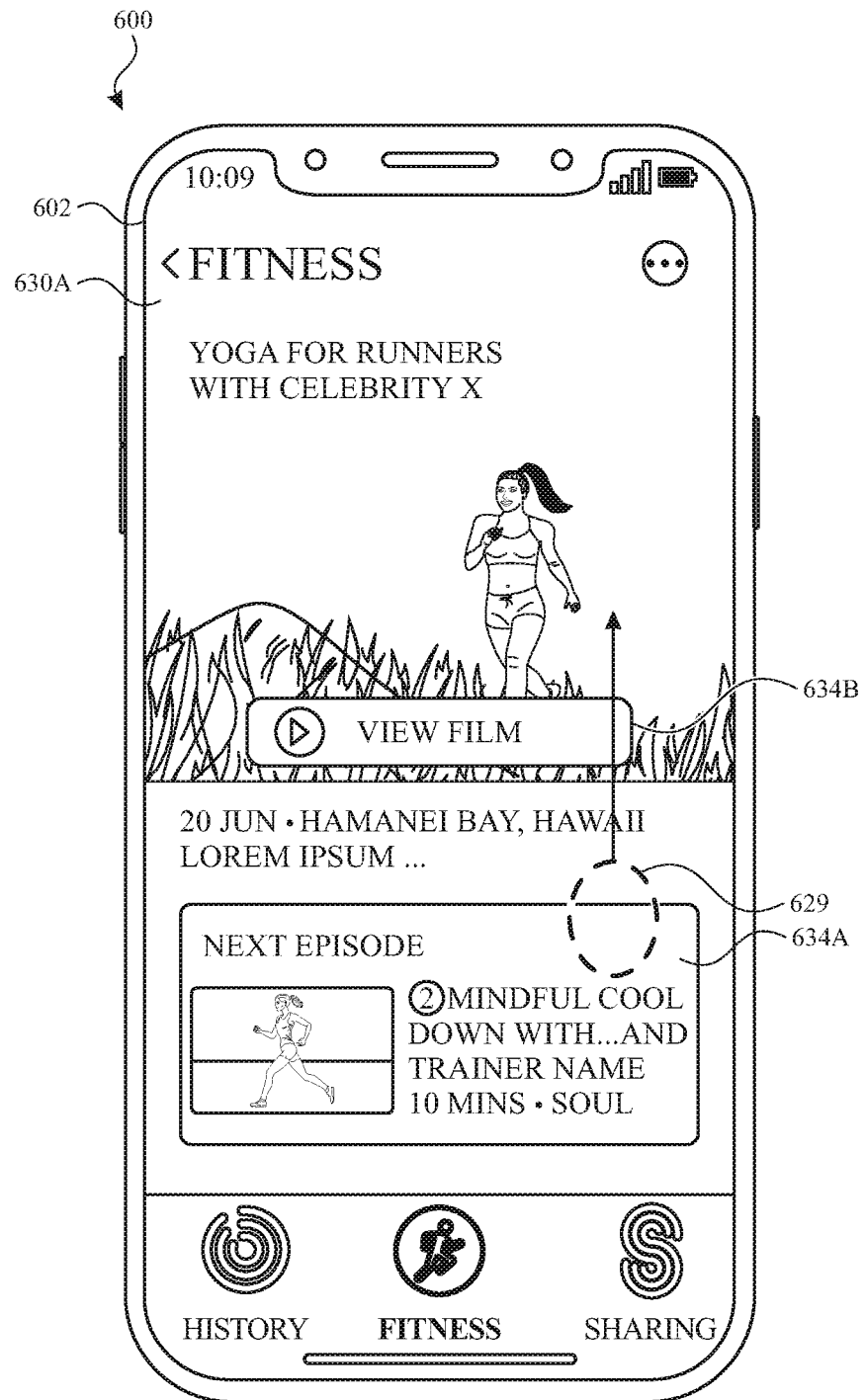
Figure 6C:
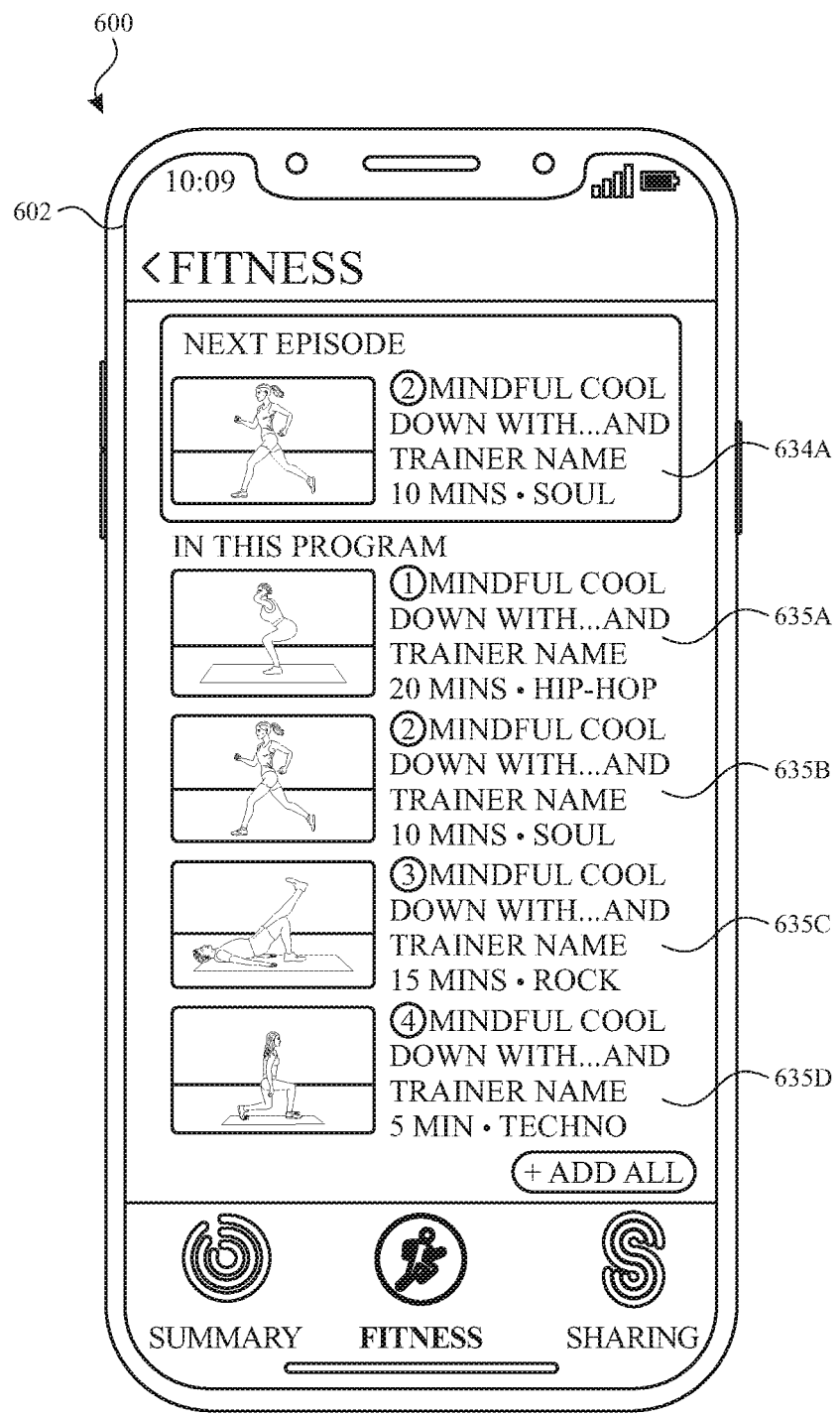
Figure 6D:
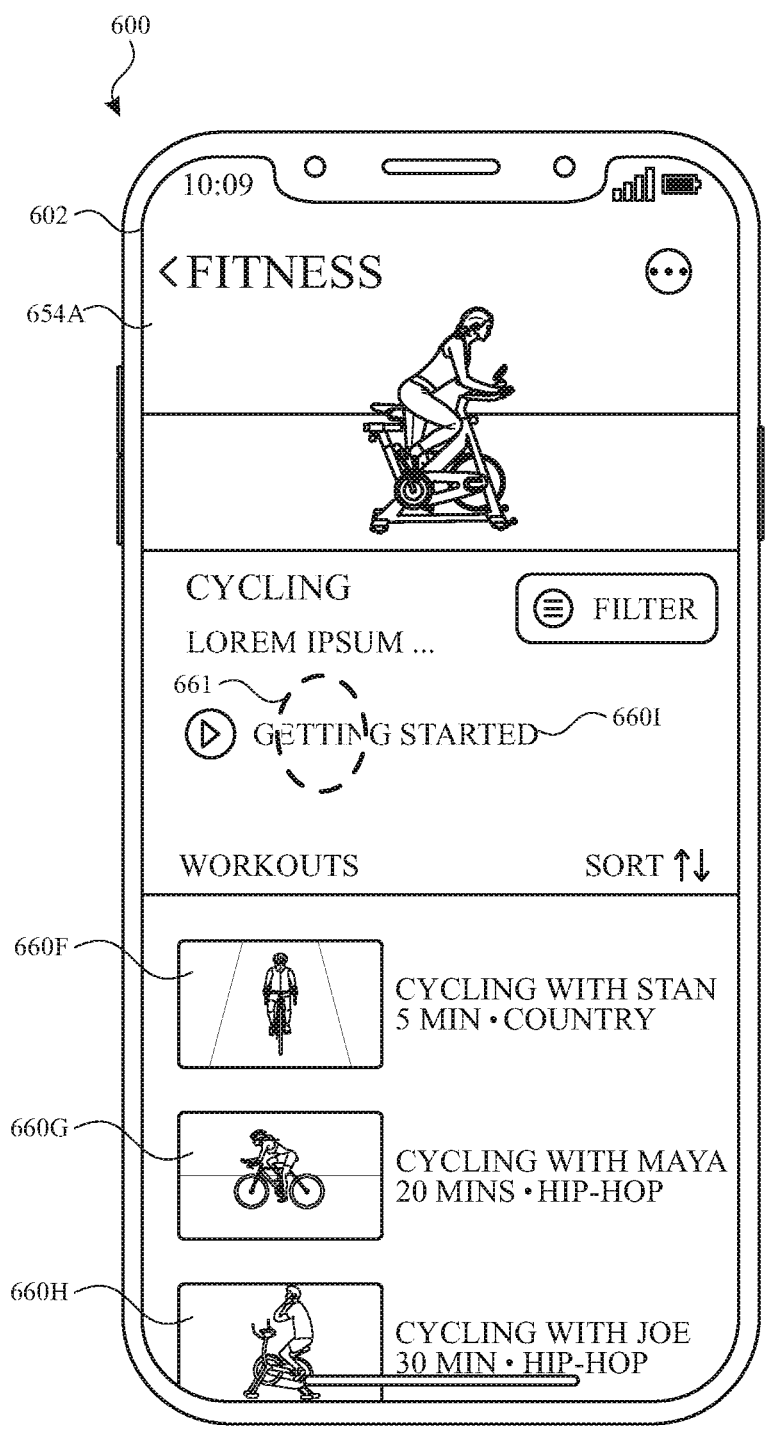
Figure 6E:
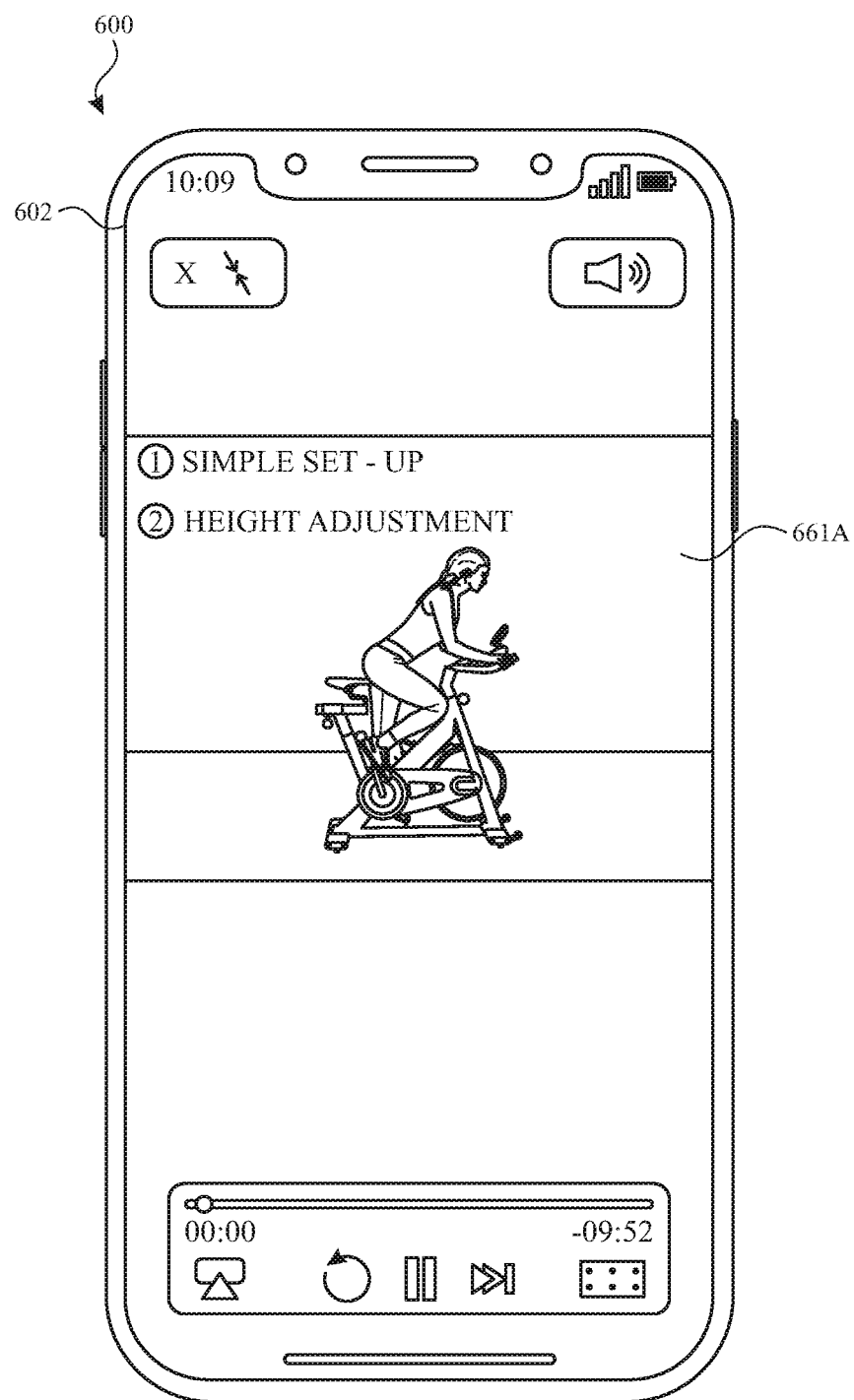

At FIG. 6Z, in response to detecting input 621, electronic device 600 scrolls workout user interface 612A. Scrolling workout user interface 612A includes sliding workout suggestions 616AA, and saved workouts 646A, 646B onto display 602. Workout suggestion 616AA is similar to workout suggestion 616R of FIG. 6K, and is a workout suggestion representing an audio workout. Saved workouts 646A, 646B are identical to saved workouts 646A, 646B of FIG. 6L. While displaying workout user interface 623, electronic device 600 detects input 623 with movement in a downward direction.

At FIG. 6AA, in response to detecting input 623, electronic device 600 scrolls workout user interface 612A to once again reveal workout suggestions 616J, 616K, 616V, and 616W (as were previously depicted in FIG. 6X). While displaying workout user interface 612A, electronic device 600 detects input 627 at a location corresponding to workout suggestion 616W.

At FIG. 6BB, in response to detecting input 627, electronic device 600 replaces display of workout user interface 612A with program user interface 630A. Program user interface 630A is similar to program user interface 630 of FIG. 6G. Various features of program user interface 630A can be incorporated into program user interface 630, and various features of program user interface 630 can be incorporated into program user interface 630A. Program user interface 630A includes a plurality of workout suggestions corresponding to a particular workout program (e.g., Yoga for Runners with Celebrity X). Scrolling down in the program user interface 630A (e.g., via user input 629) reveals a plurality of workout suggestions 635A-D in FIG. 6CC. The workout program consists of a plurality of workout content items that are ordered in a predefined sequence. In accordance with a determination that a workout in the workout program has been completed, electronic device 600 visually emphasizes, using a border, the workout suggestion corresponding to the workout that comes next in the predefined sequence of workouts in the workout program. For example, electronic device 600 visually emphasizes workout suggestion 634A in accordance with a determination that the workout corresponding to workout suggestion 635A has been completed. Workout suggestion 634A, which matches workout suggestion 635B, corresponds to the workout that is next in the sequence of workouts. Program user interface 630 also includes an option 634B that is selectable by a user to open and play a program introduction video. The program introduction video is separate and different from the workouts in the workout program. In some embodiments, the program introduction video comprises audio and/or visual clips (e.g., images or video clips) from some or all of the workouts in the workout program. In some embodiments, selection of a particular workout suggestion 634A, 635A-635D causes display of a corresponding detail user interface (similar to the detail user interface 620 of FIG. 6D). In some embodiments, the detail user interface for each workout can include a selectable option for playing video content corresponding to the workout, and a separate selectable option for playing the program introduction video (e.g., similar to options 623A and 623B in FIG. 6D).

FIG. 6DD displays a workout modality user interface 654A. Workout modality user interface 654A is similar to filter user interface 654 of FIG. 6N. Various features of workout modality user interface 654A can be incorporated into filter user interface 654, and various features of filter user interface 654 can be incorporated into workout modality user interface 654A. In some embodiments, workout modality user interface 654A can be displayed in response to a user input corresponding to 614B (e.g., in FIG. 6W or in FIG. 6M). Workout modality user interface 654A includes filtered workout suggestions 660F-660H based on selected option 614B. In the depicted scenario, the filtered workout suggestions 660F-660H all have a particular workout type (or workout modality) in common (e.g., cycling). The workout modality user interface 654A includes an option 660I that is selectable by a user to open and play a workout modality introduction video. The workout modality introduction video is separate and different from the workouts corresponding to filtered workout suggestions 660F-660H. In some embodiments, the workout modality introduction video can identify for a user any equipment that is required for the workout modality (e.g., a stationary bike can be required for the cycling workouts). While displaying workout modality user interface 654A, electronic device 600 detects input 661 at a location corresponding to option 660I.

At FIG. 6EE, in response to detecting input 661, electronic device 600 initiates playback of workout modality introduction video 661A.

FIG. 7 is a flow diagram illustrating a method for navigating and displaying workout suggestions using an electronic device, in accordance with some embodiments. Method 700 is performed at an electronic device (e.g., 100, 300, 500, 600) with a display (e.g., 602). Some operations in method 700 are, optionally, combined, the orders of some operations are, optionally, changed, and some operations are, optionally, omitted.

As described below, method 700 provides an intuitive way for navigating and displaying workout suggestions. The method reduces the cognitive burden on a user for navigating and displaying workout suggestions, thereby creating a more efficient human-machine interface. For battery-operated computing devices, enabling a user to navigate and display workout suggestions faster and more efficiently conserves power and increases the time between battery charges.

In some embodiments, the electronic device (e.g., 100, 300, 500, 600, 800) is a computer system. The computer system is optionally in communication (e.g., wired communication, wireless communication) with a display generation component and with one or more input devices. The display generation component is configured to provide visual output, such as display via a CRT display, display via an LED display, or display via image projection. In some embodiments, the display generation component is integrated with the computer system. In some embodiments, the display generation component is separate from the computer system. The one or more input devices are configured to receive input, such as a touch-sensitive surface receiving user input. In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

The electronic device displays (702), on the display (e.g., 602), a selectable user interface object (e.g., 610A, affordance) for displaying workout suggestions. The electronic device detects (704) (e.g., via a touch-sensitive display) a user input (e.g., 610B) corresponding to the selectable user interface object for displaying workout suggestions.

In response to (706) detecting the user input corresponding to the selectable user interface object for displaying workout suggestions, the electronic device displays (708), on the display, a user interface (e.g., 612) for displaying workout suggestions that includes concurrently displaying: a plurality of selectable options (710) that includes a first option (e.g., 614A-614D, selectable user interface object, affordance) that, when selected, causes the electronic device to initiate a process for displaying workout suggestions that share a first common workout parameter and a second option (e.g., 614A-614D, selectable user interface object, affordance) that, when selected, causes the electronic device to initiate a process for displaying workout suggestions that share a second common workout parameter; and a plurality of workout suggestions (712) (e.g., 616A-616D), wherein the plurality of workout suggestions are selected for display based on a workout history of a user of the electronic device. Concurrently displaying the plurality of selectable options and the plurality of workout suggestions enables a user to quickly gain access to the desired workout, thereby reducing the number of inputs needed for selecting a workout. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first common workout parameter and the second common workout parameter both correspond to a first type of workout parameter (e.g., exercise type, music type/genre, trainer, duration). In some embodiments, a workout suggestion corresponds to (e.g., represents) a workout (e.g., audio and/or video content that guides a user to perform a physical activity). In some embodiments, selecting a workout suggestion initiates a process for playback of a workout corresponding to the workout suggestion.

In some embodiments, the plurality of workout suggestions (e.g., 616A-616D) includes (714): a first workout suggestion (e.g., 616A-616B, a graphical representation of a workout), wherein the first workout suggestion corresponds to a first subset (e.g., the most recent/last workout that was completed, a workout that is part of a program/series) of a collection of completed workouts. In some embodiments, the first workout suggestion is selected for display based on correspondence between the first workout suggestion and the first subset of the collection of completed workouts. In some embodiments, the collection of completed workouts are workouts (e.g., audio/video content for a workout) that have been completed by a user of the electronic device. In some embodiments, the first workout suggestion (e.g., 616A) is displayed in a region of the display above the region occupied by the second workout suggestion (e.g., 616C). In some embodiments, the first workout suggestion (e.g., 616A) corresponds to the first subset when the first workout suggestion shares one or more characteristics (e.g., workout type, trainer, music genre, duration, required equipment, series/program) with the last completed workout. For example, the first workout suggestion has the same workout type and trainer as the last workout that was completed by the user. As another example, a user recently completed one of the workouts in a workout series/program, so the first workout suggestion (e.g., 616B) is the next workout in the series/program. Automatically suggesting a workout based on a collection of completed workouts improves the quality of suggestions to the user, thereby providing a means for selection by the user. Otherwise, additional inputs would be required to further locate the desired workout. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first subset of the collection of completed workouts includes at least one workout in a predefined series of workouts. In some embodiments, the first workout suggestion (e.g., 616B) corresponds to a next workout that has not been completed (e.g., a workout that is next in sequence after the at least one workout in the first subset) in the predefined series of workouts.

In some embodiments, the first subset of the collection of completed workouts excludes (e.g., does not include) at least one workout in a predefined series of workouts. In some embodiments, the first workout suggestion (e.g., 616A) corresponds to the workout that was most recently completed. In some embodiments, the first workout suggestion corresponds to the most recently completed workout based on one or more of: trainer, exercise type, duration of workout, music, and required equipment.)

In some embodiments, the electronic device detects a user input (e.g., 628) corresponding to the first workout suggestion (e.g., 616B) that corresponds to the next workout that has not been completed in the predefined series of workouts. In some embodiments, in response to detecting the user input corresponding to the first workout suggestion that corresponds to the next workout that has not been completed in the predefined series of workouts: the electronic device displays one or more workout suggestions (e.g., 634, 632A-632C) in the predefined series of workouts. In some embodiments, in response to detecting the user input corresponding to the first workout suggestion that corresponds to the next workout that has not been completed in the predefined series of workouts: in accordance with a determination that at least one workout in the predefined series of workouts has been completed, the electronic device visually emphasizes a workout suggestion (e.g., 634) of the one or more workout suggestions in the predefined series of workouts without visually emphasizing a different workout suggestion (e.g., 632A, 632C) of the one or more workout suggestions in the predefined series of workouts. Automatically visually emphasizing the next workout in a predefined series of workouts when a workout in the predefined series has been completed allows the user to quickly select the desired workout. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the plurality of workout suggestions includes: a second workout suggestion (e.g., 616C-616D, a graphical representation of a workout), wherein the second workout suggestion corresponds to a second subset (e.g., the workouts that have been completed during a predetermined duration of time (e.g., last 30, 60, or 90 days)) of a collection of completed workouts, wherein the first subset is different from the second subset. In some embodiments, the second workout suggestion is selected for display based on correspondence between the second workout suggestion and the second subset of the collection of completed workouts. In some embodiments, the second workout suggestion (e.g., 616C-616D) is displayed in a region of the display below the region occupied by the first workout suggestion (e.g., 616A-616B). In some embodiments, the second workout suggestion corresponds to the second subset in that the second workout suggestion shares one or more characteristics (e.g., workout type, trainer, music genre, duration, required equipment, series/program) with the workouts that have been completed in the last 30, 60, or 90 days. For example, the user has completed ten workouts in the past 30 days, and the second workout suggestion is a yoga workout because yoga was the most common workout type among the ten workouts. As another example, the user has completed thirty workouts in the past 90 days, and the second workout suggestion is a workout by a particular trainer because that particular trainer was the most common trainer among the thirty workouts. In some embodiments, the second workout suggestion is selected based on more than one characteristic (e.g., workout type and duration). Automatically suggesting a workout based on a collection of completed workouts improves the quality of suggestions to the user, thereby providing a means for selection by the user. Otherwise, additional inputs would be required to further locate the desired workout. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the plurality of selectable options (e.g., 614A-614D) and the plurality of workout suggestions (e.g., 616A-616D), the electronic device detects a first scroll gesture (e.g., 636). In some embodiments, after (e.g., in response to) detecting the first scroll gesture, the electronic device displays, on the display, a third workout suggestion (e.g., 616J), wherein the third workout suggestion corresponds to a third subset (e.g., workouts of the most common exercise type performed by the user, the workouts that have been completed during a predetermined duration of time (e.g., last 30, 60, or 90 days), the most recent/last workout that was completed, all of the completed workouts or a portion thereof) of a collection of completed workouts. In some embodiments, the third workout suggestion is selected for display based on the third workout suggestion not sharing a third common workout parameter (e.g., trainer, exercise type, duration, and the like) with the third subset of a collection of completed workouts.

In some embodiments, the third workout suggestion (e.g., 616J) is selected for display also based on the third workout suggestion sharing a fourth common workout parameter with the third subset. In some embodiments, the third workout suggestion is selected for display also based on the third workout suggestion being complementary (e.g., has a predefined correspondence/connection) with the third subset of a collection of completed workouts. For example, the user has primarily completed running workouts, so the device suggests yoga as a complementary workout to running.

In some embodiments, while displaying the plurality of selectable options (e.g., 614A-614D) and the plurality of workout suggestions (e.g., 616A-616D), the electronic device detects a second scroll gesture (e.g., 636). In some embodiments, after (e.g., in response to) detecting the second scroll gesture, the electronic device displays, on the display, a fourth workout suggestion (e.g., 616K), wherein the fourth workout suggestion corresponds to a fourth subset (e.g., workout(s) of a particular type (e.g., no corresponding video/audio for the workout), workout(s) that are not selectable as part of the plurality of workout suggestions) of a collection of completed workouts. In some embodiments, the fourth workout suggestion is selected for display based on correspondence between the fourth workout suggestion and the fourth subset. In some embodiments, the fourth subset is different from the first, second, and/or third subset. In some embodiments, the fourth suggestion (e.g., 616K) is displayed instead of the third suggestion (e.g., 616J), or vice-versa. In some embodiments, after detecting the second scroll gesture (e.g., a vertical scroll gesture), the electronic device detects a horizontal scroll gesture at a location corresponding to the third workout suggestion. In some embodiments, in response to detecting the horizontal scroll gesture, the electronic device displays the fourth suggestion.

In some embodiments, the plurality of workout suggestions includes a workout suggestion (e.g., 616A-616U) for a workout (e.g., audio and/or video content that guides a user to perform a physical activity) that corresponds to a predefined list of audio items (e.g., music playlist (e.g., as depicted in FIG. 6D)).

In some embodiments, the plurality of workout suggestions includes a workout suggestion (e.g., 616A-616Q) for a workout with metadata that causes output (e.g., at the electronic device and/or an external device) of prompts (e.g., coaching, audio or visual content prompting the user to perform certain actions or attempt to accomplish a goal) during playback of the workout.

In some embodiments, the plurality of workout suggestions includes a workout suggestion (e.g., 616A-616U) for a workout that, when selected for playback (e.g., start of video/audio content), causes recording (e.g., via one or more sensors) of one or more physical activity metrics at an external device (e.g., smartwatch, heart rate monitor, and/or fitness tracker). Automatically causing recording of one or more physical activity metrics when a workout is selected for playback allows the user to track their physical activity without requiring additional input. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the plurality of workout suggestions includes a workout suggestion (e.g., 616J) that has a physical activity type that is different than a physical activity type (e.g., the most common physical activity type among completed workouts (e.g., running, yoga, HIIT, and the like)) of a completed workout. In some embodiments, the workout suggestion has a predefined correspondence (e.g., complementary relationship) with a fifth subset (e.g., workouts of the most common exercise type performed by the user, the workouts that have been completed during a predetermined duration of time (e.g., last 30, 60, or 90 days), the most recent/last workout that was completed, all of the completed workouts or a portion thereof) of a collection of completed workouts.

In some embodiments, while displaying the plurality of selectable options (e.g., 614A-614D) and the plurality of workout suggestions (e.g., 616A-616D), the electronic device detects one or more inputs (e.g., 652, 658B). In some embodiments, in response to detecting the one or more inputs: the electronic device ceases display of the plurality of selectable operations and the plurality of workout suggestions. In some embodiments, in response to detecting the one or more inputs: the electronic device displays, on the display, a third option (e.g., 664A-664H, 666A-666E, 668A-668F, selectable user interface object, affordance) that, when selected, configures the electronic device to display workout suggestions that share a third common workout parameter and a fourth option (e.g., 664A-664H, 666A-666E, 668A-668F, selectable user interface object, affordance) that, when selected, configures the electronic device to display workout suggestions that share a fourth common workout parameter. In some embodiments, the third common workout parameter corresponds to a second type of workout parameter (e.g., exercise type, music type/genre, trainer, duration). In some embodiments, the fourth common workout parameter corresponds to a third type of workout parameter different from the second type of workout parameter (e.g., exercise type, music type/genre, trainer, duration).

In some embodiments, the electronic device detects selection of the third option (e.g., 664E in FIG. 6O). In some embodiments, in response to detecting selection of the third option, the electronic device changes one or more visual characteristics (e.g., dim, gray out or otherwise deemphasize) of the fourth option (e.g., 666E, 668A in FIG. 6P).

In some embodiments, the electronic device detects selection of the third option (e.g., 666D in FIG. 6Q). In some embodiments, after detecting selection of the third option (e.g., other option(s) are also selected), the electronic device displays one or more workout suggestions (e.g., 660D-660F in FIG. 6S) based on the detected selection of the third option, including a selectable user interface object (e.g., 678C) indicating that the third option has been selected. In some embodiments, while displaying the one or more workout suggestions based on the detected selection of the third option, the electronic device detects a user input (e.g., 680) corresponding to the selectable user interface object indicating that the third option has been selected. In some embodiments, in response to detecting the user input corresponding to the selectable user interface object indicating that the third option has been selected, the electronic device displays, on the display, one or more workout suggestions (e.g., 660G-660E in FIG. 6T) that were not displayed prior to detection of the user input corresponding to the selectable user interface object indicating that the third option has been selected.

In some embodiments, the electronic device displays a fifth workout suggestion (e.g., 616L-616Q), wherein the fifth workout suggestion is selected for display based on a frequency (e.g., within a predefined period of time (e.g., last 7, 14, or 30 days)) at which the fifth workout suggestion is selected by a group of users (e.g., users of external electronic devices). In some embodiments, the fifth workout suggestion corresponds to a popular or trending workout. In some embodiments, the fifth workout suggestion is displayed in response to (e.g., after) detecting a scroll gesture while the electronic device displays the plurality of selectable options and the plurality of workout suggestions.

In some embodiments, in accordance with a determination that a workout corresponding to a sixth workout suggestion (e.g., 616A, 616L) has been completed (e.g., a user has watched the workout (e.g., audio and/or video content of a workout)), the electronic device displays, on the display, an indication (e.g., 622F in FIG. 6D, check mark on 616L in FIG. 6J) that the workout corresponding to the sixth workout suggestion has been completed. In some embodiments, in accordance with a determination that the workout corresponding to the sixth workout suggestion has not been completed, the electronic device forgoes displaying the indication that the workout corresponding to the sixth workout suggestion has been completed. In some embodiments, the indication is displayed in response to detecting a user input (e.g., 618 in FIG. 6C) corresponding to the sixth workout suggestion. In some embodiments, the sixth workout suggestion is displayed in response to (e.g., after) detecting a scroll gesture while the electronic device displays the plurality of selectable options and the plurality of workout suggestions.

In some embodiments, the indication that the workout corresponding to the sixth workout suggestion has been completed is a visual check mark overlaid on the sixth workout suggestion (e.g., check mark on 616L in FIG. 6J).

In some embodiments, the electronic device detects a user input (e.g., 618) corresponding to a seventh workout suggestion (e.g., 616A). In some embodiments, in response to detecting the user input corresponding to the seventh workout suggestion, the electronic device displays, on the display, a detail user interface (e.g., 620) for the seventh workout suggestion, wherein the detail user interface includes one or more workout characteristics selected from a group consisting of equipment (e.g., 622C), duration (e.g., 622B), music genre (e.g., 622D), exercise type (e.g., 622A), and a number of times a workout corresponding to the seventh workout suggestion has been completed (e.g., 622F). In some embodiments, the one or more workout characteristics are associated with the workout corresponding to the seventh workout suggestion. In some embodiments, the seventh workout suggestion is displayed in response to (e.g., after)

detecting a scroll gesture while the electronic device displays the plurality of selectable options and the plurality of workout suggestions.

In some embodiments, the electronic device detects a user input (e.g., 618) corresponding to an eighth workout suggestion (e.g., 616A). In some embodiments, in response to detecting the user input corresponding to the eighth workout suggestion, the electronic device displays, on the display, an audio selectable user interface object (e.g., "Listen in Music" in FIG. 6D) that, when selected, initiates a process (e.g., launches a music application for playing audio items) for causing playback of one or more audio items (e.g., music file(s)) that are part of a predefined collection of audio items (e.g. playlist). In some embodiments, the predefined collection of audio items is associated with a workout corresponding to the eighth workout suggestion. In some embodiments, the electronic device detects a user input corresponding to the audio selectable user interface object. In some embodiments, in response to detecting the user input corresponding to the audio selectable user interface object, the electronic device launches a music application with a save option that, when selected, initiates a process for saving the predefined collection of audio items to a user library of the music application. In some embodiments, in response to detecting a user input corresponding to the save option, the electronic device displays a download option that, when selected, initiates a process for storing, at the electronic device, data corresponding to the predefined collection of audio items. In some embodiments, the eighth workout suggestion is displayed in response to (e.g., after) detecting a scroll gesture while the electronic device displays the plurality of selectable options and the plurality of workout suggestions.

In some embodiments, the electronic device causes an external device to display a ninth workout suggestion. In some embodiments, the ninth workout suggestion is based on one or more physical activity metrics of the user of the electronic device. In some embodiments, the one or more physical activity metrics are captured via one or more sensors of the external device.

In some embodiments, the electronic device displays, within the user interface for displaying workout suggestions (e.g., 612, 612A), a fifth option (e.g., 615A, 615B) (e.g., selectable user interface object, affordance) that, when selected, causes the electronic device to initiate a process for playing a new content introduction media (e.g., audio and/or video) corresponding to a plurality of new (e.g., previously unavailable to the user) workouts that have been made available to the user of the electronic device within a predefined period of time (e.g., within the last day, within the last week). In some embodiments, the new content video identifies each new workout suggestion of the plurality of new workout suggestions (e.g., by identifying a trainer, title, and/or workout type associated with the new workout suggestion. In some embodiments, the new content video comprises one or more images and/or video clips from each of the plurality of new workout suggestions. In some embodiments, the new content video object is concurrently displayed within the user interface with the plurality of selectable options and the plurality of workout suggestions. Displaying an option that, when selected, causes the electronic device to initiate a process for playing a new content introduction media corresponding to a plurality of new workouts provides the user with feedback about the current state of the device and provides feedback to the user indicating what is required to view the new content introduction media. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the electronic device detects a user input corresponding to a tenth workout suggestion (e.g., 616A). In response to detecting the user input corresponding to the tenth workout suggestion, the electronic device concurrently displays, on the display: a first audio selectable user interface object (e.g., 623C) that, when selected, initiates a process (e.g., launches a music application for playing audio items) for causing playback of a plurality of audio items (e.g., a plurality of music files) that are part of a predefined collection of audio items (e.g., a music playlist), wherein the predefined collection of audio items is associated with a workout corresponding to the tenth workout suggestion; a second audio selectable user interface object (e.g., 623D) that, when selected, initiates a process (e.g., launches a music application for playing audio items) for causing playback of a first audio item (e.g., a first music file) of the plurality of audio items (e.g., without causing playback of the other audio items of the plurality of audio items); and a third audio selectable user interface object (e.g., 623E) that, when selected, initiates a process (e.g., launches a music application for playing audio items) for causing playback of a second audio item (e.g., a second music file different from the first music file) of the plurality of audio items different from the first audio item (e.g., without causing playback of the other audio items of the plurality of audio items). Displaying different selectable user interface objects that, respectively, allow a user to play back a plurality of audio items in a predefined collection of audio items or, alternatively, allow a user to play back individual audio items (e.g., a first audio item or a second audio item), provides the user with feedback about the current state of the device and provides feedback to the user indicating what is required to play back the entire predefined collection of audio items or individual audio items within the collection. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first option (e.g., 614A, 614B, 614C, 614D), when selected, causes the electronic device to initiate a process for displaying workout suggestions that share a first common workout type (e.g., a workout modality (e.g., HIIT, yoga, cycling, running, core, rowing, dance)) (e.g., FIG. 6N, FIG. 6DD). In some embodiments, the electronic device detects a user input corresponding to the first option. In response to detecting the user input corresponding to the first option, the electronic device concurrently displays: one or more workout suggestions that share the first common workout type (e.g., 660A-660D, 660F-660H) (e.g., without displaying workout suggestions that do not share the first common workout type), and a workout type introduction object (e.g., 660E, 660I) (e.g., a selectable user interface object, an affordance) that, when selected, causes the electronic device to initiate a process for playing a workout type introduction video corresponding to the first common workout type, wherein the workout type introduction video identifies one or more pieces of workout equipment (e.g., dumbbells, yoga mat, treadmill, stationary bike)

required for the first common workout type. In some embodiments, the second option, when selected, causes the electronic device to initiate a process for displaying workout suggestions that share a second common workout type different from the first common workout type (e.g., a workout modality (e.g., HIIT, yoga, cycling, running, core, rowing, dance)), and the method further comprises: detecting a user input corresponding to the second option; in response to detecting the user input corresponding to the second option, concurrently displaying: one or more workout suggestions that share the second common workout type (e.g., without displaying workout suggestions that do not share the second common workout type), and a second workout type introduction option (e.g., a selectable user interface object, an affordance) that, when selected, causes the electronic device to initiate a process for playing a second workout type introduction video (e.g., different from the workout type introduction video) corresponding to the second common workout type, wherein the second workout type introduction video identifies one or more pieces of workout equipment (e.g., dumbbells, yoga mat, treadmill, stationary bike) required for the second common workout type). Concurrently displaying the workout type introduction object and the one or more workout suggestions enables a user to quickly gain access to the desired workout, thereby reducing the number of inputs needed for selecting a workout. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the electronic device displays, within the user interface for displaying workout suggestions, a sixth option (e.g., 616B, 616W) (e.g., selectable user interface object, affordance) that, when selected, causes the electronic device to initiate a process for displaying workout suggestions for a plurality of workouts in a predefined series of workouts (e.g., FIG. 6G, FIG. 6BB, FIG. 6CC) (in some embodiments, a plurality of workouts in a predefined ordered sequence) (e.g., without displaying workout suggestions for workouts that are not in the predefined series of workouts). The electronic device detects a user input corresponding to the sixth option. In response to detecting the user input corresponding to the sixth option, the electronic device concurrently displays: workout suggestions for the plurality of workouts in the predefined series of workouts (e.g., without displaying workout suggestions that do not correspond to the plurality of workouts in the predefined series of workouts), and a workout series introduction object (e.g., a selectable user interface object, an affordance) that, when selected, causes the electronic device to initiate a process for playing a workout series introduction media (e.g., audio and/or video) corresponding to the predefined series of workouts. In some embodiments, each workout in the predefined series of workouts corresponds to a unique workout video, and the workout series introduction video is different from the plurality of workout videos in the workout series. In some embodiments, the workout series introduction video includes one or more video clips and/or one or more images from at least a subset of the predefined series of workouts. In some embodiments, the method further comprises displaying, within the user interface for displaying workout suggestions, a seventh option (e.g., selectable user interface object, affordance) that, when selected, causes the electronic device to initiate a process for displaying workout suggestions for a second plurality of workouts in a second predefined series of workouts (in some embodiments, a second plurality of workouts in a second predefined ordered sequence different from the plurality of workouts in the predefined ordered sequence) (e.g., without displaying workout suggestions for workouts that are not in the second predefined series of workouts), wherein the second plurality of workouts in the second predefined series of workouts is different from the plurality of workouts in the predefined series of workouts; detecting a user input corresponding to the seventh option; and in response to detecting the user input corresponding to the seventh option, concurrently displaying: workout suggestions for the plurality of workouts in the second predefined series of workouts (e.g., without displaying workout suggestions that do not correspond to the second plurality of workouts in the second predefined series of workouts), and a second workout series introduction object (e.g., a selectable user interface object, an affordance) that, when selected, causes the electronic device to initiate a process for playing a second workout series introduction video (e.g., different from the workout series introduction video) corresponding to the second predefined series of workouts. In some embodiments, each workout in the second predefined series of workouts corresponds to a unique workout video, and the second workout series introduction video is different from the plurality of workout videos in the second workout series. In some embodiments, the second workout series introduction video includes one or more video clips and/or one or more images from at least a subset of the second predefined series of workouts. Concurrently displaying the workout series introduction object and the plurality of workouts in the predefined series of workouts enables a user to quickly gain access to the desired workout, thereby reducing the number of inputs needed for selecting a workout. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Note that details of the processes described above with respect to method 700 (e.g., FIG. 7) are also applicable in an analogous manner to the methods described below. For example, method 700 optionally includes one or more of the characteristics of the various methods described below with reference to method 900. For example, the plurality of workout suggestions in method 700 optionally includes workout suggestions 616R-616U, as described with reference to method 900. For brevity, these details are not repeated below.

FIGS. 8A-8S illustrate exemplary user interfaces for starting an audio-based workout, in accordance with some embodiments. The user interfaces in these figures are used to illustrate the processes described below, including the processes in FIG. 9.

FIG. 8A depicts electronic device 600, which is a smartphone with display 602. Display 602 of electronic device 600 includes a touch-sensitive surface on which electronic device 600 can detect user gestures (e.g., tap, swipe, drag). In some embodiments, electronic device 600 includes one or more features of electronic device 100, 300, and/or 500.

At FIG. 8A, electronic device 600 displays workout user interface 612 with workout suggestions 616R-616U. Workout suggestions 616R-616S represent audio content (e.g., workout content) that has a duration corresponding to the amount of time required to walk a predefined distance (e.g., 1, 2, or 3 miles). Workout suggestions 616T-616U represent audio content (e.g., workout content) corresponding to a predefined route at or near one or more physical locations (e.g., a 5K route in Hackney). While displaying workout user interface 612, electronic device 600 detects input 802B at a location corresponding to option 802A. In some embodiments, electronic device 600 displays workout user interface 612 in response to an input (e.g., 640 at FIG. 6J).

At FIG. 8B, in response to detecting input 802B, electronic device 600 replaces display of workout user interface 612 with display of library user interface 804. Library user interface 804 includes a plurality of workout suggestions (e.g., 806A-806D). Workout suggestions 806A-806D represent audio content (e.g., content that has a duration corresponding to the amount of time required to walk a predefined distance (e.g., 1, 2, or 3 miles)). Workout suggestion 806A of FIG. 8B corresponds to workout suggestion 616R of FIG. 8A. In some embodiments, selection of workout suggestion 616R of FIG. 8A and selection of workout suggestion 806A of FIG. 8B both result in display of the same user interface with details/information about the same workout. Similarly, workout suggestion 806B of FIG. 8B corresponds to workout suggestion 616S of FIG. 8A. While displaying workout user interface 612, electronic device 600 detects input 808 at a location corresponding to workout suggestion 806A.

At FIG. 8C, in response to detecting input 808, electronic device 600 replaces display of library user interface 804 with display of detail user interface 810. Detail user interface 810 includes information about the selected workout corresponding to workout suggestion 806A. Detail user interface 810 includes music item representations 814A-814E, which represent one or more music items of a playlist. In some embodiments, after playback of the workout content (e.g., corresponding to workout suggestion 806A) ends, electronic device 600 automatically starts playback of the playlist (e.g., causes audio output at an external device for playing back audio). Detail user interface 810 includes add option 812A for causing the workout content to be stored (e.g., downloaded) to electronic device 800. While displaying detail user interface 810, electronic device 600 detects input 812B at a location corresponding to add option 812A.

At FIG. 8C1, in response to detecting input 812B, electronic device 600 initiates a process for causing electronic device 800 to store, at electronic device 800, workout content (e.g., media) corresponding to workout suggestion 806A. In response to detecting input 812B, electronic device 600 visually modifies add option 812A to indicate that the workout content has been queued to be stored at electronic device 800 (e.g., queued to be downloaded). In some embodiments, the workout content remains in a queued state until the electronic device 800 is connected to and/or is drawing power from a charger.

At FIG. 8D, electronic device 600 continues the process for causing electronic device 800 to store, at electronic device 800, workout content corresponding to workout suggestion 806A. In response to detecting input 812B and/or in accordance with a determination that a set of downloading criteria have been satisfied (e.g., in accordance with a determination that the electronic device 800 is being charged), electronic device 600 visually modifies add option 812A to indicate that the workout content has been stored at electronic device 800. While displaying detail user interface 810, electronic device 600 detects input 815 which corresponds to an upward swipe gesture.

At FIG. 8D1, in response to detecting input 815, electronic device 600 displays additional content in detail user interface 810, including additional music item representations 814F-814K.

FIGS. 8E-8Q depict techniques related to playback of workout content at electronic device 800. In particular, the workout content that is played is the same workout content that was selected at electronic device 600 in FIGS. 8A-8D (e.g., corresponding to workout suggestion 806A). FIG. 8E depicts electronic device 800, which is a smartwatch with display 801. Electronic device 800 is operably connected to (e.g., wirelessly paired with) electronic device 600. For example, electronic device 600 is configured to wirelessly communicate with electronic device 800, and vice-versa. In some embodiments, electronic device 600 and electronic device 800 are both signed into the same account (e.g., an account associated with a user that enables the user to access features/functions that are otherwise limited without the account). Display 801 of electronic device 800 includes a touch-sensitive surface on which electronic device 800 can detect user gestures (e.g., tap, swipe, and/or drag). In some embodiments, electronic device 800 includes one or more features of electronic device 100, 300, and/or 500.

At FIG. 8E, electronic device 800 displays workout user interface 816 with representation 818. Representation 818 represents audio workout content (e.g., corresponding to workout suggestion 806A). While displaying workout user interface 816, electronic device 800 detects input 820 at a location corresponding to option 819.

At FIG. 8E1, in response to detecting input 820, electronic device 800 replaces display of workout user interface 816 with library user interface 821. Library user interface 821 includes workout representations 823A-823C. Workout representation 823A corresponds to representation 818 of FIG. 8E. In the depicted example, library user interface 821 presents workout representations 823A-823C that represent audio workout content that has been stored on (e.g., downloaded to) electronic device 800. Library user interface 821 includes option 827 that is selectable by a user for a user to view additional audio workout content, including audio workout content that is available but has not been stored on (e.g., downloaded to) electronic device 800. While displaying library user interface 821, electronic device 800 detects input 829A, which corresponds to a leftward swipe gesture at a location corresponding to workout representation 823C.

At FIG. 8E2, in response to detecting input 829A, electronic device 800 shifts workout representation 823C horizontally to reveal a remove option 831. Selection of the remove option 831 removes audio workout content represented by workout representation 823C from electronic device 800, and removes workout representation 823C from library user interface 821. At FIG. 8E2, electronic device 800 detects input 829B, which corresponds to a rightward swipe gesture at a location corresponding to workout representation 823C.

At FIG. 8E3, in response to detecting input 829B, electronic device 800 shifts workout representation 823C horizontally back to its original position. While displaying library user interface 821, electronic device 800 detects input 829C at a location corresponding to workout representation 823A.

At FIG. 8E4, in response to detecting input 829C, electronic device 800 replaces display of library user interface 821 with detail user interface 833. Detail user interface 833 includes information about the selected workout corresponding to workout representation 823A. Detail user interface 833 includes music item representations, which represent one or more music items of a playlist that is associated with the workout (e.g., an ordered list of songs selected to accompany the workout such as songs selected by or in consultation with the celebrity who is featured in the workout). In some embodiments, the playlist is a predetermined playlist (e.g., is not a user-selected playlist). In some embodiments, after playback of the workout content (e.g., corresponding to workout representation 823A) ends, electronic device 800 automatically starts playback of the playlist (e.g., causes audio output at an external device for playing back audio). Detail user interface 833 includes start option 835A for causing playback of workout content (e.g., corresponding to workout representation 823A). Detail user interface 833 also includes download option 835B for causing workout content corresponding to workout representation 823A to be stored on electronic device 800. Detail user interface 833 also includes open playlist option 835C for causing a music playlist associated with workout representation 823A to begin playing in a separate music application. While displaying detail user interface 833, electronic device 800 detects input 829D at a location corresponding to start option 835A.

At FIG. 8F, in response to detecting input 829D, electronic device 800 replaces display of detail user interface 833 with media user interface 822. Media user interface 822 includes a set of playback controls, including play/pause button 824A, skip back button 824B, skip forward button 824C, and title indication 824D. Title indication 824D provides an indication of the audio content that is queued for playback or is currently playing. Electronic device 800 has not caused audio playback to start in response to detecting input 820, as indicated by the state of play/pause button 824A. In some embodiments, in response to detecting input 820, electronic device 800 automatically causes audio playback of the workout content and causes recording of physical activity metrics during playback of the workout content.

While displaying media user interface 822, electronic device 800 detects input 825 at a location corresponding to play/pause button 824A. In response to detecting input 825, electronic device 800 causes audio playback of the workout content and causes recording of physical activity metrics during playback of the workout content. Prior to detection of input 825, one or more sensors (e.g., GPS, accelerometer, gyroscope, and/or heart rate) of electronic device 800 are disabled. The one or more sensors are used to capture physical activity of the user. In response to detecting input 825, electronic device 800 causes the one or more sensors to be enabled so as to improve accurate measurements of the physical activity of the user during the workout.

In some embodiments, audio playback of the workout content occurs at an external device (e.g., speakers, headphones) that is in communication with electronic device 800. In some embodiments, the physical activity metrics are recorded (e.g., captured) via one or more sensors (e.g., GPS, accelerometer, gyroscope, and/or heart rate) of electronic device 800.

At media user interface 822 of FIG. 8G, in response to detecting input 825, electronic device 800 visually updates play/pause button 824A to indicate that audio playback is occurring. Surrounding play/pause button 824A is a playback progress indicator 824AA, which visually indicates progress of audio playback. While displaying media user interface 822, electronic device 800 detects input 826 with movement in the left-to-right direction. In response to detecting input 826, electronic device 800 replaces display of media user interface 822 with display of workout user interface 830, as shown on the right side of FIG. 8G.

Workout user interface 830 includes distance indication 832A, which indicates the distance the user has traveled since the beginning of the workout (e.g., the start of playback of the workout content). Workout user interface 830 includes time indication 832B, which indicates the amount of time that has elapsed since the beginning of the workout (e.g., the start of playback of the workout content). In some embodiments, while displaying workout user interface 830, electronic device 800 detects input 828 with movement in the right-to-left direction. In response to detecting input 828, electronic device 800 replaces display of workout user interface 830 with display of media user interface 822. In some embodiments, while displaying workout user interface 830, if electronic device 800 detects an input with movement in the left-to-right direction (rather than the right-to-left input 828 shown in FIG. 8G), electronic device 800 replaces display of workout user interface 830 with a workout management user interface (not shown). The workout management user interface can include a pause/resume option that is selectable to pause and/or resume a workout (e.g., pause and/or resume audio playback associated with a workout, pause and/or resume recordation of physical metrics associated with a workout) and an end option that is selectable to end a workout (e.g., end audio playback associated with a workout, end recordation of physical metrics associated with a workout). The workout management user interface can also include a water lock option that is selectable to enable or disable a water lock feature. Enabling the water lock option disables touch-screen display 801 to prevent accidental input on touch-screen display 801 caused by moisture, while disabling the water lock option re-enables touch-screen display 801.

Figure 8J:
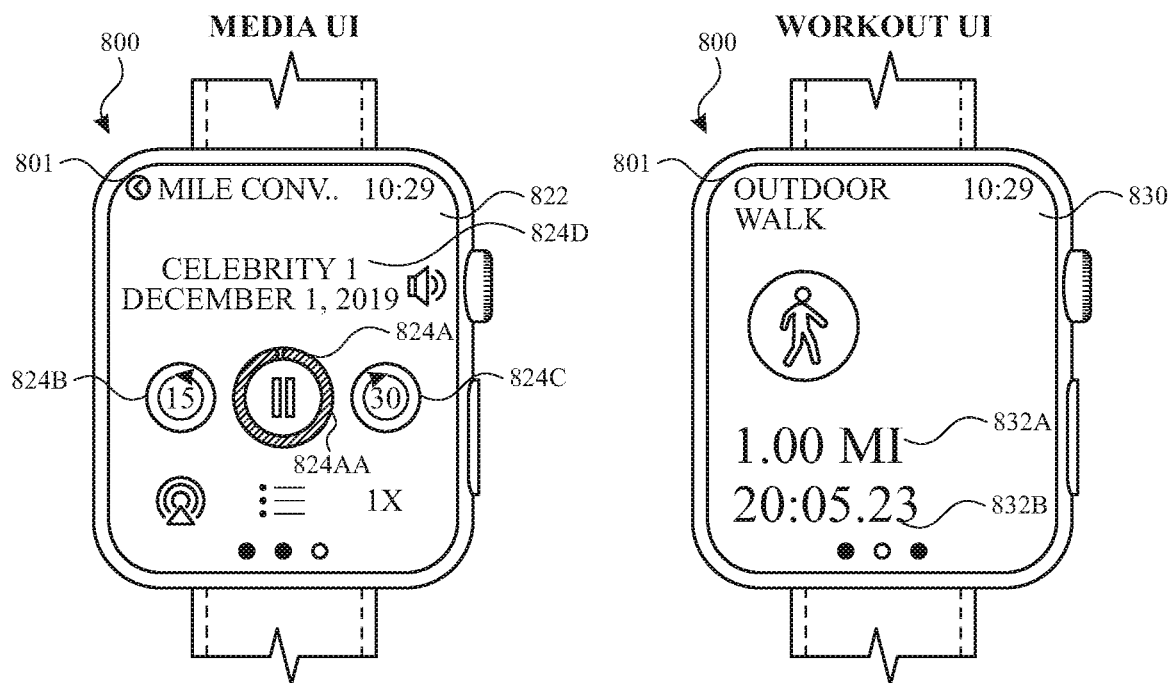
Figure 8K:
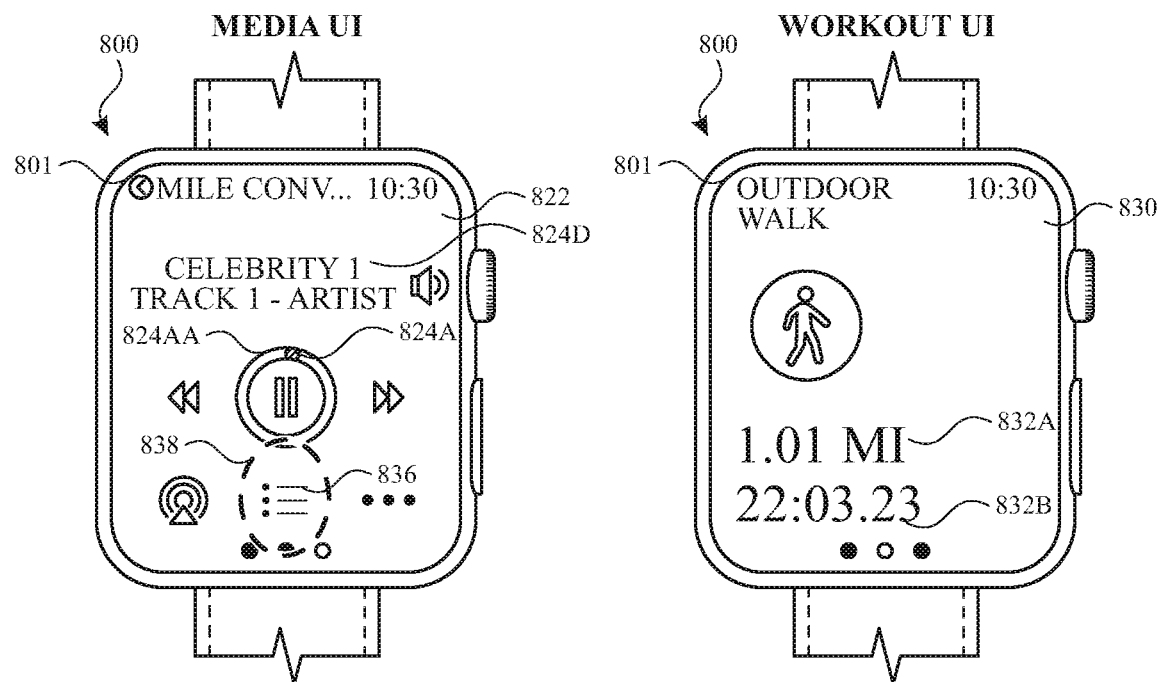

FIGS. 8H and 8J-8K depict both media user interface 822 and workout user interface 830 to illustrate how the user interfaces would progress, respectively, as playback of the workout content continues. In some embodiments, electronic device 800 transitions between display of media user interface 822 and display of workout user interface 830 in response to inputs analogous to inputs 826 and 828, as discussed above.

At FIG. 8H, electronic device 800 displays media user interface 822 or, alternatively, workout user interface 830 after playback of a portion of the workout content has occurred. Playback progress indicator 824AA indicates that the audio workout content is approximately at the halfway point. In response to a determination that a predetermined point in time has been reached (e.g., halfway point) during playback of audio content (e.g., corresponding to workout suggestion 616R), electronic device 800 causes, via an audio output device (e.g., speakers, headphones), an audible indication that the halfway point in the audio content has been reached.

At FIG. 8I, in response to a determination that a predetermined point in time has been reached during playback of audio content (e.g., corresponding to workout suggestion 616R), electronic device 800 displays visual content 834 that corresponds to the audio content of the workout. For example, electronic device 800 causes a portion of audio playback, where the narrator is describing a physical location (e.g., vineyard), and displays visual content corresponding to the portion of audio playback. In some embodiments, electronic device 800 displays visual content 834 based on metadata of the workout content. For example, the metadata is configured to cause electronic device 800 to display visual content 834 at a particular time during playback of the workout content. As shown in FIG. 8I, if media user interface 822 was displayed, visual content 834 replaces display of media user interface 822. Alternatively, if workout user interface 830 was displayed, visual content 834 replaces display of workout user interface 830. In some embodiments, when electronic device 800 displays visual content 834, electronic device 800 also produces an audio output and/or a haptic output to indicate to a user that visual content 834 is being displayed. Electronic device 800 also displays a done option 837 that is selectable by a user to cause the electronic device 800 to replace display of the visual content 834 with the media user interface 822 or the workout user interface 830.

At FIG. 8J, electronic device 800 displays media user interface 822 or, alternatively, workout user interface 830 at the end of the workout (e.g., playback of the workout content has finished). Playback progress indicator 824AA indicates that playback of the audio workout content is nearly complete. At FIG. 8K, in response to a determination that the end of the workout content has been reached, electronic device 800 causes audio playback of a playlist (e.g., one or more music items (e.g., songs)) that is associated with the workout content (e.g., the playlist is configured to play automatically after the workout content ends). In some embodiments, the one or more music items (e.g., represented by 814A-814E) are part of a playlist that is automatically played back after the workout content ends. In response to the determination that the end of the workout content has been reached, electronic device 800 updates title indication 824D to indicate the change from audio playback of the workout content to audio playback of the playlist (e.g., one or more music items). Playback progress indicator 824AA indicates that playback of the first music item in the playlist has just begun. While displaying media user interface 822, electronic device 800 detects input 838 at a location corresponding to option 836.

Figures 8L, 8M:
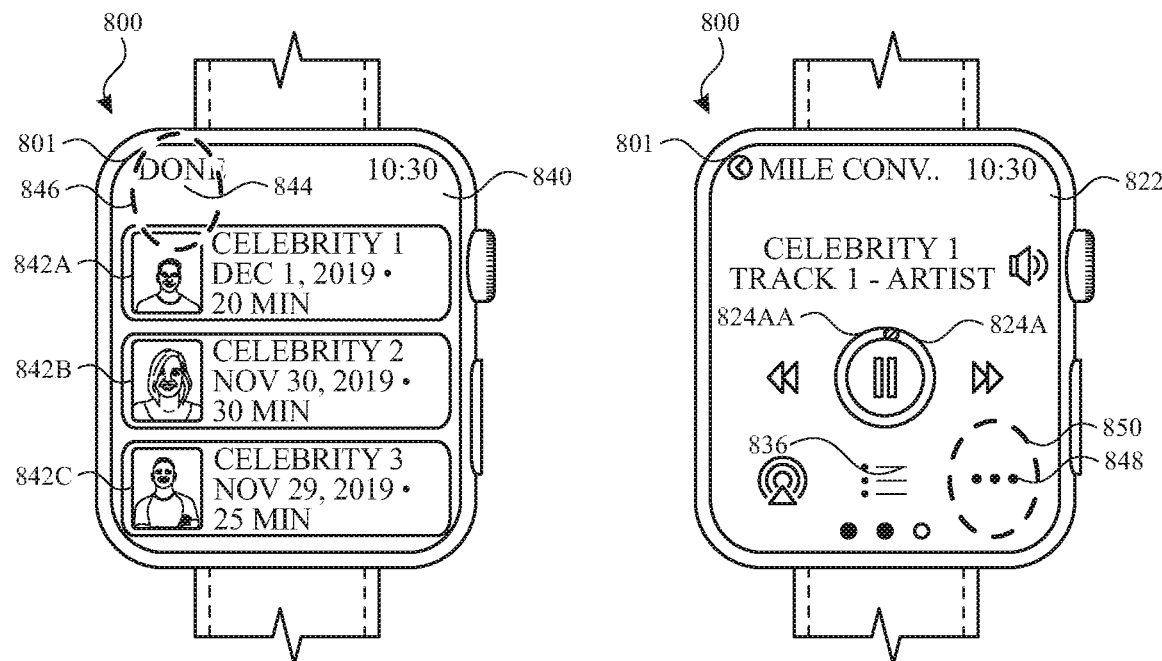

At FIG. 8L, in response to detecting input 838, electronic device 800 replaces display of media user interface 822 with display of library user interface 840. Library user interface 840 includes a plurality of workout suggestions (e.g., 842A-842C). Workout suggestions 842A, 842B, and 842C correspond to workout suggestions 806A, 806B, and 806C of FIG. 8B, respectively. While displaying library user interface 840, electronic device 800 detects input 846 at a location corresponding to option 844.

At FIG. 8M, in response to detecting input 846, electronic device 800 replaces display of library user interface 840 with media user interface 822. While displaying media user interface 822, electronic device 800 detects input 850 at a location corresponding to option 848.

In the embodiments depicted in FIGS. 8G-8M, the playback progress indicator 824AA depicts playback progress for individual content items separately, such as the audio workout content, and each music item in the playlist. Accordingly, in FIGS. 8J and 8K, when the audio workout content ends and the first music item begins playing, the playback progress indicator 824AA went from being completely full (indicating the end of playback of the audio workout content) to nearly empty (indicating the start of playback of the first music item). In some embodiments, the playback progress indicator 824AA can indicate playback progress for all of the audio content items corresponding to an audio workout as if they were a single content item. For example, the playback progress indicator 824AA can indicate playback progress for the audio workout content as well as all of the music tracks in the playlist. Such an embodiment is depicted in FIGS. 8M1-8M3. In the depicted scenario, the audio workout content is 20 minutes in duration, while the music tracks total 23 minutes in duration (as shown in FIG. 8E4). In FIG. 8M1, the audio workout content has reached its halfway point (e.g., approximately 10 minutes) (as was the case in FIG. 8H). However, the playback progress indicator 824AA indicates that the playback of content is only approximately 25% complete. This is because the playback progress indicator 824AA is representative of all audio content in the audio workout. The audio content can include both the audio workout content and the music playlist, and in the depicted scenario in FIGS. 8M1-8M3 the total runtime for all the audio content is approximately 43 minutes. Similarly, in FIG. 8M2, the audio workout content is nearing its end, and the playback progress indicator 824AA indicates that playback of content is approximately 50% complete, and in FIG. 8M3, the first music item in the playlist has begun, and the playback progress indicator 824AA indicates that playback is approximately at 60% complete.

Figure 8N:
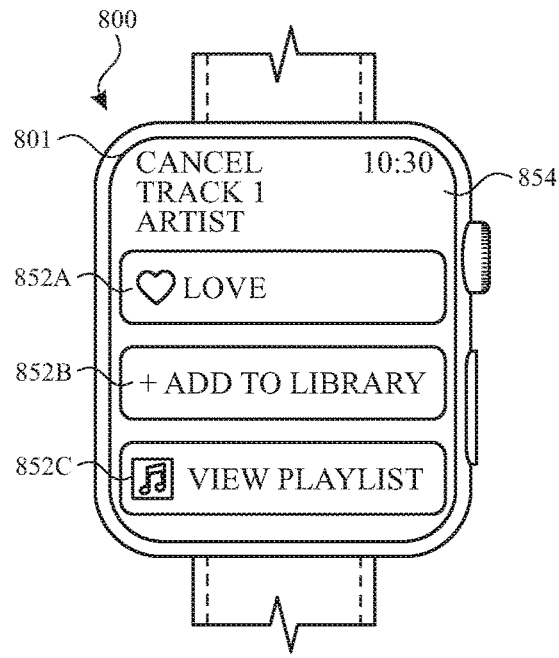

At FIG. 8N, in response to detecting input 850, electronic device 800 replaces display of media user interface 822 with action user interface 854. Action user interface 854 includes options 852A-852C for performing a respective operation based on the music item that is currently playing. In some embodiments, the respective operation is performed on the currently playing music item without being performed on a different music item, where the currently playing music item and the different music item are part of the same playlist. In some embodiments, selection of option 852A causes the currently playing music item to be favorited (e.g., favoriting a music item can affect which music items are suggested to the user at a later time). In some embodiments, selection of option 852B causes the currently playing music item to be added to a particular playlist (e.g., library). In some embodiments, selection of option 852C results in display of a plurality of representations corresponding to the one or more music items. In some embodiments, while displaying action user interface 854, electronic device 800 detects an input, and in response, replaces display of action user interface 854 with media user interface 822.

Figure 8O:
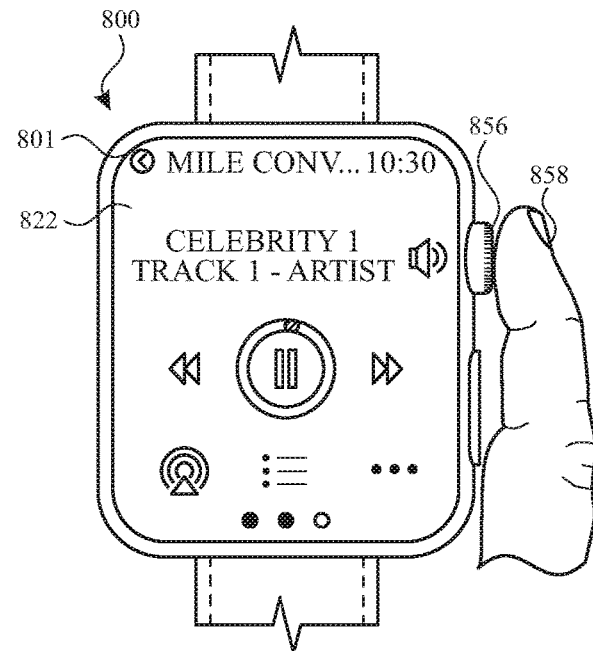

At FIG. 8O, while displaying media user interface 822, electronic device 800 detects one or more inputs, including input 858 at input mechanism 856. In some embodiments, input mechanism includes one or more features of input mechanism 506.

Figure 8P:
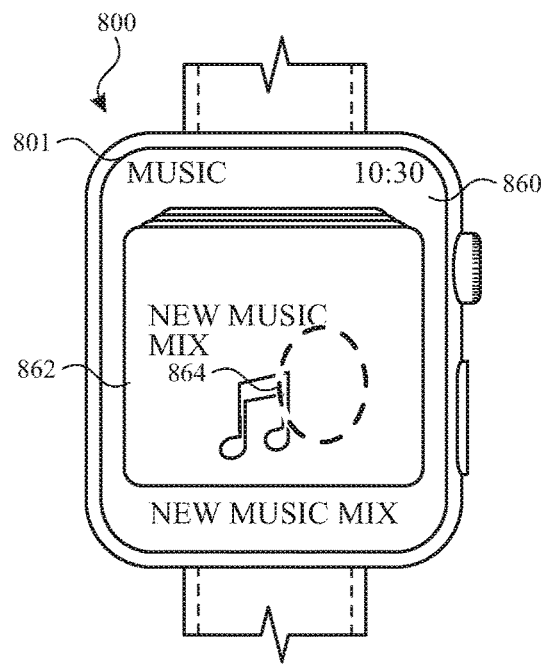

At FIG. 8P, in response to detecting the one or more inputs, electronic device 800 displays music user interface 860. Music user interface 860 includes representation 862 corresponding to a playlist that is not associated with the workout content. While displaying music user interface 860, electronic device 800 detects input 864 at a location corresponding to representation 862.

Figure 8Q:
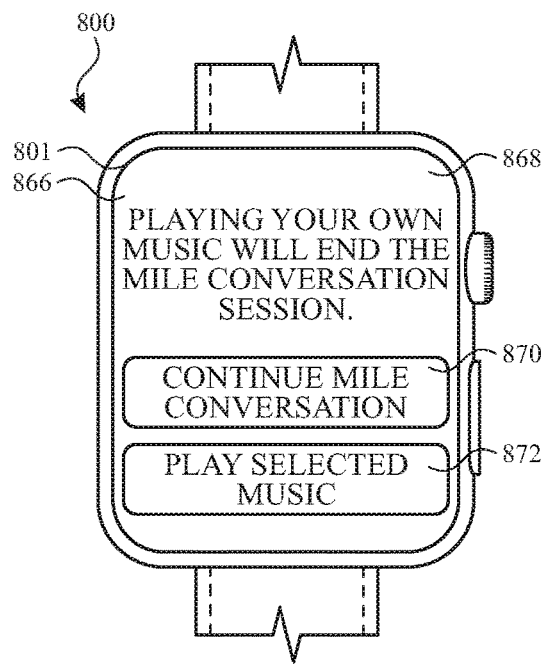

At FIG. 8Q, in response to detecting input 864, electronic device 800 displays prompt user interface 866 with indication 868. Indication 868 indicates that proceeding with playing one or more music items of the playlist that is not associated with the workout content will cause the current workout session to end (e.g., cease playback of the current playing audio content, cease recording of one or more physical activity metrics via one or more sensors of electronic device 800). In some embodiments, while displaying prompt user interface 866, electronic device 800 detects an input. In some embodiments, in response to detecting the input: in accordance with a determination that the input corresponds to option 870, electronic device 800 continues playback of the currently playing audio content without playing one or more music items of the playlist that is not associated with the workout content. In some embodiments, in response to detecting the input: in accordance with a determination that the input corresponds to option 872, electronic device 800 ceases playback of the currently playing audio content, initiates playback of the one or more music items of the playlist that is not associated with the workout content, and/or ceases recording of one or more physical activity metrics via one or more sensors of electronic device 800.

As discussed above with reference to FIG. 8K, in some embodiments, in response to a determination that the end of the workout content has been reached, electronic device 800 causes audio playback of a playlist (e.g., one or more music items (e.g., songs)) that is associated with the workout content (e.g., the playlist is configured to play automatically after the workout content ends). In some embodiments, in response to a determination that the end of the workout content has been reached and/or in response to a determination that the end of the playlist has been reached, electronic device 800 causes display of a summary user interface, as depicted in FIG. 8Q1. In FIG. 8Q1, summary user interface 880 includes information 885 pertaining to a user's measured physical activity during the workout (e.g., total time of the workout, distance walked during the workout, active and total calories burned during the workout, elevation gain, maximum and minimum elevation, average heart rate during the workout, average pace during the workout). Summary user interface 880 also includes visual content 882A, 882B associated with the workout. Visual content 882A, 882B can include visual content that was presented during the workout. For example, visual content 882A corresponds to visual content 834 of FIG. 8I. Summary user interface 880 also includes done option 884A for closing the summary user interface 880, and add playlist option 884B for adding the music playlist associated with the workout to a separate music application.

In FIG. 8Q2, electronic device 600 displays summary user interface 886. Summary user interface 886 is substantially similar to summary user interface 880, but is displayed on electronic device 600 rather than on electronic device 800. In some embodiments, electronic device 600 display summary user interface 886 in response to a determination that the end of workout content has been reached on electronic device 600. Similar to summary user interface 880, summary user interface 886 includes information 887 pertaining to a user's measured physical activity during the workout and visual content items 888A, 888B associated with the workout.

FIGS. 8R-8S depict selection of a different type of workout (e.g., corresponding to workout suggestions 616T-616U) as compared to workout selection in FIGS. 8A-8C (e.g., corresponding to workout suggestions 616R-616S). While displaying workout user interface 612, electronic device 800 detects input 874 at a location corresponding to workout suggestion 616T. As discussed above, workout suggestions 616T represents audio content (e.g., workout content) corresponding to a predefined route at or near one or more physical locations (e.g., a 5K route in Hackney).

At FIG. 8S, in response to detecting input 874, electronic device 800 displays detail user interface 876 with information about the selected workout. Detail user interface 876 includes music item representations 878A-878D, which represent one or more music items of a playlist. In some embodiments, after playback of the workout content (e.g., corresponding to workout suggestion 616T) ends, electronic device 600 automatically starts playback of one or more music items of the playlist (e.g., causes audio output at an external device for playing back audio).

In some embodiments, the techniques described above in FIGS. 8E-8Q are analogous to techniques that can be performed for workout content corresponding to workout suggestion 616T. For example, analogous to FIG. 8I, in response to a determination a predetermined point in time has been reached during playback of audio content (e.g., corresponding to workout suggestion 616T), electronic device 800 displays visual content that corresponds to the audio content of the workout, in accordance with some embodiments. As another example, analogous to FIG. 8L, electronic device 800 displays a user interface with a plurality of workout suggestions, including a workout suggestion that corresponds to workout suggestion 616T.

FIG. 9 is a flow diagram illustrating a method for starting an audio-based workout using an electronic device, in accordance with some embodiments. Method 900 is performed at an electronic device (e.g., 100, 300, 500, 600, 800) with a display (e.g., 801). Some operations in method 900 are, optionally, combined, the orders of some operations are, optionally, changed, and some operations are, optionally, omitted.

As described below, method 900 provides an intuitive way for starting an audio-based workout. The method reduces the cognitive burden on a user for starting an audio-based workout, thereby creating a more efficient human-machine interface. For battery-operated computing devices, enabling a user to start an audio workout faster and more efficiently conserves power and increases the time between battery charges.

In some embodiments, the electronic device (e.g., 100, 300, 500, 600, 800) is a computer system. The computer system is optionally in communication (e.g., wired communication, wireless communication) with a display generation component and with one or more input devices. The display generation component is configured to provide visual output, such as display via a CRT display, display via an LED display, or display via image projection. In some embodiments, the display generation component is integrated with the computer system. In some embodiments, the display generation component is separate from the computer system. The one or more input devices are configured to receive input, such as a touch-sensitive surface receiving user input. In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

The electronic device (e.g., 800) displays (902), on the display (e.g., 801), a selectable user interface object (e.g., 824A, 818, affordance) for starting audio playback.

The electronic device detects (904) (e.g., via a touch-sensitive display) a user input (e.g., 825, 820, a single user input, a single user input without intervening user input (e.g., input that is detected after the detection of the user input corresponding to the selectable user interface object for starting audio playback and before causing audio playback)) corresponding to selection of the selectable user interface object for starting audio playback.

In response to (906) detecting the user input corresponding to selection of the selectable user interface object for starting audio playback: the electronic device (e.g., 800) causes (908) audio playback of audio associated with a workout (e.g., physical activity performed by the user) at an audio output device that is in communication with the electronic device (e.g., at an external device (e.g., headphones, speakers), at the electronic device).

In response to (906) detecting the user input corresponding to selection of the selectable user interface object for starting audio playback: the electronic device (e.g., 800) causes (912) recording (e.g., tracking, logging, collecting) of physical activity metrics (e.g., calories, heart rate, distanced traveled, and/or stairs climbed) corresponding to the workout (e.g., physical activity metrics are recorded during audio playback of audio associated with the workout), wherein the physical activity metrics are recorded (e.g., captured) by one or more sensors that are monitoring an activity level of a user of the electronic device. Automatically performing two operations (e.g., causing audio playback and causing recording of physical activity metrics) allows the user to track their physical activity during audio playback via a single input. Performing two operations in response to a single input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the physical activity metrics are measured using one or more sensors (e.g., GPS, accelerometer, gyroscope, and/or heart rate) of the electronic device or an external device that is in communication with the electronic device.) In some embodiments, the physical activity metrics were not being recorded or were being recorded at a lower frequency or lower degree of precision prior to detecting (e.g., immediately prior to detecting) the user input (e.g., 825, 820) corresponding to selection of the selectable user interface object (e.g., 824A, 818) for starting audio playback (e.g., user heart rate is detected at multiple times per minute instead of once per minute or a longer time threshold, or additional sensors are used to detect steps more accurately than they were being detected prior to detection of the user input corresponding to selection of the selectable user interface object for starting audio playback). In some embodiments, in response to detecting the user input (e.g., 825, 820), causing one or more sensors of an external device to be enabled/activated so as to improve accurate measurements of the user during the workout. In some embodiments, the one or more sensors are not enabled/activated prior to detecting of the user input (e.g., 825, 820). In some embodiments, a subset of the one or more sensors are enabled/activated based on the type of workout. In some embodiments, in accordance with a determination that a workout is of a first type (e.g., exercise type), a first subset of the one or more sensors are enabled/activated based on the first type. In some embodiments, in accordance with a determination that a workout is of a second type (e.g., exercise type), a second subset of the one or more sensors are enabled/activated based on the second type. Automatically enabling the one or more sensors at the start of audio playback improves the battery life of the device, as the one or more sensors consume less power and/or battery life prior to the start of audio playback. Enabling the one or more sensors when a set of conditions are met enhances the operability of the device which, additionally, reduces power usage and improves battery life of the device by enabling the user to use the device more quickly and efficiently.

In some embodiments, the audio (910) associated with the workout (e.g., represented by 616R-616S) has a duration based on an amount of time required to complete the workout (e.g., the amount of time required to walk a predefined distance (e.g., 1, 3, or 5 miles); an amount of time required to complete the workout by a narrator of the audio associated with the workout).

In some embodiments, the audio associated with the workout includes an audio indication configured to be output at the audio output device at a predefined time (e.g., halfway point of the duration of the audio) during playback of the audio associated with the workout (e.g., as discussed above with respect to FIG. 8H). Outputting an audio indication provides the user with feedback about the current state of the device (e.g., playback of audio file has reached halfway point). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the audio associated with the workout corresponds to one or more visual content items (e.g., 834) that are configured to be output (e.g., displayed) during playback of the audio associated with the workout. In some embodiments, the one or more visual content items are displayed at the electronic device (e.g., 800) or an external device in communication with the electronic device. In some embodiments, the one or more visual content items are associated with metadata that determine a time at which the one or more visual content items are output during playback of the audio associated with the workout. For example, a visual content item of the one or more visual content items is configured to be output at a particular point in time during playback.

In some embodiments, each visual content item of the one or more visual content items (e.g., 834, 882A, 882B) is configured to be output (e.g., displayed) at a respective predetermined time during playback of the audio associated with the workout, including a first visual content item (e.g., 834) configured to be output at a first predetermined time during playback of the audio associated with the workout (e.g., FIG. 8I). In some embodiments, the electronic device displays, via the display generation component, a workout summary user interface (e.g., 880) that includes one or more graphical representations of the workout (e.g., 882A, 882B) (e.g., a non-textual representation, an image of a speaker (e.g., narrator) of the audio associated with the workout). In some embodiments, the workout summary user interface includes representations of physical activity metrics that are based on physical activity of a user during the workout (e.g., route walked, active calories, total calories, total time, average heart rate, distance, average pace). In some embodiments, in accordance with a determination that the first visual content item was output (e.g., displayed) during playback of the audio associated with the workout, the workout summary user interface includes the first visual content item (e.g., 882A, 882B) (e.g., the first visual content item is displayed within and/or accessible within the workout summary user interface), and in accordance with a determination that the first visual content item was not output (e.g., displayed) during playback of the audio associated with the workout (e.g., the user terminated playback of the audio associated with the workout prior to the first predetermined time associated with the first visual content item), the workout summary user interface does not include the first visual content item (e.g., the first visual content item is not displayed within and/or accessible within the workout summary user interface). In some embodiments, the one or more visual content items includes a second visual content item (e.g., different from the first visual content item) configured to be output at a second predetermined time (e.g., different from the first predetermined time) during playback of the audio associated with the workout, and the method further comprises: in accordance with a determination that the second visual content item was output during playback of the audio associated with the workout, the workout summary user interface includes the second visual content item (e.g., the second visual content item is displayed within and/or accessible within the workout summary user interface), and in accordance with a determination that the second visual content item was not output (e.g., displayed) during playback of the audio associated with the workout (e.g., the user terminated playback of the audio associated with the workout prior to the second predetermined time associated with the second visual content item), the workout summary user interface does not include the second visual content item (e.g., the second visual content item is not displayed within and/or accessible within the workout summary user interface). Displaying a workout summary user interface that includes the one or more visual content items configured to be output during playback of the audio associated with the workout provides the user with the ability to access the visual content items that were presented during playback of the audio. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while causing audio playback of the audio associated with the workout, the electronic device (e.g., 800) displays, via the display generation component, the one or more visual content items (e.g., 834). In some embodiments, the electronic device generates tactile output (e.g., a sequence of a number of individual tactile outputs), wherein the tactile output is provided concurrently with display of the one or more visual content items (e.g., FIG. 8I). In some embodiments, the tactile output is output by the computer system or an external device in communication with the computer system. In some embodiments, the tactile output is associated with metadata that determine a time at which the tactile output is output during playback of the audio associated with the workout. For example, tactile output is configured to be output at a particular point in time during playback (e.g., tactile output is configured to be output each time a visual content item of the one or more visual content items is output). In some embodiments, the one or more visual content items are presented full screen on the computer system (e.g., displayed on the computer system without additional content) or presented full screen on an external device in communication with the computer system. Generating tactile output, and providing the tactile output concurrently with display of the one or more visual content items, provides the user with feedback about the current state of the device (e.g., notifying the user that the device is displaying visual content items). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, after completion of the workout (in some embodiments, after completion of the audio associated with the workout), the electronic device (e.g., 800) displays, via the display generation component, a first workout summary user interface (e.g., 880, FIG. 8Q1) that includes the one or more visual content items (e.g., 882A, 882B) configured to be output during playback of the audio associated with the workout. In some embodiments, the workout summary user interface also includes physical activity metrics corresponding to the workout. Displaying a workout summary user interface that includes the one or more visual content items configured to be output during playback of the audio associated with the workout provides the user with the ability to access the visual content items that were presented during playback of the audio. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the audio associated with the workout corresponds to a predefined list of audio items (e.g., music playlist) that includes a first audio item (e.g., represented by 824D in FIG. 8K, music file) and a second audio item (e.g., music file). In some embodiments, a speaker (e.g., narrator) of the audio associated with the workout generated the predefined list of audio items (e.g., selected the audio items in the playlist).

In some embodiments, in accordance with a determination that audio playback of the audio associated with the workout has completed, the electronic device causes, at the audio output device, audio playback of the predefined list of audio items that includes the first audio item (e.g., represented by 824D in FIG. 8K) and the second audio item. In some embodiments, the predefined list of audio items (e.g., music playlist) is played in response to the audio associated with the workout ending.

In some embodiments, in response to detecting the user input (e.g., 820) corresponding to selection of the selectable user interface object (e.g., 818) for starting audio playback, the electronic device (e.g., 800) displays, on the display (e.g., 801), a first set of playback controls (e.g., 824A-824C, one or more selectable user interface objects) for modifying the audio playback of the audio associated with the workout. In some embodiments, the electronic device displays the first set of playback controls for modifying the audio playback of the audio associated with the workout in response to detecting selection of a representation (e.g., 818) of the audio content. In some embodiments, in response to (e.g., after) causing audio playback of the predefined list of audio items, the electronic device displays, on the display, a second set of playback controls (e.g., skip back button 824B changes to previous track button (displayed at same location) as shown in transition from FIGS. 8J-8K; skip forward button 824C changes to next track button (displayed at same location) as shown in transition from FIGS. 8J-8K) for modifying audio playback of the predefined list of audio items, wherein the second set of playback controls is different than the first set of playback controls. In some embodiments, the electronic device replaces the display of the first set of playback controls with the second set of playback controls.

In some embodiments, after audio playback of the audio associated with the workout has completed, the electronic device (e.g., 800) causes, at the audio output device, audio playback of the first audio item (e.g., represented by 824D in FIG. 8K) of the predefined list of audio items. In some embodiments, after (e.g., while) causing the audio playback of the first audio item, the electronic device detects one or more user inputs (e.g., 848, input at a location corresponding to 842A, 842B, or 842C) corresponding to the first audio item. In some embodiments, in response to detecting the one or more user inputs corresponding to the first audio item, the electronic device performs an operation for the first audio item (e.g., add to library (e.g., 852B), save, skip, play/pause) based on the detected one or more user inputs without performing the operation for the second audio item.

In some embodiments, in response to detecting the user input corresponding to selection of the selectable user interface object for starting audio playback, the electronic device displays, via the display generation component, a workout user interface (e.g., 822) comprising a playback progress indicator (e.g., 824AA), wherein the playback progress indicator visually indicates progress of playback of audio content, wherein the audio content includes the audio associated with the workout and the predefined list of audio items (e.g., as shown in FIG. 8E4) (e.g., a music playlist) (e.g., a music playlist that is played back in response to the audio associated with the workout ending). Displaying a workout user interface comprising a playback progress indicator provides the user with feedback about the current state of the device (e.g., a current state of playback of audio content). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in accordance with (914) a determination that a detected user input (e.g., 864, input at a location corresponding to option 872) results in audio playback of audio that is not associated with the workout, the electronic device causes (916) the audio playback of audio associated with the workout to cease. In some embodiments, the detected user input corresponds to selection of a song, playlist, or music file in a music application. In some embodiments, in accordance with a determination that a detected user input results in audio playback of audio that is not associated with the workout, causing the recording of physical activity metrics corresponding to the workout to cease (e.g., disable one or more sensors for recording physical activity of the user during a workout). Automatically causing the recording of physical activity metrics to cease when playback of non-workout audio occurs improves battery life of the device, as one or more sensors for recording physical activity metrics are disabled. Disabling the one or more sensors when a set of conditions are met enhances the operability of the device which, additionally, reduces power usage and improves battery life of the device by enabling the user to use the device more quickly and efficiently.

In some embodiments, a predetermined number (e.g., 3, 5, 7) of audio items of a first type (e.g., represented by 842A-842C) are stored at the electronic device, wherein the audio associated with the workout is of the first type (e.g., an audio program with interviews that last as long as it take to walk a predefined distance (e.g., 1, 3, or 5 miles)). In some embodiments, the electronic device (e.g., 800, smartwatch) detects a request to add (e.g., store) a predetermined number of audio items of the first type to the electronic device. In some embodiments, in response to detecting the request to add the audio of the first type, the electronic device downloads (e.g., stores) a predetermined number of audio items of the first type to be stored at the electronic device. In some embodiments, an external device (e.g., 600, smartphone) that is in communication with the electronic device (e.g., smartwatch) initiates the request to add the predetermined number of audio items to the electronic device.

In some embodiments, the audio (e.g., music, voice over) associated with the workout (e.g., represented by 616T-616U) corresponds to a predefined set of one or more physical locations (e.g., related to a running route at a physical location (e.g., city, landmark)). In some embodiments, the audio associated with the workout corresponds to one or more visual content items (e.g., defined route on a map, photos of places of significance (e.g., landmark)) that are configured to be output (e.g., displayed) during playback of the audio associated with the workout.

In some embodiments, after completion of the workout (in some embodiments, after completion of the audio associated with the workout), the electronic device (e.g., 800) displays, via the display generation component, a second workout summary user interface (e.g., 880, 886) that includes one or more graphical representations of the workout (e.g., FIG. 8Q1, FIG. 8Q2) (e.g., a non-textual representation, an image of a speaker (e.g., narrator) of the audio associated with the workout). In some embodiments, the second workout summary user interface includes physical activity metrics that are based on physical activity of a user during the workout (e.g., route walked, active calories, total calories, total time, average heart rate, distance, average pace). Displaying a workout summary user interface that includes one or more graphical representations of a workout provides the user with feedback about the user's physical activity. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system is in communication with (e.g., paired with) a first external device (e.g., 600 in FIG. 8C) (e.g., a smartphone), the first external device is configured to output (e.g., display, cause a display generation component to display) a selectable user interface object (e.g., 812A) for adding a workout (e.g., adding the workout to a computer system (e.g., downloading a workout to the computer system and/or a different computer system)). In some embodiments, in response to a determination that a sequence of one or more user inputs (e.g., 812B) have been detected by the first external device (e.g., at the first external device, at one or more input devices in communication with the first external device) corresponding to selection of the selectable user interface object (e.g., 812A) for adding the workout, the electronic device initiates a process for adding the workout to the computer system (e.g., in response to the determination that the sequence of one or more user inputs have been detected by the first external device, initiating a process for downloading the workout to the computer system). In some embodiments, adding the workout to the computer system comprises downloading and/or storing the audio associated with the workout to the computer system.

Automatically adding a workout to a computer system in response to a determination that a sequence of one or more user inputs have been detected by a first external device allows the user to add the workout to the computer system without requiring additional input. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Note that details of the processes described above with respect to method 900 (e.g., FIG. 9) are also applicable in an analogous manner to the methods described above. For example, method 900 optionally includes one or more of the characteristics of the various methods described above with reference to method 700. For example, the plurality of workout suggestions in method 700 optionally includes workout suggestions 616R-616U, as described with reference to method 900. For brevity, these details are not repeated below.

FIGS. 10A-10V illustrate exemplary user interfaces for displaying workout information, in accordance with some embodiments. In some embodiments, the workout information can include in-workout physical activity metrics and other information associated with a workout being performed by a user. The user interfaces in these figures are used to illustrate the processes described below, including the processes in FIG. 11.

FIG. 10A depicts electronic device 600, which is a smartphone with display 602. Display 602 of electronic device 600 includes a touch-sensitive surface on which electronic device 600 can detect user gestures (e.g., tap, swipe, drag). In some embodiments, electronic device 600 includes one or more features of electronic device 100, 300, and/or 500.

FIG. 10A also depicts electronic device 800, which is a smartwatch with display 801. Display 801 of electronic device 800 includes a touch-sensitive surface on which electronic device 800 can detect user gestures (e.g., tap, swipe, drag). In some embodiments, electronic device 800 includes one or more features of electronic device 100, 300, and/or 500.

At FIG. 10A, the electronic device 600 displays detail user interface 620. Detail user interface 620 includes characteristics of a workout. For example, detail user interface 620 includes exercise type 622A (e.g., core), trainer 622B (e.g., Amy Dixon), duration 622C (e.g., 20 min), music 622D (e.g., hip-hop), required equipment 622E (e.g., dumbbells), and completion indication 622F (e.g., completed 3 times).

At FIG. 10A, the electronic device 800 displays activity user interface 1002. In some embodiments, electronic device 600 causes electronic device 800 to display activity user interface 1002. The activity user interface 1002 includes physical activity metrics for a duration of time (e.g., physical activity metrics for the current day (e.g., from 12:00 am to a current time)). In the depicted embodiment, physical activity metrics are depicted in a plurality of concentric physical activity rings 1004. The plurality of concentric physical activity rings 1004 include move information (e.g., move ring 1006A) indicative of a number of calories burned by a user during the day, exercise information (e.g., exercise ring 1006B) indicative of a number of minutes the user has been active during the day, and stand information (e.g., stand ring 1006C) indicative of the number of hours during the day in which the user has stood up for a threshold amount of time or a threshold number of times. In some embodiments, including the depicted embodiment, move information (e.g., move ring 1006A) is indicative of progress towards a move goal (e.g., a target number of calories for a day), exercise information (e.g., exercise ring 1006B) is indicative of progress towards an exercise goal (e.g., a target number of exercise minutes for a day), and stand information (e.g., stand ring 1006C) is indicative of progress towards a stand goal (e.g., a target number of hours for a day). For example, in the depicted embodiment, the move ring 1006A is approximately ⅔ completed, indicating that the user is approximately ⅔ of the way to their move goal, the exercise ring 1006B is approximately ½ completed, indicating that the user is approximately ½ of the way to their exercise goal, and the stand ring 1006C is approximately ½ completed, indicating that the user is approximately ½ of the way to their stand goal. In some embodiments, including the depicted embodiment, the activity user interface 1002 also includes time-keeping elements which indicate a current time (e.g., watch hands 1010A, 1010B which indicate that the current time is 10:00).

As mentioned above, in some embodiments, move ring 1006A, exercise ring 1006B, and stand ring 1006C can be associated with (e.g., indicative of) physical activity by a user for a predetermined period of time. For example, they can be indicative of physical activity by the user for the entire day to that point (e.g., from 12:00 am until the current time in the day). For example, at FIG. 10A, the current time is 10:00 AM. Move ring 1006A, exercise ring 1006B, and stand ring 1006C can be indicative of the user's physical activity to that point in the day (e.g., from 12:00 am to 10:00 am). For example, if the user took a morning walk at 7:00 AM, move ring 1006A can include calories burned from that morning walk, exercise ring 1006B can include active calories burned from that morning walk, and stand ring 1006C can credit the user for one hour of standing during the time of the walk.

While displaying detail user interface 620, electronic device 600 detects input 1012 at a location corresponding to play button 1014.

Figure 10B:
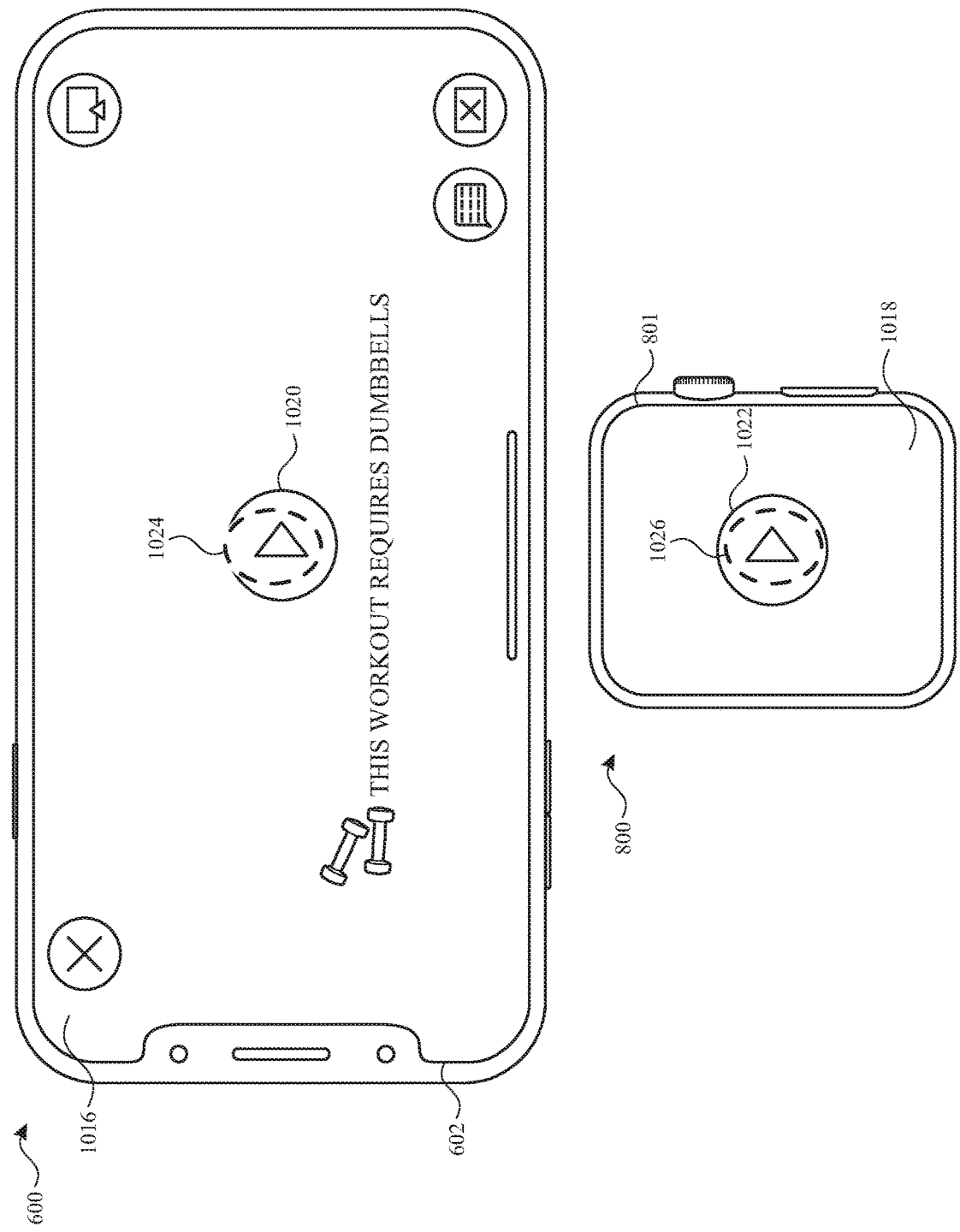

At FIG. 10B, in response to detecting input 1012, electronic device 600 replaces display of detail user interface 620 with workout start user interface 1016. Furthermore, in response to electronic device 600 detecting input 1012, electronic device 800 replaces display of activity user interface 1002 with workout start user interface 1018. In some embodiments, in response to electronic device 600 detecting input 1012, electronic device 600 causes electronic device 800 to replace display of activity user interface 1002 with workout start user interface 1018. Workout start user interface 1016 includes a play button 1020 and workout start user interface 1018 includes a play button 1022. While displaying workout start user interface 1016, electronic device 600 can detect input 1024 at a location corresponding to play button 1020 or, while displaying workout start user interface 1018, electronic device 800 can detect input 1026 at a location corresponding to play button 1022.

At FIG. 10C, in response to electronic device 600 detecting input 1024 or electronic device 800 detecting input 1026, electronic device 600 replaces display of workout start user interface 1016 with countdown user interface 1028A and electronic device 800 replaces display of workout start user interface 1018 with countdown user interface 1028B. In some embodiments, in response to electronic device 600 detecting input 1024 or electronic device 800 detecting input 1026, electronic device 600 causes electronic device 800 to replace display of workout start user interface 1018 with countdown user interface 1028B. Countdown user interface 1028A and countdown user interface 1028B display a countdown animation (e.g., counting down the number of seconds remaining) prior to initiation of a workout session.

At FIG. 10D, after a predetermined period of time after user input 1024 or user input 1026 (e.g., after conclusion of a 3-second countdown animation), electronic device 600 replaces display of countdown user interface 1028A with workout session user interface 1030 and electronic device 800 replaces display of countdown user interface 1028B with workout metrics user interface 1032. In some embodiments, electronic device 600 causes electronic device 800 to replace display of countdown user interface 1028B with workout metrics user interface 1032.

Workout session user interface 1030 includes video content 1034 that guides a user through a workout session (e.g., a video of an instructor demonstrating a workout). Workout session user interface 1030 also includes physical activity metrics indicative of a user's physical activity. The physical activity metrics include physical activity rings 1036 which include move ring 1036A, exercise ring 1036B, and stand ring 1036C. Move ring 1036A corresponds to move ring 1006A of FIG. 10A, exercise ring 1036B corresponds to exercise ring 1006B of FIG. 10A, and stand ring 1036C corresponds to stand ring 1006C of FIG. 10A. In some embodiments, physical activity rings 1036 are associated with (e.g., are indicative of) physical activity by a user for a predetermined period of time which includes a period of time preceding initiation of the workout session. For example, the physical activity rings 1036 can be indicative of physical activity by the user for the entire day to that point (e.g., from 12:00 am until the current time in the day). As discussed above, with reference to FIG. 10A, the current time when the user initiates the workout session is 10:00 AM. Move ring 1036A, exercise ring 1036B, and stand ring 1036C can be indicative of the user's physical activity to that point in the day (e.g., from 12:00 am to 10:00 am). For example, as mentioned above with reference to FIG. 10A, if the user took a morning walk at 7:00 AM, move ring 1036A can include calories burned from that morning walk, exercise ring 1036B can include active calories burned from that morning walk, and stand ring 1036C can credit the user for one hour of standing during the time of the walk. Physical activity metrics in the workout session user interface 1030 also include workout session physical activity metrics 1038 indicative of the user's physical activity during the current workout session. For example, in some embodiments, the workout session physical activity metrics 1038 include workout duration information 1040A (e.g., the workout has been in session for 1 second), heart rate information 1040B (e.g., the user's current heart rate is 61 beats per minute), and calorie information 1040C (e.g., the user has burned 0 calories so far in this workout session). The workout session physical activity metrics can also include a workout intensity representation 1040D indicative of the user's activity level in the workout session relative to other users that have previously participated in (or are currently participating in) the workout session. The workout intensity representation 1040D will be described in greater detail herein, particularly with reference to FIGS. 12A-12O.

The workout metrics user interface 1032 on electronic device 800 also includes workout session physical activity metrics, including workout duration information 1042A, heart rate information 1042B, and calorie information 1042C. In some embodiments, workout duration information 1042A corresponds to workout duration information 1040A, heart rate information 1042B corresponds to heart rate information 1040B, and calorie information 1044C corresponds to calorie information 1040C.

User physical activity metrics (including information included in physical activity rings 1036 and workout session physical activity metrics 1038) can be measured by one or more sensors in electronic device 600, one or more sensors in electronic device 800, and/or one or more sensors external to electronic device 600 and electronic device 800. Such sensors can include, for example, one or more GPS sensors, one or more accelerometers, one or more heart rate sensors, one or more gyroscopes, and the like. As the user performs a workout, the electronic device 600 and/or the electronic device 800 can receive activity data based on the physical activity of the user, and update the physical activity metrics that are displayed (e.g., in the physical activity rings 1036 and/or the workout session physical activity metrics 1038).

At FIG. 10D, while displaying workout session user interface 1030, electronic device 600 detects input 1044 at a location that corresponds to video content 1034.

At FIG. 10E, in response to detecting input 1044, electronic device 600 displays a set of playback controls overlaid on the video content 134, including play/pause button 1046A, playback progress indicator 1046B, playback volume control 1046C, closed caption icon 1046D, and edit metrics icon 1046E.

While displaying the set of playback controls, electronic device 600 detects input 1048 at a location corresponding to edit metrics icon 1046E.

Figure 10F:
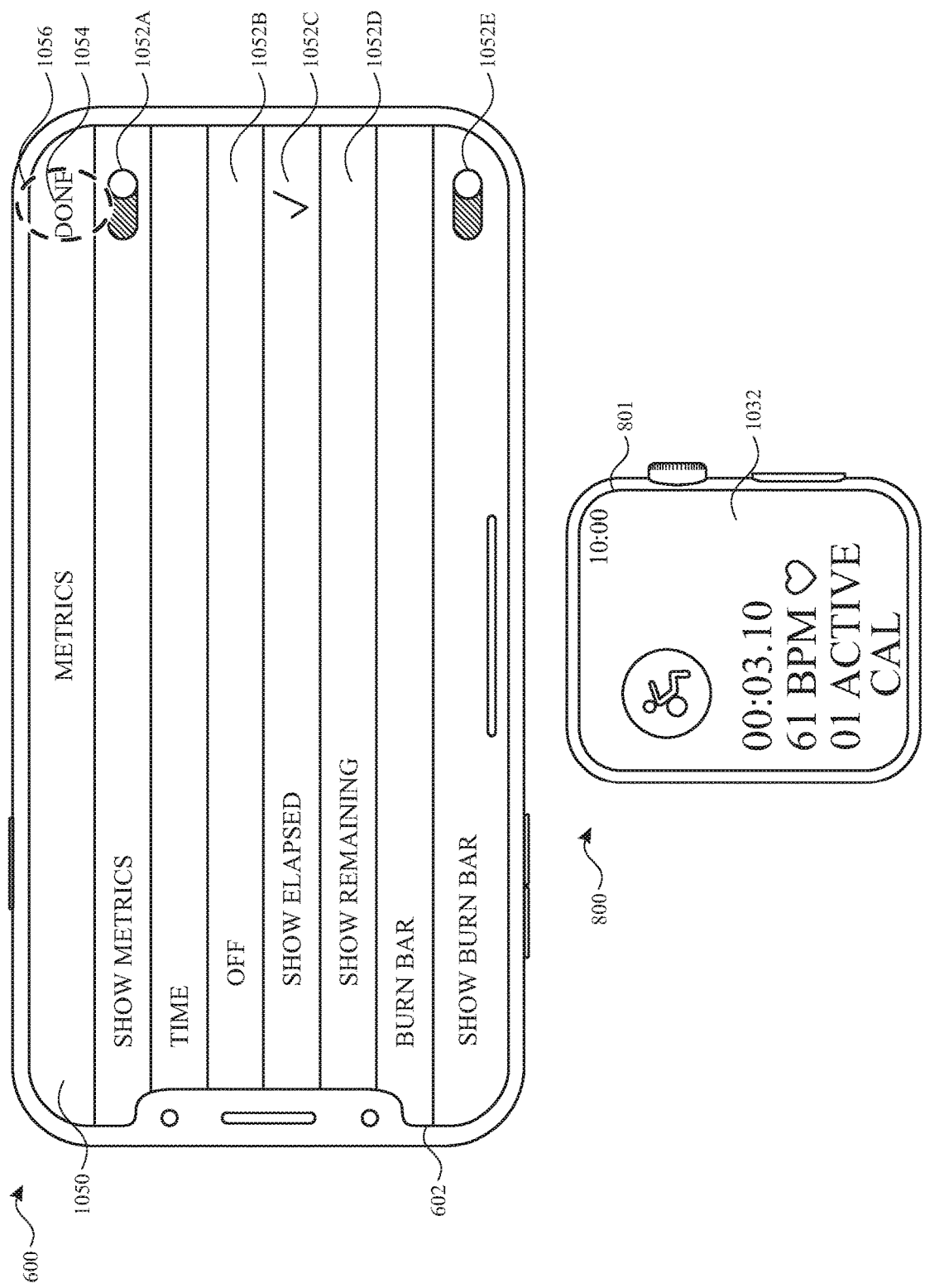

At FIG. 10F, in response to detecting input 1048, electronic device 600 replaces display of the workout session user interface 1030 and the set of playback controls with an edit metrics user interface 1050. The edit metrics user interface 1050 includes one or more selectable options for configuring display of one or more representations of physical activity metrics (e.g., workout session physical activity metrics 1038, physical activity rings 1034) on electronic device 600 and/or electronic device 800. For example, the metrics selection user interface 1050 includes an option 1052A for hiding or displaying workout session physical activity metrics, an option 1052B for hiding workout duration information 1040A, an option 1052C for showing elapsed time for workout duration information 1040A, an option 1052D for showing remaining time for workout duration information 1040A, and an option 1052E for hiding or displaying the workout intensity representation 1040D.

While displaying the metrics selection user interface 1050, the electronic device 600 detects input 1056 at a location corresponding to a "done" option 1054.

Figure 10G:
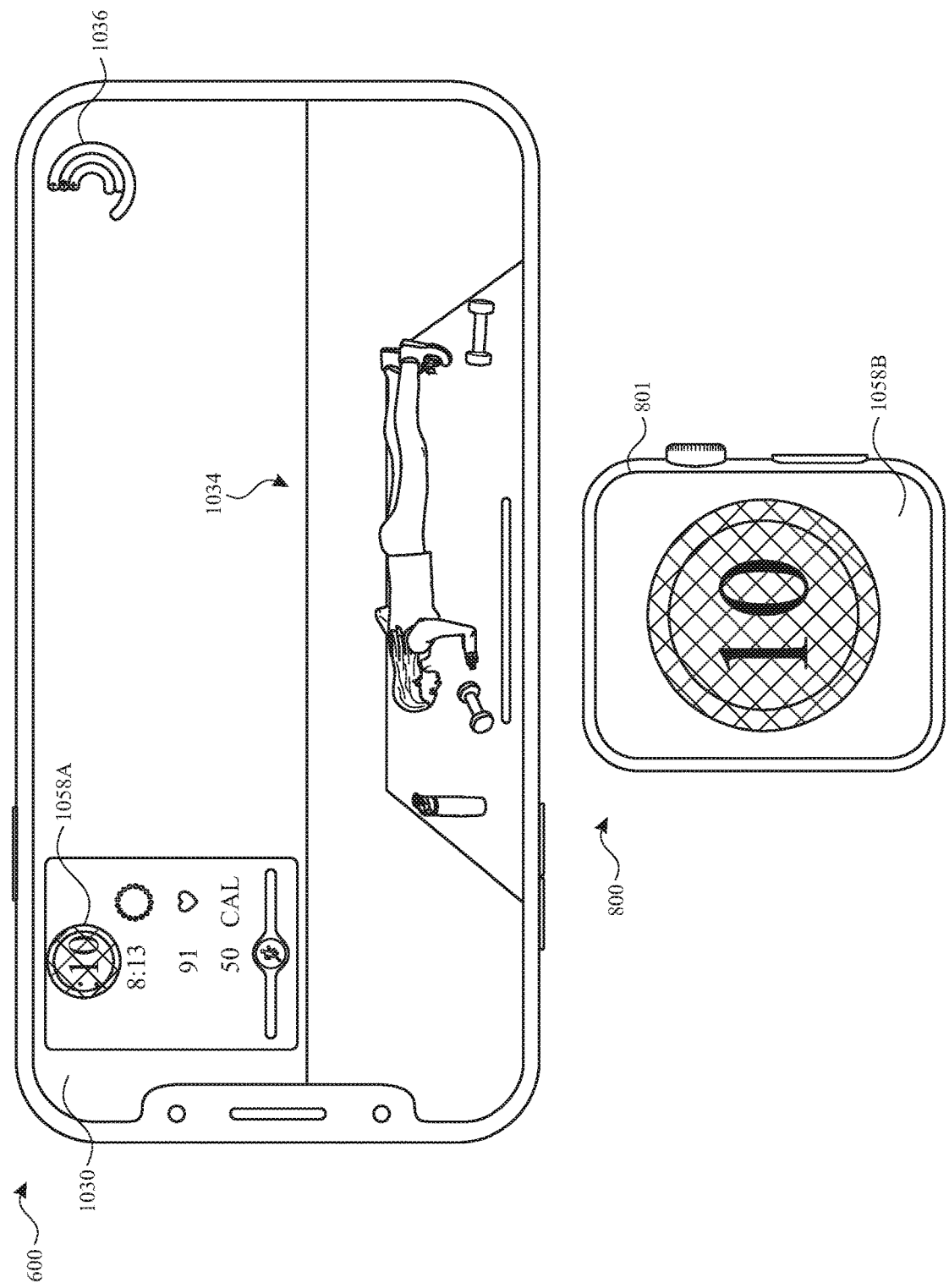

At FIG. 10G, in response to detecting input 1056, electronic device 600 replaces display of edit metrics user interface 1050 with workout session user interface 1030.

In some embodiments, a workout session can comprise one or more pre-defined events that trigger particular displays. Electronic device 600 and/or electronic device 800 can detect events based on event criteria. For example, in some embodiments, an event can occur at a particular time within a workout session (e.g., at the 3 minute mark, halfway through a workout) or when a particular milestone is achieved by a user (e.g., when the user burns a particular number of calories). Electronic device 600 and/or electronic device 800 can utilize metadata associated with a workout session to detect events associated with a workout session and take appropriate actions.

In FIG. 10G, metadata associated with the workout session can indicate that the 8 minute 15 second mark of the workout session is associated with an event that is associated with a 10-second countdown visual effect (for example, at the 8 minute 15 second mark, the trainer can instruct the user to perform as many push-ups as they can in 10 seconds). In response to determining that an event has occurred, the electronic device 600 and/or the electronic device 800 can display visual information associated with the event. For example, in FIG. 10G, the electronic device 600 displays a 10-second countdown 1058A and the electronic device 800 replaces display of the workout metrics user interface 1032 with a 10-second countdown user interface 1058B. In some embodiments, in response to detecting the event, electronic device 600 causes the electronic device 800 to replace display of the workout metrics user interface 1032 with the 10-second countdown user interface 1058B.

In some embodiments, prior to beginning the 10-second countdown, electronic device 800 can display a visual effect to visually emphasize the 10-second countdown 1058A and the 10-second countdown user interface 1058B. For example, In FIGS. 10G-10G3, although the 10-second countdown begins at the 8 minute 15 second mark, at the 8 minute 13 second mark (prior to initiating the 10-second countdown), the electronic device 600 displays the 10-second countdown 1058A, the 10-second countdown user interface 1058B replaces display of the workout metrics user interface 1032 on the electronic device 800, and a background portion of the 10-second countdown 1058A and the 10-second countdown user interface 1058B blinks (or provides some other visual indication) one or more times (e.g., the background portion can alternate different colors, vary in brightness, etc.) to draw the user's attention.

At FIG. 10H, one second has passed from FIG. 10G, and the 10-second countdown 1058A has decreased to 9 seconds, while the 10-second countdown user interface 1058B on electronic device 800 also shows 9 seconds remaining in the countdown. In this way, visual information presented on the electronic device 600 and the electronic device 800 can correspond to the video content 1034.

Figure 10I:
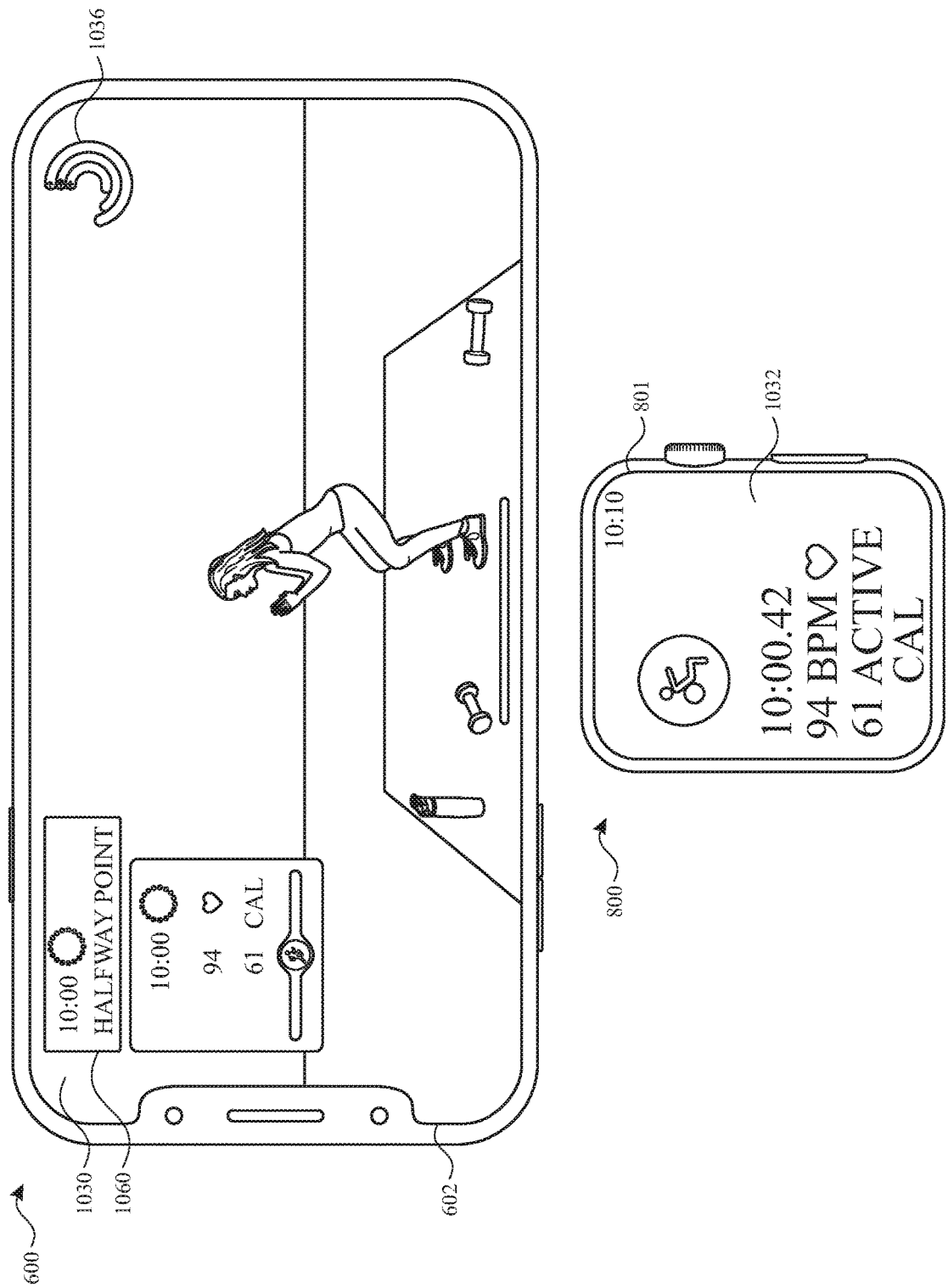

At FIG. 10I, electronic device 600 has detected another type of event. In the example shown in FIG. 10I, electronic device 600 has determined that an event associated with a halfway point in the workout session has occurred (e.g., at the 10-minute mark of a 20-minute workout). In response to this determination, the electronic device 600 displays a visual notification 1060 that the user has reached the halfway point in the workout.

Figure 10J:
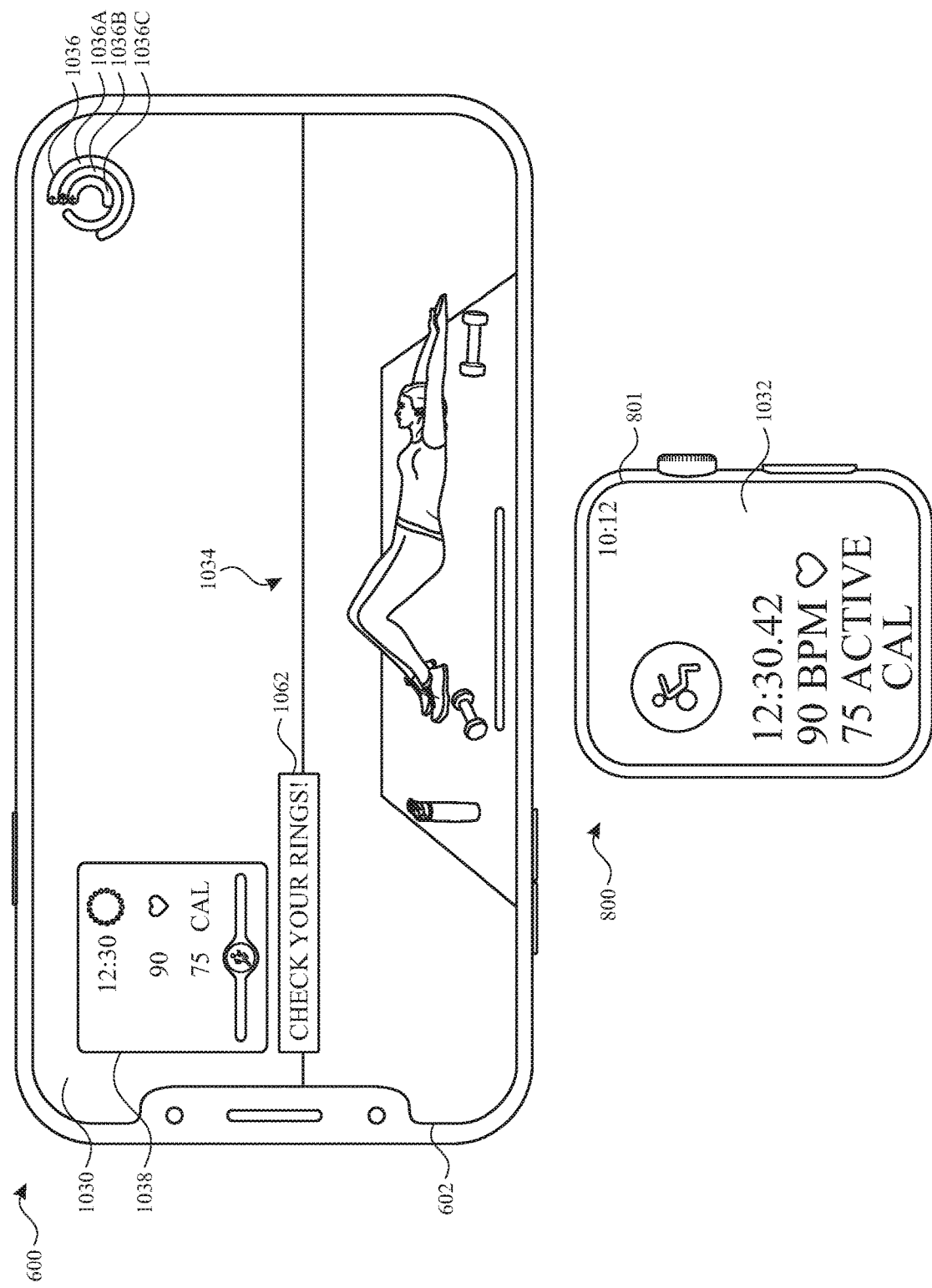
Figure 10K:
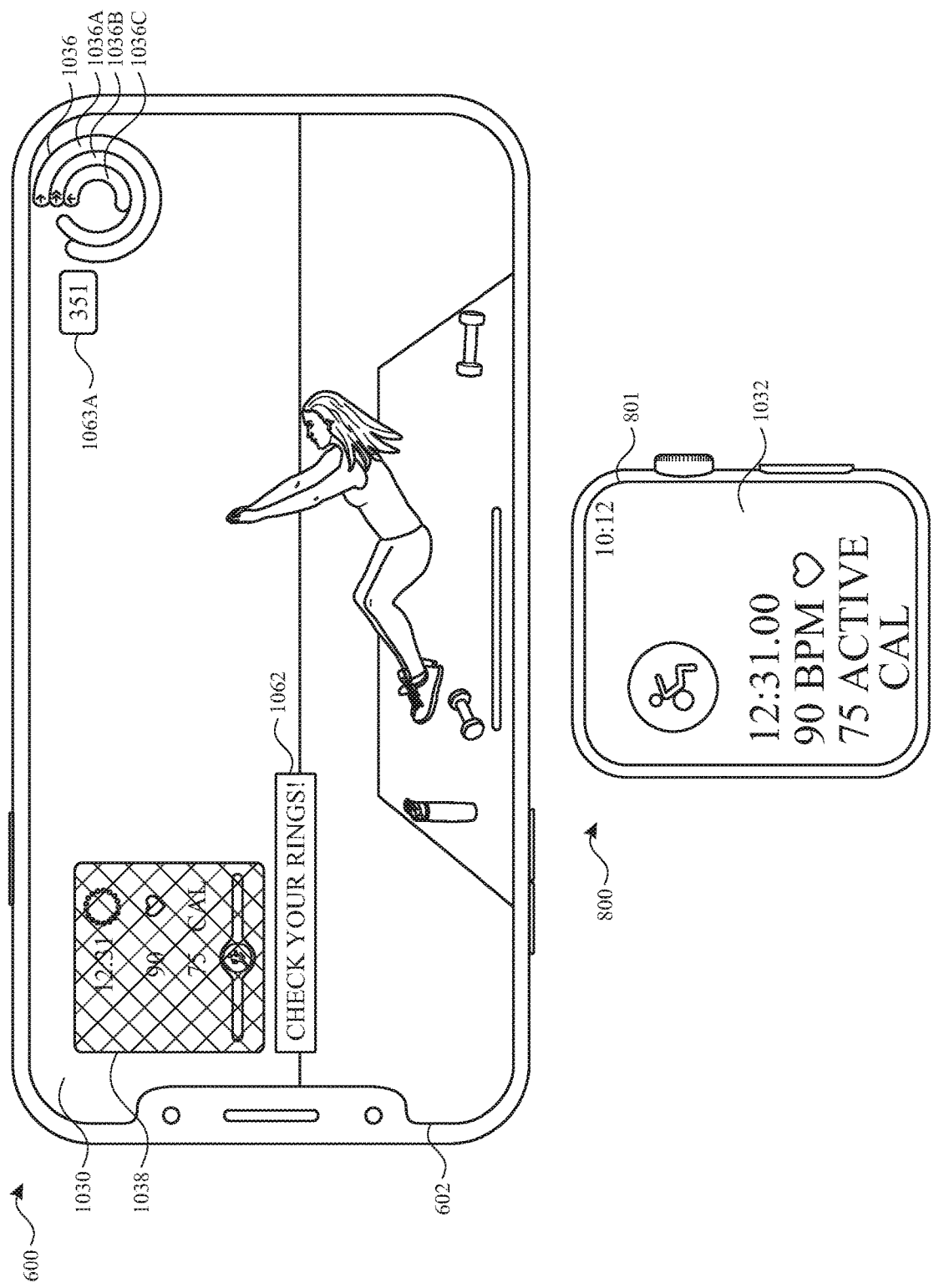
Figure 10L:
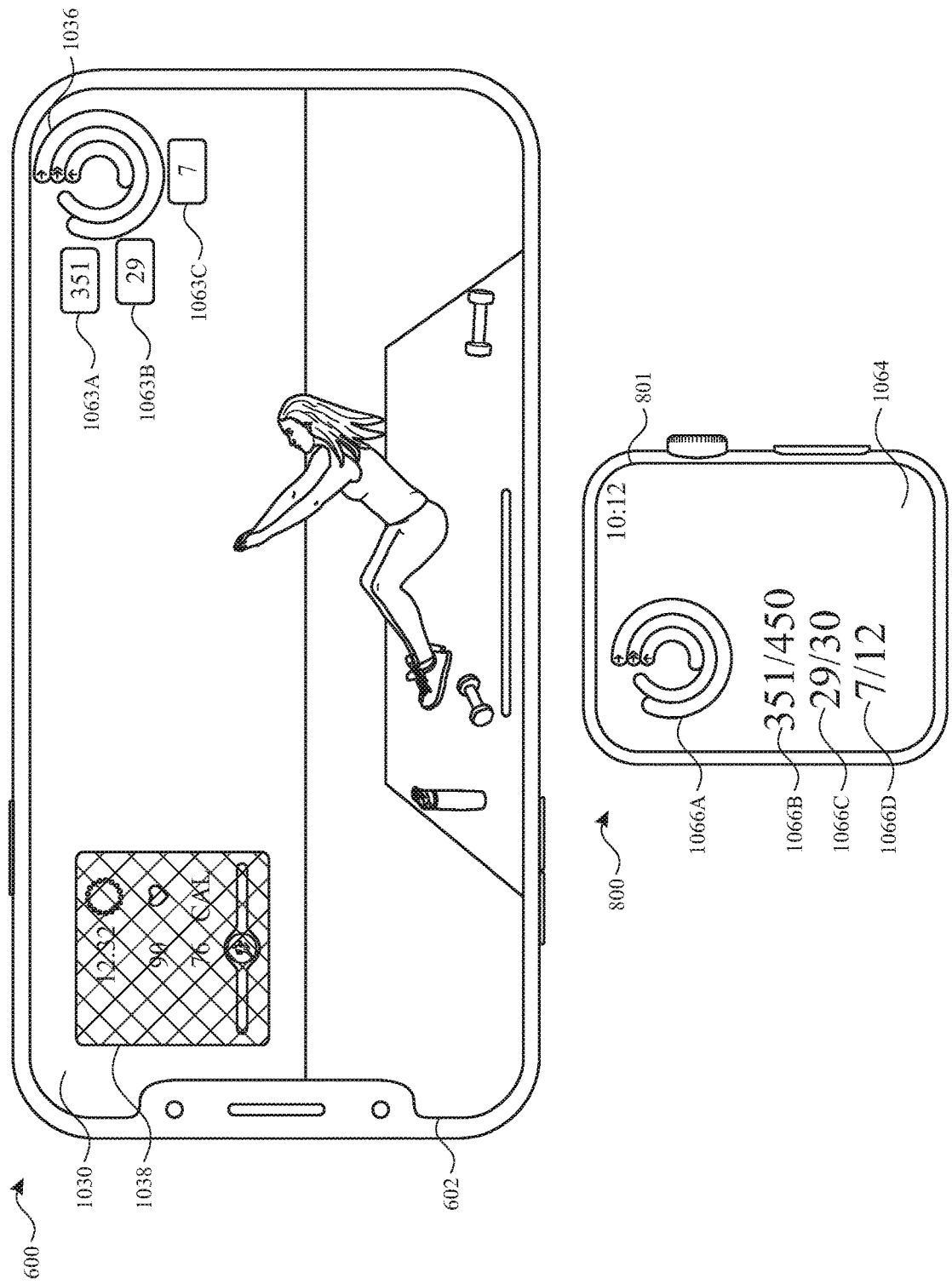

FIGS. 10J-10L demonstrate an example visual effect associated with a "check your rings" event in a workout session, according to various embodiments. At FIG. 10J, electronic device 600 has detected that one or more event criteria have been satisfied to trigger a "check your rings" events. In some embodiments, such criteria can include a time-based determination (e.g., the event occurs at a particular time within the workout session). In some embodiments, such criteria can include a user achievement-based determination (e.g., a determination that the user has nearly closed his or her exercise ring 1036B (e.g., that the user has nearly achieved his or her exercise goal for the day (e.g., that the user is within a threshold number of minutes from achieving his or her exercise goal))).

In response to detection of the "check your rings" event, the electronic device 600 can emphasize certain visual information and/or de-emphasize other visual information. In FIG. 10J, the electronic device 600 displays a visual indication 1062 instructing the user to check his or her physical activity rings 1036. In some embodiments, detection of the "check your rings" event can also cause an audio output by electronic device 600 (e.g., an audio output that instructs the user to check his or her physical activity rings 1036).

At FIG. 10K, in response to detecting the check your rings event, the electronic device 600 begins to visually emphasize the physical activity rings 1036 (e.g., by enlarging them). The electronic device 600 also begins to present additional visual information pertaining to the physical activity rings 1036 (e.g., a number value 1063A associated with the move ring 1036A). In some embodiments, in response to detecting the check your rings event, the electronic device 600 also visually de-emphasizes (e.g., hides, obscures, fades, and/or blurs) other information, such as the workout session physical activity metrics 1038.

At FIG. 10L, in response to electronic device 600 detecting the check your rings event, the electronic device 600 continues to enlarge the physical activity rings 1036, and displays additional information pertaining to the physical activity rings 1036 (e.g., numeric metrics 1063A, 1063B, 1063C associated with the physical activity rings 1036). Furthermore, in response to electronic device 600 detecting the check your rings event, electronic device 800 replaces display of the workout metrics user interface 1032 with ring information user interface 1064. In some embodiments, in response to electronic device 600 detecting the check your rings event, electronic device 600 causes electronic device 800 to replace display of the workout metrics user interface 1032 with ring information user interface 1064. The ring information user interface 1064 includes physical activity rings 1066A (which correspond to the physical activity rings 1036), move information 1066B (which corresponds to numerical value 1063A), exercise information 1066C (which corresponds to numerical value 1063B), and stand information 1066D (which correspond to numerical value 1063C).

At FIG. 10M, electronic device 600 and/or electronic device 800 detects a "ring closed" event based on a determination that the user has closed his or her exercise ring (e.g., that the user has achieved his or her exercise goal for the day). In response to detection of the ring closed event (e.g., by electronic device 600 and/or electronic device 800), electronic device 600 displays a visual indication 1068 associated with the event and electronic device 800 displays a visual indication 1070 associated with the event. In some embodiments, in response to detection of the ring closed event, electronic device 600 causes electronic device 800 to display the visual indication 1070.

In some embodiments, visual aspects of the "check your rings" event (or other events) can differ based on an orientation of the device 600. For example, in FIGS. 10J-10M, physical activity rings 1036 were displayed on a bottom portion of the device 600, away from the notch in the display. However, in FIG. 10M1, the phone is oriented in the opposite manner, such that physical activity rings 1036 are displayed on the top side, or notch side, of the device 600. When the physical activity rings 1036 are presented on the notch side of the device 600, expanding the physical activity rings 1036 can cause them to run into the notch 602A in the display 602. Accordingly, in some embodiments, when the physical activity rings 1036 are displayed on the notch side of the device 600, visually emphasizing the physical activity rings 1036 can include expanding the physical activity rings 1036 as well as translating them in a direction away from the notch 602A.

In FIG. 10M2, in response to electronic device 600 detecting the check your rings event, the electronic device

600 enlarges the physical activity rings 1036, and translates them in a left-ward direction away from the notch 602A in the display 602.

In FIG. 10M3, the physical activity rings 1036 are maintained in their translated position while the check your rings event occurs.

In FIG. 10M4, in response to electronic device 600 detecting that the check your rings event has ended, the electronic device 600 reduces the size of the physical activity rings 1036, and translates them to the right, back to their original position.

Figure 10N:
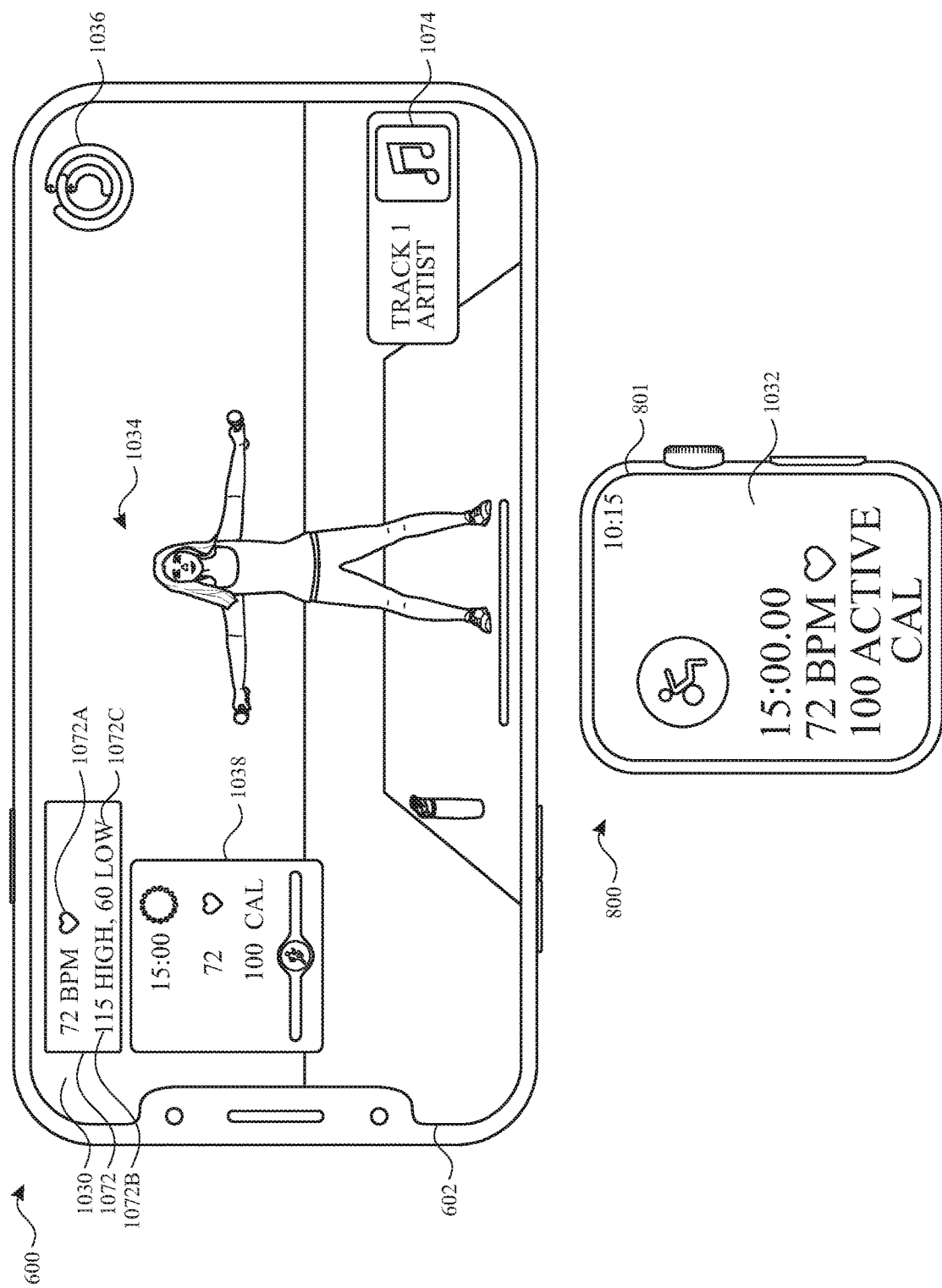

At FIG. 10N, electronic device 600 and/or electronic device 800 detects a "check your heart rate" event based on event criteria (e.g., at the 15 minute mark of the workout session). In response to detection of the check your heart rate event (e.g., by electronic device 600 and/or electronic device 800), electronic device 600 displays a visual indication 1072 associated with the event. The visual indication 1072 includes the user's current heartrate 1072A, the user's high heart rate during the workout session 1072B, and the user's low heart rate during the workout session 1072C. In some embodiments, even if a user has elected not to view certain physical activity metrics, an event can override such elections by the user and cause presentation of such information. For example, if a user has elected not to view heart rate information using the edit metrics interface 1050, a check your heart rate event can override such election, and cause display of the user's heart rate information.

In FIG. 10N, electronic device 600 also displays a visual indication 1074 based on a determination that a new song has begun playing. The visual indication 1074 identifies a track name and artist for the new song that has begun playing during the workout session.

Figure 10O:
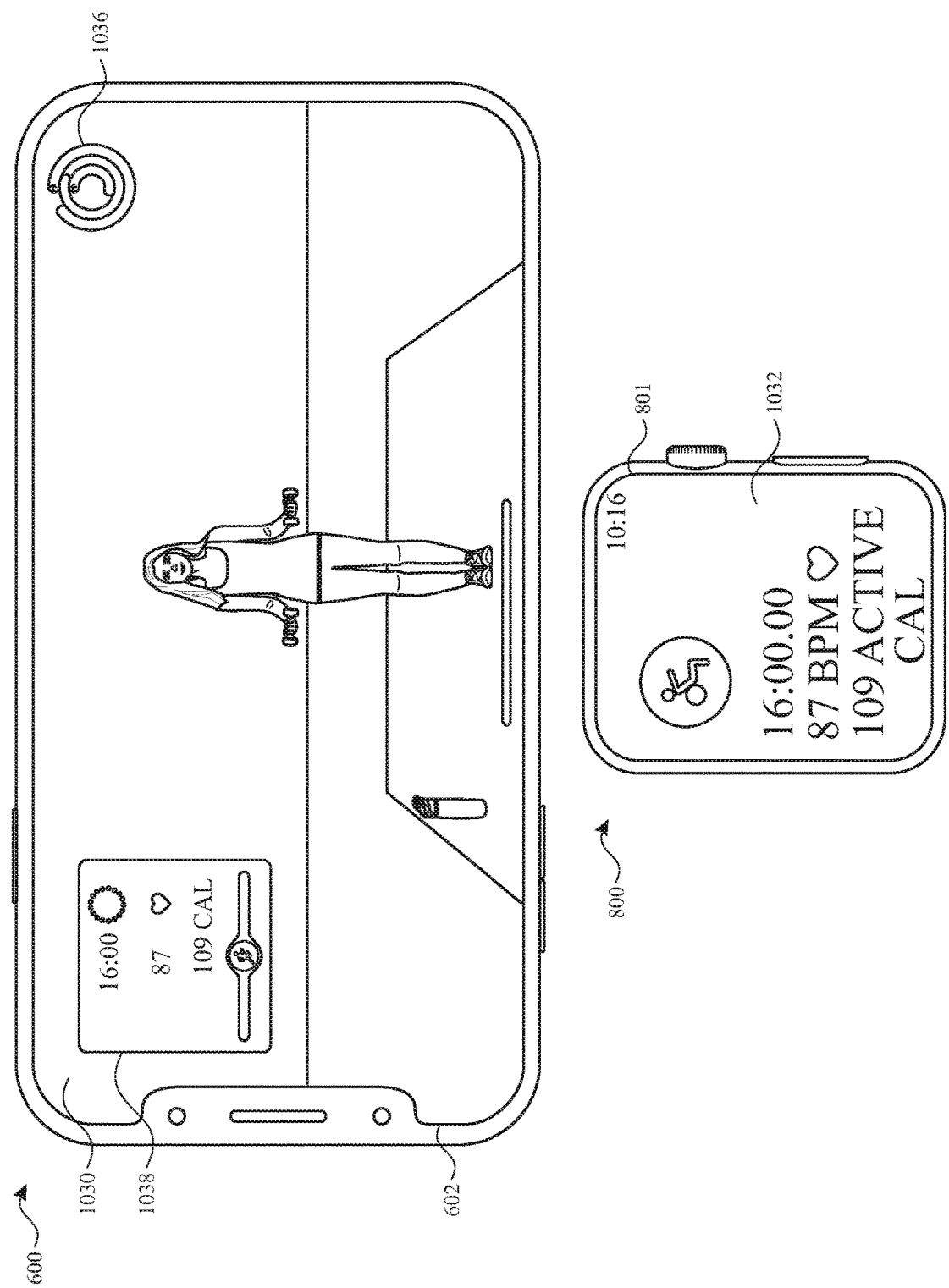

In FIG. 10O, in response to a determination that the visual indication 1072 has been displayed for a predetermined period of time, the electronic device 600 ceases display of the visual indication 1072. In FIG. 10O, in response to a determination that the visual indication 1074 has been display for a predetermined period of time, the electronic device 600 ceases display of the visual indication 1074.

Figure 10P:
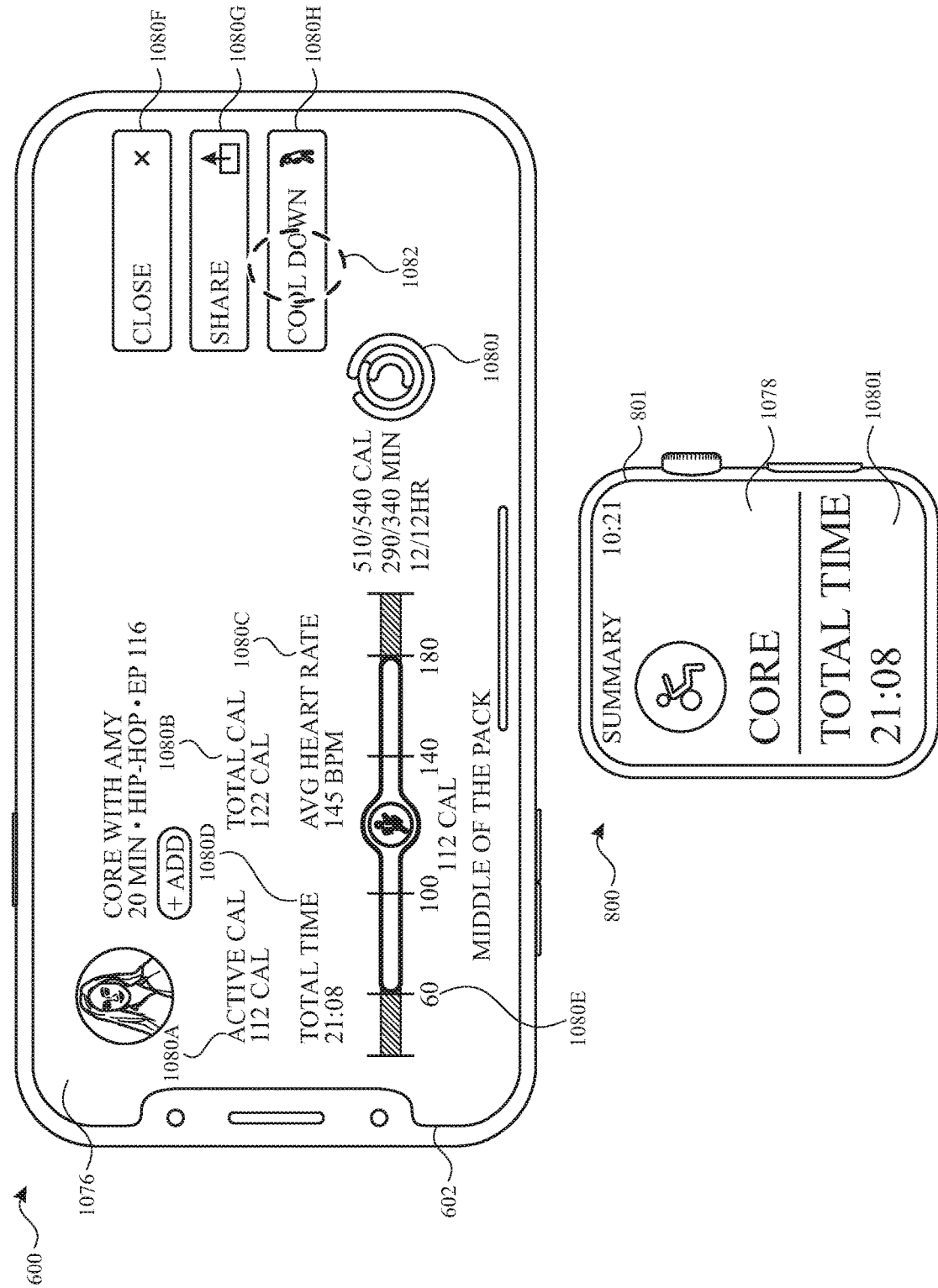

At FIG. 10P, the electronic device 600 and/or the electronic device 800 detects that the workout session has concluded. In response to detecting that the workout session has concluded, the electronic device 600 replaces display of the workout session user interface 1030 with a workout summary user interface 1076, and the electronic device 800 replaces display of the workout metrics user interface 1032 with a workout summary user interface 1078. In some embodiments, in response to detecting that the workout session has concluded, electronic device 600 causes electronic device 800 to replace display of the workout metrics user interface 1032 with the workout summary user interface 1078. The workout summary user interface 1076 optionally displays calorie information for the workout session (e.g., active calorie information 1080A, total calorie information 1080B), heart rate information for the workout session (e.g., average heart rate 1080C), duration information for the workout session (e.g., total time 1080D), and information pertaining to the user's performance relative to other users (e.g., workout intensity information 1080E (e.g., corresponds to workout intensity representation 1040D as discussed with respect to FIGS. 12A-12O)). The workout summary user interface 1076 also optionally displays physical activity ring information 1080J, which indicates the state of the user's physical activity rings 1036 after the workout. The workout summary user interface 1076 optionally also includes an option 1080F to close the workout summary user interface, an option 1080G to share workout summary information, and an option 1080H to select a cool down workout. In some embodiments, electronic device 600 can decide to display and/or decide to forgo displaying the cool down workout option 1080H based on user preferences and/or past user behavior. For example, if a user has historically chosen to go straight into another workout, or if a user historically chooses not to do a cool down workout, electronic device 600 can exclude option 1080H from the workout summary user interface 1076, whereas if a user has historically chosen to do a cool down workout, electronic device 600 can include option 1080H in the workout summary user interface 1076. The workout summary user interface 1078 displays a subset of the information in the workout summary user interface 1076 (in this case, a total workout duration 1080I, which corresponds to total time 1080D).

While displaying the workout summary user interface 1076, electronic device 600 detects an input 1082 at a location that corresponds to the cool down workout option 1080H.

Figure 10Q:
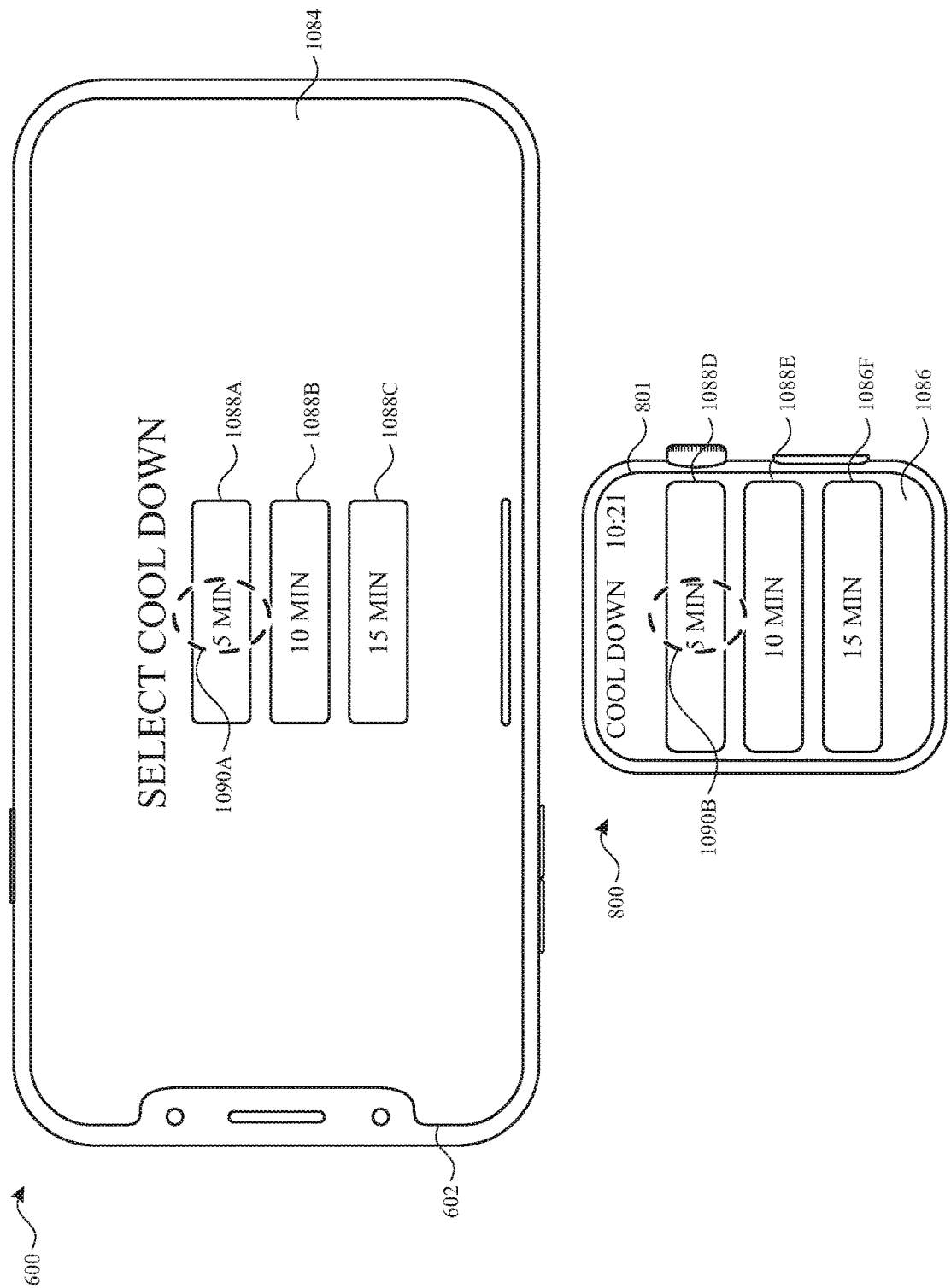

At FIG. 10Q, in response to detecting input 1082, electronic device 600 replaces display of the workout summary user interface 1076 with cool down workout selection user interface 1084. Similarly, in response to electronic device 600 detecting input 1082, electronic device 800 replaces display of workout summary user interface 1078 with cool down workout selection user interface 1086. In some embodiments, in response to detecting input 1082, electronic device 600 causes electronic device 800 to replace display of workout summary user interface 1078 with cool down workout selection user interface 1086. The cool down workout selection user interface 1084 on electronic device 600 includes selectable options 1088A, 1088B, and 1088C that can be selected by a user to select a particular cool down workout. The cool down workout selection user interface on electronic device 800 includes selectable options 1088D, 1088E, and 1088F that correspond to the selectable options 1088A, 1088B, and 1088C. A user can use the selectable options on either electronic device 600 or electronic device 800 to select his or her cool down workout. For example, if the electronic device 600 detects an input at a location corresponding to 5-minute option 1088A on electronic device 600 (e.g., user input 1090A), or if the electronic device 800 detects an input at a location corresponding to 5-minute option 1088D on electronic device 800 (e.g., user input 1090B), visual display corresponding to a 5-minute cool down workout can be initiated on electronic device 600 and corresponding display can be initiated on electronic device 800.

In the depicted embodiment, each time duration (e.g., 5-minutes, 10-minutes, 15-minutes) has only one cool down workout associated with it. However, it should be understood that in other embodiments, there can be multiple workouts for each time duration (e.g., multiple 5-minute cool down workouts, multiple 10-minute cool down workouts). In some embodiments, if the electronic device 600 determines that the cool down workout selection user interface 1084 has been displayed for a threshold period of time, a default cool down workout can automatically begin playing even without a user input. In some embodiments, the electronic device 600 can automatically select one or more cool down workouts based on characteristics of the workout that was just completed (e.g., based on the trainer of the workout, based on the workout type, based on a duration of the workout, etc.). For example, if a user has just completed a leg-intensive workout, the electronic device 600 can automatically select a cool down workout that focuses on stretching and loosening the legs. In some embodiments, a particular workout can be associated with one or more cool down workouts such that the electronic device 600 can automatically identify one or more cool down workouts that are associated with the particular workout.

Figure 10R:
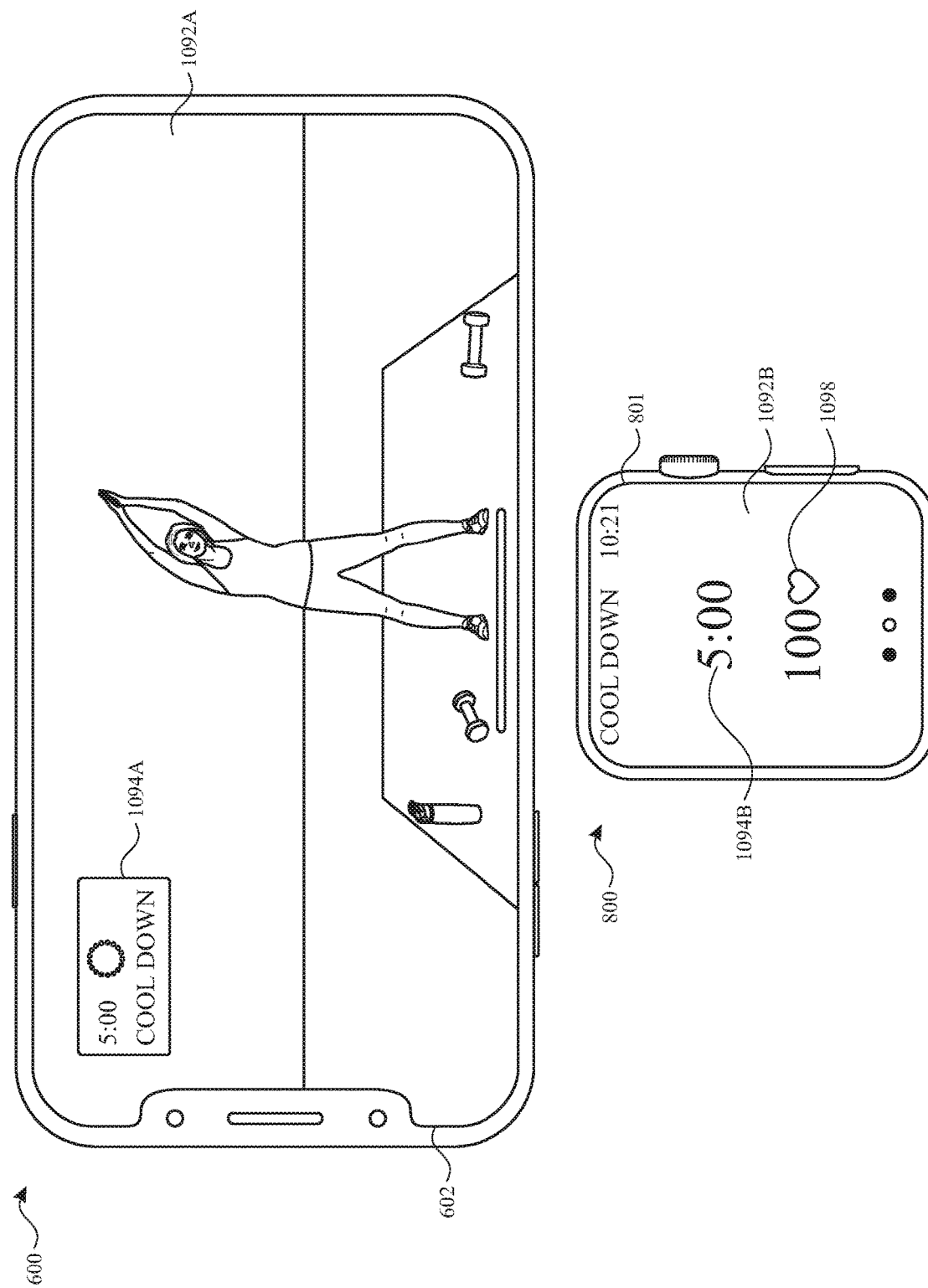

At FIG. 10R, in response to electronic device 600 detecting input 1090A or electronic device 800 detecting input 1090B, electronic device 600 replaces display of the cool down workout selection user interface 1084 with cool down workout user interface 1092A, and electronic device 800 replaces display of cool down workout selection user interface 1086 with cool down workout metrics interface 1092B. In some embodiments, electronic device 600 causes electronic device 800 to replace display of cool down workout selection user interface 1086 with cool down workout metrics interface 1092B. Cool down workout interface 1092A includes a countdown timer 1094A counting down the remaining time in the cool down workout, and cool down workout metrics interface 1092B also includes a corresponding countdown timer 1094B. The cool down workout interface 1092A includes video content 1096 that leads a user through the cool down workout. The cool down workout metrics interface 1092B includes heart rate information 1098 that presents the user with his or her current heart rate.

Figure 10S:
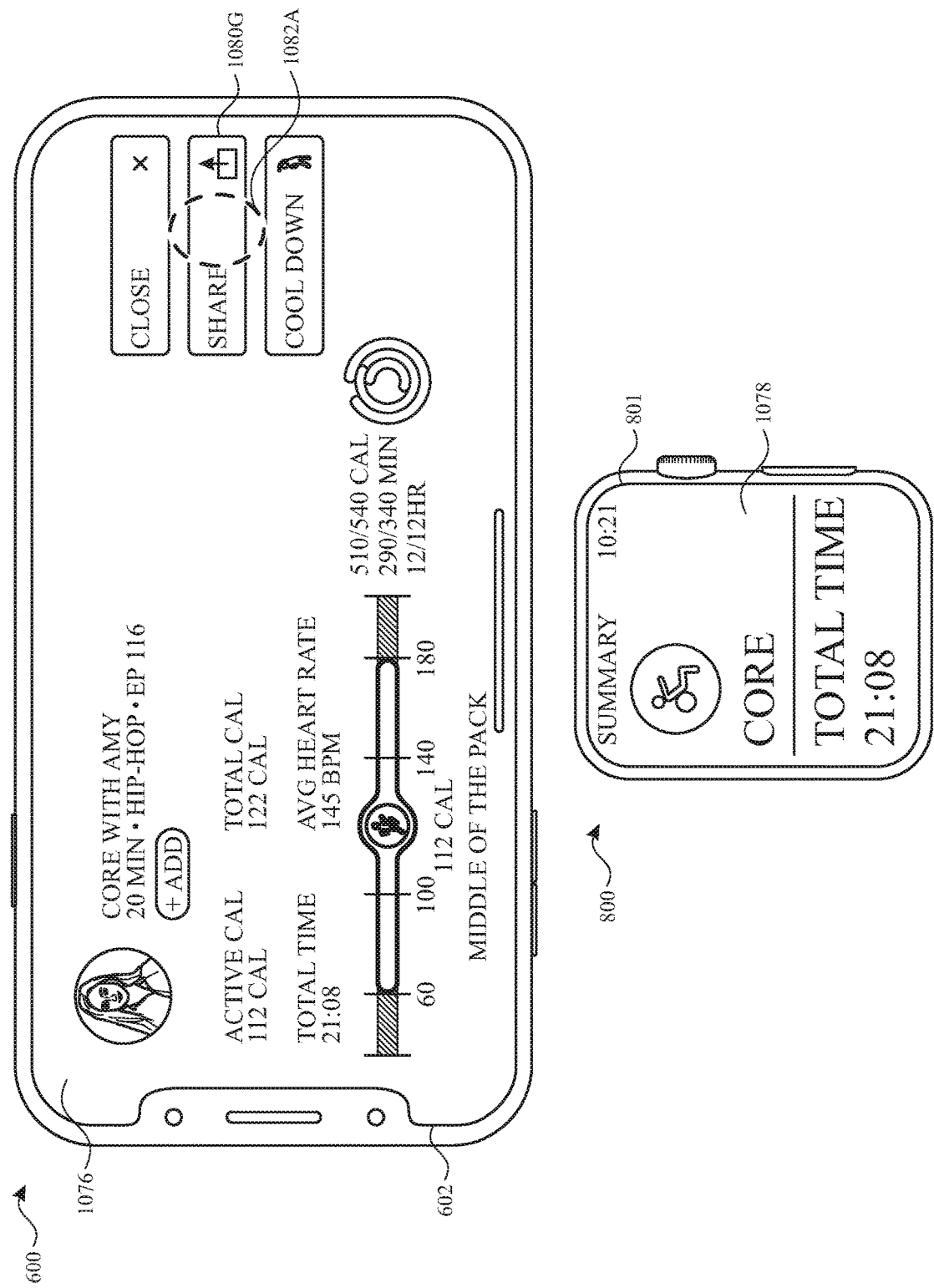

FIG. 10S depicts the workout summary user interface 1076 of FIG. 10P. However, rather than detecting selection of the cool down option 1080H, in FIG. 10S, the electronic device 600 detects a user input 1082A at a location corresponding to the share option 1080G.

Figure 10T:
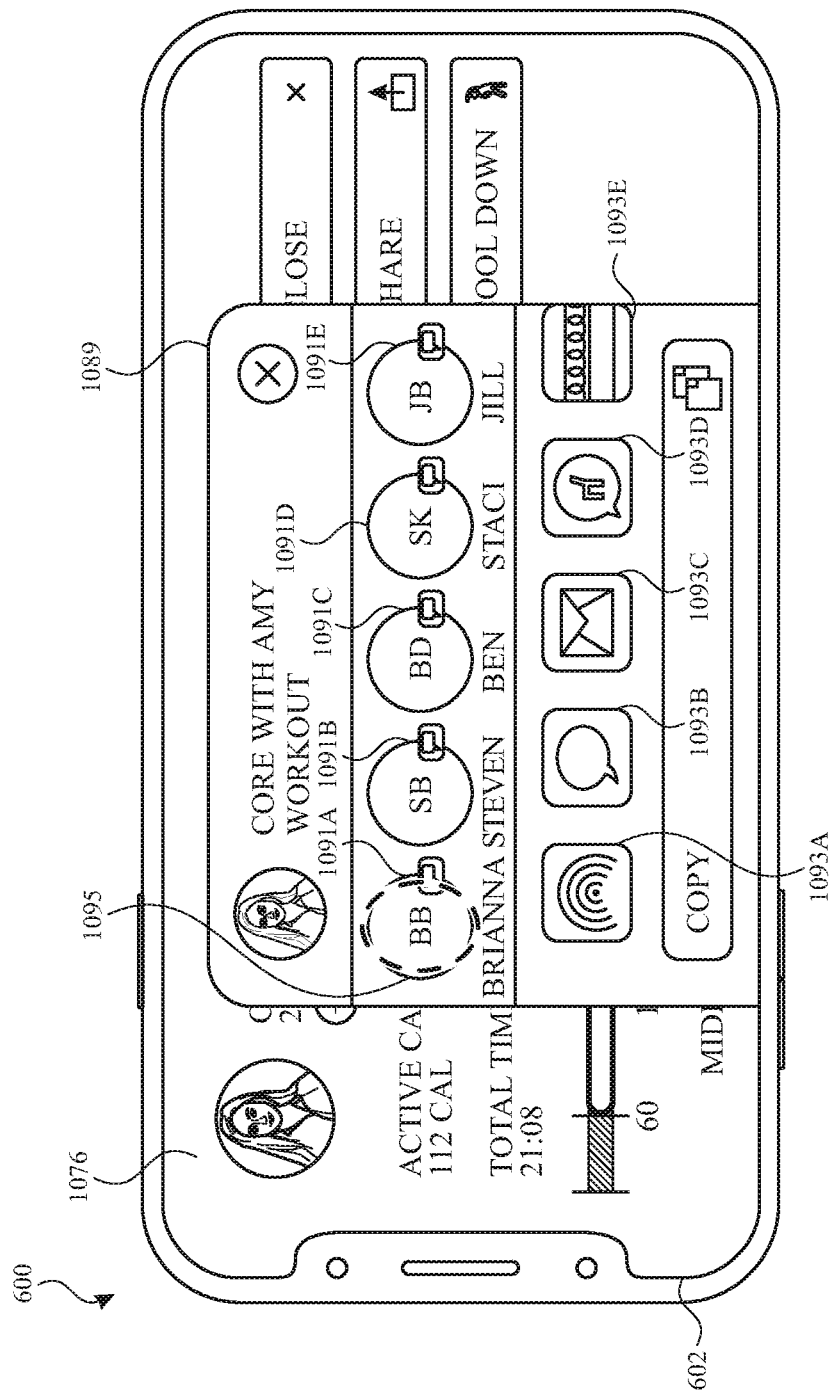

At FIG. 10T, in response to detecting input 1082A, electronic device 600 displays share user interface 1089. In the depicted embodiment, share user interface 1089 is overlaid on workout summary user interface 1076. Share user interface 1089 includes options 1091A-1091E. Each option 1091A-1091E corresponds to a respective contact, and selection of an option 1091A-1091E will open a messaging application user interface that allows the user to send workout summary information to the selected contact. Share user interface 1089 also includes application options 1093A-1093E that are selectable by a user to open a particular application for sharing workout summary information (e.g., a near-field communications transmission application (1093A), a text messaging application (1093B), an email messaging application (1093C)). While displaying share user interface 1089, electronic device 600 detects input 1095 at a location corresponding to option 1091A.

Figure 10U:
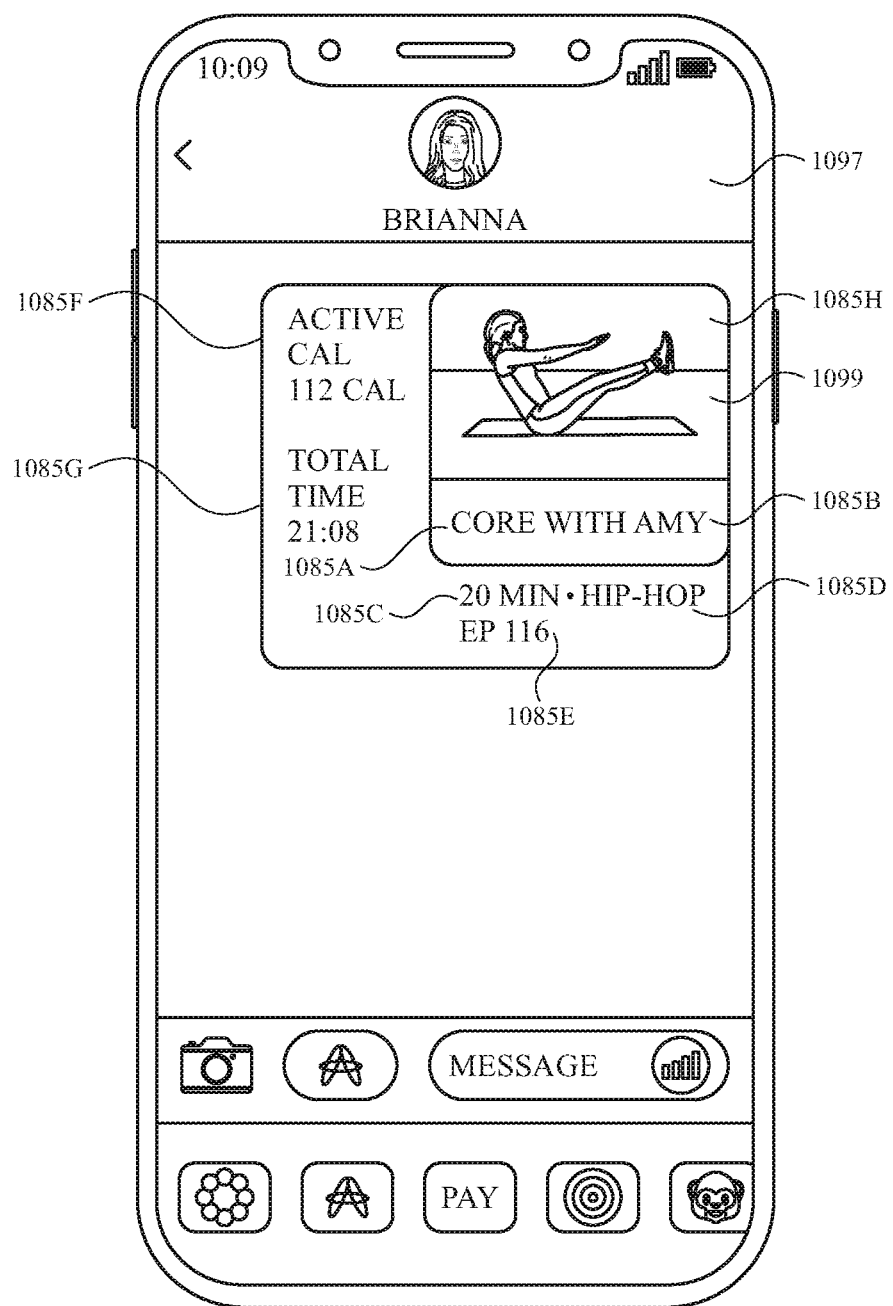
Figure 10V:
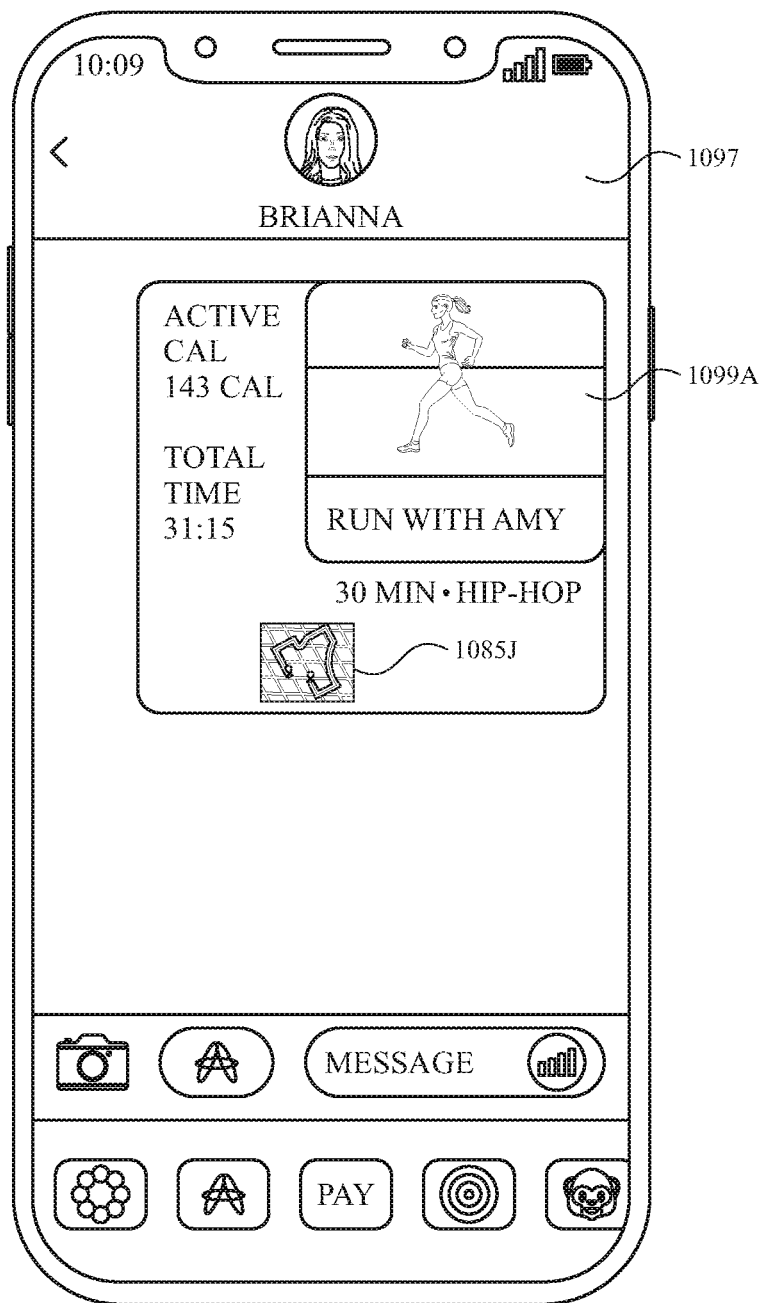

At FIG. 10U, in response to detecting input 1095, electronic device 600 initiates a process for transmitting workout summary information to the contact associated with option 1091A. In FIG. 10U, electronic device 600 has replaced display of the share user interface 1089 and the workout summary user interface 1076 with a messaging application user interface 1097, and has initiated transmission of workout summary information to the selected contact. Workout summary information is presented in the messaging application user interface 1097 as a message 1099. Workout summary information contained in message 1099 can include some or all of the information presented in workout summary user interface 1076. In FIG. 10U, the workout summary information contained in message 1099 includes workout type information 1085A ("CORE"), workout trainer information 1085B ("AMY"), workout duration information 1085C ("20 MIN"), workout music information 1085D ("HIP-HOP"), episode information 1085E ("EP 116"), active calorie information 1085F ("112 CAL"), and total workout time information 1085G ("21:08"), as well as an image representative of the workout 1085H.

In some embodiments, workout summary information presented in message 1099 can differ based on the workout. For example, in FIG. 10V, rather than sharing workout summary information for a core workout, the user has shared information for a run workout. In FIG. 10V, message 1099A includes the same workout summary information as was included in message 1099, but also includes a route map 1085J corresponding to the run workout performed by the user which was not included in message 1099 of FIG. 10U.

FIG. 11 is a flow diagram illustrating a method for displaying video content and providing workout information relating to the video content using an electronic device in accordance with some embodiments. Method 1100 is performed at an electronic device (e.g., 100, 300, 500, 600, 800) with a display (e.g., 602, 801). Some operations in method 1100 are, optionally, combined, the orders of some operations are, optionally, changed, and some operations are, optionally, omitted.

As described below, method 1100 provides an intuitive way for displaying video content and providing workout information relating to the video content. The method reduces the cognitive burden on a user for displaying video content and providing workout information relating to the video content, thereby creating a more efficient human-machine interface. For battery-operated computing devices, enabling a user to display video content and provide workout information relating to the video content faster and more efficiently conserves power and increases the time between battery charges.

In some embodiments, the electronic device (e.g., 100, 300, 500, 600, 800) is a computer system. The computer system is optionally in communication (e.g., wired communication, wireless communication) with a display generation component and with one or more input devices. The display generation component is configured to provide visual output, such as display via a CRT display, display via an LED display, or display via image projection. In some embodiments, the display generation component is integrated with the computer system. In some embodiments, the display generation component is separate from the computer system. The one or more input devices are configured to receive input, such as a touch-sensitive surface receiving user input. In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

The electronic device causes concurrent display (1102), via a display device (e.g., a display device of an electronic device (e.g., display 602 of electronic device 600), a display device of or in communication with an external device (e.g., television, set top box)), of video content (e.g., 1034, workout video) and one or more representations of physical activity metrics (e.g., 1036, 1036A-C, 1038, 1040A-D, hours in which a user has stood for at least some predetermined amount of time, minutes of activity above a certain threshold activity level, active calories, heart rate, distanced traveled, stairs climbed either based on passive background activity monitoring or activity data recorded during specific workouts) corresponding to a user. In some embodiments, the one or more representations of the physical activity metrics correspond to a predetermined amount of time that includes a period of time preceding playback of the content (1104). In some embodiments, the one or more representations of the physical activity metrics are overlaid on the video content (1106). Causing concurrent display of video content and one or more representations of physical activity metrics provides the user with feedback about physical activity metrics and other information recorded by the electronic device. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

While continuing to cause display of the video content (1108), the electronic device receives (1110) activity data based on physical activity of the user during the display of the video content. While continuing to cause display of the video content (1108) (e.g., 1034), and in response to receiving the activity data (1114), the electronic device updates (1116) the display of the one or more representations of the physical activity metrics based on the received activity data (e.g., 1036, 1036A-C, 1038, 1040A-D). In some embodiments, updating the display of the one or more representations of the physical activity metrics includes changing (e.g., highlighting, emphasizing) a visual characteristic of at least a portion of the one or more representations. Updating the display of the one or more representations of the physical activity metrics based on received activity data provides the user with updated feedback about physical activity metrics and other information recorded by the electronic device. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the video content (e.g., 1034) corresponds to a workout (e.g., a physical activity to be performed by the user), and the received activity data is based on physical activity of the user captured via one or more sensors (e.g., GPS, accelerometer, heart rate, and/or gyroscope) that is in communication with the electronic device (1112). In some embodiments, the one or more sensors correspond to (e.g., are part of) an external device. In some embodiments, the one or more sensors correspond to (e.g., are part of) the electronic device.

In some embodiments, while causing display of the video content, the electronic device causes one or more sensors of an external device to be enabled/activated so as to improve accurate measurements of the user during the workout. In some embodiments, the one or more sensors are not enabled/activated prior to display of the video content. In some embodiments, a subset of the one or more sensors are enabled/activated based on the type of workout. In some embodiments, in accordance with a determination that a workout is of a first type, a first subset of the one or more sensors are enabled/activated based on the first type. In some embodiments, in accordance with a determination that a workout is of a second type, a second subset of the one or more sensors are enabled/activated based on the second type.

In some embodiments, the one or more representations of the physical activity metrics include a plurality of (e.g., concentric) rings (e.g., 1036, 1036A-C), and a first ring (e.g., 1036A, 1036B, 1036C) of the plurality of rings corresponds to a first type of physical activity metrics (e.g., hours in which a user has stood for at least some predetermined amount of time, minutes of activity above a certain threshold activity level, active calories, heart rate, distanced traveled, stairs climbed either based on passive background activity monitoring or activity data recorded during specific workouts). In some embodiments, a second ring and a third ring of the plurality of concentric rings corresponds to a second type and a third type of physical activity metrics, respectively. In some embodiments, the one or more representations of the physical activity metrics are based on data captured from an external device (e.g., 800, smartwatch) that is in communication with the electronic device. In some embodiments, the data is captured from the external device regardless of which device (e.g., a device other than the external device and the electronic device, the electronic device) is displaying the video content.

In some embodiments, the one or more representations of the physical activity metrics include a representation of calories burned by the user (e.g., 1036A, 1040C).

In some embodiments, the one or more representations of the physical activity metrics include a representation of an amount of time that has elapsed (e.g., 1040A, corresponding to the amount of time that the video content has been playing via the display device (e.g., the amount of time the user has been physically active)).

In some embodiments, the one or more representations of the physical activity metrics include a representation of a heart rate of the user (e.g., 1040B, a real-time heart rate, a heart-rate taken at predetermined intervals (e.g., 5, 10, 30 seconds)).

In some embodiments, while continuing to cause display of the video content, the electronic device detects a first user input (e.g., 1044, anywhere on the display device, at a location corresponding to the video content); and, in response to detecting the first user input, the electronic device causes display, via the display device, of a set of one or more playback controls (e.g., 1046A-E, play/pause, close, volume, closed captions, edit which physical activity metrics are displayed) that are overlaid on the video content. Causing display of a set of one or more playback controls that are overlaid on the video content in response to a user input allows the electronic device to reveal playback controls when needed to control playback of the video content while also providing the electronic device with the ability to keep the playback controls hidden when they are not needed. Providing additional control of the device without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while causing display of the set of one or more playback controls that includes an edit selectable user interface object (e.g., 1046E), the electronic device detects a user input (e.g., 1048) corresponding to the edit selectable user interface object. In some embodiments, in response to detecting the user input corresponding to the edit selectable user interface object, the electronic device causes display, via the display device, of one or more options for configuring the display of the one or more representations of the physical activity metrics (e.g., 1052A-E). In some embodiments, the electronic device detects one or more user inputs corresponding to configuring the display of the one or more representations of the physical activity metrics, including detecting selection of a respective option of the one or more options for configuring the one or more representations of the physical activity metrics. In some embodiments, in response to detecting the one or more user inputs corresponding to configuring the display of the one or more representations of the physical activity metrics, the electronic device causes display, via the display device, of the video content and updates the display of the one or more representations of the physical activity metrics based on the detected one or more user inputs corresponding to configuring the display of the one or more representations of the physical activity metrics. In some embodiments, updating the display of the one or more representations of physical activity metrics includes modifying the format (e.g., elapsed time, remaining time) of a respective representation (e.g., options 1052C, 1052D). In some embodiments, updating the display includes ceasing to display or causing display of a respective representation (e.g., options 1052A, 1052B, 1052E). In some embodiments, the one or more options for configuring the display of the one or more representations of physical activity metrics correspond to elapsed time (e.g., 1052C), remaining time (e.g., 1052D), the plurality of rings, and workout intensity representation (e.g., 1052E, further discussed below). In some embodiments, while causing display of the video content, the electronic device overrides the configuration of the display of the one or more representations of physical activity metrics (e.g., causing display of a respective representation that would otherwise be hidden/not displayed). In some embodiments, the one or more options for configuring the one or more representations of the physical activity metrics are overlaid on the video content.

In some embodiments, while continuing to cause display of the video content, and in accordance with a determination that the a first type of event has occurred (e.g., a predefined milestone has been achieved (e.g., a threshold value has been obtained for a particular physical activity metric), a particular playback position of the video content has been reached), the electronic device visually emphasizes, via the display device, at least a portion of the one or more representations of the physical activity metrics without visually emphasizing a different portion of the one or more representations of the physical activity metrics (e.g., as depicted in FIGS. 10G-10O). In some embodiments, visually emphasizing at least the portion of the one or more representations of the physical activity metrics includes deemphasizing (e.g., obscuring, dimming) a different portion of the one or more representations of the physical activity metrics (e.g., as depicted in FIGS. 10K-M). In some embodiments, the determination is made based on metadata associated with the video content. Visually emphasizing at least a portion of the one or more representations of the physical activity metrics without visually emphasizing a different portion of the one or more representations of the physical activity metrics provides the user with feedback about the current state of the device (e.g., that the device has detected a particular event). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. Automatically visually emphasizing at least a portion of the one or more representations of the physical activity metrics in accordance with a determination that a first type of event has occurred also provides the user with feedback about the current state of the device (e.g., that the device has detected a particular event). Performing an optimized operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, visually emphasizing at least the portion of the one or more representations of the physical activity metrics includes: causing an audio output associated with the portion of the one or more representations of the physical activity metrics, wherein the portion includes a plurality of rings (e.g., 1036); and expanding the displayed size of the plurality of rings (e.g., as depicted in FIGS. 10J-10L), including causing display of information (e.g., 1063A-C, text, numerical value) about the plurality of rings. In some embodiments, the audio output is diegetic audio that occurs in the video as part of the world of the video, for example when a trainer says "check your rings" as part of leading the workout. In some embodiments, expanding the displayed size of the plurality of rings includes deemphasizing (e.g., dim, obscure, fade) other portions of the one or more representations of the physical activity metrics. In some embodiments, the electronic device emphasizes (e.g., at a specific time) at least the portion of the one or more representations of the physical activity metrics (e.g., by expanding the displayed size of the plurality of rings (e.g., as depicted in FIGS. 10J-10L)), based on data (e.g., metadata associated with the video content) that indicates when the video content advances to the portion of the video content that includes particular audio content (e.g., the diegetic audio). In some embodiments, the electronic device controls (e.g., based on metadata) the timing of when the at least a portion of the one or more representations of the physical activity metrics is visually emphasized so that the visual emphasis corresponds with, precedes, and/or follows output of specific audio content (e.g., diegetic audio content such as "a training saying "check your rings") within the video content.

In some embodiments, visually emphasizing at least the portion of the one or more representations of the physical activity metrics further includes: in accordance with a determination that the plurality of rings (e.g., 1036) are presented within a first region of the display device (e.g., in accordance with a determination that the plurality of rings are presented on a notch side of the display device (e.g., a side of the display device that includes a notch)) (e.g., FIGS. 10M1-10M4), translating the plurality of rings in a first direction (e.g., in a direction towards a center of the display device and/or away from the notch) by a first amount and expanding the displayed size of the plurality of rings (e.g., FIGS. 10M2, 10M3), and in accordance with a determination that the plurality of rings are presented within a second region of the display device different from the first region (e.g., in accordance with a determination that the plurality of rings are presented on side of the display device opposite the notch side) (e.g., FIGS. 10J-10M), expanding the displayed size of the plurality of rings without translating the plurality of rings in the first direction by the first amount (in some embodiments, with translating the plurality of rings in the first direction). Automatically translating the plurality of rings and/or not translating the plurality of rings based on the position of the plurality of rings allows the electronic device to present information to the user without additional user input. Performing an optimized operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, visually emphasizing at least the portion of the one or more representations of the physical activity metrics includes expanding the displayed size of the plurality of rings (e.g., 1036, as depicted in FIGS. 10J-10L), including causing display of a visual indication that a respective ring of the plurality of rings has closed (e.g., 1068). In some embodiments, in response to receiving activity data, the electronic device fills in an unfilled portion of one or more rings of the plurality of rings. In some embodiments, once a respective ring is completely filled in, the ring is closed, which indicates that the user has achieved their goal with respect to the physical activity metric represented by the ring.

In some embodiments, visually emphasizing at least the portion of the one or more representations of the physical activity metrics includes: while causing display, via the display device, of a first representation of time (e.g., elapsed time, remaining time) corresponding to the video content (e.g., corresponding to the overall duration of the video content), causing display, via the display device, of a second representation of time corresponding to a predefined amount of time (e.g., 10, 20, 30 seconds) (e.g., as depicted in FIGS. 10G-10H). In some embodiments, the second representation of time replaces the first representation of time.

In some embodiments, causing display of the second representation of time corresponding to a predefined amount of time comprises: causing display of an animation in which a numerical value corresponding to the predefined amount of time is overlaid on a blinking background (e.g., 1058A, 1058B, FIGS. 10G-10G3). In some embodiments, causing display of the animation comprises: causing display of the numerical value corresponding to the predefined amount of time (e.g., "10" in 1058A, 1058B, FIGS. 10G-10G3) overlaid on a background portion, wherein the background portion is displayed in a first state; and while maintaining display of the numerical value corresponding to the predefined amount of time, transitioning the background portion from the first state to a second state different from the first state (e.g., FIGS. 10G-10G3). In some embodiments, the first state and the second state comprise different visual characteristics (e.g., different colors, different brightnesses, different hues). In some embodiments, the animation is presented immediately prior to initiation of a countdown animation. Displaying an animation of the numerical value overlaid on a blinking background provides the user with feedback about the current state of the device (e.g., that a timer is about to begin). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, visually emphasizing at least the portion of the one or more representations of the physical activity metrics includes: causing display, via the display device, of one or more representations of a heart rate of the user (e.g., 1072, 1072A-C, a real-time heart rate, a heart-rate taken at predetermined intervals (e.g., 5, 10, 30 seconds), high/low/current heart rate for the duration of playback of the video content). In some embodiments, the electronic device causes an output of a (e.g., audio, visual) prompt for the user to check their heart rate. In some embodiments, the output prompt occurs while the one or more representations of the heart rate are displayed.

In some embodiments, visually emphasizing at least the portion of the one or more representations of the physical activity metrics includes: causing a second display device (e.g., 800) different from the display device to display information corresponding to the visually emphasized portion of the one or more representation of the physical activity metrics. In some embodiments, the electronic device causes the second display device (e.g., of an external device such as a smartwatch) to display a textual notification corresponding to the visually emphasized portion (e.g., as depicted in FIGS. 10G-10M). In some embodiments, in accordance with a determination that the portion that is visually emphasized is not of a particular type (e.g., heartrate or time representation), the electronic device does not cause the second display device to display information corresponding to the visually emphasized portion (e.g., as depicted in FIG. 10N). In some embodiments, the electronic device causes the second display device to display the information in accordance with a determination that the portion that is visually emphasized is of the particular type (e.g., not heartrate or time representation).

In some embodiments, visually emphasizing at least the portion of the one or more representations of the physical activity metrics includes: causing display, via the display device, of an indication that a midpoint (e.g., halfway point) in the duration of the video content has been reached (e.g., 1060).

In some embodiments, visually emphasizing at least the portion of the one or more representations of the physical activity metrics includes visually obscuring (e.g., fading, dimming) other portions of the one or more representations of the physical activity metrics (e.g., as depicted in FIGS. 10K-10M).

In some embodiments, while continuing to cause display of the video content, the electronic device causes display, via the display device, of an indication that a music track change has occurred (e.g., 1074).

In some embodiments, while continuing to cause display of the video content, the electronic device causes display, via the display device, of a new representation (e.g., 1072) of a physical activity metric, wherein the new representation of the physical activity metric was not selected for display during display of the video content (e.g., based on default or user selected settings). In some embodiments, the electronic device causes display of the new representation in accordance with a determination that the a first type of event has occurred (e.g., a predefined milestone has been achieved (e.g., a threshold value has been obtained for a particular physical activity metric), a particular playback position of the video content has been reached). Causing display of a new representation of a physical activity metric provides the user with feedback about the current state of the device (e.g., that the device has received information pertaining to the physical activity metric). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, after (e.g. in response to) the end of the video content has been reached, the electronic device causes display, via the display device, of one or more aggregate representations (e.g., active calories, total calories, total time, average heart rate, distance, average pace, workout intensity representation) of physical activity metrics that are based on physical activity of the user for the duration of the video content (e.g., 1076, 1080A-E).

In some embodiments, the one or more aggregate representations of physical activity metrics include the one or more representations of the physical activity metrics (e.g., 1080J) (e.g., a plurality of (e.g., concentric) rings) (e.g., hours in which a user has stood for at least some predetermined amount of time, minutes of activity above a certain threshold activity level, active calories, heart rate, distanced traveled, stairs climbed either based on passive background activity monitoring or activity data recorded during specific workouts). Displaying the one or more representations of the physical activity metrics provides the user with updated feedback about physical activity metrics and other information recorded by the electronic device. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, after (e.g., in response to) the end of the video content has been reached, the electronic device causes display, via the display device, of a selectable user interface object for sharing workout summary information (e.g., 1080G). In some embodiments, the selectable user interface for sharing the workout summary is concurrently displayed with the one or more aggregate representations of physical activity metrics. In some embodiments, the electronic device detects a user input (e.g., 1082A) corresponding to selection of the selectable user interface object for sharing the workout summary (e.g., 1080G). In some embodiments, in response to detecting the user input corresponding to selection of the selectable user interface object for sharing the workout summary, the electronic device initiates a process for transmitting workout summary information to a remote electronic device (e.g., FIGS. 10T-10V) (e.g., via a network), wherein the workout summary information (e.g., 1099, 1099A) includes at least one of the following: a map (e.g., 1085J) corresponding to the activity data received based on physical activity of the user during display of the video content; trainer information corresponding to the video content (e.g., 1085B, 1085H) (e.g., name of trainer, photo of trainer); workout type information corresponding to the video content (e.g., 1085A); duration information corresponding to the video content (e.g., 1085C, 1085G); and distance information corresponding to the activity data received based on physical activity of the user during display of the video content. Displaying a selectable user interface object for sharing workout summary information enables a user to quickly share workout summary information, thereby reducing the number of inputs needed for sharing workout summary information. Reducing the number of inputs needed to perform an operation enhances the operability of the device and makes the user-device interface more efficient (e.g., by helping the user to provide proper inputs and reducing user mistakes when operating/ interacting with the device) which, additionally, reduces power usage and improves battery life of the device by enabling the user to use the device more quickly and efficiently.

In some embodiments, after (e.g. in response to) the end of the video content has been reached, the electronic device causes display, via the display device, of a selectable user interface object for displaying second video content (e.g., 1080H, 1088A-C, that guides a user through a cool down routine); and in response to detecting the selectable user interface object for displaying the second video content, the electronic device initiates a process for displaying the second video content.

In some embodiments, the selectable user interface object for displaying second video content is concurrently displayed with the one or more final representations of physical activity metrics (e.g., 1080A-E). In some embodiments, the selectable user interface object for displaying second video content is displayed in accordance with a determination that the video content is of a particular type (e.g., workouts with a physical activity level above a certain threshold).

In some embodiments, while causing display of the selectable user interface object for displaying second video content (e.g., 1080H, 1088A-C) and in accordance with a determination that a predetermined amount of time has elapsed, the electronic device causes display, via the display device, of the second video content (e.g., 1092A). In some embodiments, the second video content is selected for display based one or more characteristics of the video content (e.g., trainer, duration, modality/exercise type, focus of workout (upper body or lower body), exertion/physical activity level). Automatically causing display of the second video content in accordance with a determination that a predetermined amount of time has passed allows the electronic device to present additional video content without additional user input. Performing an optimized operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, initiating the process for displaying the second video content includes causing display, via the display device, of a plurality of options (e.g., 1088A-F, selectable user interface object, affordance) for configuring the duration (e.g., 5, 10, 15 minutes) of the second video content.

In some embodiments, the electronic device selects the second video content (e.g., 1088A-1088C, 1088D-1088F, 1092A) from a plurality of available video content options (e.g., a collection of available cool down routines or workouts) based on selection criteria, wherein the selection criteria comprise at least one of: workout trainer information, workout equipment information, and user preference information. Automatically selecting the second video content based on selection criteria allows the electronic device to present additional video content without additional user input. Performing an optimized operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, after (e.g. in response to) the end of the video content has been reached: in accordance with a determination that the user satisfies a first set of criteria (e.g., in accordance with a determination that the user, based on past behavior, is not likely to perform another workout), the electronic device causes display, via the display device, of a selectable user interface object for displaying second video content (e.g., 1080H) (e.g., that guides a user through a cool down routine); and in accordance with a determination that the user satisfies a second set of criteria different from the first set of criteria (e.g., in accordance with a determination that the user, based on past behavior, is likely to perform another workout), the electronic device forgoes display of the selectable user interface object for displaying second video content. Automatically displaying a selectable user interface object and/or automatically forgoing display of the selectable user interface object based on first and second sets of criteria allows the electronic device to present optimized content for a user without additional user input. Performing an optimized operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Note that details of the processes described above with respect to method 1100 (e.g., FIG. 11) are also applicable in an analogous manner to the methods described below. For example, method 1100 optionally includes one or more of the characteristics of the various methods described below with reference to method 1300. For example, the physical activity metrics in method 1100 optionally include the workout intensity representation 1040D, as described with reference to method 1300. For brevity, these details are not repeated below.

FIGS. 12A-12O illustrate exemplary user interfaces for displaying workout information, in accordance with some embodiments. In some embodiments, the workout information can include in-workout physical activity metrics, such as workout intensity information, and other information associated with a workout being performed by a user. The user interfaces in these figures are used to illustrate the processes described below, including the processes in FIG. 13.

FIG. 12A depicts electronic device 600, which is a smartphone with display 602. Display 602 of electronic device 600 includes a touch-sensitive surface on which electronic device 600 can detect user gestures (e.g., tap, swipe, drag). In some embodiments, electronic device 600 includes one or more features of electronic device 100, 300, and/or 500.

At FIG. 12A, the electronic device 600 displays workout session user interface 1030. The workout session user interface 1030 includes video content 1034 that guides a user through a workout session (e.g., a video of an instructor demonstrating a workout). The workout session user interface 1030 also includes physical activity metrics indicative of a user's physical activity. The physical activity metrics include physical activity rings 1036 which include move ring 1036A, exercise ring 1036B, and stand ring 1036C. In some embodiments, physical activity rings 1036 are associated with (e.g., are indicative of) physical activity by a user for a predetermined period of time which includes a period of time preceding initiation of the workout session. For example, the physical activity rings 1036 can be indicative of physical activity by the user for the entire day to that point (e.g., from 12:00 am until the current time in the day). In some embodiments, the move ring 1036A is indicative of a number of calories burned by a user during the day, the exercise ring 1036B is indicative of a number of minutes the user has been active during the day, and the stand ring 1036C is indicative of the number of hours during the day in which the user has stood up for a threshold amount of time or a threshold number of times. In some embodiments, including the depicted embodiment, the move ring 1036A is indicative of progress towards a move goal (e.g., a target number of calories for a day), the exercise ring 1036B is indicative of progress towards an exercise goal (e.g., a target number of exercise minutes for a day), and the stand ring 1036C is indicative of progress towards a stand goal (e.g., a target number of hours for a day). For example, in the depicted embodiment, the move ring 1036A is approximately ⅔ completed, indicating that the user is approximately ⅔ of the way to their move goal, the exercise ring 1036B is approximately ½ completed, indicating that the user is approximately ½ of the way to their exercise goal, and the stand ring 1036C is approximately ½ completed, indicating that the user is approximately ½ of the way to their stand goal.

Physical activity metrics in the workout session user interface 1030 also include workout session physical activity metrics 1038 indicative of the user's physical activity during the current workout session. For example, in some embodiments, the workout session physical activity metrics 1038 include workout duration information 1040A (e.g., the workout has been in session for 1 second), heart rate information 1040B (e.g., the user's current heart rate is 61 beats per minute), and calorie information 1040C (e.g., the user has burned 0 calories so far in this workout session).

The workout session physical activity metrics can also include a workout intensity representation 1040D. As will be described in greater detail with reference to FIGS. 12F to 12N, the workout intensity representation 1040D is indicative of the user's workout intensity level in the workout session relative to other users that have previously participated in (or are currently participating in) the workout session. However, in FIGS. 12A to 12E, the workout session has just started (as indicated by workout duration information 1040A). As such, it can be the case that there is insufficient information to compare the user's workout intensity level relative to other users. Therefore, the workout intensity representation 1040D in FIGS. 12A to 12E depicts an initial visual effect 1202 indicating that the electronic device 600 is gathering additional information in order to compare the user's workout intensity level to other users. In the depicted embodiment, the initial visual effect 1202 is a symbol or icon moving from left to right to indicate that there is some uncertainty as to how the user's workout intensity compares the workout intensity of other users.

User physical activity metrics (including information included in physical activity rings 1036 and workout session physical activity metrics 1038) can be measured by one or more sensors in electronic device 600 and/or one or more sensors external to electronic device 600. Such sensors can include, for example, one or more GPS sensors, one or more accelerometers, one or more heart rate sensors, one or more gyroscopes, and the like. As the user performs a workout, the electronic device 600 can receive activity data based on the physical activity of the user, and update the physical activity metrics that are displayed (e.g., in the physical activity rings 1036 and/or the workout session physical activity metrics 1038).

In some embodiments, after a threshold period of time (e.g., after 30 seconds, after 1 minute), there can be sufficient information to determine the user's workout intensity level relative to other users.

At FIG. 12F, the workout session has been in session for one minute (as demonstrated by workout duration information 1040A). Based on a determination that a threshold period of time has elapsed, electronic device 600 replaces display of the initial visual effect 1202 with the workout intensity representation 1040D. The workout intensity representation 1040D comprises an icon 1204 and a bar 1206. The position of the icon 1204 can move along the bar 1206, and the position of the icon 1204 along the bar 1206 is indicative of the user's workout intensity level relative to other users that have previously participated in and/or are currently participating in the workout session. For example, in FIGS. 12A-12O, the user is viewing video content entitled "Core with Amy" (as indicated in FIG. 12O), e.g., the user is participating in a workout session entitled "Core with Amy." In some embodiments, the workout intensity representation 1040D (e.g., the position of the icon 1204 along the bar 1206) can be indicative of the user's workout intensity level during the workout session (e.g., while viewing the video content entitled "Core with Amy") relative to other users while those users were also participating in the same workout (e.g., while those users were also viewing the video content entitled "Core with Amy"). In some embodiments, positioning of the icon 1204 on the bar 1206 is determined using only data collected from users while those users were viewing the same video content. For example, data collected from users that were participating in a different workout (e.g., Cardio with Bob) can be excluded and/or ignored in the workout intensity representation 1040D for the user participating in the "Core with Amy" workout. The user's workout intensity level and the placement of the icon 1204 along the bar 1206 can be determined based on one or more physical activity metrics, such as heart rate (current heart rate, average heart rate, low heart rate, and/or high heart rate), calories burned, and the like.

In some embodiments, the workout intensity representation 1040D can correspond to a predetermined number of workout intensity groups. A user can be categorized into a particular workout intensity group based on his or her workout intensity as can be determined based on one or more physical activity metrics. For example, workout intensity can be determined based on calories burned, and there can be multiple, e.g., five, defined workout intensity groups, e.g., a fifth/lowest workout intensity group associated with a first range of burned calories (e.g., 0-40 calories burned), a fourth workout intensity group associated with a second range of burned calories (e.g., 41-60 calories burned), a third workout intensity group associated with a third range of burned calories (e.g., 61-80 calories burned), a second workout intensity group associated with a fourth range of burned calories (e.g., 81-100 calories burned), and a first workout intensity group associated with a fifth range of burned calories (e.g., 101 calories and up). It should be understood that the number of groups and the specific percentages provided herein are provided as examples for clarity of explanation, and are not meant to be limiting embodiments. Ranges of physical activity metrics and/or workout intensity thresholds used to define each workout intensity group can be defined based on previous performance by other users that participated in the workout session. For example, a fifth workout intensity group can be defined to capture a first percentage of users, a fourth workout intensity group can be defined to capture a second percentage of users, a third workout intensity group can be defined to capture a third percentage of users, and so forth. In some embodiments, a user's workout intensity level can be compared against a group of users that share one or more characteristics with the user (e.g., fitness level, age range, weight range). In other words, the workout intensity thresholds used to define particular workout intensity groups for a particular user can be defined based on a group of users that share one or more characteristics with the user (e.g., in order to normalize the workout intensity thresholds based on the fitness level and/or the demographics of the user).

In the depicted embodiment, users can be grouped into one of five different workout intensity groups. Each workout intensity group can be associated with a unique set of criteria or thresholds in order to assign users to a particular workout intensity group based on their physical activity metrics. Furthermore, each workout intensity group can be associated with a particular position along the bar 1206. For example, a fifth and lowest workout intensity group can be associated with a leftmost position on the bar 1206, a fourth workout intensity group can be associated with a center-left position on the bar 1206, a third workout intensity group can be associated with a center position on the bar 1206, a second workout intensity group can be associated with a center-right position on the bar 1206, and a first and highest workout intensity group can be associated with a right-most position on the bar 1206.

At FIG. 12F, the user's physical activity metrics indicate that the user's workout intensity falls within a third/middle workout intensity group relative to other users. As such, the icon 1204 is positioned at a first location on the bar 1206 associated with the third workout intensity group (proximate a middle position of the bar 1206).

Figure 12G:
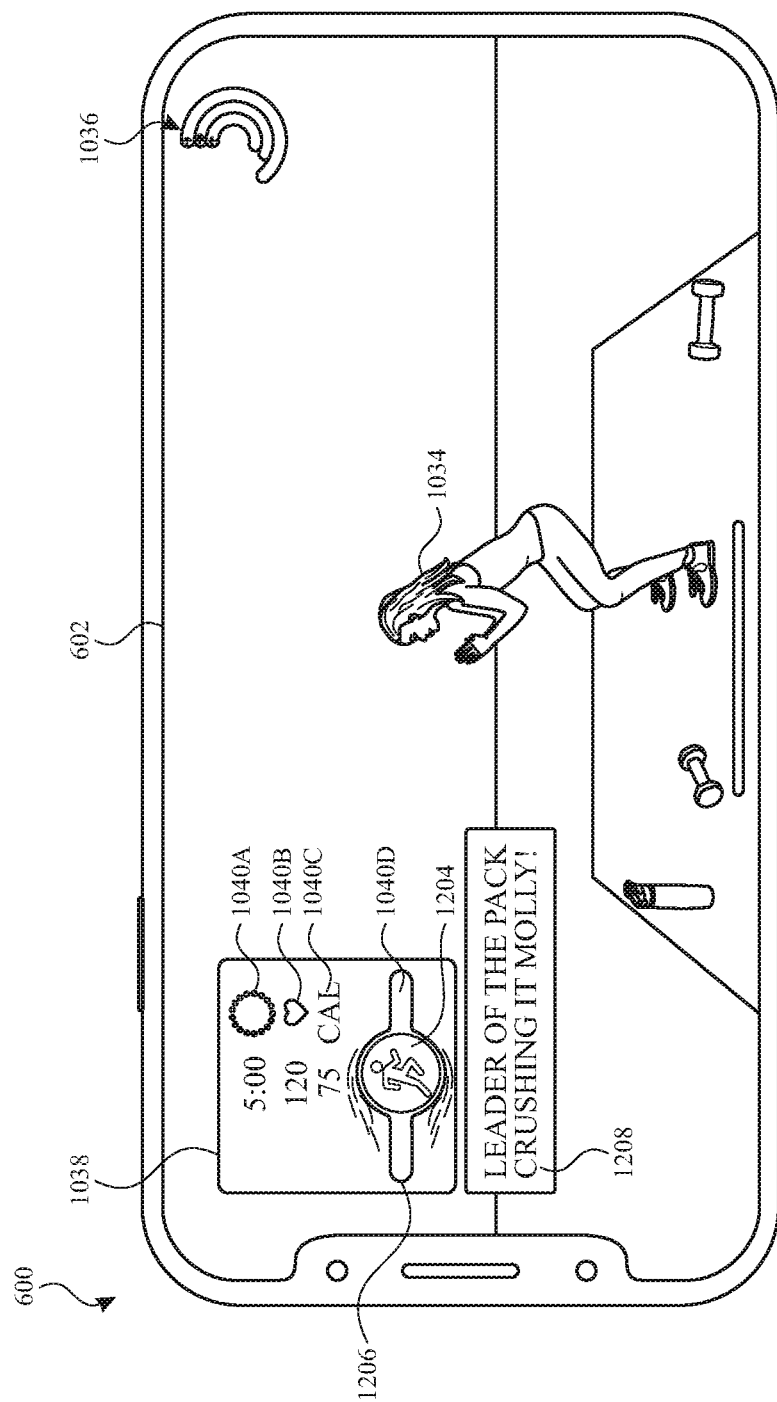

At FIG. 12G, electronic device 600 determines that the user's workout intensity now satisfies one or more workout intensity thresholds associated with the second workout intensity group. Based on this determination, the electronic device 600 initiates a visual indication that the user is moving to a higher workout intensity group. The visual indication can include enlarging the icon 1204, translating the icon to the right towards the center-right position associated with the second workout intensity group, and presenting a notification 1208.

Figure 12H:
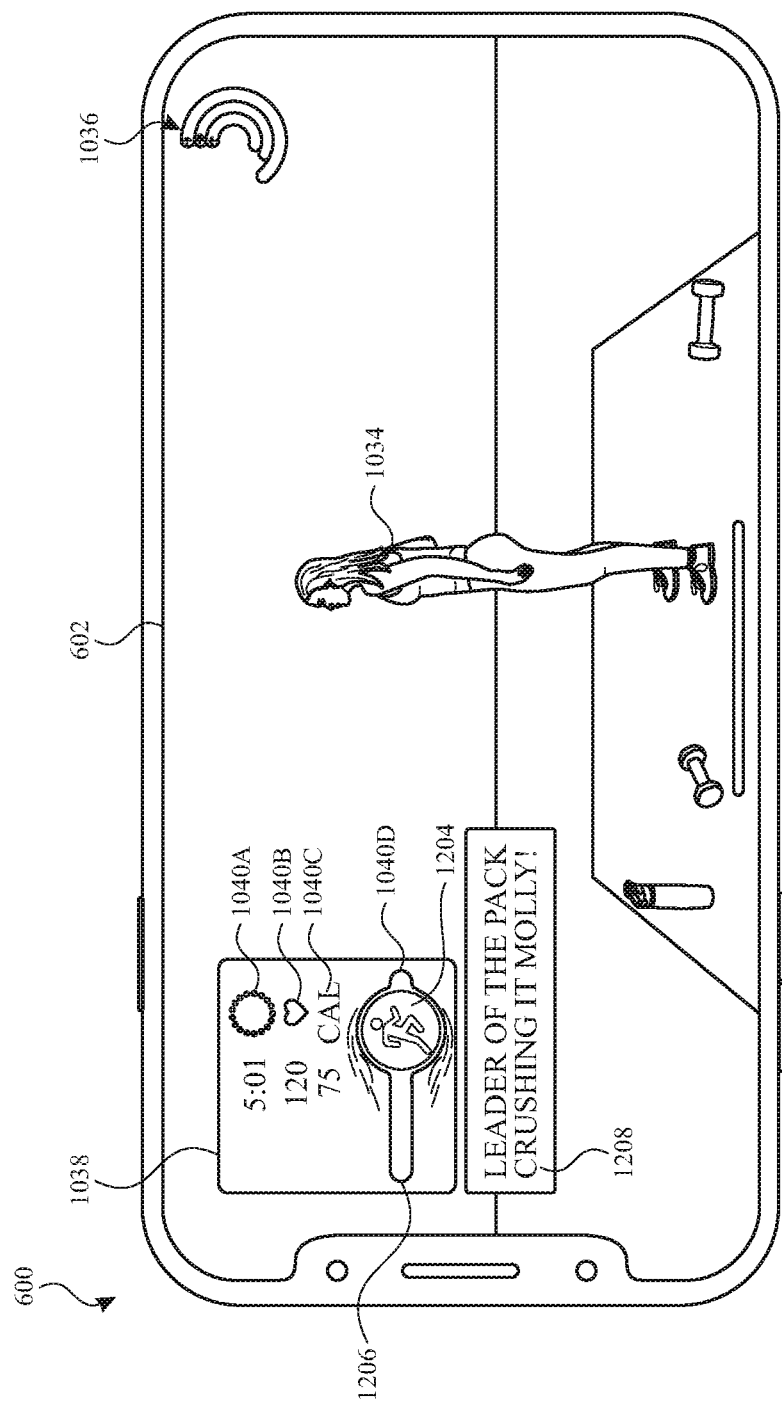

At FIG. 12H, the visual indication that the user is moving to a higher workout intensity group continues, and electronic device 600 displays the icon 1204 continuing to translate to the right along bar 1206.

Figure 12I:
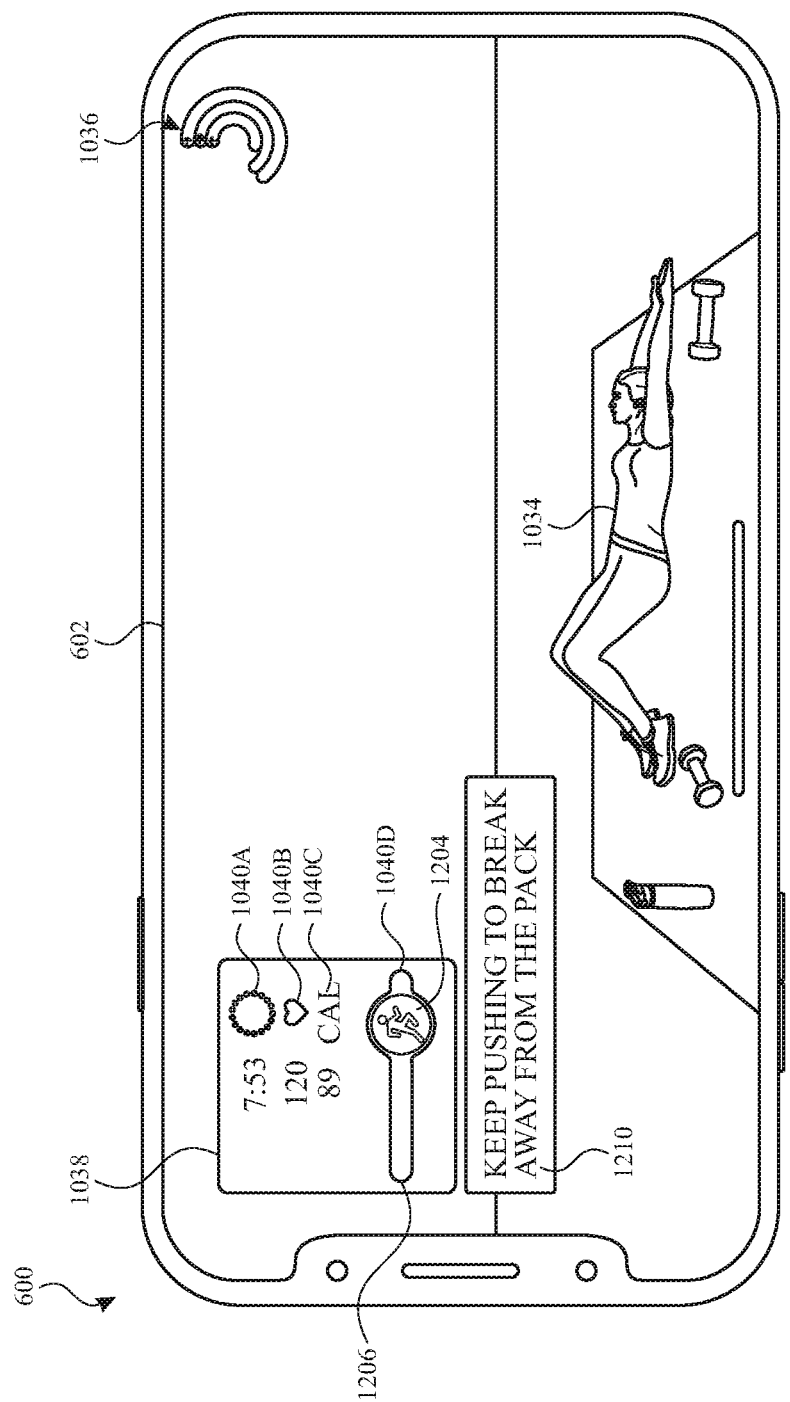

At FIG. 12I, the icon 1204 has reached a center-right position associated with the second workout intensity group. The icon 1204 returns to its smaller size and is presented at the center-right position associated with the second workout intensity group. Furthermore, a new notification 12I is presented which encourages the user to continue improving their performance to move up to the first workout intensity group.

Figure 12J:
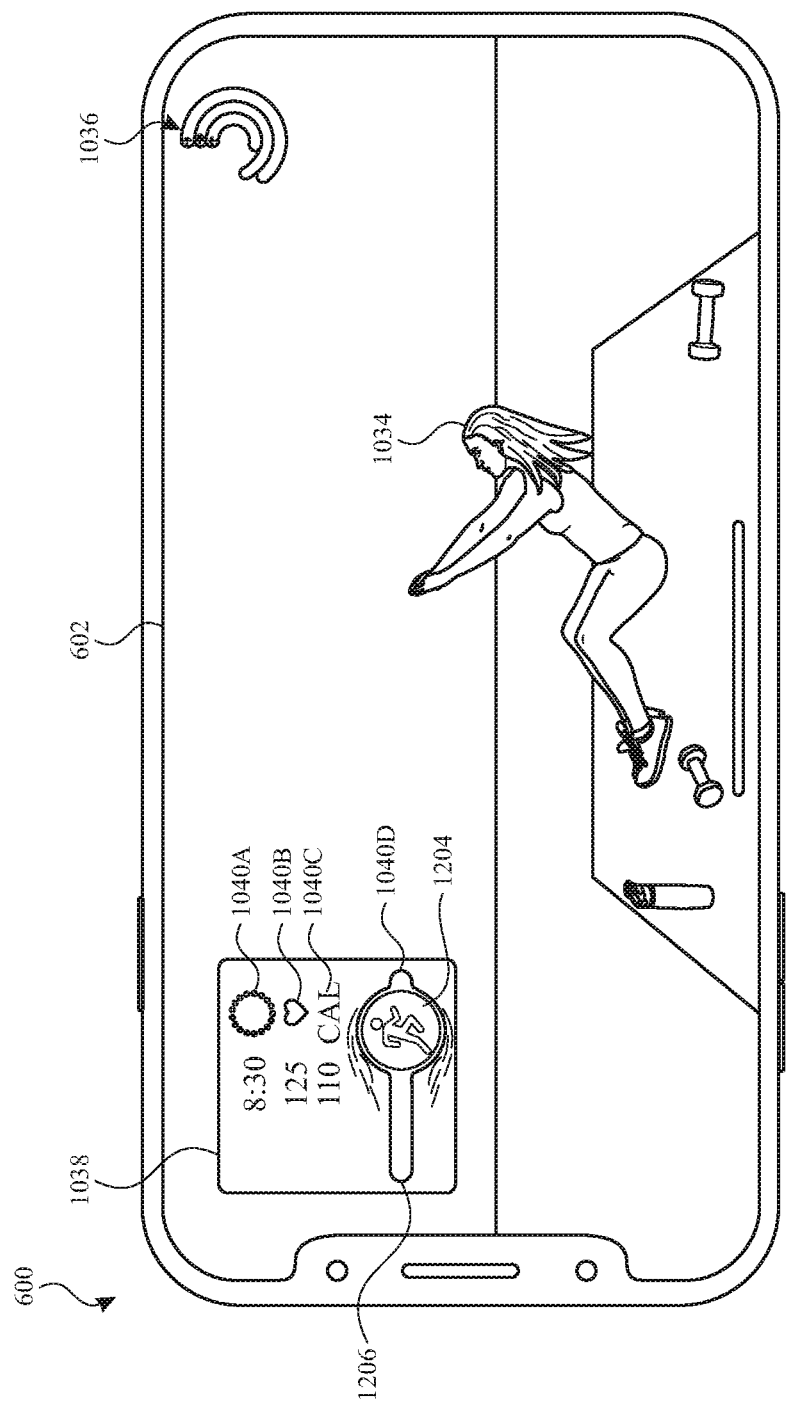
Figure 12K:
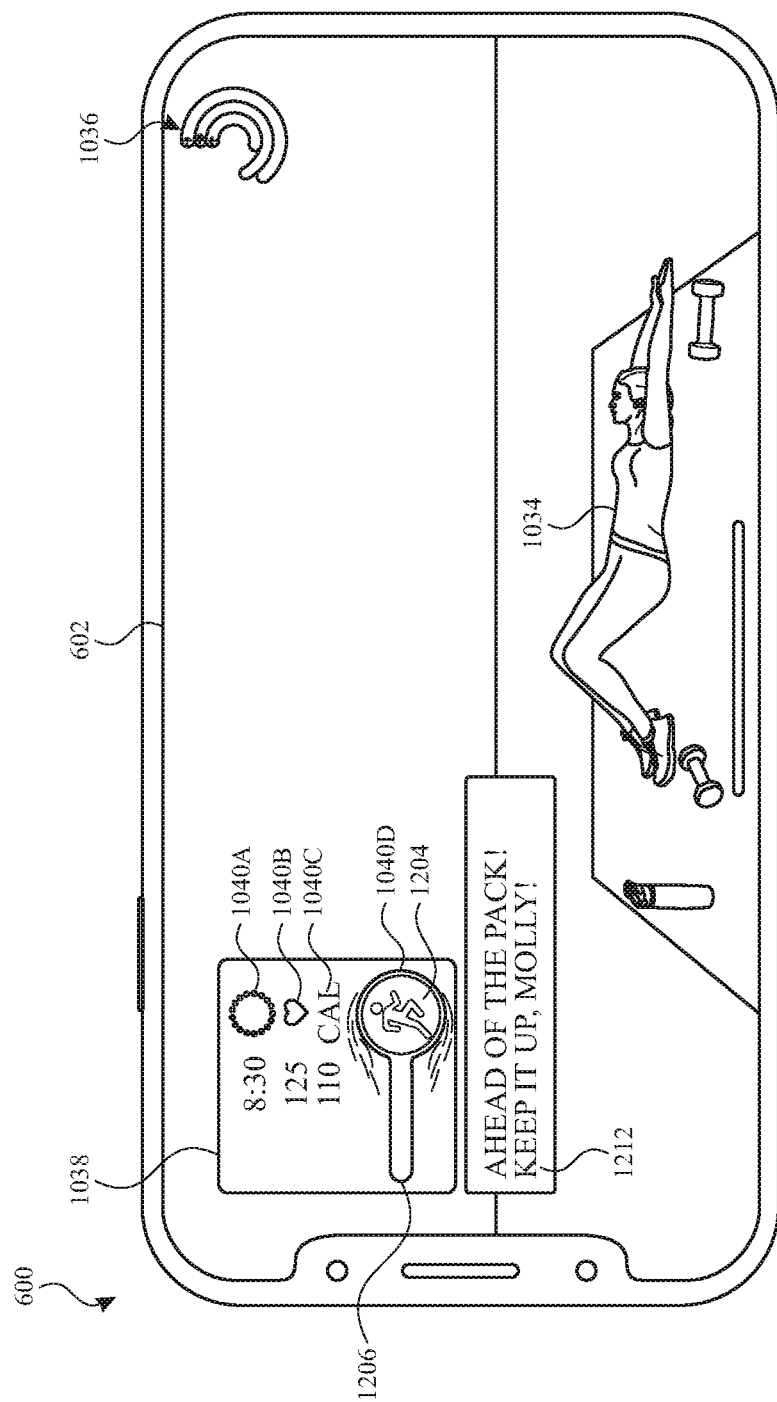

At FIG. 12J, electronic device 600 determines that the user's physical activity satisfies one or more workout intensity thresholds associated with the top workout intensity group. Based on this determination, electronic device 600 initiates a visual indication that the user is moving to a higher workout intensity group. The visual indication can once again include enlarging the icon 1204, translating the icon to the right towards a right-most position associated with the top group, and presenting a notification 1212 (shown in FIG. 12K).

Figure 12L:
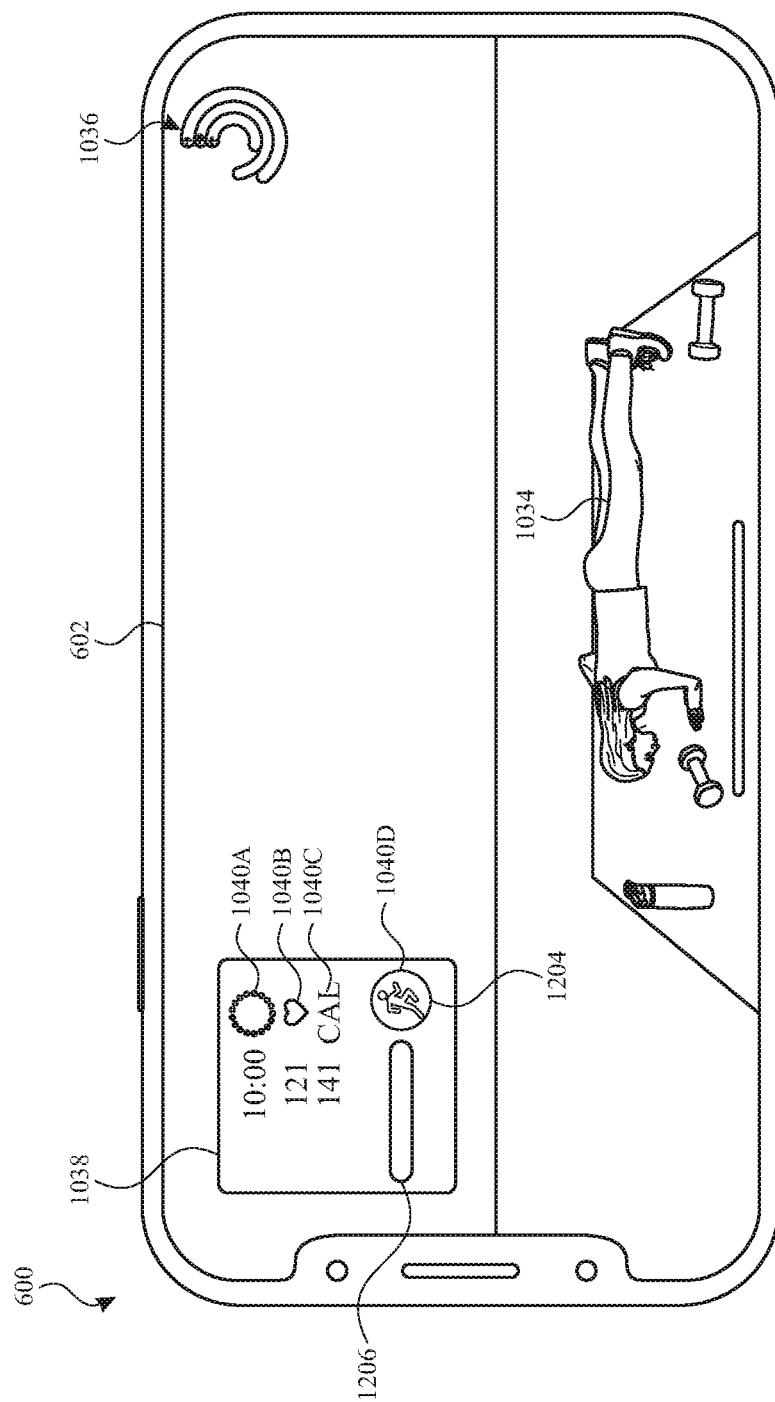

At FIG. 12L, the icon 1204 has reached a right-most position associated with the top group of users. The icon 1204 returns to its smaller size and is presented at the right-most position associated with the top tier of users.

Figure 12M:
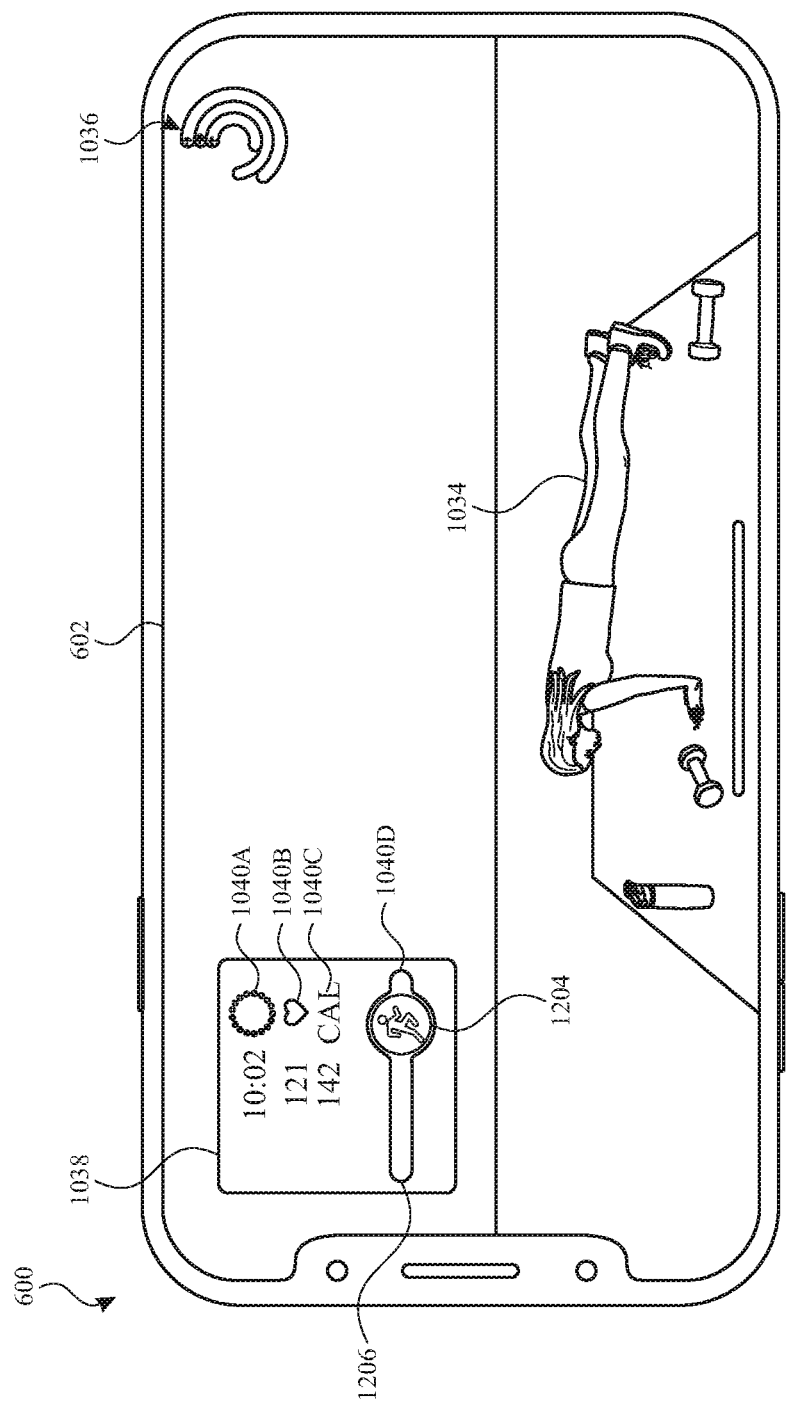

At FIG. 12M, electronic device 600 determines that the user's physical activity no longer satisfies the one or more workout intensity thresholds associated with the top group of users. Based on this determination, electronic device 600 initiates a visual indication that the user is moving to a lower workout intensity group. The visual indication can include translating the icon 1204 to the left towards a center-right position along the bar 1206 associated with the second workout intensity group. In some embodiments, including the depicted embodiment, moving the icon to a position on the bar 1206 associated with a lower group does not result in enlarging the icon 1204 or presenting an additional notification (other than translating the icon 1204). However, in other embodiments, additional, fewer, or different visual indications can be used.

Figure 12N:
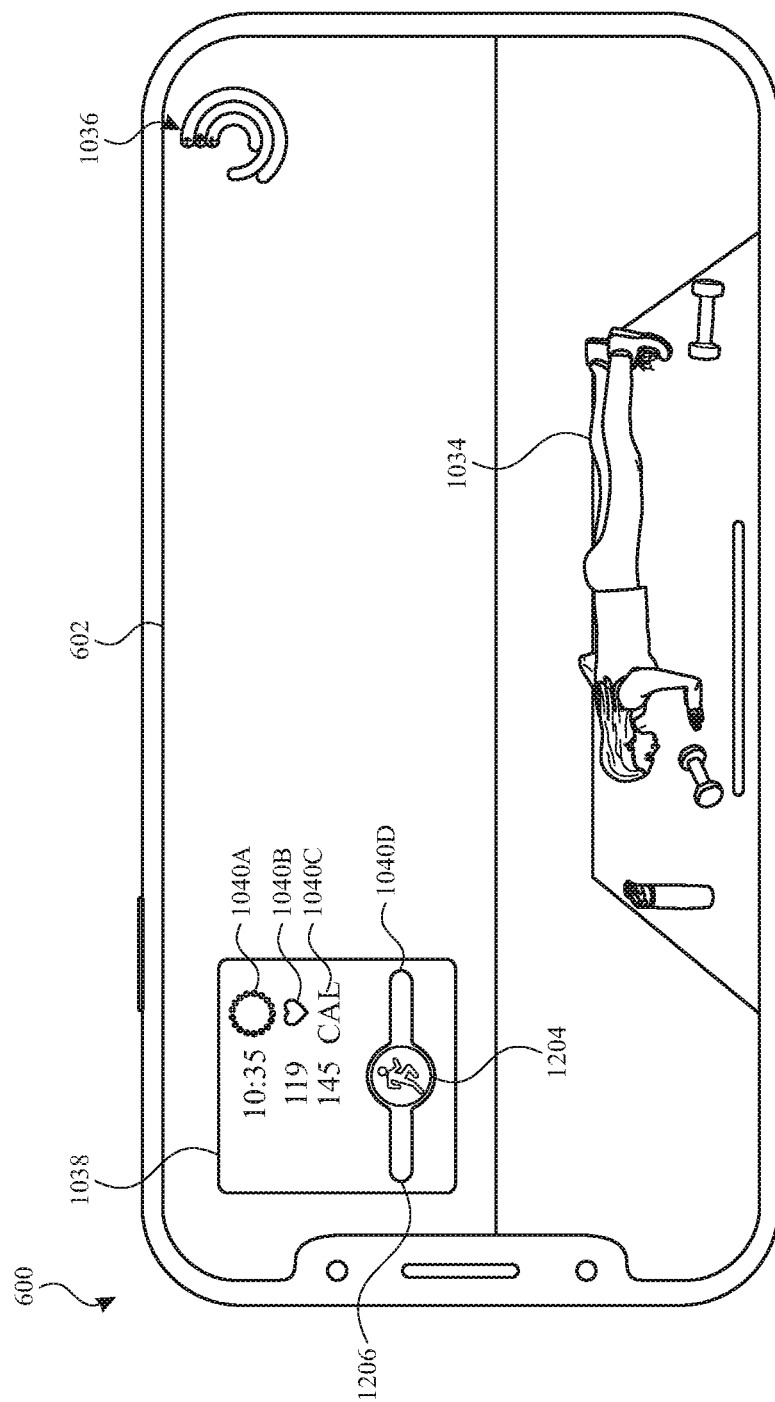
Figure 12O:
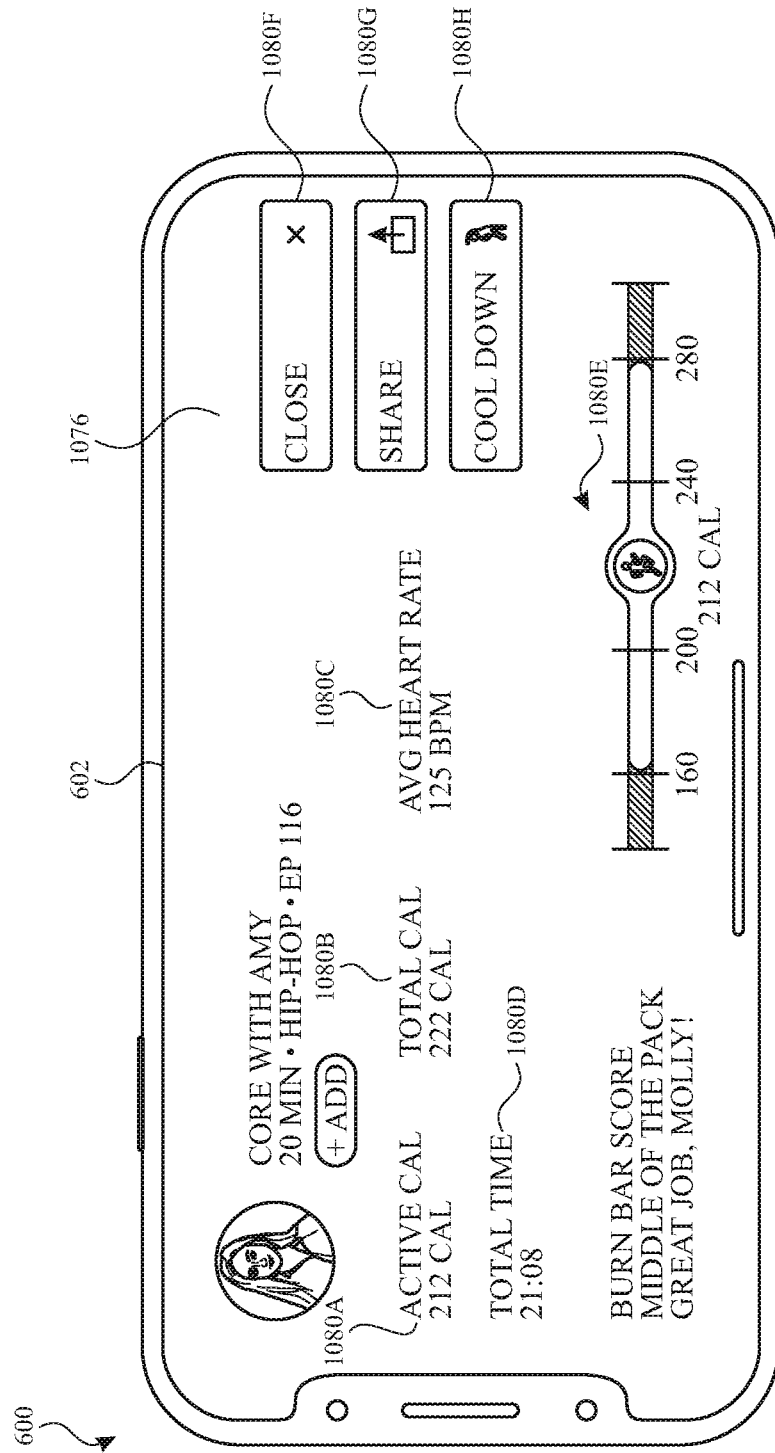

At FIG. 12N, the electronic device 600 determines that the user's physical activity does not satisfy the one or more workout intensity thresholds associated with the second group of users. Based on this determination, electronic device 600 continues to translate the icon 1204 to the left to a position on the bar 1206 associated with the third workout intensity group (in this case, a center position on the bar 1206).

At FIG. 12O, the electronic device 600 detects that the workout session has concluded. In response to detecting that the workout session has concluded, the electronic device 600 replaces display of the workout session user interface 1030 with a workout summary user interface 1076. The workout summary user interface 1076 optionally displays calorie information for the workout session (e.g., active calorie information 1080A, total calorie information 1080B), heart rate information for the workout session (e.g., average heart rate 1080C), duration information for the workout session (e.g., total time 1080D), and information pertaining to the user's performance relative to other users (e.g., workout intensity information 1080E). The workout intensity information 1080E demonstrates multiple, e.g., five, different groups or tiers of users based on active calories burned for the workout, with a lowest tier of users that burned fewer than 160 active calories, a second tier of users that burned between 160 and 200 active calories, a third tier of users that burned between 200 and 240 active calories, a fourth tier of users that burned between 240 and 280 active calories, and a fifth tier of users that burned more than 280 active calories. The workout intensity information 1080E indicates that the user has burned 212 active calories, placing the user in the third tier or group of users.

The workout summary user interface 1076 also includes an option 1080F to close the workout summary user interface, an option 1080G to share workout summary information, and an option 1080H to select a cool down workout.

FIG. 13 is a flow diagram illustrating a method for displaying video content and providing workout information relating to the video content using an electronic device in accordance with some embodiments. Method 1300 is performed at a device (e.g., 100, 300, 500, 600) with a display (e.g., 602). Some operations in method 1300 are, optionally, combined, the orders of some operations are, optionally, changed, and some operations are, optionally, omitted.

As described below, method 1300 provides an intuitive way for displaying video content and providing workout information relating to the video content. The method reduces the cognitive burden on a user for displaying video content and providing workout information relating to the video content, thereby creating a more efficient human-machine interface. For battery-operated computing devices, enabling a user to display video content and provide workout information relating to the video content faster and more efficiently conserves power and increases the time between battery charges.

In some embodiments, the electronic device (e.g., 100, 300, 500, 600, 800) is a computer system. The computer system is optionally in communication (e.g., wired communication, wireless communication) with a display generation component and with one or more input devices. The display generation component is configured to provide visual output, such as display via a CRT display, display via an LED display, or display via image projection. In some embodiments, the display generation component is integrated with the computer system. In some embodiments, the display generation component is separate from the computer system. The one or more input devices are configured to receive input, such as a touch-sensitive surface receiving user input. In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

The electronic device causes concurrent display (1302), via a display device, of (e.g., a display device of an electronic device (e.g., display 602 or electronic device 600), a display device of or in communication with an external device (e.g., television, set top box)): video content (e.g., 1034, a workout video); and a workout intensity representation (e.g., 1040D, bar and/or user icon). In some embodiments, the workout intensity representation has a visual characteristic (e.g., size, location/position, color, numerical values, and/or textual characters) based on (e.g., that varies based on) a comparison between a physical activity metric (e.g., active calories, heart rate, distanced traveled, and/or stairs climbed) for a user of the electronic device that corresponds to a first playback position of the video content (e.g., a current playback position of the video content at a first time) and the physical activity metric for a group of users who participated in a workout while watching the video content based on the physical activity of the group of users that corresponds to the first playback position of the video content (1304). Causing concurrent display of video content and a workout intensity representation provides the user with feedback about the physical activity metrics and other information recorded by the electronic device. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the physical activity metric is based on (e.g., corresponds to) data captured by one or more sensors of an external device (e.g., GPS, accelerometer, gyroscope, and/or heart rate). In some embodiments, the correspondence between the physical activity metric (for the user or group of users) and the first playback position is precise (e.g., second by second accuracy). For example, the physical activity metric is a real-time representation of physical activity at the first playback position. In some embodiments, the correspondence between the physical activity metric (for the user or group of users) and the first playback position is less precise (e.g., 30 second, 1 minute, or 5 minute intervals). For example, the physical activity metric is a representation of physical activity that is updated at predefined intervals. In some embodiments, the workout intensity representation corresponds to a plurality of workout intensity levels (e.g., optionally indicated by tick marks on a bar) based on a physical activity metric. In some embodiments, the workout intensity representation indicates that a user of the electronic device is in a first workout intensity level of the plurality of workout intensity levels. In some embodiments, the physical activity metric for the group of users corresponds to historical data for the group of users (e.g., data captured prior to the start of the current workout). In some embodiments, the physical activity metric for the group of users corresponds to current data for the group of users (e.g., data captured during the current workout). In some embodiments, the physical activity metric for the group of users corresponds to a combination of historical and current data. In some embodiments, the intensity representation includes a bar (e.g., 1206, horizontal or vertical) and a user icon (e.g., 1204) displayed at a location relative to the bar. In some embodiments, the user icon corresponds to a user of the electronic device. In some embodiments, the location of the user icon relative to the bar indicates an intensity level of the user of the electronic device relative to the group of users. In some embodiments, the intensity representation includes numerical value(s), textual character(s), or a combination thereof. In some embodiments, the intensity representation does not include textual characters or numerical values. For example, the intensity representation is a pictorial and/or graphical representation without textual characters or numerical values. In some embodiments, the intensity representation is displayed while workout video content is displayed. In some embodiments, the intensity representation is overlaid on the workout video content. In some embodiments, the user icon is displayed on the same axis as the bar. In some embodiments, the user icon changes depending on the type of workout being performed by the user. For example, the user icon can have an animated figure that appears to be running. As another example, the user icon can have an animated figure that appears to be rowing. In some embodiments, a second electronic device (e.g., different from the electronic device) also displays a workout intensity representation, where the workout intensity representation has a visual characteristic based on a comparison between a physical activity metric for a user of the second electronic device and the physical activity metric for a group of users (e.g., including the user of the electronic device). In some embodiments, the physical activity metric for the group of users is updated to include data (e.g., anonymized data) corresponding to the user of the electronic device after the user completes the workout.)

In some embodiments, after the video has advanced from the first playback position to a second playback position (1308), the electronic device receives (1310) activity data corresponding to the physical activity metric for the user. In some embodiments, the electronic device also receives activity data corresponding to the physical activity metric for the group of users.

In some embodiments, in response to receiving the activity data (1312), the electronic device causes display (1314), via the display device, of the workout intensity representation with the visual characteristic of the workout intensity representation changed based on the received activity data and based on (e.g., that varies based on) a comparison between the physical activity metric (e.g., active calories, heart rate, distanced traveled, and/or stairs climbed) for the user of the electronic device that corresponds to the second playback position of the video content and the physical activity metric for a group of users that corresponds to the second playback position of the video content. Causing display of the workout intensity representation with the visual characteristic of the workout intensity representation changed based on the received activity data provides the user with updated feedback about physical activity metrics and other information recorded by the electronic device. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in response to receiving the activity data: in accordance with a determination that the activity data corresponds to an increased intensity level of the user relative to the group of users, the electronic device moves the user icon in a first direction along the bar of the intensity representation (e.g., as depicted in FIGS. 12F-12I). In some embodiments, in response to receiving the activity data: in accordance with a determination that the activity data corresponds to a decreased intensity level of the user relative to the group of users, the electronic device moves the user icon in a second direction opposite the first direction along the bar of the intensity representation (e.g., as depicted in FIGS. 12L-12N). In some embodiments, in accordance with a determination that the activity data does not correspond to a change in intensity level of the user relative to the group of users, the electronic device maintains the location of the user icon along the bar of the intensity representation. In some embodiments, instead of moving the user icon, the electronic device changes numerical value(s) and/or textual character(s) to reflect the change in intensity level, as indicated by the received activity data. For example, a numerical value increases in response to the device receiving activity data corresponding to an increased intensity level. As another example, a numerical value decreases in response to the device receiving activity data corresponding to a decreased intensity level.

In some embodiments, the physical activity metric for the user corresponds to a representation of calories burned by the user (1306) (e.g., calories burned during the duration of the video content or a predetermined portion thereof). In some embodiments, the cumulative calories metric applies to a certain type of workout (e.g., workouts where a threshold amount of calories is expected to be burned (e.g., high intensity interval training (HIIT), treadmill, rowing, cycling)).

In some embodiments, the workout intensity representation (e.g., 1040D, 1204, 1206) corresponds to a predetermined number (e.g., 3, 5, 7) of workout intensity levels (e.g., zones) based on the physical activity metric for the group of users, including a first workout intensity level and a second workout intensity level. In some embodiments, the first workout intensity level indicates that the physical activity metric for the user is within a predetermined subset of a range (e.g., in the pack, a particular intensity level) corresponding to the physical activity metric for the group of users. In some embodiments, the second workout intensity level indicates that the physical activity metric for the user is not within the predetermined subset of the range (e.g., not in the pack (e.g., behind or ahead of the pack), not in the particular intensity level) corresponding to the physical activity metric for the group of users. In some embodiments, the first workout intensity level indicates a higher value for the physical activity metric for the user as compared to the second workout intensity level. In some embodiments, the second workout intensity level indicates a higher value for the physical activity metric for the user as compared to the first workout intensity level. In some embodiments, the "pack" consists of more than one workout intensity level and less than the predetermined number of workout intensity levels.

In some embodiments, in accordance with a determination that the physical activity metric for the user corresponds to an imminent change in workout intensity levels from the first workout intensity level to the second workout intensity level (e.g., the physical activity metric corresponds to being above a threshold value for the first workout intensity level), the electronic device causes display, via the display device, of a prompt (e.g., 1210, encouragement for the user to continue to move or to increase their movement) for the user to cause a change in workout intensity levels from the first workout intensity level to the second workout intensity level. Causing display of a prompt for the user in accordance with a determination that the physical activity metric for the user corresponds to an imminent change in workout intensity levels provides the user with feedback about the current state of the device (e.g., that the device has detected an imminent change in the user's workout intensity level). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in accordance with a determination that the user of the electronic device is at the first workout intensity level, the workout intensity representation with the changed visual characteristic indicates that the user is at the first workout intensity level (e.g., in the pack). In some embodiments, in accordance with a determination that the user of the electronic device is at the second workout intensity level, the workout intensity representation with the changed visual characteristic indicates that the user is at the second workout intensity level (e.g., not in the pack, ahead of the pack, behind the pack).

In some embodiments, in accordance with a determination that the physical activity metric for the user corresponds to an increase by at least a (e.g., predetermined) threshold amount relative to the physical activity metric for the group of users, the electronic device causes display, via the display device, of a first indication (e.g., 1208, 1212, text, graphic, and/or pictorial illustration) that the physical activity metric for the user corresponds to an increase relative to the physical activity metric for the group of users, wherein the first indication is different from the workout intensity representation. In some embodiments, the first indication is concurrently displayed with the workout intensity representation that has the changed visual characteristic. In some embodiments, the first indication is displayed while the workout intensity representation indicates a change from a lower workout intensity level to a higher workout intensity level. Causing display of an indication in accordance with a determination that the physical activity metric for the user corresponds to an increase by at least a threshold amount relative to the physical activity metric for a group of users provides the user with feedback about the current state of the device (e.g., that the device has detected that the physical activity metric for the user corresponds to an increase by a threshold amount relative to the physical activity metric for the group of users). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in accordance with a determination that the physical activity metric for the user corresponds to a decrease by at least a (e.g., predetermined) threshold amount relative to the physical activity metric for the group of users, the workout intensity representation with the changed visual characteristic is displayed without causing display of a second indication (e.g., text, graphic, and/or pictorial illustration) that the physical activity metric for the user corresponds to a decrease relative to the physical activity metric for the group of users (e.g., as depicted in FIGS. 12L-N). In some embodiments, in accordance with a determination that the physical activity metric for the user corresponds to a decrease by at least a (e.g., predetermined) threshold amount relative to the physical activity metric for the group of users, the workout intensity representation with the changed visual characteristic is displayed without causing display of any indication that the physical activity metric for the user corresponds to a decrease relative to the physical activity metric for the group of users. In some embodiments, the workout intensity representation indicates a change from a higher workout intensity level to a lower workout intensity level. Causing display of an indication in accordance with a determination that the physical activity metric for the user corresponds to a decrease by at least a threshold amount relative to the physical activity metric for a group of users provides the user with feedback about the current state of the device (e.g., that the device has detected that the physical activity metric for the user corresponds to a decrease by a threshold amount relative to the physical activity metric for the group of users). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in accordance with a determination that the physical activity metric for the user corresponds to change that is below a (e.g., predetermined) threshold amount for at least a predetermined amount of time, the electronic device visually modifies (e.g., shrinking the size of, minimizing, ceasing to display) the workout intensity representation.

In some embodiments, the user and the group of users share one or more characteristics (e.g., fitness level, demographics such as a range of ages, sex, weight), and the workout intensity representation is based on the shared one or more characteristics. In some embodiments, one or more users that do not share the one or more characteristics with the user are excluded. In some embodiments, the group of users (e.g., the data representing physical activity of the group of users) is normalized based on the fitness level and/or demographics of the user.

In some embodiments, the video content is initially displayed without causing display of the workout intensity representation, and the workout intensity representation is initially displayed with the video content in accordance with a determination that a predetermined amount of time has elapsed (e.g., as depicted in FIG. 12F).

In some embodiments, the video content is initially displayed with the workout intensity representation, where the workout intensity representation is in an unresolved state (e.g., as depicted in FIGS. 12A-E). In some embodiments, the unresolved state includes changing the displayed position of a user icon (representing the user) from a first position corresponding to a first workout intensity level to a second position corresponding to a second workout intensity level. In some embodiments, the electronic device repeatedly changes/cycles the displayed position of the user icon in a predefined manner. In some embodiments, in accordance with a determination that a sufficient amount of activity data for the user has been received (e.g. obtained), the electronic device causes display of the user icon at a particular position corresponding to a workout intensity level without repeatedly changing/cycling the displayed position of the user icon in the predefined manner.

Note that details of the processes described above with respect to method 1300 (e.g., FIG. 13) are also applicable in an analogous manner to the methods described above. For example, method 1300 optionally includes one or more of the characteristics of the various methods described above with reference to method 1100. For example, the workout intensity representation can be included in the physical activity metrics described above with reference to method 1100. For brevity, these details are not repeated below.

FIGS. 14A-14R illustrate exemplary user interfaces for coordinating display of workout content among multiple devices, in accordance with some embodiments. The user interfaces in these figures are used to illustrate the processes described below, including the processes in FIG. 15.

FIG. 14A depicts electronic device 600, which is a smartphone with display 602. Display 602 of electronic device 600 includes a touch-sensitive surface on which electronic device 600 can detect user gestures (e.g., tap, swipe, and/or drag). In some embodiments, electronic device 600 includes one or more features of electronic device 100, 300, and/or 500.

FIG. 14A also depicts electronic device 800, which is a smartwatch with display 801. In some embodiments, electronic device 800 is in communication with electronic device 600 (e.g., electronic device 800 is wirelessly paired with electronic device 600). In some embodiments, electronic device 800 communicates (e.g., transmits/receives data) with external devices via electronic device 600. In some embodiments, electronic device 800 transmits data representing physical activity of the user to electronic device 600, and vice-versa. Display 801 of electronic device 800 includes a touch-sensitive surface on which electronic device 800 can detect user gestures (e.g., tap, swipe, drag). In some embodiments, electronic device 800 includes one or more features of electronic device 100, 300, and/or 500.

FIG. 14A further depicts electronic device 1400, which is a television with display 1401. In some embodiments, electronic device 1400 is in communication with, or is capable of being in communication with electronic device 600. For example, electronic device 600 optionally transmits data representing displayed content to electronic device 1400. In some embodiments, electronic device 1400 is a set top box or a streaming device instead of a television. In some embodiments, electronic device 1400 displays content via display 1401, which is integrated as part of the television. In some embodiments, electronic device 1400 displays content via a display that is external to electronic device 1400. In some embodiments, electronic device 1400 is paired with a physical remote that can be used to operate electronic device 1400. In some embodiments, each of the devices (e.g., 600, 800, 1400) are signed into the same account (e.g., an account associated with a user that enables the user to access features/functions that are otherwise limited without the account). At FIG. 14A, electronic device 600 displays detail user interface 620, as discussed above with respect to FIG. 6D. Electronic device 800 displays activity user interface 1002, as discussed above with respect to FIG. 10A. Electronic device 1400 is not yet displaying workout (e.g., content associated with the workout represented in detail user interface 620). While displaying detail user interface 620, electronic device 600 detects input 1406 at a location corresponding to option 1404.

Figure 14B:
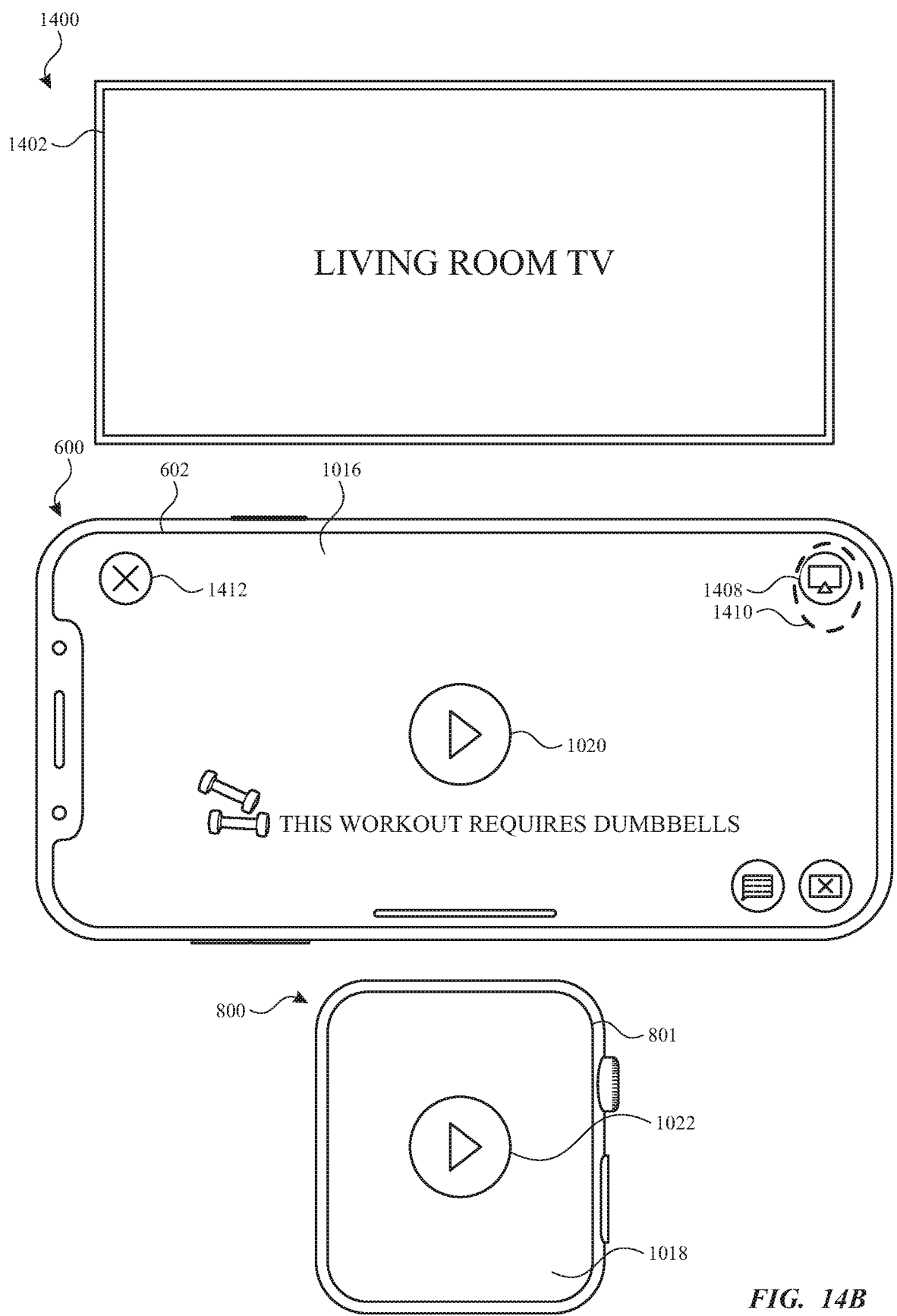

At FIG. 14B, in response to detecting input 1406, electronic device 600 initiates a process for playing workout content, including replacing display of detail user interface 620 with workout start user interface 1016, as discussed above with respect to FIG. 10B. Workout start user interface 1016 includes exit option 1412 which, when selected, causes electronic device 600 to return to displaying a previously displayed user interface. Additionally, in response to detecting input, electronic device 600 causes electronic device 800 to replace display of activity user interface 1002 with workout start user interface 1018. Workout start user interface 1016 includes play button 1020 and workout start user interface 1018 includes play button 1022, as discussed above with respect to FIG. 10B. Electronic device 1400 is still not displaying workout content. While displaying workout start user interface 1016, electronic device 600 detects input 1410 at a location corresponding to option 1408.

Figure 14C:
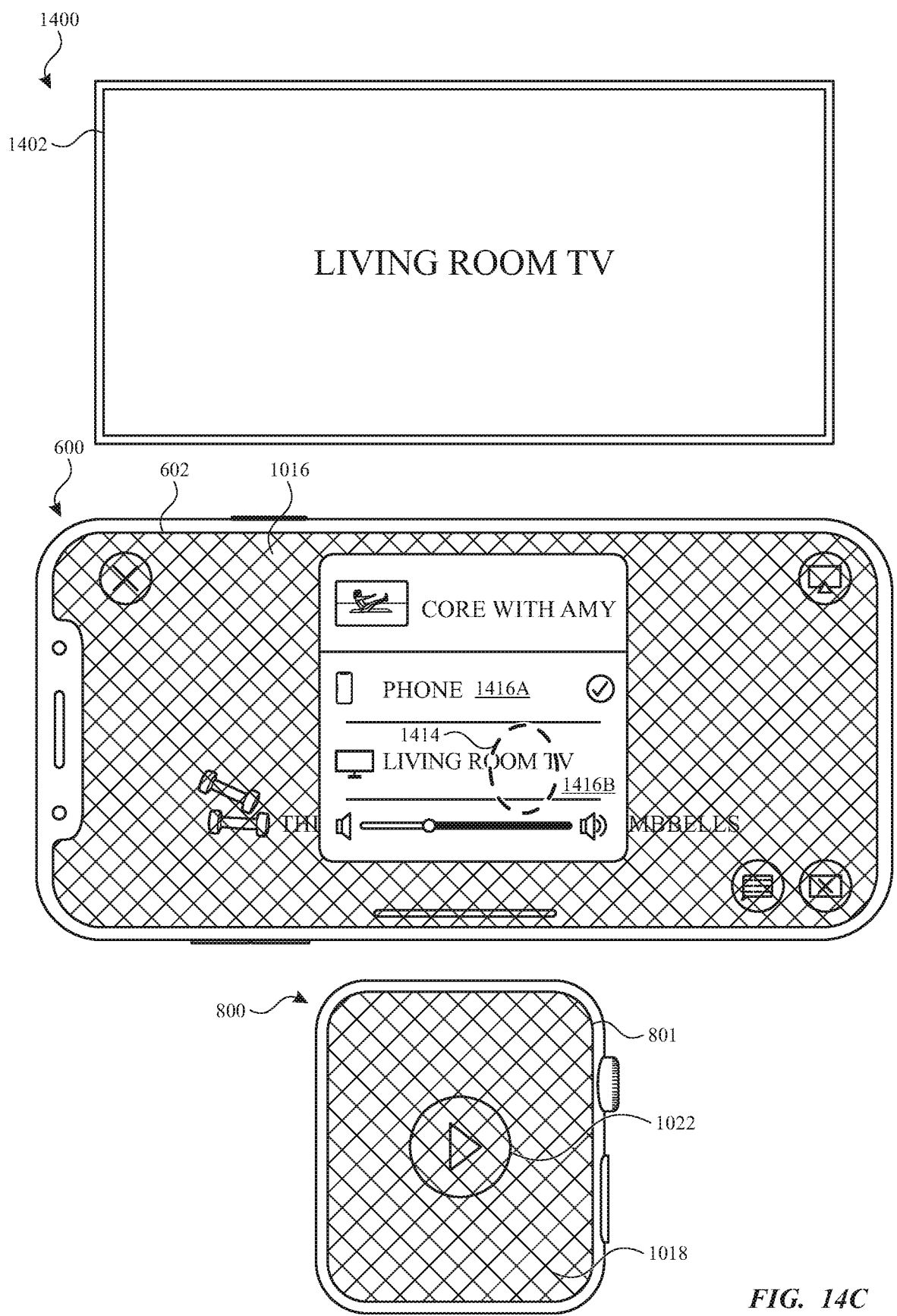

At FIG. 14C, in response to detecting input 1410, electronic device 600 initiates a process for playing workout content at a device other than electronic device 600, such as electronic device 1400, including displaying options 1416A-1416B for configuring which device displays the workout content. As shown in FIG. 14C, electronic device 600 provides device options for the user to select. As indicated by the check mark, the phone (e.g., 600) is currently configured to display the workout content. Option 1416B provides a user with the option to configure the living room TV (e.g., 1400) to display the workout content instead of the phone. In response to detecting input 1410, electronic device 600 de-emphasizes workout start user interface 1016. In response to detecting input 1410, electronic device 600 causes electronic device 600 to de-emphasize workout start user interface 1018 (e.g., causing play button 1022 to not be selectable). Electronic device 1400 is still not displaying workout content. While displaying options 1416A-1416B, electronic device 600 detects input 1414 at a location corresponding to 1416B.

Figure 14D:
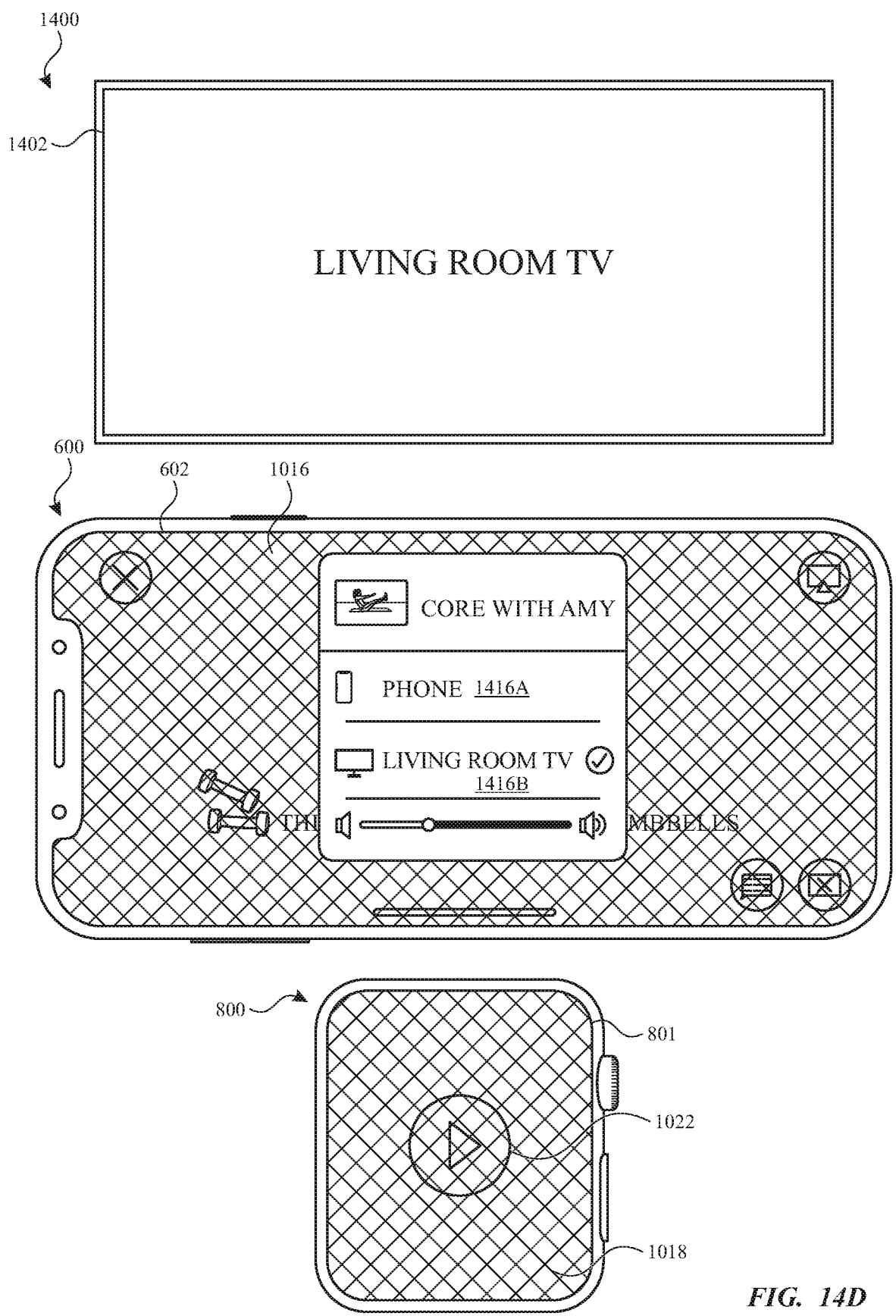

At FIG. 14D, in response to detecting input 1414, electronic device 600 initiates a process for displaying workout content at electronic device 1400 (e.g., corresponding to option 1416B). In accordance with a determination that electronic device 1400 has been successfully configured to display the workout content, electronic device 600 displays a visual indication next to option 1416B (e.g., check mark)

to indicate that electronic device 1400 has been successfully configured. Electronic device 1400 is still not displaying workout content.

Figure 14E:
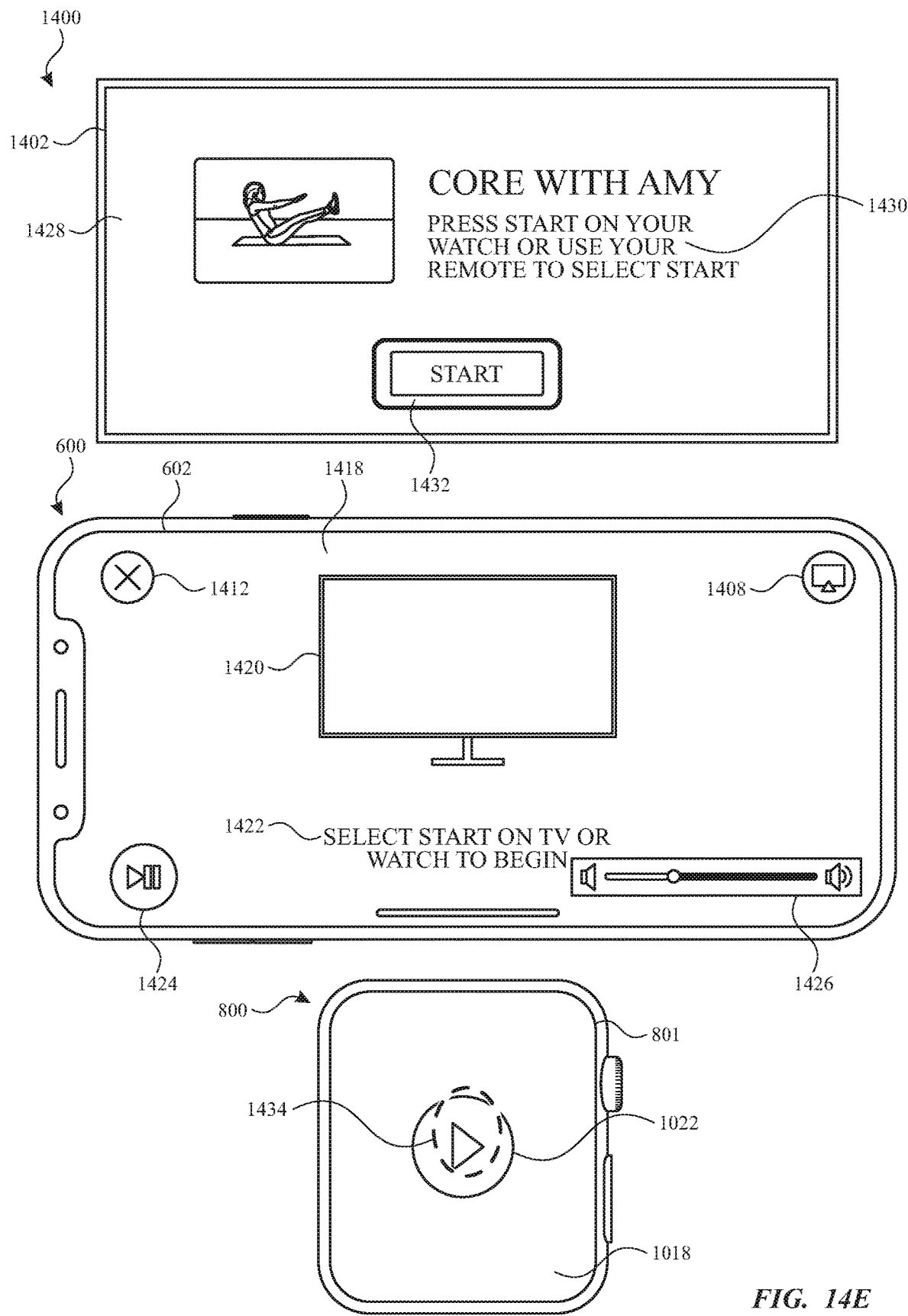

At FIG. 14E, in response to detecting input 1414 (e.g., and after displaying the visual indication), electronic device 600 replaces display of options 1416A-1416B (e.g., and deemphasized workout start user interface 1016) with status user interface 1418. Status user interface 1418 includes representation 1420, which indicates that electronic device 1400 is configured to display the workout content. Status user interface 1418 includes prompt 1422, which prompts the user to start the workout using electronic device 800 or electronic device 1400. Status user interface 1418 also includes play/pause button 1424 and volume controls 1426.

Further in response to detecting input 1414, electronic device 600 causes electronic device 1400 to display workout start user interface 1428. Workout start user interface includes prompt 1430, which prompts the user to start the workout using electronic device 800 or electronic device 1400. Workout start user interface 1428 includes option 1432 which, when selected, causes electronic device 1400 to display workout content.

Further in response to detecting input 1414, electronic device 600 causes electronic device 800 to cease de-emphasizing workout start user interface 1018. As a result, play button 1022 is selectable. While displaying workout start user interface 1018, electronic device 800 detects input 1434 at a location corresponding to play button 1022. In some embodiments, electronic device 600 detects, via input 1434 at electronic device 800, a request to start playback of the workout content.

Figure 14F:
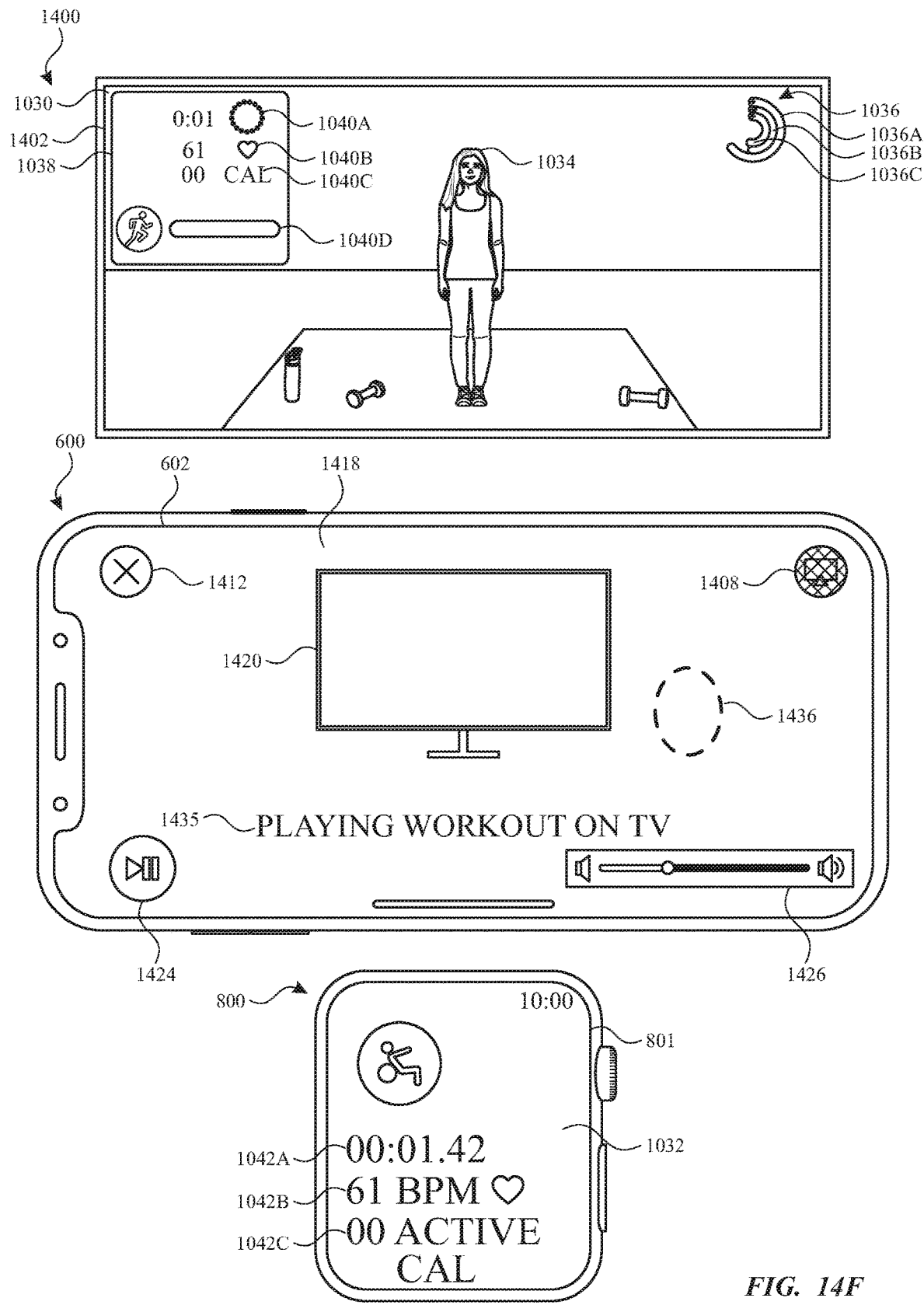

At FIG. 14F, in response to input 1434, electronic device 600 causes electronic device 1400 to display workout session user interface 1030, including video content 1034. Workout session user interface 1030 includes the elements discussed above with respect to FIG. 10D. In some embodiments, in response to detecting input 1434, electronic device 800 transmits first data to electronic device 600 indicating that a request to start playback of the workout content has been made. In some embodiments, in response to receiving the first data from electronic device 800, electronic device 600 transmits second data indicating that a request to start playback of the workout content has been made to electronic device 1400. In some embodiments, in response to receiving the second data, electronic device 1400 displays activity session user interface 1030 with video content 1034. In some embodiments, instead of electronic device 800 transmitting the data to electronic device 600, electronic device 800 transmits the data directly to electronic device 1400 without using electronic device 600 as an intermediary.

Further in response to input 1434, electronic device 800 replaces display of workout start user interface 1018 with display of workout metrics user interface 1032. Workout metrics user interface 1032 includes the elements discussed above with respect to FIG. 10D. In some embodiments, in response to input 1434, electronic device 800 begins recording (e.g., capturing) data corresponding to physical activity of the user. In some embodiments, electronic device 800 records the data via one or more sensors (e.g., GPS, accelerometer, gyroscope, and/or heart rate). Prior to input 1434, the one or more sensors of electronic device 800 are disabled. The one or more sensors are used to capture physical activity of the user. In response to detecting input 1434, electronic device 800 causes the one or more sensors to be enabled so as to improve accurate measurements of the physical activity of the user during the workout.

Further in response to input 1434, electronic device 600 updates status user interface 1418, including replacing prompt 1422 with indication 1435. Indication 1435 indicates that electronic device 1400 is currently displaying the workout content. Additionally, in response to input 1434, electronic device 600 de-emphasizes option 1408 (e.g., causes option 1408 to not be selectable). While displaying status user interface 1418, electronic device 600 detects input 1436 on display 602.

Figure 14G:
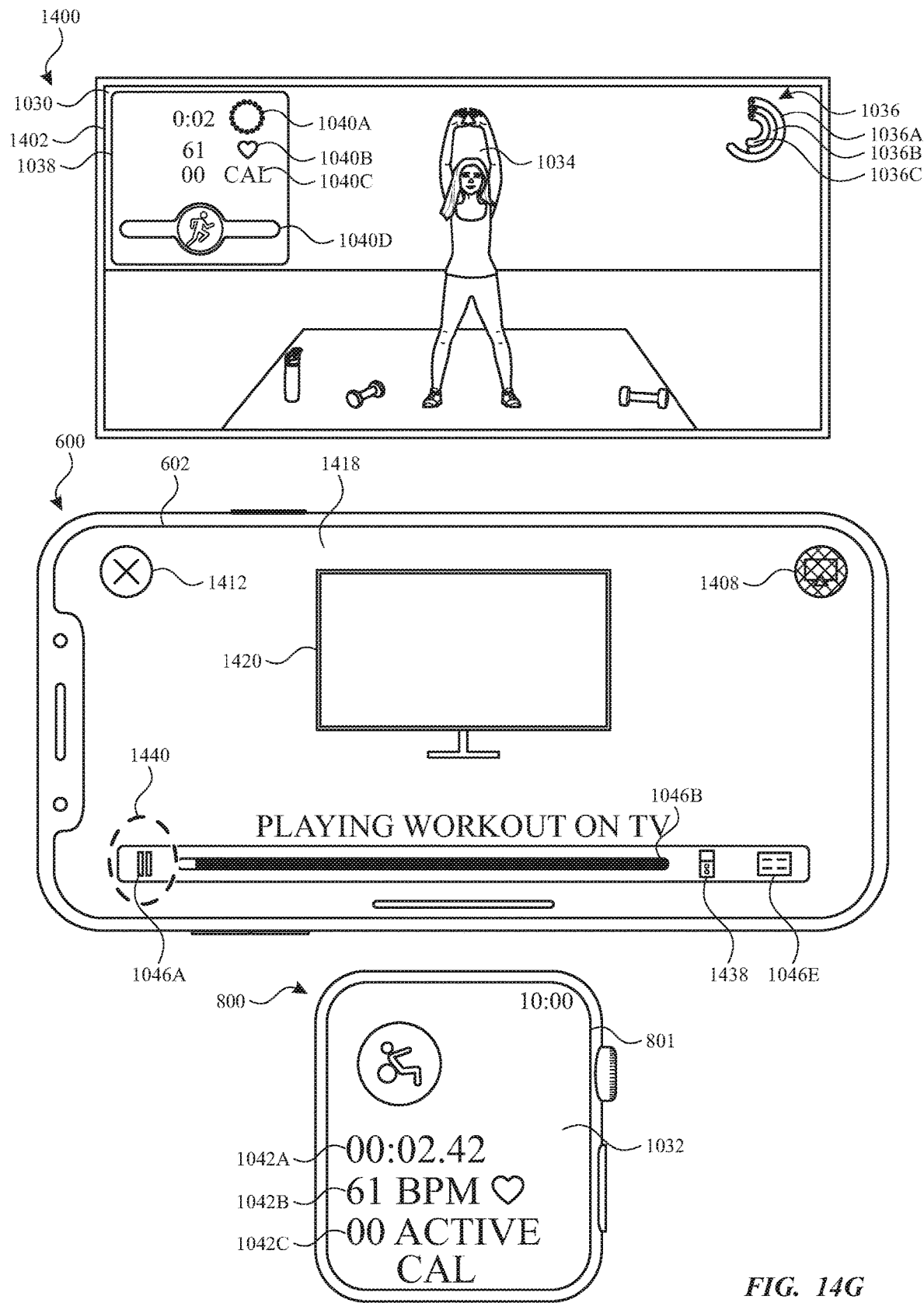

At FIG. 14G, in response to detecting input 1436, electronic device 600 displays a set of playback controls overlaid on status user interface 1418, including play/pause button 1046A, playback progress indicator 1046B, virtual remote 1438, and edit metrics icon 1046E. While displaying the set of playback controls, electronic device 600 detects input 1440 at a location corresponding to play/pause button 1046A.

Figure 14H:
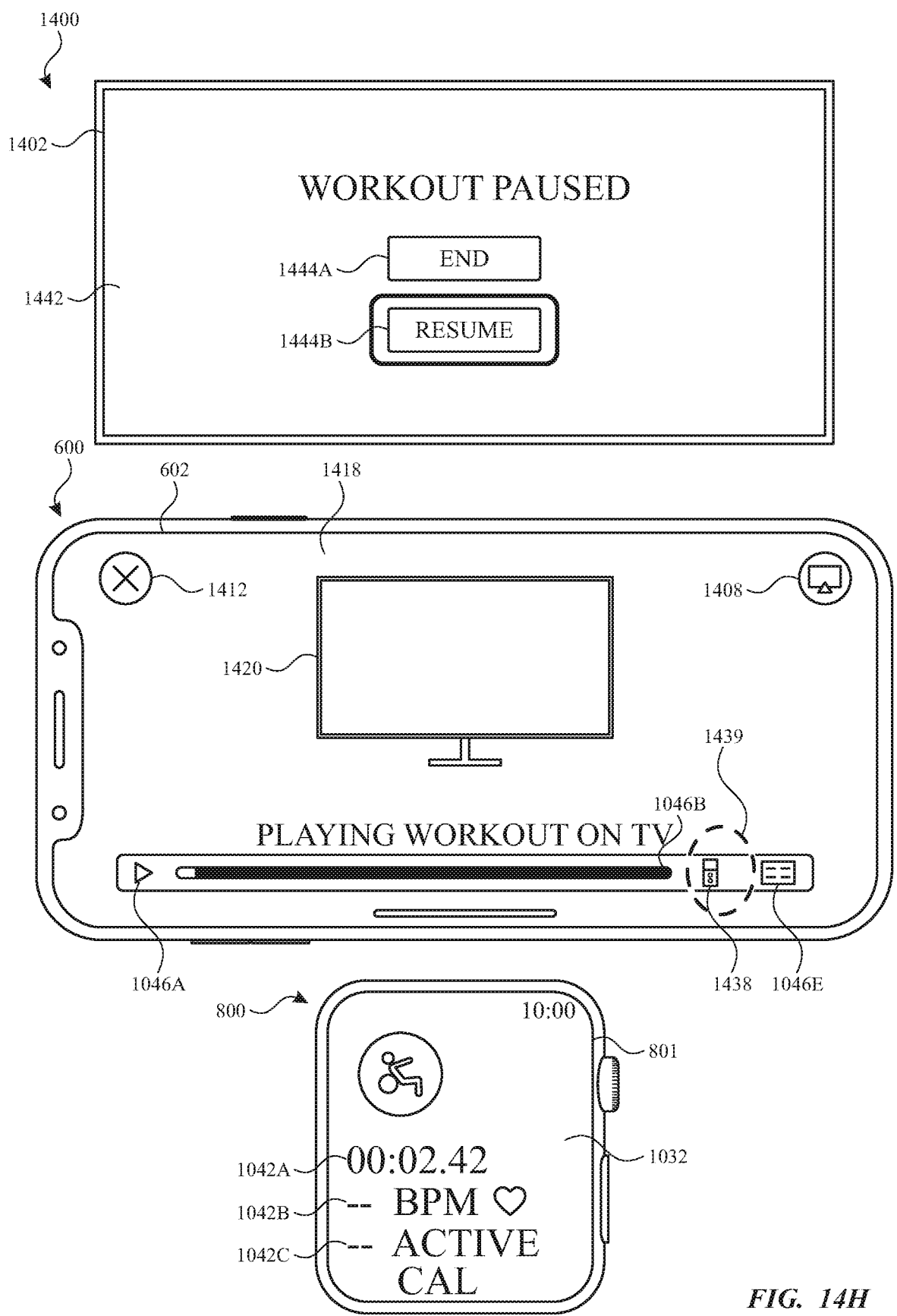

At FIG. 14H, in response to detecting input 1440, electronic device 600 causes electronic device 1400 to replace display of workout session user interface 1030 with display of paused user interface 1442. Further in response to detecting input 1440, electronic device 600 causes electronic device 800 to cease recording (e.g., capturing) data corresponding to physical activity of the user. As a result, electronic device 800 updates workout metrics user interface 1032 to indicate that electronic device 800 is not recording the data. Paused user interface 1442 includes option 1444A that, when selected, ends the current workout session (e.g., displays workout summary user interface 1452 of FIG. 14K). Paused user interface 1442 also includes option 1444B that, when selected, resumes the current workout session (e.g., returns to displaying workout session user interface 1030). In some embodiments, electronic device 1400 detects selection of one of the options (e.g., 1444A-1444B) via an input made at a physical remote paired with electronic device 1400. In some embodiments, electronic device 1400 detects selection via an input made at electronic device 600, as further discussed below. While displaying the set of playback controls overlaid on status user interface 1418, electronic device 600 detects input 1439 at a location corresponding to virtual remote 1438.

Figure 14I:
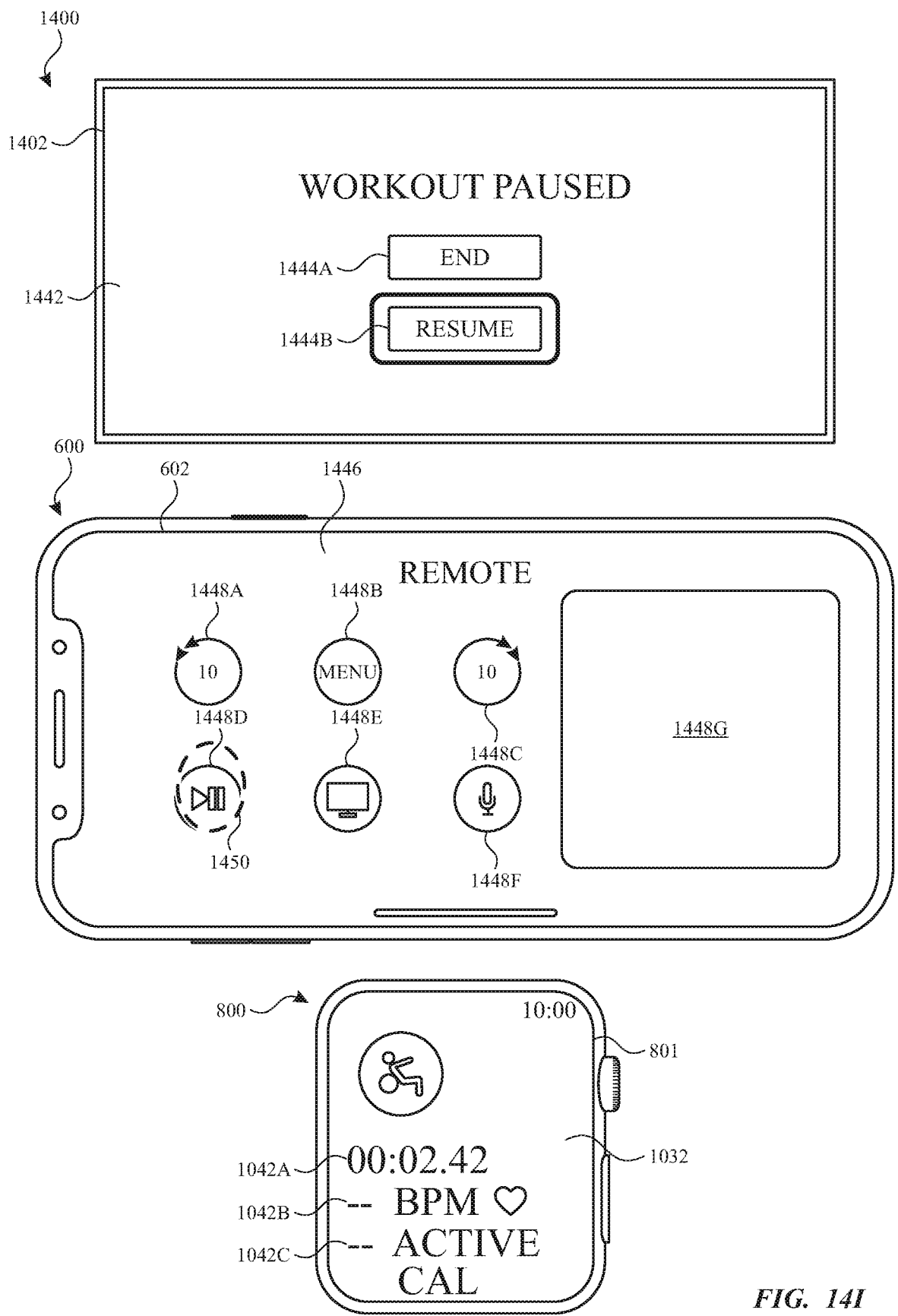

At FIG. 14I, in response to detecting input 1439, electronic device 600 replaces display of status user interface 1418 with display of virtual remote user interface 1446. Virtual remote user interface 1446 includes skip back button 1448A, menu button 1448B, skip forward button 1448C, play/pause button 1448D, screen button 1448E, virtual assistant button 1448F, and virtual trackpad 1448G. While displaying virtual remote user interface 1446, electronic device 600 detects input 1450 at a location corresponding to play/pause button 1448D.

Figure 14J:
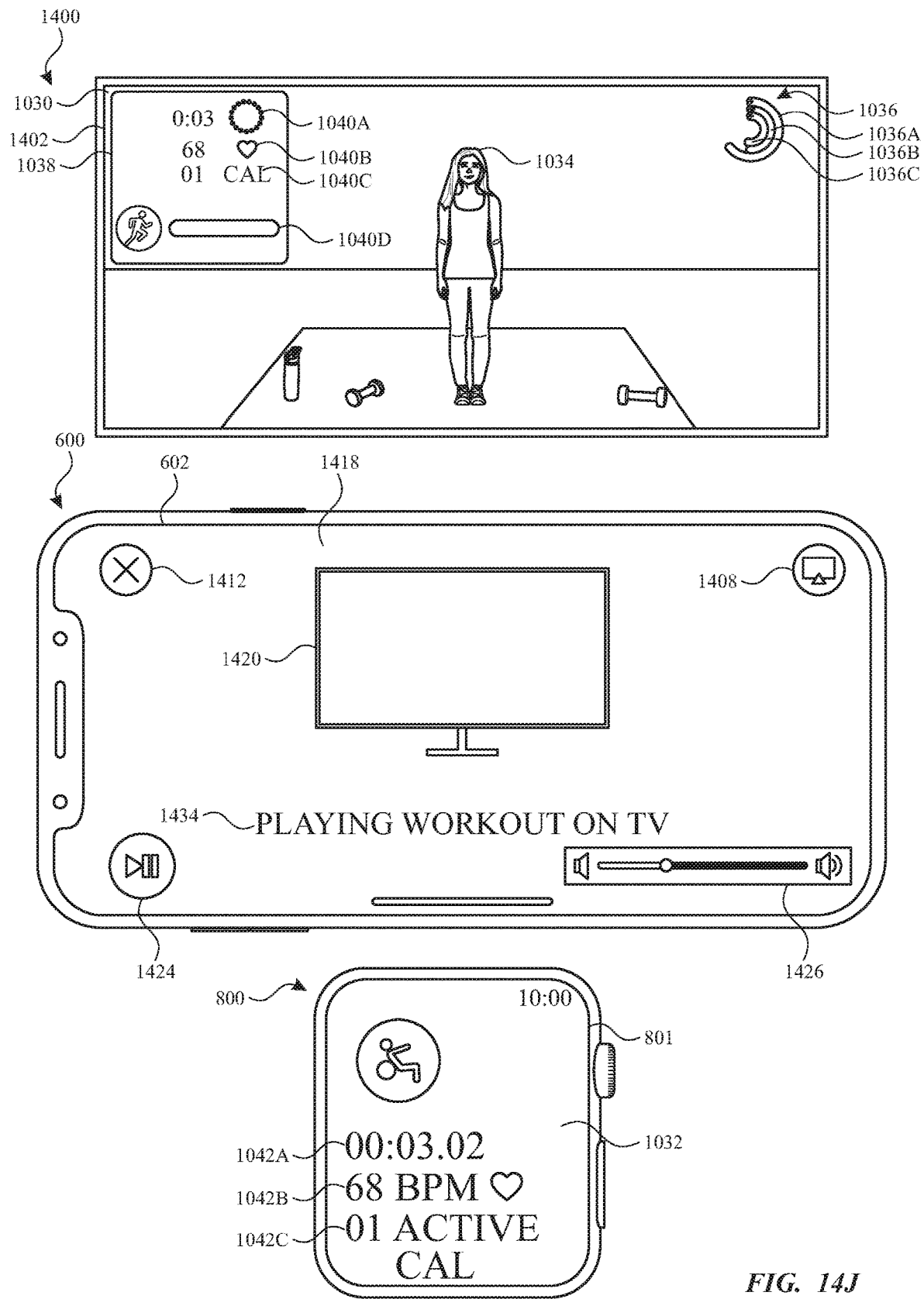

At FIG. 14J, in response to detecting input 1450, electronic device 600 returns to displaying status user interface 1418. Further in response to detecting input 1450, electronic device 600 causes electronic device 1400 to resume the workout session (e.g., return to displaying workout session user interface 1030). Further in response to detecting input 1450, electronic device 600 causes electronic device 800 to resume recording data representing physical activity of the user.

Figure 14K:
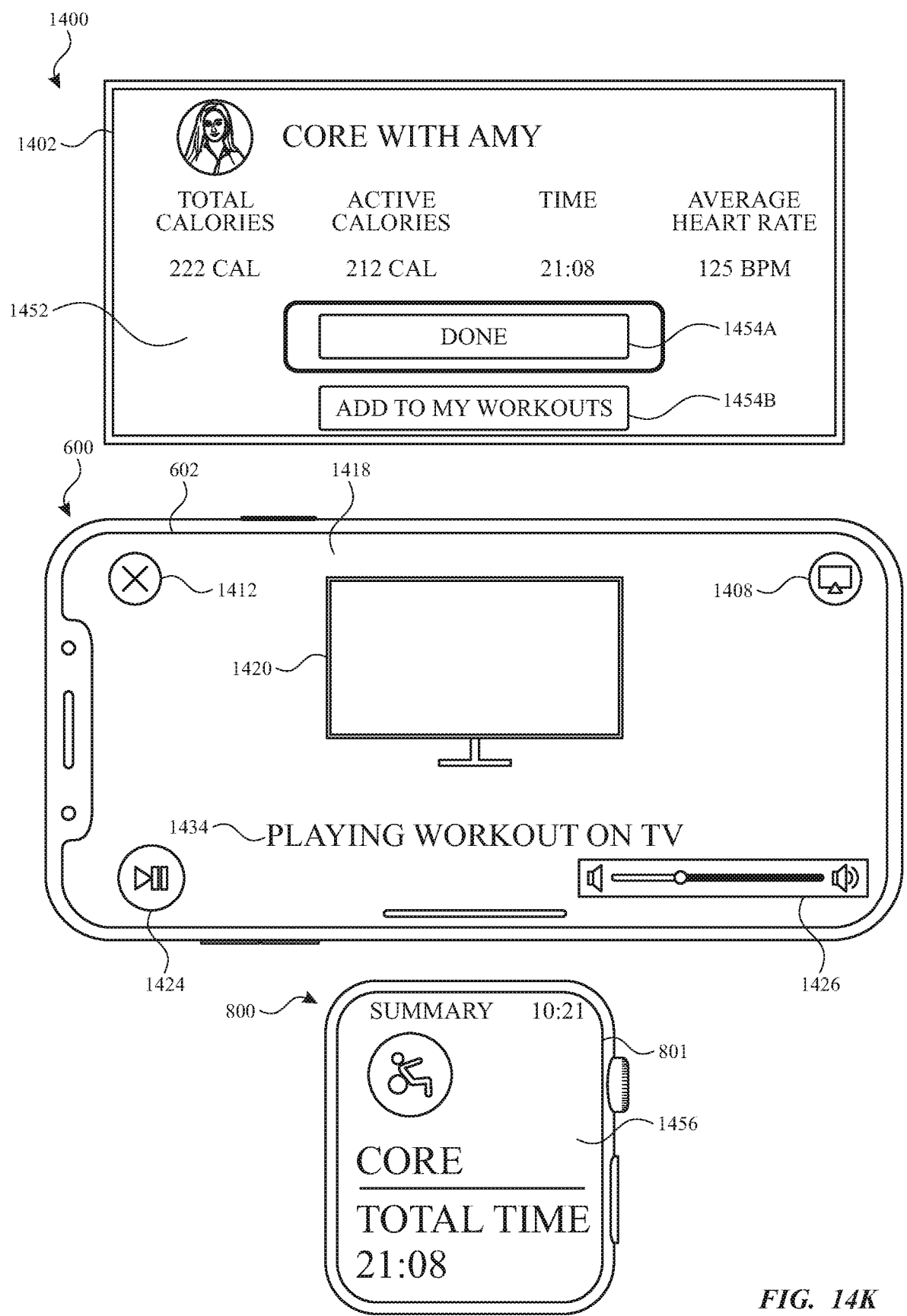

At FIG. 14K, the workout session has completed (e.g., playback of video content 1034 has ended). In accordance with a determination that the workout session has completed, electronic device 800 replaces display of workout metrics user interface 1032 with summary user interface 1456, which includes a set of metrics associated with the workout session. In accordance with a determination that the workout session has completed, electronic device 800 ceases recording data corresponding to physical activity of the user.

In accordance with a determination that the workout session has completed, electronic device 1400 replaces display of workout session user interface 1030 with workout summary user interface 1452. Workout summary user interface 1452 includes option 1454A that, when selected, causes electronic device 1400 to cease displaying workout content (e.g., and return primary control to electronic device 600). Workout summary user interface 1452 includes option 1454B that, when selected, causes the workout corresponding to video content 1034 to be added to the user's collection of workouts. While displaying workout summary user interface 1452, electronic device 1400 detects selection of option 1454A (e.g., via an input made at a physical remote paired with electronic device, or via an input made using virtual trackpad 1448G).

Figure 14L:
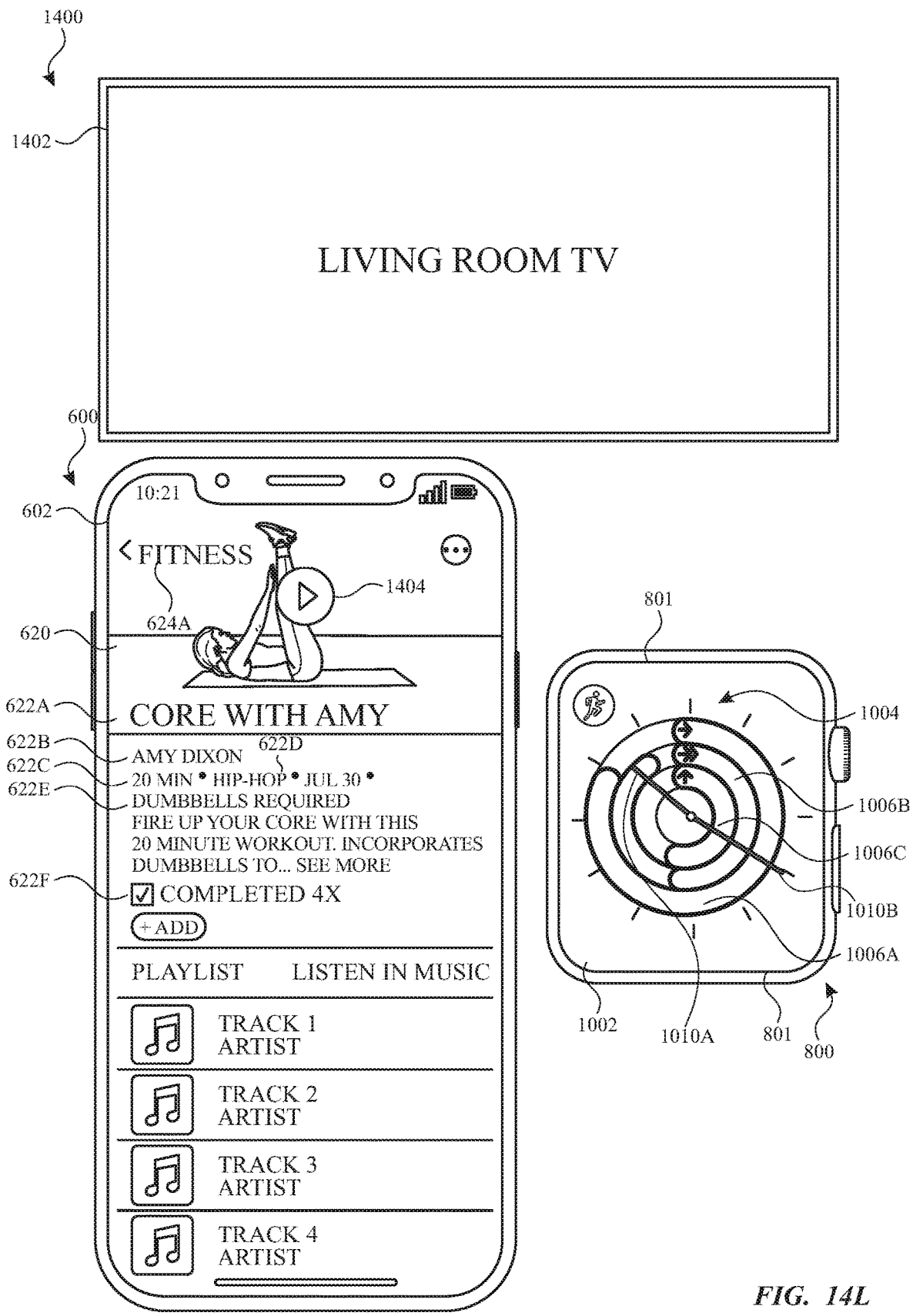

At FIG. 14L, in response to selection of option 1454A, electronic device 1400 ceases displaying workout content. In response to selection of option 1454A, electronic device 600 replaces display of status user interface 1418 with display of detail user interface 620. In response to selection of option 1454A, electronic device 800 replaces display of summary user interface 1456 with activity user interface 1002. The plurality of concentric physical activity rings 1004 have been updated in activity user interface 1002 to indicate an increase in activity as a result of the recently completed workout. For example, move ring 1006A and exercise 1006B have been visually modified to indicate an increase in number of calories burned and an increase in number of minutes exercised, respectively.

Figure 14M:
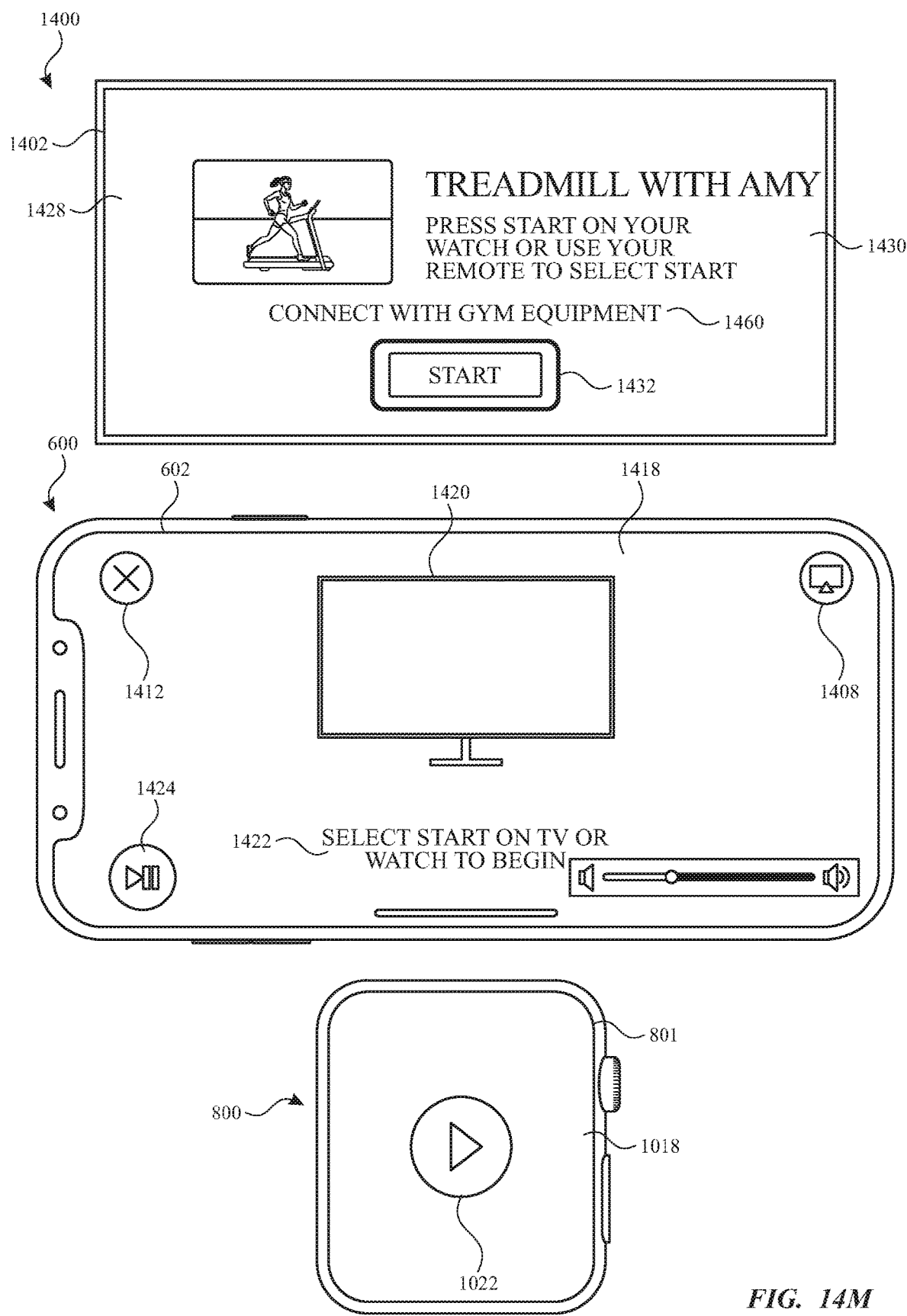

FIG. 14M depicts a scenario in which electronic exercise equipment, such as a treadmill, a stationary bike, a rowing machine, or a stair machine, can optionally be connected to (e.g., paired to) electronic devices 600, 800, and/or 1400. At FIG. 14M, similar to FIG. 14E, electronic device 600 displays a status user interface 1418, electronic device 1400 displays a workout start user interface 1428, and electronic device 800 displays a workout start user interface 1018. However, in FIG. 14M, workout start user interface 1428 on electronic device 1400 includes a prompt 1460. Prompt 1460 can indicate to the user that the selected workout is compatible with connection to electronic exercise equipment, if such exercise equipment is available (in this case, a treadmill). In the depicted embodiments, a user can optionally begin his or her workout without connecting to any exercise equipment (e.g., by selecting option 1432 or option 1022). At FIG. 14M, electronic device 600, electronic device 800, and/or electronic device 1400 determines that electronic device 800 satisfies proximity criteria relative to a compatible exercise equipment device (e.g., based on signal strength, based on an input at the exercise equipment device, and/or other proximity indications).

Figure 14N:
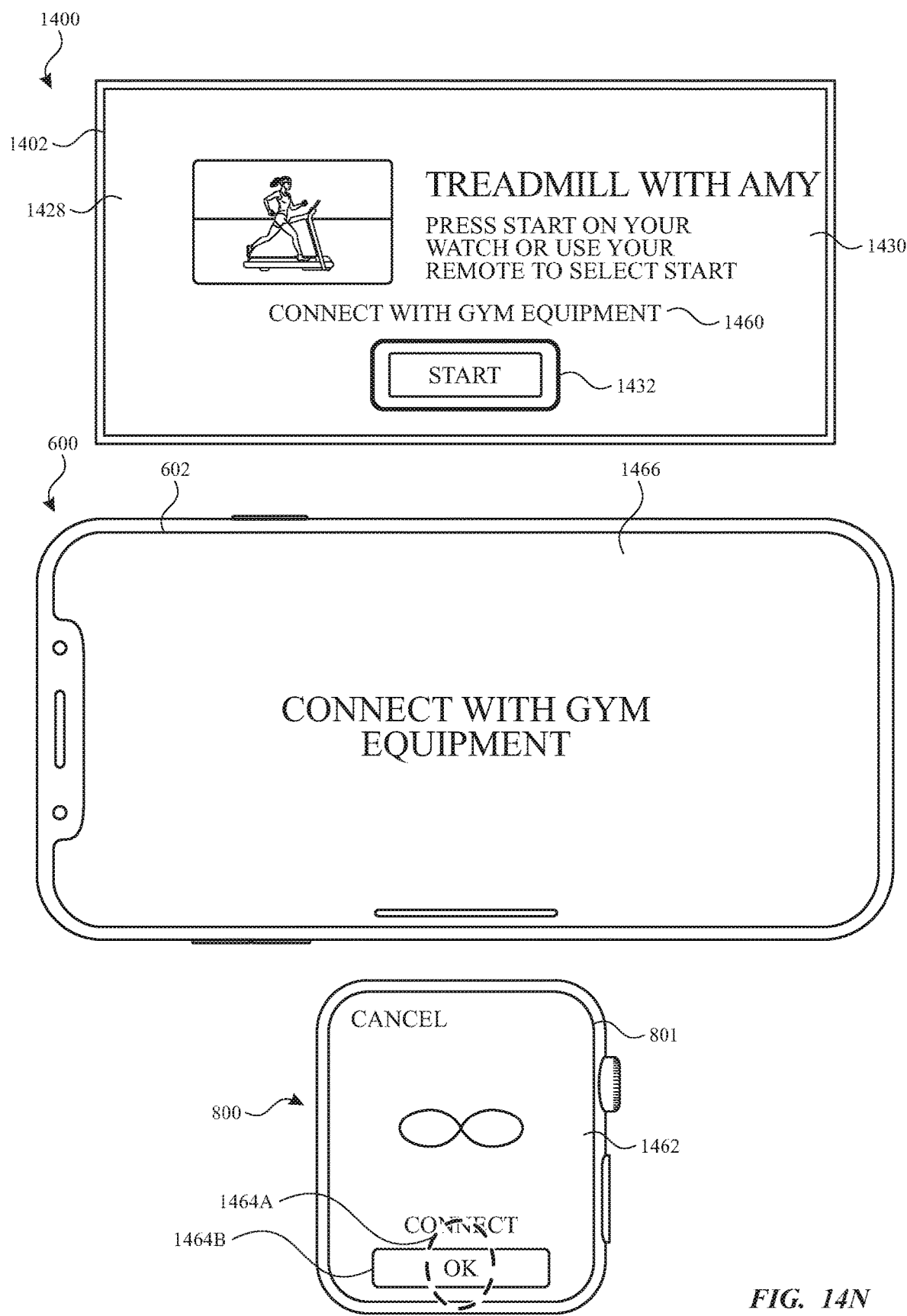

At FIG. 14N, in response to the determination that electronic device 800 satisfies proximity criteria relative to a compatible exercise equipment device, electronic device 800 replaces display (e.g., electronic device 600 causes electronic device 800 to replace display) of workout start user interface 1018 with pairing user interface 1462, and electronic device 600 replaces display of status user interface 1418 with status user interface 1466. Pairing user interface 1462 includes an option 1464A that is selectable by a user to proceed with pairing electronic device 800 with a compatible exercise equipment device. At FIG. 14N, while displaying pairing user interface 1462, electronic device 800 detects input 1464B at a location corresponding to option 1464A.

Figure 14O:
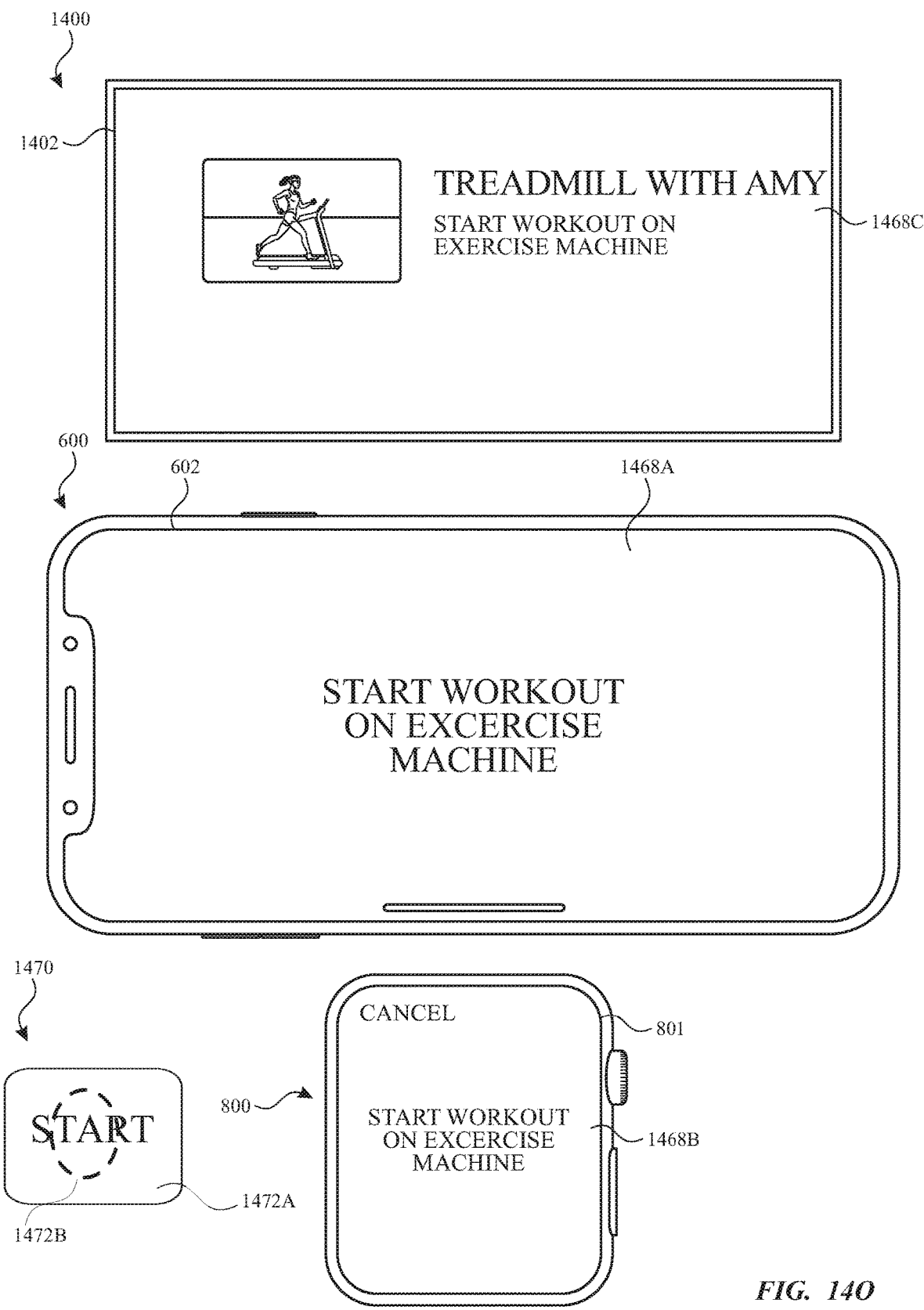

At FIG. 14O, in response to input 1464B, electronic device 800 is paired with a compatible exercise equipment device 1470 (e.g., a treadmill). In response to a determination that electronic device 800 is successfully paired with exercise equipment device 1470, electronic device 600 replaces display of status user interface 1466 with status user interface 1468, electronic device 800 replaces display (e.g., electronic device 600 causes electronic device 800 to replace display) of pairing user interface 1462 with status user interface 1468B, and electronic device 1400 replaces display (e.g., electronic device 600 and/or 800 causes electronic device 1400 to replace display) of workout start user interface 1428 with status user interface 1468C. Each of status user interface 1468A, 1468B, and 1468C instruct the user to begin the workout on the paired exercise equipment device 1470. At FIG. 14O, while electronic devices 600, 800, and 1400 display status user interfaces 1468A, 1468B, 1468C, respectively, paired exercise equipment device 1470 detects a user input 1472B at a "START" option 1472A, indicating user intent to begin the workout.

Figure 14P:
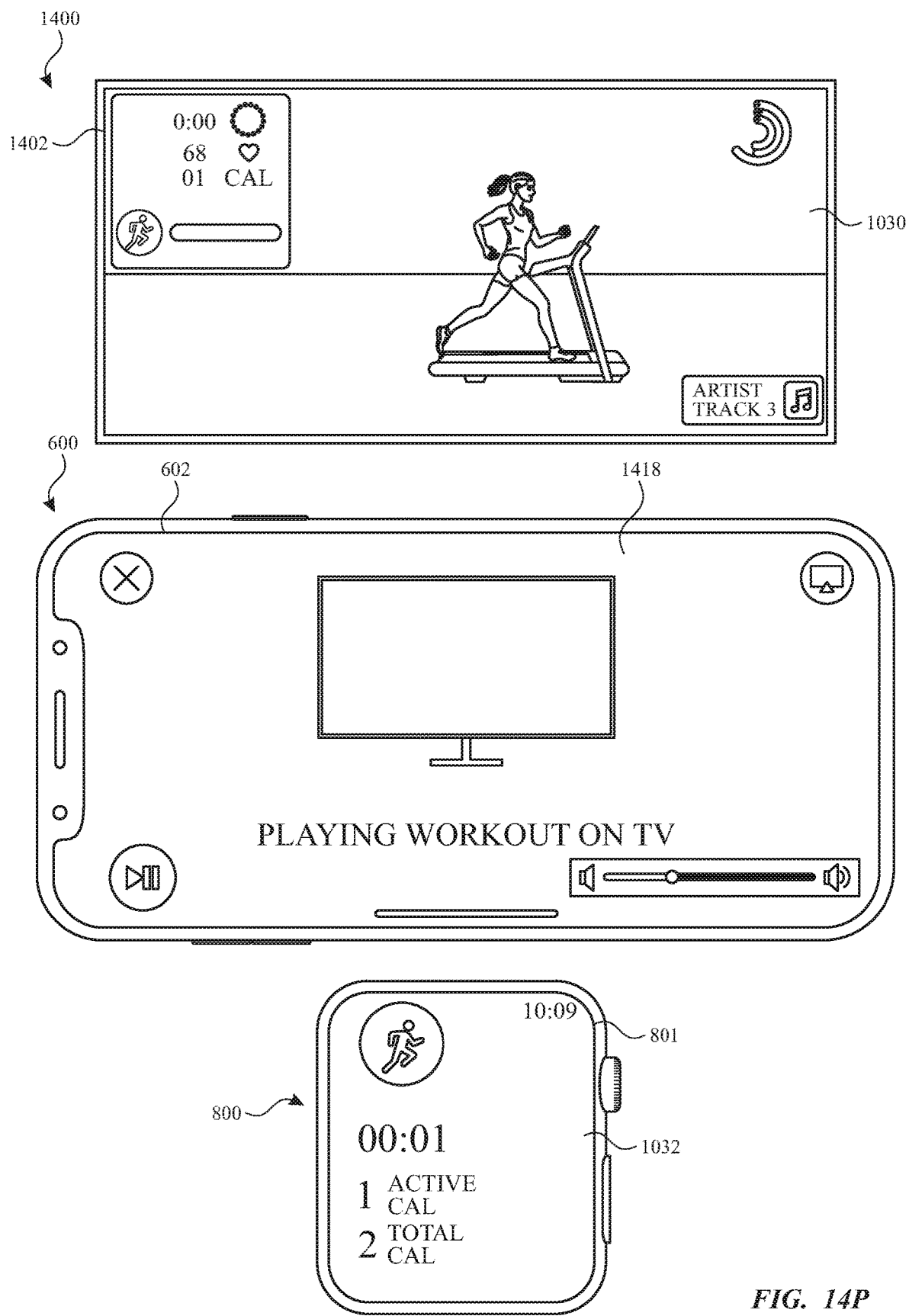

At FIG. 14P, in response to input 1472B (e.g., in response to a determination that a user input has been received at the paired exercise equipment device 1470 indicative of user intent to begin the workout), electronic device 600 replaces display of status user interface 1468A with status user interface 1418, electronic device 800 replaces display (e.g., electronic device 600 causes electronic device 800 to replace display) of status user interface 1468B with workout metrics user interface 1032, and electronic device 1400 replaces display (e.g., electronic device 600 and/or 800 causes electronic device 1400 to replace display) of status user interface 1468C with workout session user interface 1030, each of which have been described in greater detail above (e.g., with reference to FIG. 14F).

Figure 14Q:
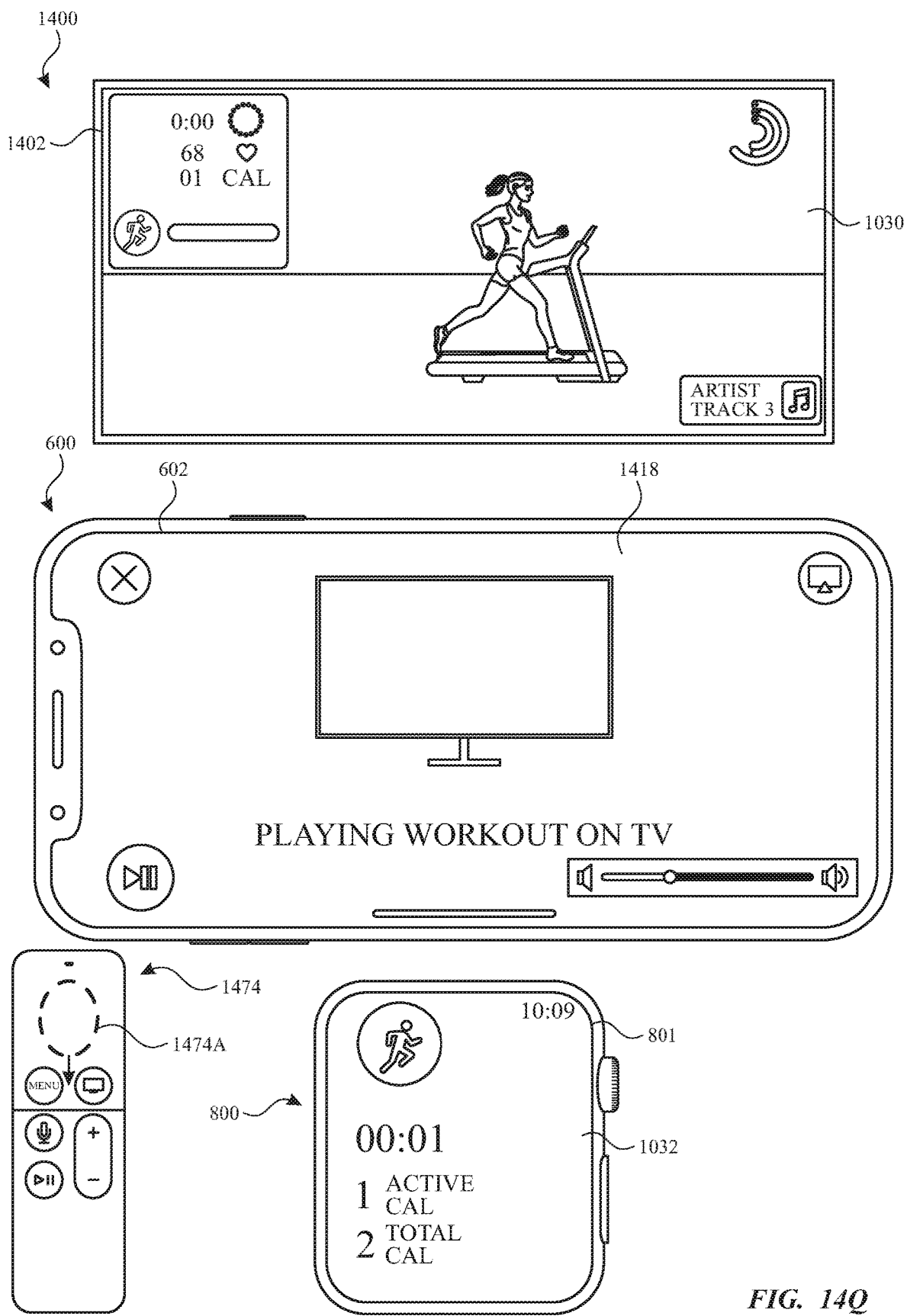

At FIG. 14Q, while electronic device 1400 is displaying workout session user interface 1030, a user input 1474A that includes a downward motion is received at a remote control device 1474 that is paired to electronic device 1400.

At FIG. 14R, in response to input 1474A, electronic device 1400 displays display settings user interface 1476. A user can navigate the display settings user interface 1476 and select various selectable options to control what information is displayed in the workout session user interface 1030. For example, a user can choose to display or not display physical activity metrics (via options 1478A and 1478B), turn off time display (1478C), display elapsed time (1478D), display remaining time (1478E), turn off display of the burn bar (1478F), or turn on display of the burn bar (1478G). Electronic device 1400 can update display of the workout session user interface 1030 based on user inputs and selections in display settings user interface 1476.

FIG. 15 is a flow diagram illustrating a method for coordinating display of workout content among multiple devices, in accordance with some embodiments. Method 1500 is performed at an electronic device (e.g., 100, 300, 500, 600) with a display (e.g., 602), wherein the electronic device is in communication with a first external device (e.g., 1400, television, laptop, tablet, set top box, streaming device) and a second external device (e.g., 800, smartwatch, fitness tracking device, wearable electronic device). Some operations in method 1500 are, optionally, combined, the orders of some operations are, optionally, changed, and some operations are, optionally, omitted.

As described below, method 1500 provides an intuitive way for coordinating display of workout content among multiple devices. The method reduces the cognitive burden on a user for coordinating display of workout content among multiple devices, thereby creating a more efficient human-machine interface. For battery-operated computing devices, enabling a user to coordinate display of workout content among multiple devices faster and more efficiently conserves power and increases the time between battery charges.

In some embodiments, the electronic device (e.g., 100, 300, 500, 600, 800) is a computer system. The computer system is optionally in communication (e.g., wired communication, wireless communication) with a display generation component and with one or more input devices. The display generation component is configured to provide visual output, such as display via a CRT display, display via an LED display, or display via image projection. In some embodiments, the display generation component is integrated with the computer system. In some embodiments, the display generation component is separate from the computer system. The one or more input devices are configured to receive input, such as a touch-sensitive surface receiving user input. In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

The electronic device (e.g., 600) displays, on the display (e.g., 602) of the electronic device, a user interface (e.g., 1016) corresponding to video content (e.g., 1034) including a first selectable user interface object (e.g., 1408) for enabling display of an activity session user interface (e.g., 1030) associated with the video content on a display device (e.g., 1402) that is in communication with the first external device (e.g., a display that is part of a device (e.g., television, laptop, tablet), a display that is external to a device (e.g., set top box, streaming device)). In some embodiments, the user interface corresponding to video content is a detail page (e.g., 620) for a particular workout. In some embodiments, the user interface includes one or more of: a representation (e.g., image) of the video content, duration of video content, music genre for corresponding audio content, required equipment, workout description, audio playlist, and an option for adding the workout to a library. In some embodiments, the user interface includes a selectable user interface object for starting the activity session (e.g., displaying workout content on the display of the electronic device, e.g., without displaying workout content on the display device that is in communication with the first external device.

The electronic device (e.g., 600) detects a first sequence of one or more user inputs (e.g., 1410, 1414) including selection of the first selectable user interface object.

In response to detecting the first sequence of one or more user inputs (e.g., 1410, 1414) including selection of the first selectable user interface object: the electronic device (e.g., 600) causes the display device (e.g., 1402) that is in communication with the first external device (e.g., 1400) to display (e.g., by transmitting, to the first external device, a command or instruction) a first graphical user interface (e.g., 1428) that is associated with the activity session.

While the display device (e.g., 1402) is displaying the first graphical user interface (e.g., 1428) that is associated with the activity session, a display device (e.g., 801) that is in communication with the second external device (e.g., a display that is part of a device (e.g., smartwatch, fitness tracking device, wearable electronic device), a display that is external to the device) displays (e.g., by transmitting, to the first external device, a command or instruction) a second graphical user interface (e.g., 1018) that is associated with starting the activity session and is different from the first graphical user interface, wherein a selection input (e.g., 1434) directed to a portion (e.g., 1022) of the second graphical user interface (e.g., 1018) causes the display device that is in communication with the first external device (e.g., 1402) to display an activity session user interface (e.g., 1030) associated with the video content.

In some embodiments, the portion of the second graphical user interface (e.g., 1018) corresponds to a second selectable user interface object (e.g., 1022) that, when selected, causes the display device (e.g., 1402) that is in communication with the first external device to display the activity session user interface (e.g., 1030) associated with the video content. In some embodiments, selection of the second selectable user interface object causes the second external device to output haptic feedback.

In some embodiments, in accordance with a determination that a third external device (e.g., 1470) (e.g., an exercise device (e.g., treadmill, stair machine, rowing machine, stationary bike, elliptical, etc.)) is available to connect to (e.g., be paired to) the second external device (e.g., 800) (e.g., smartwatch, fitness tracking device, wearable electronic device) (e.g., directly connect, indirectly connect via another device (e.g., via the electronic device)) (e.g., in accordance with a determination that the third external device satisfies proximity criteria (e.g., is within a threshold distance and/or proximity (e.g., based on signal strength)) with respect to the second external device), the display device (e.g., 801) that is in communication with the second external device (e.g., 800) displays an indication (e.g., 1462) that the third external device is available to connect to the second external device. In some embodiments, the display device that is in communication with the second external device displays a selectable user interface object that, when selected, initiates a process for connecting the second external device to the third external device. In some embodiments, connecting the second external device to the third external device allows for transmission of workout information from the third external device to the second external device and/or transmission of workout information from the second external device to the third external device. Displaying a selectable user interface object in accordance with a determination that a third external device is available to connect to the second external device provides the user with feedback about the current state of the device (e.g., that a third external device is available to connect to the second external device). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in response to a determination that a third external device (e.g., 1470) (e.g., an exercise device (e.g., treadmill, stair machine, rowing machine, stationary bike, elliptical, etc.)) is available to connect to (e.g., be paired to) the second external device (e.g., 800) (e.g., smartwatch, fitness tracking device, wearable electronic device) (e.g., directly connect, indirectly connect via another device (e.g., via the electronic device)) (e.g., in accordance with a determination that the third external device satisfies proximity criteria (e.g., is within a threshold distance and/or proximity (e.g., based on signal strength)) with respect to the second external device), the display device (e.g., 801) that is in communication with the second external device (e.g., 800) ceases to display the second selectable user interface object (e.g., 1022, 1464A) and displays a visual prompt (e.g., 1468B) (e.g., text, graphics, pictorial illustration) to start the activity session using the third external device. Displaying a visual prompt in accordance with a determination that a third external device is connected to the second external device provides the user with feedback about the current state of the device (e.g., that a third external device is connected to the second external device). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in response to a determination that a user input (e.g., 1472B) has been received at the third external device (e.g., 1470) (e.g., in response to a determination that a user input corresponding to a request and/or command to begin a workout has been received at the third external device): the display device (e.g., 1402) that is in communication with the first external device (e.g., 1400) displays the activity session user interface associated with the video content (e.g., 1030). Displaying an activity session user interface in response to a determination that a user input has been received at the third external device provides the user with feedback about the current state of the device (e.g., that a particular user input has been received at the third external device). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the electronic device (e.g., 600) displays, on the display (e.g., 602) of the electronic device, a visual prompt (e.g., 1422, text, graphics, and/or pictorial illustration) to start the activity session using the second external device. In some embodiments, displaying the visual prompt occurs in response to detecting the first sequence of one or more user inputs. In some embodiments, displaying the visual prompt occurs prior to detecting the first sequence of one or more user inputs. Providing a prompt to start the activity session using the second external device provides the user with feedback about the current state of the devices and provides feedback to the user indicating what is required to start the activity session. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the visual prompt (e.g., 1422) includes a prompt to start the activity session using the first external device (e.g., 1400).

In some embodiments, the display (e.g., 602) of the electronic device (e.g., 600) is configured to display content at a first size. In some embodiments, the display device (e.g., 1402) that is in communication with the first external device (e.g., 1400) is configured to display content at a second size that is larger than the first size.

In some embodiments, the first graphical user interface (e.g., 1428) that is associated with the activity session includes a visual prompt (e.g., 1430, text, graphics, and/or pictorial illustration) to start the activity session using the first external device (e.g., 1400) or the second external device (e.g., 800). Providing a prompt to start the activity session using the first external device provides the user with feedback about the current state of the devices and provides feedback to the user indicating what is required to start the activity session. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in response to detecting the first sequence of one or more user inputs (e.g., 1410, 1414), the electronic device (e.g., 600) displays, on the display (e.g., 602) of the electronic device, a visual indication (e.g., 1420, text, graphics, pictorial illustration, and/or visual representation (e.g., of the first external device)) that the display device (e.g., 1402) that is in communication with the first external device (e.g., 1400) is configured to display the activity session user interface (e.g., 1030) associated with the video content.

In some embodiments, a selection input directed to a portion (e.g., 1432) of the first graphical user interface (e.g., 1428) that is associated with the activity session causes the display device that is in communication with the first external device to display the activity session user interface (e.g., 1030) associated with the video content.

In some embodiments, the display device (e.g., 801) that is in communication with the second external device displays one or more physical activity metrics (e.g., 1042A-1042C, based on data captured via one or more sensors of the second external device) based on physical activity of a user during the activity session (e.g., and ceases to display the second graphical user interface (e.g., 1018)) while the display device (e.g., 1402) that is in communication with the first external device displays the activity session user interface (e.g., 1030) associated with the video content.

In some embodiments, the display device (e.g., 801) that is in communication with the second external device displays the one or more physical activity metrics (e.g., 1042A-1042C) for the user of the second external device in response to a determination that the activity session has started (e.g., as a result of selection input (e.g., 1434) at the second external device or at the first external device).

In some embodiments, while the display device (e.g., 1402) that is in communication with the first external device (e.g., 1400) displays the activity session user interface (e.g., 1030) associated with the video content, the electronic device (e.g., 600) displays, on the display (e.g., 602) of the electronic device, a visual indication (e.g., 1435, 1420, text, graphics, and/or pictorial illustration) that the display device (e.g., 1402) that is in communication with the first external device (e.g., 1400) is displaying the activity session user interface (e.g., 1030) associated with the video content. Displaying a visual indication that the display device in communication with the first external device is displaying the activity session user interface provides the user with feedback as to the status of which device is displaying the workout content. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while the display device (e.g., 1402) that is in communication with the first external device (e.g., 1400) displays the activity session user interface (e.g., 1030) associated with the video content, a second sequence of one or more user inputs at a physical remote device associated with (e.g., paired with) the first external device (e.g., 1400) causes the display device (e.g., 1402) that is in communication with the first external device to cease display of the activity session user interface (e.g., 1030) associated with the video content.

In some embodiments, a third sequence of one or more user inputs at a physical remote device associated with (e.g., paired with) the first external device (e.g., 1400) causes the display device (e.g., 1402) that is in communication with the first external device to display the activity session user interface (e.g., 1030) associated with the video content.

In some embodiments, while the display device (e.g., 1402) that is in communication with the first external device (e.g., 1400) displays the activity session user interface (e.g., 1030) associated with the video content, the electronic device (e.g., 600) displays, on the display (e.g., 602) of the electronic device, a selectable user interface object (e.g., 1046A, 1412) that, when selected, causes the display device that is in communication with the first external device to cease display of the activity session user interface (e.g., 1030) associated with the video content.

In some embodiments, while the display device (e.g., 1402) that is in communication with the first external device (e.g., 1400) displays the activity session user interface (e.g., 1030) associated with the video content, the electronic device (e.g., 600) displays, on the display (e.g., 602) of the electronic device, a selectable user interface object (e.g., 1438) that, when selected, causes display of a set of options (e.g., 1448A-1448G) for controlling display of the activity session user interface (e.g., 1030) associated with the video content.

In some embodiments, the set of options includes a first option (e.g., 1448B) that, when selected, causes the display device (e.g., 1402) that is in communication with the first external device to cease display of the activity session user interface (e.g., 1030) associated with the video content. In some embodiments, while the activity session is paused, selection of the first option causes the first external device to resume the activity session.

In some embodiments, the set of options includes a second option (e.g., 1448B) that, when selected via an input that includes contact with the display for at least a predetermined amount of time, causes the display device (e.g., 1402) that is in communication with the first external device to cease display of the activity session user interface (e.g., 1030) associated with the video content and to display one or more application icons (e.g., on a homescreen) for launching a respective application.

In some embodiments, the set of options includes a third option (e.g., 1448E) that, when selected, causes the display device (e.g., 1402) that is in communication with the first external device to cease display of the activity session user interface (e.g., 1030) associated with the video content and to display one or more application icons (e.g., on a homescreen) for launching a respective application.

In some embodiments, the set of options includes a fourth option (e.g., 1448E) that, when selected via an input that includes contact with the display for at least a predetermined amount of time, causes the first external device (e.g., 1400) to overlay, on the activity session user interface (e.g., 1030), a plurality of options, including an option for turning off the first external device.

In some embodiments, the set of options includes a fifth option (e.g., 1448D) that, when selected, causes: the display device (e.g., 1402) that is in communication with the first external device (e.g., 1400) to cease display of the activity session user interface (e.g., 1030) associated with the video content; and the second external device (e.g., 800) to cease updating the display of one or more physical activity metrics (e.g., 1042A-1042C, based on data captured via one or more sensors of the second external device) for a user of the second external device.

In some embodiments, a physical remote device is paired with the first external device (e.g., 1400, television, laptop, tablet, set top box, streaming device). In some embodiments, the physical remote device has one or more of the features discussed above with respect to the set of options (e.g., 1448A-1448G) for controlling display of the activity session user interface associated with the video content. In some embodiments, the physical remote device has a physical button corresponding to each of the options in the set of options. For example, analogous to the first option (e.g., 1448B), the physical remote device has a first physical button that, when pressed, causes the first external device (e.g., 1400) to cease display of the activity session user interface (e.g., 1030) associated with the video content. As another example, analogous to the fourth option (e.g., 1448E), the physical remote device has a second physical button that, when pressed for at least a predetermined amount of time, causes the first external device (e.g., 1400) to overlay, on the activity session user interface (e.g., 1030), a plurality of options, including an option for turning off the first external device.

In some embodiments, after (e.g. in response to) the end of the activity session has been reached (e.g., video content 1034 has ended), the display device (e.g., 1402) that is in communication with the first external device (e.g., 1400) displays: one or more aggregate representations (e.g., active calories, total calories, total time, average heart rate, distance, average pace, workout intensity representation) of physical activity metrics (e.g., as shown in workout summary user interface 1452) that are based on physical activity of a user during the activity session, and a selectable user interface object (e.g., 1454B) that, when selected, causes a workout corresponding to the video content to be added to a collection of workouts for the user. In some embodiments, instead of the display device that is in communication with the first external device, the electronic device displays, on the display, the one or more aggregate representations and the selectable user interface object.

In some embodiments, after (e.g. in response to) the end of the activity session has been reached (e.g., video content 1034 has ended), the display device (e.g., 1402) that is in communication with the first external device (e.g., 1400) displays a selectable user interface object (e.g., 1454A) that, when selected, causes: the display device (e.g., 1402) that is in communication with the first external device to return to displaying a graphical user interface that was displayed prior to the first graphical user interface (e.g., 1428), and the electronic device (e.g., 600) to return to displaying a graphical user interface that was displayed prior to the user interface (e.g., 1016) corresponding to the video content.

In some embodiments, after (e.g. in response to) the end of the activity session has been reached (e.g., video content 1034 has ended), the display device (e.g., 1402) that is in communication with the first external device (e.g., 1400): in accordance with a determination that the first external device satisfies trust criteria (e.g., the first external device has been paired with the electronic device previously, confirmed selection to save the first external device as a trusted device), displays an option (e.g., selectable user interface object, affordance) for configuring the displayed content (e.g., restarting the video content, selecting new content to be displayed); and in accordance with a determination that the first external device does not satisfy the trust criteria, forgoes displaying the option for configuring the displayed content. Forgoing display of the option for configuring the displayed content when trust criteria are not satisfied provides security and can prevent unauthorized users from initiating sensitive operations. Providing improved security enhances the operability of the device and makes the user-device interface more efficient and/or secure (e.g., by restricting unauthorized access) which, additionally, reduces power usage and improves battery life of the device by limiting the performance of restricted operations.

In some embodiments, while the display device (e.g., 1402) that is in communication with the first external device (e.g., 1400) displays the activity session user interface (e.g., 1030) associated with the video content, the electronic device (e.g., 600) displays, on the display of the electronic device, a selectable user interface object (e.g., 1046E as discussed with respect to FIGS. 10E-10F) that, when selected, causes display of one or more options for configuring the display of physical activity metrics that are based on physical activity of a user during the activity session.

In some embodiments, the electronic device (e.g., 600) detects a request to start the activity session (e.g., via input (e.g., 1434) at the second graphical user interface (e.g., 1018) or at the electronic device (e.g., via input at play button 1020)). In some embodiments, in response to detecting the request to start the activity session, the electronic device causes: the display device (e.g., 1402) that is in communication with the first external device (e.g., 1400) to display a countdown animation (e.g., such as the countdown animation in countdown user interface 1028A as discussed with respect to FIG. 10C) prior to display of the activity session user interface (e.g., 1030), and the display device (e.g., 801) that is in communication with the second external device (e.g., 800) to display the countdown animation prior to display of one or more physical activity metrics (e.g., 1042A-1042C) that are based on physical activity of a user during the activity session. In some embodiments, in response to detecting the request to start the activity session, the electronic device displays the countdown animation (e.g., in addition to the countdown animations on the first external device and/or the second external device).

In some embodiments, while the display device (e.g., 1402) that is in communication with the first external device (e.g., 1400) displays the activity session user interface (e.g., 1030) associated with the video content, the electronic device detects a request to pause the activity session (e.g., input 1440 at play/pause button 1046A, input 1450 at play/pause button 1448D). In some embodiments, in response to detecting the request to pause the activity session, the electronic device (e.g., 600) causes the second external device (e.g., 800) to cease recording data based on physical activity of the user during the activity session (e.g., via one or more sensors of the second external device). In some embodiments, the background collection of activity data continues even after the workout stops. In some embodiments, in response to detecting the request to pause the activity session, the electronic device does not cause the second external device to cease recording data based on physical activity of the user. Automatically causing the recording of physical activity metrics to cease when the activity session is paused improves battery life of the device, as one or more sensors for recording physical activity metrics are disabled. Disabling the one or more sensors when a set of conditions are met enhances the operability of the device which, additionally, reduces power usage and improves battery life of the device by enabling the user to use the device more quickly and efficiently.

In some embodiments, in response to detection of a user input (e.g., 1474A) (in some embodiments, detection of a user input at and/or by the first external device) (in some embodiments, a user input comprising a downward swipe gesture) (in some embodiments, the user input is received at a physical remote device associated with (e.g., paired with) the first external device), the display device (e.g., 1402) that is in communication with the first external device (e.g., 1400) displays, while displaying the activity session user interface (e.g., 1030) associated with the video content, a selectable user interface object (e.g., "METRICS" in FIG. 14R) that, when selected, causes display of one or more options (e.g., 1478A-1478G) for configuring the display of physical activity metrics that are based on physical activity of the user during the activity session. Displaying a selectable user interface object in response to detection of a user input provides the user with feedback about the current state of the device (e.g., that a particular user input has been received). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

FIGS. 16A-16R illustrate exemplary user interfaces for displaying workout information, in accordance with some embodiments. The user interfaces in these figures are used to illustrate the processes described below, including the processes in FIGS. 17A-17B.

FIGS. 16A-16R illustrate exemplary devices and user interfaces. At FIG. 16A, computer system 1600 (e.g., device 100, 300, 500) is displaying workout user interface 1606 on display 1601 (e.g., a television). In some embodiments, display 1601 is an integrated part of computer system 1600. In some embodiments, computer system 1600 is a separate digital media player that is in communication (e.g., wireless, wired) with display 1601 (e.g., as depicted in FIG. 18A).

FIG. 16A also illustrates remote control 1602, which is configured to transmit data (e.g., via RF communication, via Bluetooth, via infrared) to computer system 1600 based on user input that is detected at remote control 1602. Remote control 1602 includes a selection region 1604a, which includes a touch-sensitive surface for detecting tap, press, and swipe gestures, a menu button 1604b, a television button 1604c, a microphone button 1604d, a play/pause button 1604e, and volume control buttons 1604f.

At FIG. 16A, computer system 1600 causes display 1601 to display a workout user interface 1606. Workout user interface 1606 includes workout suggestions 1608a-1608d for a user. In some embodiments, workout suggestions 1608a-1608d are based on one or more workouts that have been completed by the user. For example, workout suggestion 1608a represents a workout that shares one or more characteristics with a subset of workouts completed by the user (e.g., the most recently completed workout). In the depicted scenario, the user most recently completed a core workout with trainer Amy. Accordingly, computer system 1600 provides workout suggestion 1608a, as it represents a workout that has a shared characteristic with the user's most recently completed workout (e.g., workout suggestion 1608a has the same type of workout (core) as the user's most recently completed workout, workout suggestion 1608a has the same trainer (Amy) as the user's most recently completed workout). In FIG. 16A, a focus is on browse option 1610, as indicated by the bold outline around option 1610. While computer system 1600 causes display of workout user interface 1606 with the focus on browse option 1610, remote control 1602 detects activation of selection region 1604a via button press input 1611 corresponding to selection of option 1610 and transmits an indication of the input to computer system 1600. Computer system 1600 receives, from remote control 1602, the indication of input 1611 corresponding to selection of option 1610.

Figure 16B:
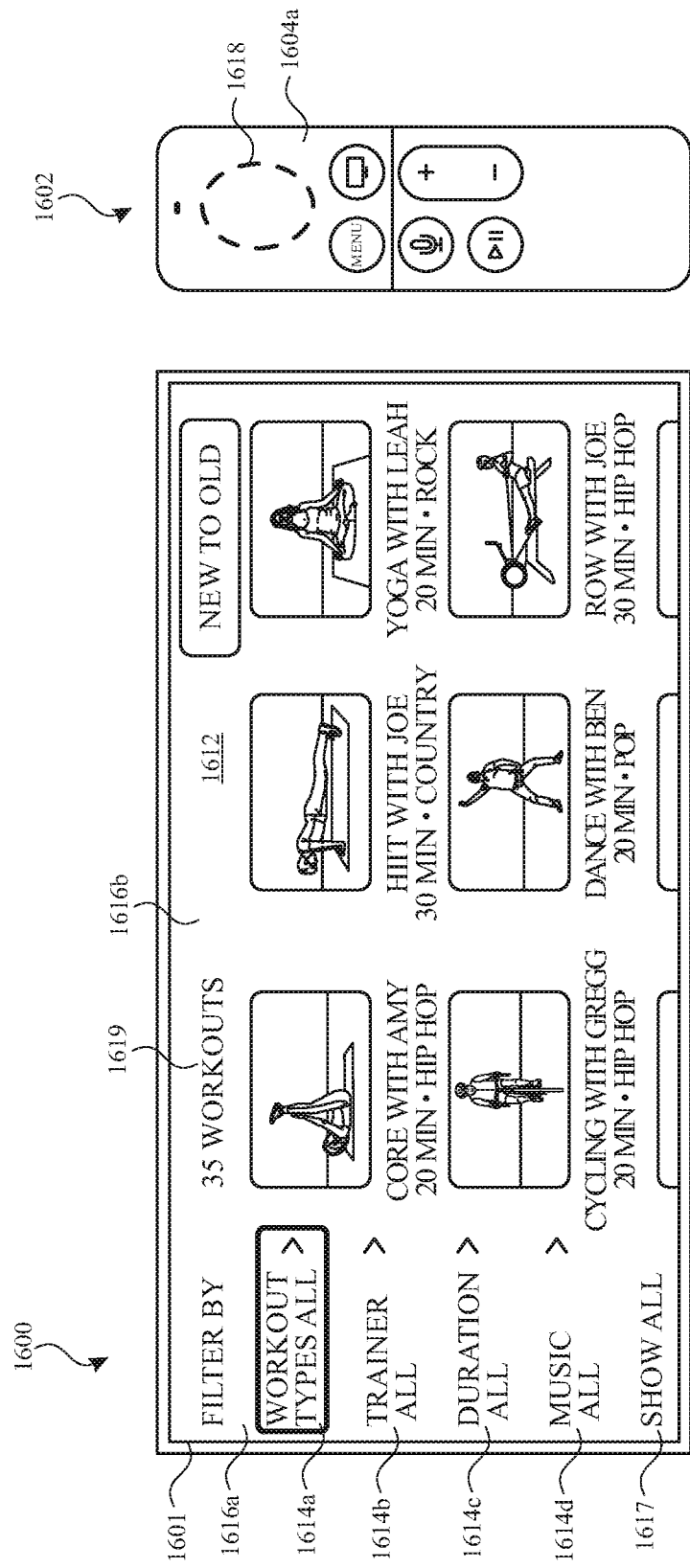

At FIG. 16B, in response to detecting (e.g., receiving the indication of) input 1611, computer system 1600 causes display 1601 to replace display of workout user interface 1606 with workout browse user interface 1612. Workout browse user interface 1612 includes a first region 1616a that includes various filtering category options 1614a-1614d. Workout browse user interface 1612 also includes a second region 1616b that includes a plurality of workout suggestions. Each workout suggestion represents a respective workout, and each workout suggestion is selectable by a user to initiate a process for presenting workout content (e.g., audio content, video content) associated with the selected workout to the user. Workout browse user interface 1612 also includes an option 1617 that is selectable by a user to clear all currently applied filters, and an indication 1619 that provides an indication of how many workout suggestions are currently included in the second region 1616b. In FIG. 16B, the focus is on filtering category option 1614a. While computer system 1600 is causing display of workout browse user interface 1612 with the focus on filtering category option 1614a, remote control 1602 detects activation of selection region 1604a via press input 1618 corresponding to selection of option 1614a. Remote control 1602 transmits an indication of the input to computer system 1600. Computer system 1600 receives, from remote control 1602, the indication of input 1618 corresponding to selection of option 1614a.

Figure 16C:
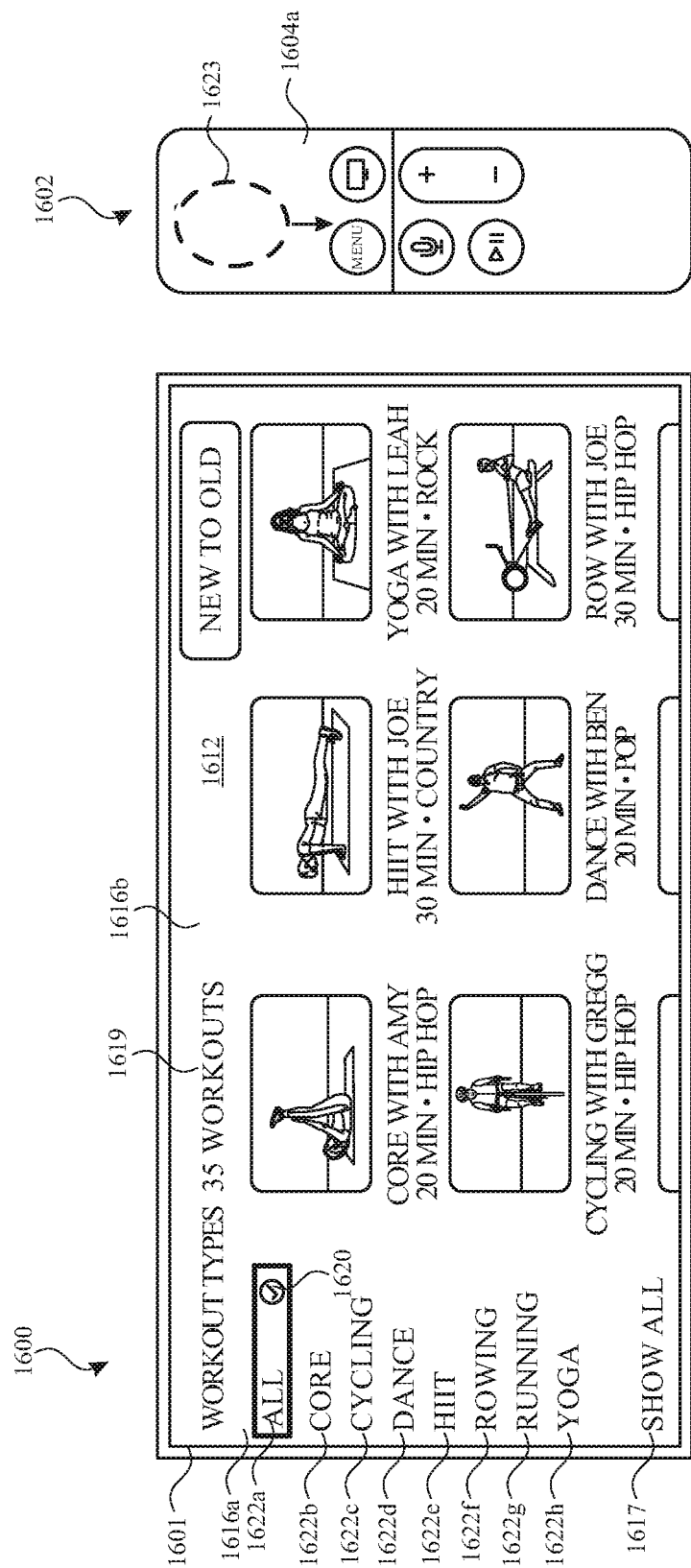

At FIG. 16C, in response to detecting (e.g., receiving the indication of) input 1618, computer system 1600 causes display 1601 to display replacement of filtering category options 1614a-1614d with filtering options 1622a-1622h. Filtering options 1622a-1622h are associated with filtering category 1614a (e.g., are grouped into filtering category 1614a), and can be selected by a user to filter workout suggestions displayed in region 1616b. In FIG. 16C, filtering options 1622a-1622h represent different workout types such that a user can select a filtering option to filter workout suggestions by workout type. In FIG. 16C, the focus is on "ALL" filtering option 1622a, and a selection indication 1620 indicates that the "ALL" filtering option is currently applied (e.g., indicating that workout suggestions have not been filtered by workout type). While filtering options 1622a-1622h are being displayed with the focus on filtering option 1622a, remote control 1602 detects input 1623 corresponding to a downward swipe gesture on selection region 1604a. Remote control 1602 transmits an indication of the input to computer system 1600. Computer system 1600 receives, from remote control 1602, the indication of input 1623 corresponding to a downward swipe gesture.

Figure 16D:
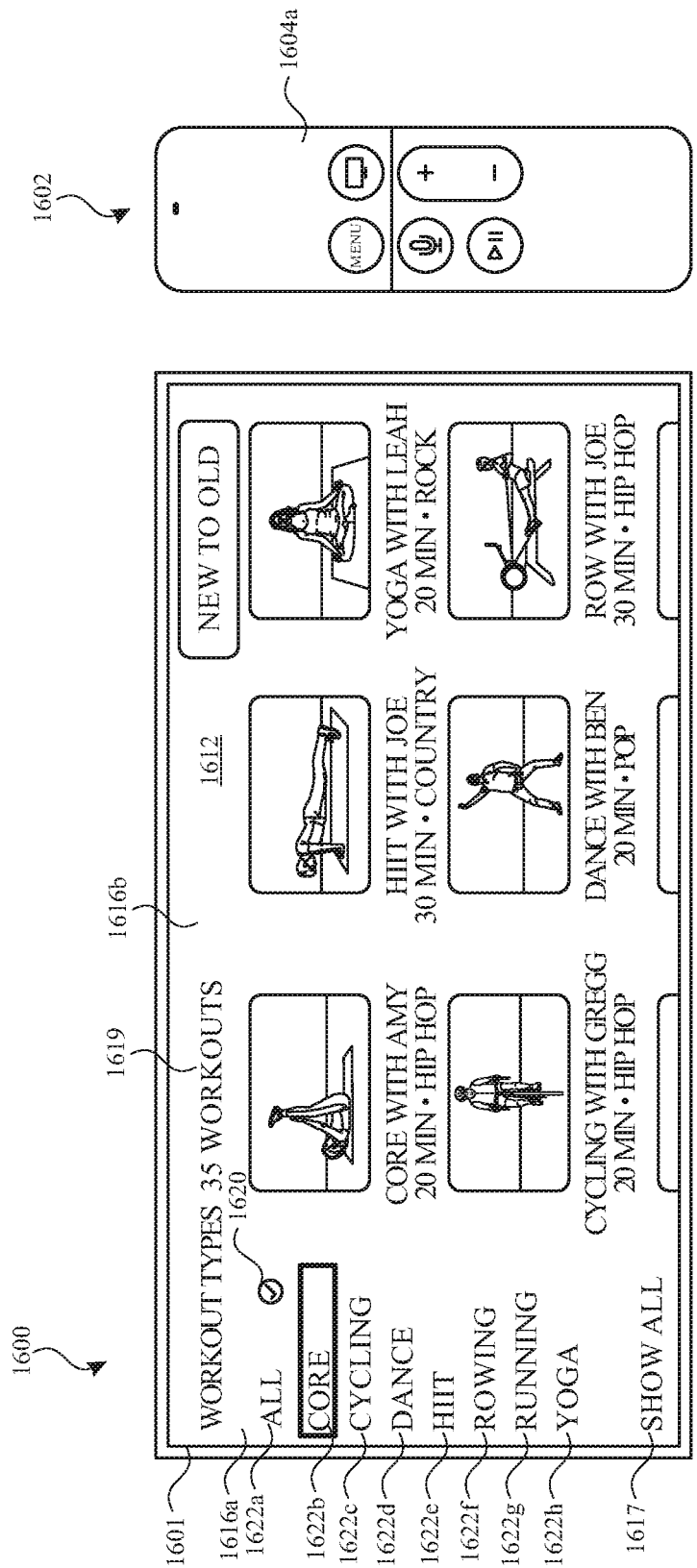

At FIG. 16D, in response to detecting (e.g., receiving the indication of) input 1623, computer system 1600 causes display 1601 to display movement of the focus in a downward direction, such that the focus moves to "CORE" filtering option 1622b. While the focus has moved to "CORE" filtering option 1622b, selection indication 1620 is still positioned at "ALL" filtering option 1622a, as a different filtering option has not yet been selected or applied.

Figure 16E:
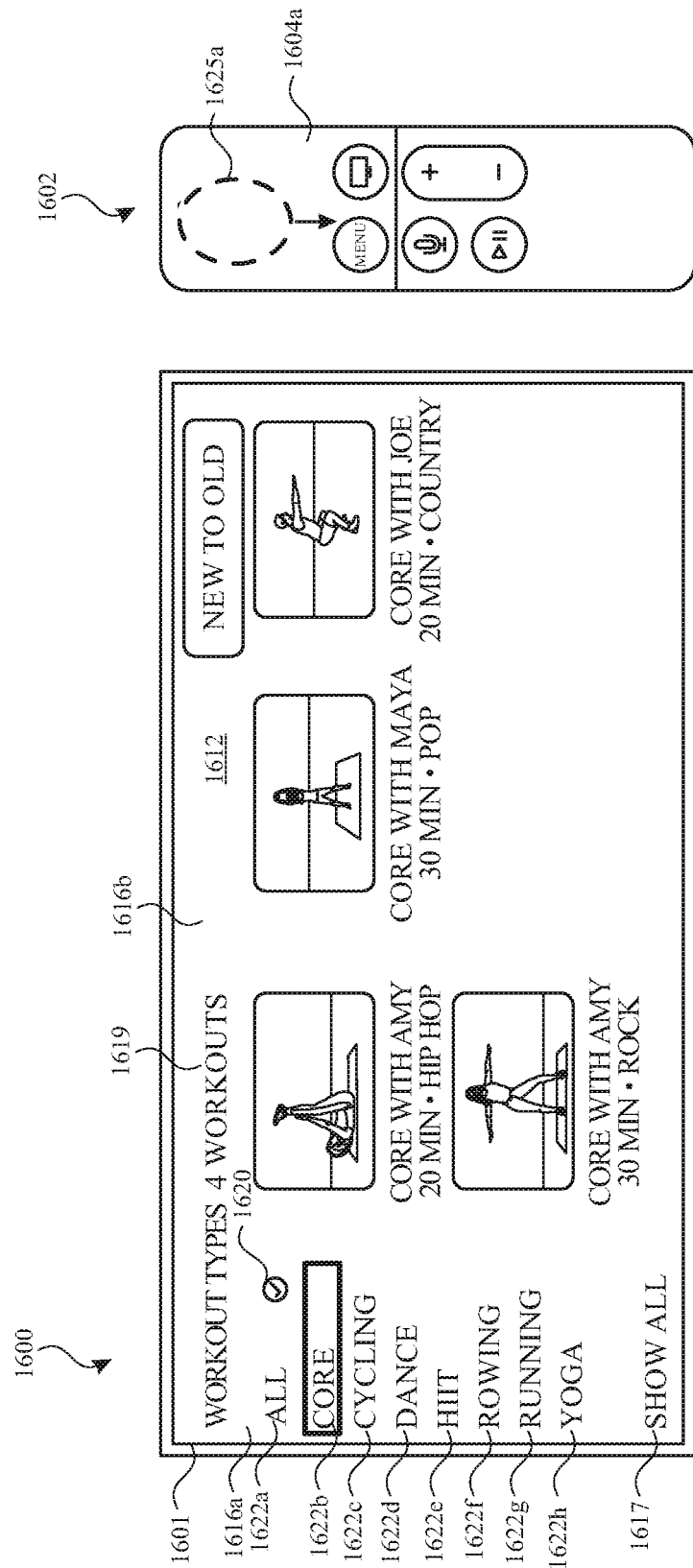

At FIG. 16E, the focus has been maintained on the "CORE" filtering option 1622b for at least a threshold period of time (e.g., 1 second). In response to a determination that the focus has been maintained on the "CORE" filtering option 1622b for the threshold period of time, computer system 1600 causes display 1601 to update display of region 1616b such that region 1616b only displays workout suggestions associated with "CORE" filtering option 1622b. As can be seen in FIG. 16E, computer system 1600 has caused display 1601 to cease displaying workout suggestions that are not associated with the "CORE" workout type, and only workout suggestions that are associated with the "CORE" workout type are displayed in region 1616b. While the user has not yet selected or applied the "CORE" workout type filtering option (as indicated by selection indication 1620 maintaining its position next to the "ALL" filtering option), region 1616b has been updated to display a preview of workout suggestions that are associated with "CORE" filtering option 1622b. While computer system 1600 causes display of workout suggestions associated with "CORE" filtering option 1622b, remote control 1602 detects input 1625a corresponding to a downward swipe gesture on selection region 1604a. Remote control 1602 transmits an indication of the input to computer system 1600. Computer system 1600 receives, from remote control 1602, the indication of input 1625a corresponding to a downward swipe gesture.

Figure 16F:
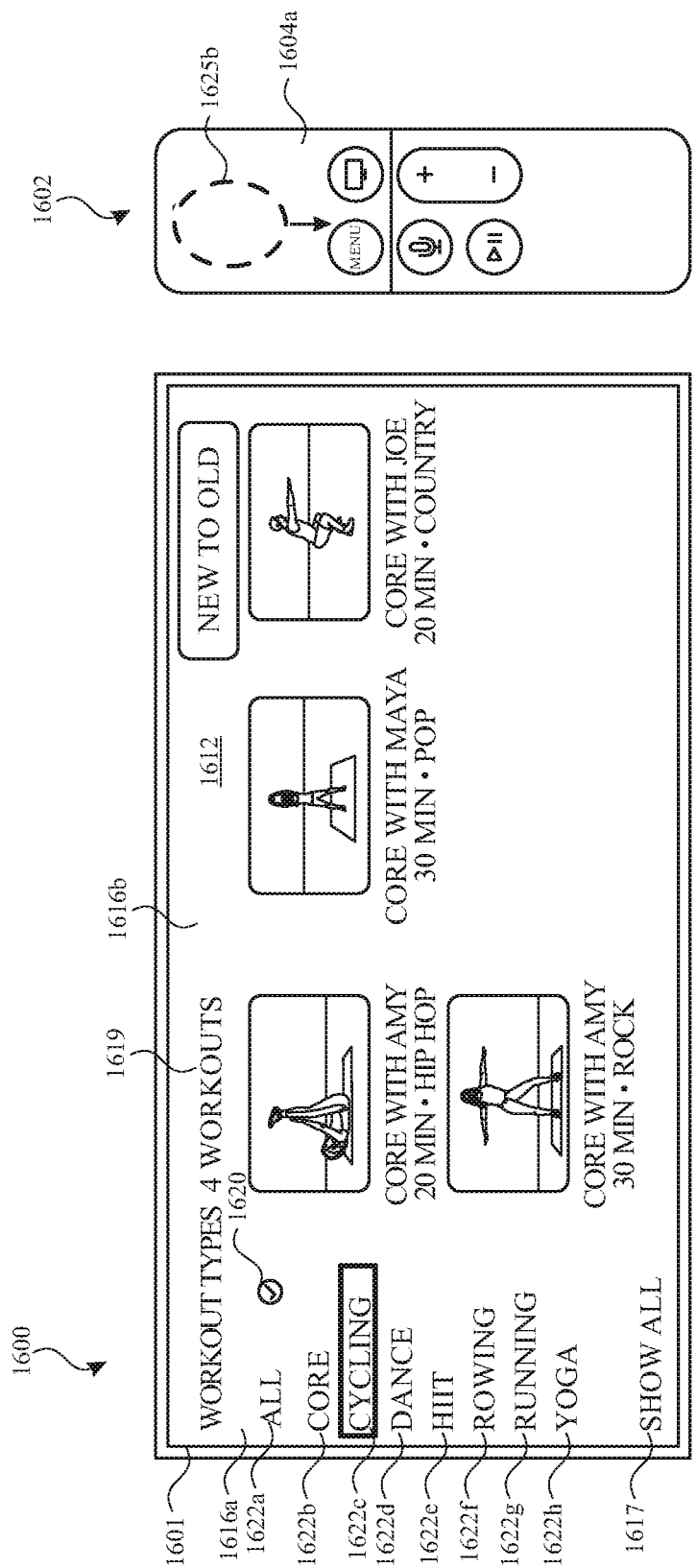

At FIG. 16F, in response to detecting (e.g., receiving the indication of) input 1625a, computer system 1600 causes display 1601 to display movement of the focus in a downward direction such that the focus moves from "CORE" filtering option 1622b to "CYCLING" filtering option 1622c. While the focus is on "CYCLING" filtering option 1622c, remote control 1602 detects input 1625b corresponding to a downward swipe gesture on selection region 1604a. Input 1625b can be a continuation of input 1625a, or can be a separate, subsequent input. Remote control 1602 transmits an indication of the input to computer system 1600. Computer system 1600 receives, from remote control 1602, the indication of input 1625b corresponding to a downward swipe gesture.

Figure 16G:
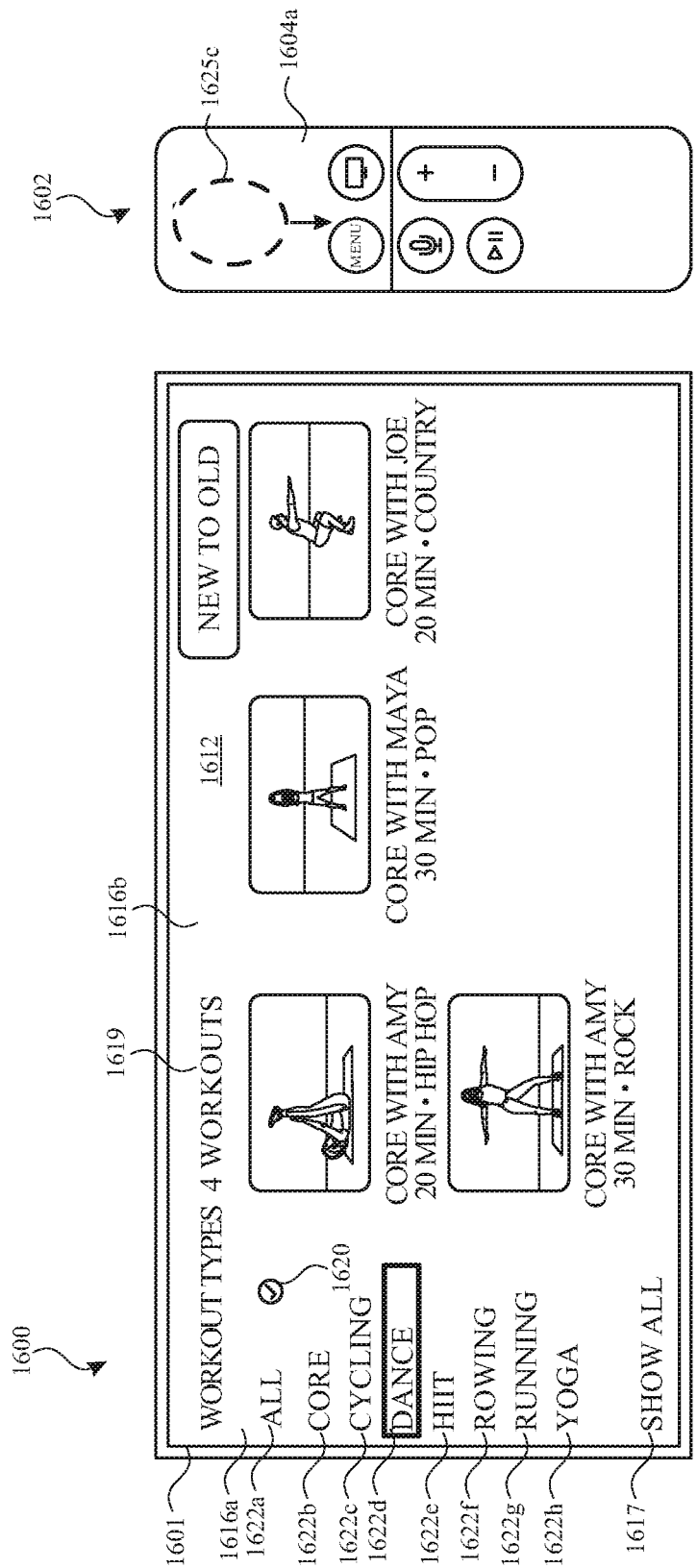

At FIG. 16G, in response to detecting (e.g., receiving the indication of) input 1625b, computer system 1600 causes display 1601 to display movement of the focus in a downward direction such that the focus moves from "CYCLING" filtering option 1622c to "DANCE" filtering option 1622d. While the focus is on "DANCE" filtering option 1622d, remote control 1602 detects input 1625c corresponding to a downward swipe gesture. Input 1625c is, optionally, a continuation of input 1625b, or is, optionally, a separate, subsequent input. Remote control 1602 transmits an indication of the input to computer system 1600. Computer system 1600 receives, from remote control 1602, the indication of input 1625c corresponding to a downward swipe gesture.

Figure 16H:
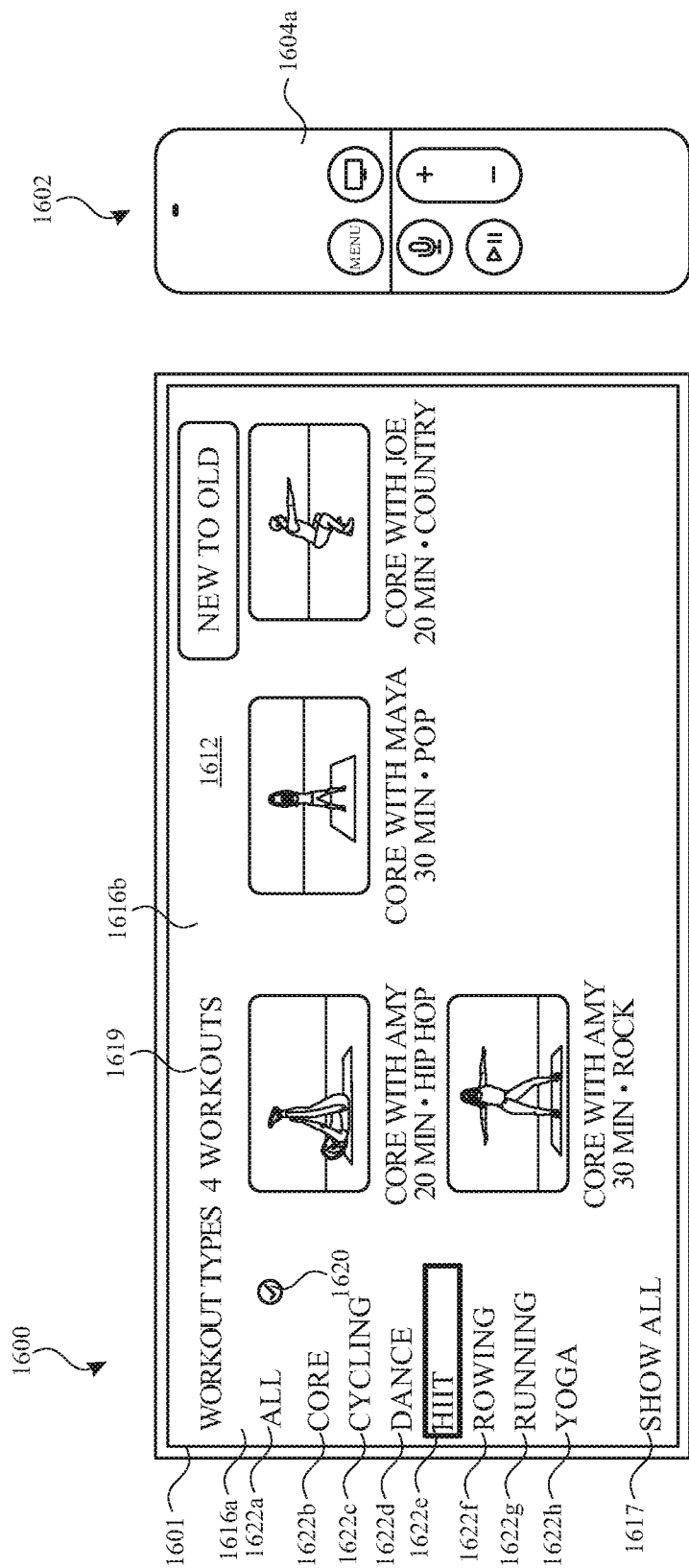

At FIG. 16H, in response to detecting (e.g., receiving the indication of) input 1625c, computer system 1600 causes display 1601 to display movement of the focus in a downward direction such that the focus moves from "DANCE" filtering option 1622d to "HIIT" filtering option 1622e. Although the focus has moved from filtering option 1622b down to filtering options 1622c, 1622d, and 1622e, region 1616b continues to display the four workout suggestions associated with "CORE" filtering option 1622b. Computer system 1600 maintains display of the four workout suggestions in region 1616b based on a determination that the focus has not been maintained on any of filtering options 1622c, 1622d, or 1622e for at least the threshold period of time. However, at FIG. 16H, computer system 1600 determines that the focus has been maintained on filtering option 1622e for at least the threshold period of time.

Figure 16I:
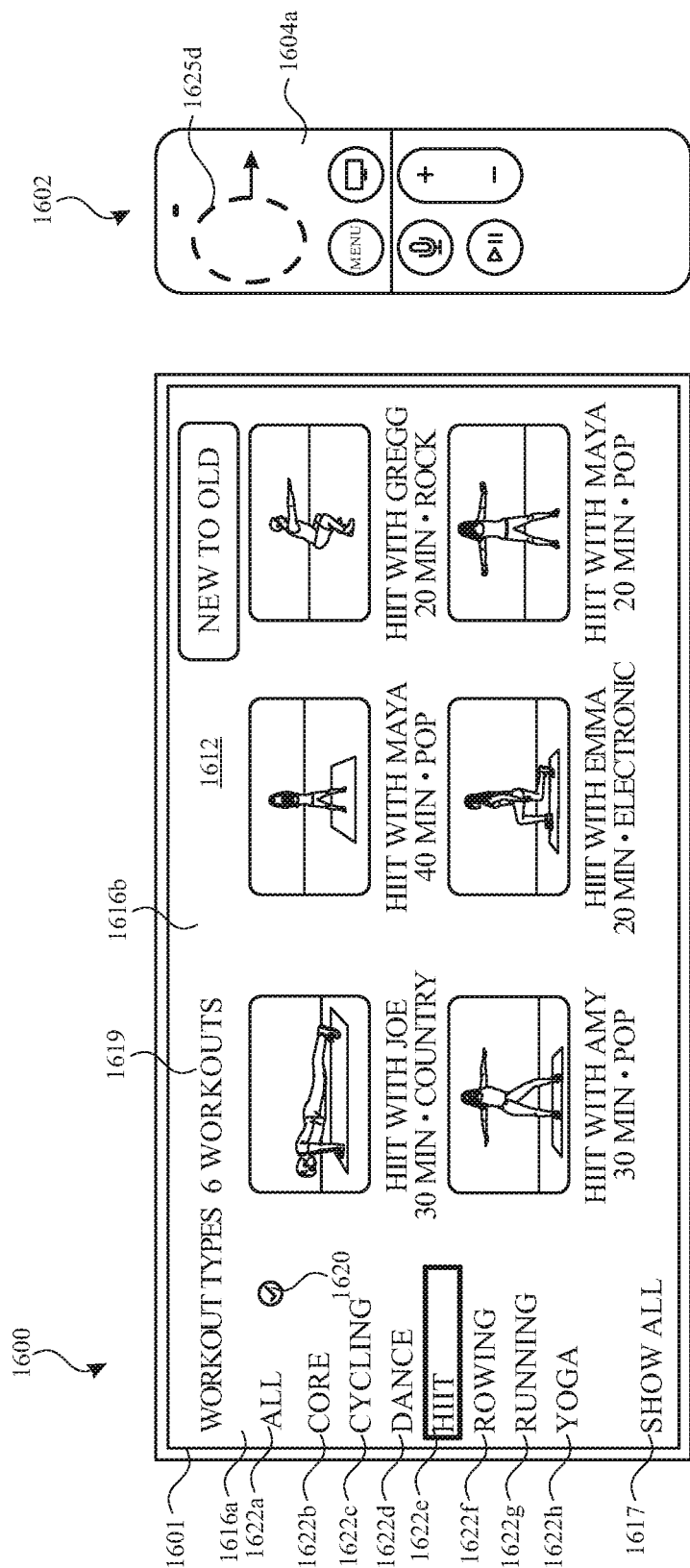

At FIG. 16I, in response to the determination that the focus has been maintained on filtering option 1622e for at least the threshold period of time, computer system 1600 causes display 1602 to update display of region 1616b such that the four workout suggestions associated with "CORE" filtering option 1622b are replaced by six workout suggestions associated with "HIIT" filtering option 1622e. While the six workout suggestions associated with "HIIT" filtering option 1622e are displayed, remote control 1602 detects input 1625d corresponding to a rightward swipe gesture on selection region 1604a. Remote control 1602 transmits an indication of the input to computer system 1600. Computer system 1600 receives, from remote control 1602, the indication of input 1625d corresponding to a rightward swipe gesture.

Figure 16J:
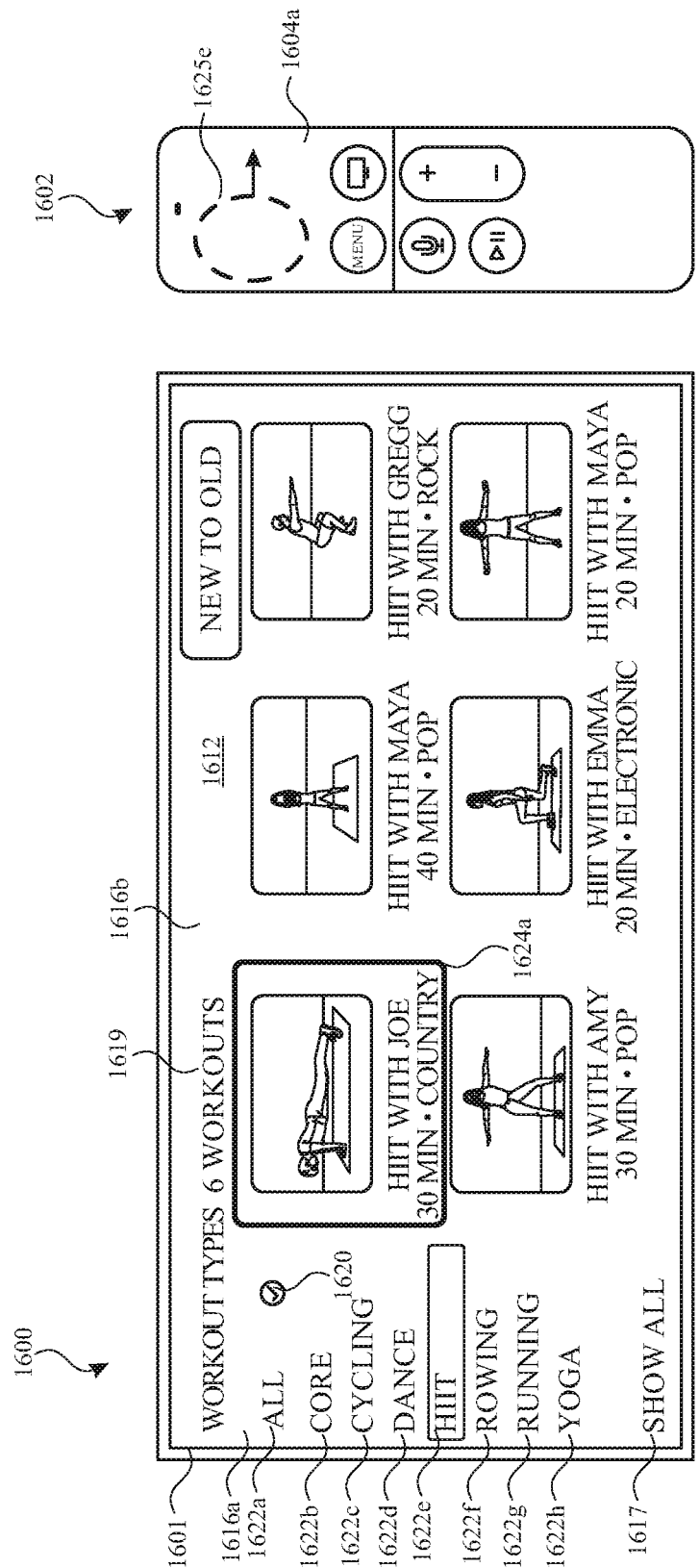

At FIG. 16J, in response to detecting (e.g., receiving the indication of) input 1625d, computer system 1600 causes display 1601 to display movement of the focus in a rightward direction to workout suggestion 1624a. While the focus is on workout suggestion 1624a, remote control 1602 detects input 1625e corresponding to a rightward swipe gesture on selection region 1604a. Input 1625e can be a continuation of input 1625d, or a separate, subsequent input. Remote control 1602 transmits an indication of the input to computer system 1600. Computer system 1600 receives, from remote control 1602, the indication of input 1625e corresponding to a rightward swipe gesture.

Figure 16K:
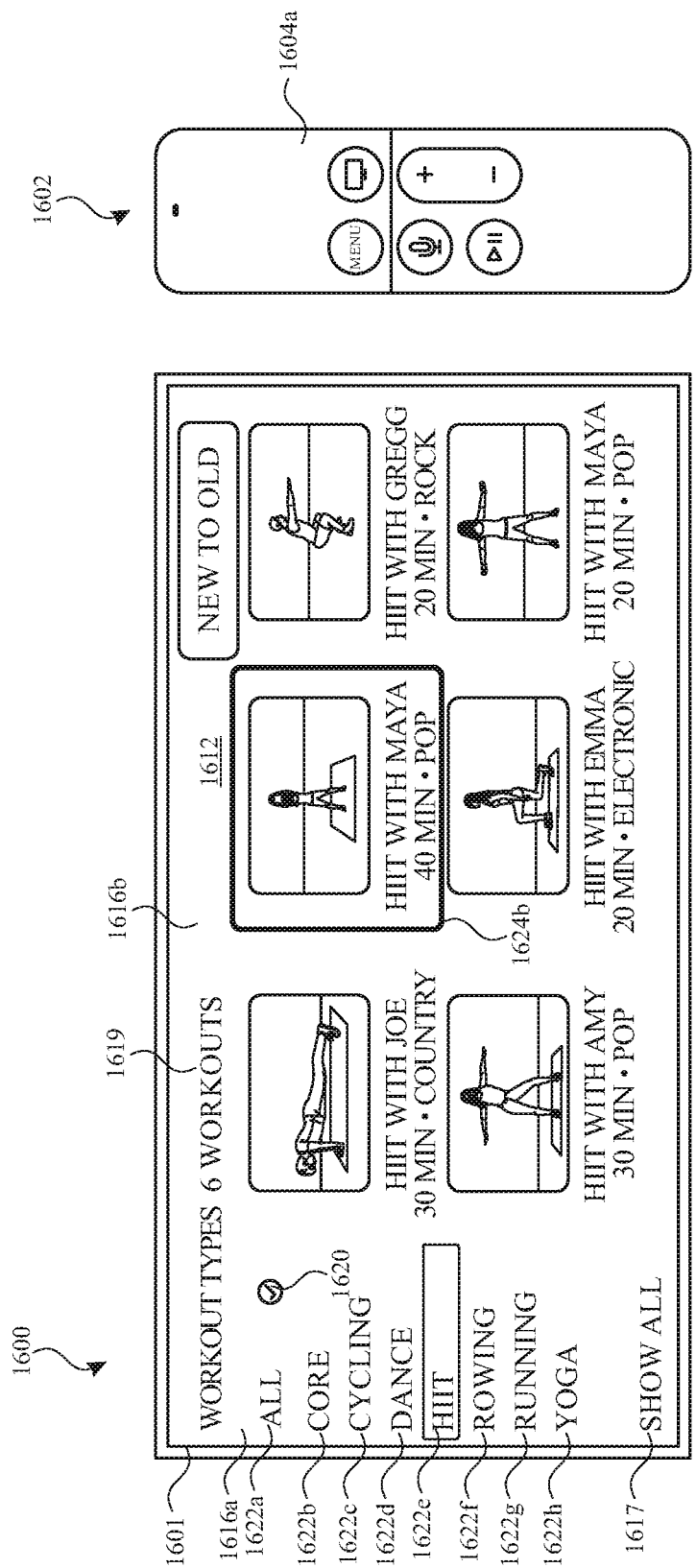

At FIG. 16K, in response to detecting (e.g., receiving the indication of) input 1625e, computer system 1600 causes display 1601 to display movement of the focus in a rightward direction to workout suggestion 1624b. At FIG. 16K, computer system 1600 determines that the focus has been maintained on workout suggestion 1624b for at least a second threshold period of time.

Figure 16L:
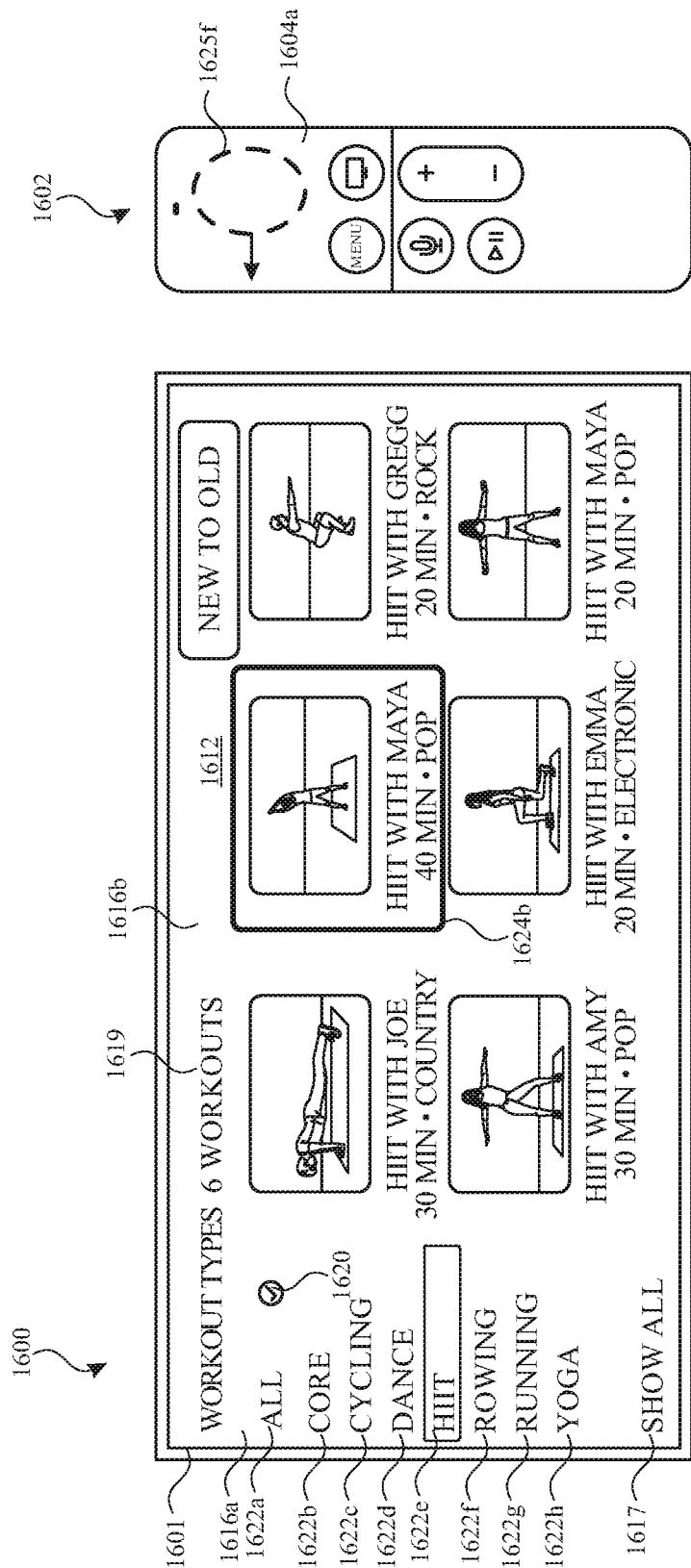

At FIG. 16L, in response to determining that focus selector 1611a has been maintained on workout suggestion 1624b for at least the second threshold period of time, computer system 1600 causes display 1601 to display a visual indication that the focus has been maintained on workout suggestion 1624b for at least the second threshold period of time. In FIG. 16L, the visual indication includes animating workout suggestion 1624b. For example, after the second threshold period of time, workout suggestion 1624b can present a video preview of the workout associated with workout suggestion 1624b. In some embodiments, as long as the focus is continuously maintained on workout suggestion 1624b, the video preview of the workout can continue to play. While computer system 1600 causes display of the video preview of workout suggestion 1624b, remote control 1602 detects input 1625f corresponding to a leftward swipe gesture on selection region 1604a. Remote control 1602 transmits an indication of the input to computer system 1600. Computer system 1600 receives, from remote control 1602, the indication of input 1625f corresponding to a leftward swipe gesture.

Figure 16M:
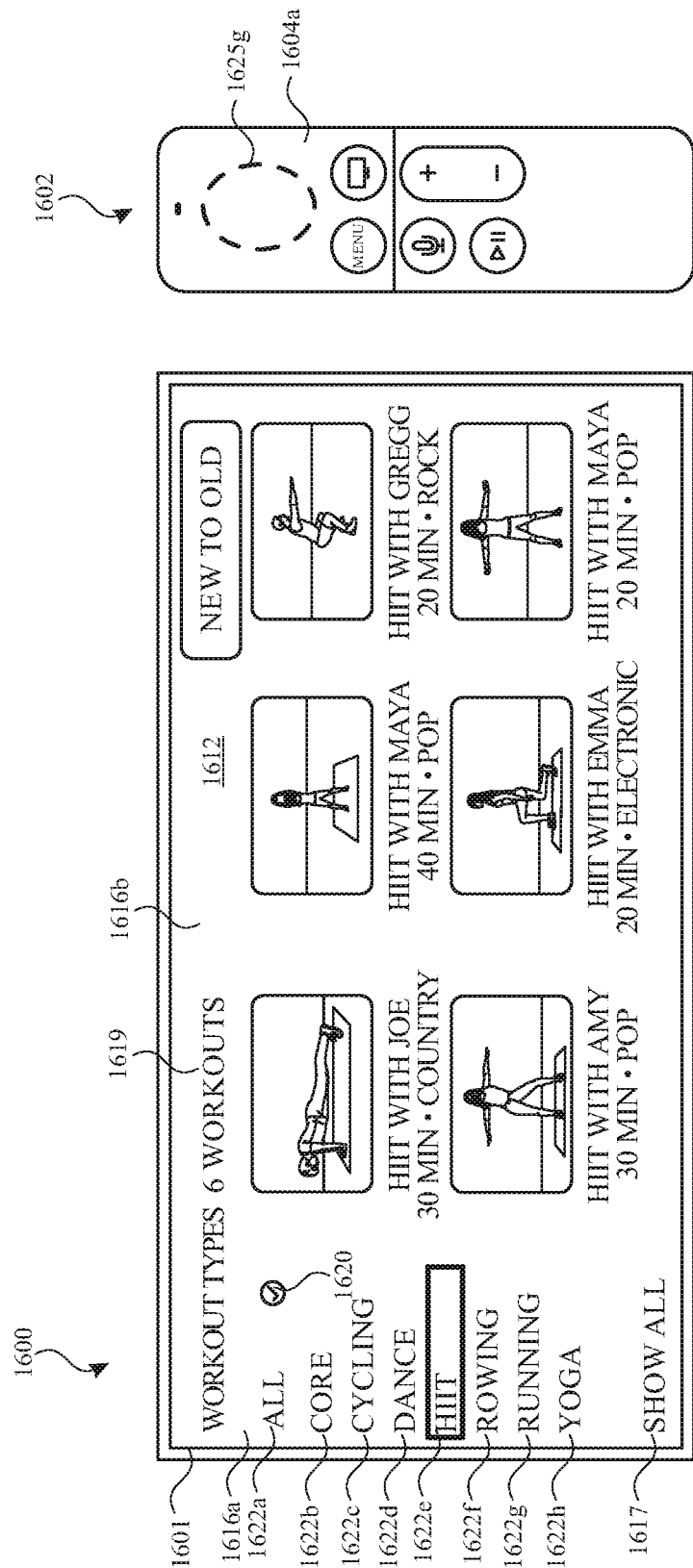

At FIG. 16M, in response to detecting (e.g., receiving the indication of) input 1625f, computer system 1600 causes display 1601 to display movement of the focus in a leftward direction to "HIIT" filtering option 1622d. While the focus is on "HIIT" filtering option 1622d, remote control 1602 detects activation of selection region 1604a via press input 1625g corresponding to selection of "HIIT" filtering option 1622d. Remote control 1602 transmits an indication of the input to computer system 1600. Computer system 1600 receives, from remote control 1602, the indication of input 1625g corresponding to selection of "HIIT" filtering option 1622d.

Figure 16N:
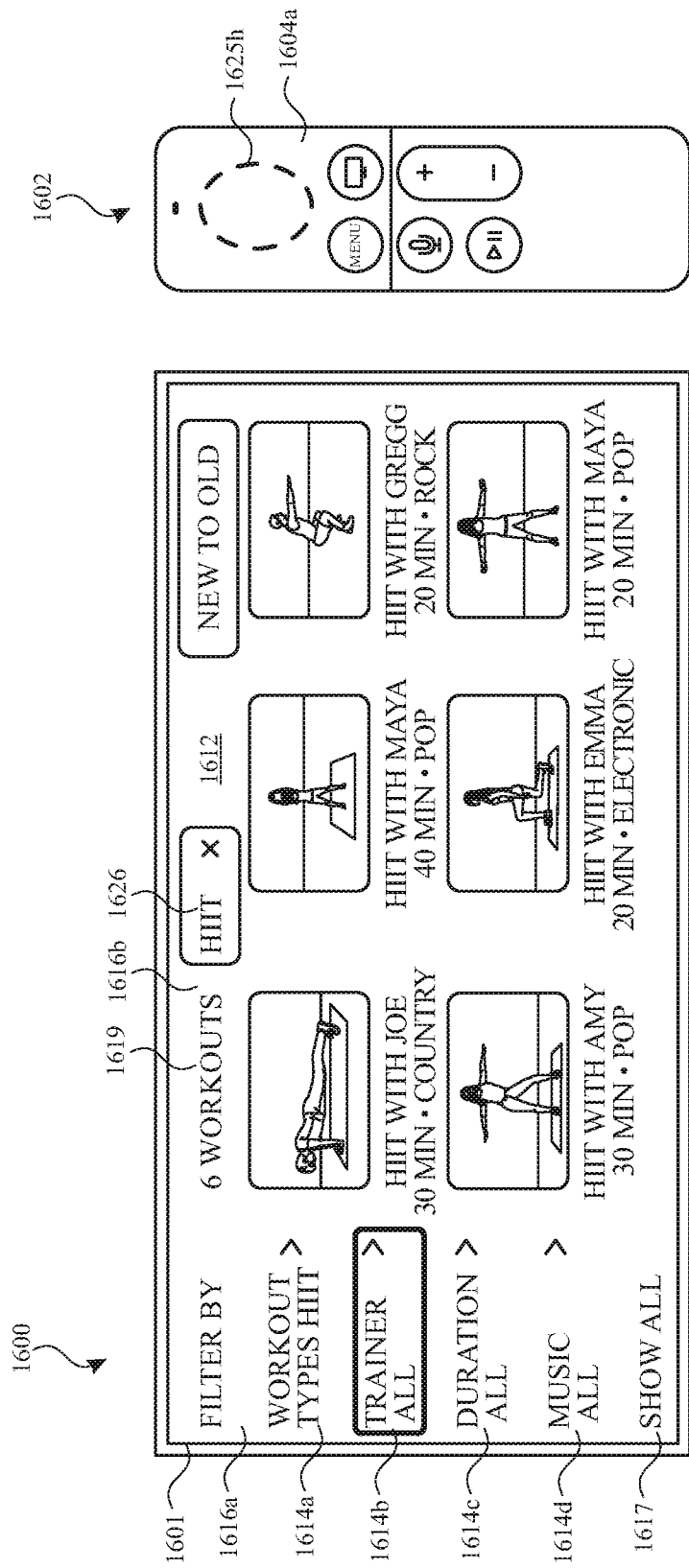

At FIG. 16N, in response to detecting (e.g., receiving the indication of) input 1625g, computer system 1600 causes display 1601 to replace display of filtering options 1622a-h in region 1616a with filtering category options 1614a-1614d. Furthermore, in response to input 1625g, computer system 1600 has visually modified filtering category option 1614a to indicate that the "HIIT" filtering option has been selected for the "WORKOUT TYPES" filtering category, and computer system 1600 has also added button 1626 to workout browse user interface 1612. Button 1626 is selectable by a user to remove the currently applied "HIIT" filtering option. Additionally, in response to detecting input 1625g corresponding to selection of the "HIIT" filtering option for the "WORKOUT TYPES" filtering category, the focus is automatically positioned on a next filtering category, "TRAINER" filtering category 1614b. While the focus is on "TRAINER" filtering category 1614b, remote control 1602 detects activation of selection region 1604a via press input 1625h corresponding to selection of filtering category 1614b. Remote control 1602 transmits an indication of the input to computer system 1600. Computer system 1600 receives, from remote control 1602, the indication of input 1625h corresponding to selection of filtering category 1614b.

Figure 16O:
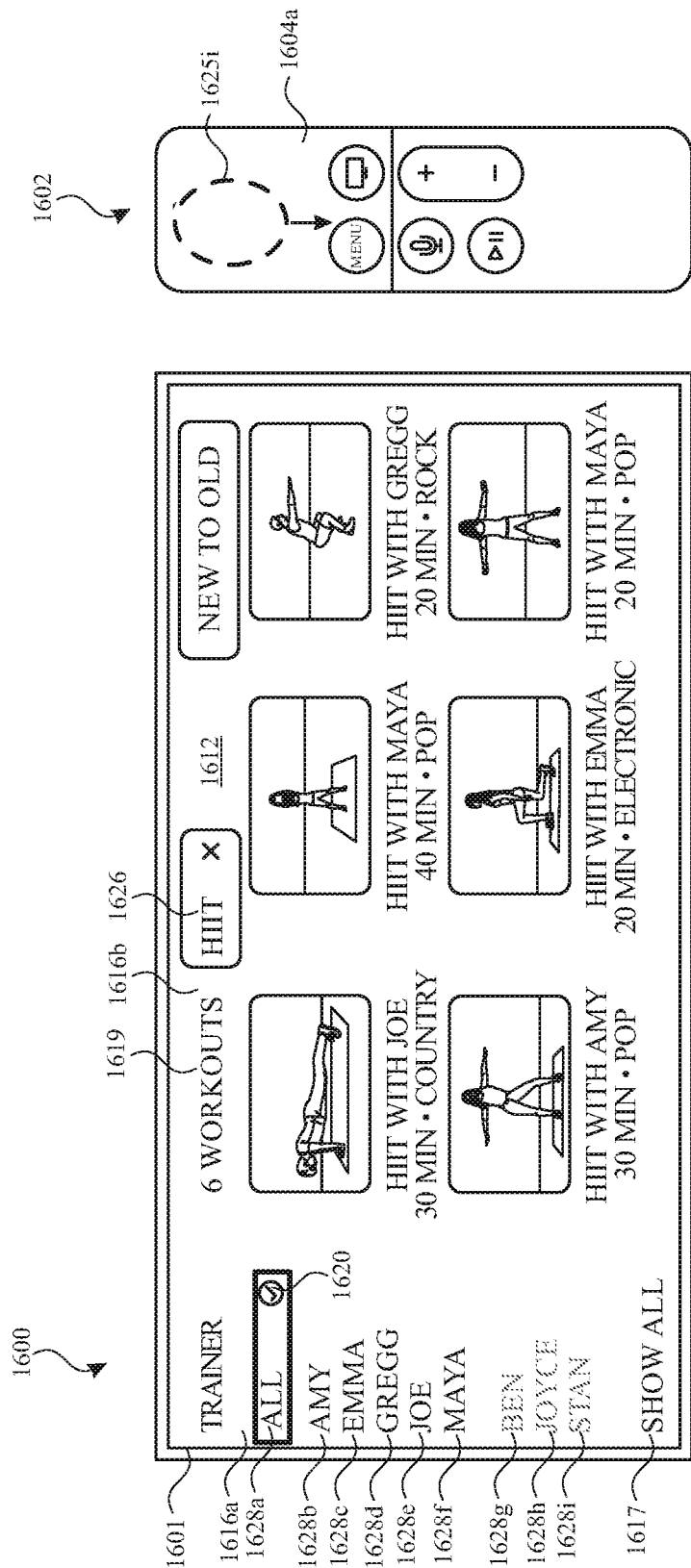

At FIG. 16O, in response to detecting (e.g., receiving the indication of) input 1625h, computer system 1600 causes display 1601 to display replacement of filtering category options 1614a-1614d with filtering options 1628a-1628i. Filtering options 1628a-1628i are associated with filtering category 1614b (e.g., are grouped into filtering category 1614b), and can be selected by a user to filter the workout suggestions displayed in region 1616b. In FIG. 16O, filtering options 1628a-1628i represent different trainers such that a user can select a filtering option to filter workout suggestions by trainer. In FIG. 16O, filtering options 1628g, 1628h, and 1628i are visually distinct from filtering options 1628a-1628f. Filtering options 1628g-1628i are displayed in a visual style indicating that those filtering options are not compatible with the currently applied filtering options (e.g., the "HIIT" filtering option). For example, the three trainers associated with those filtering options (Ben, Joyce, and Stan) may not have any HIIT workouts. In some embodiments, filtering options 1628g-1628i may not be selectable. In some embodiments, filtering options 1628g-1628i can be selectable, but selection of these filtering options can result in de-selection of one or more (e.g., all) currently applied filtering options.

In FIG. 16O, the focus is on the "ALL" filtering option 1628a, and selection indication 1620 indicates that the "ALL" filtering option is currently applied (e.g., indicating that workout suggestions have not been filtered by trainer). While computer system 1600 causes display of filtering options 1628*a*-1628*i* with the focus on "ALL" filtering option 1628*a*, remote control 1602 detects input 1625*i* corresponding to a downward swipe gesture on selection region 1604*a*. Remote control 1602 transmits an indication of the input to computer system 1600. Computer system 1600 receives, from remote control 1602, the indication of input 1625*i* corresponding to a downward swipe gesture.

Figure 16P:
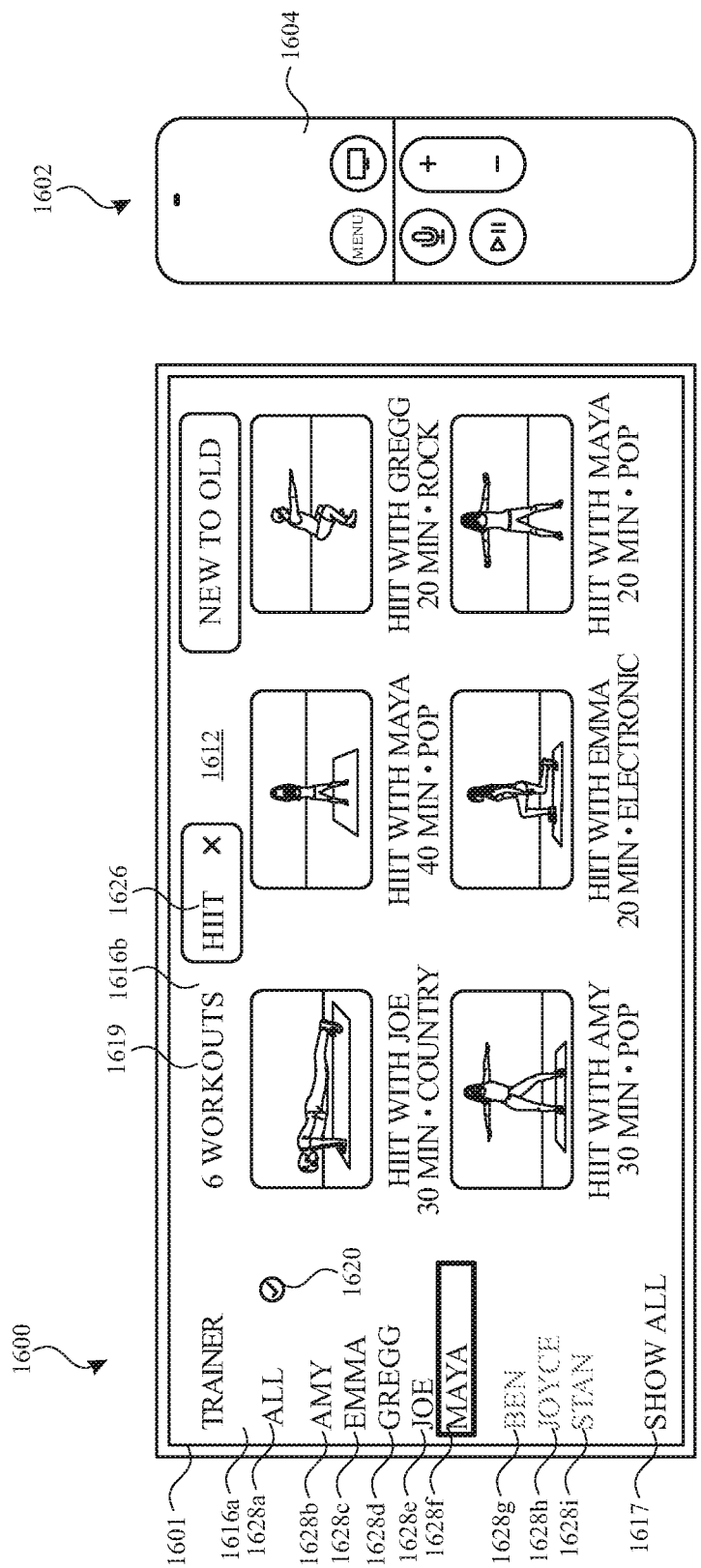

At FIG. 16P, in response to detecting (e.g., receiving the indication of) input 1625*i*, computer system 1600 causes display 1601 to display downward movement of the focus through filtering options 1628*b*, 1628*c*, 1628*d*, 1628*e*, and finally to filtering option 1628*f* ("MAYA"). At FIG. 16P, computer system 1600 determines that the focus has been maintained on filtering option 1628*f* for a threshold period of time.

Figure 16Q:
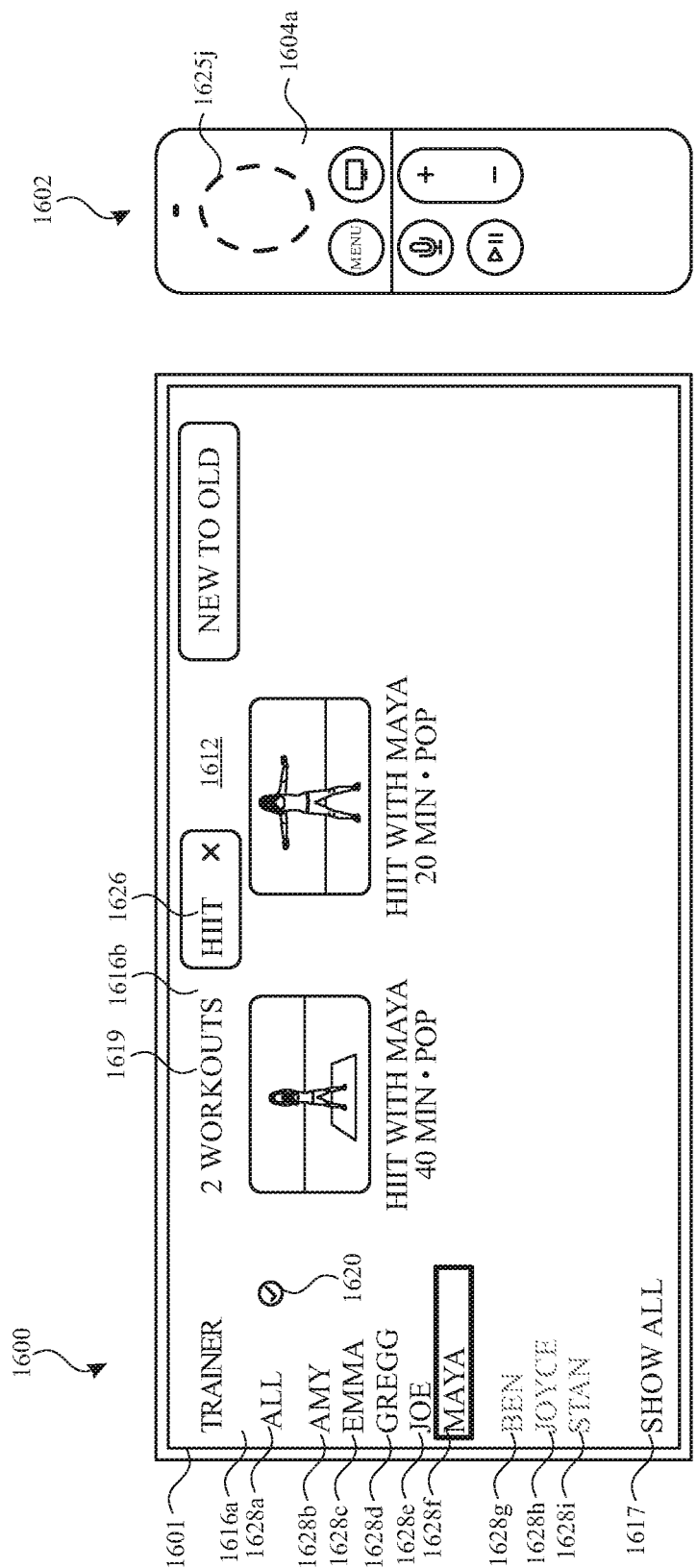

At FIG. 16Q, in response to determining that the focus has been maintained on filtering option 1628*f* for the threshold period of time, computer system 1600 causes display 1601 to update workout browse user interface 1612 such that region 1616*b* ceases to display any workout suggestions that are not associated with filtering option 1628*f*. In FIG. 16Q, region 1616*b* displays only those HIIT workouts that are also associated with trainer Maya. While computer 1600 causes display of only those workout suggestions that are associated with filtering option 1628*f*, remote control 1602 detects activation of selection region 1604*a* via press input 1625*j* corresponding to selection of filtering option 1628*f*. Remote control 1602 transmits an indication of the input to computer system 1600. Computer system 1600 receives, from remote control 1602, the indication of input 1625*j* corresponding to selection of filtering option 1628*f*.

At FIG. 16R, in response to detecting (e.g., receiving the indication of) input 1625*j*, computer system 1600 causes display 1601 to replace display of filtering options 1628*a*-1628*i* in region 1616*a* with filtering category options 1614*a*-1614*d*. Furthermore, in response to input 1625*j*, computer system 1600 has visually modified filtering category option 1614*b* to indicate that the "MAYA" filtering option has been selected for the "TRAINER" filtering category, and computer system 1600 has also added a button 1630 to workout browse user interface 1612. Button 1630 is selectable by a user to remove the currently applied "MAYA" filtering option. Additionally, in response to detecting input 1625*j* corresponding to selection of the "MAYA" filtering option for the "TRAINER" filtering category, the focus is automatically positioned on a next filtering category, e.g., the "DURATION" filtering category 1614*c*.

FIGS. 17A-17B are a flow diagram illustrating a method for displaying workout information in accordance with some embodiments. Method 1700 is performed at a device (e.g., 100, 300, 500, 600, 800, 1600) with a display. Some operations in method 1700 are, optionally, combined, the orders of some operations are, optionally, changed, and some operations are, optionally, omitted.

In some embodiments, the electronic device (e.g., 600, 800, 1600) is a computer system. The computer system is optionally in communication (e.g., wired communication, wireless communication) with a display generation component and with one or more input devices. The display generation component is configured to provide visual output, such as display via a CRT display, display via an LED display, or display via image projection. In some embodiments, the display generation component is integrated with the computer system. In some embodiments, the display generation component is separate from the computer system. The one or more input devices are configured to receive input, such as a touch-sensitive surface receiving user input.

In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

As described below, method 1700 provides an intuitive way for displaying workout information. The method reduces the cognitive burden on a user for displaying workout information, thereby creating a more efficient human-machine interface. For battery-operated computing devices, enabling a user to display camera views faster and more efficiently conserves power and increases the time between battery charges.

Computer system 1600 (e.g., an electronic device, a set top device; a digital media player) that is in communication with (e.g., wired communication, wireless communication) a display generation component and one or more input devices: causes display (1702), via the display generation component, of a user interface (e.g., 1612), wherein the user interface includes: a plurality of workout suggestions (e.g., workout suggestions displayed in region 1616*b*) displayed in a first region (e.g., 1616*b*) of the user interface, and one or more filtering options (e.g., 1622*a*-1622*h*, 1628*a*-1628*i*) (e.g., one or more workout types, trainers, durations, music options) for filtering workout suggestions displayed concurrently with the plurality of workout suggestions. In some embodiments, a workout suggestion corresponds to (e.g., represents) a workout (e.g., audio and/or video content that guides a user to perform a physical activity). In some embodiments, selecting a workout suggestion initiates a process for playback of a workout corresponding to the workout suggestion. In some embodiments, only a portion of the plurality of workout suggestions are displayed at a given time and scrolling within the user interface causes display of additional workout suggestions of the plurality of workout suggestions. Displaying the plurality of workout suggestions and one or more filtering options for filtering workout suggestions enables a user to quickly filter workouts and gain access to a particular workout, thereby reducing the number of inputs needed for selecting a workout. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Computer system 1600 detects (1704), via the one or more input devices, a first user input (e.g., 1623, 1625*c*, 1625*i*) (e.g., on a remote control, smartphone, tablet, and/or watch in communication with (e.g., operably connected to) the computer system) directed to a first filtering option (e.g., 1622*a*, 1622*e*, 1628*f*) of the one or more filtering options.

In accordance with a determination that the first user input directed to the first filtering option has been maintained for at least a predefined period of time (1706) (e.g., the focus selector has been maintained on the first filtering option without navigating away from the first filtering option for a predefined period of time (e.g., and without actively selecting (e.g., tapping on, clicking) the first filtering option)) (e.g., hovering on the first filtering option for a predefined period of time), computer system 1600 ceases to display (1708) at least a portion of the plurality of workout suggestions within the first region of the user interface, so that the first region of the user interface includes a first subset of workout suggestions (e.g., FIG. 16E depicting a subset of workout suggestions associated with filtering option 1622*a*, FIG. 16I depicting a subset of workout suggestions associated with filtering option 1622*e*, FIG. 16Q depicting a subset of workout suggestions associated with filtering option 1628*f*) from the plurality of workout suggestions that are associated with the first filtering option and does not include workout suggestions that are not associated with the first filtering option (e.g., satisfies the first filtering option) (in some embodiments, only a portion of the first subset of workout suggestions is displayed at a given time, and scrolling within the user interface causes display of additional workout suggestions of the first subset of workout suggestions). Ceasing display of at least a portion of the plurality of workout suggestions such that the user interface includes workout suggestions that are associated with the first filtering option enables a user to quickly view and gain access to a particular workout, thereby reducing the number of inputs needed for selecting a workout. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

While the first subset of workout suggestions is displayed in the first region (e.g., 1616*b*) of the user interface (1710), computer system 1600 detects (1712), via the one or more input devices, a second user input (e.g., 1625*d*, 1625*e*) (e.g., on a remote control, smartphone, tablet, and/or watch in communication with (e.g., operably connected to) the computer system) corresponding to navigation to a first workout suggestion (e.g., 1624*b*) of the first subset of workout suggestions.

In response to detecting the second user input (1714), computer system 1600 causes display (1716), via the display generation component, of a visual indication that the input is directed to the first workout suggestion (e.g., FIG. 16K-16L depicting movement/animation of workout suggestion 1624*b*) while display of the first subset of workout suggestions is maintained in the first region (e.g., 1616*b*) of the user interface.

In some embodiments, while causing display of the first subset of workout suggestions in the first region (e.g., 1616*b*) of the user interface (1718), computer system 1600 detects (172), via the one or more input devices, a third user input (e.g., 1625*c*) (e.g., on a remote control, smartphone, tablet, and/or watch in communication with (e.g., operably connected to) the computer system) directed to a second filtering option (e.g., 1622*e*) of the one or more filtering options.

In some embodiments, in accordance with a determination that the input directed to the second filtering option has been maintained for at least a second predefined period of time (1722) (e.g., the focus selector has been maintained on the second filtering option without navigating away from the second filtering option for a second predefined period of time (e.g., a predetermined period of time that is the same as the predetermined period of time) (e.g., and without actively selecting (e.g., tapping on, clicking) the second filtering option)) (e.g., hovering on the second filtering option for a predefined period of time), computer system 1600 ceases to display (1724) at least a portion of the first subset of workout suggestions (e.g., FIGS. 16H-16I, depicting replacement of a first set of workout suggestions associated with "CORE" filtering option 1622*a* with a second set of workout suggestions associated with "HIIT" filtering option 1622*e*), so that the first region of the user interface includes a second subset of workout suggestions from the plurality of workout suggestions that are associated with the second filtering option and does not include workout suggestions that are not associated with the second filtering option (e.g., satisfies the second filtering option). In some embodiments, only a portion of the second subset of workout suggestions is displayed at a given time, and scrolling within the user interface causes display of additional workout suggestions of the second subset of workout suggestions. Ceasing display of at least a portion of the first subset of workout suggestions so that the first region of the user interface includes a second subset of workout suggestions from the plurality of workout suggestions that are associated with the second filtering option enables a user to quickly view and gain access to a particular workout, thereby reducing the number of inputs needed for selecting a workout. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the one or more filtering options (e.g., 1622*a*-1622*h*) are grouped into a first filtering category (e.g., 1614*a*) (e.g., filtering categories can include workout type, trainer, duration, music genre), the first filtering category is one of a plurality of filtering categories (e.g., 1614*a*-1614*d*) (e.g., workout type, trainer, duration, music genre), and the first filtering category (e.g., 1614*a*) includes a plurality of filtering options (e.g., 1622*a*-1622*h*) and a second filtering category (e.g., 1614*b*) of the plurality of filtering categories includes a plurality of filtering options (e.g., 1628*a*-1628*i*) (1726). In some embodiments, each filtering category of the plurality of filtering categories comprises a plurality of filtering options (e.g., the "workout type" filtering category includes a plurality of workout types, the "trainer" filtering category includes a plurality of trainers, the "duration" filtering category includes a plurality of workout durations, the "music genre" filtering category includes a plurality of music genres). Grouping filtering options into various filtering categories enables a user to quickly gain access to and apply filtering options, thereby reducing the number of inputs needed to apply a filtering option. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while causing display of the one or more filtering options of the first filtering category in the user interface, computer system 1600 detects a fourth user input (e.g., 1625*g*) (e.g., a selection of a different filtering category).

In some embodiments, in response to detecting the fourth user input, computer system 1600 causes ceasing of display of the one or more filtering options of the first filtering category (e.g. in FIG. 16N, filtering options 1622a-1622h are no longer displayed).

In some embodiments, computer system 1600 causes, via the display generation component, display of the plurality of filtering categories (e.g., in FIG. 16N, filtering categories 1614a-1614d are displayed) (e.g., workout type, trainer, duration, music genre/type) including the first filtering category.

In some embodiments, computer system 1600 detects a fifth user input (e.g., 1625h) corresponding to selection of a second filtering category from the plurality of filtering categories (e.g., tapping on the second filtering category, clicking on the second filtering category).

In some embodiments, in response to detecting the fifth user input (e.g., 1625h), computer system 1600 causes the second filtering category to be expanded so that a second plurality of filtering options of the second filtering category are displayed (e.g., in FIG. 16O, filtering options 1628a-1628i are displayed). In some embodiments, causing the second filtering category to be expanded so that the second plurality of filtering options of the second filtering category are displayed comprises causing replacement of display of the plurality of filtering categories with display of the second plurality of filtering options. Ceasing display of filtering options in one filtering category before displaying filtering options in a different category allows a user to more efficiently navigate and apply filtering options, thereby reducing the number of inputs needed to apply filtering options. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the fourth user input corresponds to selection of the first filtering option of the one or more filtering options (e.g., tapping on the first filtering option, clicking on the first filtering option) (e.g., 1625g in FIG. 16M). Ceasing display of the one or more filtering options of the first category and causing display of the plurality of filtering categories in response to a user selection of a first filtering option within the first category allows a user to more quickly and efficiently navigate filtering options with fewer inputs. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in response to the first user input (e.g., 1623), computer system 1600 maintains display of the one or more filtering options of the first filtering category (e.g., FIGS. 16C-16E, display of filtering options 1622a-1622h is maintained). Maintaining display of one or more filtering options prior to selection of a filtering options, and then ceasing display of the one or more filtering options and causing display of the plurality of filtering categories in response to a user selection of a first filtering option allows a user to more quickly and efficiently navigate filtering options in multiple filtering categories with fewer inputs. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in response to detecting the fifth user input (e.g., 1625h) and in accordance with a determination that a third filtering option (e.g., a trainer filtering option) (e.g., 1628g, 1628h, 1628i) of the second plurality of filtering options (e.g., 1628a-1628i) is incompatible with a set of currently applied filtering options (e.g., in FIG. 16O, a "HIIT" filtering option is applied) (e.g., a selected filtering option from the first filtering category) (in some embodiments, no workout suggestions associated with the third filtering option are also associated with the currently applied filtering options, there is no overlap between the subset of workout suggestions that are associated with the third filtering option and the subset of workout suggestions that are associated with the currently applied filtering options), and while the second plurality of filtering options of the second filtering category are displayed, computer system 1600 causes display, via the display generation component, of a visual indication that the third filtering option is incompatible with the set of currently applied filtering options (e.g., filtering options 1628g-1628i in FIG. 16O are visually distinct from filtering options 1628a-1628f) (e.g., displaying the third filtering option in a particular visual style indicative of the third filtering option being incompatible with the currently applied filtering options (e.g., as a "grayed out" or otherwise visually deemphasized option), displaying the third filtering option separately from one or more filtering options that are compatible with the currently applied filtering options (e.g., that have associated workout suggestions that are also associated with the currently applied filtering options)). In some embodiments, based on the determination that the third filtering option is incompatible with the set of currently applied filtering options, the third filtering option is unavailable for selection by a user. In some embodiments, the third filtering option is still selectable, but selection of the third filtering option results in the currently applied filtering options being removed (e.g., the currently applied filtering options are removed, and the third filtering option is applied). Displaying a visual indication that a particular filtering option is incompatible with the set of currently applied filtering options allows a user to more quickly and efficiently navigate and apply filtering options with fewer inputs. Otherwise, a user may spend one or more inputs attempting to apply filtering options that are incompatible with currently applied filtering options. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in response to detecting the fourth user input (e.g., 1625g), computer system 1600 causes display, via the display generation component, of a selectable user interface object (e.g., selectable option, affordance) (e.g., 1626) that indicates that the first filtering option has been selected and applied, wherein the selectable user interface object, when selected, removes application of the first filtering option (e.g., selection of the selectable user interface object results in the first region of the user interface including workout suggestions that are not associated with the first filtering option). Displaying selectable user interface objects that can be selected to remove application of an applied filtering option allows a user to more quickly and efficiently remove application of applied filtering options with fewer inputs. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, after detecting the first user input and in accordance with a determination that the first user input directed to the first filtering option has not been maintained for at least the predefined period of time (e.g., the focus selector has not been maintained on the first filtering option for the predefined period of time (e.g., the focus selector has been navigated away from the first filtering option before the predefined period of time has elapsed)), computer system 1600 maintains display, via the display generation component, of the plurality of workout suggestions in the first region of the user interface (e.g., FIGS. 16E-16F, user input 1625*a* does not cause a change in the plurality of workout suggestions shown in region 1616*b*) (e.g., maintaining display of the plurality of workout suggestions in the first region of the user interface such that the first region of the user interface remains unchanged). Maintaining display of workout suggestions when a user input has not been maintained for at least a predefined period of time reduces the number of times the objects and/or components displayed in a user interface must be updated or changed. Reducing unnecessary visual changes in a UI makes the user-device interface more efficient (e.g., by minimizing visual confusion and helping the user to provide proper inputs and reducing user mistakes when operating/interacting with the device) which, additionally, reduces power usage and improves battery life of the device by enabling the user to use the device more quickly and efficiently.

In some embodiments, each filtering option of the one or more filtering options is associated with a respective workout trainer of one or more workout trainers (e.g., trainer filtering options 1628*a*-1628*i*). In some embodiments, the first filtering option is associated with a first workout trainer of the one or more workout trainers. In some embodiments, ceasing to display at least a portion of the plurality of workout suggestions within the first region of the user interface comprises ceasing to display workout suggestions that are not associated with the first workout trainer (e.g., FIG. 16Q), so that the first region of the user interface includes a first subset of workout suggestions from the plurality of workout suggestions that are associated with the first workout trainer and does not include workout suggestions that are not associated with the first workout trainer. Ceasing display of workout suggestions that are not associated with the first workout trainer provides the user with feedback as to which workouts correspond to the selected trainer. Providing improved feedback to the user enhances the operability of the device and makes the user-device interface more efficient (e.g., by helping the user to provide proper inputs and reducing user mistakes when operating/ interacting with the device) which, additionally, reduces power usage and improves battery life of the device by enabling the user to use the device more quickly and efficiently.

In some embodiments, causing display of a visual indication that the input is directed to the first workout suggestion while display of the first subset of workout suggestions is maintained in the first region of the user interface comprises causing display, via the display generation component, of a preview video associated with the first workout suggestion while display of the first subset of workout suggestions is maintained in the first region of the user interface (e.g., FIGS. 16K-16L). In some embodiments, the preview video comprises video and/or audio footage of a workout trainer associated with the workout suggestion. In some embodiments, the preview video associated with the first workout suggestion comprises selected portions of the first workout suggestion. In some embodiments, each workout suggestion of the plurality of workout suggestions is associated with a respective preview video, and each preview video has the same, predetermined duration. Causing display of the preview video associated with the first workout suggestion provides the user with feedback about the current state of the device (e.g., the device has detected a user input directed to the first workout suggestion). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the user interface (e.g., 1612) further includes a second selectable user interface object (e.g., selectable option, affordance) (e.g., 1617) that, when selected, removes one or more (or all) applied filtering options In some embodiments, selection of the selectable user interface object results in the first region of the user interface including an unfiltered (e.g., complete) listing of available workout suggestions. Providing a selectable user interface object that can be selected to remove application of an applied filtering option allows a user to more quickly and efficiently remove application of applied filtering options with fewer inputs. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Note that details of the processes described above with respect to method 1700 (e.g., FIGS. 17A-17B) are also applicable in an analogous manner to the methods described below. For example, method 1900 optionally includes one or more of the characteristics of the various methods described above with reference to method 1700. For example, the workout suggestion user interfaces as discussed below with respect to method 1900 may include various browsing and filtering features, as set forth in method 1700. For brevity, these details are not repeated below.

FIGS. 18A-18V illustrate exemplary user interfaces for displaying workout information, in accordance with some embodiments. The user interfaces in these figures are used to illustrates the processes described below, including the processes in FIGS. 19A-19C.

FIGS. 18A-18V illustrate exemplary devices and user interfaces. At FIG. 18A, computer system 1600 (e.g., device 100, 300, 500) is displaying a home screen user interface 1810 on display 1601 (e.g., a television) that includes selectable graphical user interface objects for launching one or more different applications or viewing different content. In some embodiments, display 1601 is an integrated part of computer system 1600. In some embodiments, computer system 1600 is in communication (e.g., wireless, wired) with display 1601 (e.g., as depicted in FIG. 18A) (e.g., the computer system is a set top box or computer that is in communication with display 1601).

FIG. 18A also illustrates remote control 1602, which is configured to transmit data (e.g., via RF communication, via Bluetooth, via infrared) to computer system 1600 based on user input that is detected at remote control 1602. Remote control 1602 includes a selection region 1604a, which includes a touch-sensitive surface for detecting tap, press, and swipe gestures, a menu button 1604b, a television button 1604c, a microphone button 1604d, a play/pause button 1604e, and volume control buttons 1604f.

Figure 18B:
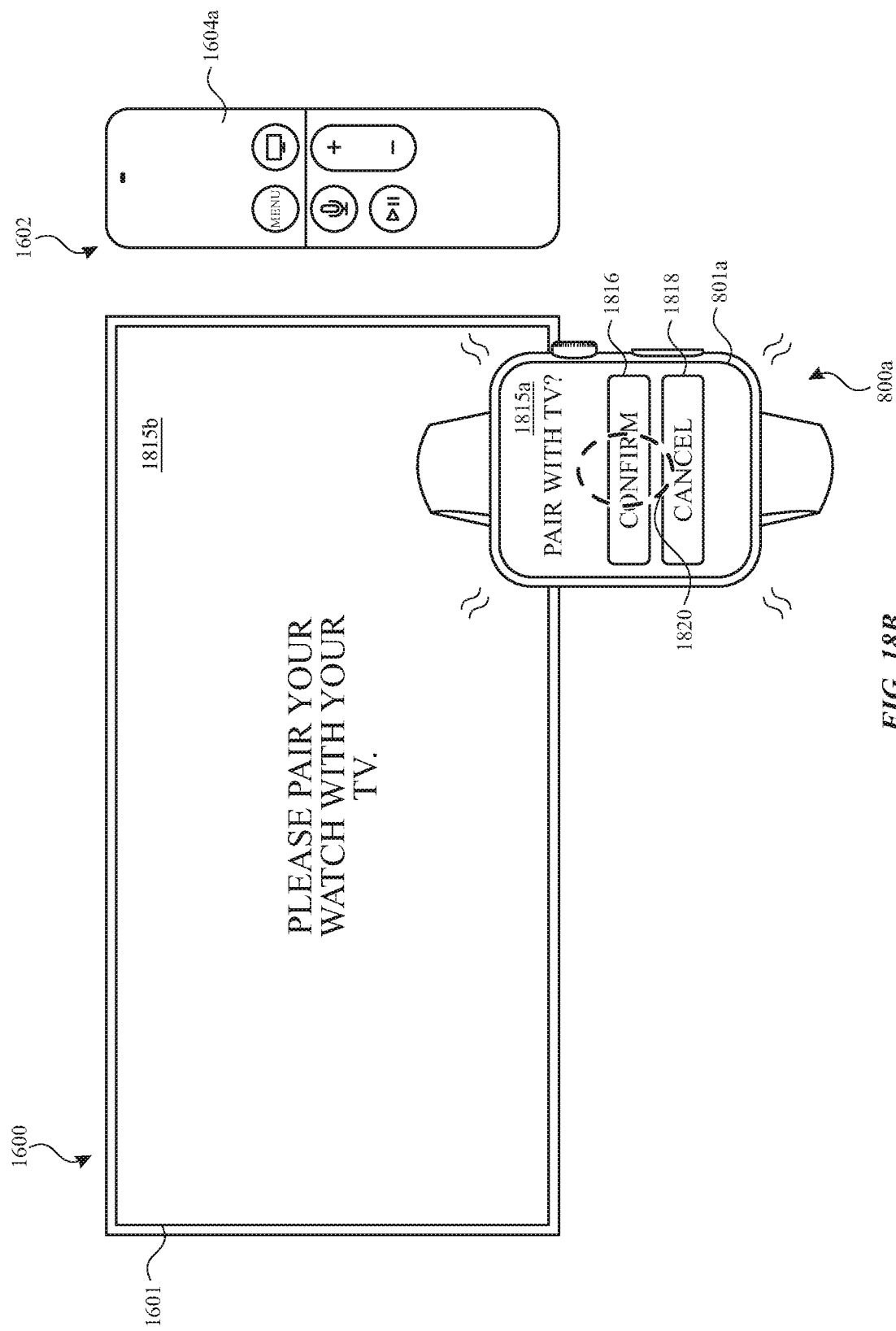
Figure 18C:
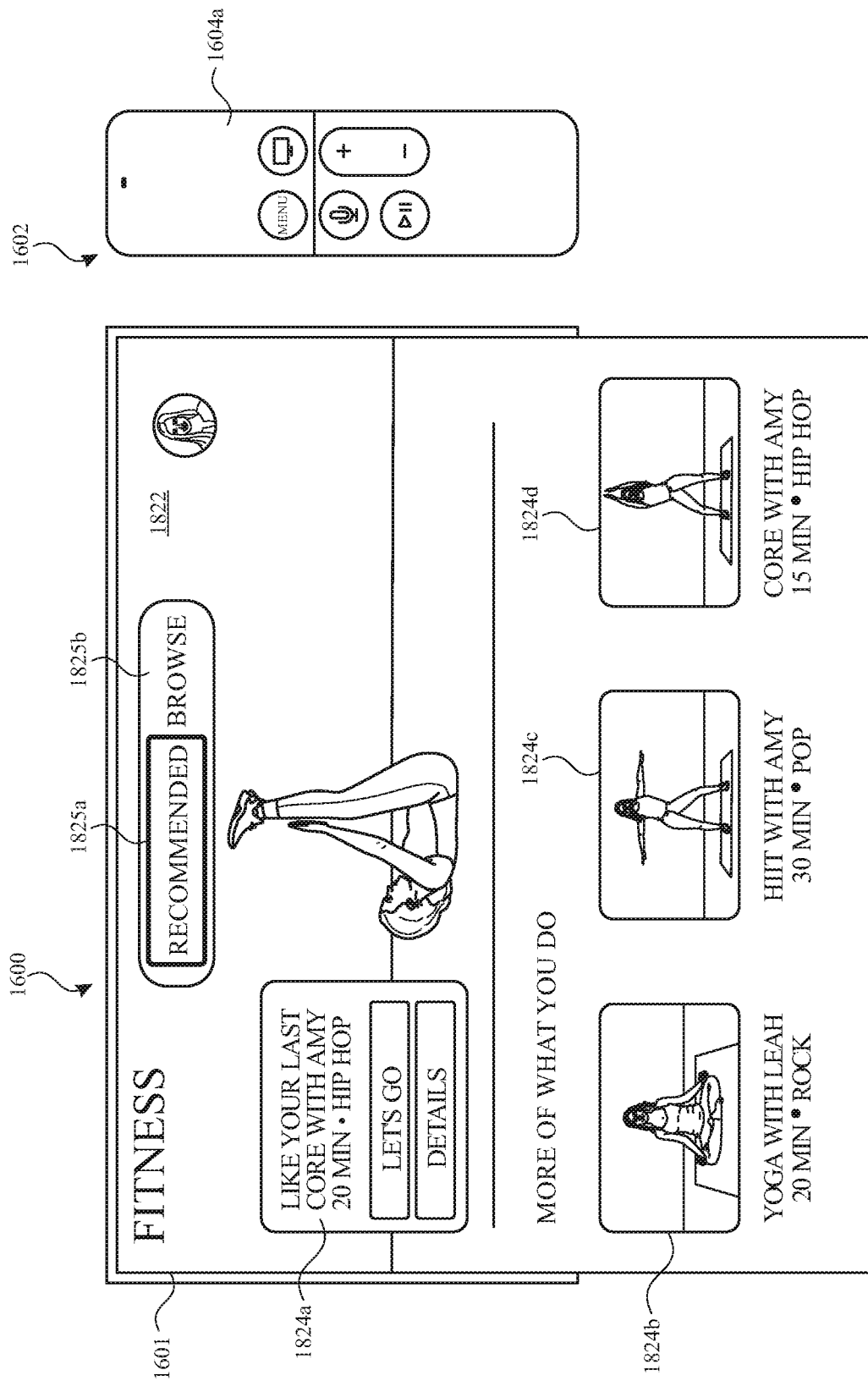

FIGS. 18A-18C depict an example scenario 1802, in which a user is automatically presented with a personalized workout user interface. In the example scenario 1802, a determination is made by computer system 1600 that there is a single recognized user (1806a) within a proximity of computer system 1600 (e.g., there is a single recognized (e.g., previously paired) electronic device associated with a user within a proximity of the computer system). Based on that determination, computer system 1600 displays a personalized workout user interface for that recognized user. More details will now be provided with reference to FIGS. 18A-18C.

At FIG. 18A, computer system 1600 causes display 1601 to display a home screen user interface 1810. Home screen user interface 1810 includes application representations 1812a-1812d that are selectable by a user to open a corresponding application.

FIG. 18A also depicts a scenario 1802 in which a user 1806a is in the same room as computer system 1600. User 1806a is wearing an electronic device 800a (e.g., device 800) (e.g., a watch). Computer system 1600 determines that there is one device (e.g., a device of a particular type (e.g., one watch)) that is within a predefined proximity of computer system 1600 (e.g., in the same room, within a threshold distance, etc.). Furthermore, in scenario 1802, computer system 1600 also determines that the device 800a has previously been paired with computer system 1600 (e.g., the user 800a has previously caused device 800a to connect to (e.g., wirelessly) computer system 1600)).

In home screen user interface 1810 as depicted in FIG. 18A, a focus is on application representation 1812a that corresponds to a fitness application. While computer system 1600 causes display, via display 1601, of home screen user interface 1810 with the focus on application representation 1812a, remote control 1602 detects activation of selection region 1604a via button press input 1814 corresponding to selection of application representation 1812a, and transmits an indication of the input to computer system 1600. Computer system 1600 receives, from remote control 1602, the indication of input 1814 corresponding to selection of application representation 1812a.

At FIG. 18B, in response to detecting (e.g., receiving the indication of) input 1814, and based on (e.g., in response to, in accordance with) the determination that there is a single device 800a that is within the predefined proximity of computer system 1600, and further based on (e.g., in response to, in accordance with) the determination that the single device 800a is a recognized device that has previously been paired with computer system 1600, computer system 1600 causes device 800a to display, via display 801a, a notification 1815a. The notification 1815a requests confirmation from user 800a that the user would like to pair device 800a with computer system 1600. Notification 1815a includes option 1816 to confirm pairing of device 800a with computer system 1600, and option 1818 to cancel pairing. In some embodiments, computer system 1600 also causes device 800a to output a haptic output to notify the user of notification 1815a. In response to input 1814 and based on the determination that there is a single previously-paired device within the proximity of computer system 1600, computer system 1600 also causes display 1601 to display notification 1815b instructing the user to pair their device with computer system 1600.

In FIG. 18B, electronic device 800a detects an input 1820 corresponding to the location of option 1816 indicating confirmation of the user's intent to pair device 800a with computer system 1600. Device 800a transmits an indication of the input to computer system 1600. Computer system 1600 receives, from device 800a, the indication of input 1820. In some embodiments, rather than requiring a single tap to confirm pairing of device 800a with computer system 1600, computer system 1600 can require entry of additional information, such as a PIN number, to confirm pairing (e.g., as shown in FIG. 18M).

At FIG. 18C, in response to detecting (e.g., receiving the indication of) input 1820, computer system 1600 causes display 1601 to display a new user interface. Furthermore, based on (e.g., in response to, in accordance with) the determination that there is a single previously-paired device 800a (e.g., a single previously-paired device of a particular type (e.g., a watch)) that is within the predefined proximity of computer system 1600, computer system 1600 causes display, via display 1601, of a workout user interface 1822 that is associated with device 800a and/or user 1806a. Workout user interface 1822 has substantially similar functionality to workout user interface 1606 of FIG. 16A. Workout user interface 1822 includes workout suggestions 1824a-1824d for a user (e.g., user 1806a). In some embodiments, workout user interface 1822 is associated with electronic device 800a in that electronic device 800a is associated with user 1806a, and workout suggestions 1824a-1824d are selected based on one or more workouts that have been completed by user 1806a. For example, workout suggestion 1824a represents a workout that shares one or more characteristics with a subset of workouts completed by user 1806a (e.g., the most recently completed workout). In the depicted scenario, user 1806a most recently completed a core workout with trainer Amy. Accordingly, computer system 1600 provides workout suggestion 1824a, as it represents a workout that has a shared characteristic with user 1806a's most recently completed workout (e.g., workout suggestion 18024a has the same type of workout (core) as the user's most recently completed workout, workout suggestion 18024a has the same trainer (Amy) as the user's most recently completed workout). Workout user interface 1822 also includes option 1825a, which is selectable to present workout user interface 1822, and option 1825b, which is selectable to present a different workout browse user interface (e.g., user interface 1612 of FIG. 16B).

Whereas FIGS. 18A-18C demonstrate a scenario in which a single recognized device is identified, FIGS. 18D-18H demonstrate a scenario in which multiple recognized (e.g., previously-paired) devices are identified as being within a proximity of computer system 1600.

Figure 18D:
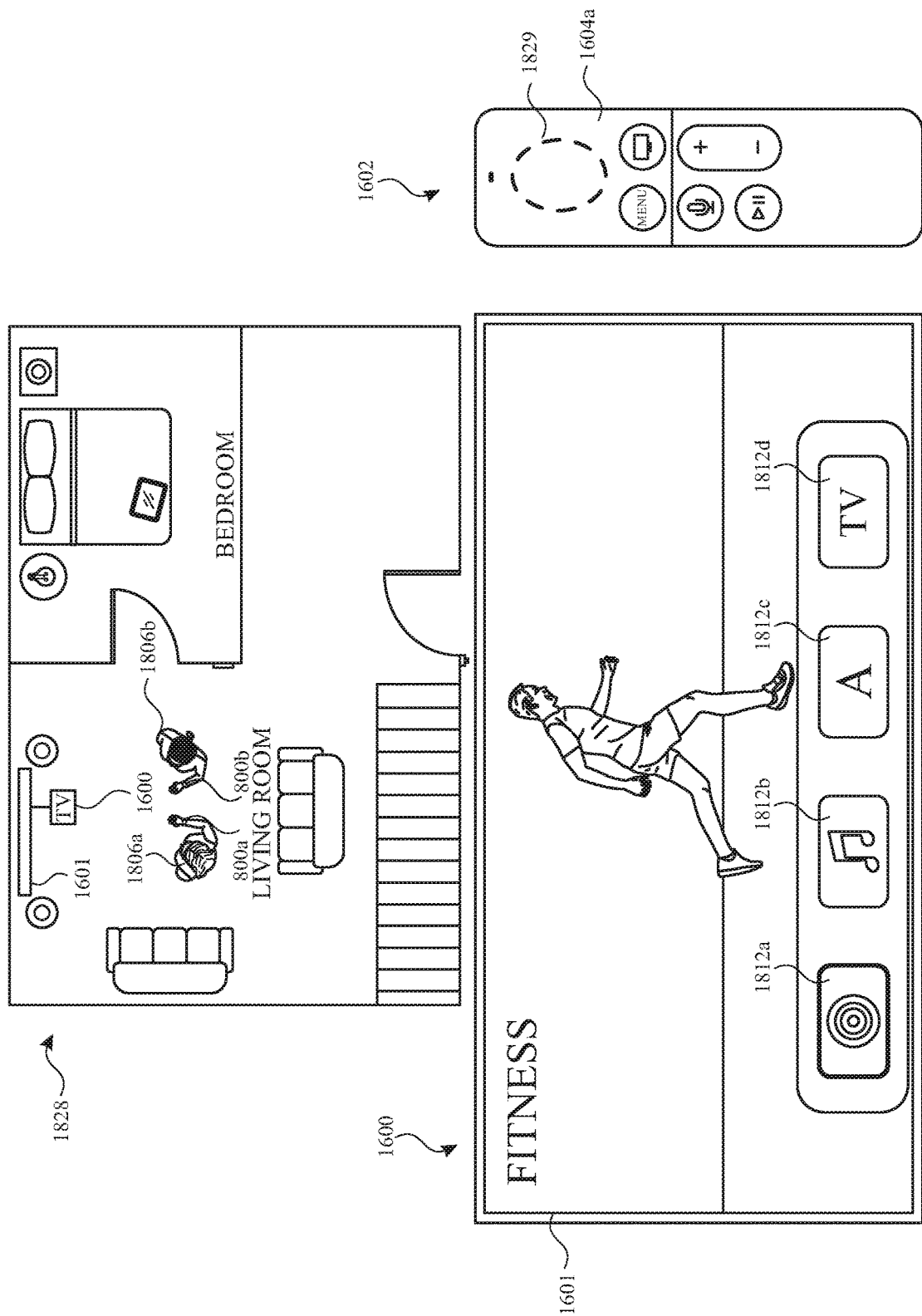

At FIG. 18D, computer system 1600 causes display 1601 to display home screen user interface 1810.

FIG. 18D also depicts a scenario 1828 in which two users 1806a, 1806b are in the same room as computer system

1600. User 1806*a* is wearing an electronic device 800*a* (e.g., device 800) (e.g., a watch) and user 1806*b* is wearing an electronic device 800*b* (e.g., device 800) (e.g., a watch). Computer system 1600 determines that there are multiple (e.g., two) devices (e.g., devices of a particular type (e.g., two watches)) that are within a predefined proximity of computer system 1600 (e.g., in the same room, within a threshold distance, etc.). Furthermore, in scenario 1828, computer system 1600 also determines that both devices 800*a*, 800*b* have previously been paired with computer system 1600.

In home screen user interface 1810 as depicted in FIG. 18D, the focus is on application representation 1812*a* that corresponds to a fitness application. While computer system 1600 causes display, via display 1601, of home screen user interface 1810 with the focus on application representation 1812*a*, remote control 1602 detects activation of selection region 1604*a* via button press input 1829 corresponding to selection of application representation 1812*a*, and transmits an indication of the input to computer system 1600. Computer system 1600 receives, from remote control 1602, the indication of input 1829 corresponding to selection of application representation 1812*a*.

At FIG. 18E, in response to detecting (e.g., receiving the indication of) input 1829, and based on (e.g., in response to, in accordance with) the determination that there is are multiple recognized (e.g., previously-paired) devices 800*a*, 800*b* that are within the predefined proximity of computer system 1600, computer system 1600 causes device display 1601 to replace display of home screen user interface 1810 with disambiguation user interface 1830. Disambiguation user interface 1830 includes three selectable options 1832*a*, 1832*b*, 1832*c*. Option 1832*a* is associated with (e.g., corresponds to) user 1806*b* and device 800*b*, and is presented based on a determination that device 800*b* is within the predefined proximity of computer system 1600. Option 1832*a*, when selected, presents a workout user interface associated with user 1806*b* and device 800*b*. Option 1832*b* is associated with (e.g., corresponds to) user 1806*a* an device 800*a*, and is presented based on a determination that device 800*a* is within the predefined proximity of computer system 1600. Option 1832*b*, when selected, presents a workout user interface associated with user 1806*a* and device 800*a*. Option 1832*c* is selectable to pair a new device that has not been previously paired with computer system 1600.

In FIG. 18E, the focus is on option 1832*b*, and remote control 1602 detects activation of selection region 1604*a* via button press input 1834 corresponding to selection of option 1832*b*. Remote control 1602 transmits an indication of the input to computer system 1600. Computer system 1600 receives, from remote control 1602, the indication of input 1834.

Figure 18F:
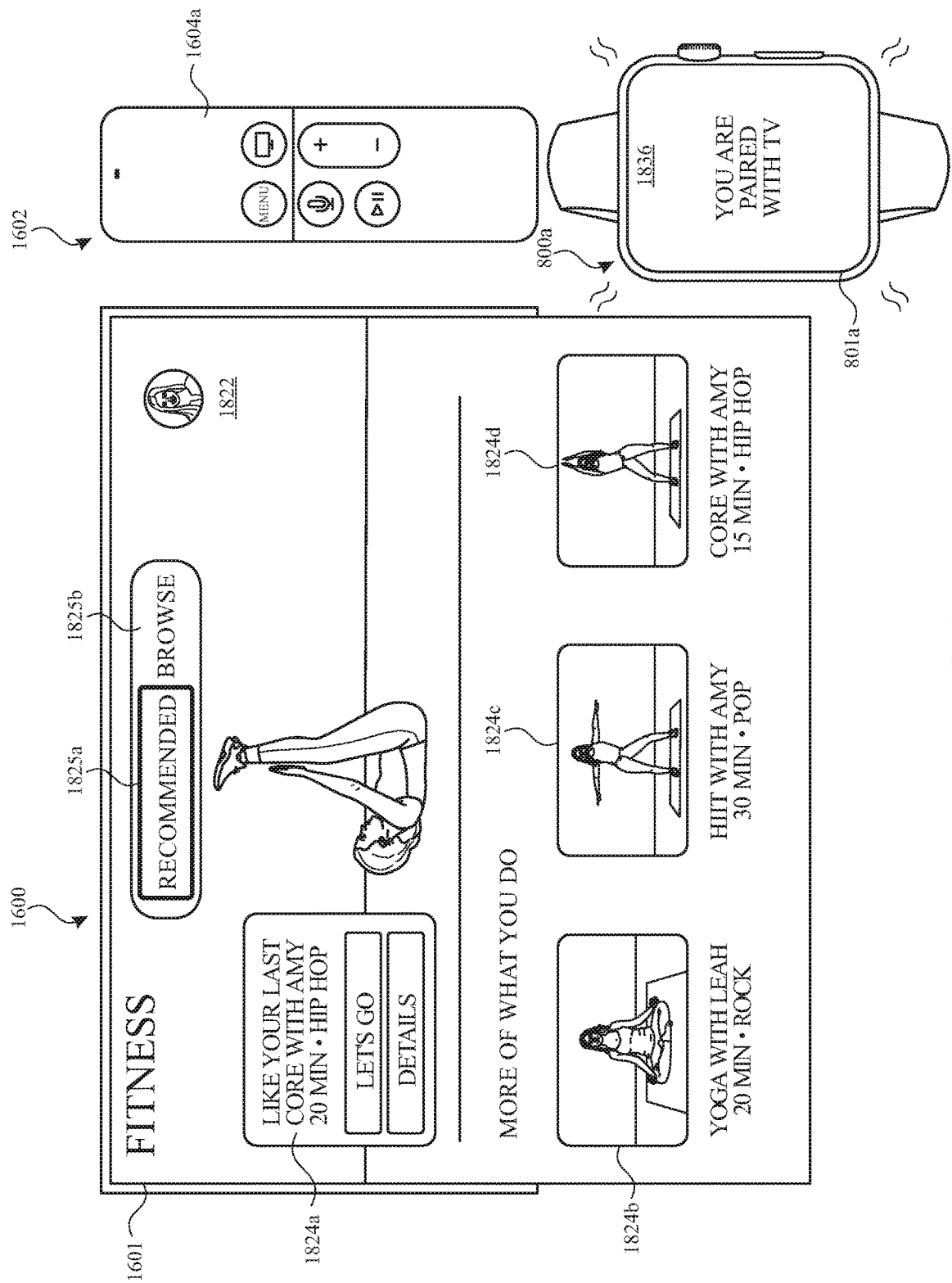

At FIG. 18F, in response to detecting (e.g., receiving the indication of) input 1834, computer system 1600 causes replacement of display of disambiguation user interface 1830 with workout user interface 1822. Workout user interface 1822 is the same as workout user interface 1822 in FIG. 18C. As discussed above with reference to FIG. 18C, workout user interface 1822 is associated with (e.g., corresponds to, is personalized for) user 1806*a* and device 800*a*. For example, workout suggestions 1824*a*-1824*d* presented in workout user interface 1822 are selected based on one or more workouts that have been completed by user 1806*a*.

In response to detecting input 1834, computer system 1600 also causes device 800*a* to display a notification 1836 and output a haptic output confirming that device 800*a* has been paired with computer system 1600. In some embodiments, before causing display of user interface 1822, computer system 1600 causes display of a notification on device 800*a* confirming that the user would like to pair device 800*a* with computer system 1600 (as was shown in FIG. 18B).

Figure 18G:
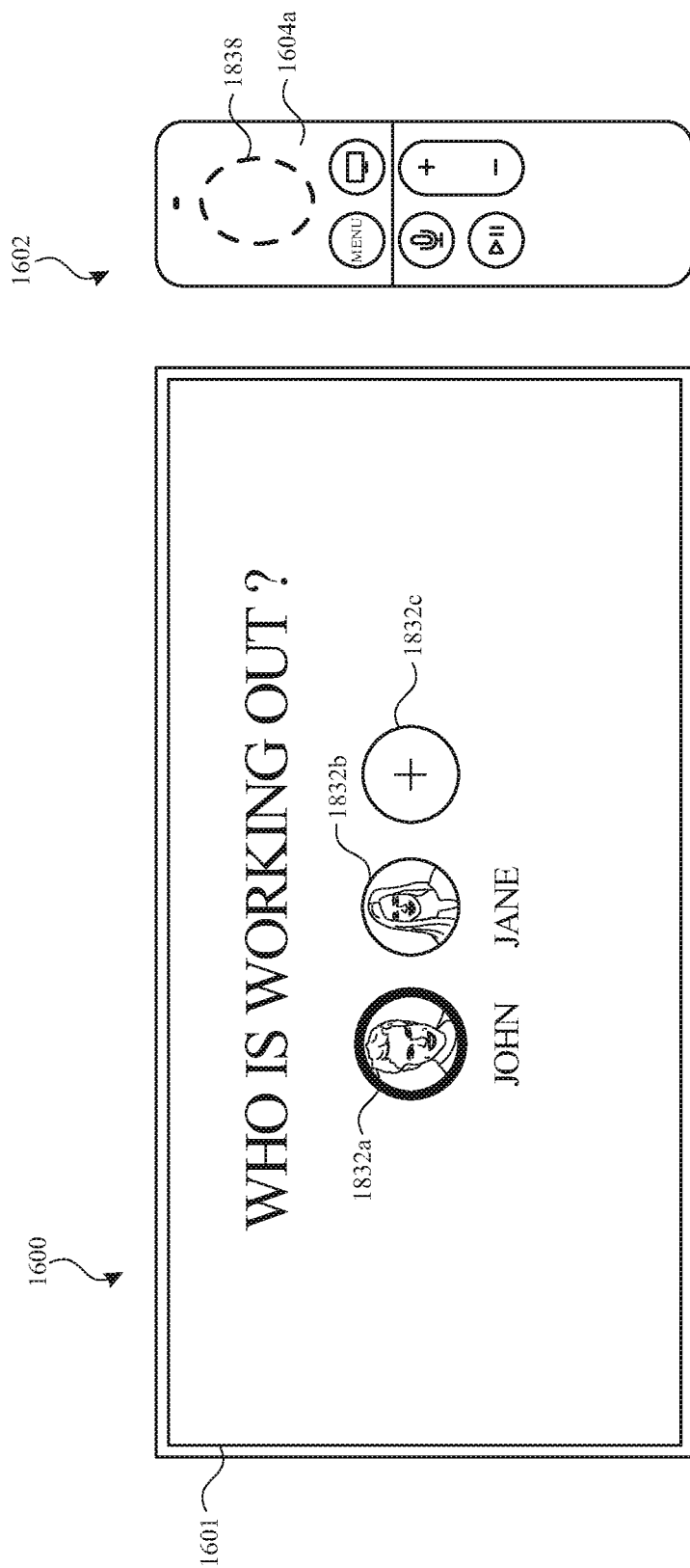

In FIG. 18G, returning to disambiguation user interface 1830, the focus is on option 1832*a*, and remote control 1602 detects activation of selection region 1604*a* via button press input 1838 corresponding to selection of option 1832*a*. Remote control 1602 transmits an indication of the input to computer system 1600. Computer system 1600 receives, from remote control 1602, the indication of input 1838.

Figure 18H:
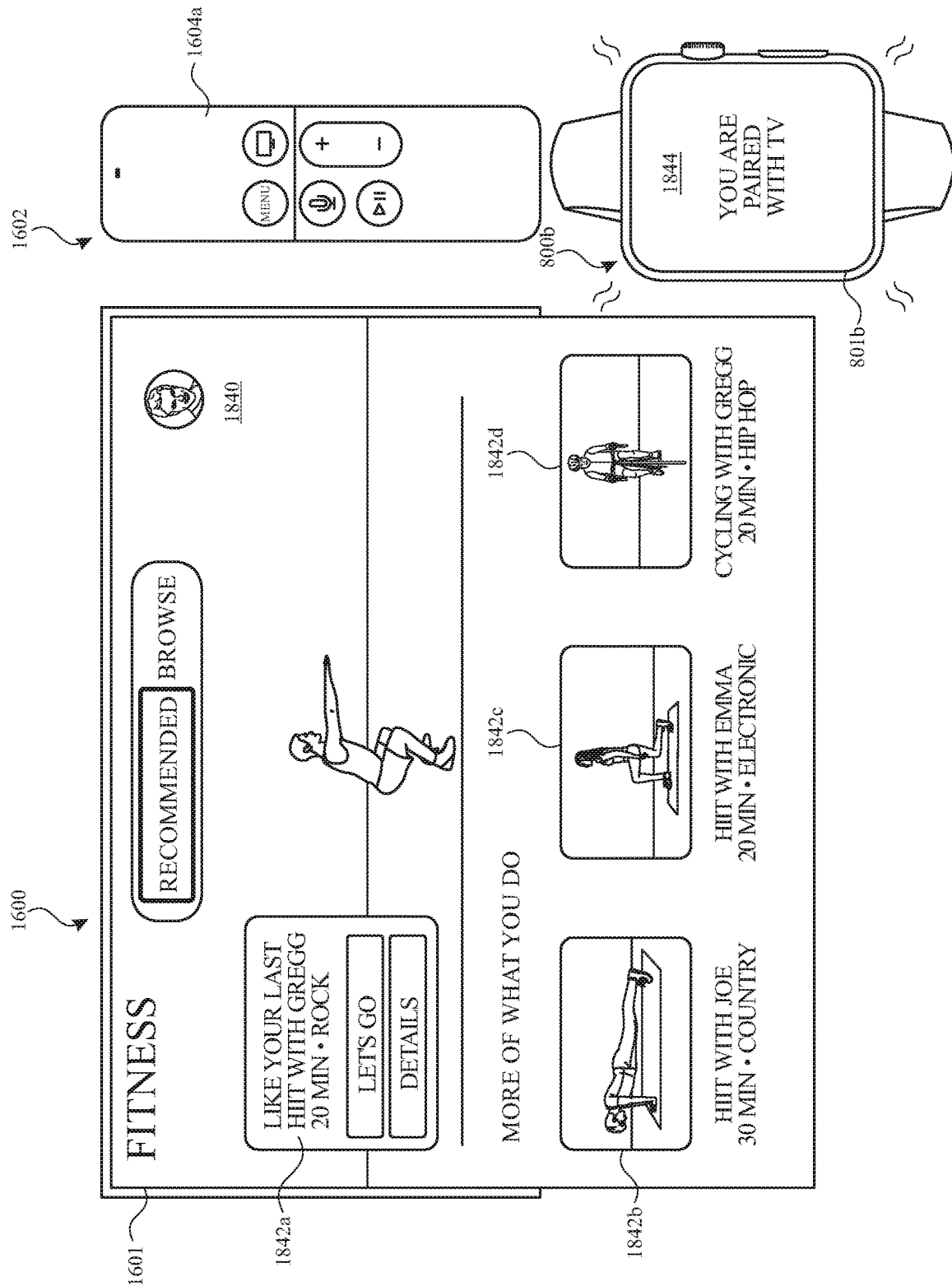

At FIG. 18H, in response to detecting (e.g., receiving the indication of) input 1838, computer system 1600 causes replacement of display of disambiguation user interface 1830 with workout user interface 1840. Functionality of user interface 1840 is substantially the same as workout user interface 1822 in FIGS. 18C and 18F. Workout user interface 1840 is associated with (e.g., corresponds to, is personalized for) user 1806*b* and device 800*b*. For example, workout suggestions 1842*a*-1842*d* presented in workout user interface 1840 are selected based on one or more workouts that have been completed by user 1806*a*.

In response to detecting input 1838, computer system 1600 also causes device 800*b* to display a notification 1844 and output a haptic output confirming that device 800*b* has been paired with computer system 1600. In some embodiments, before causing display of user interface 1840, computer system 1600 causes display of a notification on device 800*a* confirming that the user would like to pair device 800*b* with computer system 1600 (similar to notification 1815*a* shown in FIG. 18B).

Whereas FIGS. 18A-18C demonstrate a scenario in which a single recognized device (e.g., a smartphone or smart watch or other device that is associated with a particular user) is identified, and FIGS. 18D-18H demonstrate a scenario in which multiple recognized (e.g., previously-paired) devices are identified as being within a proximity of computer system 1600, FIGS. 18I-18N demonstrate a scenario in which one or more devices are within a proximity of computer system 1600, but none of the devices are recognized devices (e.g., none of the devices have been previously-paired with computer system 1600). In some embodiments, the recognized device is a device that includes one or more sensors (e.g., biometric sensors such as heart rate or blood oxygenation sensors or motion sensors such as gyroscopes or accelerometers) that enable more accurate tracking of user activity levels during a workout.

Figure 18I:
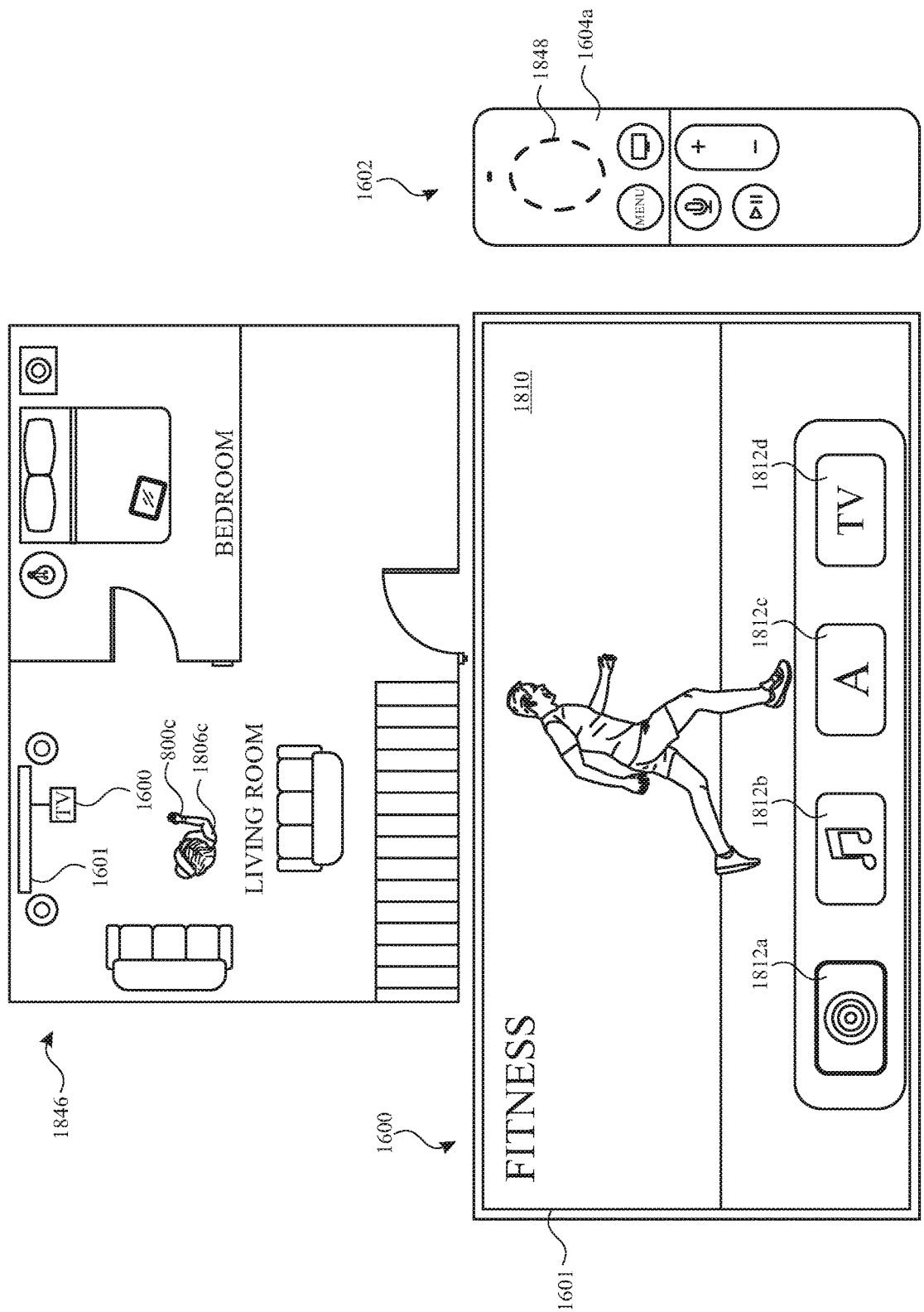

At FIG. 18I, computer system 1600 causes display 1601 to display home screen user interface 1810.

FIG. 18I also depicts a scenario 1846 in which a user 1806*c* is in the same room as computer system 1600. User 1806*c* is wearing an electronic device 800*c* (e.g., device 800) (e.g., a watch). Computer system 1600 determines that there is a single device 800*c* within a predefined proximity of computer system 1600 (e.g., in the same room, within a threshold distance, etc.), but also determines that device 800*c* has not been previously paired with computer system 1600.

In home screen user interface 1810 as depicted in FIG. 18I, the focus is on application representation 1812*a* that corresponds to a fitness application. While computer system 1600 causes display, via display 1601, of home screen user interface 1810 with the focus on application representation 1812*a*, remote control 1602 detects activation of selection region 1604*a* via button press input 1848 corresponding to selection of application representation 1812*a*, and transmits an indication of the input to computer system 1600. Computer system 1600 receives, from remote control 1602, the indication of input 1848 corresponding to selection of application representation 1812*a*.

Figure 18J:
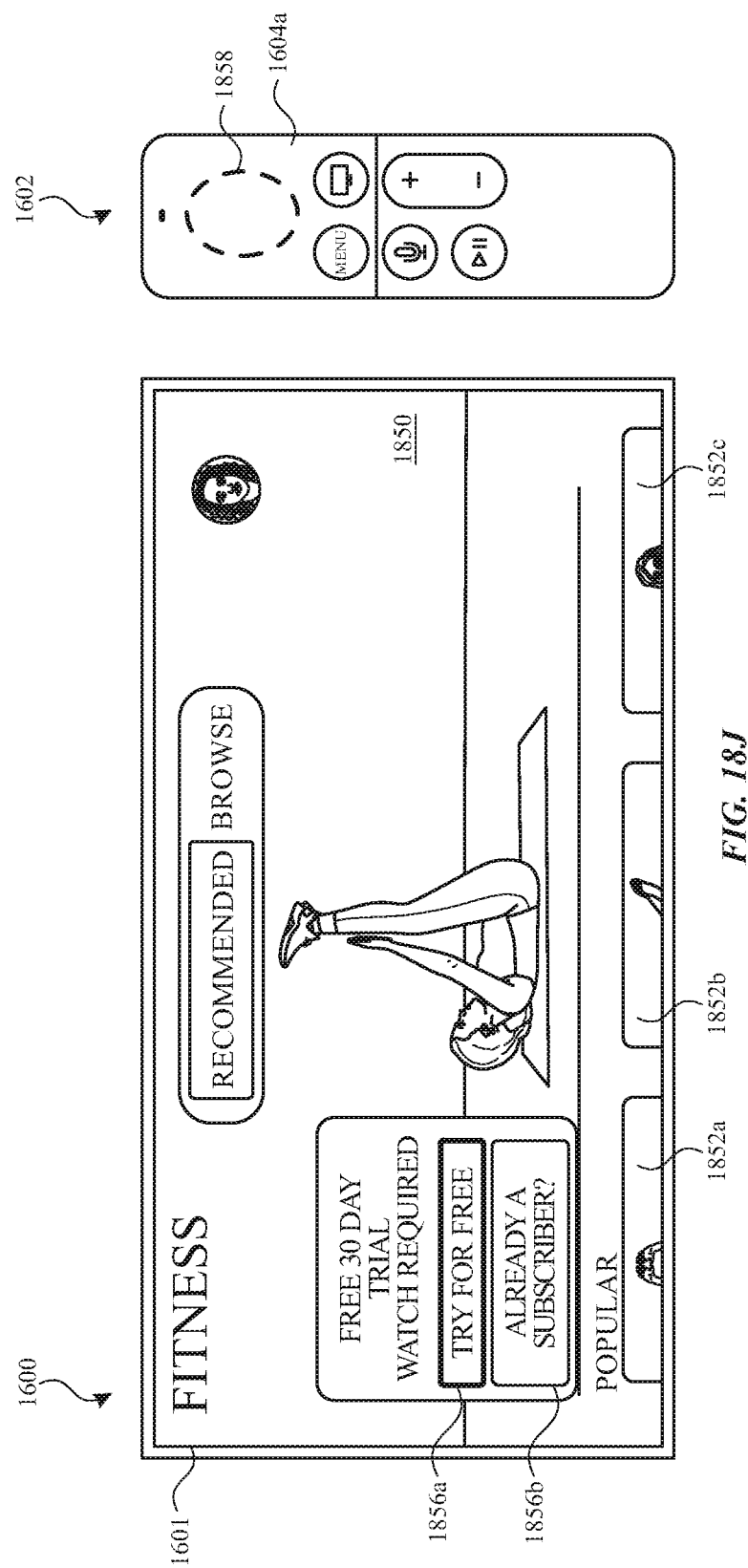

At FIG. 18J, in response to detecting (e.g., receiving the indication of) input 1848, and based on (e.g., in response to, in accordance with) the determination that there is are no recognized (e.g., previously-paired) devices that are within the predefined proximity of computer system 1600, computer system 1600 causes display 1601 to replace display of home screen user interface 1810 with logged-out workout user interface 1850. In contrast to workout user interfaces 1822, 1840 discussed above, logged-out workout user interface 1850 is not associated with any particular user or user account. User interface 1850 displays workout suggestions 1852*a*-1852*c*, but workout suggestions 1852*a*-1852*c* may not be selectable by a user until the user logs into and/or signs up for a fitness application account. User interface 1850 provides option 1856*a* that is selectable to sign up for a free trial of the fitness application, and option 1856*b* that is selectable to log in to a fitness application account if the user already has an account.

In FIG. 18J, the focus is on option 1856*a*. While computer system 1600 causes display of user interface 1850 with the focus on option 1856*a*, remote control 1602 detects activation of selection region 1604*a* via button press input 1858 corresponding to selection of option 1856*a*, and transmits an indication of the input to computer system 1600. Computer system 1600 receives, from remote control 1602, the indication of input 1858 corresponding to selection of option 1856*a*.

Figure 18K:
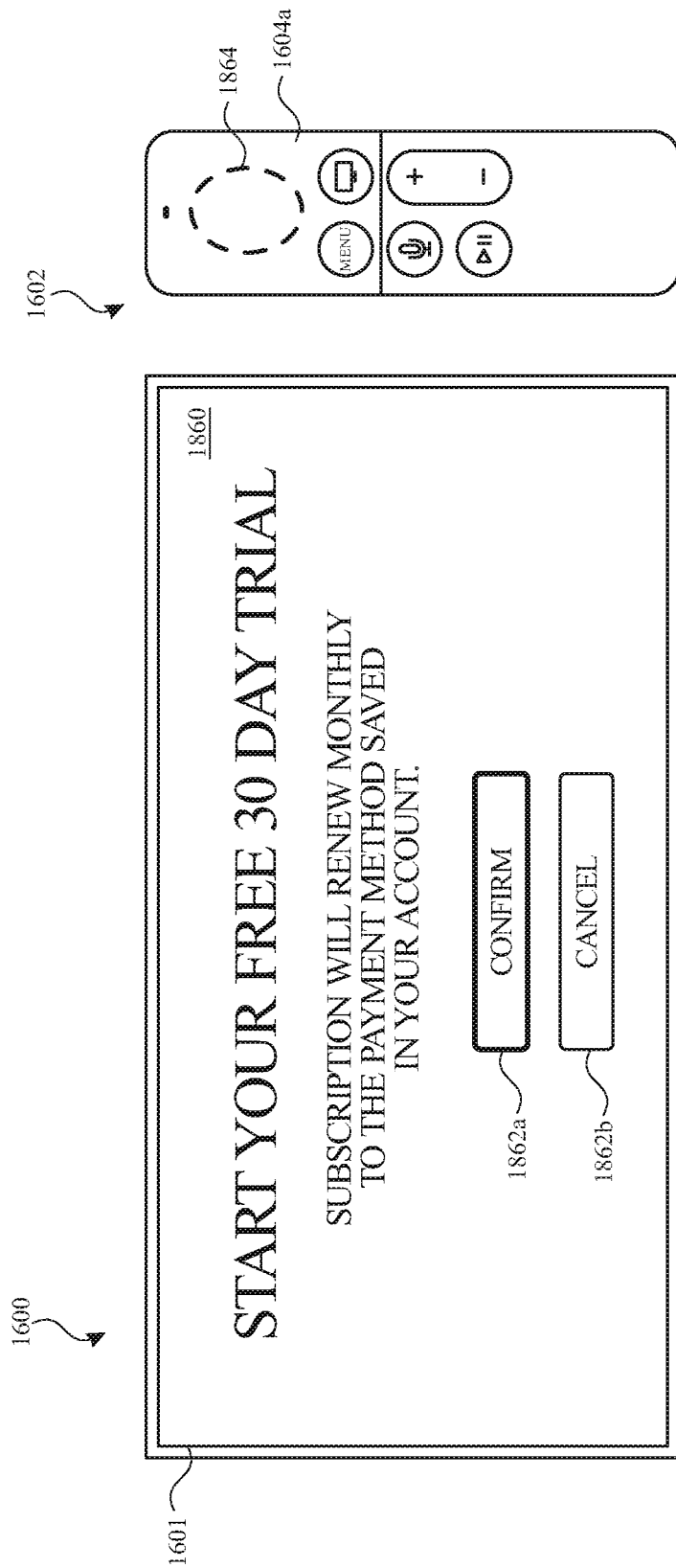

In FIG. 18K, in response to detecting (e.g., receiving the indication of) input 1858, computer system 1600 causes display 1601 to replace display of user interface 1850 with user interface 1860. User interface 1860 includes an option 1862*a* that is selectable to confirm a free trial of the fitness application, and an option 1862*b* that is selectable to cancel signing up for the free trial of the fitness application. In FIG. 18K, the focus is on option 1862*a*. While computer system 1600 causes display of user interface 1860 with the focus on option 1862*a*, remote control 1602 detects activation of selection region 1604*a* via button press input 1864 corresponding to selection of option 1862*a*, and transmits an indication of the input to computer system 1600. Computer system 1600 receives, from remote control 1602, the indication of input 1864 corresponding to selection of option 1862*a*.

Figure 18L:
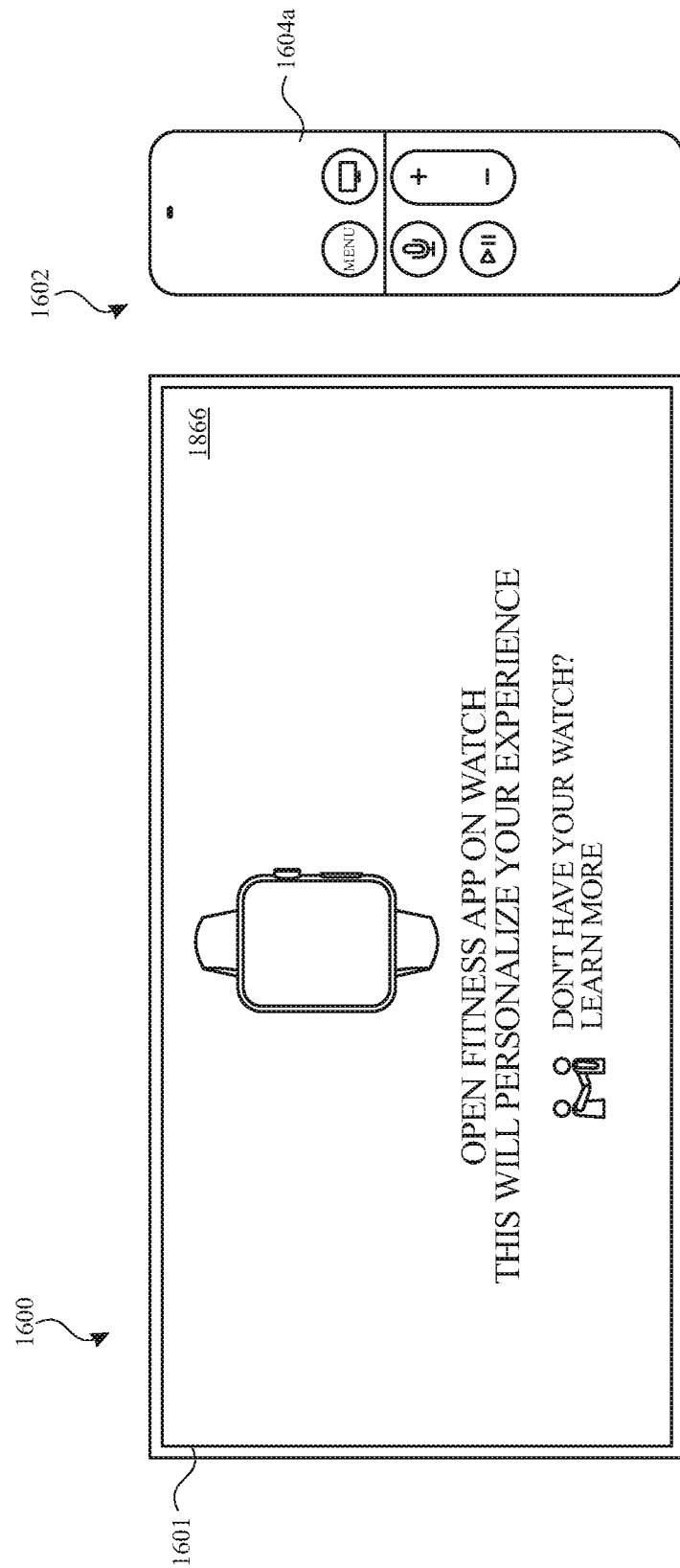
Figure 18M:
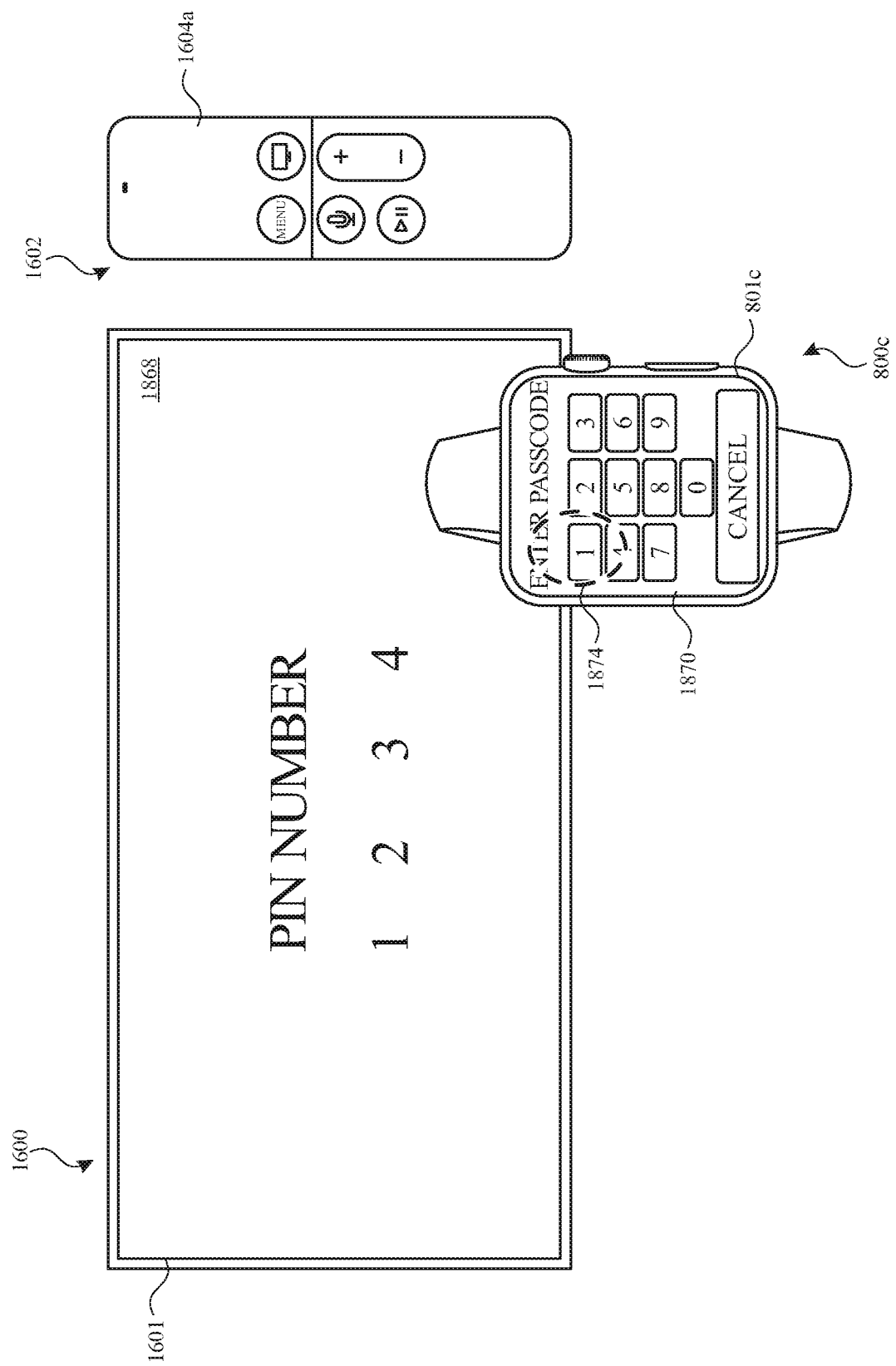

In FIG. 18L, in response to detecting (e.g., receiving the indication of) input 1864, computer system 1600 causes display 1601 to replace display of user interface 1860 with user interface 1866. User interface 1866 instructs the user 1806*c* to open the fitness application on device 800*c*.

In FIG. 18M, in response to a determination that the user has opened the fitness application on device 800*c*, computer system 1600 causes display 1601 to replace display of user interface 1860 with user interface 1868. User interface 1868 display a PIN number. Computer system 1600 also causes device 800*c* to display, via display 801*c*, a number pad 1870. User 1806*c* can use the number pad 1870 to enter the PIN number shown in user interface 1868 to confirm his or her intention to pair device 800*c* with computer system 1600. In FIG. 18M, device 800*c* detects user input 1874 corresponding to entry of the number sequence "1 2 3 4", and transmits an indication of the input to computer system 1600. Computer system 1600 receives, from device 800*c*, the indication of input 1874 corresponding to entry of the number sequence "1 2 3 4." In some embodiments, rather than entering a PIN number, other inputs can be received to confirm user intent to pair device 800*c* with computer system 1600.

In FIG. 18N, in response to detecting (e.g., receiving the indication of) input 1874, computer system 1600 causes display 1601 to replace display of user interface 1868 with workout user interface 1876. Like workout user interfaces 1822, 1840 discussed with reference to FIGS. 18B, 18F, and 18H, workout user interface 1876 includes workout suggestions 1852*a*-1852*c* that are each associated with a particular workout, and are selectable to access workout content (e.g., video content, audio content) for the workout. In some embodiments, workout user interface 1876 is a default workout user interface that is not personalized to user 1806*a*. This can be because user 1806*a* has not performed any workouts in the fitness application and, as such, there is insufficient data to generate a personalized workout user interface for the user 1806*a*. Workout user interface 1876 also includes option 1853*a* that is selectable to present workout user interface 1876, and option 1853*b* that is selectable to present a different workout browse user interface (e.g., user interface 1612 of FIG. 16B).

FIGS. 18O-18V demonstrate a scenario in which a user can log out of his or her account to allow for pairing of a new device with the computer system 1600.

Figure 18O:
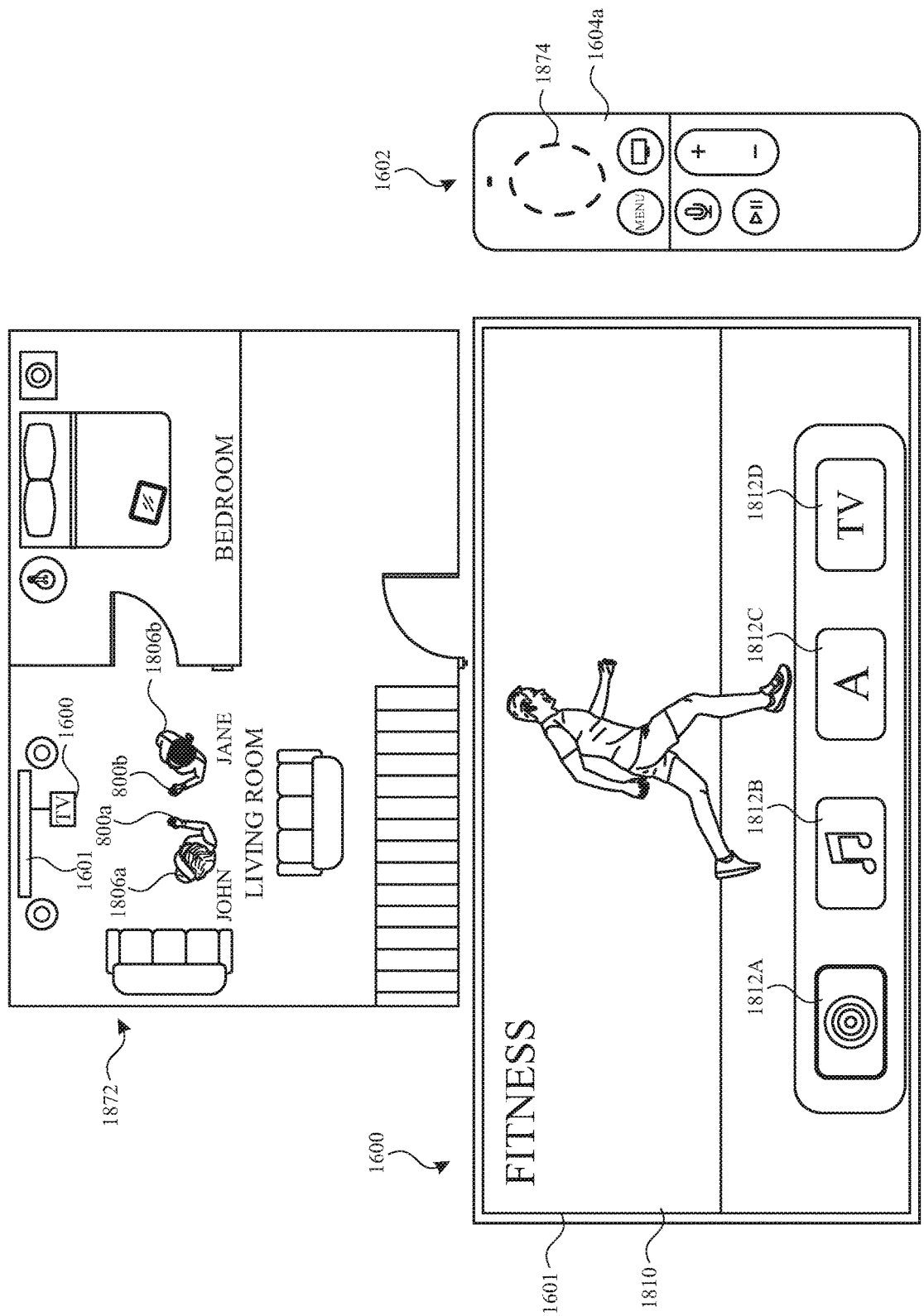

At FIG. 18O, computer system 1600 causes display 1601 to display home screen user interface 1810.

FIG. 18O also depicts a scenario 1872, in which the two users 1806*b* ("JANE"), 1806*a* ("JOHN") from FIGS. 18D-18H are in the same room as computer system 1600. As was the case in FIGS. 18D-18H, user 1806*a* is wearing an electronic device 800*a* (e.g., device 800) (e.g., a watch) and user 1806*b* is wearing an electronic device 800*b* (e.g., device 800) (e.g., a watch). However, in scenario 1872, only user 1806*b*'s electronic device 800*b* has been previously paired with computer system 1600. User 1806*a*'s electronic device 800*a* has never been previously paired with computer system 1600. Computer system 1600 determines that there is only one device (e.g., devices of a particular type (e.g., one watch)) that is within a predefined proximity of computer system 1600 (e.g., in the same room, within a threshold distance, etc.) and has previously been paired with computer system 1600.

In home screen user interface 1810 as depicted in FIG. 18O, the focus is on application representation 1812*a* that corresponds to a fitness application. While computer system 1600 causes display, via display 1601, of home screen user interface 1810 with the focus on application representation 1812*a*, remote control 1602 detects activation of selection region 1604*a* via button press input 1874 corresponding to selection of application representation 1812*a*, and transmits an indication of the input to computer system 1600. Computer system 1600 receives, from remote control 1602, the indication of input 1874 corresponding to selection of application representation 1812*a*.

Figure 18P:
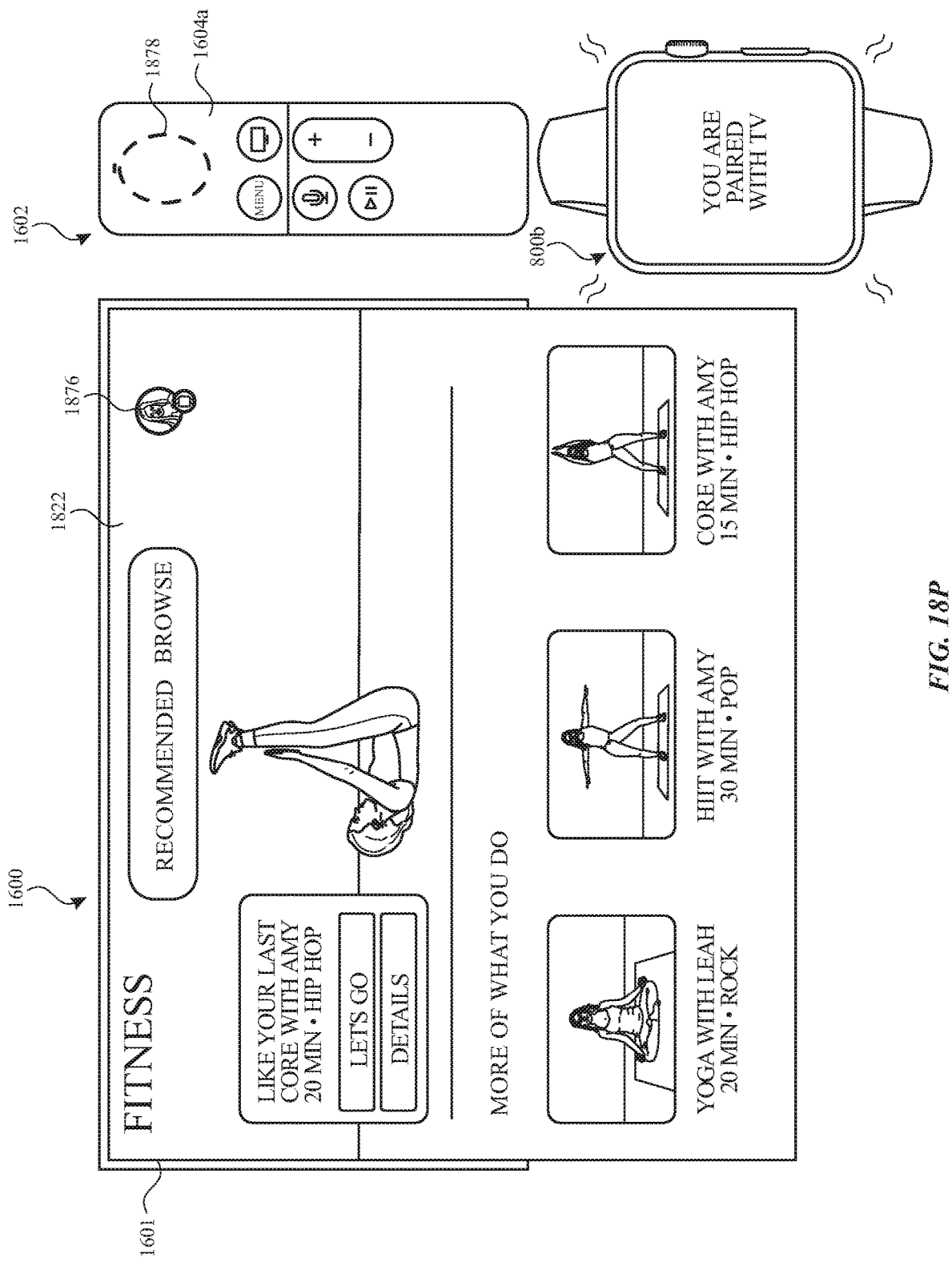

At FIG. 18P, in response to detecting (e.g., receiving the indication of) input 1874, and based on (e.g., in response to, in accordance with) the determination that there is only one previously-paired device 800*d* that is within the predefined proximity of computer system 1600, computer system 1600 causes display 1601 to replace display of home user interface 1810 with workout user interface 1822 which, as described above, is a personalized workout user interface that is associated with electronic device 800*b* and/or user 1806*b*. Similarly, in response to detecting (e.g., receiving the indication of) input 1874, and based on (e.g., in response to, in accordance with) the determination that there is only one previously-paired device 800*d* that is within the predefined proximity of computer system 1600, computer system 1600 causes electronic device 800*b* to display a notification and output a haptic output indicating that electronic device 800*b* is now paired to computer system 1600.

At FIG. 18P, the focus is on option 1876 that corresponds to an avatar/image representation of user 1806*b*. While computer system 1600 causes display, via display 1601, of workout user interface 1822 with the focus on option 1876, remote control 1602 detects activation of selection region 1604*a* via button press input 1878 corresponding to selection of option 1876, and transmits an indication of the input to computer system 1600. Computer system 1600 receives, from remote control 1602, the indication of input 1878 corresponding to selection of option 1876.

Figure 18Q:
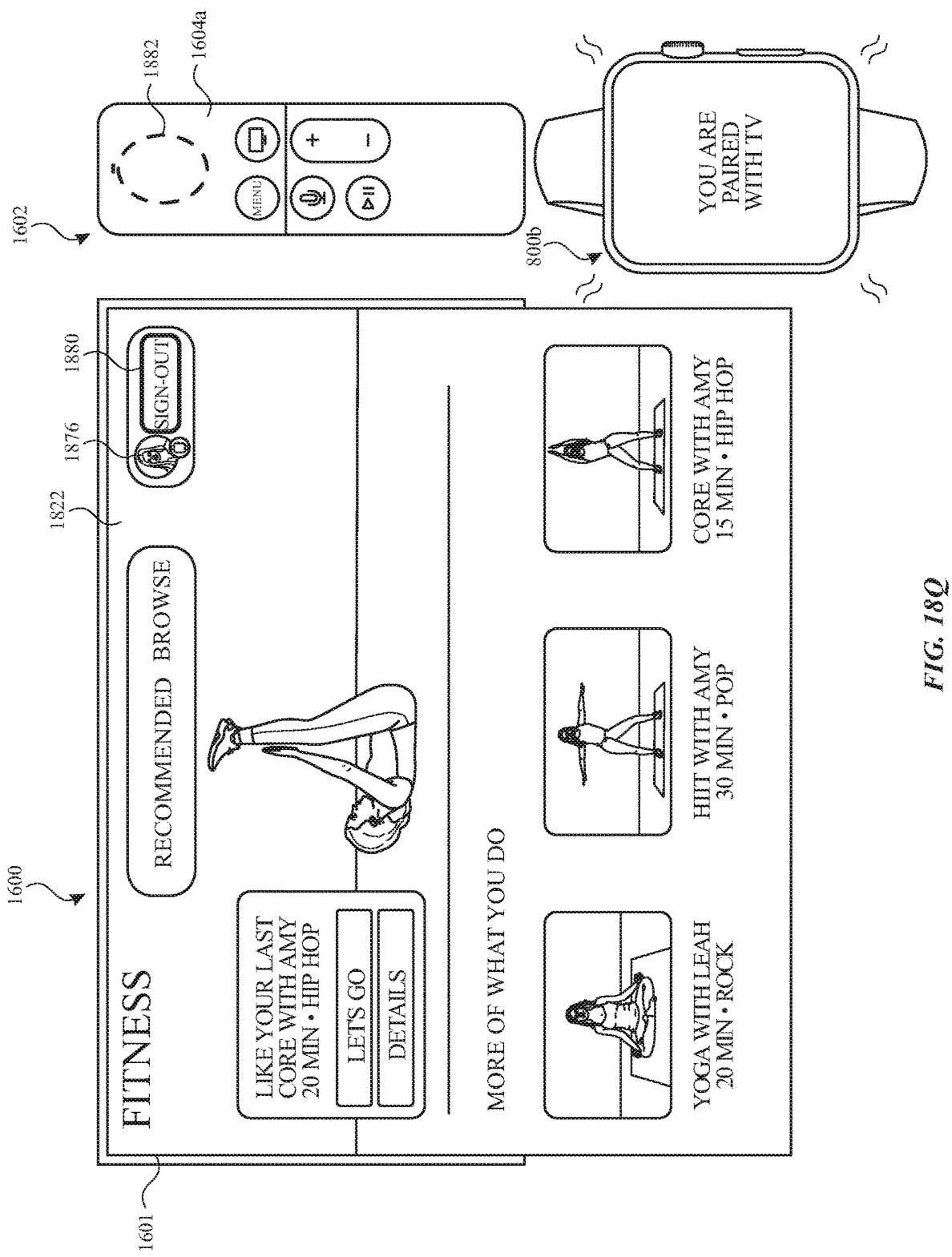

At FIG. 18Q, in response to detecting (e.g., receiving the indication of) input 1878, computer system 1600 causes display 1601 to display a sign-out option 1880. At FIG. 18Q, the focus is on option 1880. While computer system 1600 causes display, via display 1601, of workout user interface 1822 with the focus on option 1880, remote control 1602 detects activation of selection region 1604*a* via button press input 1882 corresponding to selection of option 1880, and transmits an indication of the input to computer system 1600. Computer system 1600 receives, from remote control 1602, the indication of input 1882 corresponding to selection of option 1880.

Figure 18R:
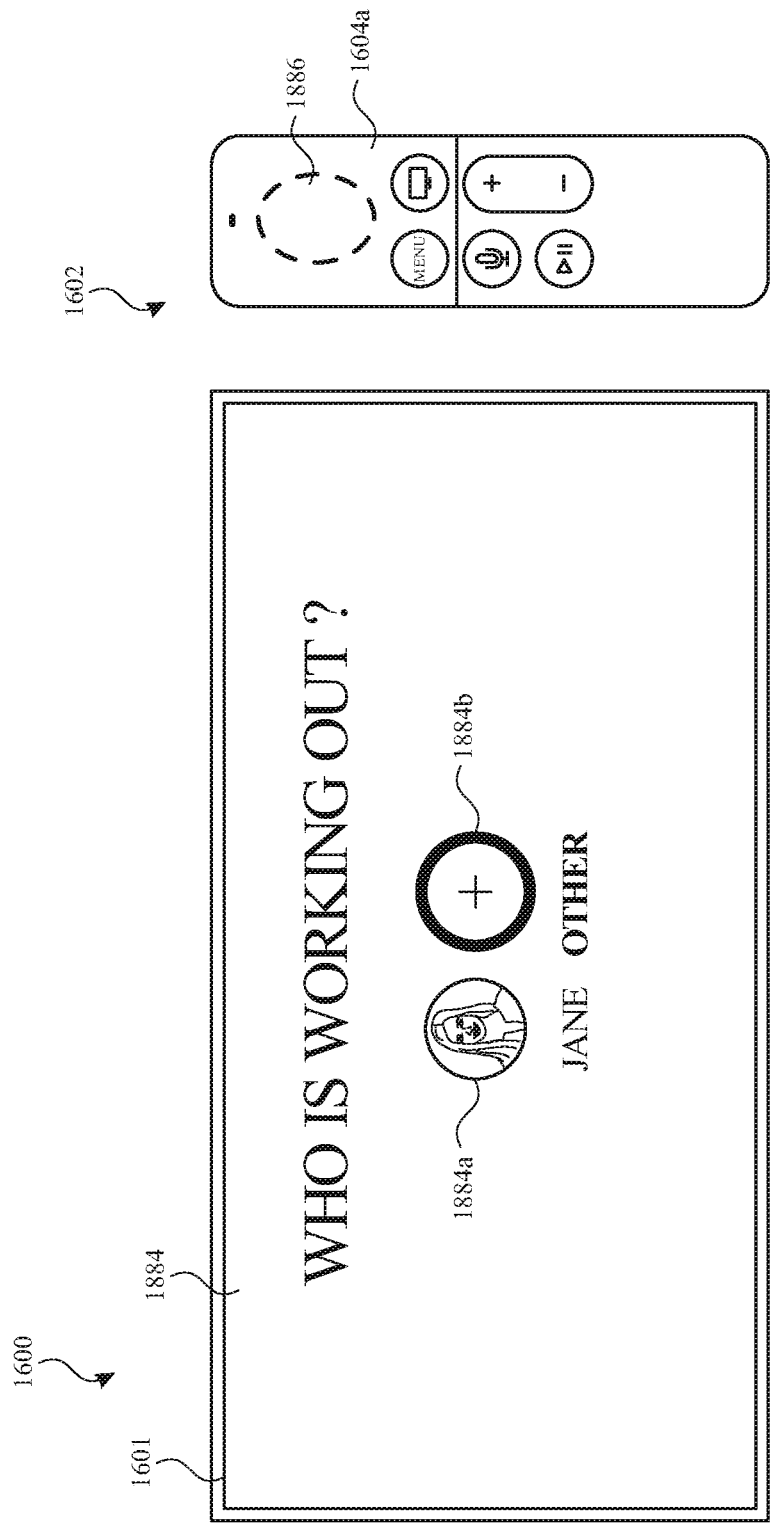

At FIG. 18R, in response to detecting (e.g., receiving the indication of) input 1882, computer system 1600 causes display 1601 to replace display of workout user interface 1822 with disambiguation user interface 1884. Disambiguation user interface 1884 includes two selectable options 1884*a*, 1884*b*. Option 1884*a* is associated with (e.g., corresponds to) user 1806*b* and device 800*b*, and is presented based on a determination that device 800*b* is within the predefined proximity of computer system 1600. Option 1884*a*, when selected, presents workout user interface 1822 associated with user 1806*b* and device 800*b*. Option 1884*b* is selectable to pair a new device that has not been previously paired with computer system 1600. In some embodiments, if additional previously-paired electronic devices of a particular type are determined to be within the predefined proximity of computer system 1600, disambiguation user interface 1884 could include additional selectable options for each of the detected devices.

In FIG. 18R, the focus is on option 1884*b*, and remote control 1602 detects activation of selection region 1604*a* via button press input 1886 corresponding to selection of option 1884*b*. Remote control 1602 transmits an indication of the input to computer system 1600. Computer system 1600 receives, from remote control 1602, the indication of input 1886.

Figure 18S:
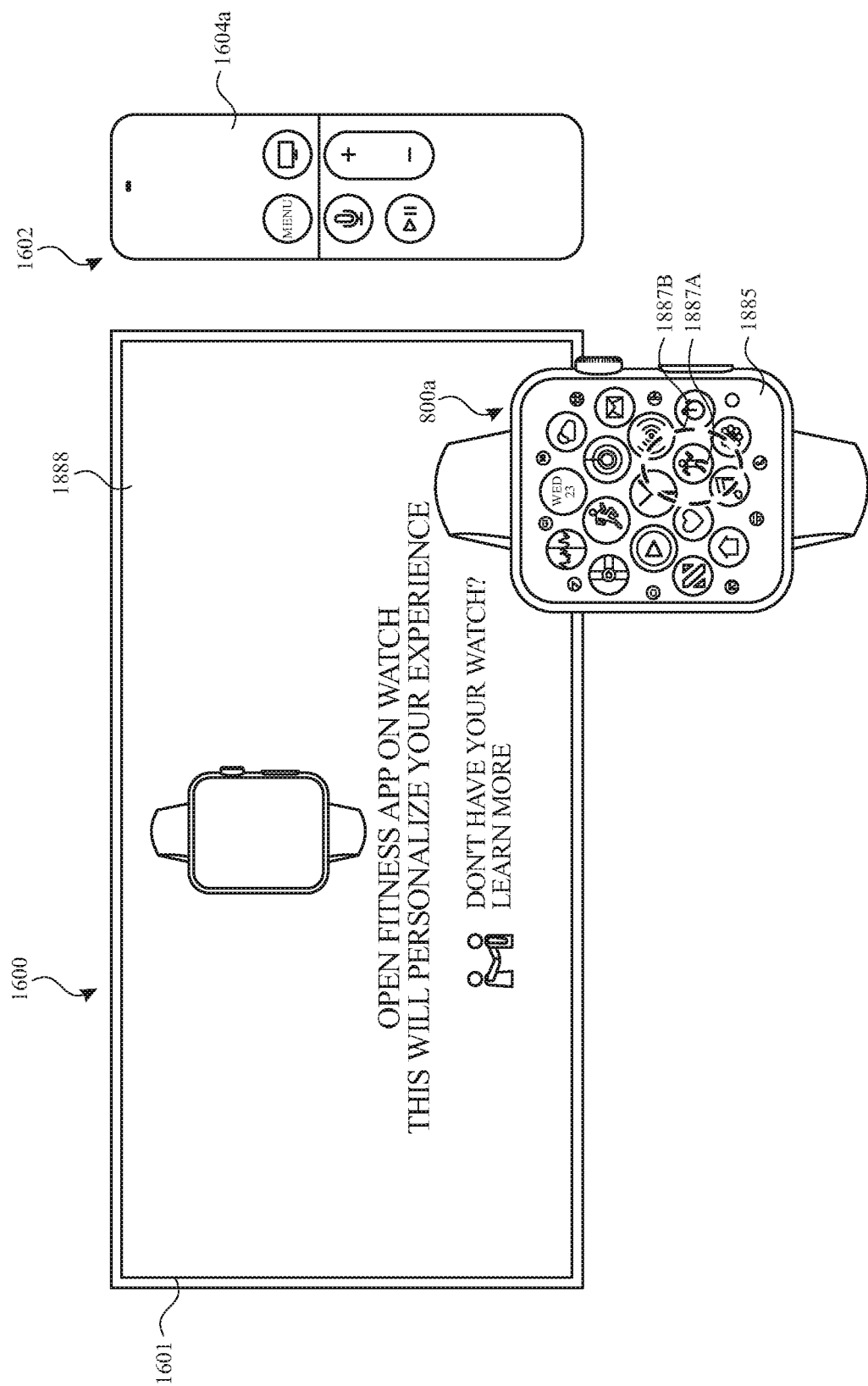

At FIG. 18S, in response to detecting (e.g., receiving the indication of) input 1886, computer system 1600 causes display 1601 to replace display of disambiguation user interface 1884 with status user interface 1888. Status user interface 1888 instructs the user to open a fitness application on the new device (e.g., the new watch) that the user wishes to pair with computer system 1600. User 1806*a* wishes to pair device 800*a* with computer system 1600. In FIG. 18S, device 800*a* displays a home user interface 1885 comprising a plurality of application icons representing different applications installed on device 800*a*. Device 800*a* detects a user input 1887B at a location corresponding to a fitness application icon 1887A.

Figure 18T:
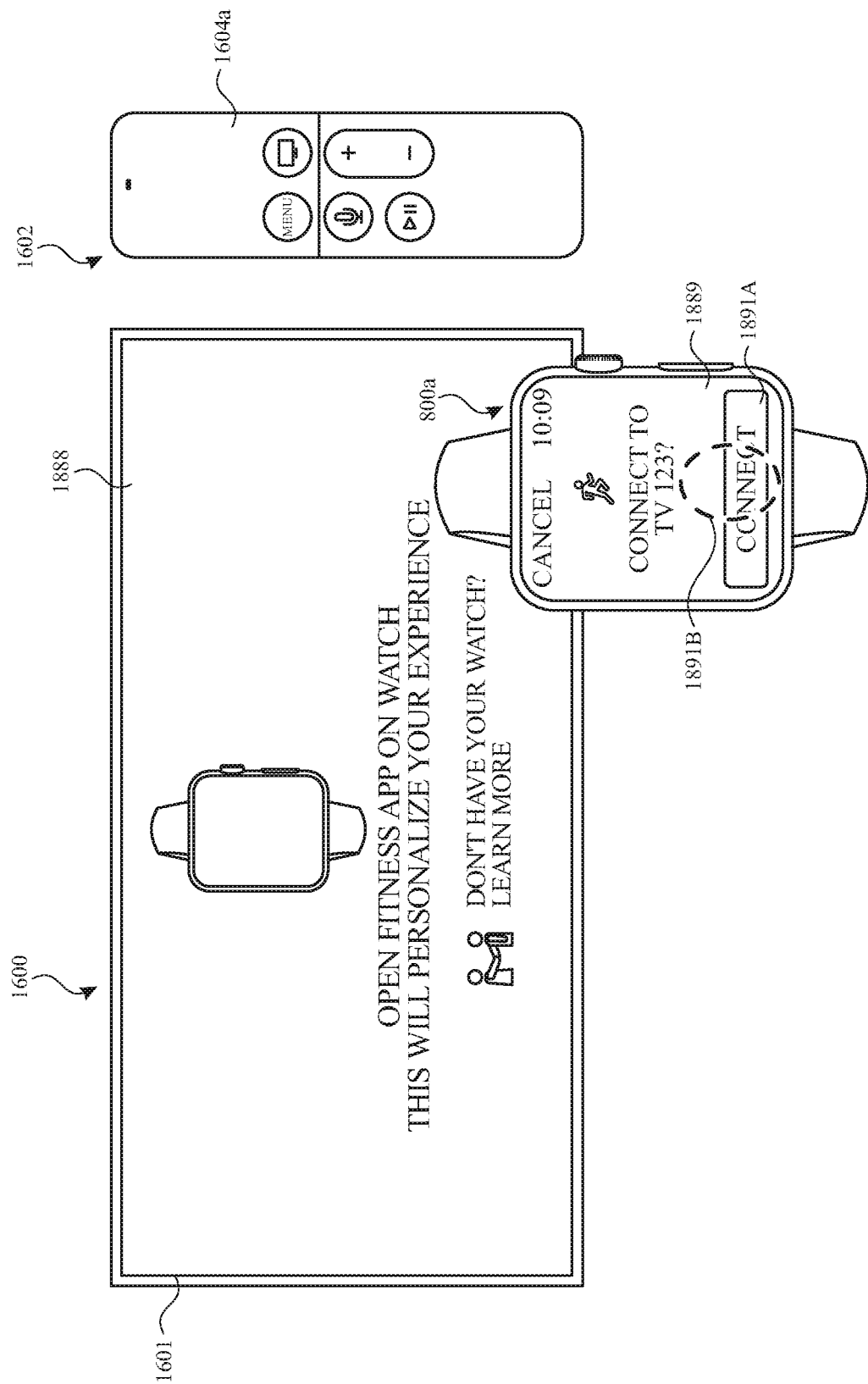

At FIG. 18T, in response to input 1887B, device 800*a* replaces display of home user interface 1885 with pairing user interface 1889. Pairing user interface 1889 includes an option 1891A. While displaying pairing user interface 1889, device 800*a* detects a user input 1891B at a location corresponding to option 1891A.

Figure 18U:
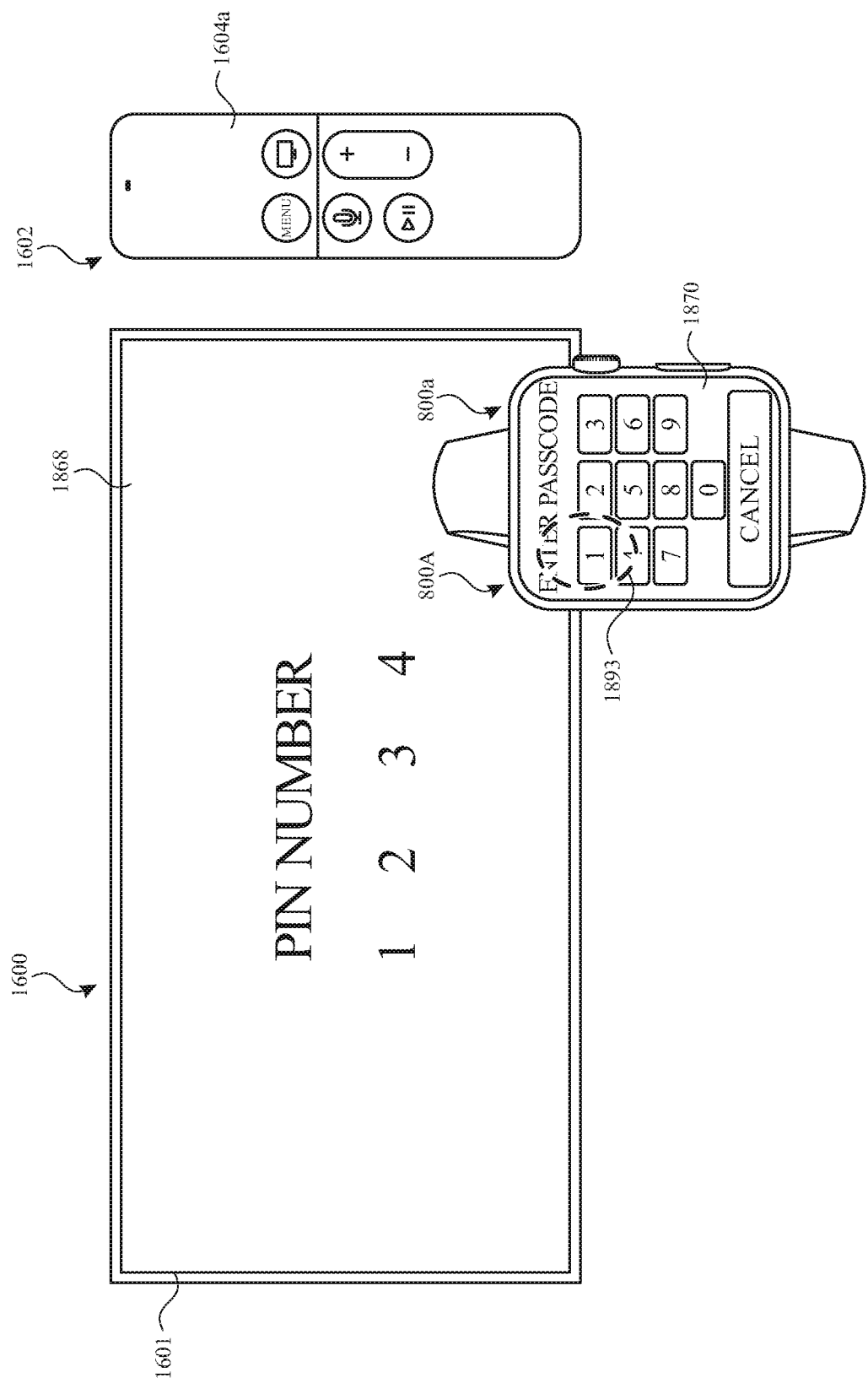

At FIG. 18U, in response to input 1891B, device 800*a* replaces display of pairing user interface 1889 with number pad 1870, as was described above with reference to FIG. 18M. Furthermore, in response to input 1891B (e.g., in response to a communication from device 800*a* indicating detection of input 1891B), device 1600 replaces display of status user interface 1888 with user interface 1868, which was described above with reference to FIG. 18M. User interface 1868 displays a PIN number. User 1806*a* can use the number pad 1870 to enter the PIN number shown in user interface 1868 to confirm his or her intention to pair device 800*a* with computer system 1600. In FIG. 18U, device 800*a* detects user input 1893 corresponding to entry of the number sequence "1 2 3 4", and transmits an indication of the input to computer system 1600. Computer system 1600 receives, from device 800*c*, the indication of input 1874 corresponding to entry of the number sequence "1 2 3 4."

In FIG. 18V, in response to detecting (e.g., receiving the indication of) input 1893, computer system 1600 causes display 1601 to replace display of user interface 1868 with workout user interface 1840. Workout user interface 1840 was described in greater detail with reference to FIG. 18H, and represents a personalized workout user interface associated with device 800*a* and/or user 1806*a*. In the depicted embodiments, device 800*a* is associated with a subscription account and a personalized workout user interface can be presented for device 800*a* based on past workouts associated with device 800*a* and/or user 1806*a*. In other scenarios (e.g., in scenarios in which the device and/or user are not subscribed, or have not performed any past workouts), a different user interface can be presented (e.g., user interface 1850 of FIG. 18J).

FIGS. 19A-19C are a flow diagram illustrating a method for displaying workout information in accordance with some embodiments. Method 1900 is performed at a device (e.g., 100, 300, 500, 600, 800, 1600) with a display. Some operations in method 1900 are, optionally, combined, the orders of some operations are, optionally, changed, and some operations are, optionally, omitted.

In some embodiments, the electronic device (e.g., 600, 800, 1600) is a computer system. The computer system is optionally in communication (e.g., wired communication, wireless communication) with a display generation component and with one or more input devices. The display generation component is configured to provide visual output, such as display via a CRT display, display via an LED display, or display via image projection. In some embodiments, the display generation component is integrated with the computer system. In some embodiments, the display generation component is separate from the computer system. The one or more input devices are configured to receive input, such as a touch-sensitive surface receiving user input. In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

As described below, method 1900 provides an intuitive way for displaying workout information. The method reduces the cognitive burden on a user for displaying workout information, thereby creating a more efficient human-machine interface. For battery-operated computing devices, enabling a user to display camera views faster and more efficiently conserves power and increases the time between battery charges.

Computer system 1600 (e.g., an electronic device, a set top device; a digital media player) that is in communication with (e.g., wired communication, wireless communication) a display generation component and one or more input devices detects (1902), via the one or more input devices, a user input (e.g., 1814, 1829, 1848) corresponding to a request to display a workout user interface.

In response to the request to display the workout user interface (1906), and in accordance with a determination that the computer system meets proximity criteria relative to (e.g., is determined to be in approximately the same location or within a threshold distance based on connection signal strength, based on connection to a common device associated with the location, based on self-identification as being located at the approximately the same location or within a threshold distance, based on a determination that the computer system is within a predetermined distance of the external electronic device) a single external electronic device of a first type (1906) (e.g., 800*a* in FIG. 18A, 800*c* in FIG. 18I) (e.g., not more than one external electronic device of the first type) (e.g., a wearable electronic device (e.g., a watch)) (in some embodiments, in accordance with a determination that the computer system is in the same location with a single previously-paired external electronic device of a first type (e.g., external electronic devices that have previously been paired with the computer system)), computer system 1600 initiates (1908) a process to display, via the display generation component, a first workout suggestion user interface (e.g., 1822) (e.g., a personalized workout suggestion user interface (e.g., workout user interface 612 of FIGS. 6C-6M)) (in some embodiments, without displaying or causing display of a disambiguation user interface), wherein the first workout suggestion user interface displays one or more workout suggestions (e.g., 1824*a*-1824*d*) associated with the single external electronic device (e.g., associated with a user associated with the external electronic device). In some embodiments, a workout suggestion corresponds to (e.g., represents) a workout (e.g., audio and/or video content that guides a user to perform a physical activity). In some embodiments, selecting a workout suggestion initiates a process for playback of a workout corresponding to the workout suggestion. Displaying one or more workout suggestions associated with the single electronic device in accordance with a determination that the computer system meets proximity criteria relative to the single electronic device enables a user to quickly gain access to a particular workout, thereby reducing the number of inputs needed for selecting a workout. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In response to the request to display the workout user interface (1906), and in accordance with a determination that the computer system meets proximity criteria relative to at least a first external electronic device of the first type and a second external electronic device of the first type (1910) (e.g., 800*a*, 800*b* in FIG. 18D) (e.g., a first wearable electronic device and a second wearable electronic device (e.g., a first watch and a second watch)) (in some embodiments, in accordance with a determination that the computer system is in the same location with at least a first previously-paired external electronic device of the first type and a second previously-paired external electronic device of the first type (e.g., external electronic devices that have previously been paired with the computer system)), computer system 1600 initiates (1912) a process to display, via the display generation component, a disambiguation user interface (e.g., 1830) different from the first workout suggestion user interface (in some embodiments, without displaying or causing display of the first workout suggestion user interface). The disambiguation user interface includes: a first selectable user interface object (e.g., 1832*a*) that, when selected, initiates a process for displaying a second workout suggestion user interface (e.g., 1840) associated with the first external electronic device (e.g., 800*b*) (e.g., a personalized workout suggestion user interface associated with the first external electronic device), wherein the second workout suggestion user interface displays one or more workout suggestions (e.g., 1842*a*-1842*d*) associated with the first external electronic device (e.g., associated with a user associated with the first external electronic device) (1914), and a second selectable user interface object (1832*b*) that, when selected, initiates a process for displaying a third workout suggestion user interface (e.g., 1822, FIG. 18F) different from the second workout suggestion user interface and associated with the second external electronic device (e.g., 800*a*) (e.g., a personalized workout suggestion user interface associated with the second external electronic device), wherein the third workout suggestion user interface displays one or more workout suggestions (e.g., 1824*a*-1824*d*) associated with the second external electronic device (1916) (e.g., associated with a user associated with the second external electronic device). In some embodiments, the first workout suggestion user interface includes one or more workout suggestions that are not included in the second and/or third workout suggestion user interfaces. In some embodiments, the second workout suggestion user interface includes one or more workout suggestions that are not included in the first and/or third workout suggestion user interfaces. In some embodiments, the third workout suggestion user interface includes one or more workout suggestions that are not included in the first and/or second workout suggestion user interfaces. Displaying a disambiguation user interface in accordance with a determination that the computer system meets proximity criteria relative to multiple external electronic devices enables a user to quickly and efficiently identify a particular external electronic device and access workout suggestions associated with the particular external electronic device, thereby reducing the number of inputs needed for selecting a workout. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, initiating the process to display the first workout suggestion user interface includes: in accordance with a determination that the single external electronic device is associated with an authorized user account (e.g., a user account that is registered for a workout service or workout application), computer system 1600 causes display, via the display generation component, of the first workout suggestion user interface (e.g., 1822, FIG. 18C) (e.g., a personalized workout suggestion user interface) (in some embodiments, without displaying or causing display of a disambiguation user interface), wherein the first workout suggestion user interface displays one or more workout suggestions associated with the authorized user account (In some embodiments, a workout suggestion corresponds to (e.g., represents) a workout (e.g., audio and/or video content that guides a user to perform a physical activity. In some embodiments, selecting a workout suggestion initiates a process for playback of a workout corresponding to the workout suggestion), and in accordance with a determination that the single external electronic device is not associated with an authorized user account, computer system 1600 causes display, via the display generation component, of an authorization user interface (e.g., 185) that is different from the first workout suggestion user interface (e.g., a default landing page user interface associated with unregistered users (e.g., a user registration interface, a user login interface, a free-trial registration interface)). In some embodiments, the authorization interface includes a selectable user interface object that, when selected, initiates a process to authorize a user account associated with the single external electronic device. In some embodiments, after the user account is authorized, the first workout suggestion user interface is displayed. In some embodiments, the authorization user interface is displayed without displaying or causing display of the first workout suggestion user interface or the disambiguation user interface. Displaying one or more workout suggestions associated with the single electronic device in accordance with a determination that the single external electronic device is associated with an authorized user account enables a user to quickly gain access to a particular workout, thereby reducing the number of inputs needed for selecting a workout. Displaying an authorization user interface in accordance with a determination that the single external electronic device is not associated with an authorized user account enhances security and privacy. Reducing the number of inputs needed to perform an operation and providing improved security enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while the authorization user interface is displayed on the display device, computer system 1600 detects a second user input (e.g., 1858) corresponding to a request to authorize a user account associated with the single external electronic device (e.g., authorize the user account to access a workout application and/or workout suggestions) (e.g., selection of an option or affordance to start a free trial or to register a user account).

In some embodiments, in response to detecting the second user input (e.g., 1858), computer system 1600 initiates a process to display a notification on the single external electronic device, wherein the notification requests authentication of the user intent to authorize the user account associated with the single external electronic device (e.g., FIG. 18M) (e.g., a notification requesting a user input on the single external electronic device to authenticate user intent to authorize the user account associated with the single external electronic device). Displaying the notification on the single external electronic device requesting authentication of the user intent to authorize the user account associated with the single external device provides the user with feedback about the current state of the device (e.g., that a user input corresponding to a request to authorize the user account associated with the single external electronic device has been received). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, initiating the process to display the first workout suggestion user interface includes (1918): prior to display of the first workout suggestion user interface, computer system 1600 causes (1920) the single external electronic device to output a notification (e.g., haptic, visual) (e.g., 1815a, FIG. 18B, FIG. 18M) requesting user confirmation to pair the single external electronic device with the computer system (e.g., requesting that a user perform a gesture on the single external electronic device (e.g., entering a PIN number, tapping on an option indicative of a user intent to pair the single external electronic device with the computer system). In some embodiments, the first workout suggestion user interface is displayed after confirmation is received to pair the single external electronic device with the computer system. In some embodiments, the single external electronic device is uniquely paired with the computer system. For example, the single external electronic device has a special relationship with the computer system in that the single external electronic device is only paired with the computer system and is not paired with any other devices. In some embodiments, pairing two electronic devices includes establishing a means of communication between the two devices. The means of communication may include those described in U.S. Patent Publication No. 2015/0350865, "Predefined Wireless Pairing," filed Sep. 2, 2014 and published Dec. 3, 2015, which is incorporated in this disclosure by reference. Once the devices are paired, they may exchange data including data that may be used for device configuration. Pairing may also allow a device to be configured using a user interface provided by the other paired device. For example, recent advances in computer technology have enabled manufacturers to produce powerful computing devices in relatively small form factors. However, small devices may be unable to provide a user interface large enough to be suitable for user configuration. Instead, the device being configured may be paired with an external device with a larger user interface that provides the ability to set parameters on the device being configured. Such techniques can reduce the time and effort required to begin using the device and can make the device more useful to the user. In some embodiments, pairing two electronic devices includes registering the two electronic devices with one another for future wireless communications. For example, when a first device is paired with a second device, the second device may be registered (e.g., on the first device) as a paired device, and/or the first device may be registered (e.g., on the second device) as a paired device). In some embodiments, if two devices are paired with one another, the two devices are registered with one another and can perform two-way wireless communication. In some embodiments, wireless communication, for purposes of a paired relationship, occurs over a peer-to-peer wireless communication protocol such as Bluetooth and/or Bluetooth Low Energy (BTLE). In some embodiments, the wireless communication uses more than one wireless communication protocol. For example, WiFi may be used in addition to BTLE. In these embodiments, an initial communication between two devices may occur over a lower powered protocol, such as BTLE, even if the protocol yields a slower data transfer speed. Subsequent communications may occur over a secondary network that is relatively faster, such as WiFi. Additional exemplary techniques related to initiating and operating in a paired relationship are described in the following applications: U.S. Patent Publication No. 2015/035081 titled "Companion Application for Activity Cooperation," filed Dec. 30, 2014 and published Dec. 3, 2015; U.S. Patent Publication No. 2015/0350865 titled "Predefined Wireless Pairing," filed Sep. 2, 2014 and published Dec. 3, 2015; and U.S. Patent Publication No. 2016/0062572 titled "Reduced-size Configuration Interface," filed Aug. 28, 2015 and published Mar. 3, 2016. Outputting a notification on the single external electronic device requesting user confirmation to pair the single external electronic device with the computer system provides the user with feedback about the current state of the device (e.g., that the computer system is attempting to pair with the single external electronic device). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, user confirmation to pair the single external electronic device with the computer system includes user input of a personal identification number (1922) (e.g., FIG. 18M). In some embodiments, a PIN number is displayed for the user (e.g., on the display generation component, on the computer system, and/or on the single external electronic device), and user confirmation to pair the single external electronic device with the computer system is determined based on receiving a user input corresponding to the PIN number (e.g., user input of the PIN number on the display generation component, on the computer system, and/or on the single external electronic device) (e.g., the single external electronic device is paired with the computer system and/or the first workout suggestion user interface is displayed on the display generation component in accordance with a determination that the user has entered the PIN number (e.g., on the display generation component, on the computer system, and/or on the single external electronic device)). Receiving user confirmation to pair the single external electronic device via user input of a personal identification number enhances security. Providing improved security enhances the operability of the device and makes the user-device interface more efficient (e.g., by restricting unauthorized access) which, additionally, reduces power usage and improves battery life of the device by limiting the performance of restricted operations.

In some embodiments, user confirmation to pair the single external electronic device with the computer system includes a user input on a selectable user interface object (1924) (e.g., a tap gesture) (e.g., FIG. 18B). In some embodiments, in accordance with a determination that the single external electronic device has been previously paired with the computer system, user confirmation to pair the single external electronic device with the computer system is determined based on receiving a first user gesture on the single external electronic device (e.g., a tap gesture), and in accordance with a determination that the single external electronic device has not been previously paired with the computer system, user confirmation to pair the single external electronic device with the computer system is determined based on receiving a second user gesture different from the first user gesture on the single external electronic device (e.g., entry of a PIN number)). Receiving user confirmation to pair the single external electronic device via a user input on a selectable user interface object enhances security. Providing improved security enhances the operability of the device and makes the user-device interface more efficient (e.g., by restricting unauthorized access) which, additionally, reduces power usage and improves battery life of the device by limiting the performance of restricted operations.

In some embodiments, initiating the process to display the first workout suggestion user interface comprises causing display, via the display generation component, of the first workout suggestion user interface (e.g., 1822) without user input (e.g., the first workout suggestion user interface is displayed on the display generation component automatically once the determination is made that the computer system meets proximity criteria relative to (e.g., is in the same location with) the single external electronic device of the first type). In some embodiments, initiating the process to display the disambiguation user interface includes causing display, via the display generation component, of the disambiguation user interface (e.g., 1830) without user input (e.g., the disambiguation user interface is displayed on the display generation component automatically once the determination is made that the computer system meets proximity criteria relative to (e.g., is in the same location with) the first external electronic device of the first type and the second external electronic device of the first type). Automatically displaying a first workout suggestions user interface or a disambiguation user interface without user input allows the user to quickly select a particular workout. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, initiating the process to display the first workout suggestion user interface includes (1918) causing (1926) the single external electronic device to generate a tactile output (e.g., a sequence of a number of individual tactile outputs) indicating that the single external electronic device is paired with the computer system (e.g., device 800*a* in FIG. 18F, device 800*b* in FIG. 18H). Causing the single external electronic device to generate a tactile output indicating that the single external electronic device is paired with the computer system provides the user with feedback about the current state of the device (e.g., that the computer system is paired with the single external electronic device). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in response to the request to display the workout user interface and in accordance with a determination that the computer system does not satisfy the proximity criteria relative to (e.g., is determined not to be in approximately the same location or within a threshold distance based on connection signal strength, based on lack of connection to a common device associated with the location, based on self-identification as not being located at the approximately the same location or within a threshold distance, based on a determination that the computer system is not within a predetermined distance of any external electronic device) any external electronic device of the first type (e.g., a wearable electronic device (e.g., a watch)) (in some embodiments, in accordance with a determination that the computer system is not in the same location with any previously-paired external electronic device of the first type), computer system 1600 initiates a process to display, via the display generation component, an application demonstration user interface (e.g., 1850) different from each of the first workout suggestion user interface (e.g., 1822 in FIG. 18C), the disambiguation user interface (e.g., 1830), the second workout suggestion user interface (e.g., 1822 in FIG. 18F), and the third workout suggestion user interface (e.g., 1840) (in some embodiments, without displaying or causing display of the first workout suggestion user interface, the disambiguation user interface, the second workout suggestion user interface, or the third workout suggestion user interface). Initiating the process to display the application demonstration user interface in accordance with a determination that the computer system does not satisfy proximity criteria relative to any external electronic device of the first type provides the user with feedback about the current state of the device (e.g., that the computer system does not satisfy proximity criteria relative to any external electronic device of the first type). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in response to the request to display the workout user interface and in accordance with a determination that the computer system does not satisfy the proximity criteria relative to (e.g., is determined not to be in approximately the same location or within a threshold distance based on connection signal strength, based on lack of connection to a common device associated with the location, based on self-identification as not being located at the approximately the same location or within a threshold distance, based on a determination that the computer system is not within a predetermined distance of any previously-paired external electronic device) any previously-paired external electronic device of the first type (e.g., a wearable electronic device (e.g., a watch)), computer system 1600 initiates a process to display, via the display generation component, a device pairing user interface (e.g., 1866, 1868) that includes a prompt to pair an external electronic device of the first type (in some embodiments, without displaying or causing display of the first workout suggestion user interface, the disambiguation user interface, the second workout suggestion user interface, or the third workout suggestion user interface). In some embodiments, the device pairing user interface is different from the first workout suggestion user interface, the disambiguation user interface, the second workout suggestion user interface, and the third workout suggestion user interface. In some embodiments, the device pairing user interface comprises one or more instructions for a user to pair an external electronic device of the first type with the computer system. Initiating the process to display the device pairing user interface in accordance with a determination that the computer system does not satisfy proximity criteria relative to any previously-paired external electronic device of the first type provides the user with feedback about the current state of the device (e.g., that the computer system does not satisfy proximity criteria relative to any previously-paired external electronic device of the first type). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the device pairing user interface (e.g., 1866) comprises one or more instructions for a user to pair an external electronic device of the first type (e.g., a wearable electronic device (e.g., a watch)) with the computer system. In some embodiments, the one or more instructions include an instruction to open an application (e.g., a specific application; an application of a first type; a workout application) (e.g., "OPEN FITNESS APP ON WATCH" in FIG. 18L) on an external electronic device of the first type. Displaying instructions for the user to pair an external device of the first type with the computer system allows a user to more quickly and efficiently pair an external device with the computer system, thereby reducing the number of inputs required to pair the external device with the computer system. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the disambiguation user interface (e.g., 1830) further includes a third selectable user interface object (e.g., 1832c) that, when selected, initiates a process for pairing a previously-unpaired external electronic device of the first type with the computer system. Displaying a selectable user interface object that, when selected, initiates a process for pairing a previously-unpaired external electronic device with the computer system enables a user to more efficiently pair an external electronic device with the computer system, thereby reducing the number of inputs required to pair the external device with the computer system. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first selectable user interface object (e.g., 1832a), when selected, causes the first external electronic device to output a notification (e.g., visual, haptic) (e.g., on the first external electronic device) (e.g., 1836, device 800a in FIG. 18F, 1844, device 800b in FIG. 18H) indicating that the first external electronic device has been selected.

In some embodiments, the second selectable user interface object, when selected, causes the second external electronic device to output a notification (e.g., visual, haptic) (e.g., on the second external electronic device) (e.g., 1836, device 800a in FIG. 18F, 1844, device 800b in FIG. 18H) indicating that the second external electronic device has been selected. Causing the second external electronic device to output a notification indicating that the second external electronic device has been selected provides the user with feedback about the current state of the device (e.g., that the computer system has received a user input selecting the second external electronic device). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first workout suggestion user interface (e.g., 1822) includes one or more workout suggestions (e.g., 1824a-1824d) associated with the single external electronic device (e.g., 800a) based on user information (e.g., locally stored information) received from the single external electronic device (e.g., based on user health application information stored locally on the single external electronic device). Suggesting a workout based on user information received from the single external electronic device improves the quality of suggestions to the user, thereby providing a means for selection by the user. Otherwise, additional inputs would be required to further locate a particular workout. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, after initiating the process to display, via the display generation component, the first workout suggestion user interface (e.g., 1822), the electronic device displays, via the display generation component, the first workout suggestion user interface (e.g., 1822) associated with the first external electronic device (e.g., 800b) (e.g., associated with a user associated with the first external electronic device). In some embodiments, while displaying the first workout suggestion user interface (e.g., 1822), the electronic device detects one or more user inputs (e.g., 1878, 1882) corresponding to a request to sign out of the first workout suggestion user interface (e.g., a request to sign out of an account associated with the user associated with the first external electronic device). In some embodiments, in response to detecting the one or more user inputs corresponding to the request to sign out of the first workout suggestion user interface, the electronic device (e.g., 1600) displays a second disambiguation user interface (e.g., 1884) different from the first workout suggestion user interface (e.g., 1822) and the disambiguation user interface (e.g., 1830) (e.g., without displaying the first workout suggestion user interface) (in some embodiments, replacing display of the first workout suggestion user interface with the second disambiguation user interface), wherein the second disambiguation user interface includes: a fourth selectable user interface object (e.g., 1884a) that, when selected, initiates a process for displaying the first workout suggestion user interface, and a fifth selectable user interface object (e.g., 1884b) that, when selected, initiates a process for pairing a previously-unpaired external electronic device of the first type with the computer system. Displaying a selectable user interface object that, when selected, initiates a process for pairing a previously-unpaired external electronic device with the computer system enables a user to more efficiently pair an external electronic device with the computer system, thereby reducing the number of inputs required to pair the external device with the computer system. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in accordance with a determination that the computer system (e.g., 1600) meets proximity criteria relative to (e.g., is determined to be in approximately the same location or within a threshold distance based on connection signal strength, based on connection to a common device associated with the location, based on self-identification as being located at the approximately the same location or within a threshold distance, based on a determination that the computer system is within a predetermined distance of the external electronic device) one or more additional external electronic devices of the first type (e.g., wearable electronic devices (e.g., watches)) (in some embodiments, in accordance with a determination that the computer system is in the same location with one or more additional previously-paired external electronic devices of the first type (e.g., external electronic devices that have previously been paired with the computer system)), the second disambiguation user interface (e.g., 1884) further comprises, for each external electronic device of the one or more additional external electronic device of the first type, a respective selectable user interface object that, when selected, initiates a process for displaying a workout suggestion user interface associated with the external electronic device. Automatically causing display of additional selectable user interface objects in a disambiguation user interface in accordance with a determination that the computer system meets proximity criteria relative to one or more additional external electronic devices allows a user to access those selectable user interface objects without additional user input. Performing an optimized operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the second disambiguation user interface (e.g., 1884), the electronic device (e.g., 1600) detects, via the one or more input devices, one or more user inputs (e.g., 1886) corresponding to selection of the fifth selectable user interface object (e.g., 1884b); in response to detecting the one or more user inputs corresponding to selection of the fifth selectable user interface object, displaying one or more instructions (e.g., 1888) for a user to pair an external electronic device of the first type (e.g., a wearable electronic device (e.g., a watch)) with the computer system, wherein the one or more instructions include an instruction to open an application (e.g., a specific application; an application of a first type; a workout application) on an external electronic device of the first type. Displaying instructions for the user to pair an external device of the first type with the computer system allows a user to more quickly and efficiently pair an external device with the computer system, thereby reducing the number of inputs required to pair the external device with the computer system. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the second disambiguation user interface (e.g., 1884), the electronic device (e.g., 1600) determines that the computer system meets proximity criteria relative to (e.g., is determined to be in approximately the same location or within a threshold distance based on connection signal strength, based on connection to a common device associated with the location, based on self-identification as being located at the approximately the same location or within a threshold distance, based on a determination that the computer system is within a predetermined distance of the external electronic device) a third external electronic device of the first type (e.g., 800*a*) (e.g., a third wearable electronic device (e.g., a watch)) (in some embodiments, in accordance with a determination that the computer system is in the same location with at least the third external electronic device of the first type), wherein opening the application on the third external electronic device causes display, on the third external electronic device (e.g., on a display built into the third external electronic device, on a display in communication with the third external electronic device), of a selectable user interface object (e.g., 1891A) that, when selected, initiates a process for pairing the third external electronic device with the computer system. Displaying an affordance for pairing an external device of the first type with the computer system allows a user to more quickly and efficiently pair an external device with the computer system, thereby reducing the number of inputs required to pair the external device with the computer system. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the second disambiguation user interface (e.g., 1884), and in accordance with a determination that the computer system meets proximity criteria relative to (e.g., is determined to be in approximately the same location or within a threshold distance based on connection signal strength, based on connection to a common device associated with the location, based on self-identification as being located at the approximately the same location or within a threshold distance, based on a determination that the computer system is within a predetermined distance of the external electronic device) a third external electronic device of the first type (e.g., 800*a*) (e.g., a third wearable electronic device (e.g., a watch)) (in some embodiments, in accordance with a determination that the computer system is in the same location with at least the third external electronic device of the first type), the electronic device causes the third external electronic device to display (e.g., on a display built into the third external electronic device, on a display in communication with the third external electronic device), within the application, a selectable user interface object (e.g., 1891A) that, when selected, initiates a process for pairing the third external electronic device with the computer system. Causing a selectable user interface object to be displayed in accordance with a determination that the computer system meets proximity criteria relative to the third external electronic device provides the user with feedback about the current state of the device (e.g., that the computer system meets proximity criteria relative to the third external electronic device). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the second disambiguation user interface (e.g., 1884), the electronic device detects one or more user inputs (e.g., 1886) corresponding to selection of the fifth selectable user interface object (e.g., 1884*b*). After detecting the one or more user inputs corresponding to selection of the fifth selectable user interface object, the electronic device determines that the computer system has been successfully paired with a third external electronic device of the first type (e.g., FIG. 18V). In response to determining that the computer system has been successfully paired with the third external electronic device of the first type, the electronic device initiates a process to display, via the display generation component, a third workout suggestion user interface (e.g., 1840) (e.g., a personalized workout suggestion user interface), wherein the third workout suggestion user interface displays one or more workout suggestions associated with the third external electronic device (e.g., associated with a user associated with the third external electronic device). In some embodiments, a workout suggestion corresponds to (e.g., represents) a workout (e.g., audio and/or video content that guides a user to perform a physical activity). In some embodiments, selecting a workout suggestion initiates a process for playback of a workout corresponding to the workout suggestion. Automatically causing a third workout suggestion user interface to be displayed in accordance with a determination that the computer system has been successfully paired with the third external electronic device provides the user with feedback about the current state of the device (e.g., that the computer system has been successfully paired with the third external electronic device). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Note that details of the processes described above with respect to method 1900 (e.g., FIGS. 19A-19C) are also applicable in an analogous manner to the methods described above. For example, method 1700 optionally includes one or more of the characteristics of the various methods described above with reference to method 1900. For example, the workout suggestion user interfaces as discussed above with respect to method 1900 may include various browsing and filtering features, as set forth in method 1700. For brevity, these details are not repeated.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery of workout content to a user. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver better personalized workout suggestions to the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of personalizing workout suggestions, the present technology can be configured to allow users to select to "opt in" or "opt out" of participation in the collection of personal information data during registration for services or anytime thereafter. In another example, users can select not to provide workout data for targeted workout suggestions. In yet another example, users can select to limit the length of time workout data is collected from the user. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, workout suggestions can be selected and delivered to users by inferring preferences based on non-personal information data or a bare minimum amount of personal information, such as the content being requested by the device associated with a user, other non-personal information available to the workout content services, or publicly available information.

What is claimed is:

1. An electronic device, comprising:
   a display;
   one or more processors; and
   memory storing one or more programs configured to be executed by the one or more processors, the one or more programs including instructions for:
   displaying, on the display, a selectable user interface object for displaying workout suggestions;
   detecting a user input corresponding to the selectable user interface object for displaying workout suggestions; and
   in response to detecting the user input corresponding to the selectable user interface object for displaying workout suggestions, displaying, on the display, a user interface for displaying workout suggestions that includes concurrently displaying:
- a plurality of workout affordances that includes a first affordance that, when selected, causes the electronic device to initiate a process for displaying workout suggestions that share a first common workout parameter and a second affordance that, when selected, causes the electronic device to initiate a process for displaying workout suggestions that share a second common workout parameter, wherein the plurality of workout affordances are displayed at a first area of the display; and
- a plurality of workout suggestion affordances, wherein the plurality of workout suggestion affordances are selected for display based on a workout history of a user of the electronic device, and wherein the plurality of workout suggestion affordances are displayed at a second area of the display different from the first area of the display.

2. The electronic device of claim 1, wherein the plurality of workout suggestion affordances includes:
a first workout suggestion affordance, wherein the first workout suggestion affordance corresponds to a first subset of a collection of completed workouts.

3. The electronic device of claim 2, wherein:
the first subset of the collection of completed workouts includes at least one workout in a predefined series of workouts, and
the first workout suggestion affordance corresponds to a next workout that has not been completed in the predefined series of workouts.

4. The electronic device of claim 2, wherein:
the first subset of the collection of completed workouts excludes at least one workout in a predefined series of workouts, and
the first workout suggestion affordance corresponds to the workout that was most recently completed.

5. The electronic device of claim 2, wherein the one or more programs further include instructions for:
detecting a user input corresponding to the first workout suggestion affordance that corresponds to a next workout that has not been completed in a predefined series of workouts; and
in response to detecting the user input corresponding to the first workout suggestion affordance that corresponds to the next workout that has not been completed in the predefined series of workouts:
displaying one or more workout suggestions in the predefined series of workouts; and
in accordance with a determination that at least one workout in the predefined series of workouts has been completed, visually emphasizing a workout suggestion of the one or more workout suggestions in the predefined series of workouts without visually emphasizing a different workout suggestion of the one or more workout suggestions in the predefined series of workouts.

6. The electronic device of claim 2, wherein the plurality of workout suggestion affordances includes:
a second workout suggestion affordance, wherein the second workout suggestion affordance corresponds to a second subset of a collection of completed workouts, wherein the first subset is different from the second subset.

7. The electronic device of claim 6, wherein the one or more programs further include instructions for:

while displaying the plurality of workout affordances and the plurality of workout suggestion affordances, detecting a first scroll gesture; and
after detecting the first scroll gesture, displaying, on the display, a third workout suggestion affordance, wherein the third workout suggestion affordance corresponds to a third subset of a collection of completed workouts.

8. The electronic device of claim 7, wherein the one or more programs further include instructions for:
while displaying the plurality of workout affordances and the plurality of workout suggestion affordances, detecting a second scroll gesture; and
after detecting the second scroll gesture, displaying, on the display, a fourth workout suggestion affordance, wherein the fourth workout suggestion affordance corresponds to a fourth subset of a collection of completed workouts.

9. The electronic device of claim 1, wherein the plurality of workout suggestion affordances includes a workout suggestion affordance for a workout that corresponds to a predefined list of audio items.

10. The electronic device of claim 1, wherein the plurality of workout suggestion affordances includes a workout suggestion affordance for a workout with metadata that causes output of prompts during playback of the workout.

11. The electronic device of claim 1, wherein the plurality of workout suggestion affordances includes a workout suggestion affordance for a workout that, when selected for playback, causes recording of one or more physical activity metrics at an external device.

12. The electronic device of claim 1, wherein the plurality of workout suggestion affordances includes a workout suggestion affordance that has a physical activity type that is different than a physical activity type of a completed workout.

13. The electronic device of claim 1, wherein the one or more programs further include instructions for:
while displaying the plurality of workout affordances and the plurality of workout suggestion affordances, detecting one or more inputs; and
in response to detecting the one or more inputs:
ceasing display of the plurality of workout affordances and the plurality of workout suggestion affordances; and
displaying, on the display, a third affordance that, when selected, configures the electronic device to display workout suggestion affordances that share a third common workout parameter and a fourth affordance that, when selected, configures the electronic device to display workout suggestion affordances that share a fourth common workout parameter.

14. The electronic device of claim 13, wherein the one or more programs further include instructions for:
detecting selection of the third affordance;
after detecting selection of the third affordance, displaying one or more workout suggestion affordances based on the detected selection of the third affordance, including a selectable user interface object indicating that the third affordance has been selected;
while displaying the one or more workout suggestion affordances based on the detected selection of the third affordance, detecting a user input corresponding to the selectable user interface object indicating that the third affordance has been selected; and
in response to detecting the user input corresponding to the selectable user interface object indicating that the third affordance has been selected, displaying, on the display, one or more workout suggestion affordances that were not displayed prior to detection of the user input corresponding to the selectable user interface object indicating that the third affordance has been selected.

15. The electronic device of claim 1, wherein the one or more programs further include instructions for:
    displaying a fifth workout suggestion affordance, wherein the fifth workout suggestion affordance is selected for display based on a frequency at which the fifth workout suggestion affordance is selected by a group of users.

16. The electronic device of claim 1, wherein the one or more programs further include instructions for:
    detecting a user input corresponding to a seventh workout suggestion affordance; and
    in response to detecting the user input corresponding to the seventh workout suggestion affordance, displaying, on the display, a detail user interface for the seventh workout suggestion affordance, wherein the detail user interface includes one or more workout characteristics selected from a group consisting of equipment, duration, music genre, exercise type, and a number of times a workout corresponding to the seventh workout suggestion affordance has been completed,
        wherein the one or more workout characteristics are associated with the workout corresponding to the seventh workout suggestion affordance.

17. The electronic device of claim 1, wherein the one or more programs further include instructions for:
    detecting a user input corresponding to an eighth workout suggestion affordance;
    in response to detecting the user input corresponding to the eighth workout suggestion affordance, displaying, on the display, an audio selectable user interface object that, when selected, initiates a process for causing playback of one or more audio items that are part of a predefined collection of audio items, wherein the predefined collection of audio items is associated with a workout corresponding to the eighth workout suggestion affordance;
    detecting a user input corresponding to the audio selectable user interface object; and
    in response to detecting the user input corresponding to the audio selectable user interface object, launching a music application with a save affordance that, when selected, initiates a process for saving the predefined collection of audio items to a user library of the music application.

18. The electronic device of claim 1, wherein the one or more programs further include instructions for:
    causing an external device to display a ninth workout suggestion affordance, wherein the ninth workout suggestion affordance is based on one or more physical activity metrics of the user of the electronic device.

19. The electronic device of claim 1, wherein the one or more programs further include instructions for:
    displaying, within the user interface for displaying workout suggestion, a fifth affordance that, when selected, causes the electronic device to initiate a process for playing a new content introduction media corresponding to a plurality of new workouts that have been made available to the user of the electronic device within a predefined period of time.

20. The electronic device of claim 1, wherein the one or more programs further include instructions for:
    detecting a user input corresponding to a tenth workout suggestion affordance;
    in response to detecting the user input corresponding to the tenth workout suggestion affordance, concurrently displaying, on the display:
        a first audio selectable user interface object that, when selected, initiates a process for causing playback of a plurality of audio items that are part of a predefined collection of audio items, wherein the predefined collection of audio items is associated with a workout corresponding to the tenth workout suggestion affordance;
        a second audio selectable user interface object that, when selected, initiates a process for causing playback of a first audio item of the plurality of audio items; and
        a third audio selectable user interface object that, when selected, initiates a process for causing playback of a second audio item of the plurality of audio items different from the first audio item.

21. The electronic device of claim 1, wherein the first affordance, when selected, causes the electronic device to initiate a process for displaying workout suggestion affordances that share a first common workout type, and the one or more programs further include instructions for:
    detecting a user input corresponding to the first affordance; and
    in response to detecting the user input corresponding to the first affordance, concurrently displaying:
        one or more workout suggestion affordances that share the first common workout type, and
        a workout type introduction object that, when selected, causes the electronic device to initiate a process for playing a workout type introduction video corresponding to the first common workout type, wherein the workout type introduction video identifies one or more pieces of workout equipment required for the first common workout type.

22. The electronic device of claim 1, wherein the one or more programs further include instructions for:
    displaying, within the user interface for displaying workout suggestion affordances, a sixth affordance that, when selected, causes the electronic device to initiate a process for displaying workout suggestion affordances for a plurality of workouts in a predefined series of workouts;
    detecting a user input corresponding to the sixth affordance; and
    in response to detecting the user input corresponding to the sixth affordance, concurrently displaying:
        workout suggestion affordances for the plurality of workouts in the predefined series of workouts, and
        a workout series introduction object that, when selected, causes the electronic device to initiate a process for playing a workout series introduction media corresponding to the predefined series of workouts.

23. A non-transitory computer-readable storage medium storing one or more programs configured to be executed by one or more processors of an electronic device with a display, the one or more programs including instructions for:
    displaying, on the display, a selectable user interface object for displaying workout suggestions;
    detecting a user input corresponding to the selectable user interface object for displaying workout suggestions; and
    in response to detecting the user input corresponding to the selectable user interface object for displaying workout suggestions, displaying, on the display, a user interface for displaying workout suggestions that includes concurrently displaying:
- a plurality of workout affordances that includes a first affordance that, when selected, causes the electronic device to initiate a process for displaying workout suggestions that share a first common workout parameter and a second affordance that, when selected, causes the electronic device to initiate a process for displaying workout suggestions that share a second common workout parameter, wherein the plurality of workout affordances are displayed at a first area of the display; and
- a plurality of workout suggestion affordances, wherein the plurality of workout suggestion affordances are selected for display based on a workout history of a user of the electronic device, and wherein the plurality of workout suggestion affordances are displayed at a second area of the display different from the first area of the display.

24. A method, comprising:
at an electronic device with a display:
- displaying, on the display, a selectable user interface object for displaying workout suggestions;
- detecting a user input corresponding to the selectable user interface object for displaying workout suggestions; and
- in response to detecting the user input corresponding to the selectable user interface object for displaying workout suggestions, displaying, on the display, a user interface for displaying workout suggestions that includes concurrently displaying:
  - a plurality of workout affordances that includes a first affordance that, when selected, causes the electronic device to initiate a process for displaying workout suggestions that share a first common workout parameter and a second affordance that, when selected, causes the electronic device to initiate a process for displaying workout suggestions that share a second common workout parameter, wherein the plurality of workout affordances are displayed at a first area of the display; and
  - a plurality of workout suggestion affordances, wherein the plurality of workout suggestion affordances are selected for display based on a workout history of a user of the electronic device, and wherein the plurality of workout suggestion affordances are displayed at a second area of the display different from the first area of the display.

25. The non-transitory computer-readable storage medium of claim 23, wherein the plurality of workout suggestion affordances includes:
a first workout suggestion affordance, wherein the first workout suggestion affordance corresponds to a first subset of a collection of completed workouts.

26. The non-transitory computer-readable storage medium of claim 25, wherein:
the first subset of the collection of completed workouts includes at least one workout in a predefined series of workouts, and
the first workout suggestion affordance corresponds to a next workout that has not been completed in the predefined series of workouts.

27. The non-transitory computer-readable storage medium of claim 25, wherein:
the first subset of the collection of completed workouts excludes at least one workout in a predefined series of workouts, and the first workout suggestion affordance corresponds to the workout that was most recently completed.

28. The non-transitory computer-readable storage medium of claim 25, wherein the one or more programs further include instructions for:
detecting a user input corresponding to the first workout suggestion affordance that corresponds to a next workout that has not been completed in a predefined series of workouts; and
in response to detecting the user input corresponding to the first workout suggestion affordance that corresponds to the next workout that has not been completed in the predefined series of workouts:
displaying one or more workout suggestions in the predefined series of workouts; and
in accordance with a determination that at least one workout in the predefined series of workouts has been completed, visually emphasizing a workout suggestion of the one or more workout suggestions in the predefined series of workouts without visually emphasizing a different workout suggestion of the one or more workout suggestions in the predefined series of workouts.

29. The non-transitory computer-readable storage medium of claim 25, wherein the plurality of workout suggestion affordances includes:
a second workout suggestion affordance, wherein the second workout suggestion affordance corresponds to a second subset of a collection of completed workouts, wherein the first subset is different from the second subset.

30. The non-transitory computer-readable storage medium of claim 29, wherein the one or more programs further include instructions for:
while displaying the plurality of workout affordances and the plurality of workout suggestion affordances, detecting a first scroll gesture; and
after detecting the first scroll gesture, displaying, on the display, a third workout suggestion affordance, wherein the third workout suggestion affordance corresponds to a third subset of a collection of completed workouts.

31. The non-transitory computer-readable storage medium of claim 30, wherein the one or more programs further include instructions for:
while displaying the plurality of workout affordances and the plurality of workout suggestion affordances, detecting a second scroll gesture; and
after detecting the second scroll gesture, displaying, on the display, a fourth workout suggestion affordance, wherein the fourth workout suggestion affordance corresponds to a fourth subset of a collection of completed workouts.

32. The non-transitory computer-readable storage medium of claim 23, wherein the plurality of workout suggestion affordances includes a workout suggestion affordance for a workout that corresponds to a predefined list of audio items.

33. The non-transitory computer-readable storage medium of claim 23, wherein the plurality of workout suggestion affordances includes a workout suggestion affordance for a workout with metadata that causes output of prompts during playback of the workout.

34. The non-transitory computer-readable storage medium of claim 23, wherein the plurality of workout suggestion affordances includes a workout suggestion affordance for a workout that, when selected for playback, causes recording of one or more physical activity metrics at an external device.

35. The non-transitory computer-readable storage medium of claim 23, wherein the plurality of workout suggestion affordances includes a workout suggestion affordance that has a physical activity type that is different than a physical activity type of a completed workout.

36. The non-transitory computer-readable storage medium of claim 23, wherein the one or more programs further include instructions for:
while displaying the plurality of workout affordances and the plurality of workout suggestion affordances, detecting one or more inputs; and
in response to detecting the one or more inputs:
ceasing display of the plurality of workout affordances and the plurality of workout suggestion affordances; and
displaying, on the display, a third affordance that, when selected, configures the electronic device to display workout suggestion affordances that share a third common workout parameter and a fourth affordance that, when selected, configures the electronic device to display workout suggestion affordances that share a fourth common workout parameter.

37. The non-transitory computer-readable storage medium of claim 36, wherein the one or more programs further include instructions for:
detecting selection of the third affordance;
after detecting selection of the third affordance, displaying one or more workout suggestion affordances based on the detected selection of the third affordance, including a selectable user interface object indicating that the third affordance has been selected;
while displaying the one or more workout suggestion affordances based on the detected selection of the third affordance, detecting a user input corresponding to the selectable user interface object indicating that the third affordance has been selected; and
in response to detecting the user input corresponding to the selectable user interface object indicating that the third affordance has been selected, displaying, on the display, one or more workout suggestion affordances that were not displayed prior to detection of the user input corresponding to the selectable user interface object indicating that the third affordance has been selected.

38. The non-transitory computer-readable storage medium of claim 23, wherein the one or more programs further include instructions for:
displaying a fifth workout suggestion affordance, wherein the fifth workout suggestion affordance is selected for display based on a frequency at which the fifth workout suggestion affordance is selected by a group of users.

39. The non-transitory computer-readable storage medium of claim 23, wherein the one or more programs further include instructions for:
detecting a user input corresponding to a seventh workout suggestion affordance; and
in response to detecting the user input corresponding to the seventh workout suggestion affordance, displaying, on the display, a detail user interface for the seventh workout suggestion affordance, wherein the detail user interface includes one or more workout characteristics selected from a group consisting of equipment, duration, music genre, exercise type, and a number of times a workout corresponding to the seventh workout suggestion affordance has been completed,
wherein the one or more workout characteristics are associated with the workout corresponding to the seventh workout suggestion affordance.

40. The non-transitory computer-readable storage medium of claim 23, wherein the one or more programs further include instructions for:
detecting a user input corresponding to an eighth workout suggestion affordance;
in response to detecting the user input corresponding to the eighth workout suggestion affordance, displaying, on the display, an audio selectable user interface object that, when selected, initiates a process for causing playback of one or more audio items that are part of a predefined collection of audio items, wherein the predefined collection of audio items is associated with a workout corresponding to the eighth workout suggestion affordance;
detecting a user input corresponding to the audio selectable user interface object; and
in response to detecting the user input corresponding to the audio selectable user interface object, launching a music application with a save affordance that, when selected, initiates a process for saving the predefined collection of audio items to a user library of the music application.

41. The non-transitory computer-readable storage medium of claim 23, wherein the one or more programs further include instructions for:
causing an external device to display a ninth workout suggestion affordance, wherein the ninth workout suggestion affordance is based on one or more physical activity metrics of the user of the electronic device.

42. The non-transitory computer-readable storage medium of claim 23, wherein the one or more programs further include instructions for:
displaying, within the user interface for displaying workout suggestion, a fifth affordance that, when selected, causes the electronic device to initiate a process for playing a new content introduction media corresponding to a plurality of new workouts that have been made available to the user of the electronic device within a predefined period of time.

43. The non-transitory computer-readable storage medium of claim 23, wherein the one or more programs further include instructions for:
detecting a user input corresponding to a tenth workout suggestion affordance;
in response to detecting the user input corresponding to the tenth workout suggestion affordance, concurrently displaying, on the display:
a first audio selectable user interface object that, when selected, initiates a process for causing playback of a plurality of audio items that are part of a predefined collection of audio items, wherein the predefined collection of audio items is associated with a workout corresponding to the tenth workout suggestion affordance;
a second audio selectable user interface object that, when selected, initiates a process for causing playback of a first audio item of the plurality of audio items; and
a third audio selectable user interface object that, when selected, initiates a process for causing playback of a second audio item of the plurality of audio items different from the first audio item.

44. The non-transitory computer-readable storage medium of claim 23, wherein the first affordance, when selected, causes the electronic device to initiate a process for displaying workout suggestion affordances that share a first common workout type, and the one or more programs further include instructions for:
  detecting a user input corresponding to the first affordance; and
  in response to detecting the user input corresponding to the first affordance, concurrently displaying:
    one or more workout suggestion affordances that share the first common workout type, and
    a workout type introduction object that, when selected, causes the electronic device to initiate a process for playing a workout type introduction video corresponding to the first common workout type, wherein the workout type introduction video identifies one or more pieces of workout equipment required for the first common workout type.

45. The non-transitory computer-readable storage medium of claim 23, wherein the one or more programs further include instructions for:
  displaying, within the user interface for displaying workout suggestion affordances, a sixth affordance that, when selected, causes the electronic device to initiate a process for displaying workout suggestion affordances for a plurality of workouts in a predefined series of workouts;
  detecting a user input corresponding to the sixth affordance; and
  in response to detecting the user input corresponding to the sixth affordance, concurrently displaying:
    workout suggestion affordances for the plurality of workouts in the predefined series of workouts, and
    a workout series introduction object that, when selected, causes the electronic device to initiate a process for playing a workout series introduction media corresponding to the predefined series of workouts.

46. The method of claim 24, wherein the plurality of workout suggestion affordances includes:
  a first workout suggestion affordance, wherein the first workout suggestion affordance corresponds to a first subset of a collection of completed workouts.

47. The method of claim 46, wherein:
  the first subset of the collection of completed workouts includes at least one workout in a predefined series of workouts, and
  the first workout suggestion affordance corresponds to a next workout that has not been completed in the predefined series of workouts.

48. The method of claim 46, wherein:
  the first subset of the collection of completed workouts excludes at least one workout in a predefined series of workouts, and
  the first workout suggestion affordance corresponds to the workout that was most recently completed.

49. The method of claim 46, further comprising:
  detecting a user input corresponding to the first workout suggestion affordance that corresponds to a next workout that has not been completed in a predefined series of workouts; and
  in response to detecting the user input corresponding to the first workout suggestion affordance that corresponds to the next workout that has not been completed in the predefined series of workouts:
    displaying one or more workout suggestions in the predefined series of workouts; and
    in accordance with a determination that at least one workout in the predefined series of workouts has been completed, visually emphasizing a workout suggestion of the one or more workout suggestions in the predefined series of workouts without visually emphasizing a different workout suggestion of the one or more workout suggestions in the predefined series of workouts.

50. The method of claim 46, wherein the plurality of workout suggestion affordances includes:
  a second workout suggestion affordance, wherein the second workout suggestion affordance corresponds to a second subset of a collection of completed workouts, wherein the first subset is different from the second subset.

51. The method of claim 50, further comprising:
  while displaying the plurality of workout affordances and the plurality of workout suggestion affordances, detecting a first scroll gesture; and
  after detecting the first scroll gesture, displaying, on the display, a third workout suggestion affordance, wherein the third workout suggestion affordance corresponds to a third subset of a collection of completed workouts.

52. The method of claim 51, further comprising:
  while displaying the plurality of workout affordances and the plurality of workout suggestion affordances, detecting a second scroll gesture; and
  after detecting the second scroll gesture, displaying, on the display, a fourth workout suggestion affordance, wherein the fourth workout suggestion affordance corresponds to a fourth subset of a collection of completed workouts.

53. The method of claim 24, wherein the plurality of workout suggestion affordances includes a workout suggestion affordance for a workout that corresponds to a predefined list of audio items.

54. The method of claim 24, wherein the plurality of workout suggestion affordances includes a workout suggestion affordance for a workout with metadata that causes output of prompts during playback of the workout.

55. The method of claim 24, wherein the plurality of workout suggestion affordances includes a workout suggestion affordance for a workout that, when selected for playback, causes recording of one or more physical activity metrics at an external device.

56. The method of claim 24, wherein the plurality of workout suggestion affordances includes a workout suggestion affordance that has a physical activity type that is different than a physical activity type of a completed workout.

57. The method of claim 24, further comprising:
  while displaying the plurality of workout affordances and the plurality of workout suggestion affordances, detecting one or more inputs; and
  in response to detecting the one or more inputs:
    ceasing display of the plurality of workout affordances and the plurality of workout suggestion affordances; and
    displaying, on the display, a third affordance that, when selected, configures the electronic device to display workout suggestion affordances that share a third common workout parameter and a fourth affordance that, when selected, configures the electronic device to display workout suggestion affordances that share a fourth common workout parameter.

58. The method of claim 57, further comprising:
detecting selection of the third affordance;
after detecting selection of the third affordance, displaying one or more workout suggestion affordances based on the detected selection of the third affordance, including a selectable user interface object indicating that the third affordance has been selected;
while displaying the one or more workout suggestion affordances based on the detected selection of the third affordance, detecting a user input corresponding to the selectable user interface object indicating that the third affordance has been selected; and
in response to detecting the user input corresponding to the selectable user interface object indicating that the third affordance has been selected, displaying, on the display, one or more workout suggestion affordances that were not displayed prior to detection of the user input corresponding to the selectable user interface object indicating that the third affordance has been selected.

59. The method of claim 24, further comprising:
displaying a fifth workout suggestion affordance, wherein the fifth workout suggestion affordance is selected for display based on a frequency at which the fifth workout suggestion affordance is selected by a group of users.

60. The method of claim 24, further comprising:
detecting a user input corresponding to a seventh workout suggestion affordance; and
in response to detecting the user input corresponding to the seventh workout suggestion affordance, displaying, on the display, a detail user interface for the seventh workout suggestion affordance, wherein the detail user interface includes one or more workout characteristics selected from a group consisting of equipment, duration, music genre, exercise type, and a number of times a workout corresponding to the seventh workout suggestion affordance has been completed,
wherein the one or more workout characteristics are associated with the workout corresponding to the seventh workout suggestion affordance.

61. The method of claim 24, further comprising:
detecting a user input corresponding to an eighth workout suggestion affordance;
in response to detecting the user input corresponding to the eighth workout suggestion affordance, displaying, on the display, an audio selectable user interface object that, when selected, initiates a process for causing playback of one or more audio items that are part of a predefined collection of audio items, wherein the predefined collection of audio items is associated with a workout corresponding to the eighth workout suggestion affordance;
detecting a user input corresponding to the audio selectable user interface object; and
in response to detecting the user input corresponding to the audio selectable user interface object, launching a music application with a save affordance that, when selected, initiates a process for saving the predefined collection of audio items to a user library of the music application.

62. The method of claim 24, wherein the one or more programs further include instructions for:
causing an external device to display a ninth workout suggestion affordance, wherein the ninth workout suggestion affordance is based on one or more physical activity metrics of the user of the electronic device.

63. The method of claim 24, further comprising:
displaying, within the user interface for displaying workout suggestion, a fifth affordance that, when selected, causes the electronic device to initiate a process for playing a new content introduction media corresponding to a plurality of new workouts that have been made available to the user of the electronic device within a predefined period of time.

64. The method of claim 24, further comprising:
detecting a user input corresponding to a tenth workout suggestion affordance;
in response to detecting the user input corresponding to the tenth workout suggestion affordance, concurrently displaying, on the display:
a first audio selectable user interface object that, when selected, initiates a process for causing playback of a plurality of audio items that are part of a predefined collection of audio items, wherein the predefined collection of audio items is associated with a workout corresponding to the tenth workout suggestion affordance;
a second audio selectable user interface object that, when selected, initiates a process for causing playback of a first audio item of the plurality of audio items; and
a third audio selectable user interface object that, when selected, initiates a process for causing playback of a second audio item of the plurality of audio items different from the first audio item.

65. The method of claim 24, wherein the first affordance, when selected, causes the electronic device to initiate a process for displaying workout suggestion affordances that share a first common workout type, the method further comprising:
detecting a user input corresponding to the first affordance; and
in response to detecting the user input corresponding to the first affordance, concurrently displaying:
one or more workout suggestion affordances that share the first common workout type, and
a workout type introduction object that, when selected, causes the electronic device to initiate a process for playing a workout type introduction video corresponding to the first common workout type, wherein the workout type introduction video identifies one or more pieces of workout equipment required for the first common workout type.

66. The method of claim 24, further comprising:
displaying, within the user interface for displaying workout suggestion affordances, a sixth affordance that, when selected, causes the electronic device to initiate a process for displaying workout suggestion affordances for a plurality of workouts in a predefined series of workouts;
detecting a user input corresponding to the sixth affordance; and
in response to detecting the user input corresponding to the sixth affordance, concurrently displaying:
workout suggestion affordances for the plurality of workouts in the predefined series of workouts, and
a workout series introduction object that, when selected, causes the electronic device to initiate a process for playing a workout series introduction media corresponding to the predefined series of workouts.

* * * * *